(12) United States Patent
Cha et al.

(10) Patent No.: US 12,041,848 B2
(45) Date of Patent: Jul. 16, 2024

(54) HETEROCYCLIC COMPOUND AND ORGANIC LIGHT EMITTING ELEMENT COMPRISING SAME

(71) Applicant: LG Chem, Ltd., Seoul (KR)

(72) Inventors: Yongbum Cha, Daejeon (KR); Seongmi Cho, Daejeon (KR); Jin Joo Kim, Daejeon (KR)

(73) Assignee: LG Chem, Ltd., Seoul (KR)

(*) Notice: Subject to any disclaimer, the term of this patent is extended or adjusted under 35 U.S.C. 154(b) by 476 days.

(21) Appl. No.: 15/780,880

(22) PCT Filed: Dec. 7, 2016

(86) PCT No.: PCT/KR2016/014307
§ 371 (c)(1),
(2) Date: Jun. 1, 2018

(87) PCT Pub. No.: WO2017/099471
PCT Pub. Date: Jun. 15, 2017

(65) Prior Publication Data
US 2018/0287069 A1    Oct. 4, 2018

(30) Foreign Application Priority Data

Dec. 8, 2015 (KR) .......... 10-2015-0174341
Nov. 7, 2016 (KR) .......... 10-2016-0147542

(51) Int. Cl.
*H10K 85/60* (2023.01)
*C07D 307/91* (2006.01)
(Continued)

(52) U.S. Cl.
CPC ......... *H10K 85/636* (2023.02); *C07D 307/91* (2013.01); *C09K 11/025* (2013.01);
(Continued)

(58) Field of Classification Search
CPC .............. H01L 51/0061; H01L 51/006; H01L 51/0074; H01L 2251/5338; H01L 51/0073;
(Continued)

(56) References Cited

U.S. PATENT DOCUMENTS 5,025,008 A     6/1991   DiNinno et al.
2011/0248246 A1  10/2011  Ogita et al.
(Continued)

FOREIGN PATENT DOCUMENTS

CN  102219774 A  10/2011
CN  103288656 A   9/2013
(Continued)

OTHER PUBLICATIONS

Katsuhiko Ono "Synthesis and Electroluminescence Properties of fac-Tris(2-phenylpyridine)-iridium Derivatives Containing Hole-Trapping Moieties" Eur. J. Inorg. Chem. 2006, 3676-3683 (Year: 2006).*
(Continued)

*Primary Examiner* — Michael Y Sun
(74) *Attorney, Agent, or Firm* — Lerner David LLP

(57) ABSTRACT

The present specification provides a heterocyclic compound and an organic light emitting device including the same.

15 Claims, 1 Drawing Sheet

(51) Int. Cl.
- *C09K 11/02* (2006.01)
- *H10K 50/11* (2023.01)
- *H10K 50/15* (2023.01)
- *H10K 50/16* (2023.01)
- *H10K 50/17* (2023.01)
- *H10K 50/18* (2023.01)
- *H10K 71/00* (2023.01)
- *H10K 71/16* (2023.01)
- *H10K 101/10* (2023.01)
- *H10K 102/00* (2023.01)

(52) U.S. Cl.
CPC ........... H10K 85/633 (2023.02); *H10K 50/11* (2023.02); *H10K 50/15* (2023.02); *H10K 50/16* (2023.02); *H10K 50/17* (2023.02); *H10K 50/171* (2023.02); *H10K 50/18* (2023.02); *H10K 71/00* (2023.02); *H10K 71/164* (2023.02); *H10K 85/615* (2023.02); *H10K 85/6574* (2023.02); *H10K 85/6576* (2023.02); *H10K 2101/10* (2023.02); *H10K 2102/311* (2023.02)

(58) Field of Classification Search
CPC ............. H01L 51/0052; H01L 51/5016; H01L 51/5072; H01L 51/5092; H01L 51/5056; H01L 51/5096; H01L 51/5088; H01L 51/56; H01L 51/001; C09K 11/025; C09K 11/06; C09K 2211/1014; C09K 2211/1088; C09K 2211/1092; C07D 307/91; C07D 333/76; H10K 85/636; H10K 85/633; H10K 50/11; H10K 50/15; H10K 50/16; H10K 50/17; H10K 50/171; H10K 50/18; H10K 71/00; H10K 71/164; H10K 85/615; H10K 85/6574; H10K 85/6576; H10K 2101/10; H10K 2102/311; H10K 50/181; C07C 211/54

See application file for complete search history.

(56) References Cited

U.S. PATENT DOCUMENTS

| | | | |
|---|---|---|---|
| 2012/0119197 A1* | 5/2012 | Nishimura | H01L 51/0072 257/40 |
| 2013/0228752 A1 | 9/2013 | Shin et al. | |
| 2015/0137080 A1 | 5/2015 | Tsai et al. | |
| 2016/0020405 A1* | 1/2016 | Ito | H01L 51/0067 257/40 |
| 2016/0028021 A1* | 1/2016 | Zeng | C07D 251/24 257/40 |
| 2018/0226585 A1* | 8/2018 | Park | C07D 405/04 |
| 2018/0358563 A1* | 12/2018 | Park | H01L 51/0061 |
| 2019/0044071 A1* | 2/2019 | Parham | C07D 405/10 |

FOREIGN PATENT DOCUMENTS

| | | | | |
|---|---|---|---|---|
| JP | 2011153201 A | * | 8/2011 | |
| KR | 20110041725 A | | 4/2011 | |
| KR | 2013-0007441 A | | 1/2013 | |
| KR | 2013-0100633 A | | 9/2013 | |
| KR | 20150010016 A | | 1/2015 | |
| KR | 10-1535606 B1 | | 7/2015 | |
| KR | 101535606 B1 | * | 7/2015 | ............. C09K 11/06 |
| KR | 2016-0057018 A | | 5/2016 | |
| KR | 20170001830 A | | 1/2017 | |
| WO | 2015009076 A1 | | 1/2015 | |
| WO | WO-2015041492 A1 | * | 3/2015 | ............ C07D 405/04 |

OTHER PUBLICATIONS

Taiwanese Search Report for Application No. 105140604, dated Jul. 24, 2019, 1 pg.

Tolkunov et al., Reactions Of 1,3-Substituted Benzothieno[2,3-C]Pyrylium Salts With Primary Amines, Chemistry of Heterocyclic Compounds, 2004, pp. 1082-1086, vol. 40, No. 8.

International Search Report From PCT/KR2016/014307 dated Mar. 15, 2017.

Chinese Search Report for Application No. 201680072920.1, dated Jul. 8, 2021, 3 pages.

\* cited by examiner

【FIG. 1】
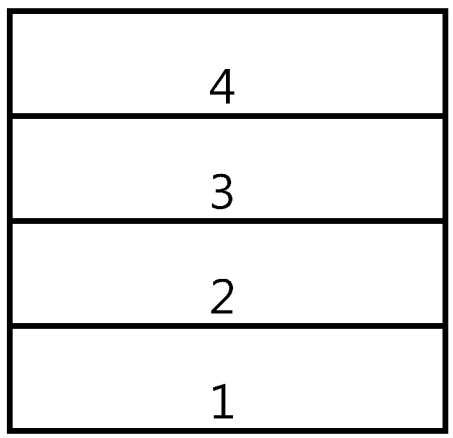
【FIG. 2】
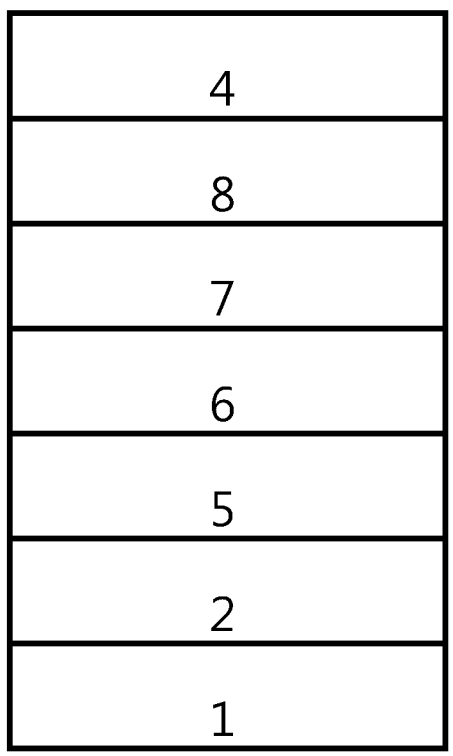

HETEROCYCLIC COMPOUND AND ORGANIC LIGHT EMITTING ELEMENT COMPRISING SAME

CROSS-REFERENCE TO RELATED APPLICATIONS

This application is a national phase entry under 35 U.S.C. § 371 of International Application No. PCT/KR2016/014307, filed Dec. 7, 2016, which claims priority to Korean Patent Application No. 10-2015-0174341, filed Dec. 8, 2015 and Korean Patent Application No. 10-2016-0147542, filed Nov. 7, 2016, the disclosures of which are incorporated herein by reference.

TECHNICAL FIELD

The present specification relates to a heterocyclic compound and an organic light emitting device including the same.

BACKGROUND ART

An organic light emission phenomenon generally refers to a phenomenon converting electrical energy to light energy using an organic material. An organic light emitting device using an organic light emission phenomenon normally has a structure including an anode, a cathode, and an organic material layer therebetween. Herein, the organic material layer is often formed in a multilayer structure formed with different materials in order to increase efficiency and stability of the organic light emitting device, and for example, may be formed with a hole injection layer, a hole transfer layer, an electron blocking layer, a light emitting layer, an electron transfer layer, an electron injection layer and the like. When a voltage is applied between the two electrodes in such an organic light emitting device structure, holes and electrons are injected to the organic material layer from the anode and the cathode, respectively, and when the injected holes and electrons meet, excitons are formed, and light emits when these excitons fall back to the ground state.

Development of new materials for such an organic light emitting device has been continuously required.

DISCLOSURE

Technical Problem

The present specification describes a heterocyclic compound and an organic light emitting device including the same.

Technical Solution

One embodiment of the present specification provides a compound represented by the following Chemical Formula 1:

[Chemical Formula 1]

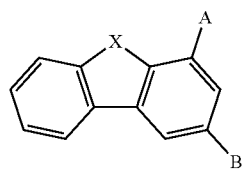

in Chemical Formula 1,
X is O or S,
at least one of A and B has a structure of the following Chemical Formula 1-1, and the remaining one is a substituted or unsubstituted aryl group; or a substituted or unsubstituted heterocyclic group,

[Chemical Formula 1-1]

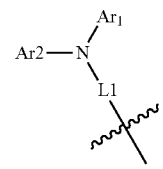

in Chemical Formula 1-1, L1 is a direct bond; or a substituted or unsubstituted arylene group, and
Ar1 and Ar2 are the same as or different from each other, and each independently hydrogen; deuterium; a halogen group; a nitrile group; a nitro group; a hydroxyl group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylphosphine group; a substituted or unsubstituted phosphine oxide group; a substituted or unsubstituted aryl group; or a substituted or unsubstituted heterocyclic group.

Chemical Formula 1 may be represented by the following Chemical Formula 1-A or Chemical Formula 1-B,

[Chemical Formula 1-A]

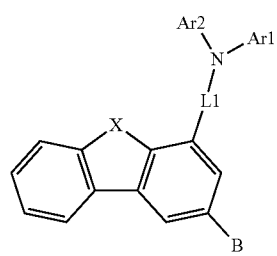

[Chemical Formula 1-B]

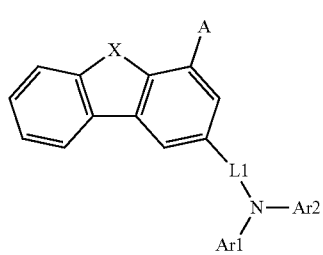

In Chemical Formulae 1-A and 1-B,
definitions of X, L1, A, B, Ar1 and Ar2 are the same as in Chemical Formula 1 and Chemical Formula 1-1.

Another embodiment of the present specification provides an organic light emitting device including a first electrode, a second electrode, and one or more organic material layers disposed between the first electrode and the second electrode, wherein one or more layers of the organic material layers include the compound of Chemical Formula 1.

Advantageous Effects

Compounds described in the present specification may be used as a material of an organic material layer of an organic light emitting device. Compounds according to at least one embodiment are capable of efficiency enhancement, low driving voltage and/or lifespan property enhancement in an organic light emitting device. Particularly, compounds described in the present specification can be used as materials of hole injection, hole transfer, hole injection and hole transfer, electron blocking, light emitting, hole blocking, electron transfer, or electron injection.

DESCRIPTION OF DRAWINGS

FIG. 1 is a diagram illustrating an organic light emitting device formed with a substrate (1), an anode (2), a light emitting layer (3) and a cathode (4).

FIG. 2 is a diagram illustrating an organic light emitting device formed with a substrate (1), an anode (2), a hole injection layer (5), a hole transfer layer (6), a light emitting layer (7), an electron transfer layer (8) and a cathode (4).

1: Substrate
2: Anode
3: Light Emitting Layer
4: Cathode
5: Hole Injection Layer
6: Hole Transfer Layer
7: Electron Transfer Layer

MODE FOR DISCLOSURE

Hereinafter, the present specification will be described in more detail.

One embodiment of the present specification provides a compound represented by Chemical Formula 1.

In the present specification,

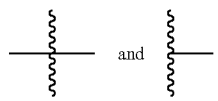

and mean a site linking to other substituents.

Examples of the substituents are described below, however, the substituents are not limited thereto.

The term "substituted or unsubstituted" in the present specification means being substituted with one or more substituents selected from the group consisting of deuterium; a halogen group; a nitrile group; a nitro group; a hydroxyl group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a heterocyclic group, or being unsubstituted, or being substituted with a substituent linking two or more substituents among the substituents illustrated above, or being unsubstituted. For example, "a substituent linking two or more substituents" may include a biphenyl group. In other words, a biphenyl group may be an aryl group, or interpreted as a substituent linking two phenyl groups.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

In the present specification, examples of the halogen group may include fluorine, chlorine, bromine or iodine.

In the present specification, the number of carbon atoms of the carbonyl group is not particularly limited, but is preferably from 1 to 40. Specifically, compounds having structures as below may be included, but the carbonyl group is not limited thereto.

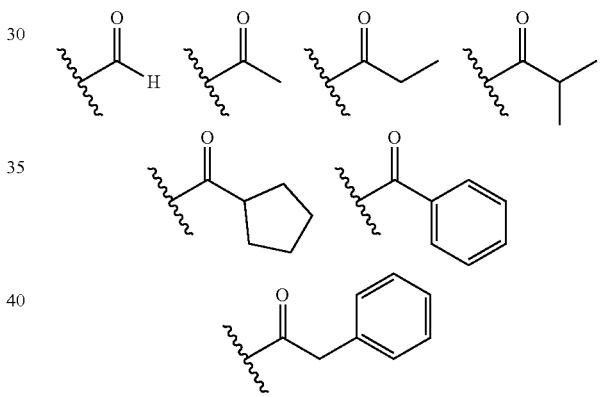

In the present specification, in the ester group, the oxygen of the ester group may be substituted with a linear, branched or cyclic alkyl group having 1 to 25 carbon atoms or an aryl group having 6 to 25 carbon atoms. Specifically, compounds having the following structural formulae may be included, but the ester group is not limited thereto.

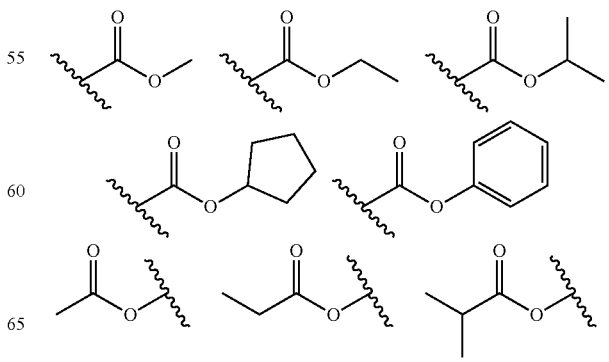

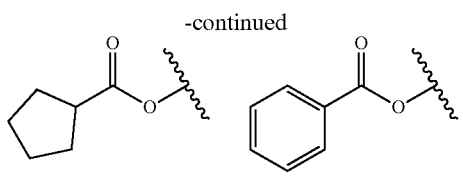

In the present specification, the number of carbon atoms of the imide group is not particularly limited, but is preferably from 1 to 25. Specifically, compounds having structures as below may be included, but the imide group is not limited thereto.

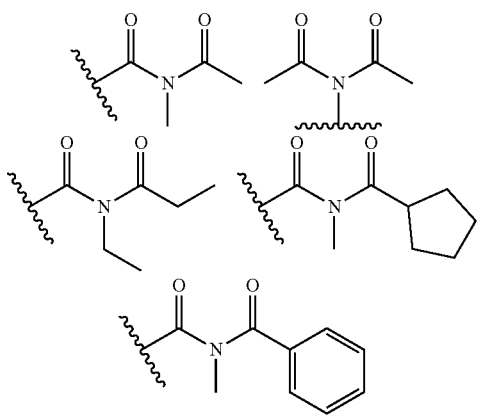

In the present specification, the silyl group may be represented by the chemical formula of —SiRR'R", and R' and R" may each be hydrogen; a substituted or unsubstituted alkyl group; or a substituted or unsubstituted aryl group. Specific examples of the silyl group may include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the boron group may be represented by the chemical formula of —BR'R", and R, R' and R" may each be hydrogen; a substituted or unsubstituted alkyl group; or a substituted or unsubstituted aryl group. Specific examples of the boron group may include a trimethylboron group, a triethylboron group, a t-butyldimethylboron group, a triphenylboron group, a phenylboron group and the like, but are not limited thereto.

In the present specification, a germanium group may be represented by the chemical formula of —GeR$_a$R$_b$R$_c$, and R$_a$, R$_b$ and R$_c$ may each be hydrogen; a substituted or unsubstituted alkyl group; or a substituted or unsubstituted aryl group. Specific examples of the germanium group may include a trimethylgermanium group, a triethylgermanium group, a t-butyldimethylgermanium group and the like, but are not limited thereto.

In the present specification, the alkyl group may be linear or branched, and the number of carbon atoms is not particularly limited, but is preferably from 1 to 40. According to one embodiment, the number of carbon atoms of the alkyl group is from 1 to 20. According to another embodiment, the number of carbon atoms of the alkyl group is from 1 to 10. According to still another embodiment, the number of carbon atoms of the alkyl group is from 1 to 6. Specific examples of the alkyl group may include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 4-methylhexyl, 5-methylhexyl and the like, but are not limited thereto.

In the present specification, the cycloalkyl group is not particularly limited, but preferably has 3 to 60 carbon atoms, and according to one embodiment, the number of carbon atoms of the cycloalkyl group is from 3 to 30. According to another embodiment, the number of carbon atoms of the cycloalkyl group is from 3 to 20. According to still another embodiment, the number of carbon atoms of the cycloalkyl group is from 3 to 6. Specific examples thereof may include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the alkoxy group may be linear, branched or cyclic. The number of carbon atoms of the alkoxy group is not particularly limited, but is preferably from 1 to 20. Specific examples thereof may include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

The alkyl group, the alkoxy group and other substituents including the alkyl group parts described in the present specification include all of linear or branched forms.

In the present specification, the alkenyl group may be linear or branched, and although not particularly limited thereto, the number of carbon atoms is preferably from 2 to 40. According to one embodiment, the number of carbon atoms of the alkenyl group is from 2 to 20. According to another embodiment, the number of carbon atoms of the alkenyl group is from 2 to 10. According to still another embodiment, the number of carbon atoms of the alkenyl group is from 2 to 6. Specific examples thereof may include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group and the like, but are not limited thereto.

In the present specification, examples of the arylamine group include a substituted or unsubstituted monoarylamine group, a substituted or unsubstituted diarylamine group, or a substituted or unsubstituted triarylamine group. The aryl group in the arylamine group may be a monocyclic aryl group or a multicyclic aryl group. The arylamine group including two or more aryl groups may include monocyclic aryl groups, multicyclic aryl groups, or both monocyclic aryl groups and multicyclic aryl groups.

Specific examples of the arylamine group may include phenylamine, naphthylamine, biphenylamine, anthracenylamine, 3-methyl-phenylamine, 4-methyl-naphthylamine, 2-methyl-biphenylamine, 9-methyl-anthracenylamine, a diphenylamine group, a phenylnaphthylamine group, a ditolylamine group, a phenyltolylamine group, carbazole, a triphenylamine group and the like, but are not limited thereto.

In the present specification, examples of the heteroarylamine group include a substituted or unsubstituted monoheteroarylamine group, a substituted or unsubstituted diheteroarylamine group, or a substituted or unsubstituted triheteroarylamine group. The heteroaryl group in the heteroarylamine group may be a monocyclic heterocyclic group or a multicyclic heterocyclic group. The heteroarylamine group including two or more heterocyclic groups may include monocyclic heterocyclic groups, multicyclic heterocyclic groups, or both monocyclic heterocyclic groups and multicyclic heterocyclic groups.

In the present specification, the arylheteroarylamine group means an amine group substituted with an aryl group and a heterocyclic group.

In the present specification, the number of carbon atoms of the amine group is not particularly limited, but is preferably from 1 to 30. In the amine group, the N atom may be substituted with an aryl group, an alkyl group, an arylalkyl group, a heterocyclic group and the like, and specific examples of the amine group may include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a phenylnaphthylamine group, a ditolylamine group, a phenyltolylamine group, a triphenylamine group and the like, but are not limited thereto.

In the present specification, examples of the arylphosphine group include a substituted or unsubstituted monoarylphosphine group, a substituted or unsubstituted diarylphosphine group, or a substituted or unsubstituted triarylphosphine group. The aryl group in the arylphosphine group may be a monocyclic aryl group or a multicyclic aryl group. The arylphosphine group including two or more aryl groups may include monocyclic aryl groups, multicyclic aryl groups, or both monocyclic aryl groups and multicyclic aryl groups.

In the present specification, the aryl group is not particularly limited, but preferably has 6 to 60 carbon atoms, and may be a monocyclic aryl group or a multicyclic aryl group. According to one embodiment, the number of carbon atoms of the aryl group is from 6 to 40. According to one embodiment, the number of carbon atoms of the aryl group is from 6 to 20. Examples of the monocyclic aryl group may include a phenyl group, a biphenyl group, a terphenyl group, a quaterphenyl group and the like, but are not limited thereto. Examples of the multicyclic aryl group may include a naphthyl group, an anthracenyl group, a phenanthrenyl group, a perylenyl group, a fluoranthenyl group, a triphenylenyl group, a phenalenyl group, a pyrenyl group, a tetracenyl group, a chrysenyl group, a pentacenyl group, a fluorenyl group, an indenyl group, an acenaphthylenyl group, a benzofluorenyl group, a spirofluorenyl group and the like, but are not limited thereto.

In the present specification, the fluorenyl group may be substituted, and two of the substituents may bond to each other to form a spiro structure.

When the fluorenyl group is substituted, a spirofluorenyl group such as

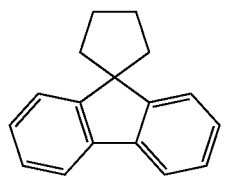 and 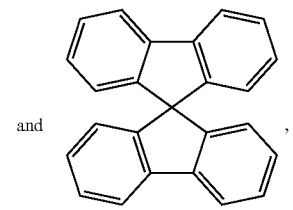, and a substituted fluorenyl group such as

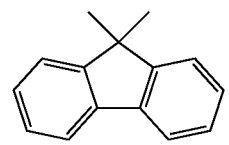

(9,9-dimethylfluorenyl group) and

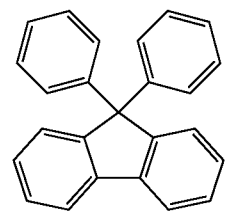 [SMILES: c1ccc(C2(c3ccccc3)c3ccccc3-c3ccccc32)cc1]

(9,9-diphenylfluorenyl group), may be included. However, the structure is not limited thereto.

In the present specification, the heterocyclic group is a heterocyclic group including one or more of N, O, P, S, Si and Se as a heteroatom, and although not particularly limited thereto, the number of carbon atoms is preferably from 2 to 60. According to one embodiment, the number of carbon atoms of the heterocyclic group is from 6 to 40. According to one embodiment, the number of carbon atoms of the heterocyclic group is from 6 to 20. Specific examples of the heterocyclic group may include a pyridyl group, a pyrrole group, a pyrimidyl group, a pyridazinyl group, a furanyl group, a thiophenyl group, an imidazole group, a pyrazole group, an oxazole group, an isoxazole group, a thiazole group, an isothiazole group, a triazole group, an oxadiazole group, a thiadiazole group, a dithiazole group, a tetrazole group, a pyranyl group, a thiopyranyl group, a pyrazinyl group, an oxazinyl group, a thiazinyl group, a dioxynyl group, a triazinyl group, a tetrazinyl group, a quinolinyl group, an isoquinolinyl group, a quinazolinyl group, a quinoxalinyl group, a naphthyridinyl group, an acridyl group, a xanthenyl group, a phenanthridinyl group, a diazanaphthalenyl group, a triazaindenyl group, an indole group, an indolinyl group, an indolizinyl group, a phthalazinyl group, a pyridopyrimidinyl group, a pyridopyrazinyl group, a pyrazinopyrazinyl group, a benzothiazole group, a benzoxazole group, a benzimidazole group, a benzothiophene group, a benzofuranyl group, a dibenzothiophene group, a dibenzofuranyl group, a carbazole group, a benzocarbazole group, a dibenzocarbazole group, an indolocarbazole group, a indenocarbazole group, a phenazinyl group, an imidazopyridine group, a phenoxazinyl group, a phenanthridine group, a phenanthroline group, a phenothiazine group, an imidazopyridine group, an imidazophenanthridine group, a benzimidazoquinazoline group, a benzimidazophenanthridine group or the like, but are not limited thereto.

In one embodiment of the present specification, the number of atoms forming the cycle is from 3 to 60 in the heterocyclic group. In another embodiment, the number of atoms forming the cycle is from 3 to 40 in the heterocyclic group. In one embodiment, the number of atoms forming the cycle is from 3 to 20 in the heterocyclic group.

In the present specification, the descriptions on the heterocyclic group provided above may be used on the heteroaryl group except that the heteroaryl group is an aromatic group.

In the present specification, the descriptions on the aryl group provided above may be used on the aryl group in the aryloxy group, the arylthioxy group, the arylsulfoxy group, the arylphosphine group, the aralkyl group, the aralkylamine group, the aralkenyl group, the alkylaryl group, the arylamine group and the arylheteroarylamine group.

In the present specification, the descriptions on the alkyl group provided above may be used on the alkyl group in the alkylthioxy group, the alkylsulfoxy group, the aralkyl group, the aralkylamine group, the alkylaryl group and the alkylamine group.

In the present specification, the descriptions on the heterocyclic group provided above may be used on the heteroaryl group in the heteroaryl group, the heteroarylamine group and the arylheteroarylamine group.

In the present specification, the descriptions on the alkenyl group provided above may be used on the alkenyl group in the aralkenyl group.

In the present specification, the descriptions on the aryl group provided above may be used on the arylene group except that the arylene group is divalent. According to one embodiment, the number of carbon atoms of the arylene is from 6 to 30.

In the present specification, bonding to an adjacent group to form a ring means bonding to an adjacent group to form a substituted or unsubstituted aliphatic hydrocarbon ring; a substituted or unsubstituted aromatic hydrocarbon ring; a substituted or unsubstituted aliphatic heteroring; a substituted or unsubstituted aromatic heteroring; or a fused ring thereof.

In the present specification, the aliphatic hydrocarbon ring means a ring that is not aromatic and formed only with carbon and hydrogen atoms. Specific examples of the aliphatic hydrocarbon ring may include cyclopropane, cyclobutane, cyclobutene, cyclopentane, cyclopentene, cyclohexane, cyclohexene, 1,4-cyclohexadiene, cycloheptane, cycloheptene, cyclooctane, cyclooctene and the like, but are not limited thereto.

In the present specification, the aromatic hydrocarbon ring means an aromatic ring formed only with carbon and hydrogen atoms. Specific examples of the aromatic hydrocarbon ring may include benzene, naphthalene, anthracene, phenanthrene, perylene, fluoranthene, triphenylene, phenalene, pyrene, tetracene, chrysene, pentacene, fluorene, indene, acenaphthylene, benzofluorene, spirofluorene and the like, but are not limited thereto.

In the present specification, the aliphatic heteroring means an aliphatic ring including one or more of heteroatoms. Specific examples of the aliphatic heteroring may include oxirane, tetrahydrofuran, 1,4-dioxane, pyrrolidine, piperidine, morpholine, oxepane, azokane, thiokane and the like, but are not limited thereto.

In the present specification, the aromatic heteroring means an aromatic ring including one or more of heteroatoms. Specific examples of the aromatic heteroring may include pyridine, pyrrole, pyrimidine, pyridazine, furan, thiophene, imidazole, pyrazole, oxazole, isoxazole, triazole, isothiazole, triazole, oxadiazole, thiadiazole, dithiazole, tetrazole, pyran, thiopyran, diazine, oxazine, triazine, dioxin, triazine, tetrazine, isoquinoline, quinoline, quinol, quinazoline, quinoxaline, naphthyridine, acridine, phenanthridine, diazanaphthalene, triazaindene, indole, indolizine, benzothiazole, benzoxazole, benzimidazole, benzothiophene, benzofuran, dibenzothiophene, dibenzofuran, carbazole, benzocarbazole, dibenzocarbazole, phenazine, imidazopyridine, phenoxazine, phenanthridine, indolocarbazole, indenocarbazole and the like, but are not limited thereto.

In the present specification, the aliphatic hydrocarbon ring, the aromatic hydrocarbon ring, the aliphatic heteroring and the aromatic heteroring may be monocyclic or multicyclic.

According to one embodiment of the present specification, Chemical Formula 1 is represented by any one of the following Chemical Formula 11 to Chemical Formula 14.

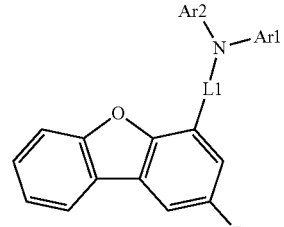

[Chemical Formula 11]

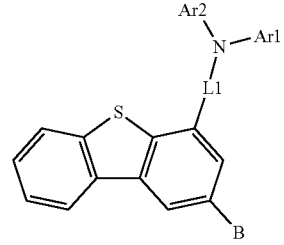

[Chemical Formula 12]

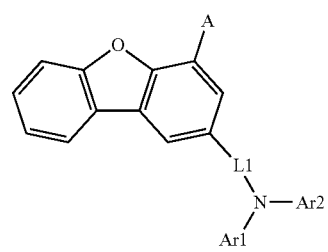

[Chemical Formula 13]

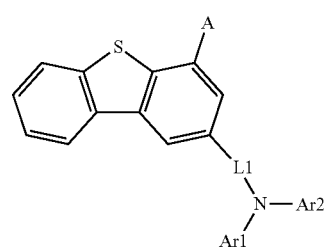

[Chemical Formula 14]

In Chemical Formulae 11 to 14,
definitions of L1, A, B, Ar1 and Ar2 are the same as in Chemical Formula 1 and Chemical Formula 1-1.

According to one embodiment of the present specification, Chemical Formula 1 is represented by any one of the following Chemical Formula 21 to Chemical Formula 24.

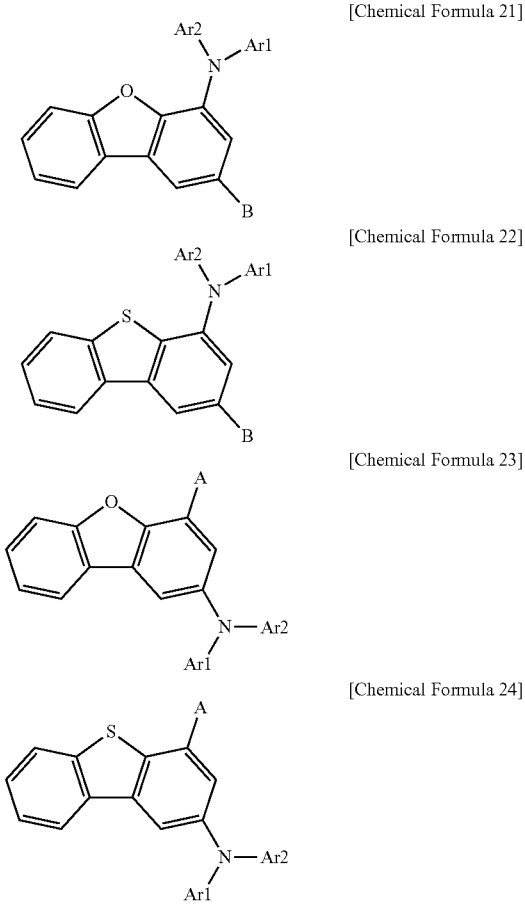

[Chemical Formula 21]

[Chemical Formula 22]

[Chemical Formula 23]

[Chemical Formula 24]

In Chemical Formulae 21 to 24,
definitions of A, B, Ar1 and Ar2 are the same as in Chemical Formula 1 and Chemical Formula 1-1.

In one embodiment of the present disclosure, the one that is not represented by the structure of Chemical Formula 1-1 among A and B is a substituted or unsubstituted aryl group; or a substituted or unsubstituted heterocyclic group.

In one embodiment of the present disclosure, the one that is not represented by the structure of Chemical Formula 1-1 among A and B is a substituted or unsubstituted monocyclic or multicyclic aryl group having 6 to 40 carbon atoms.

In one embodiment of the present disclosure, the one that is not represented by the structure of Chemical Formula 1-1 among A and B is a substituted or unsubstituted phenyl group; a substituted or unsubstituted biphenyl group; a substituted or unsubstituted terphenyl group; a substituted or unsubstituted naphthyl group; a substituted or unsubstituted anthracenyl group; a substituted or unsubstituted phenanthrenyl group; a substituted or unsubstituted perylenyl group; a substituted or unsubstituted fluoranthenyl group; a substituted or unsubstituted triphenylenyl group; a substituted or unsubstituted phenalenyl group; a substituted or unsubstituted pyrenyl group; a substituted or unsubstituted tetracenyl group; a substituted or unsubstituted chrysenyl group; a substituted or unsubstituted pentacenyl group; a substituted or unsubstituted fluorenyl group; a substituted or unsubstituted indenyl group; a substituted or unsubstituted acenaphthylenyl group; or a substituted or unsubstituted benzofluorenyl group, but are not limited thereto.

In one embodiment of the present disclosure, the one that is not represented by the structure of Chemical Formula 1-1 among A and B is a substituted or unsubstituted phenyl group; a substituted or unsubstituted biphenyl group; a substituted or unsubstituted fluorenyl group; or a substituted or unsubstituted naphthyl group.

In one embodiment of the present disclosure, the one that is not represented by the structure of Chemical Formula 1-1 among A and B is a phenyl group; a biphenyl group; a 9,9-dimethylfluorenyl group; a 9,9-dimethylfluorenyl group; a spirobifluorenyl group; or a naphthyl group.

In one embodiment of the present specification, the one that is not represented by the structure of Chemical Formula 1-1 among A and B is a substituted or unsubstituted heterocyclic group having 2 to 40 carbon atoms.

In one embodiment of the present specification, the one that is not represented by the structure of Chemical Formula 1-1 among A and B is a substituted or unsubstituted dibenzothiophene group; a substituted or unsubstituted dibenzofuranyl group; or a substituted or unsubstituted carbazole group.

In one embodiment of the present specification, the one that is not represented by the structure of Chemical Formula 1-1 among A and B is a dibenzothiophene group unsubstituted or substituted with an aryl group; a dibenzofuranyl group unsubstituted or substituted with an aryl group; or a carbazole group unsubstituted or substituted with an aryl group.

In one embodiment of the present specification, the one that is not represented by the structure of Chemical Formula 1-1 among A and B is a dibenzothiophene group; a dibenzofuranyl group; or a 9-phenylcarbazole group.

In one embodiment of the present disclosure, L1, is a direct bond or a substituted or unsubstituted arylene group.

In one embodiment of the present disclosure, L1, is a direct bond or a substituted or unsubstituted arylene group having 6 to 30 carbon atoms.

In one embodiment of the present disclosure, L1, is a direct bond or a substituted or unsubstituted monocyclic or multicyclic arylene group having 6 to 30 carbon atoms.

In another embodiment, L1, is preferably unsubstituted or substituted with one or more substituents selected from the group consisting of a substituted or unsubstituted phenylene group; a substituted or unsubstituted biphenylylene group; a substituted or unsubstituted terphenylene group; a substituted or unsubstituted quaterphenylene group; a substituted or unsubstituted naphthylene group; a substituted or unsubstituted pyrenylene group; a substituted or unsubstituted phenanthrenylene group; a substituted or unsubstituted perylenylene group; a substituted or unsubstituted tetracenylene group; a substituted or unsubstituted triphenylene group; a substituted or unsubstituted fluoranthenylene group; and a substituted or unsubstituted fluorenylene group, or unsubstituted or substituted with a substituent linking two or more substituents among the substituents illustrated above.

According to one embodiment of the present disclosure, L1 is a direct bond; a substituted or unsubstituted phenylene group; a substituted or unsubstituted biphenylylene group; a substituted or unsubstituted terphenylene group; a substituted or unsubstituted quaterphenylene group; a substituted or unsubstituted naphthylene group; a substituted or unsubstituted anthracenylene group; a substituted or unsubstituted fluorenylene group; a substituted or unsubstituted phenanthrenylene group; or a substituted or unsubstituted triphenylene group.

According to one embodiment of the present disclosure, L1 may be a phenylene group, a biphenylylene group, a terphenylene group, a quaterphenylene group, a naphthylene group, an anthracenyl group, a 9,9-dimethylfluorenylene group, a phenanthrenylene group or a triphenylene group, and these may be further substituted.

Specifically, L1 may be unsubstituted or substituted with one or more substituents selected from the group consisting of deuterium; a halogen group; a nitrile group; a nitro group; a hydroxyl group; a carbonyl group; an ester group; an imide group; an amine group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylheteroarylamine group; an arylphosphine group; and a heterocyclic group.

In addition, L1 in the present specification is preferably any one substituent selected from the following group, but is not limited thereto.

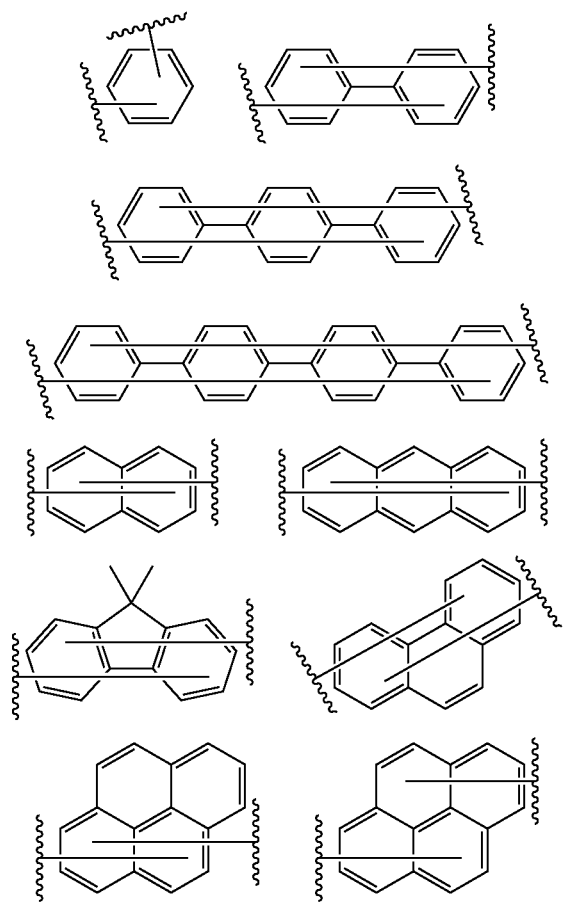

-continued

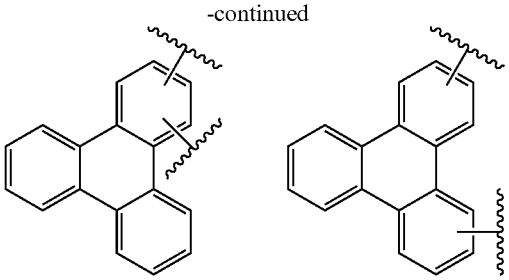

The structures may be unsubstituted or substituted with one or more substituents selected from the group consisting of deuterium; a halogen group; a nitrile group; a nitro group; a hydroxyl group; a carbonyl group; an ester group; an imide group; an amine group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylheteroarylamine group; an arylphosphine group; and a heterocyclic group.

According to one embodiment of the present specification, Ar1 and Ar2 are the same as or different from each other, and each independently hydrogen; deuterium; a halogen group; a nitrile group; a nitro group; a hydroxyl group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylphosphine group; a substituted or unsubstituted phosphine oxide group; a substituted or unsubstituted aryl group; or a substituted or unsubstituted heterocyclic group.

According to one embodiment of the present specification, Ar1 and Ar2 are the same as or different from each other, and each independently hydrogen; deuterium; a halogen group; a carbonyl group; a substituted or unsubstituted silyl group; a substituted or unsubstituted alkyl group; a substituted or unsubstituted heteroarylamine group; a substituted or unsubstituted arylamine group; a substituted or unsubstituted arylphosphine group; a substituted or unsubstituted phosphine oxide group; a substituted or unsubstituted aryl group; or a substituted or unsubstituted heterocyclic group.

According to one embodiment of the present specification, Ar1 and Ar2 are the same as or different from each other, and each independently selected from the group consisting of hydrogen, deuterium, halogen, linear or branched substituted or unsubstituted alkyl having 1 to 60 carbon atoms, linear or branched substituted or unsubstituted alkenyl having 2 to 60 carbon atoms, linear or branched substituted or unsubstituted alkynyl having 2 to 60 carbon atoms, monocyclic or multicyclic substituted or unsubstituted cycloalkyl having 3 to 60 carbon atoms, monocyclic or multicyclic substituted or unsubstituted heterocycloalkyl having 2 to 60 carbon atoms, monocyclic or multicyclic substituted or unsubstituted aryl having 6 to 60 carbon atoms, and a monocyclic or multicyclic substituted or unsubstituted heteroring having 2 to 60 carbon atoms.

According to one embodiment of the present specification, Ar1 and Ar2 are the same as or different from each other, and each independently hydrogen; deuterium; halogen; a substituted or unsubstituted alkyl group having 1 to 40 carbon atoms; a substituted or unsubstituted cycloalkyl group having 3 to 60 carbon atoms; a substituted or unsubstituted aryl group having 6 to 40 carbon atoms; or a substituted or unsubstituted heterocyclic group having 2 to 40 carbon atoms.

According to one embodiment of the present specification, Ar1 and Ar2 are the same as or different from each other, and each independently hydrogen; a substituted or unsubstituted monocyclic or multicyclic aryl group having 6 to 40 carbon atoms; or a substituted or unsubstituted monocyclic or multicyclic heterocyclic group having 2 to 40 carbon atoms.

According to one embodiment of the present specification, Ar1 and Ar2 are the same as or different from each other, and may each independently be hydrogen; an aryl group such as a phenyl group, a biphenyl group, a naphthyl group, an anthracenyl group, a chrysenyl group, a phenanthrenyl group, a triphenylenyl group, a pyrenyl group, a tetracenyl group, a pentacenyl group or a fluorenyl group; or a heteroring such as a pyridyl group, a pyrrole group, a pyridyl group, a pyridazinyl group, a furanyl group, a thiophene group, an imidazole group, a pyrazole group, an oxazole group, an isoxazole group, a thiazole group, a isothiazole group, a triazole group, a pyrazinyl group, a triazine group, a quinolinyl group, an isoquinolinyl group, a quinazoline group, a quinoxalinyl group, a naphthyridinyl group, an acridyl group, a xanthenyl group, a phenanthridinyl group, a diazanaphthalenyl group, a triazaindenyl group, an indole group, an indolinyl group, an indolizinyl group, a phthalazinyl group, a pyridopyrimidinyl group, a pyridopyrazinyl group, a pyrazinopyrazinyl group, a carbazole group, a benzothiophene group, a benzofuranyl group, a benzimidazole group, a benzothiazole group, a benzoxazole group, a benzocarbazole group, a dibenzothiophene group, a dibenzofuranyl group, a dibenzocarbazole group, an indolocarbazole group, an indenocarbazole group, a phenanthroline group, a phenazinyl group, a phenoxazinyl group, a phenothiazinyl group, an imidazopyridinyl group, an imidazophenanthridine group, a benzimidazoquinazolinyl group or a benzimidazophenanthridinyl group, and these may be further substituted.

Specifically, Ar1 and Ar2 may be unsubstituted or substituted with one or more substituents selected from the group consisting of deuterium; a halogen group; a nitrile group; a nitro group; a hydroxyl group; a carbonyl group; an ester group; an imide group; an amine group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylheteroarylamine group; an arylphosphine group; and a heterocyclic group.

According to one embodiment of the present specification, Ar1 and Ar2 are the same as or different from each other, and may each independently be any one selected from among the following structures.

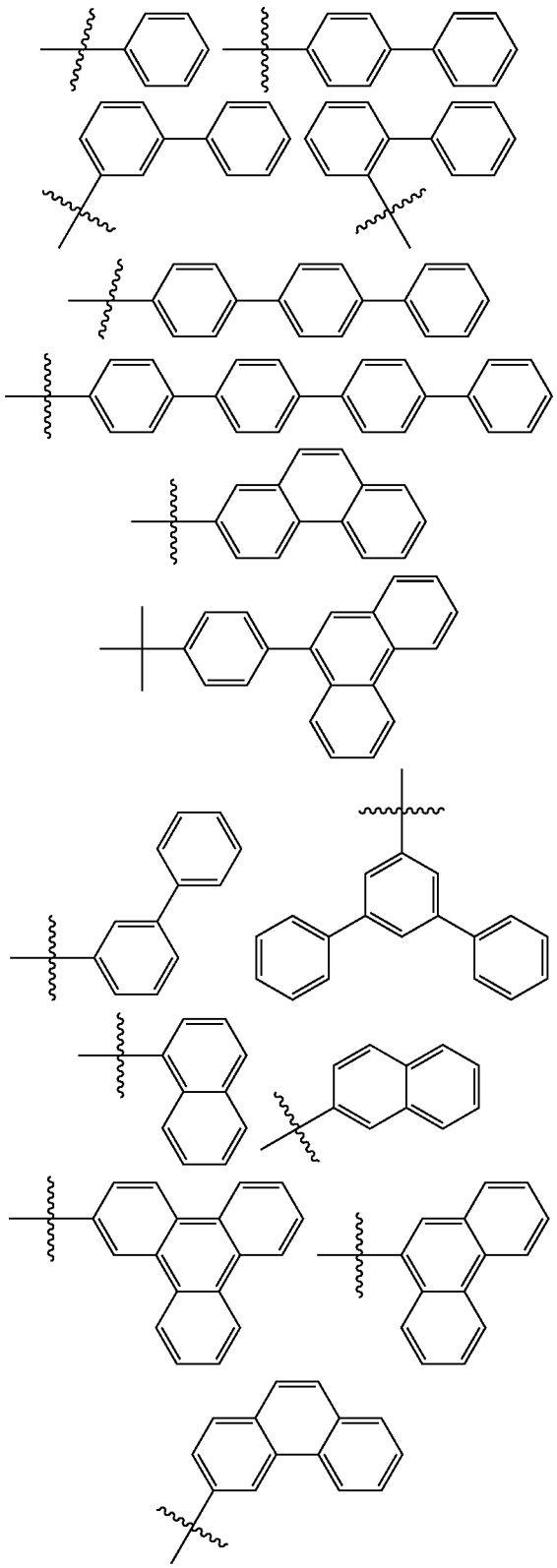

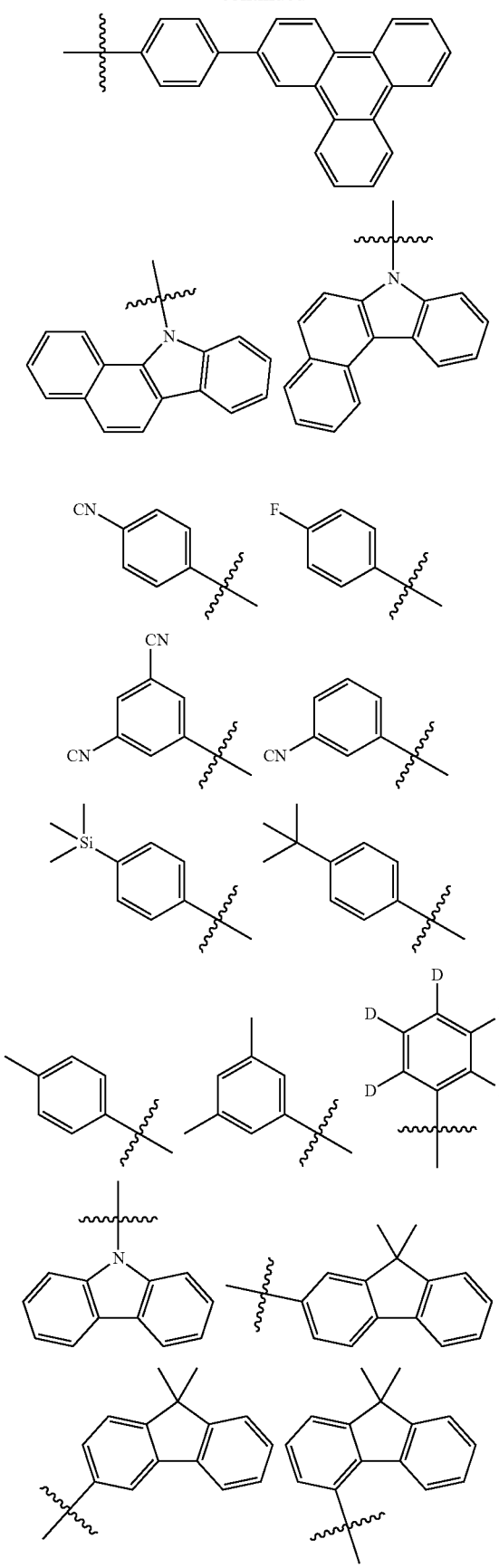
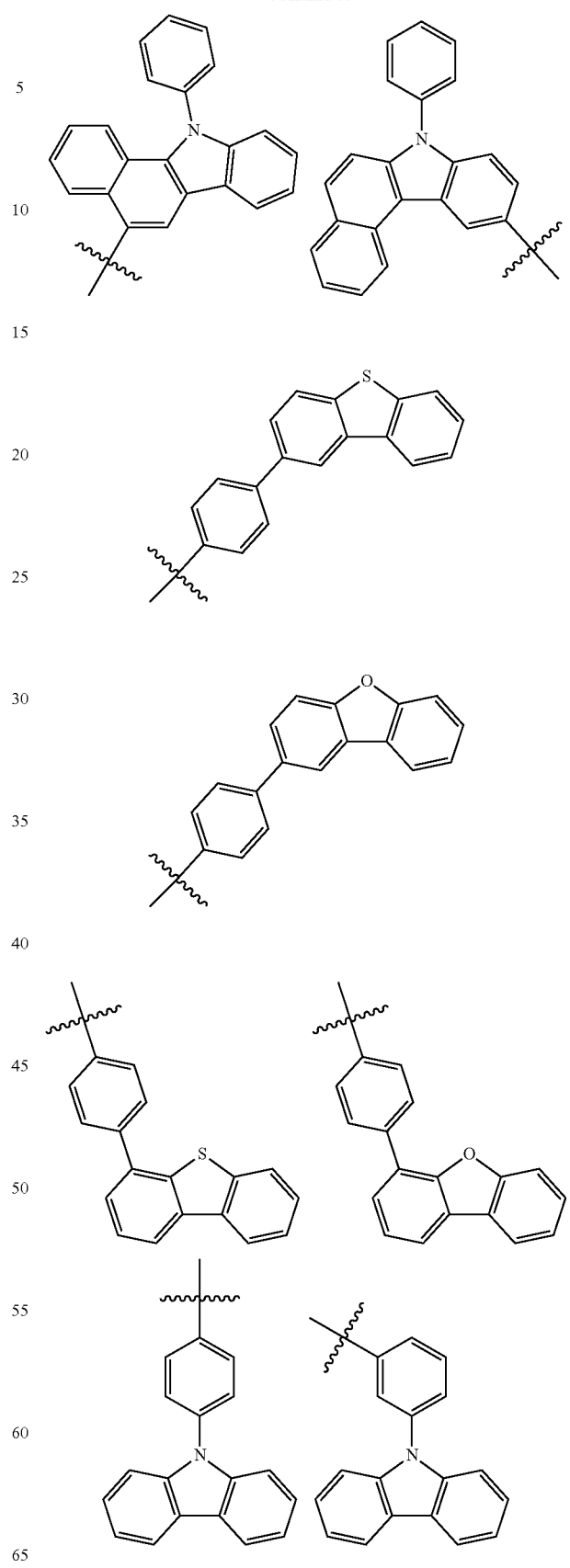

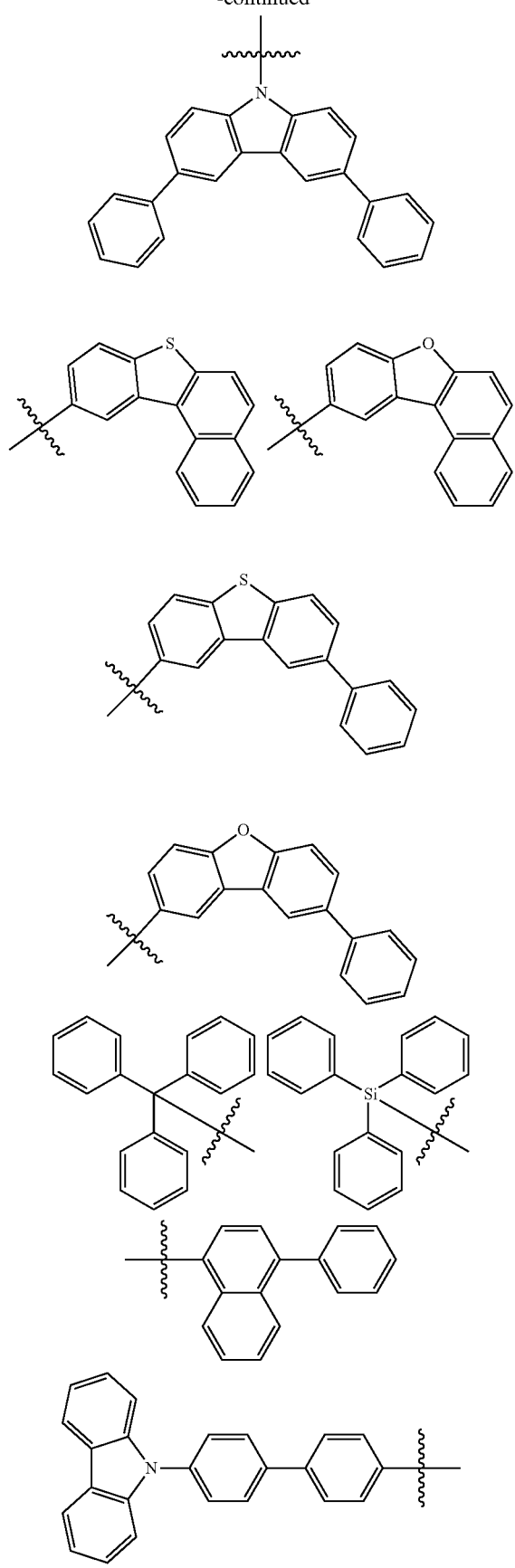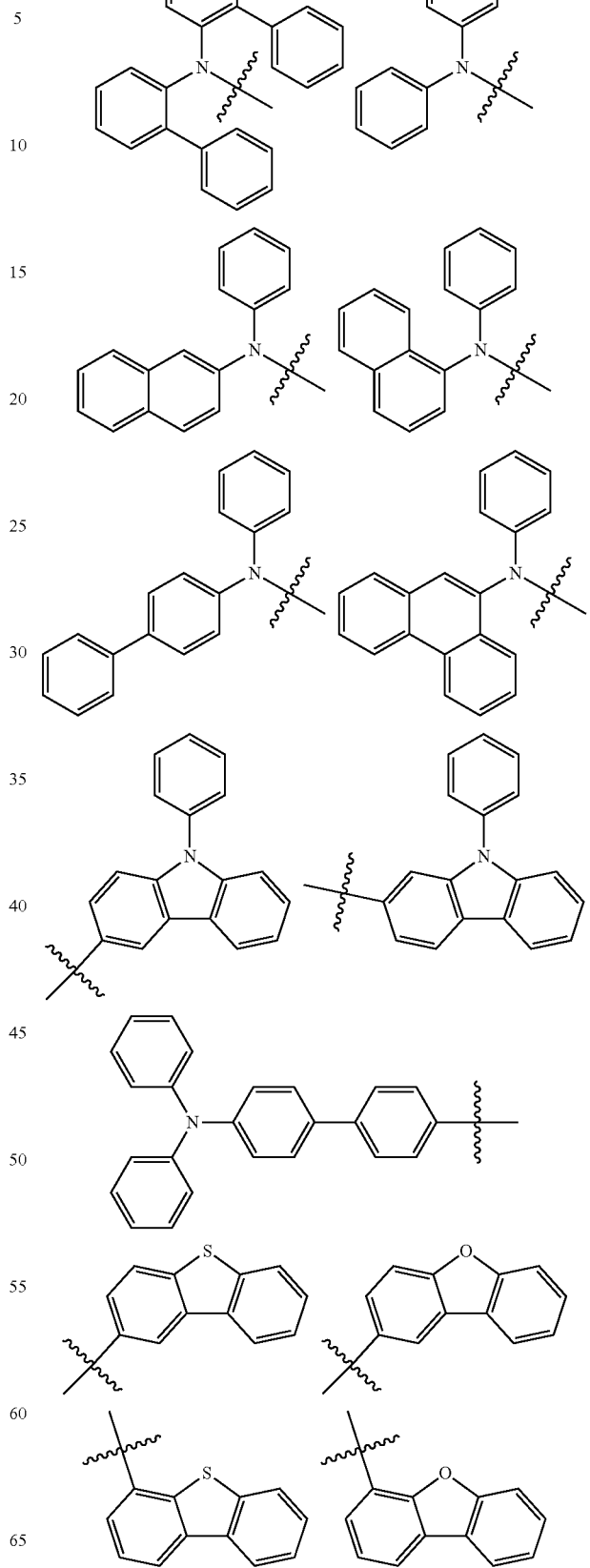

21
-continued
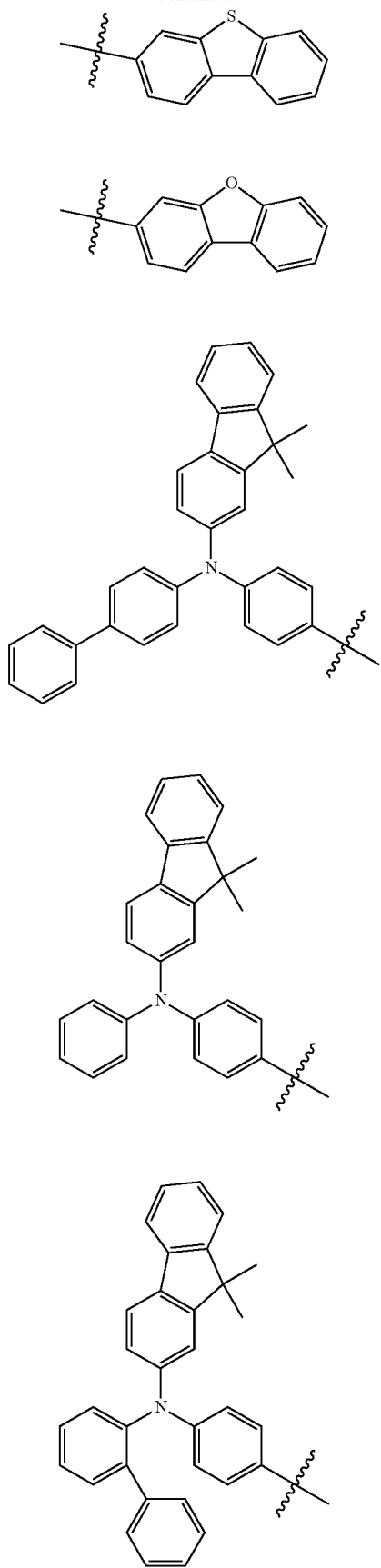
22
-continued
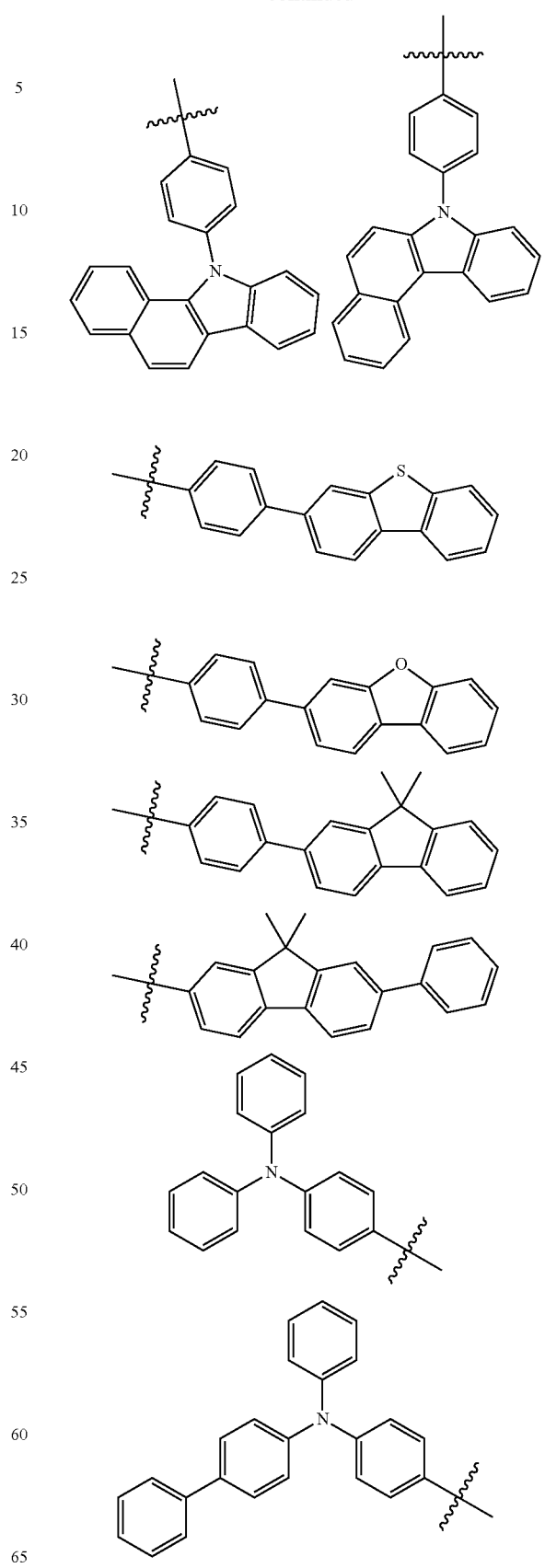

-continued
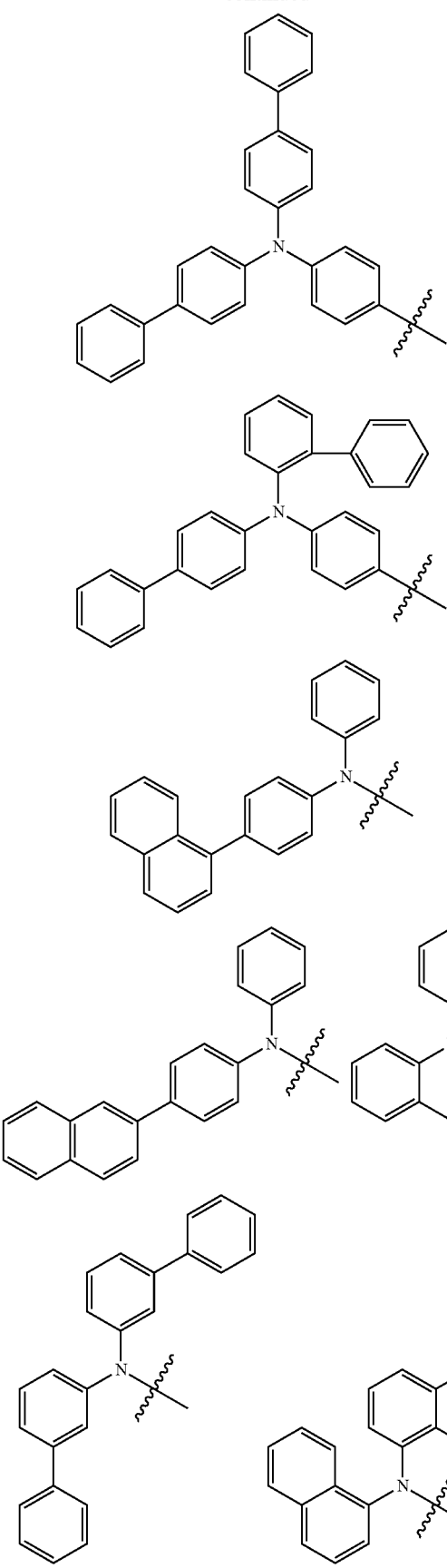
-continued
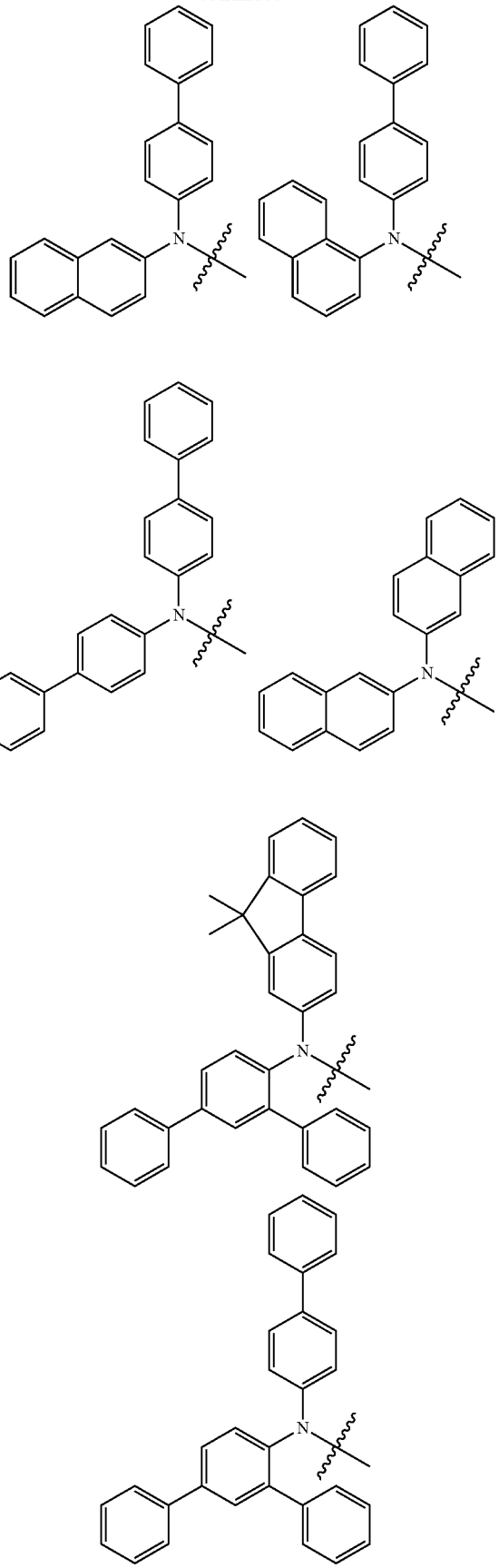

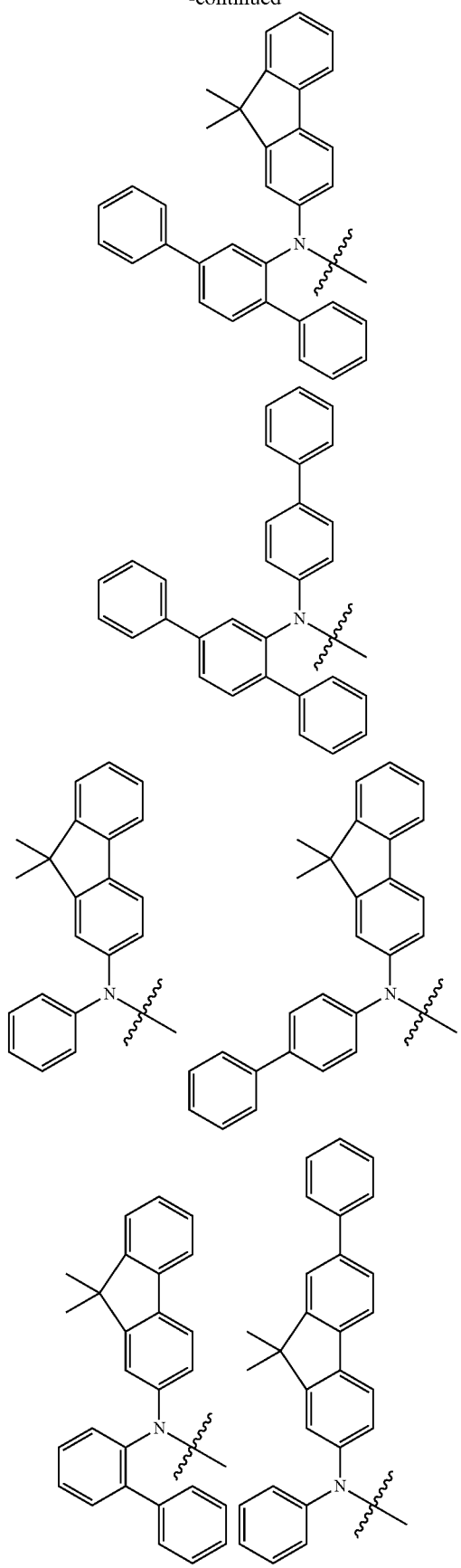
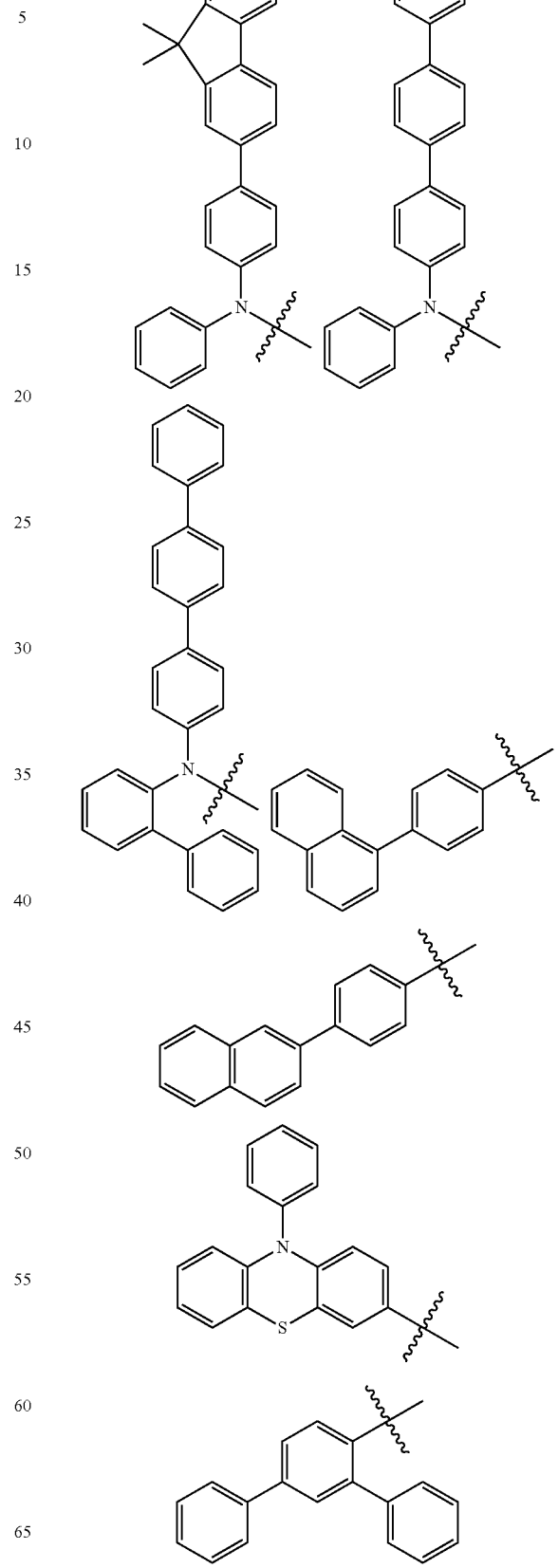

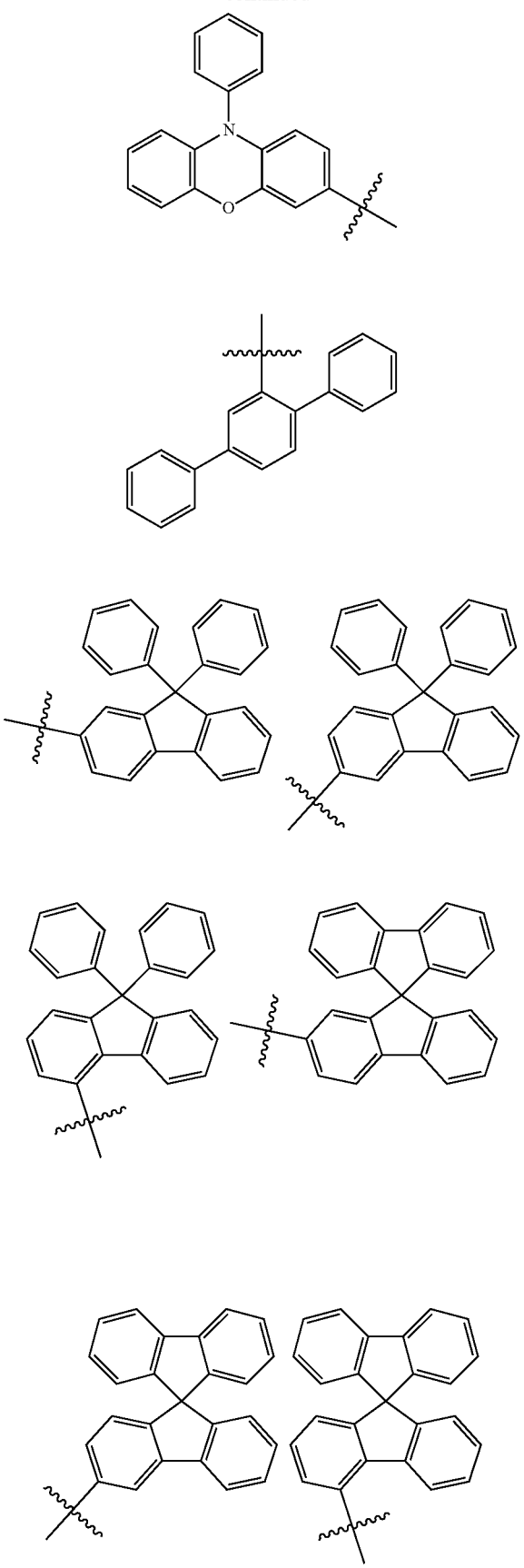

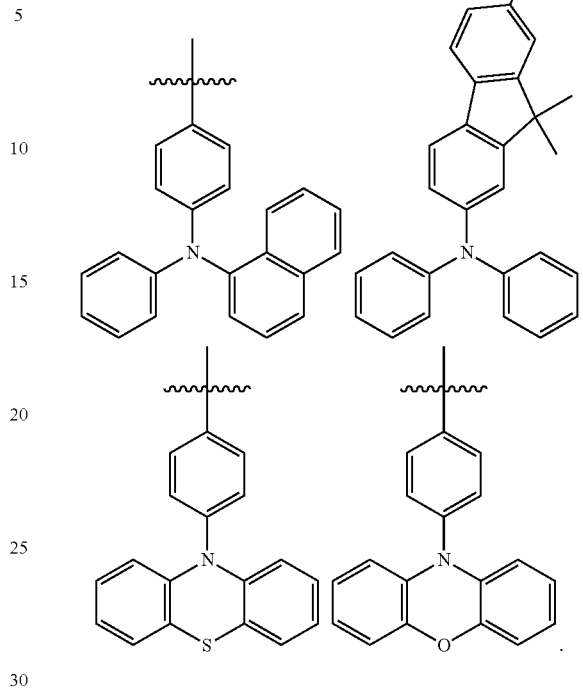

The structures may be unsubstituted or substituted with one or more substituents selected from the group consisting of deuterium; a halogen group; a nitrile group; a nitro group; a hydroxyl group; a carbonyl group; an ester group; an imide group; an amine group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylheteroarylamine group; an arylphosphine group; and a heterocyclic group.

According to one embodiment of the present disclosure, the compound of Chemical Formula 1 may be any one selected from among the following compounds.

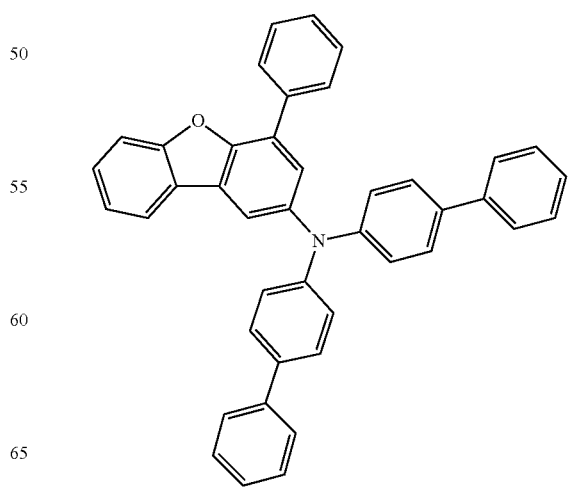

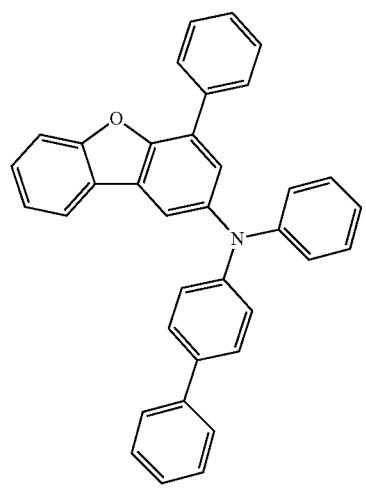
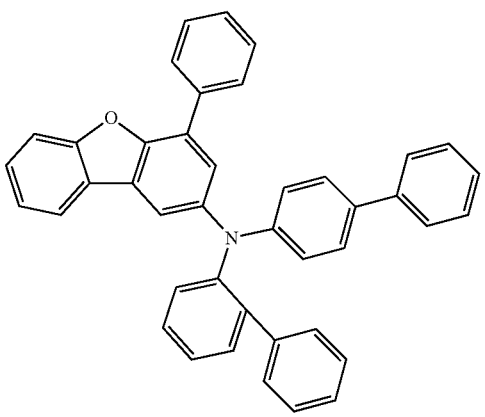
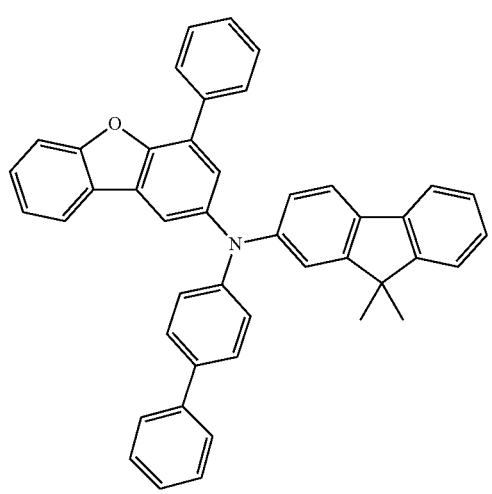
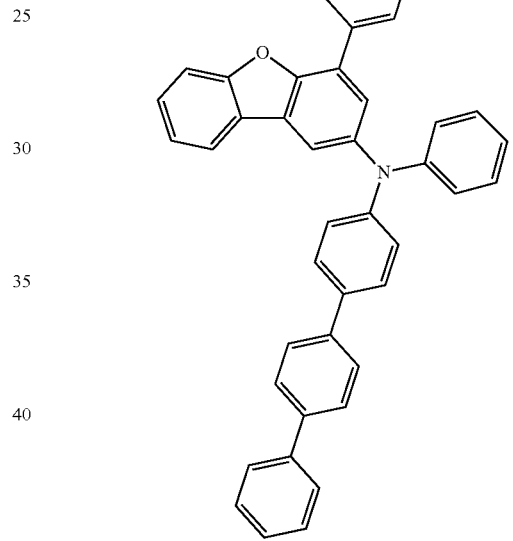
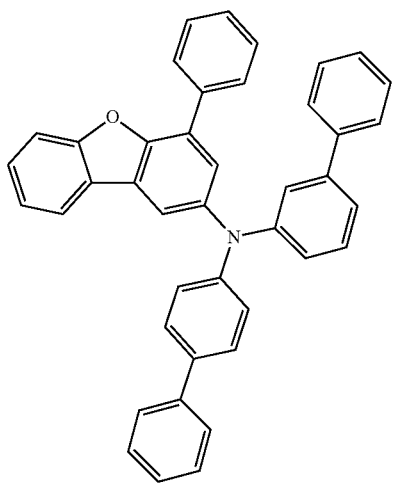
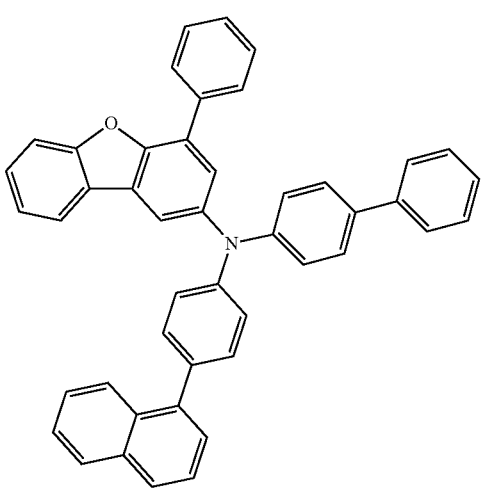

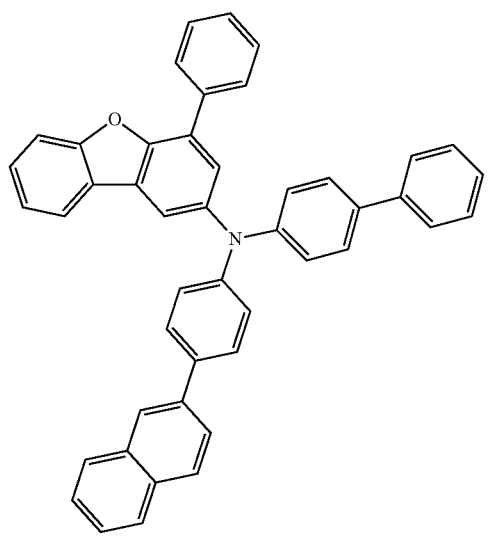
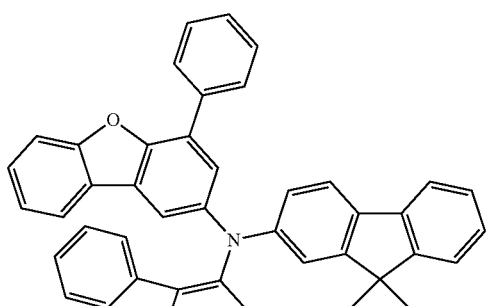
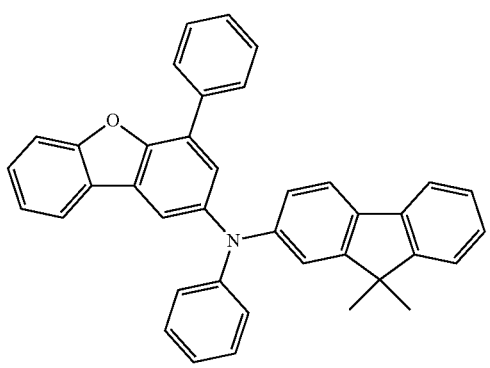
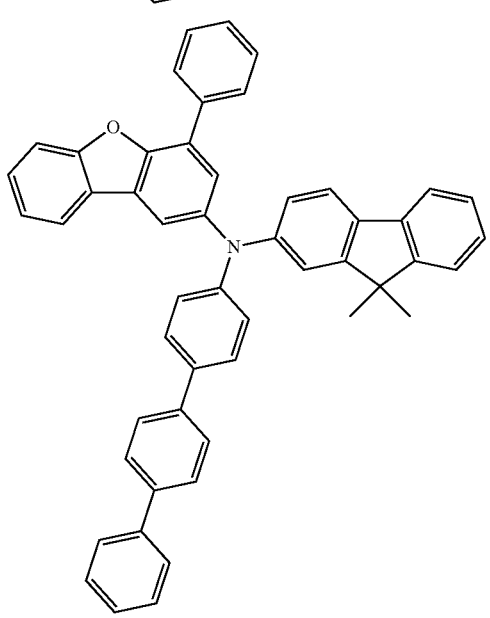
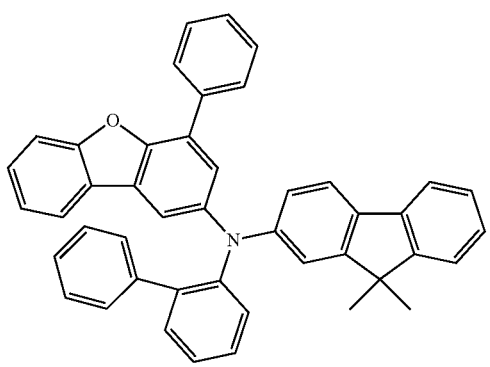
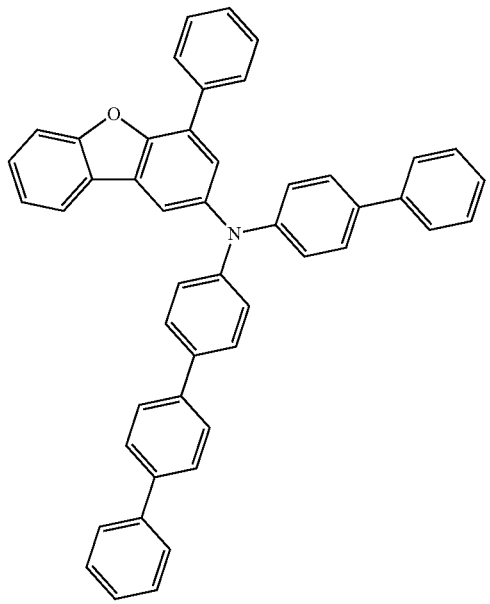

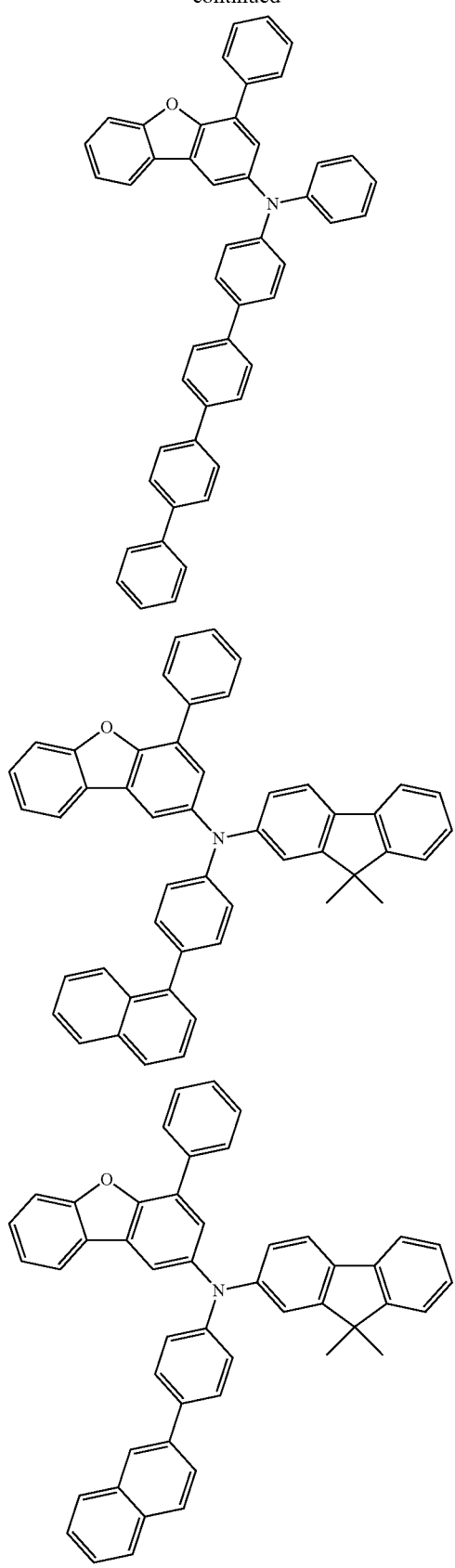
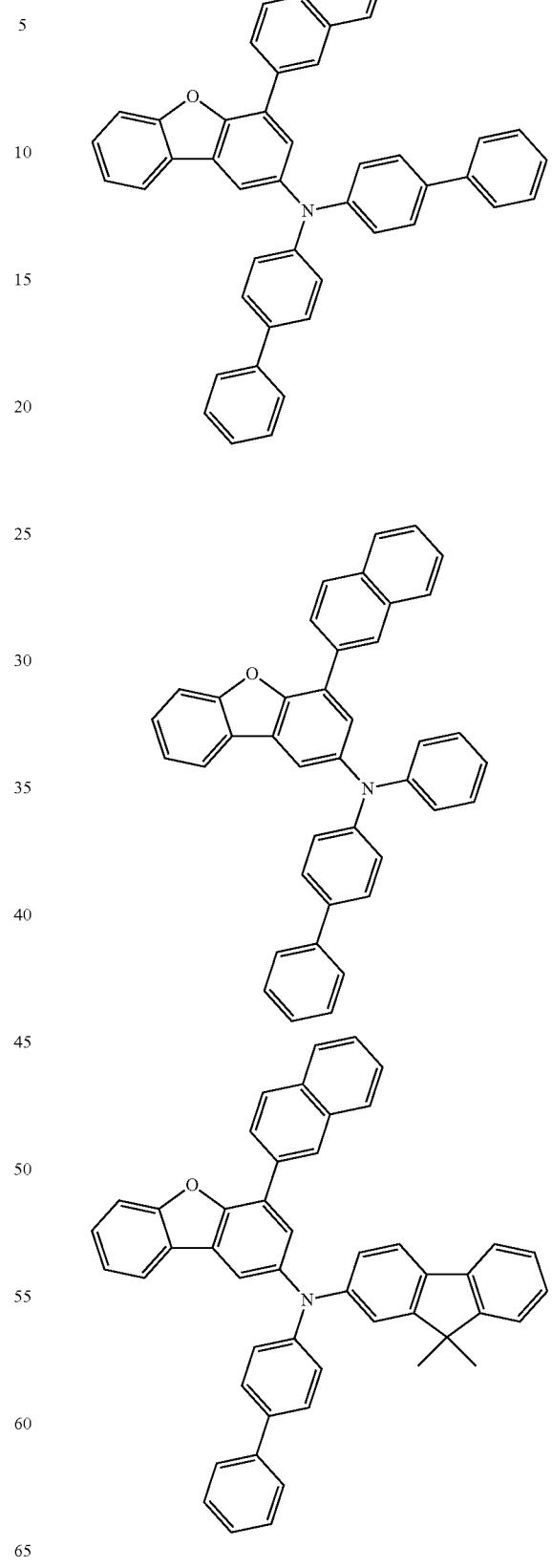

-continued
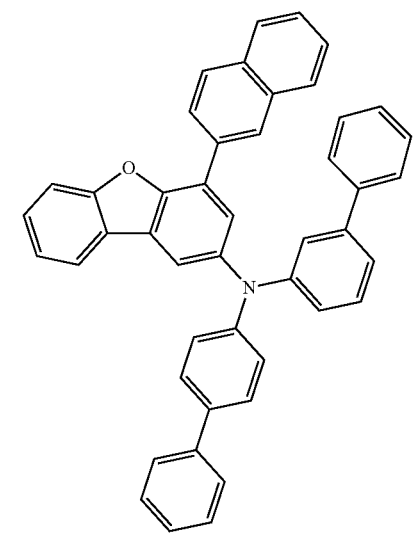
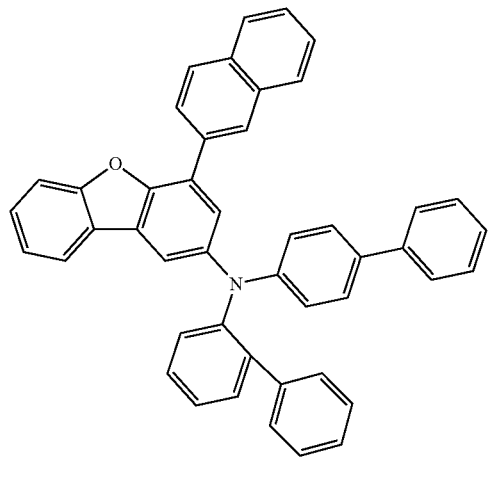
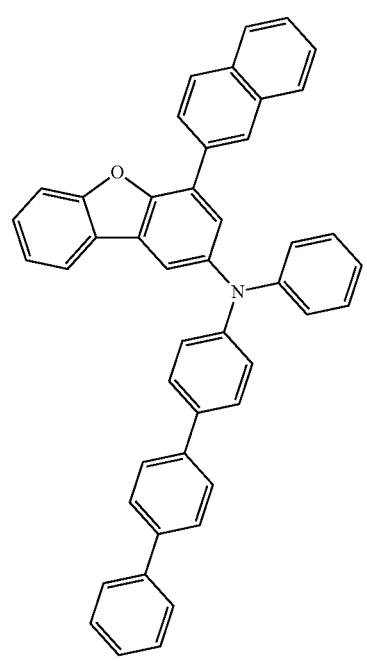
-continued
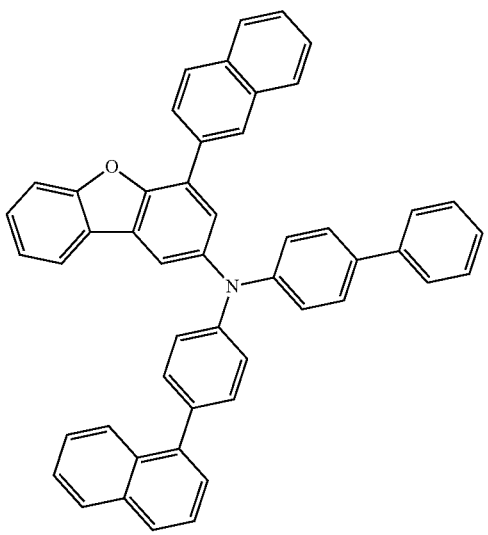
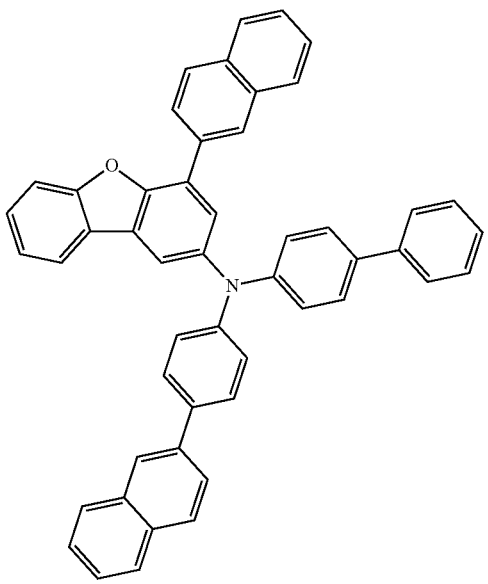
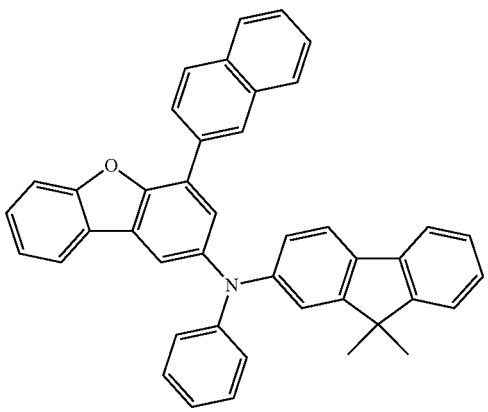

-continued
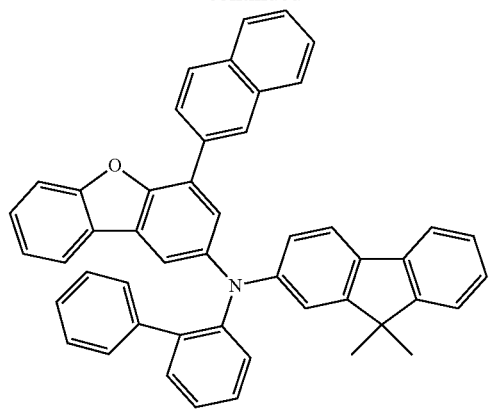
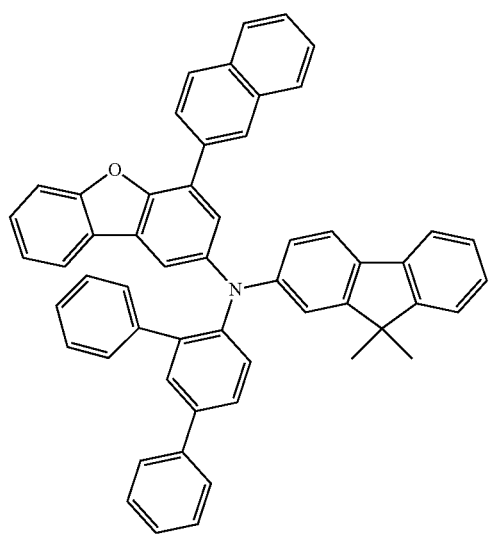
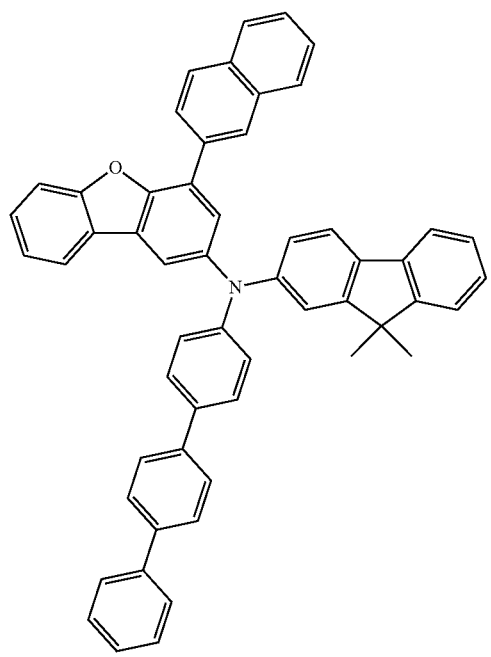
-continued
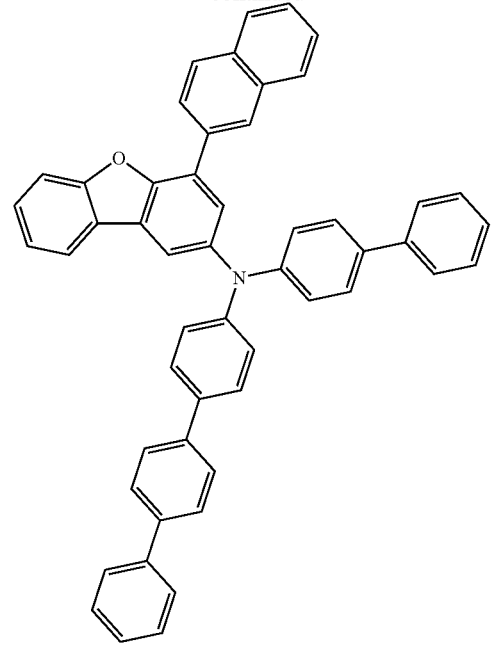
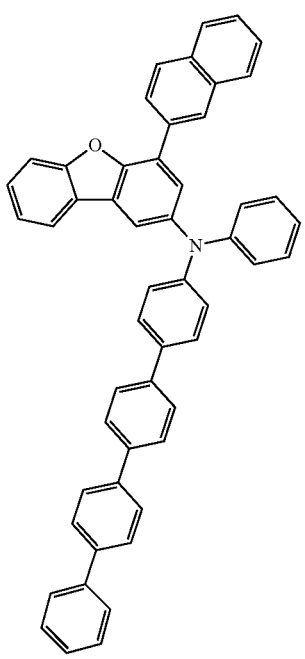

-continued
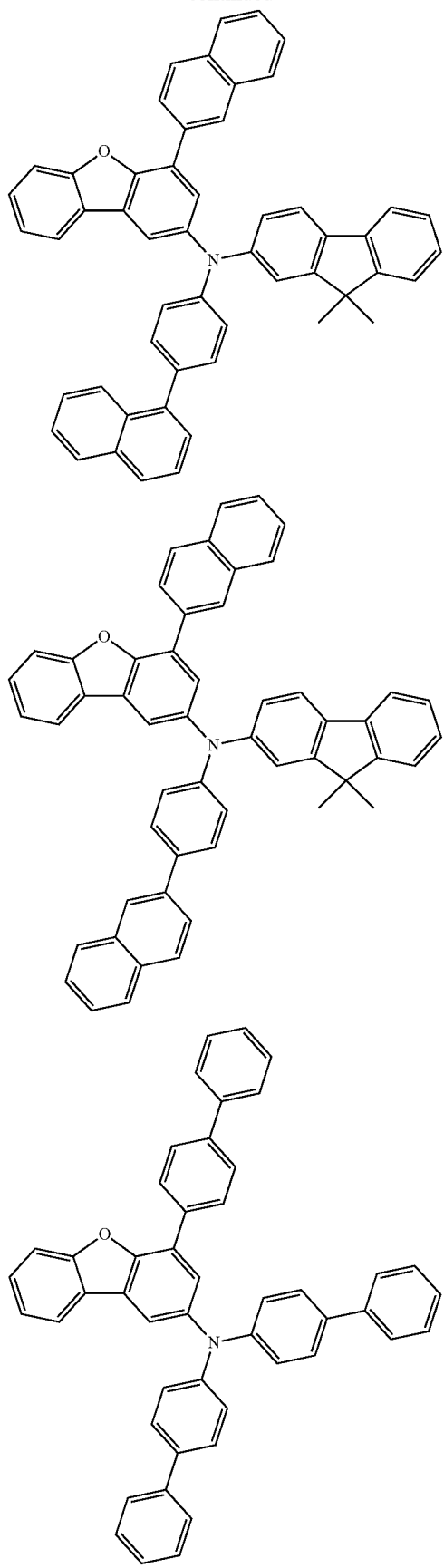
-continued

-continued
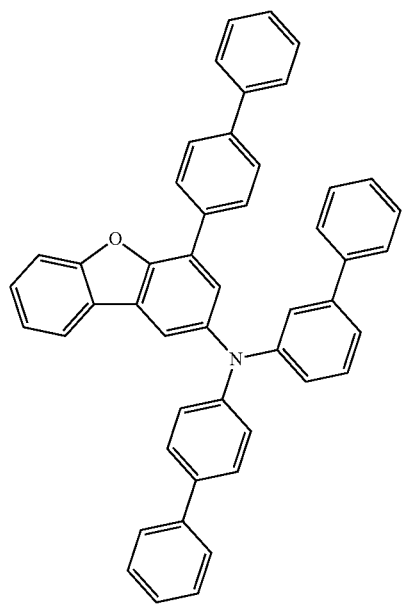
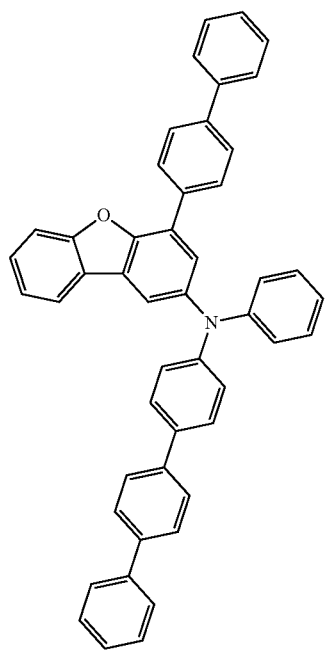
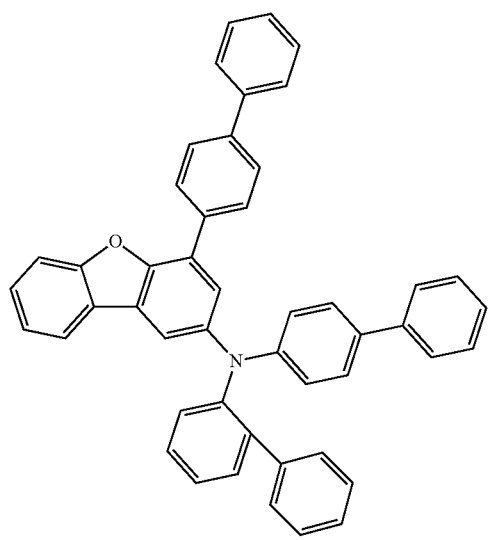
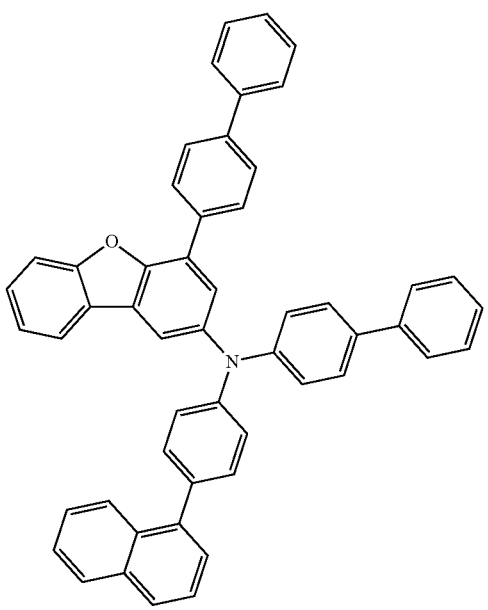

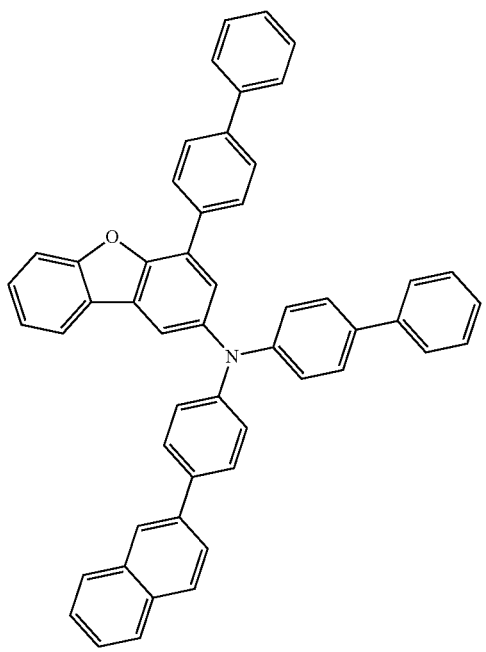
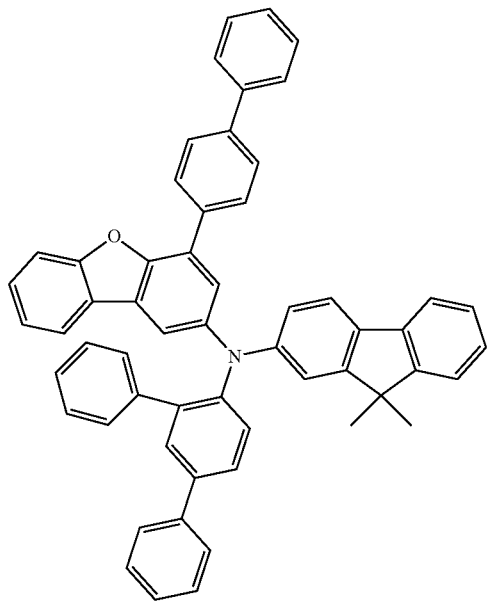
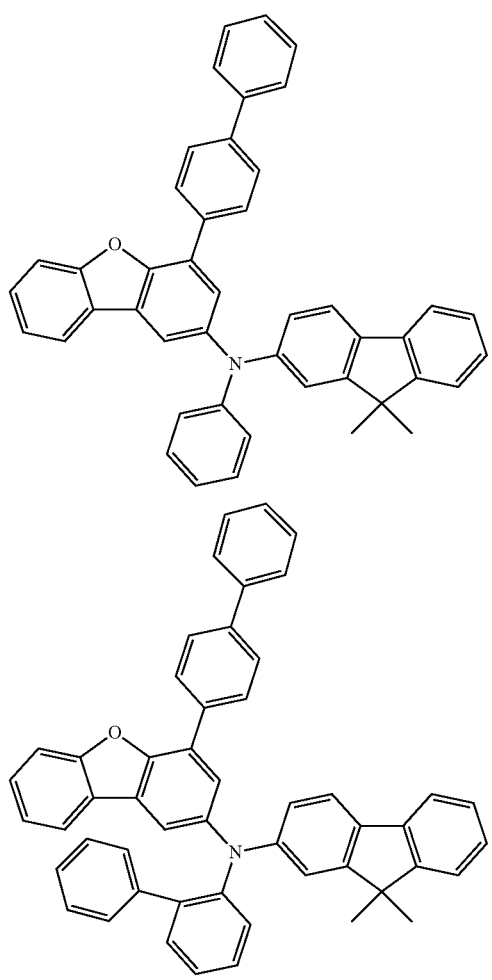
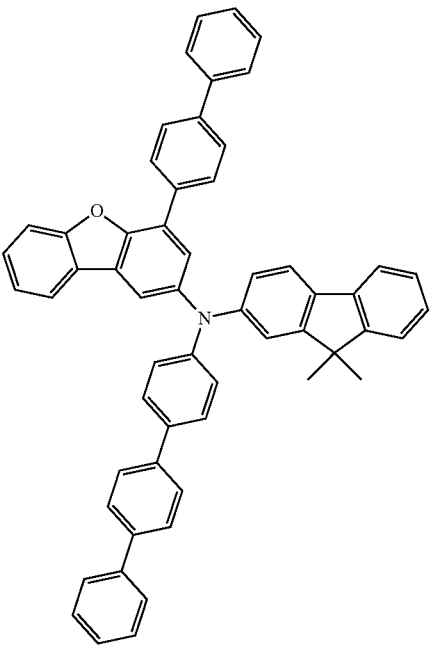

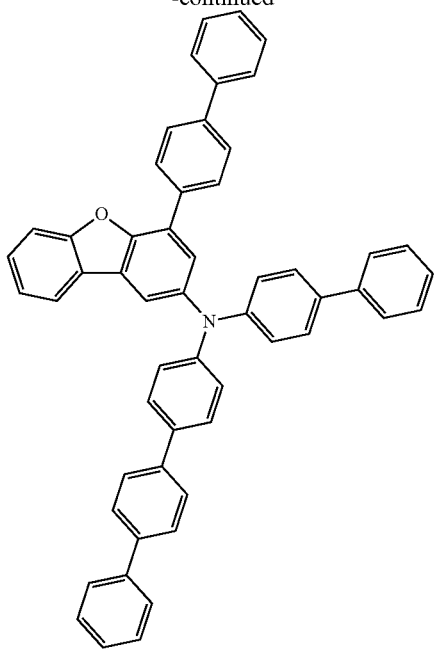
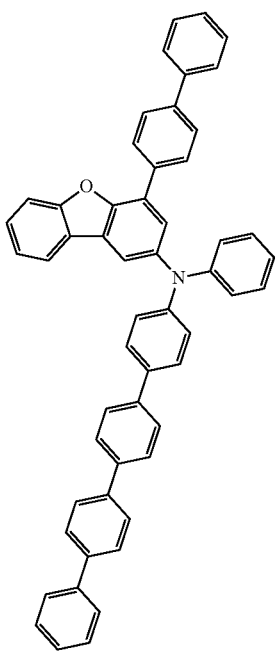
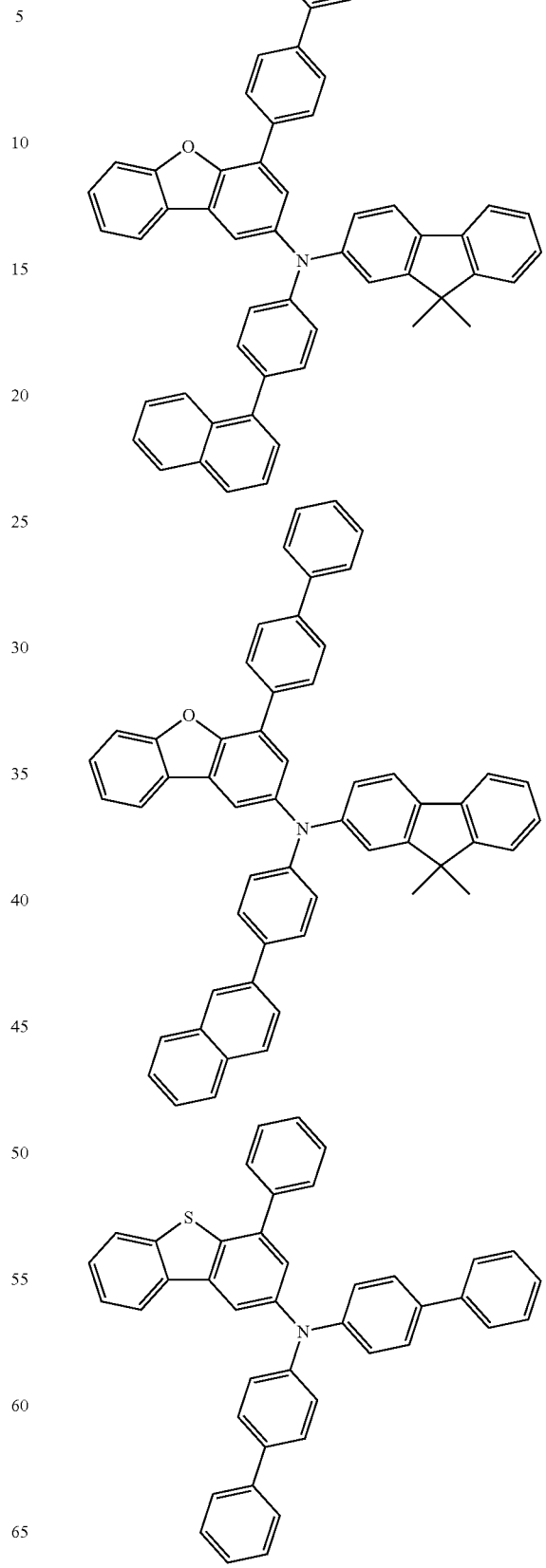

-continued
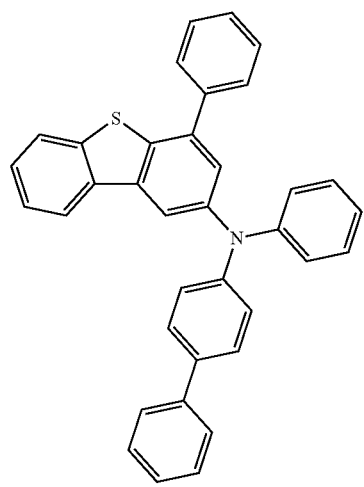
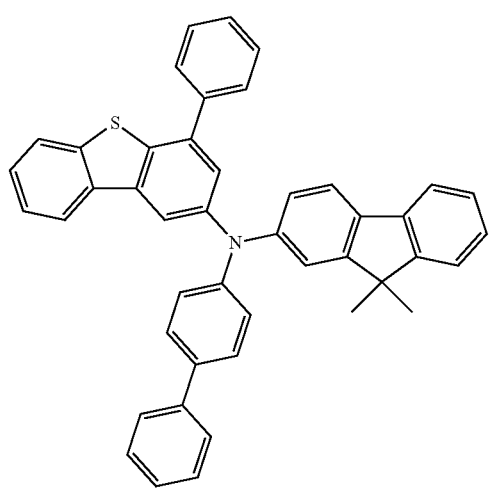
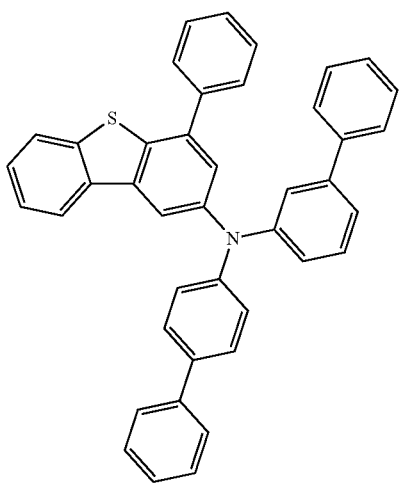
-continued
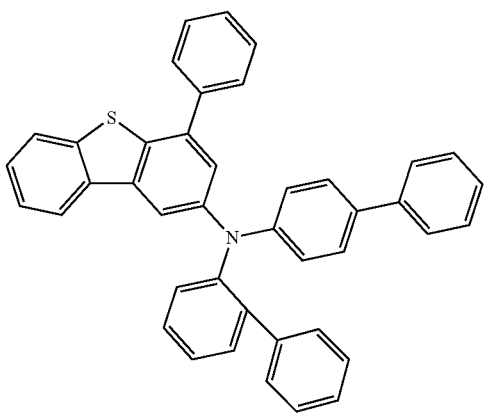
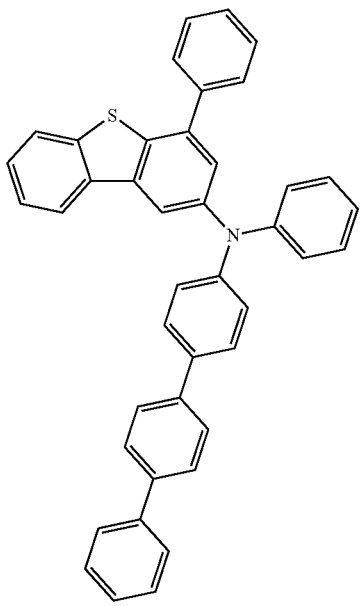
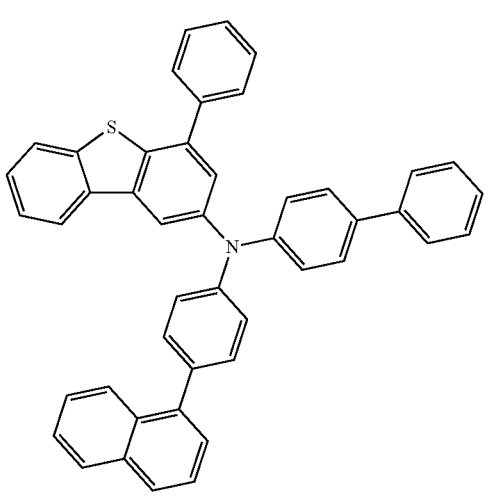

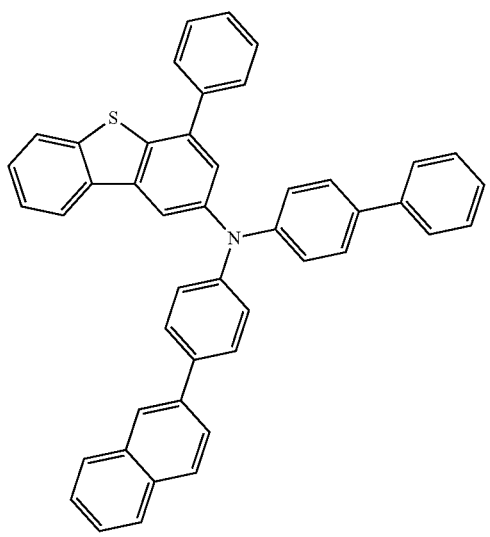
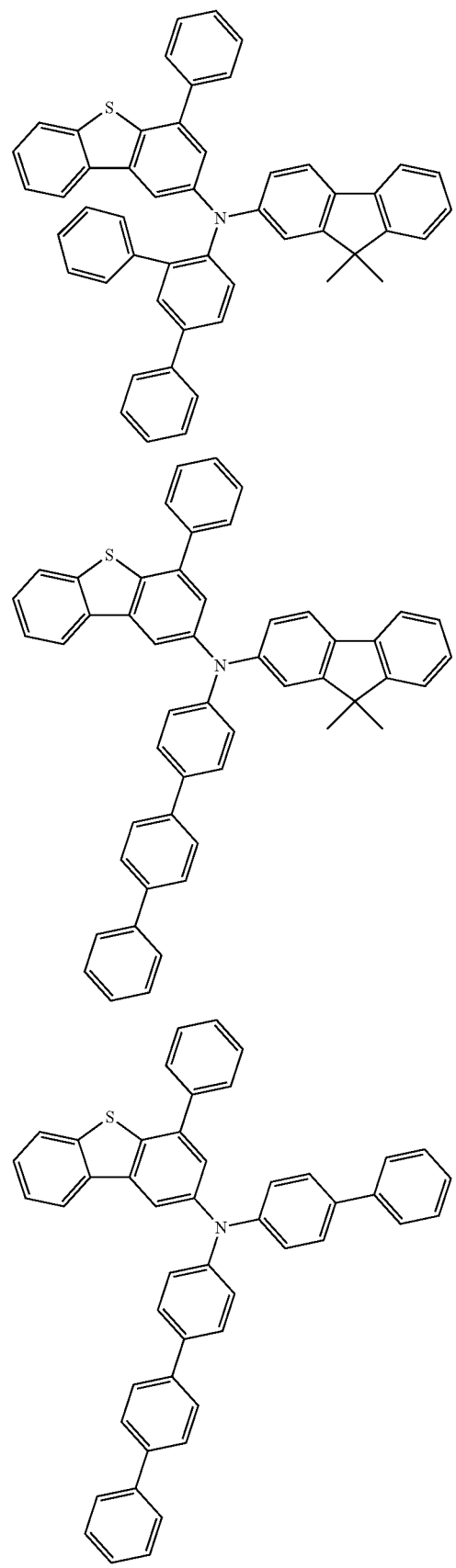

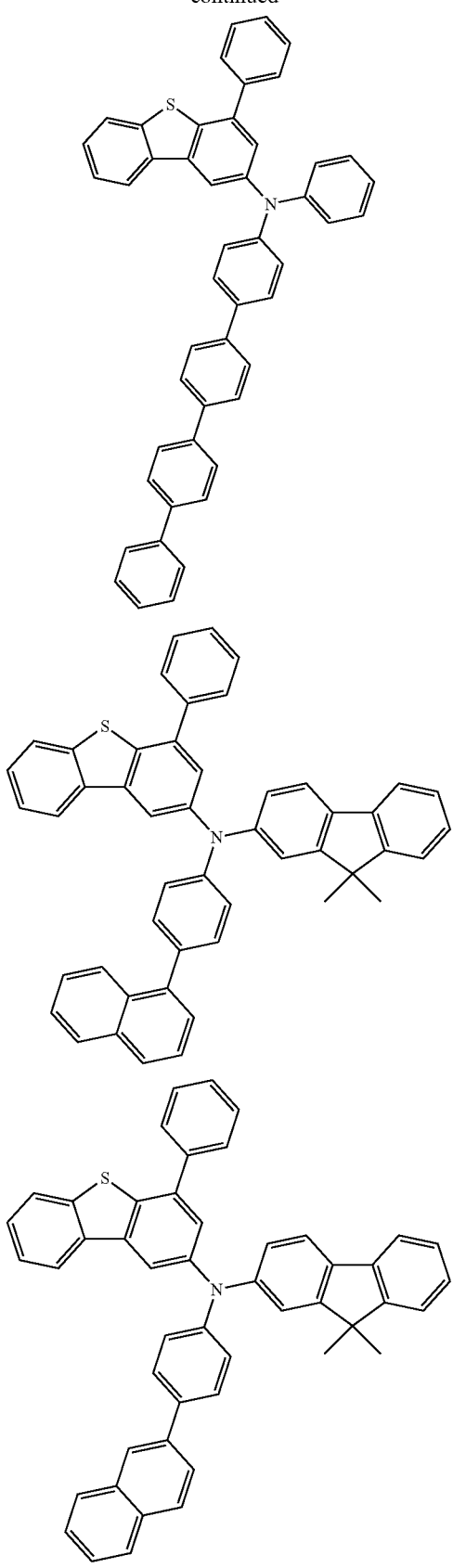
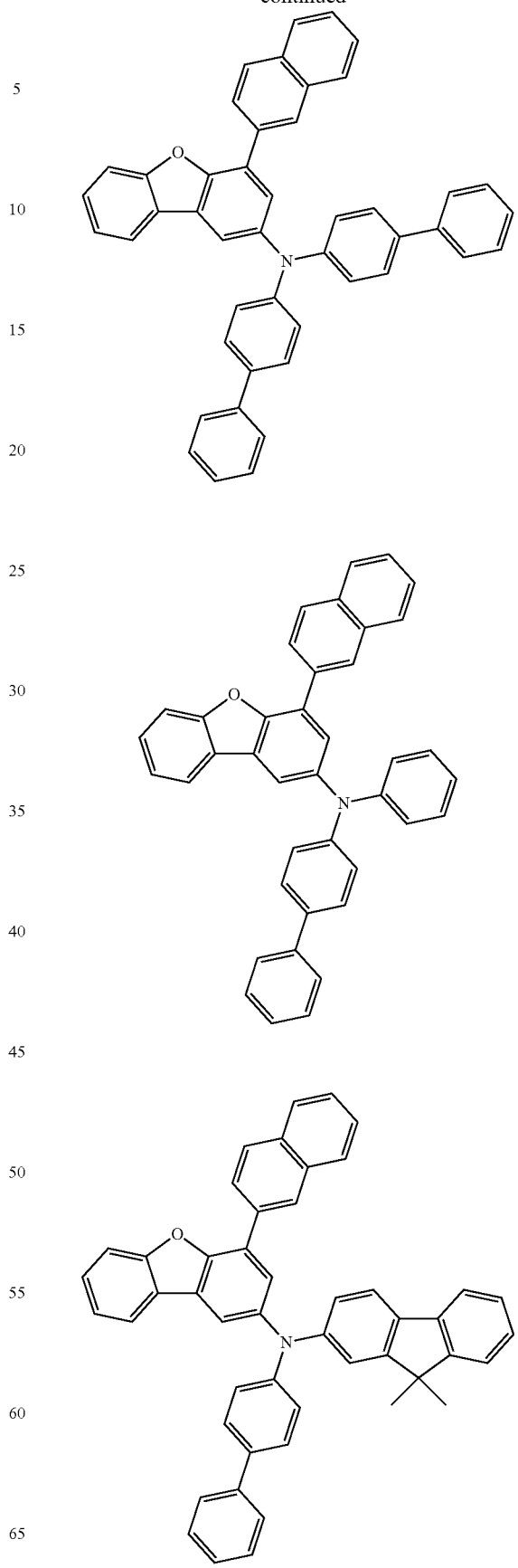

53
-continued
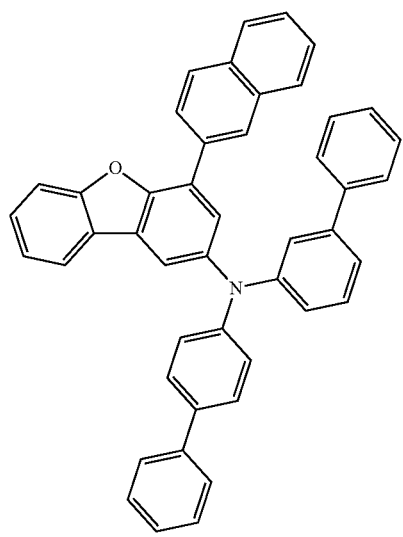
54
-continued
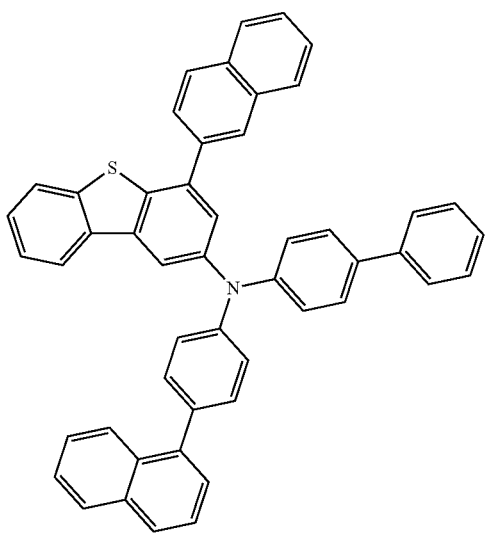
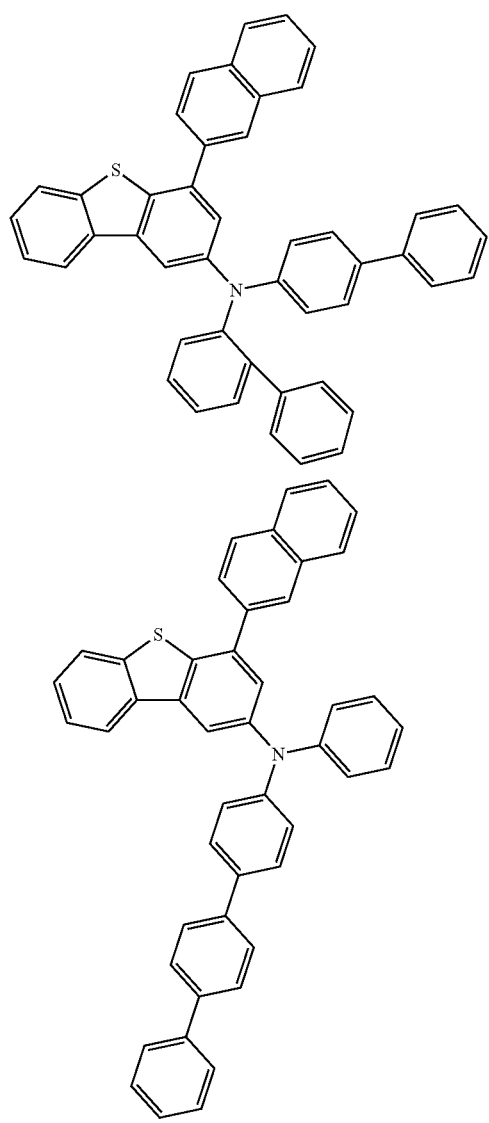
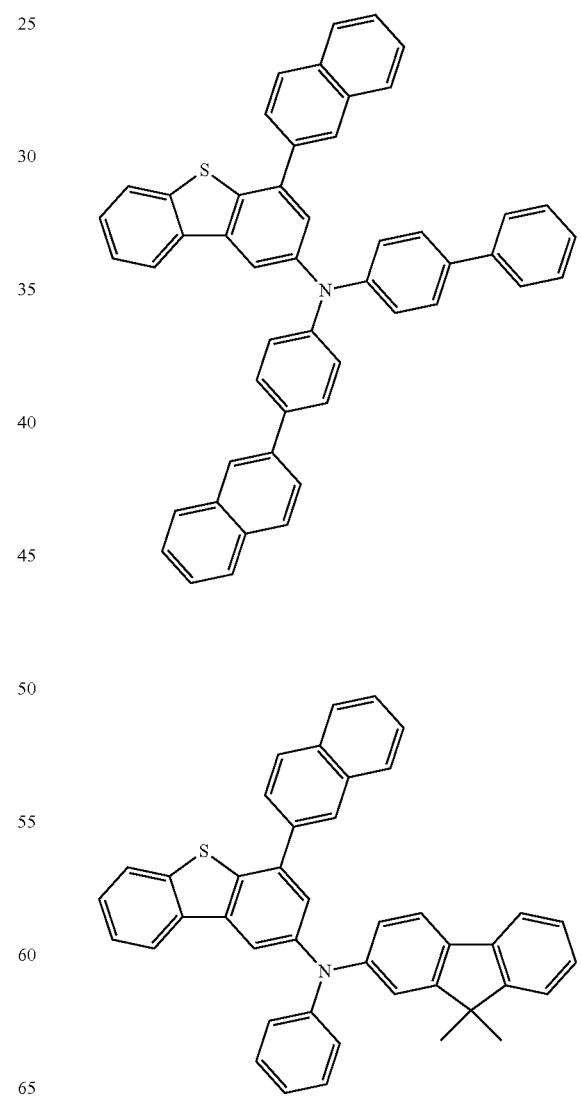

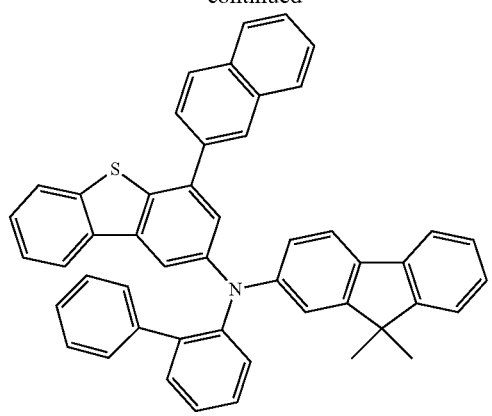
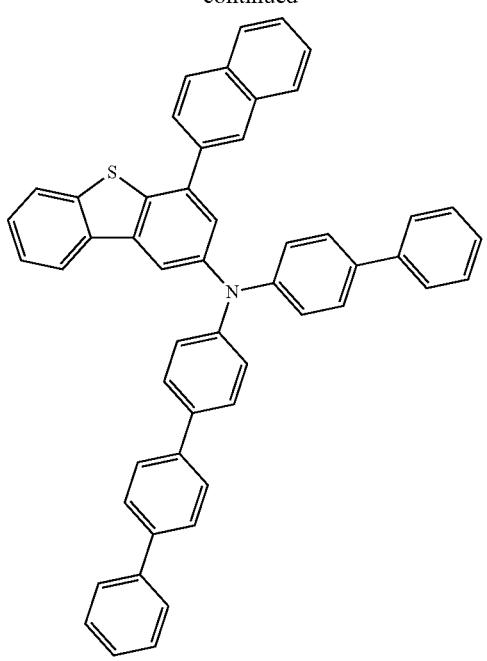
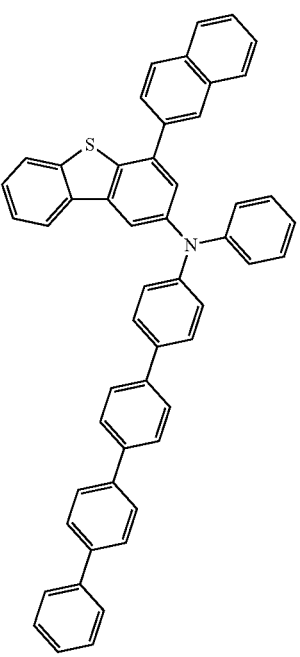

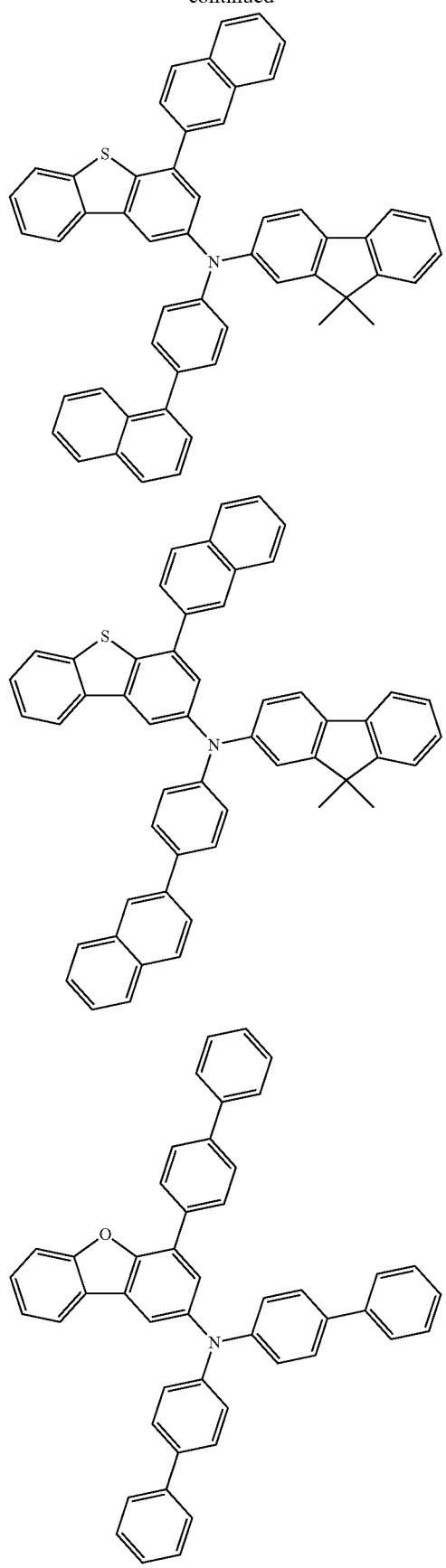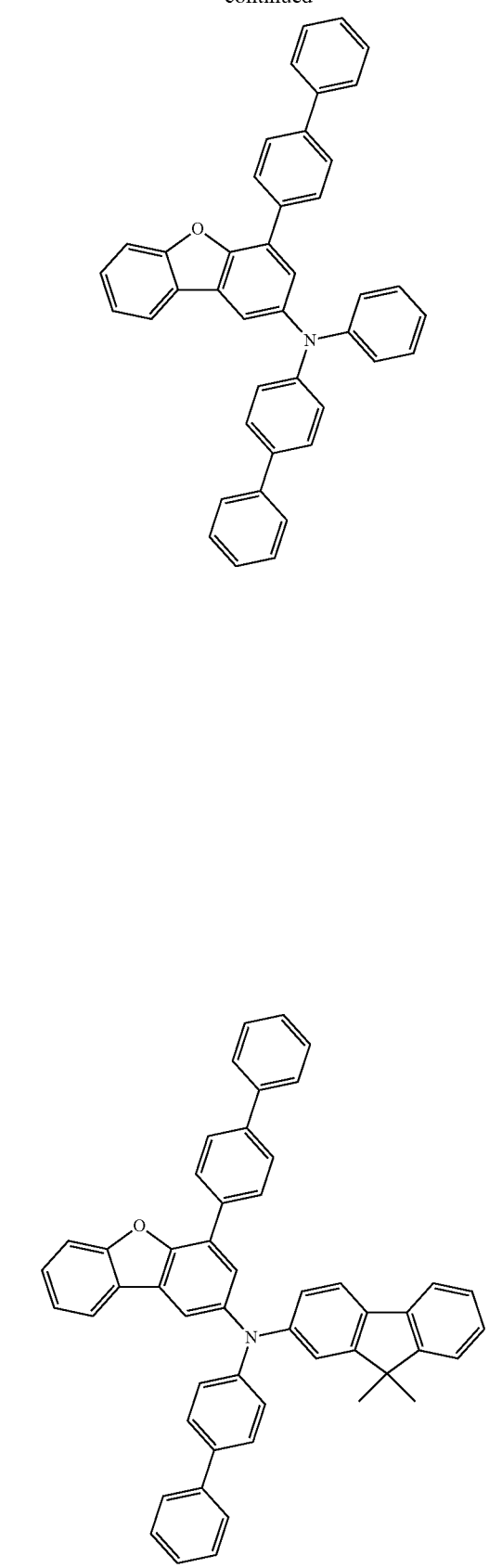

59
-continued
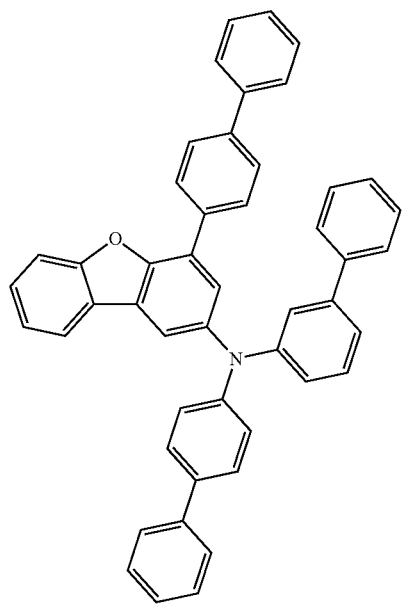
60
-continued
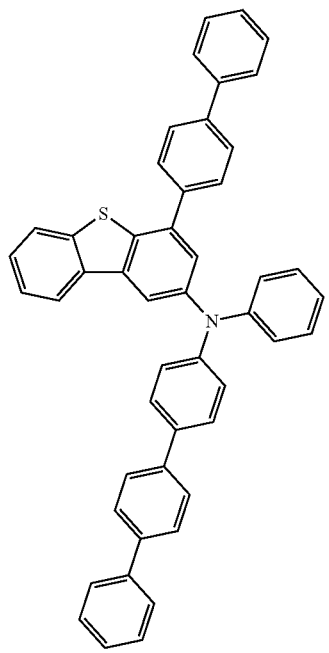
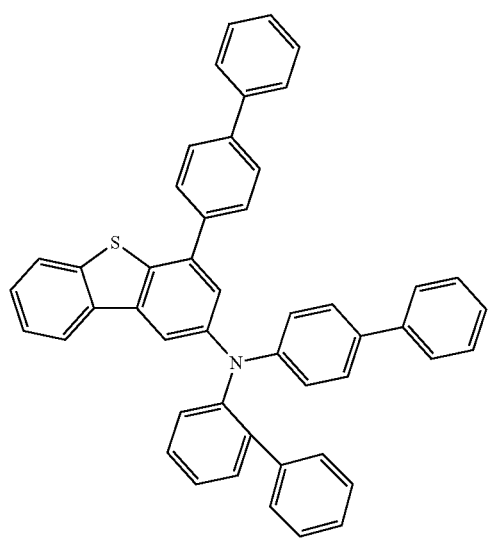
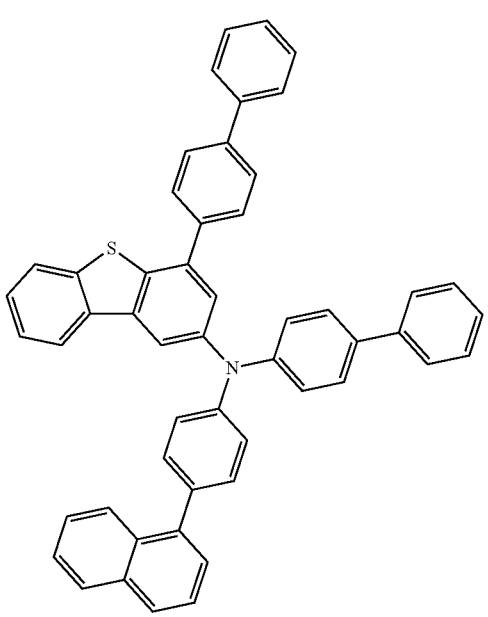

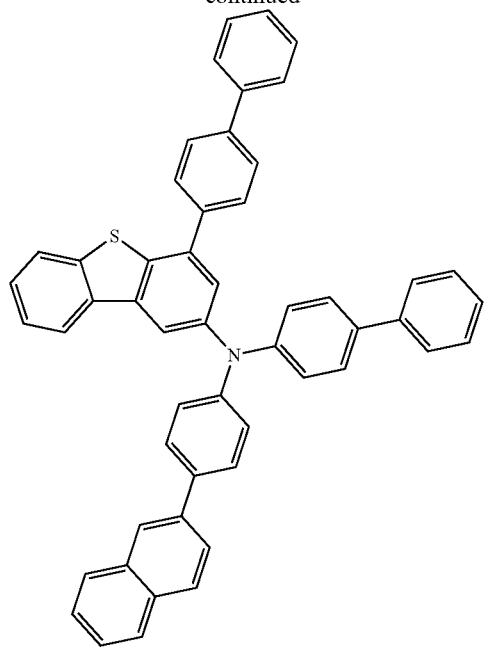
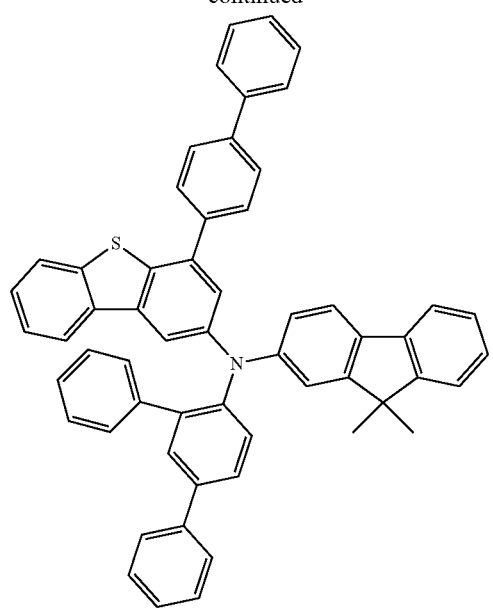
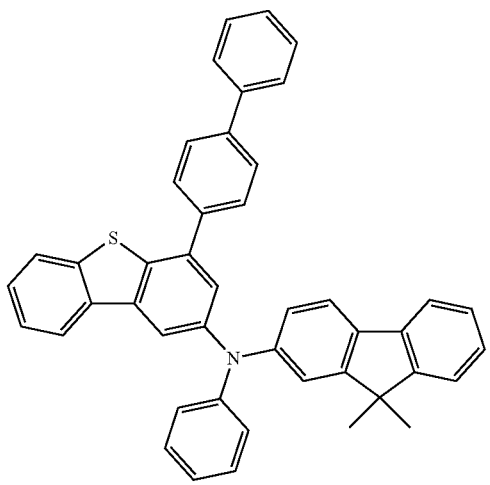
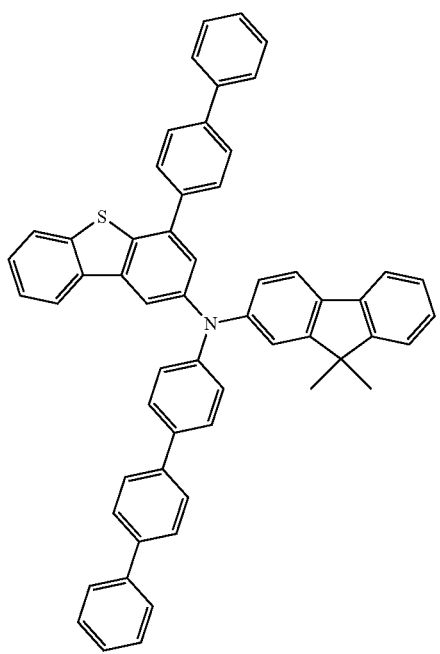

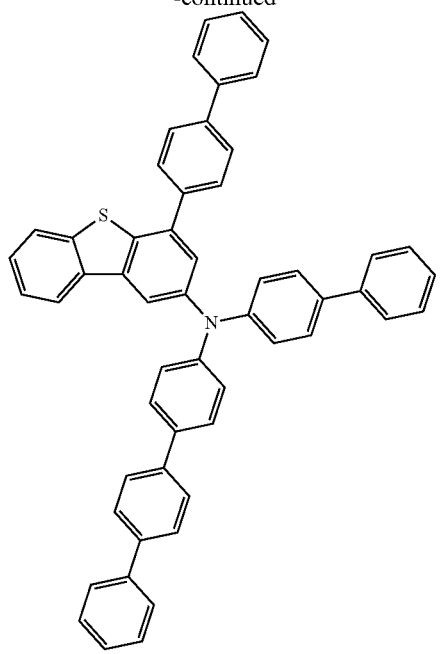
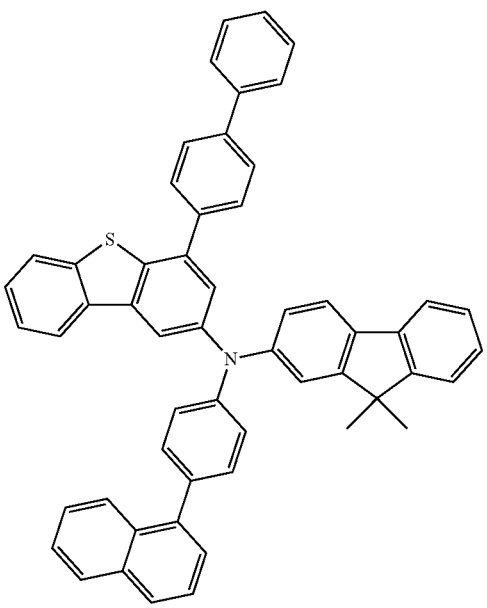
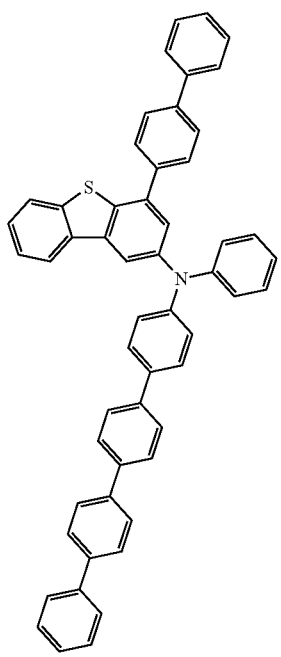

-continued
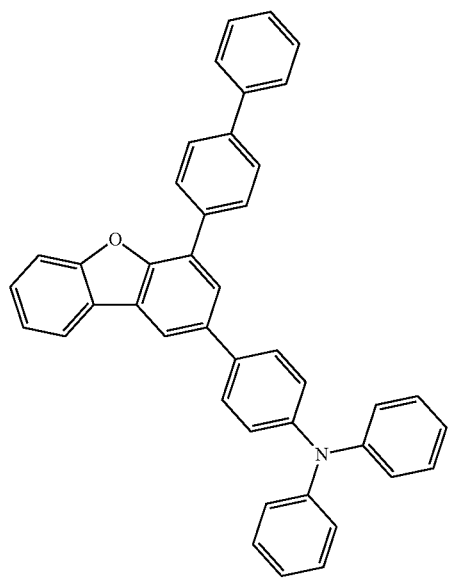
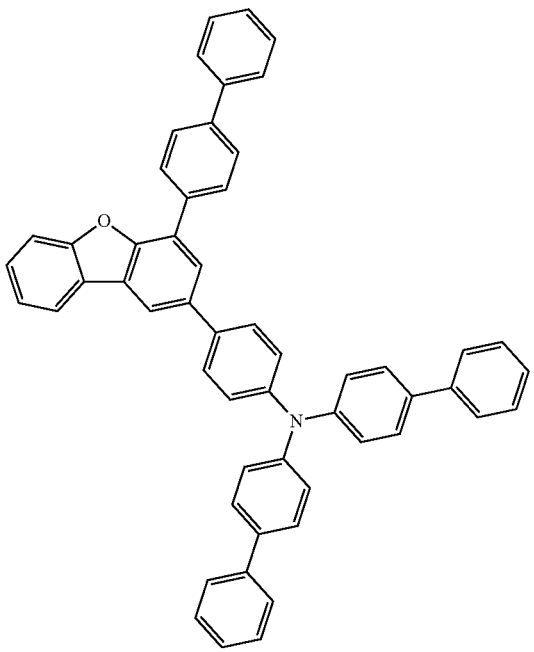
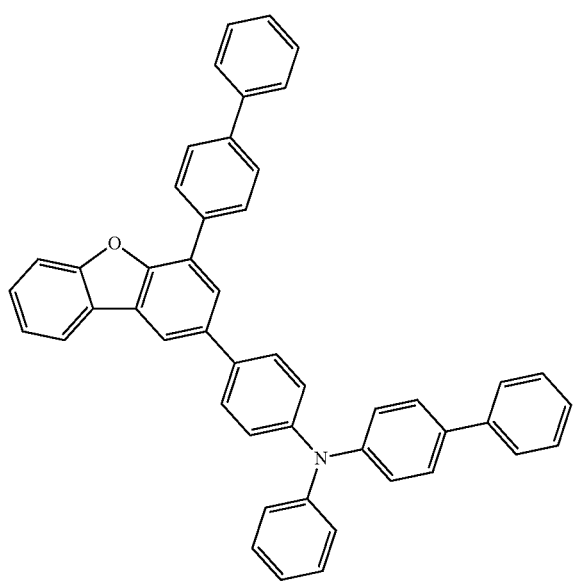
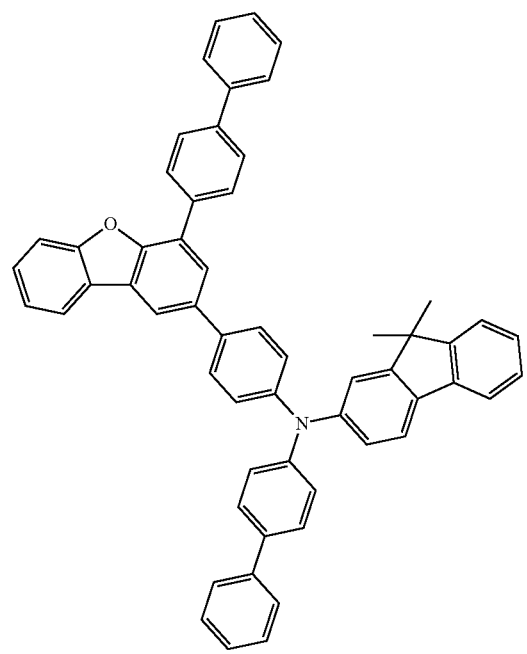

67
-continued
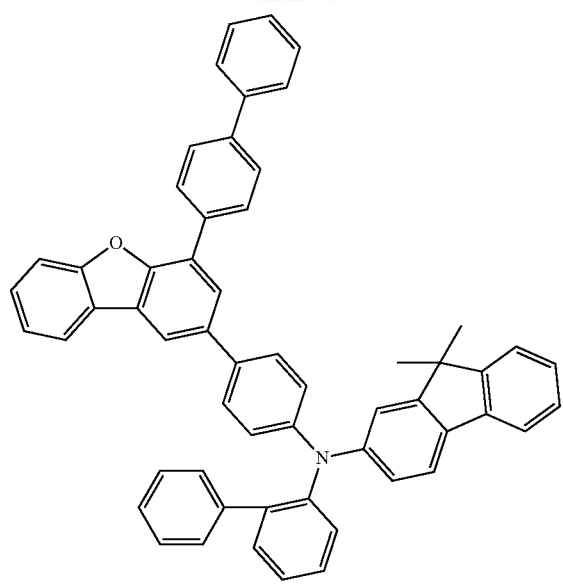
68
-continued
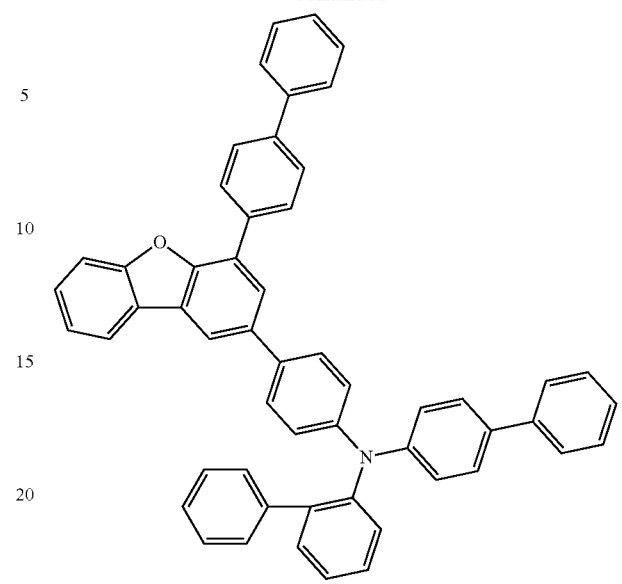
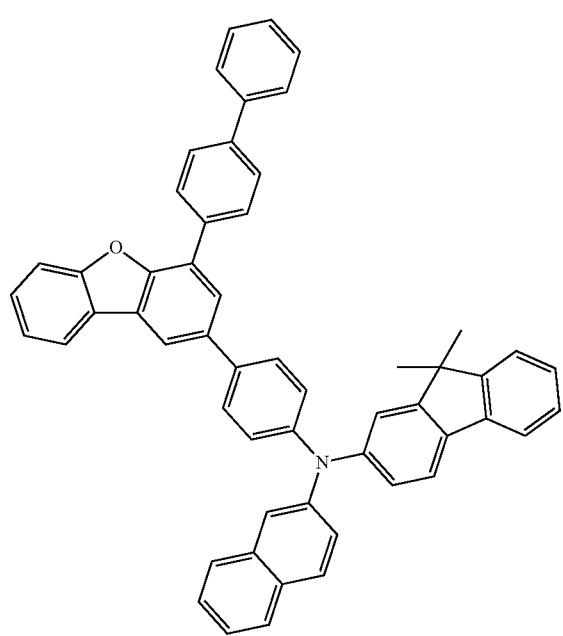
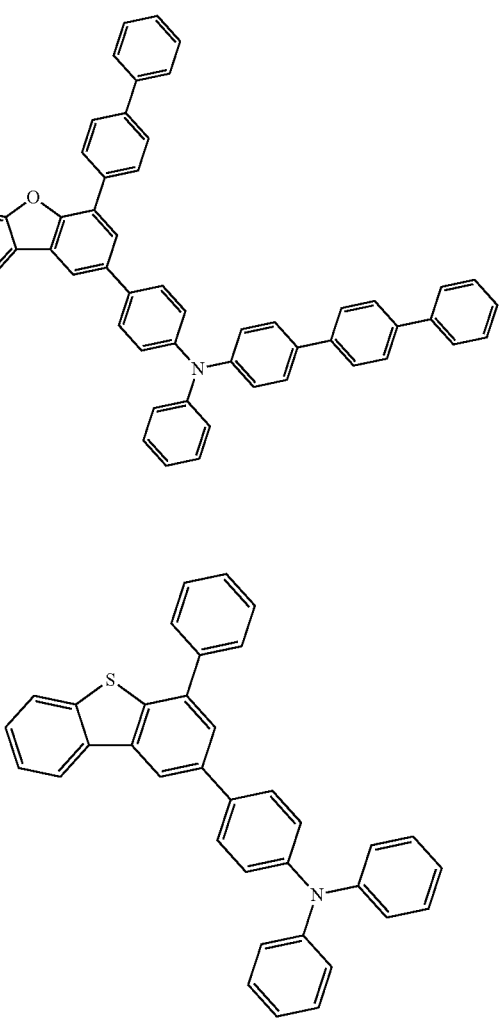

69
-continued
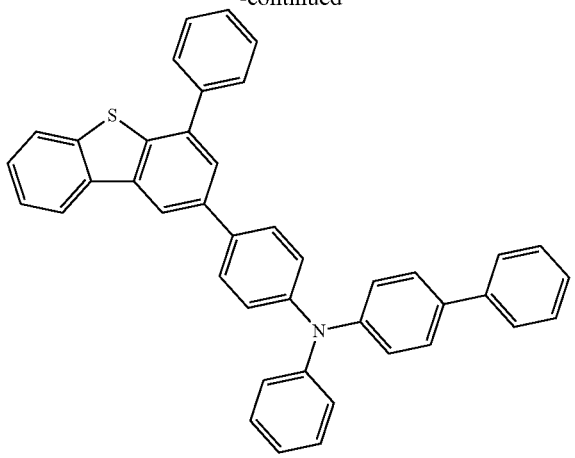
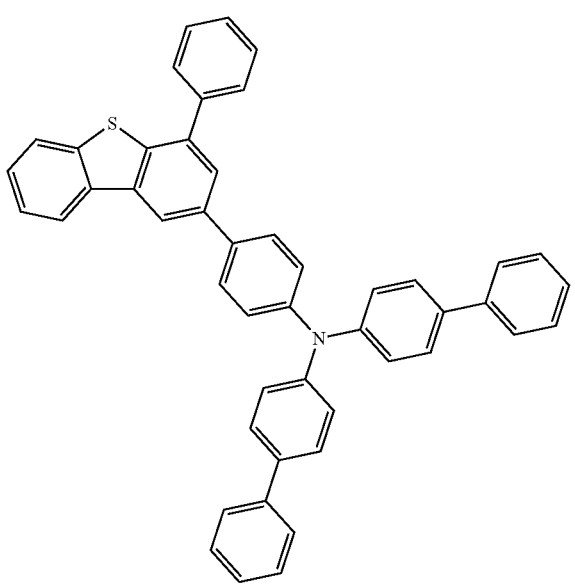
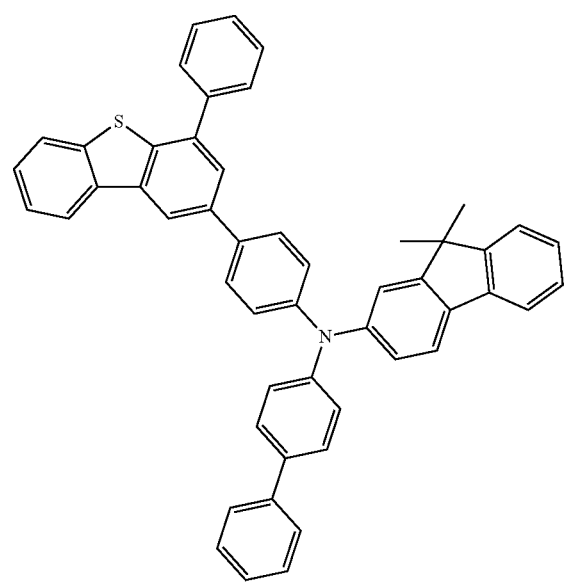
70
-continued
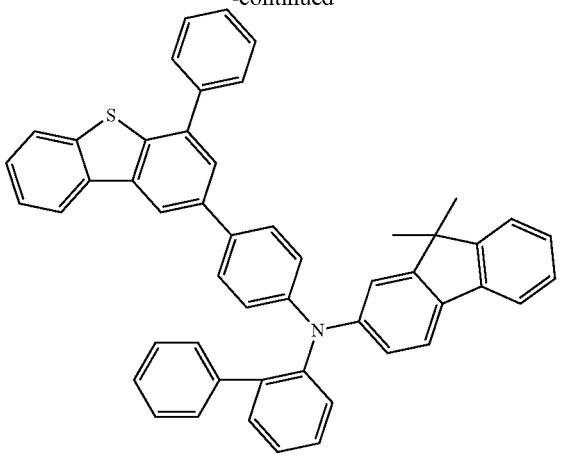
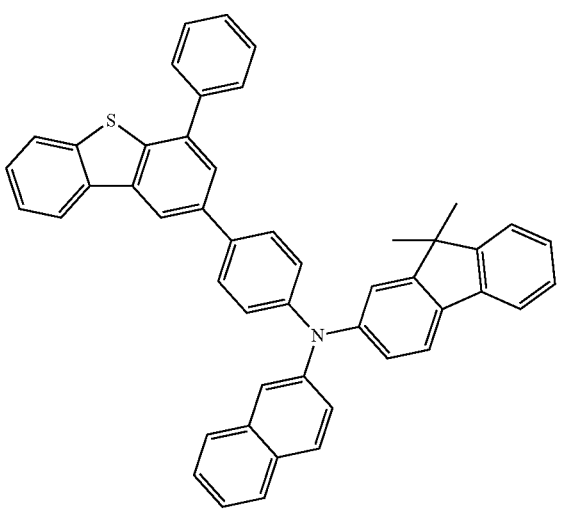
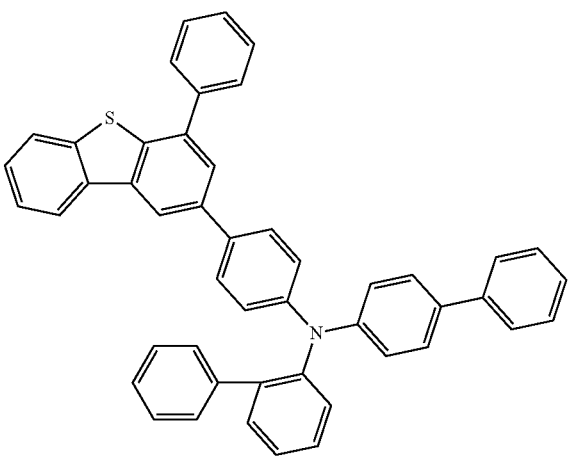

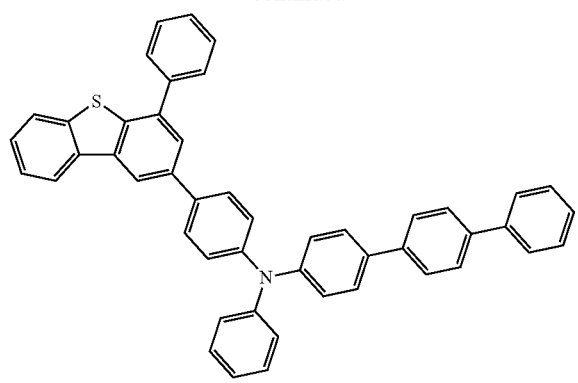
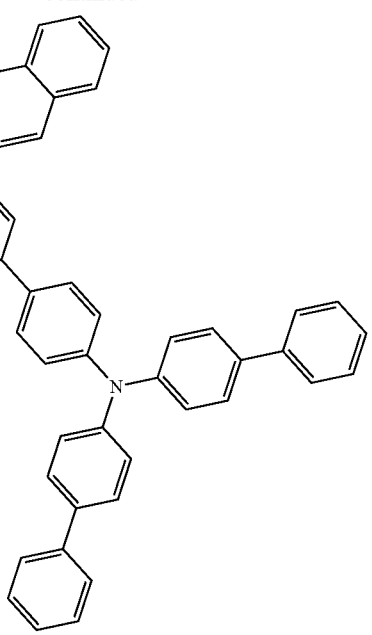
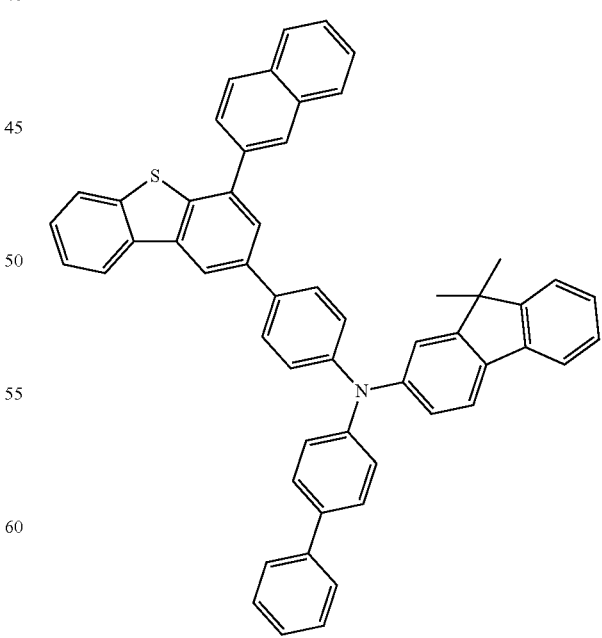

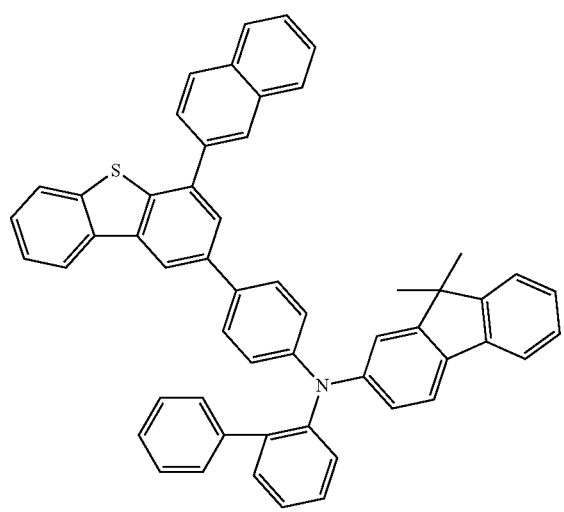
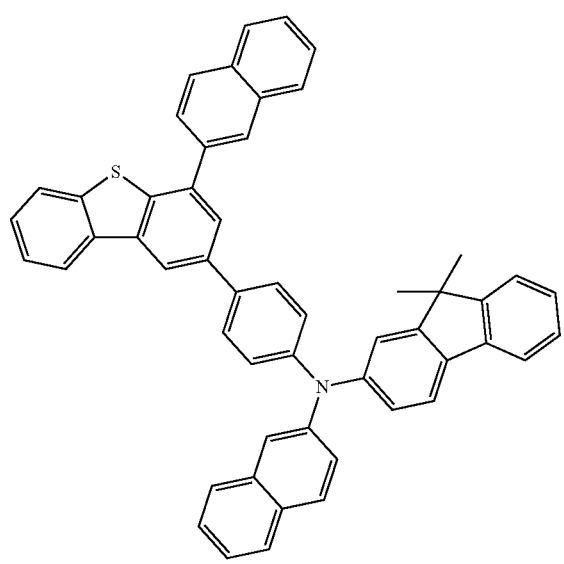
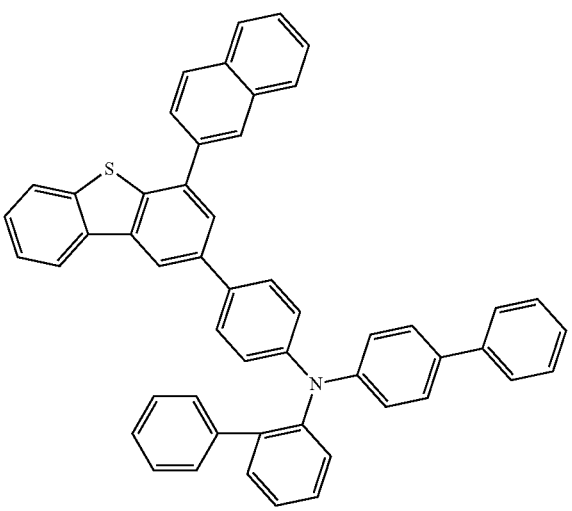
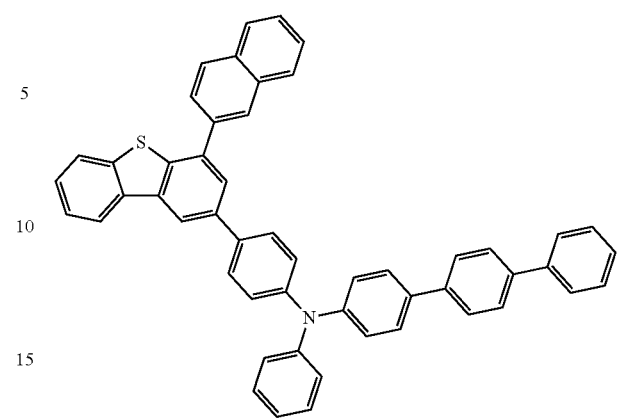
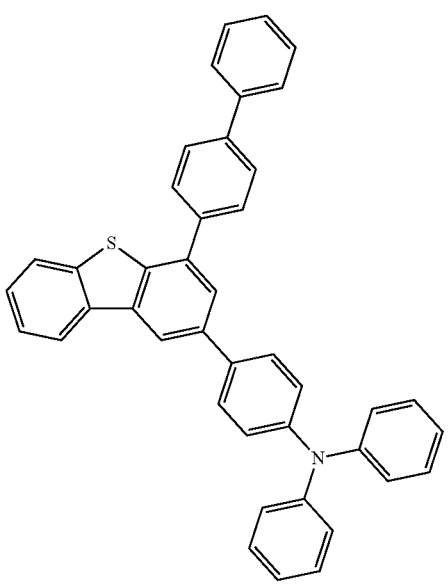
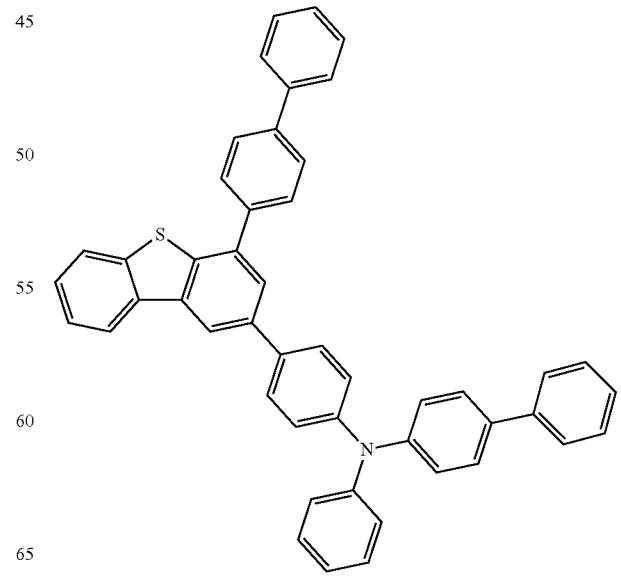

-continued
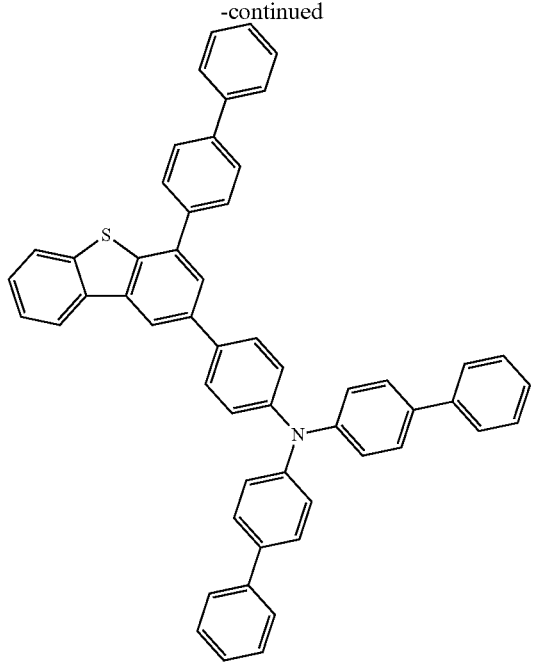
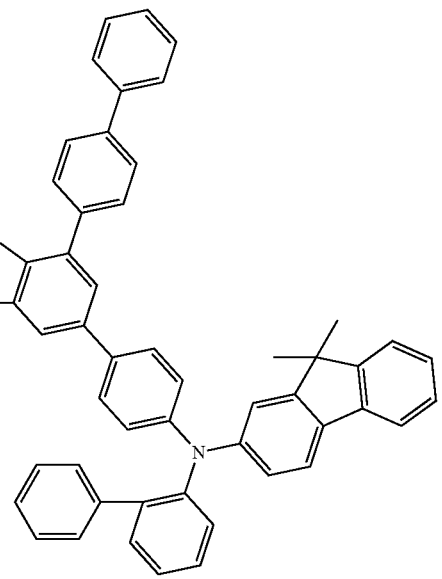
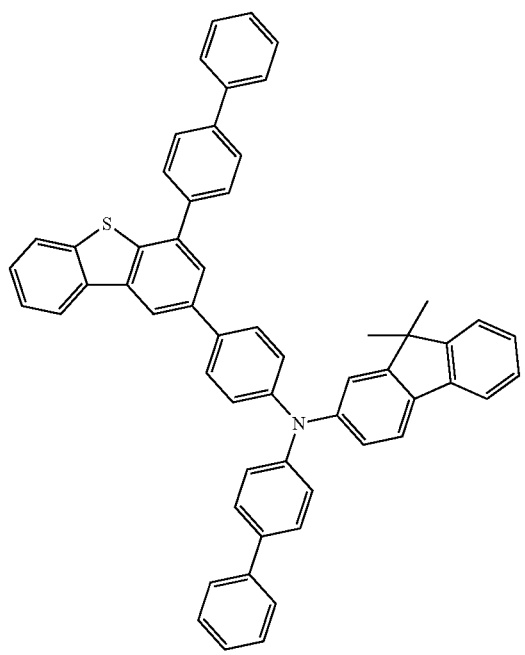
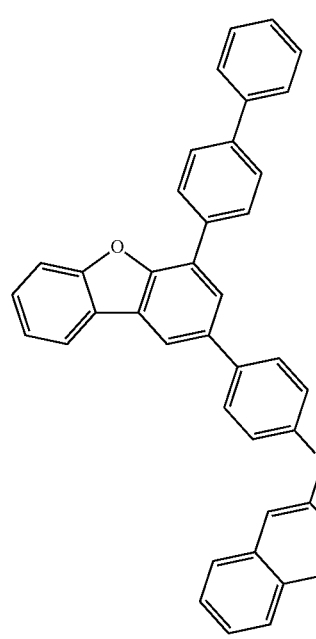

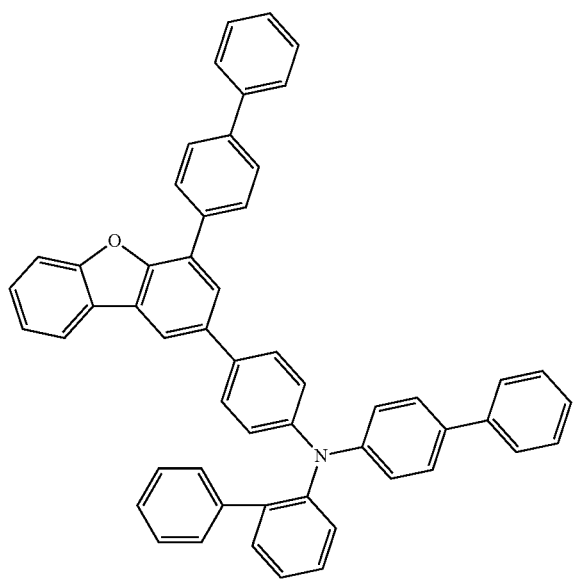
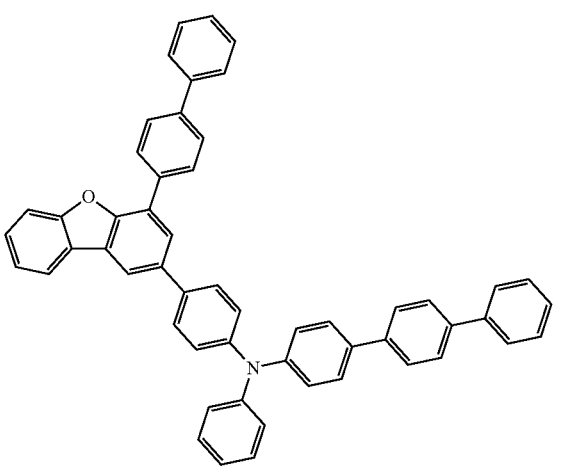
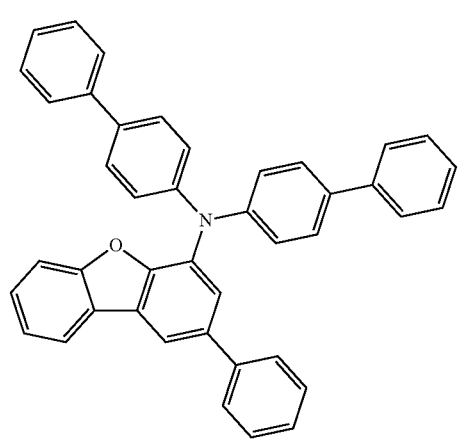
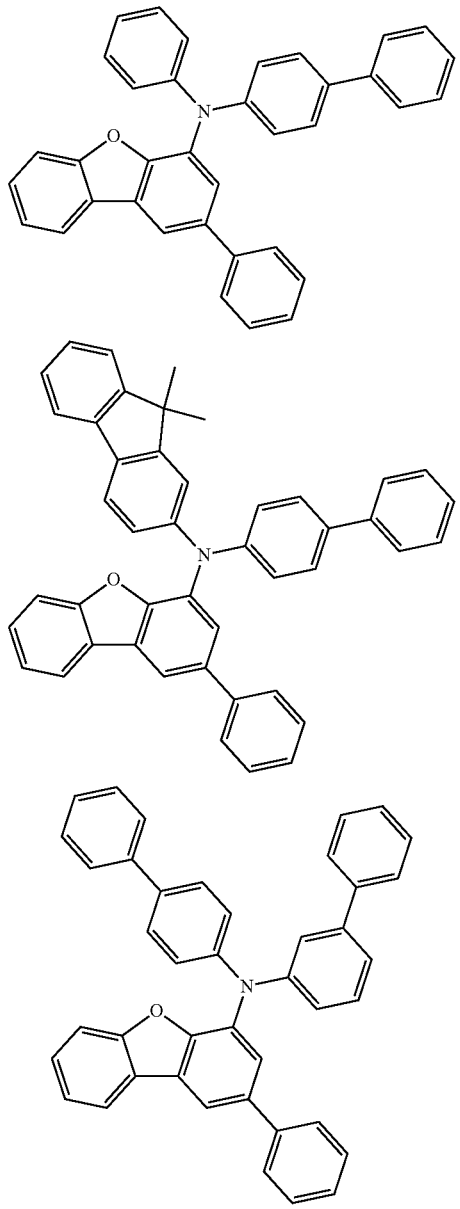
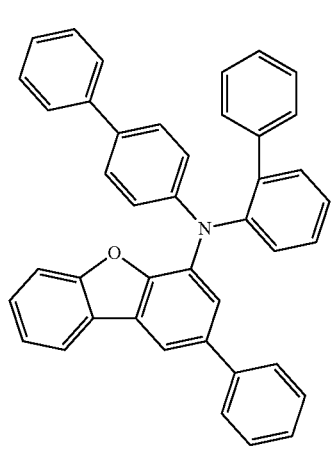

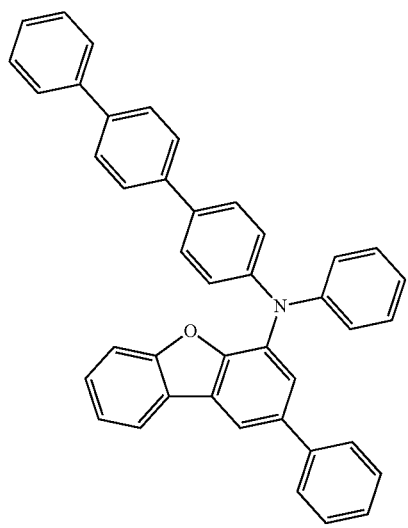
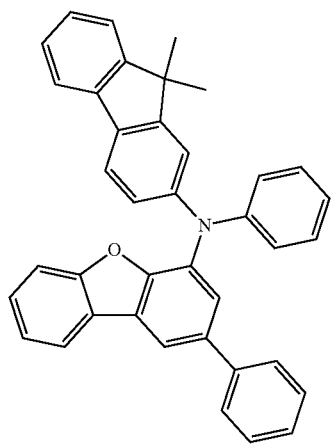
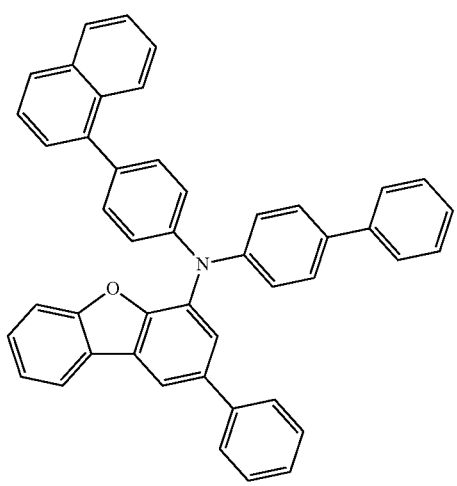
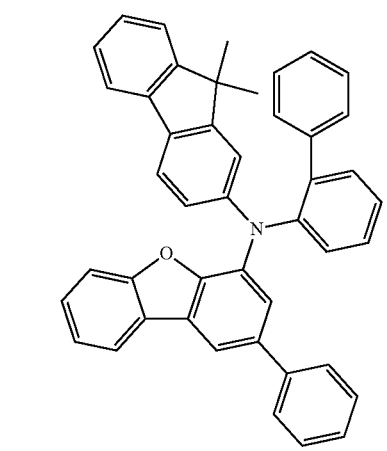
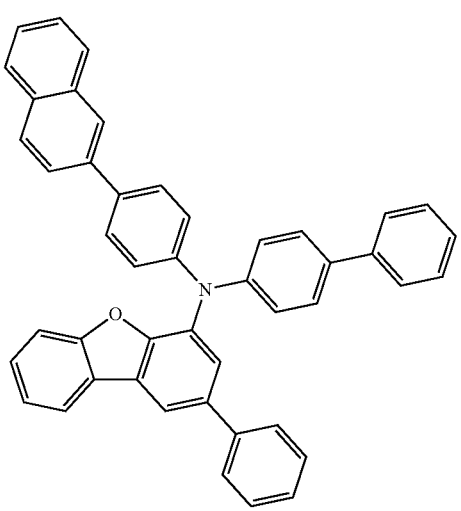
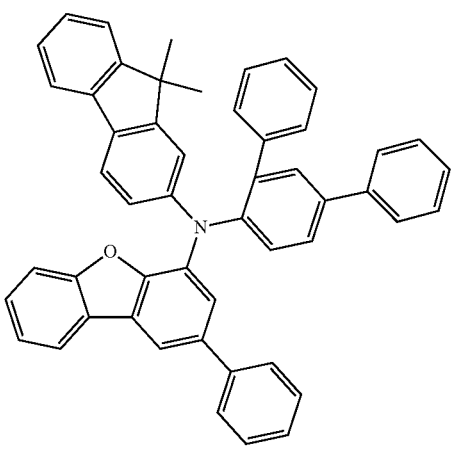

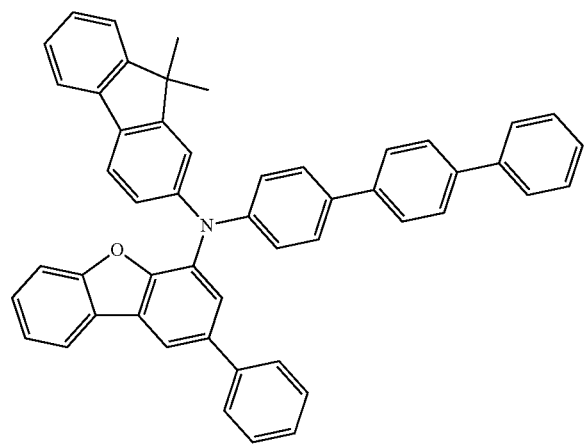
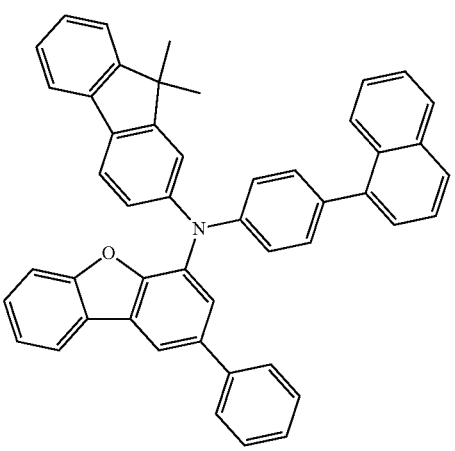
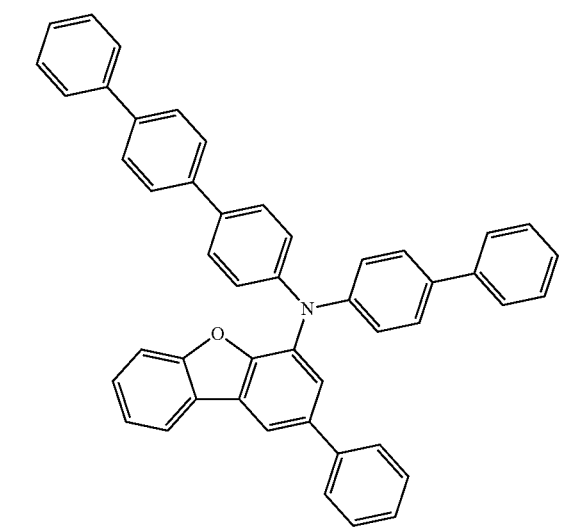
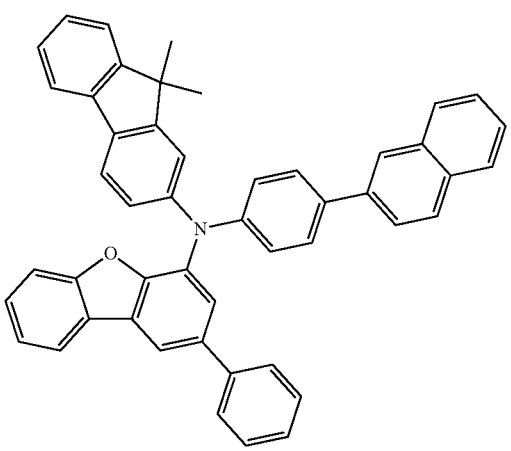
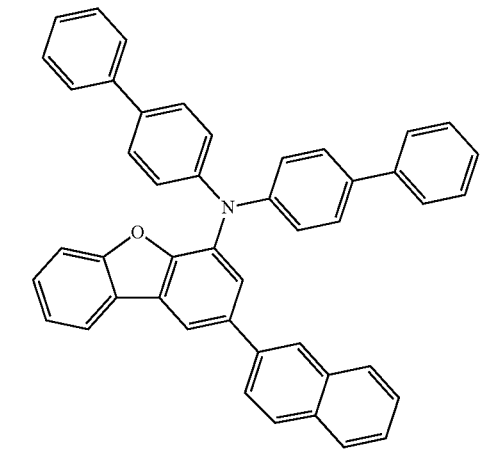
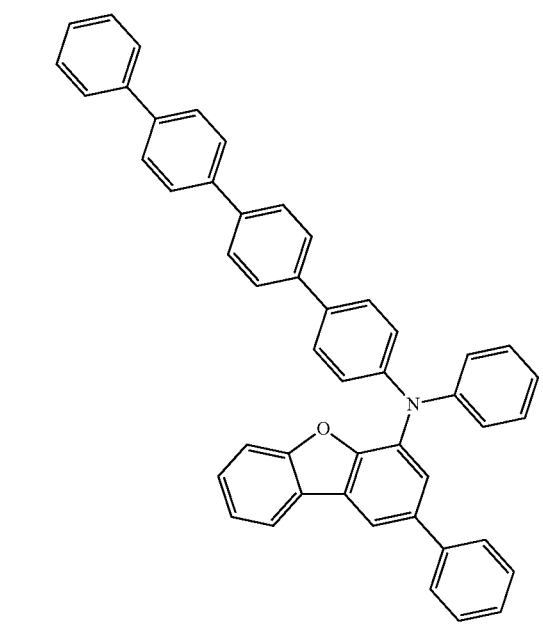
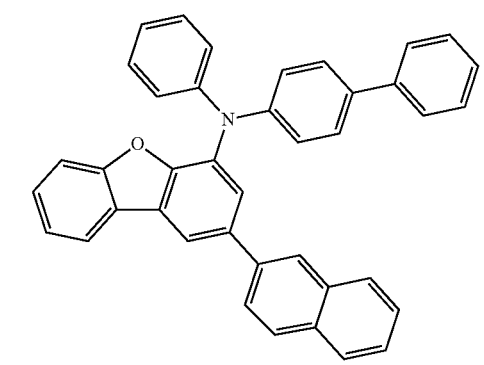

-continued
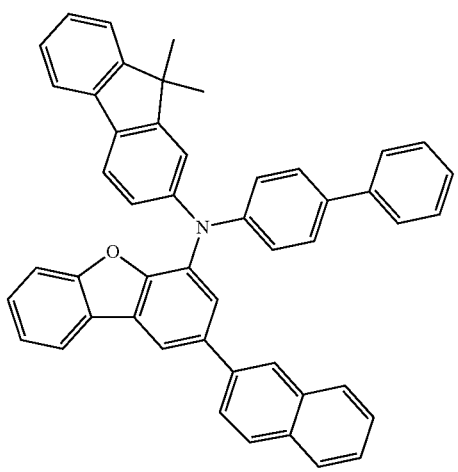
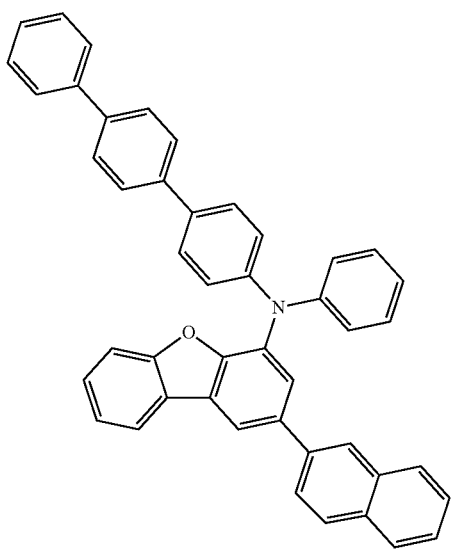
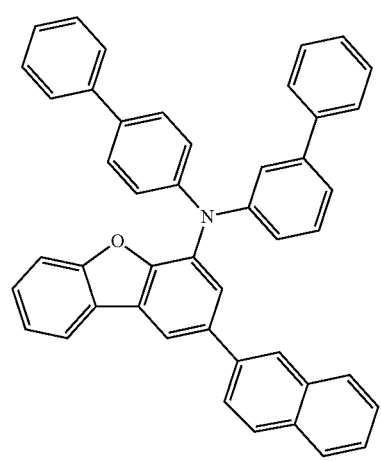
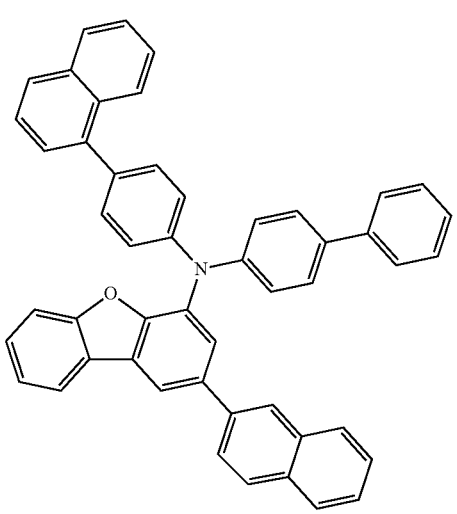
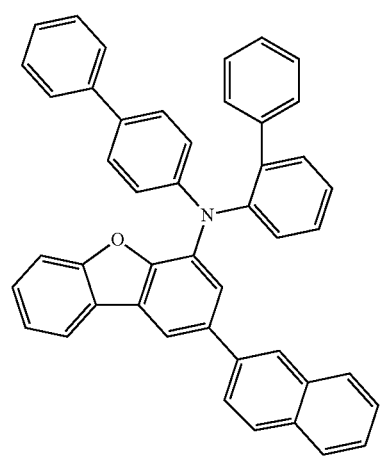
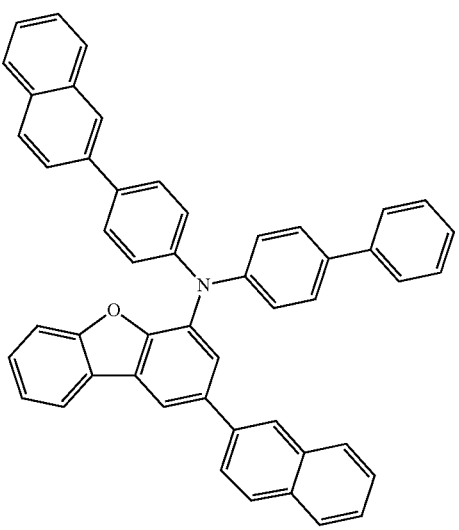

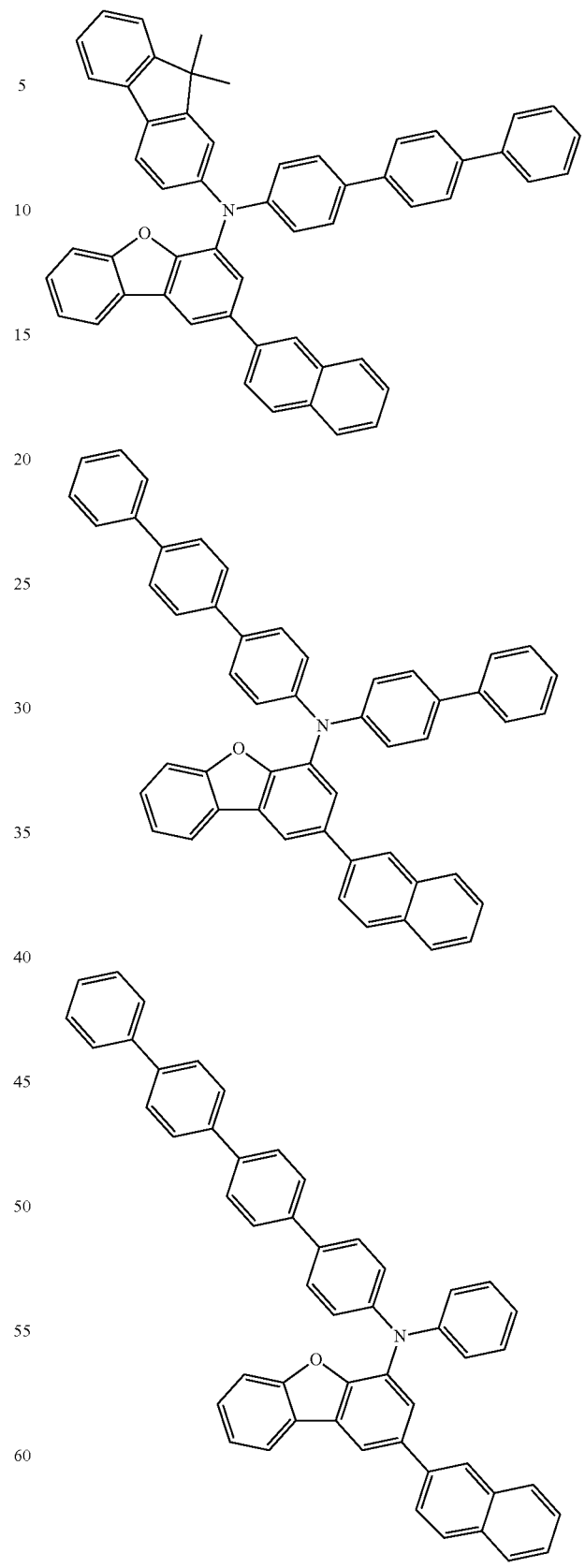

87
-continued
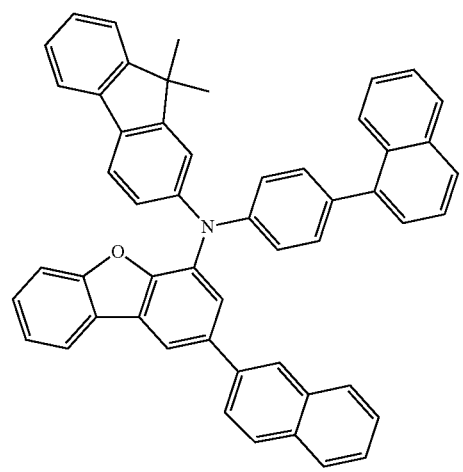
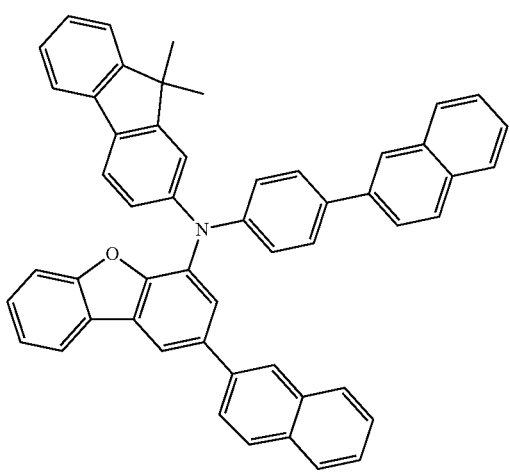
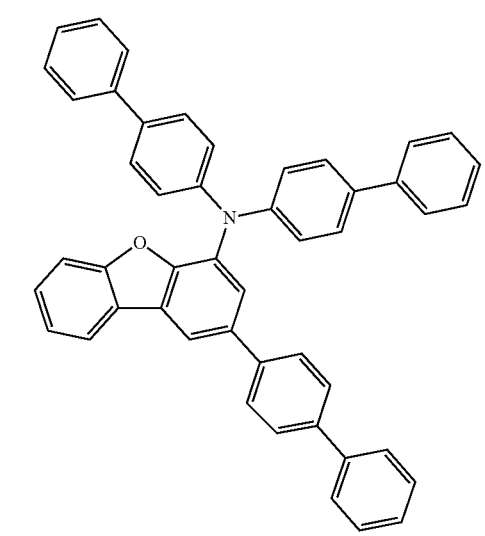
88
-continued
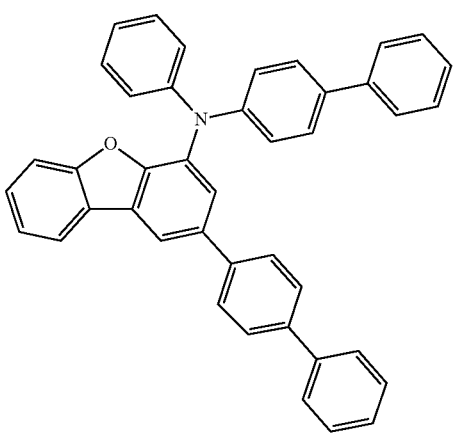
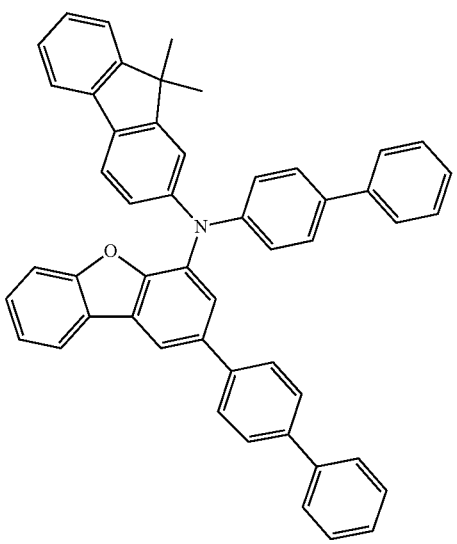
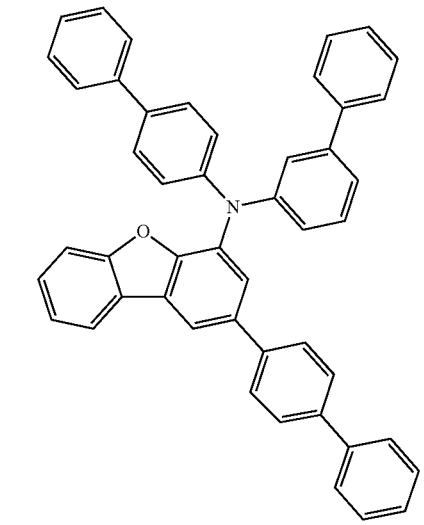

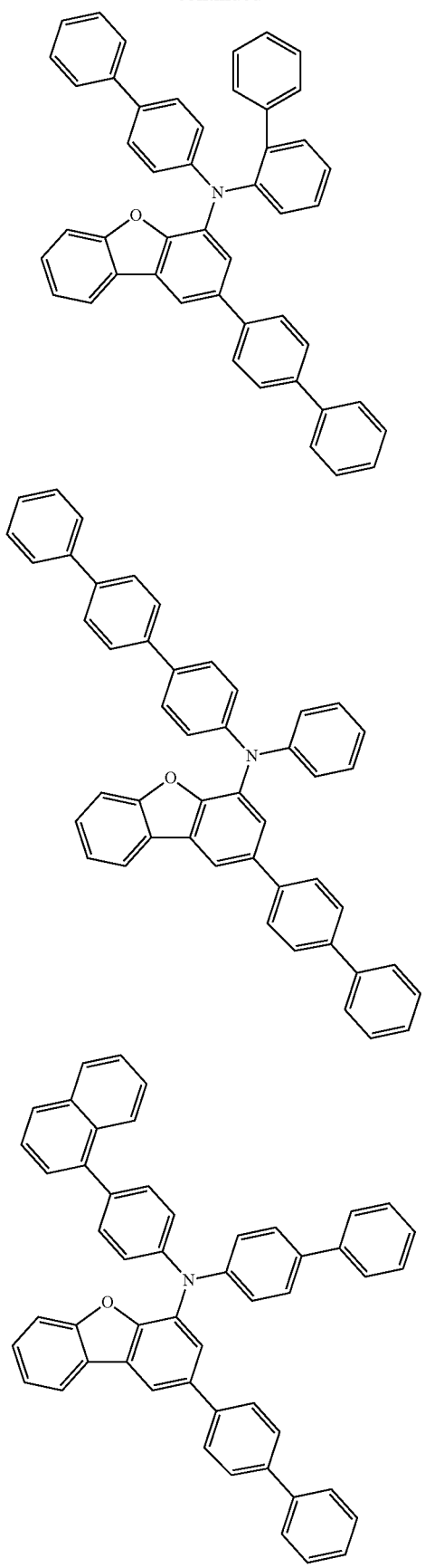
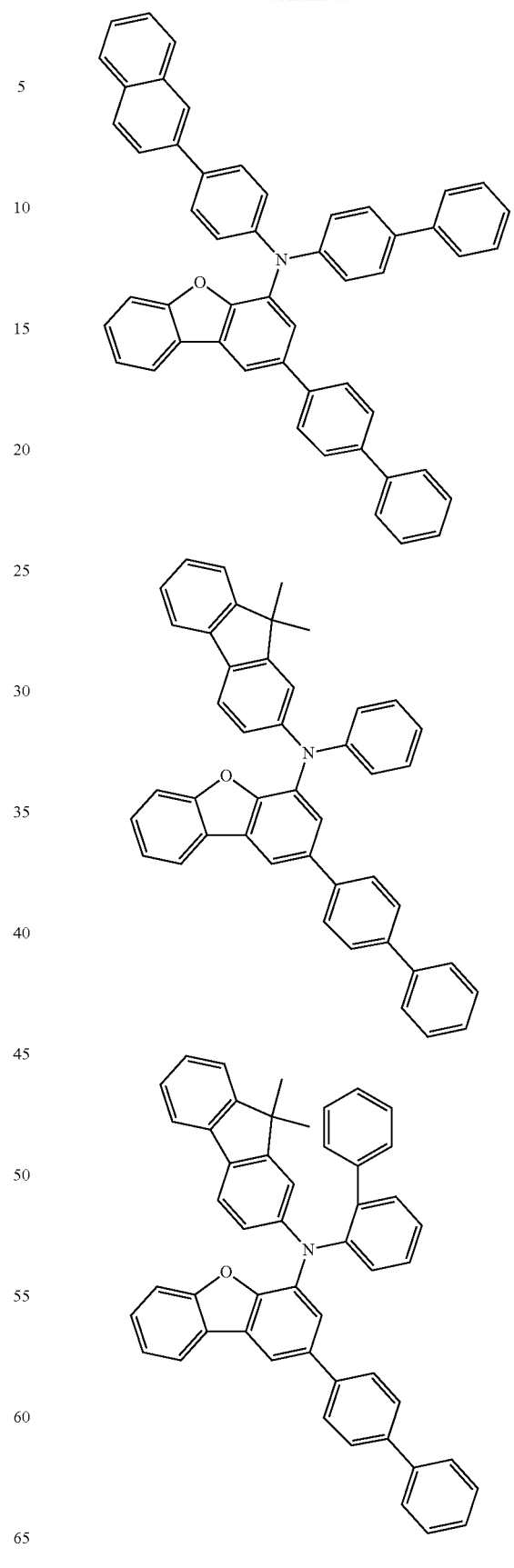

91
-continued
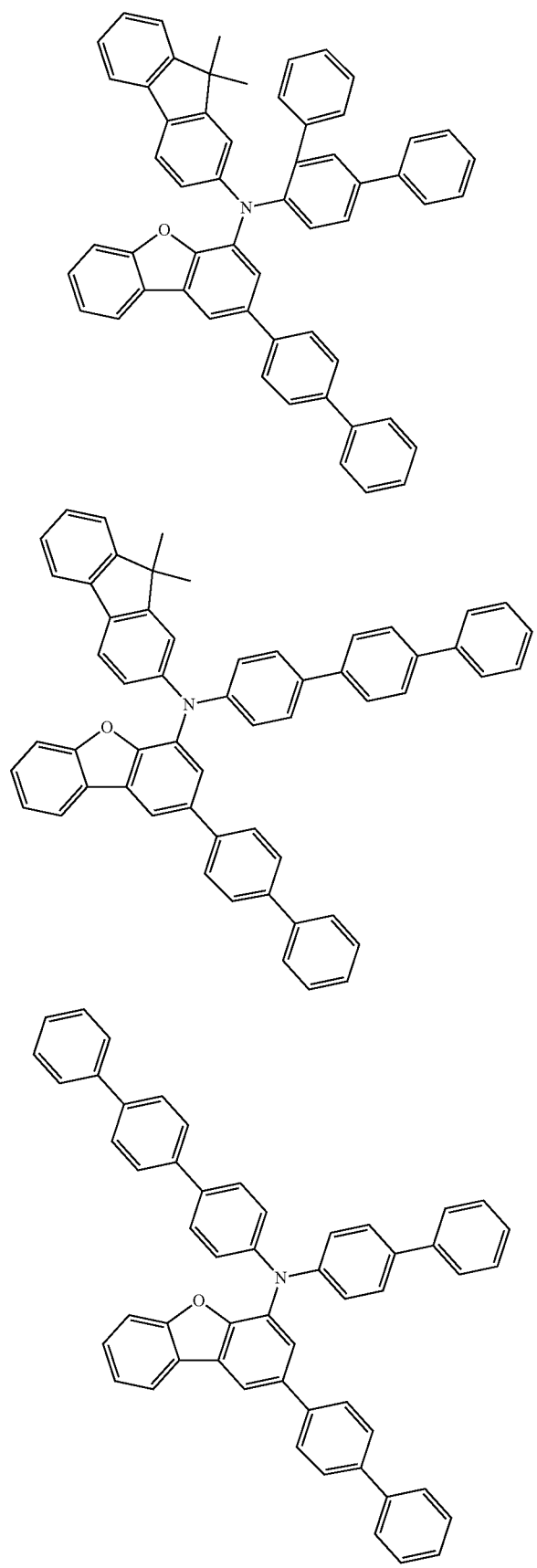
92
-continued
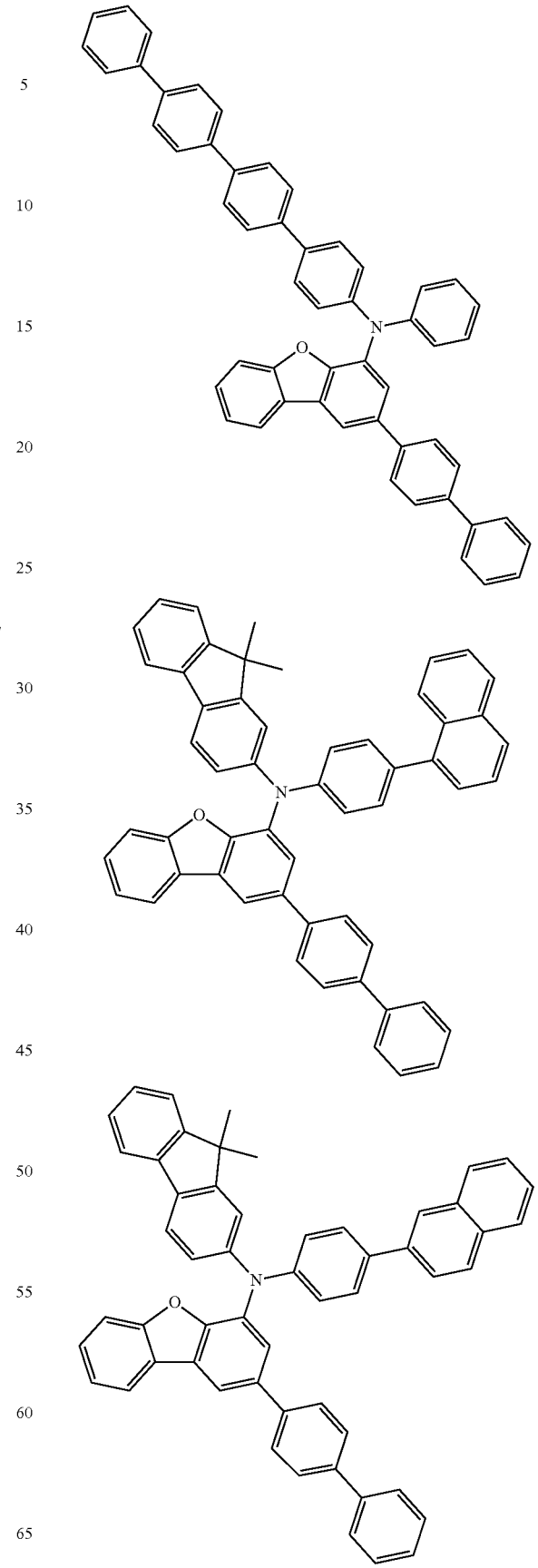

93
-continued
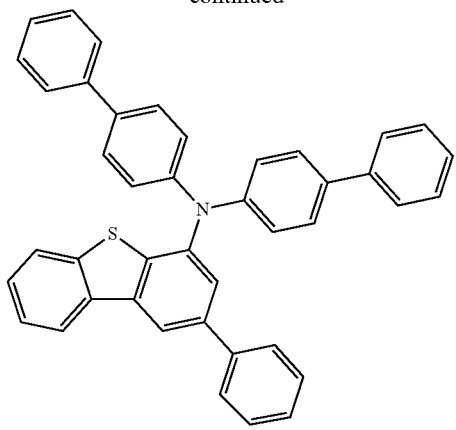
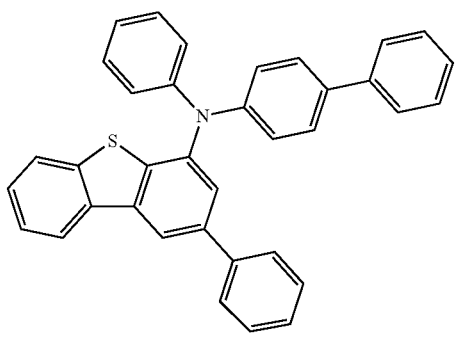
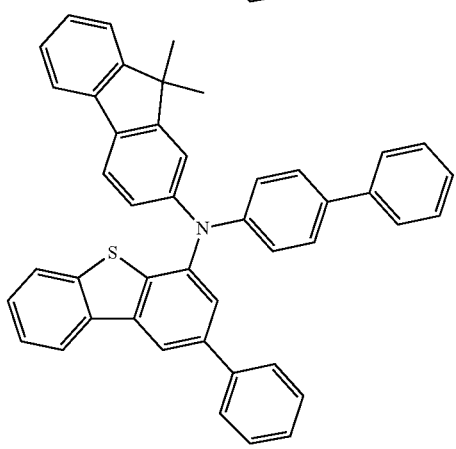
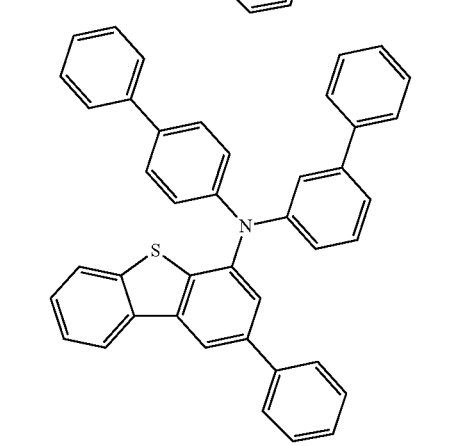
94
-continued
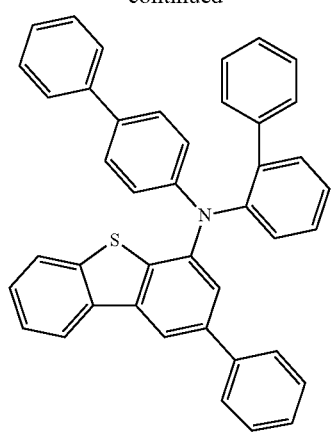
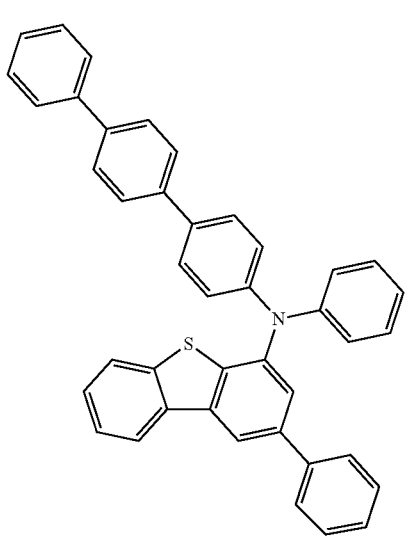
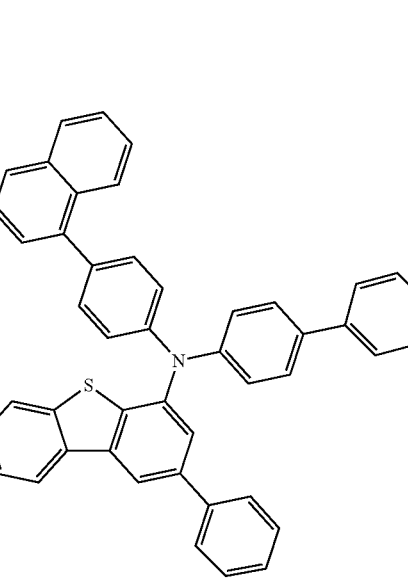

95
-continued
96
-continued
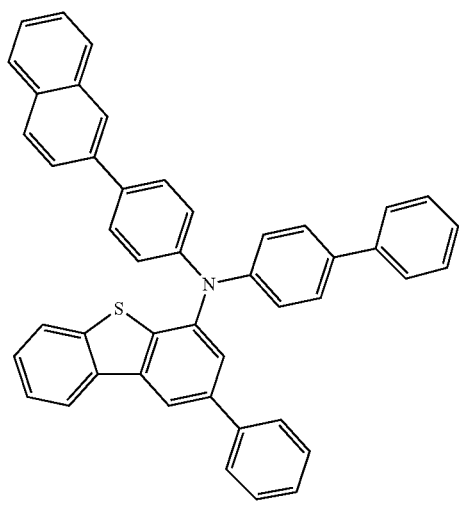
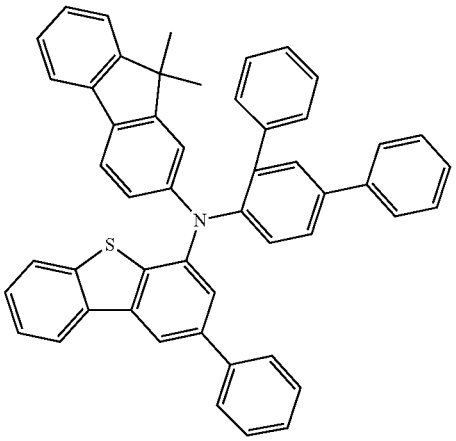
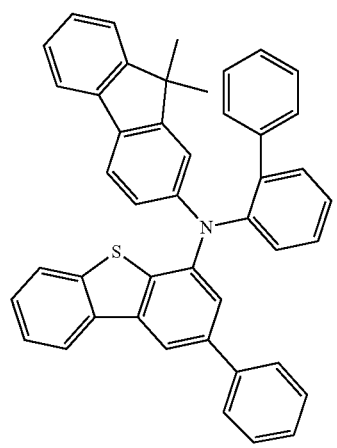
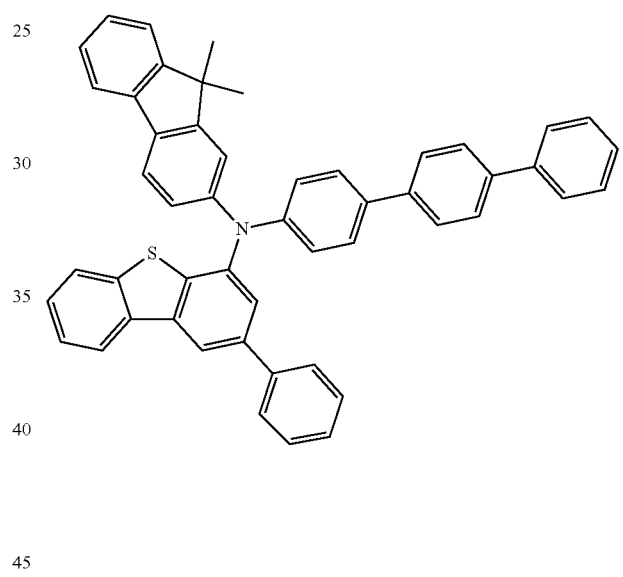
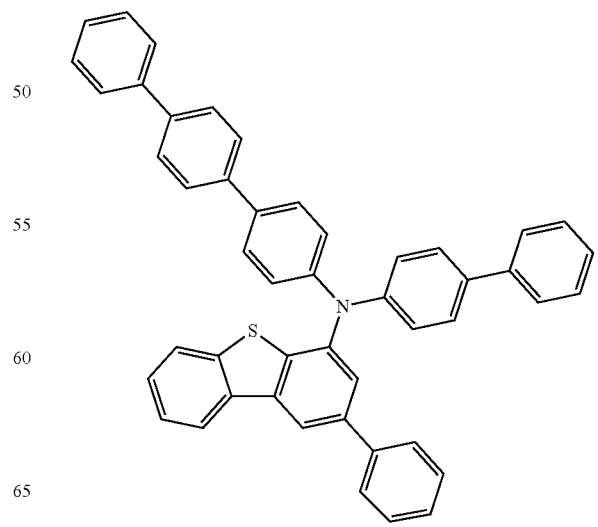

97
-continued
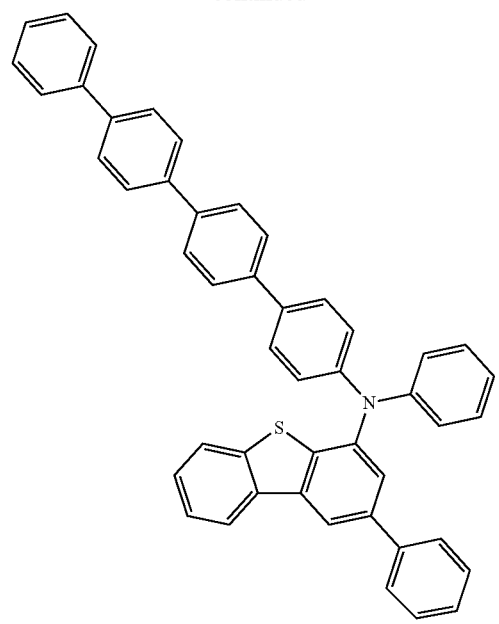
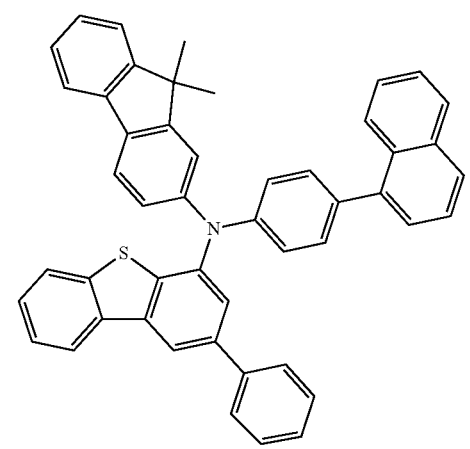
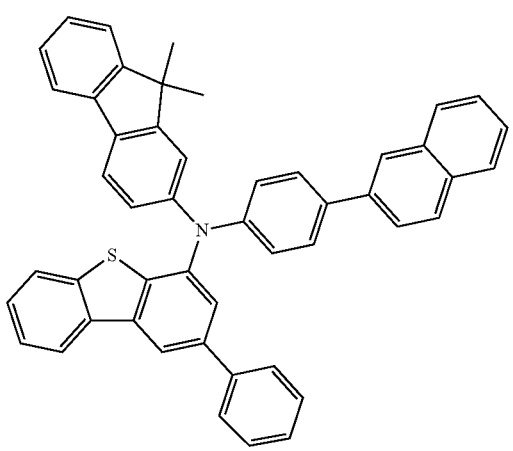
98
-continued
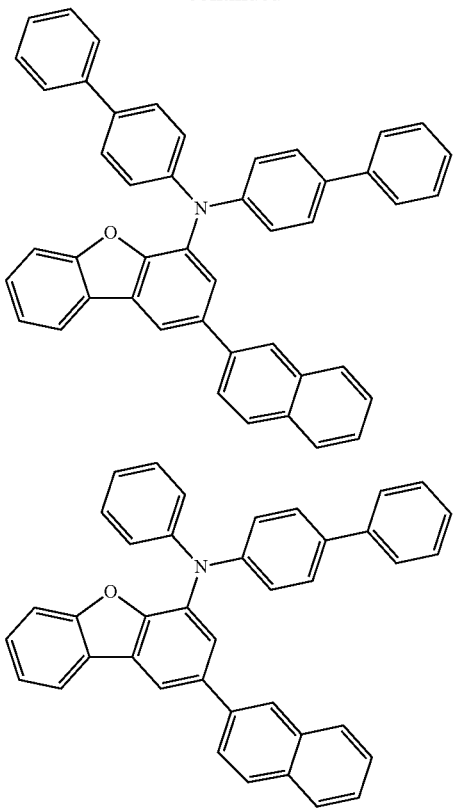
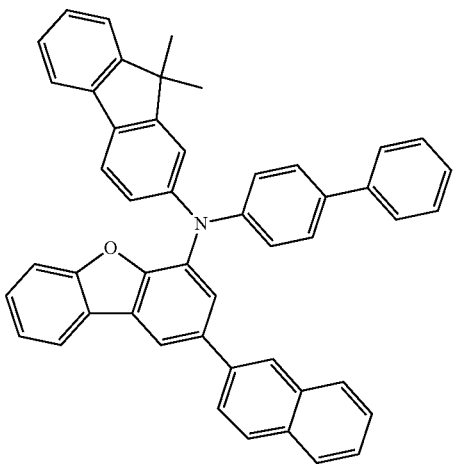
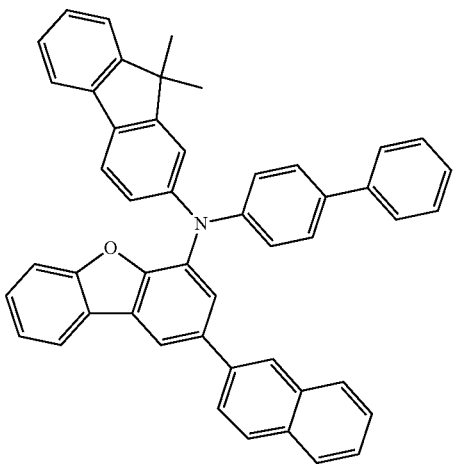
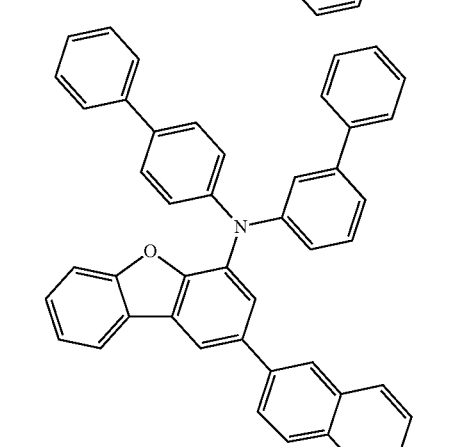

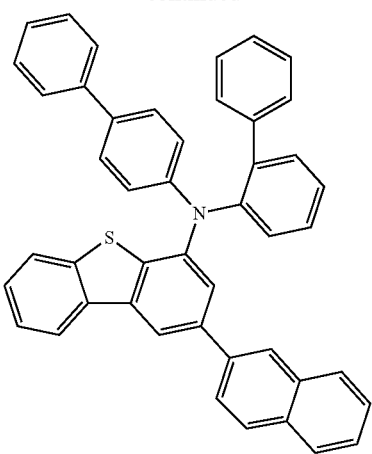
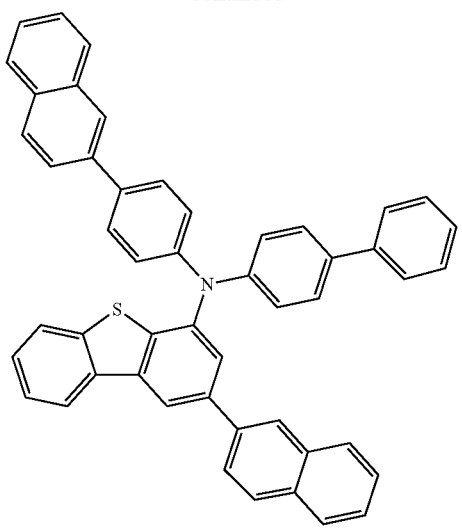
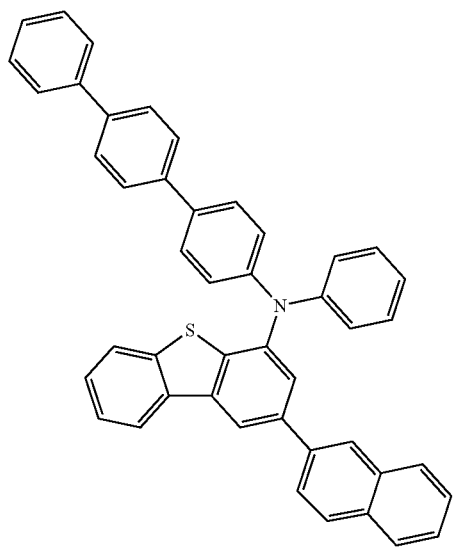
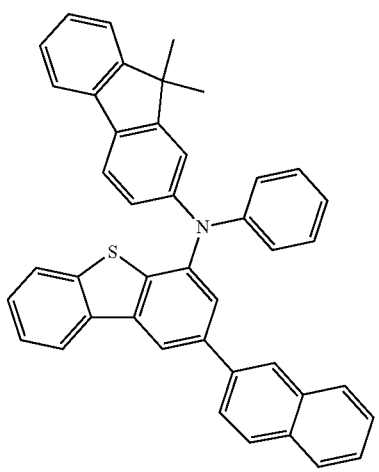
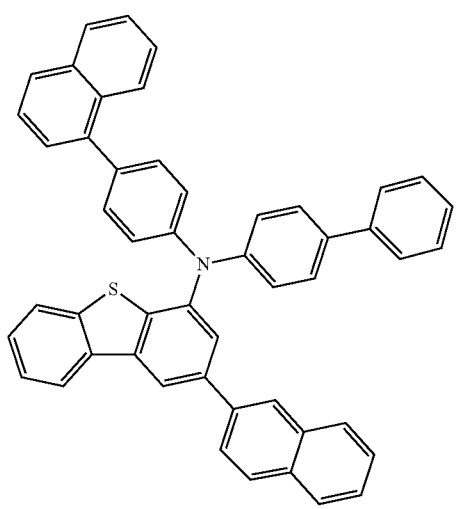
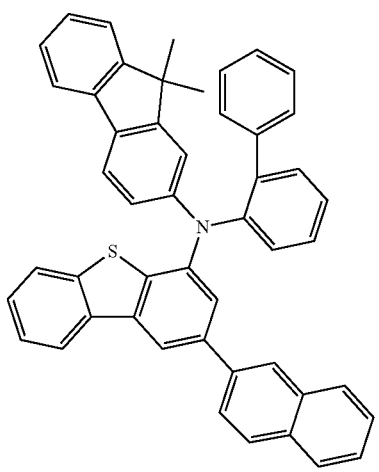

101
-continued
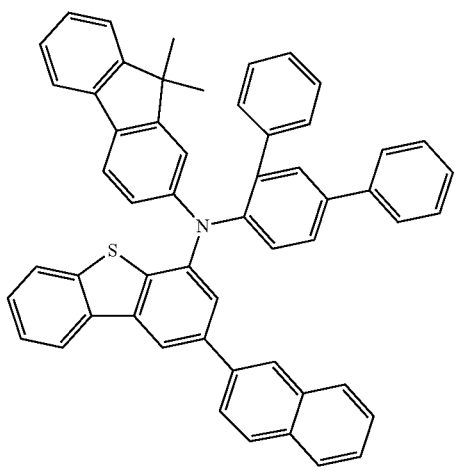
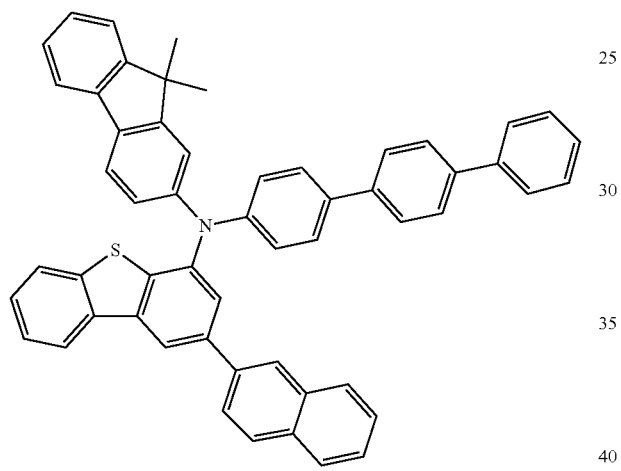
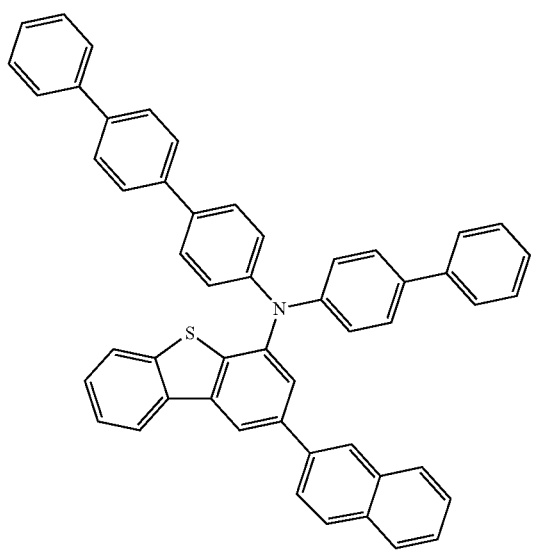
102
-continued
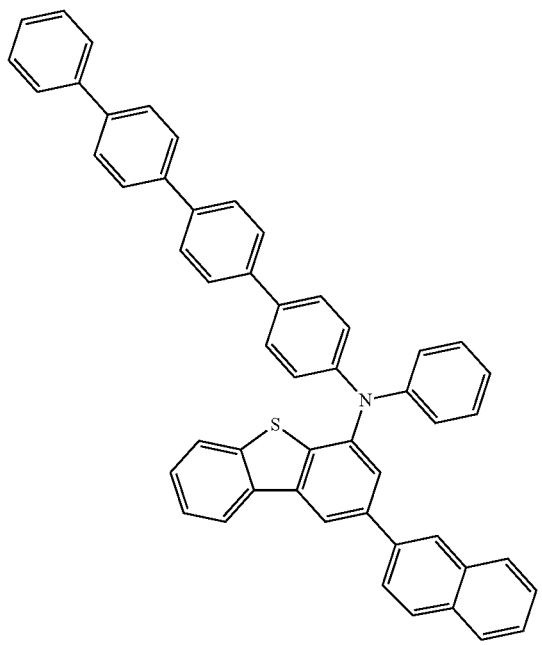
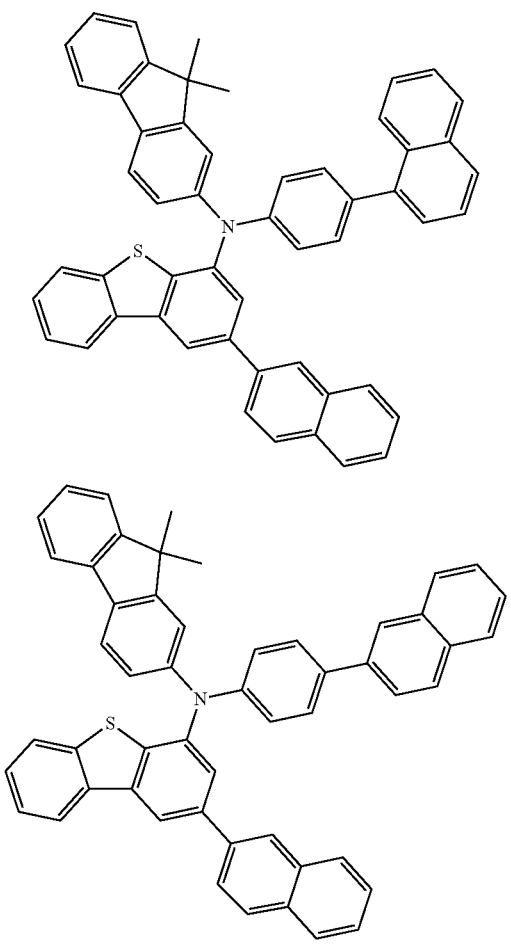

103
-continued
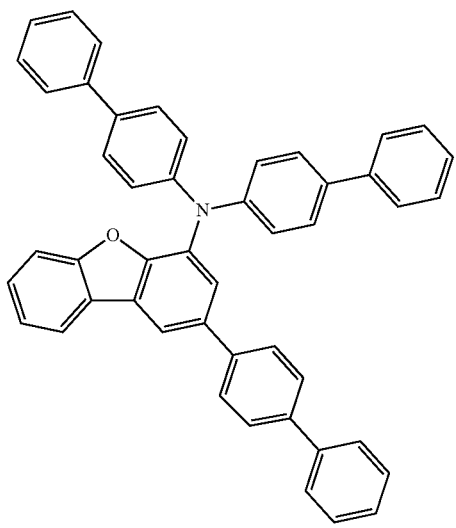
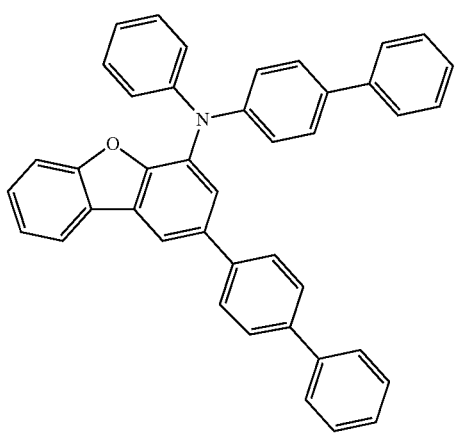
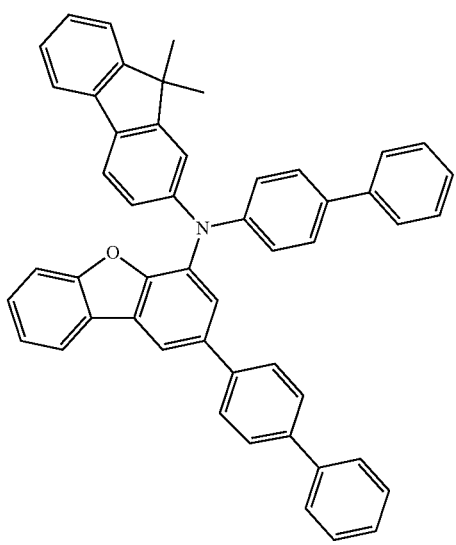
104
-continued
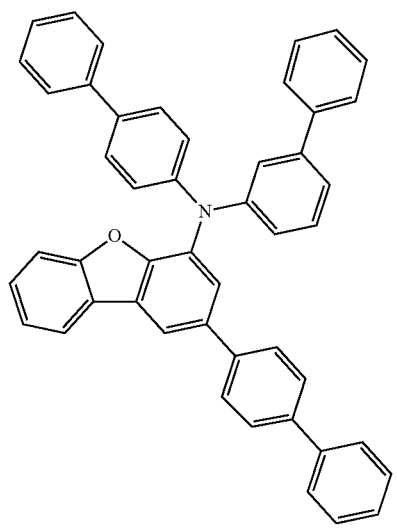
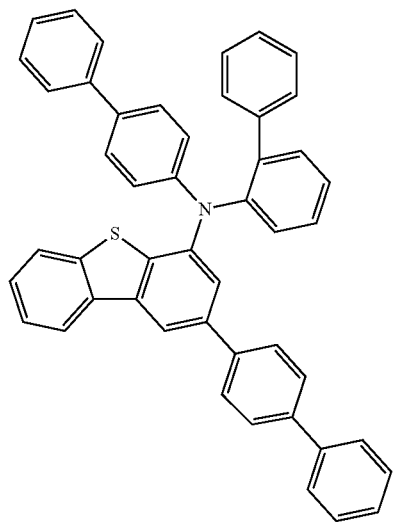
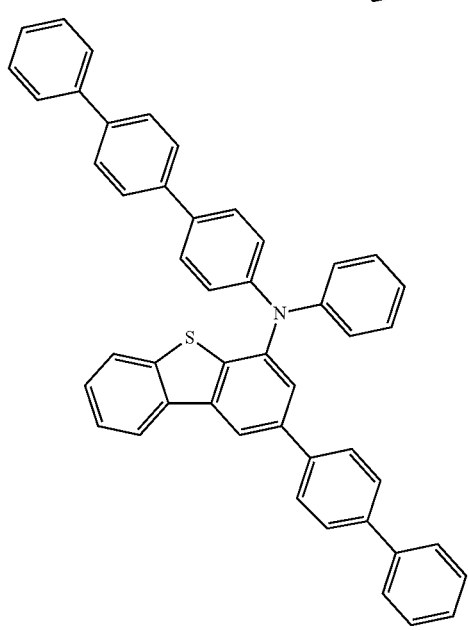

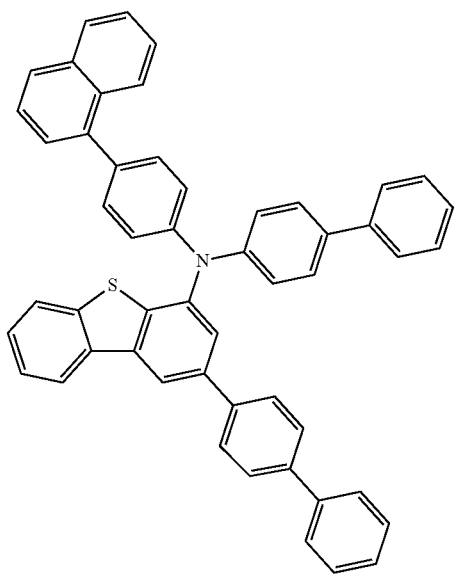
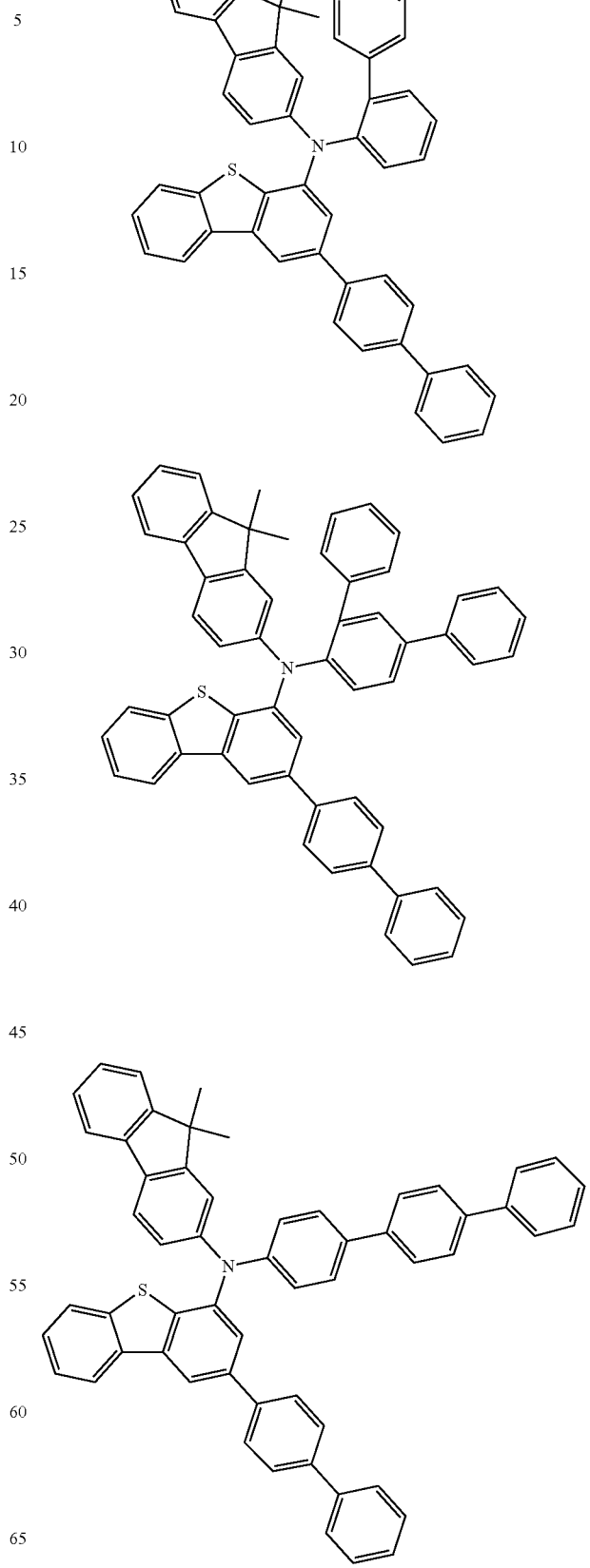

107
-continued
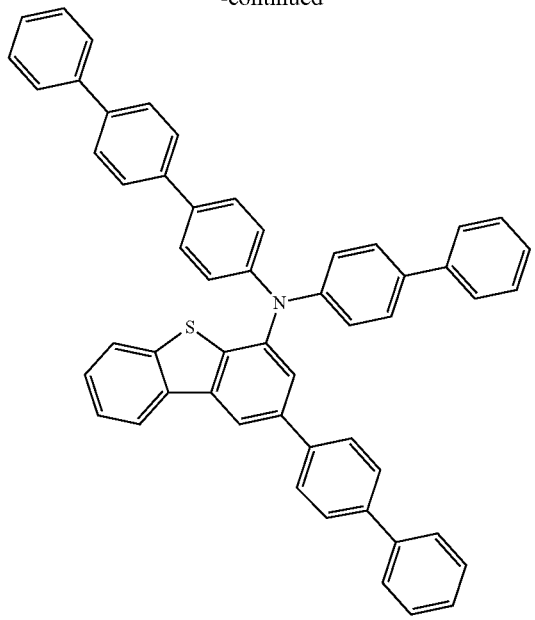
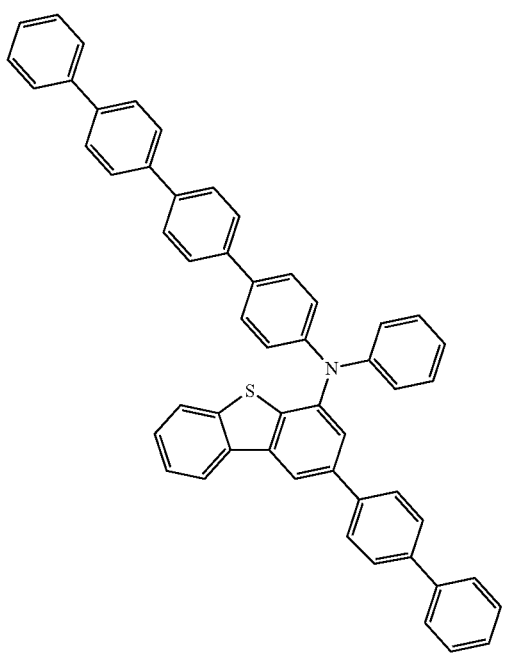
108
-continued
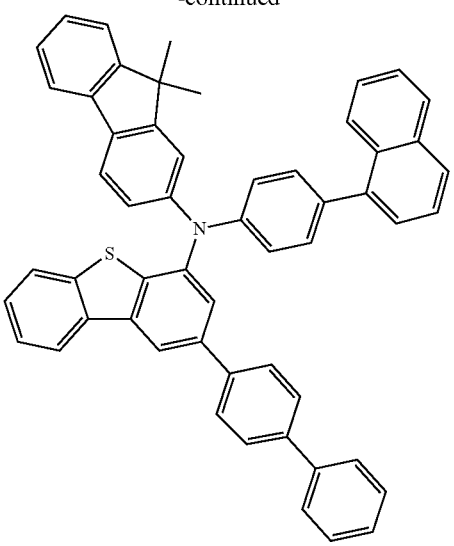
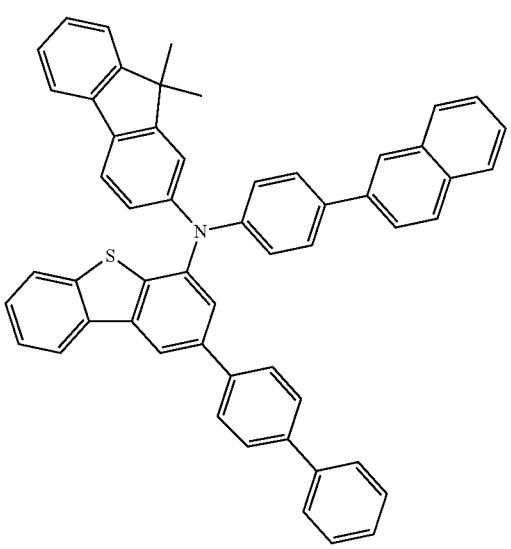
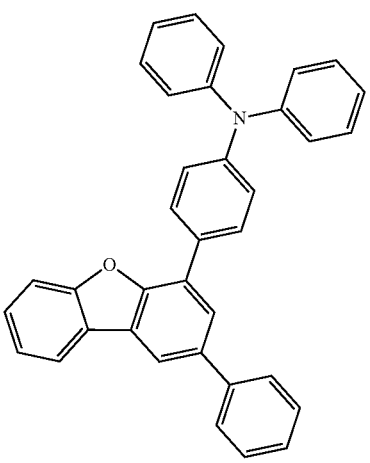

109
-continued
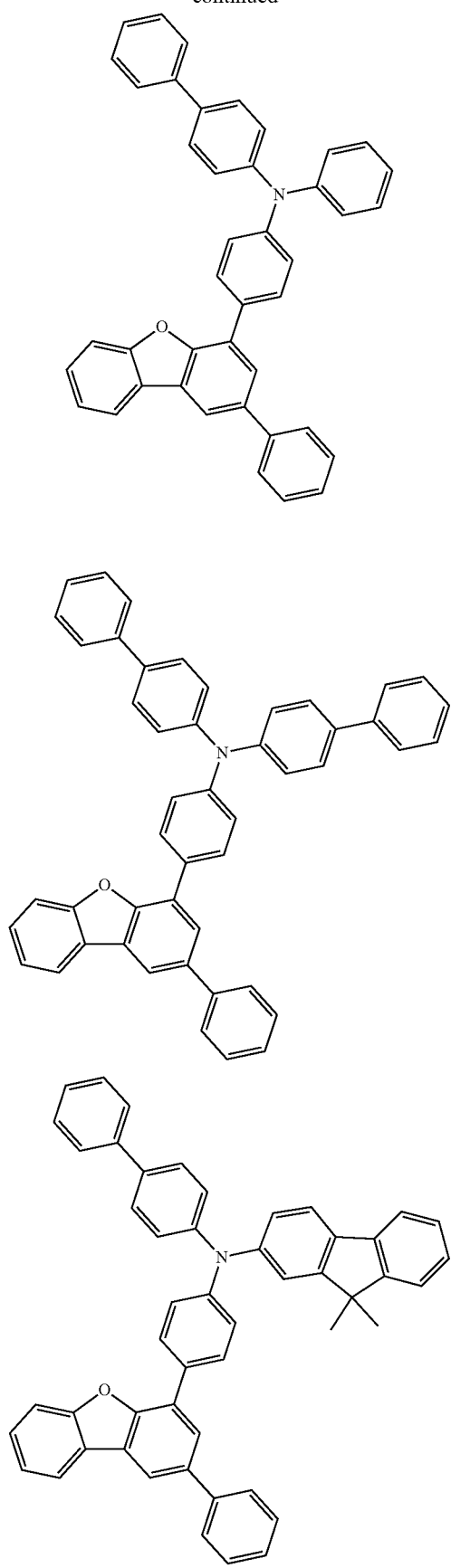
110
-continued

111
-continued
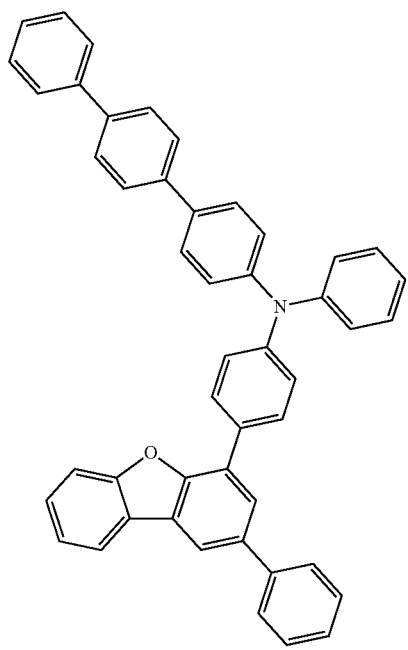
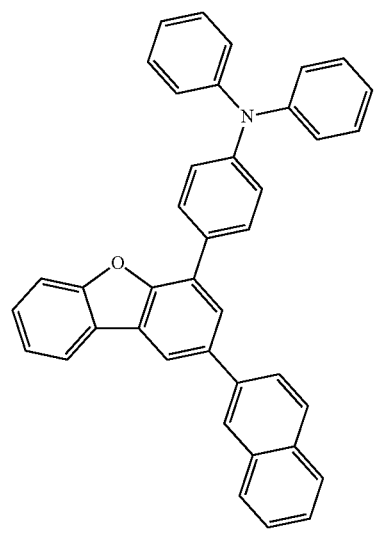
112
-continued
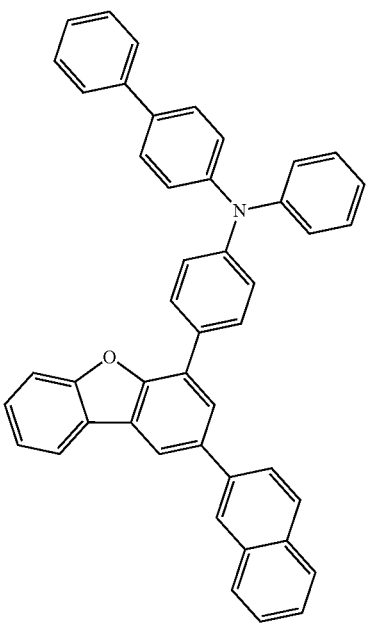
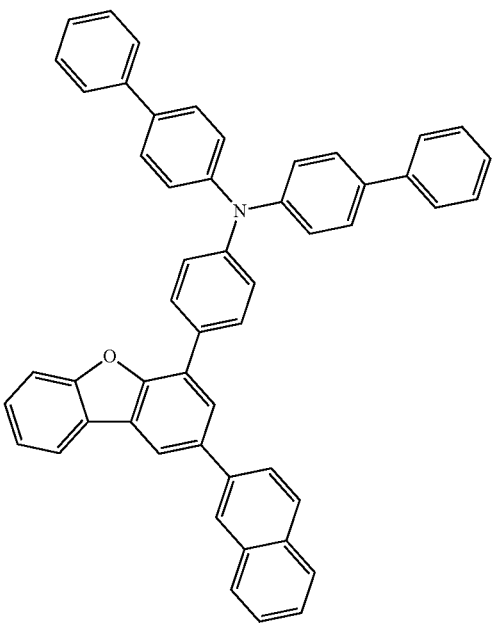

113
-continued
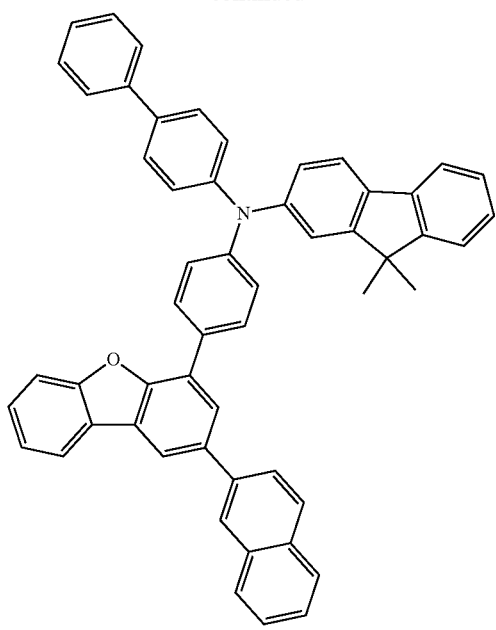
114
-continued
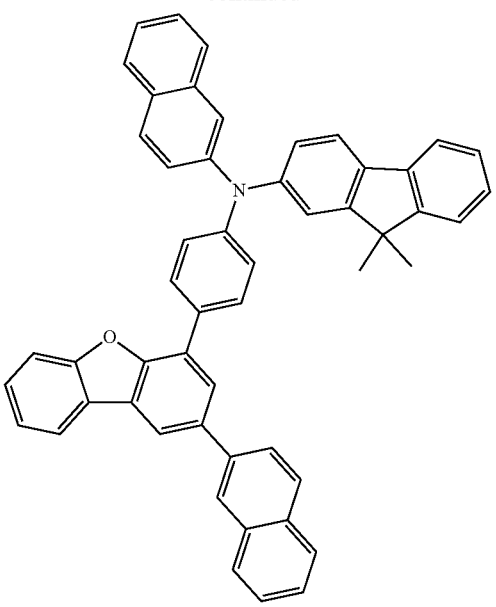
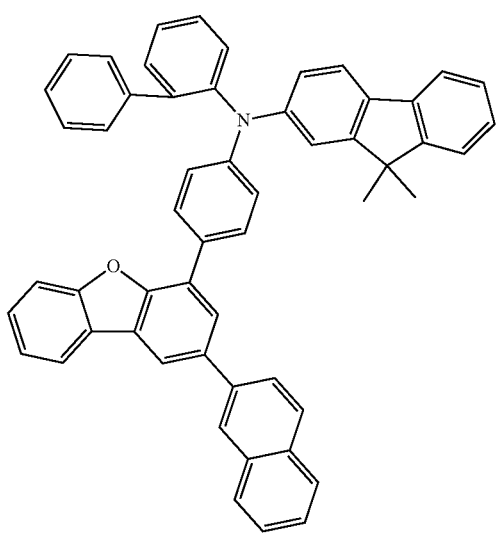
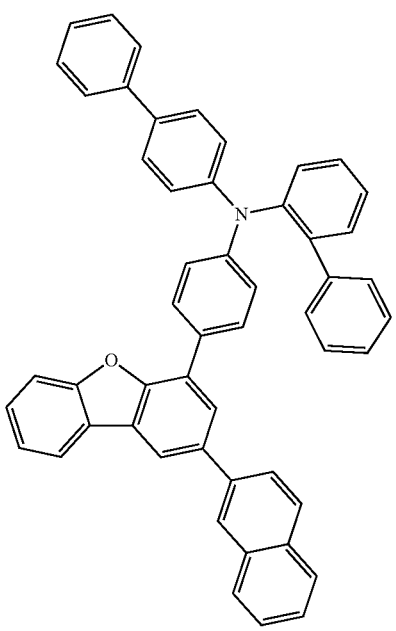

115
-continued
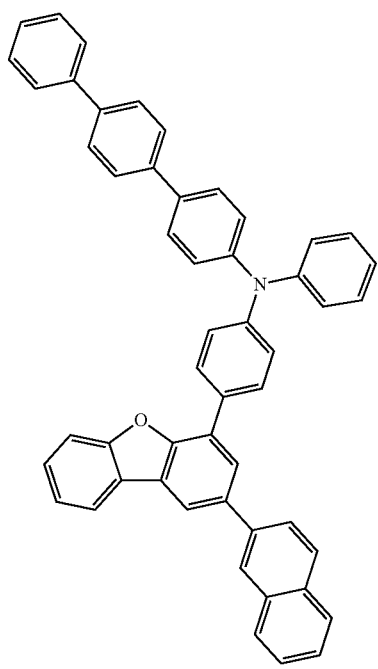
116
-continued
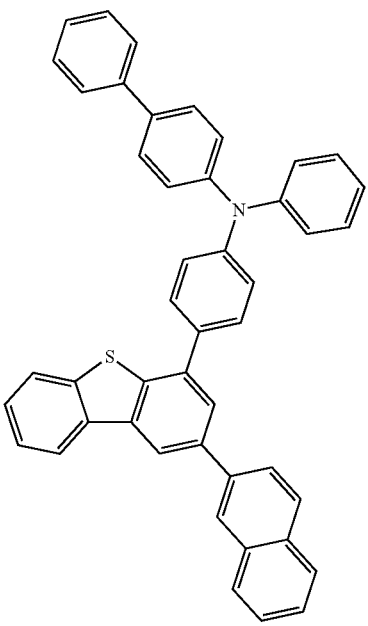
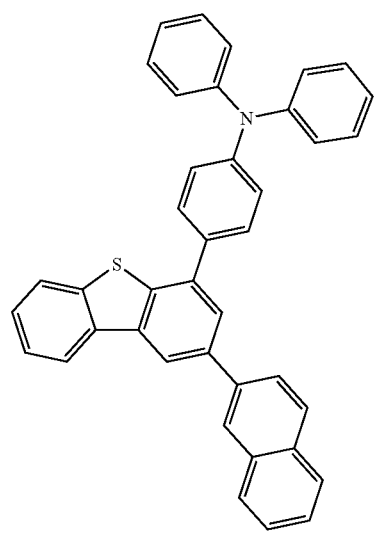
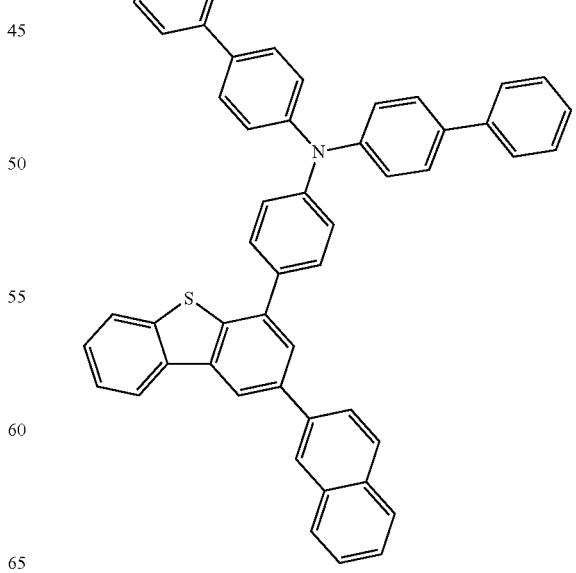

117
-continued
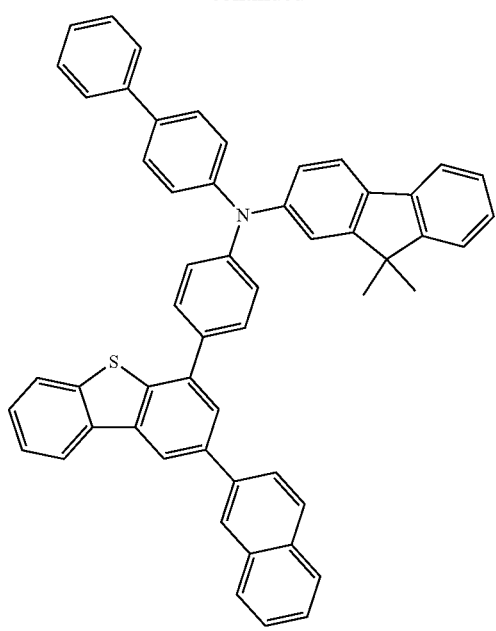
118
-continued
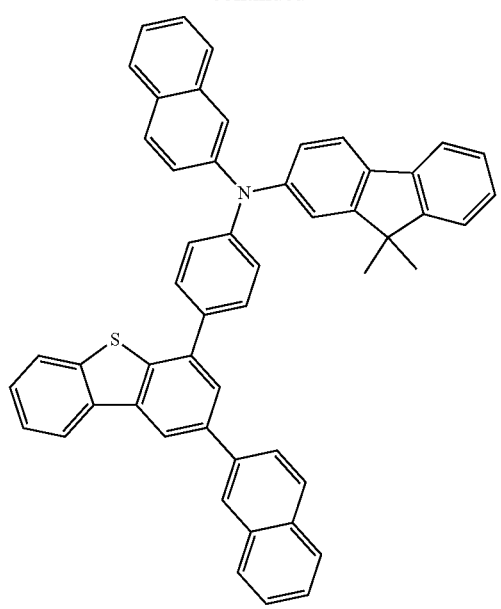
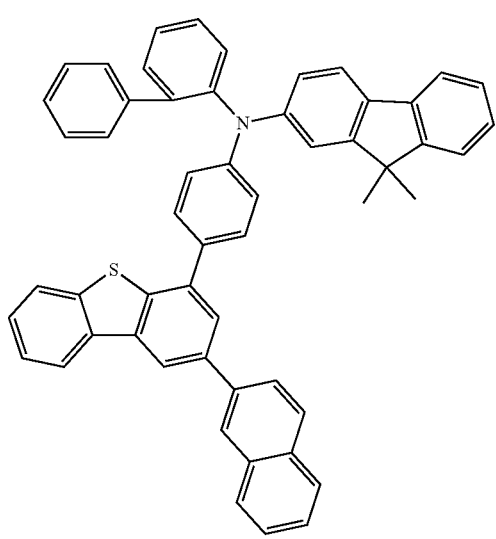
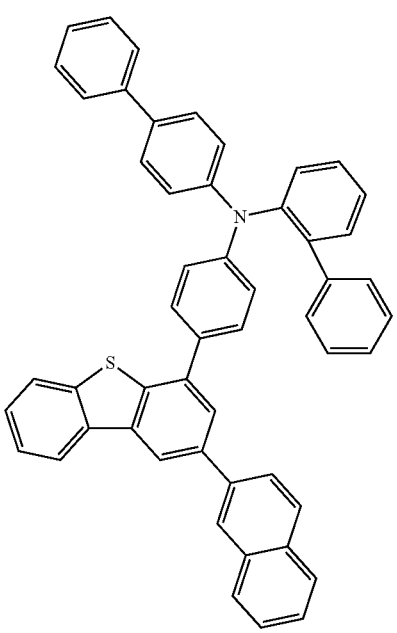

119
-continued
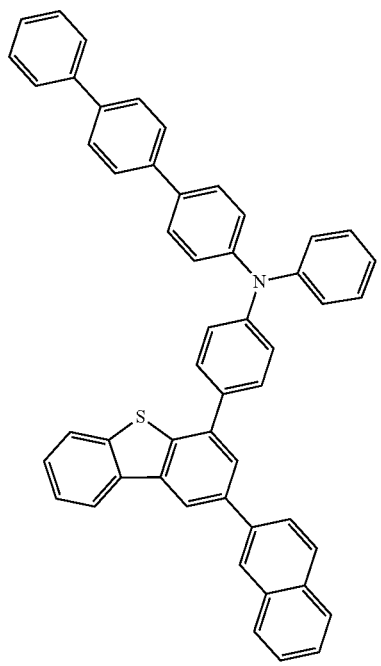
120
-continued
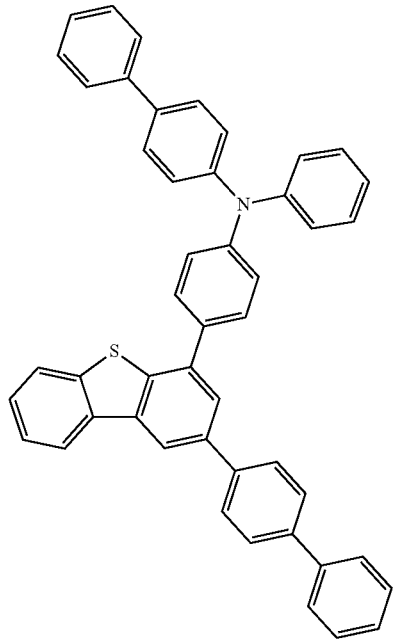
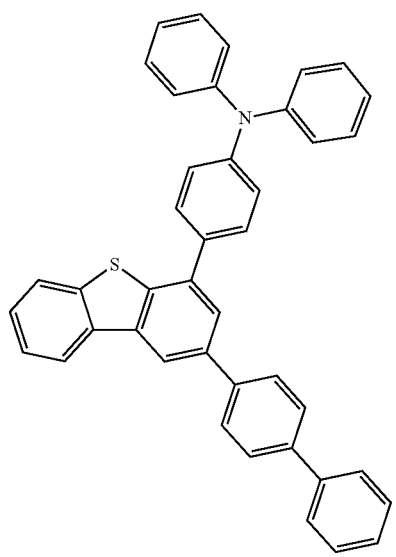
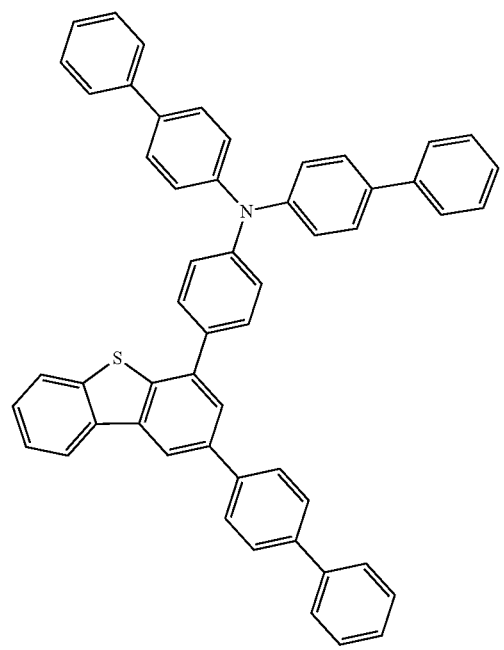

121
-continued
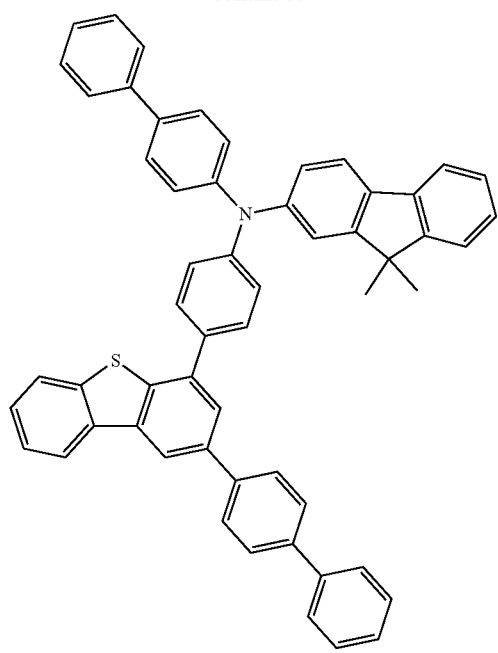
122
-continued
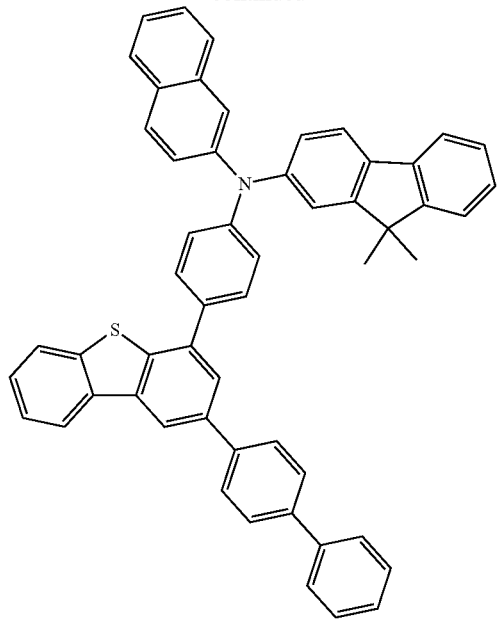
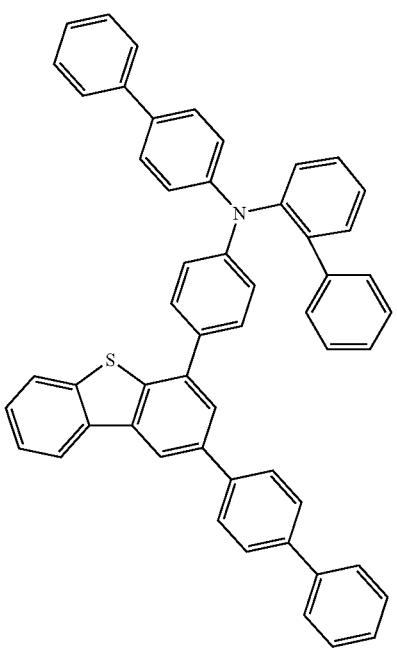

123
-continued
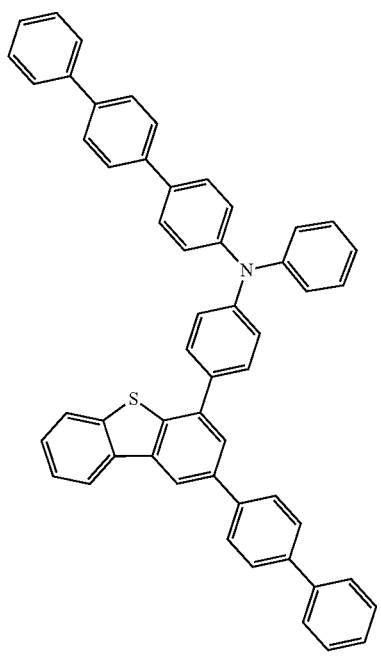
124
-continued
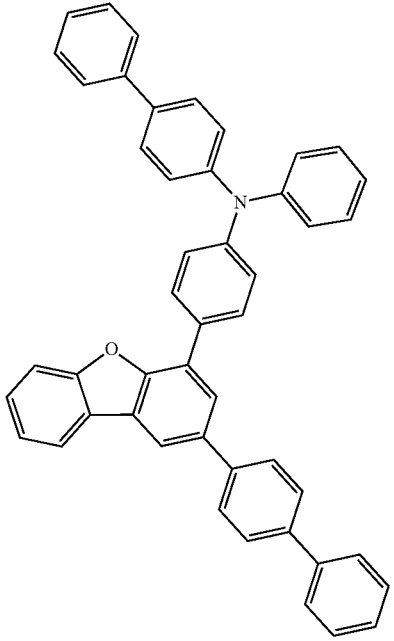
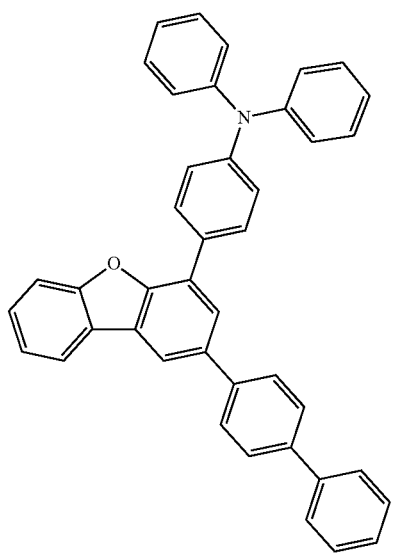
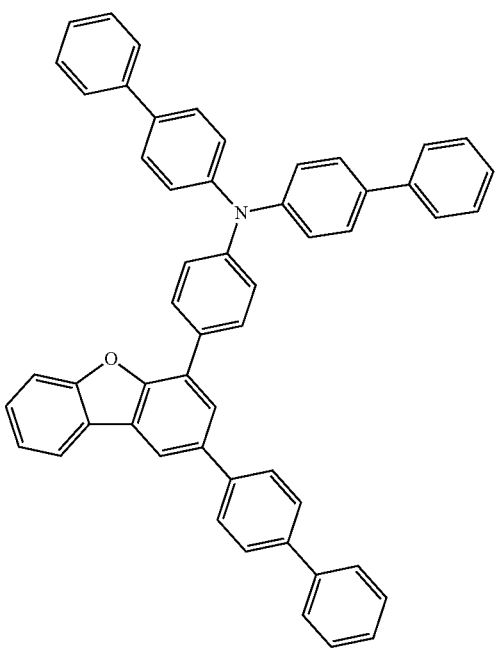

125
-continued
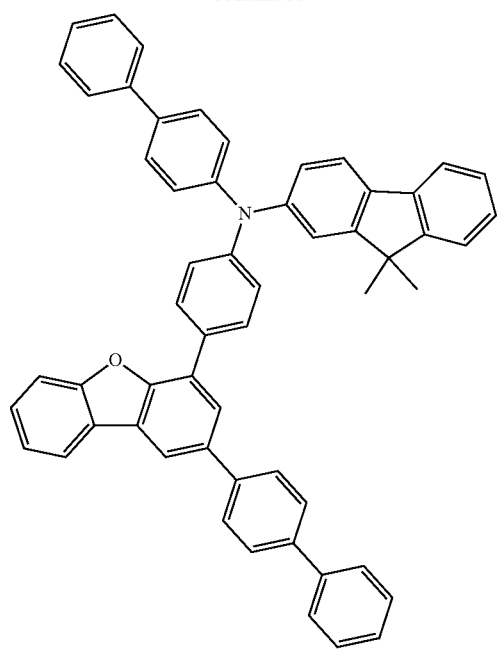
126
-continued
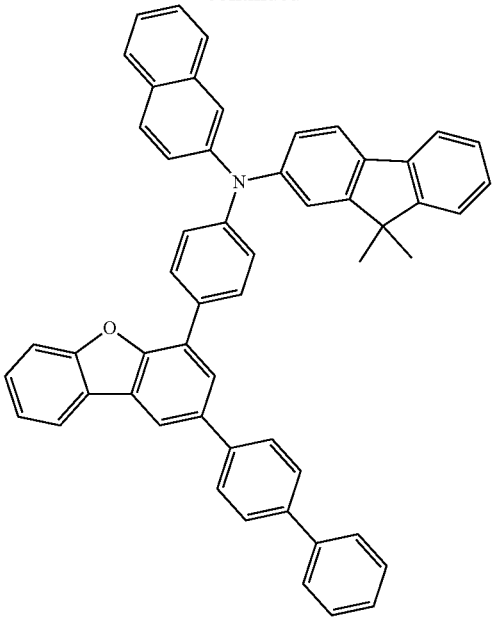
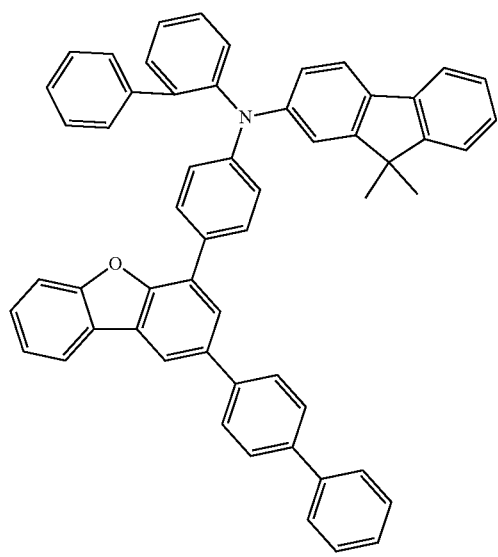
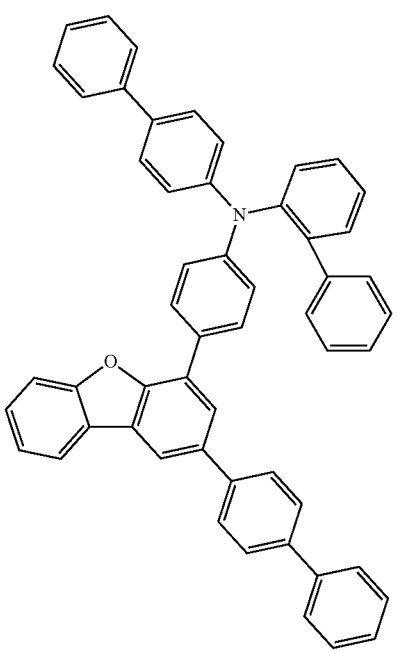

127
-continued
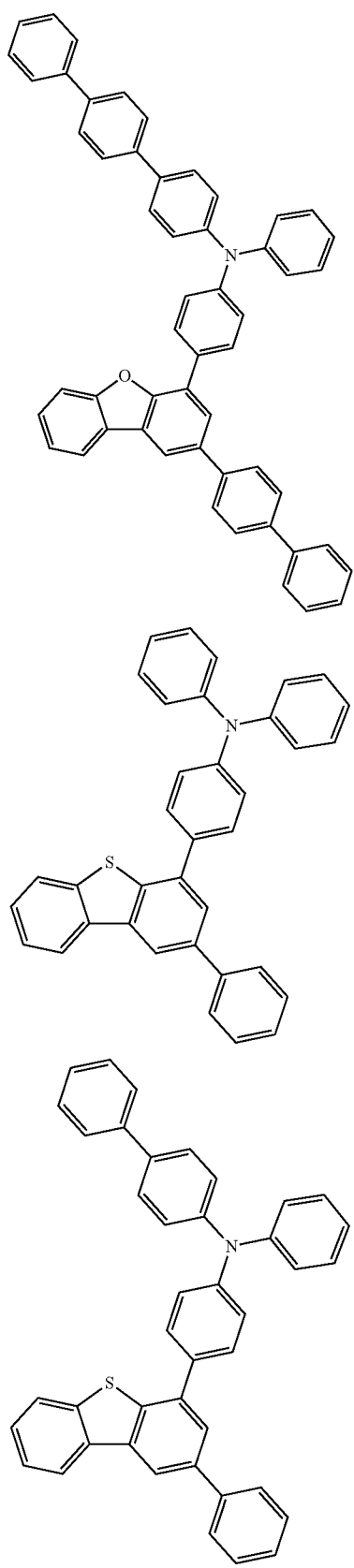
128
-continued
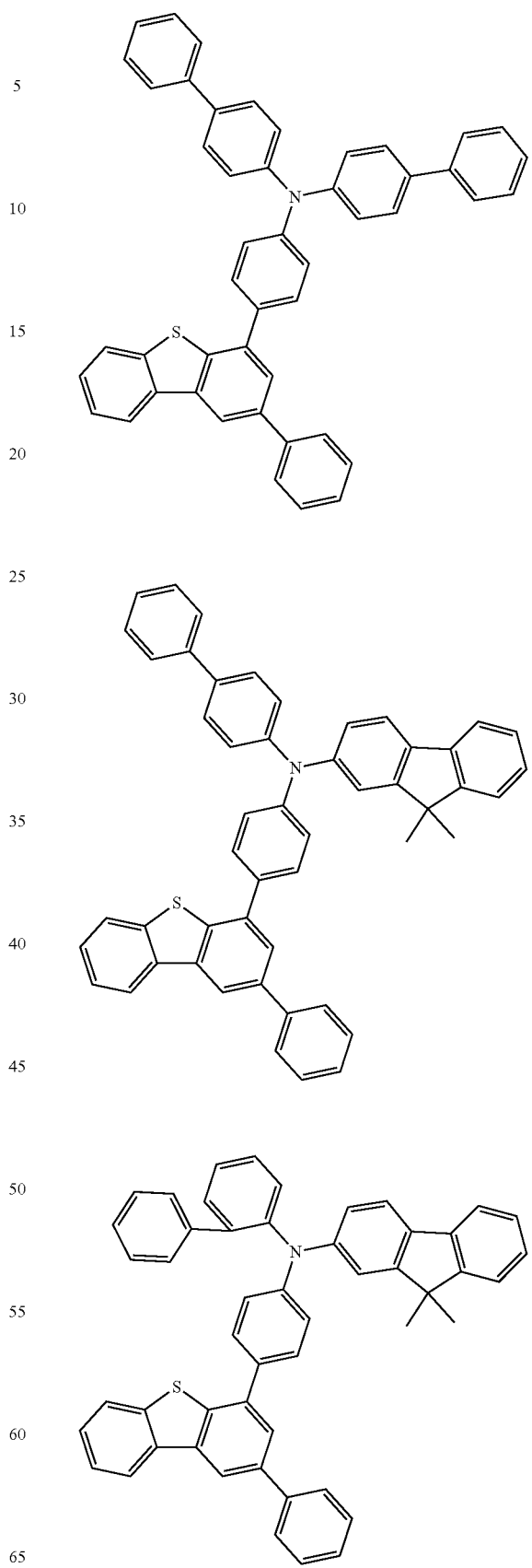

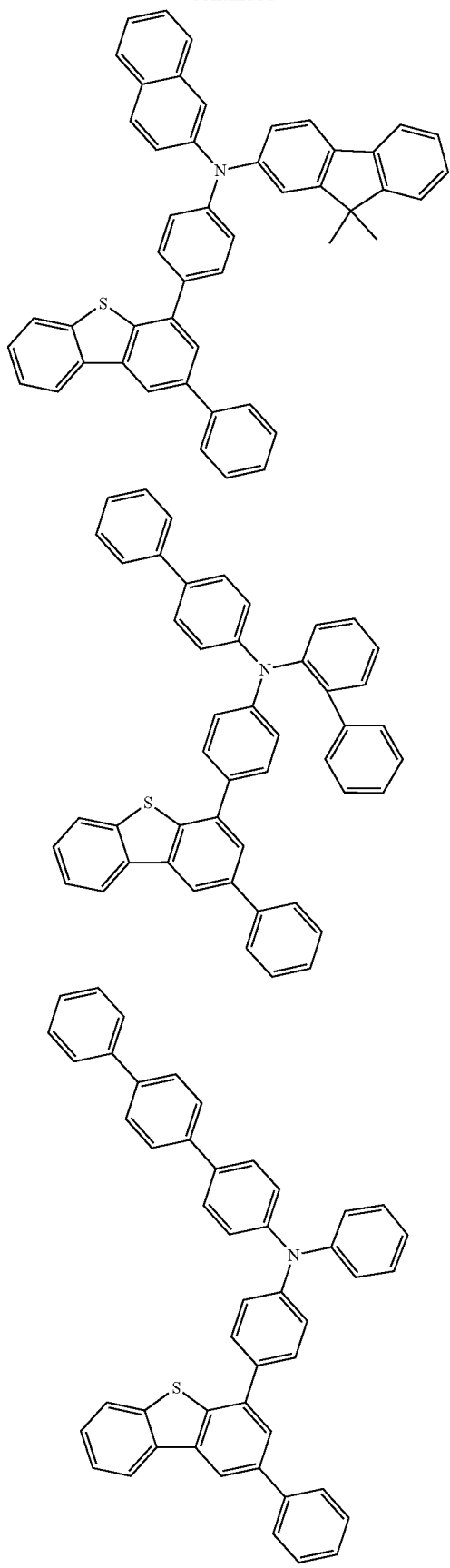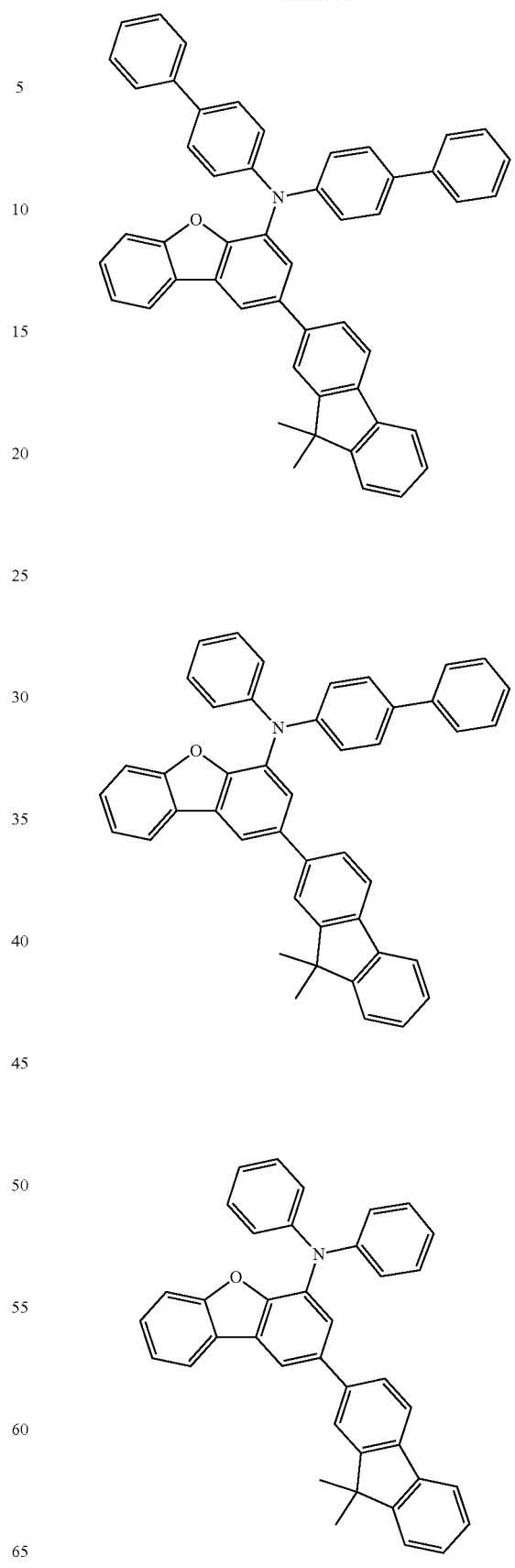

131
-continued
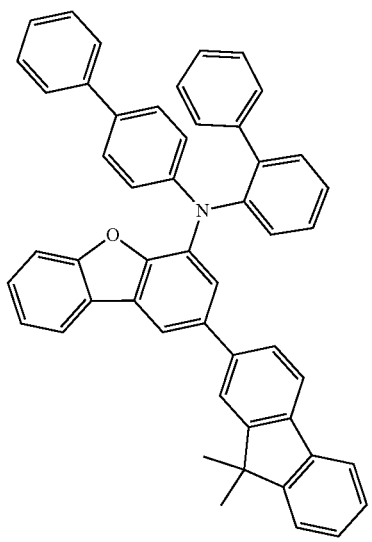
132
-continued
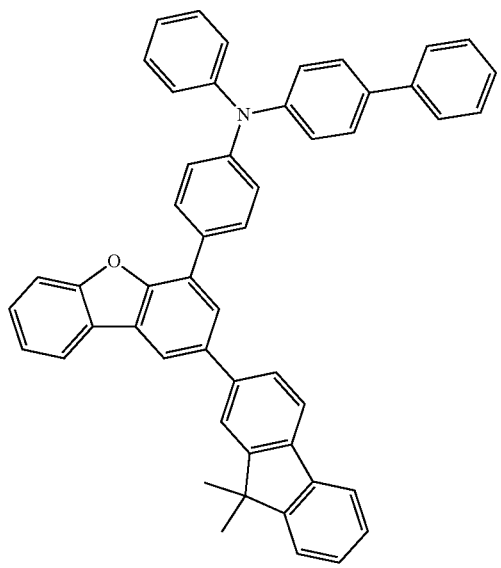
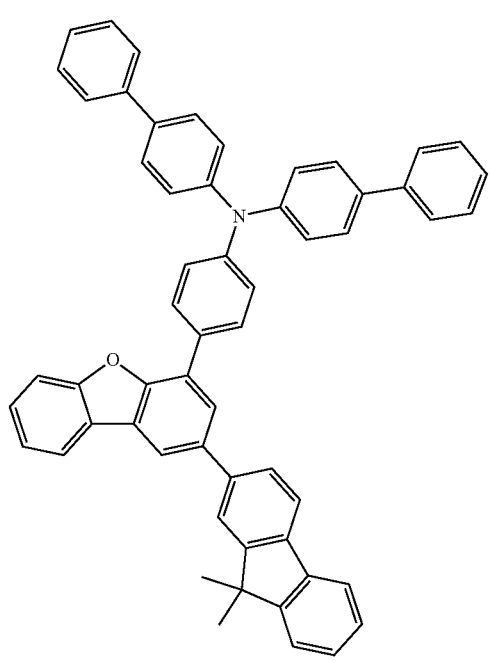
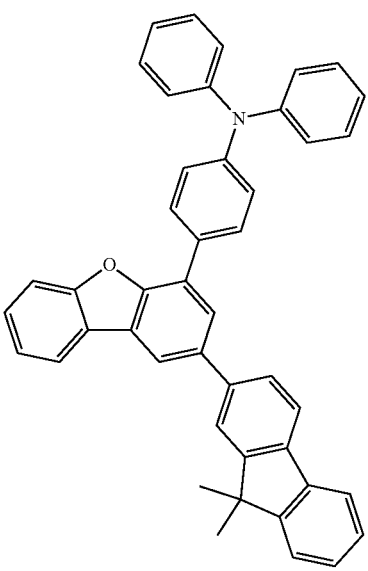

133
-continued
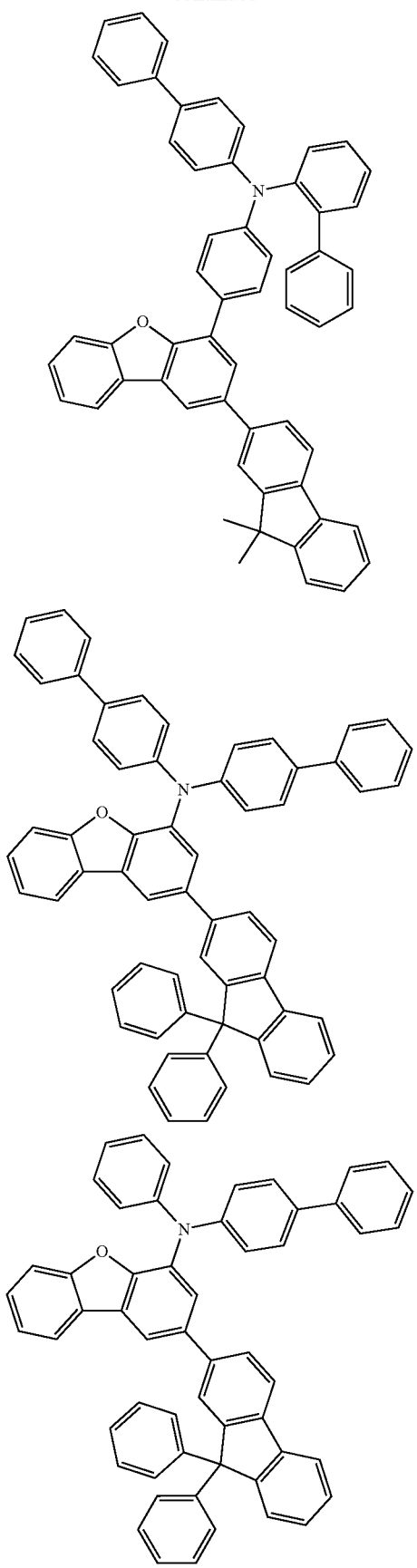
134
-continued
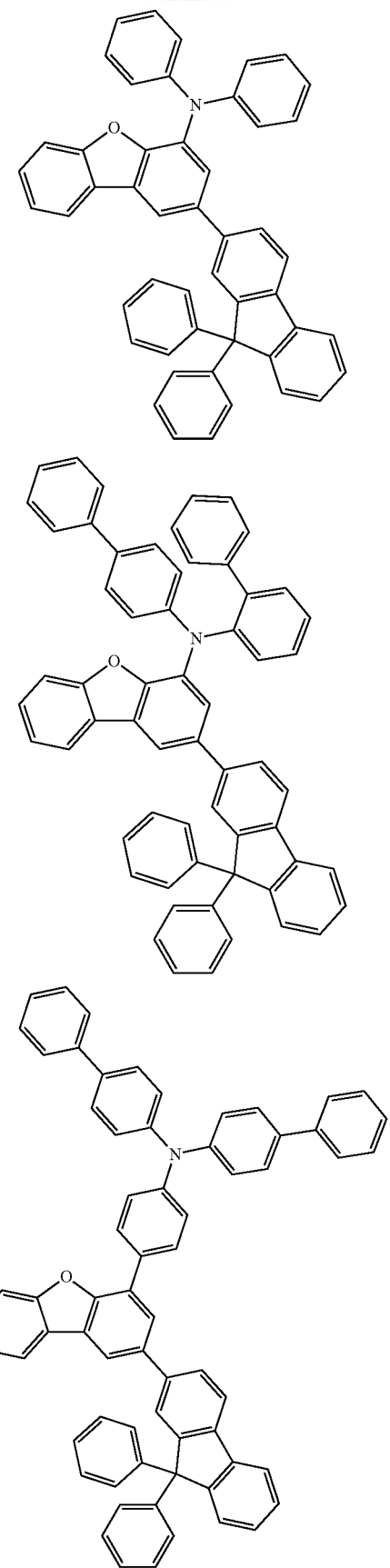

135
-continued
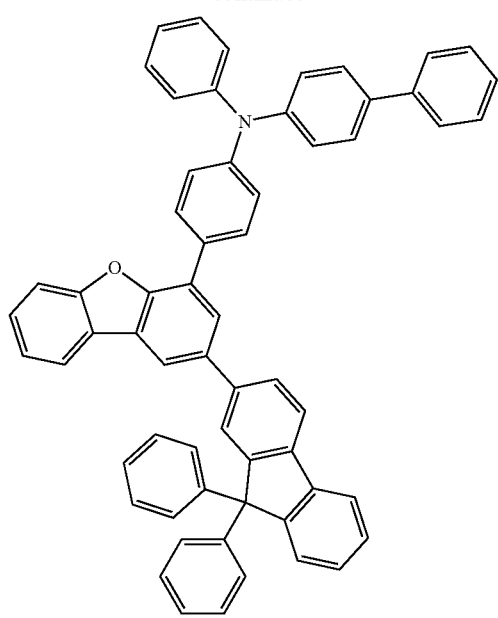
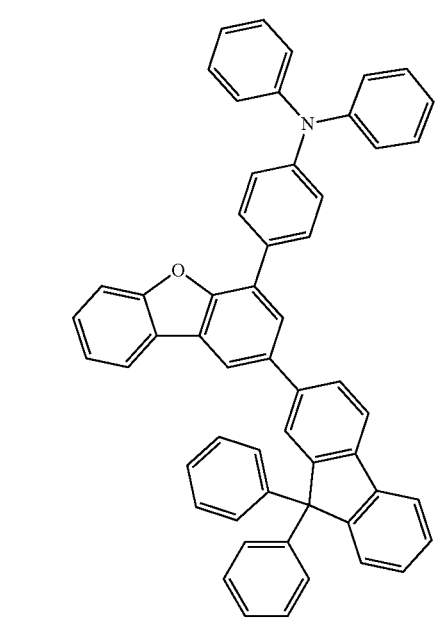
136
-continued
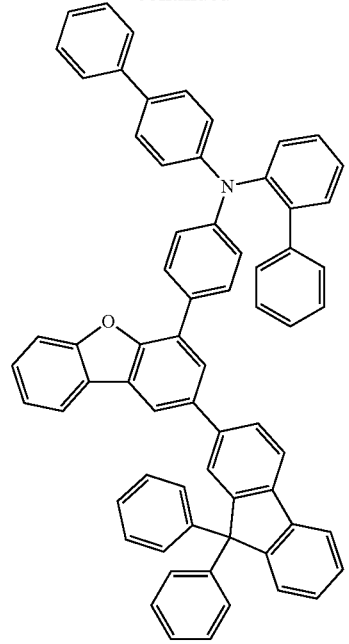
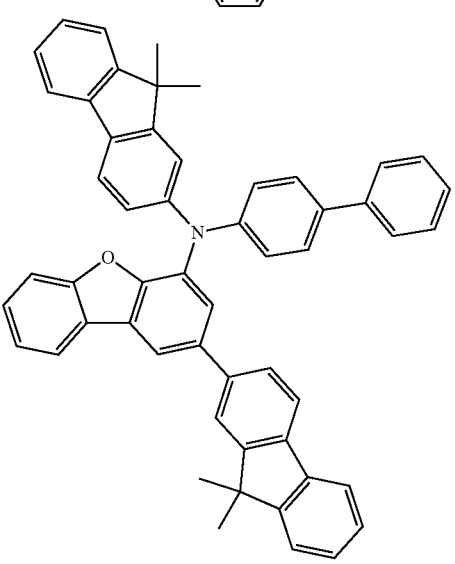
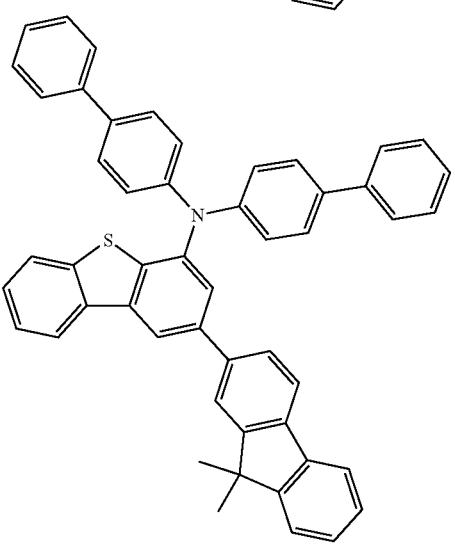

137
-continued
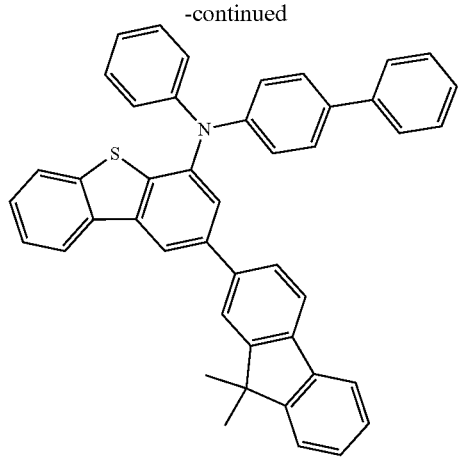
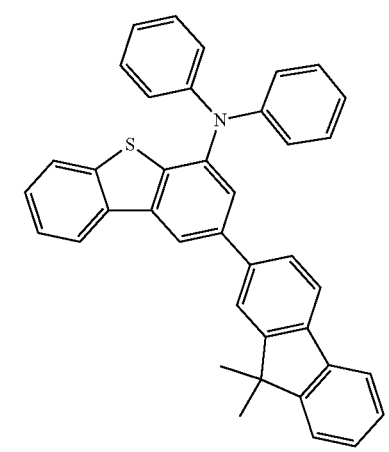
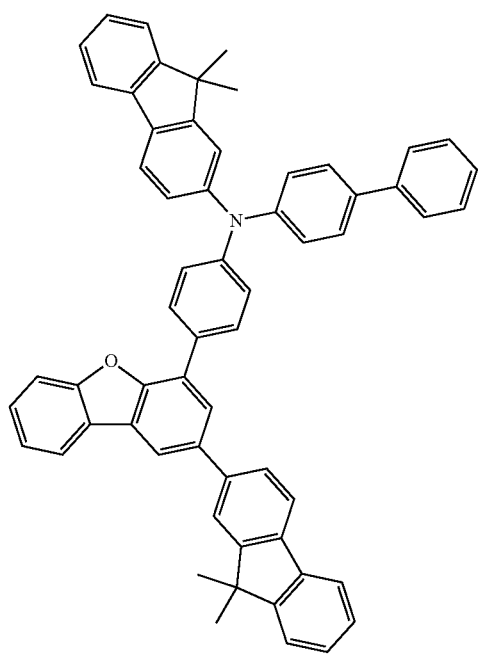
138
-continued
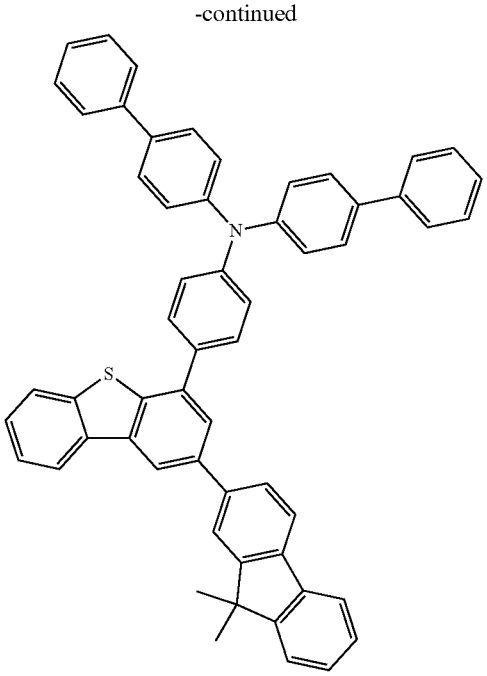
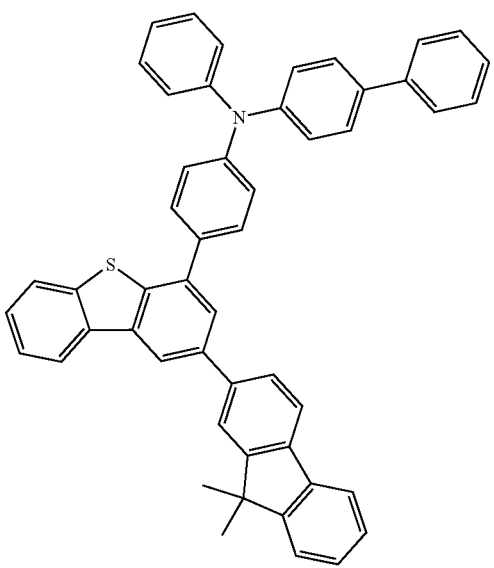

139
-continued
140
-continued
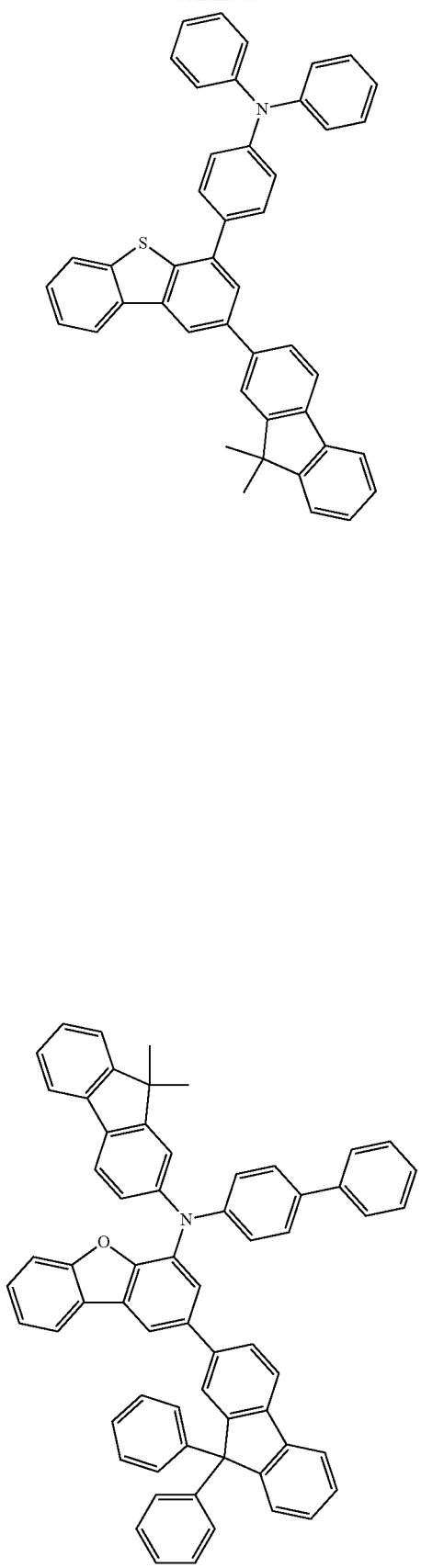
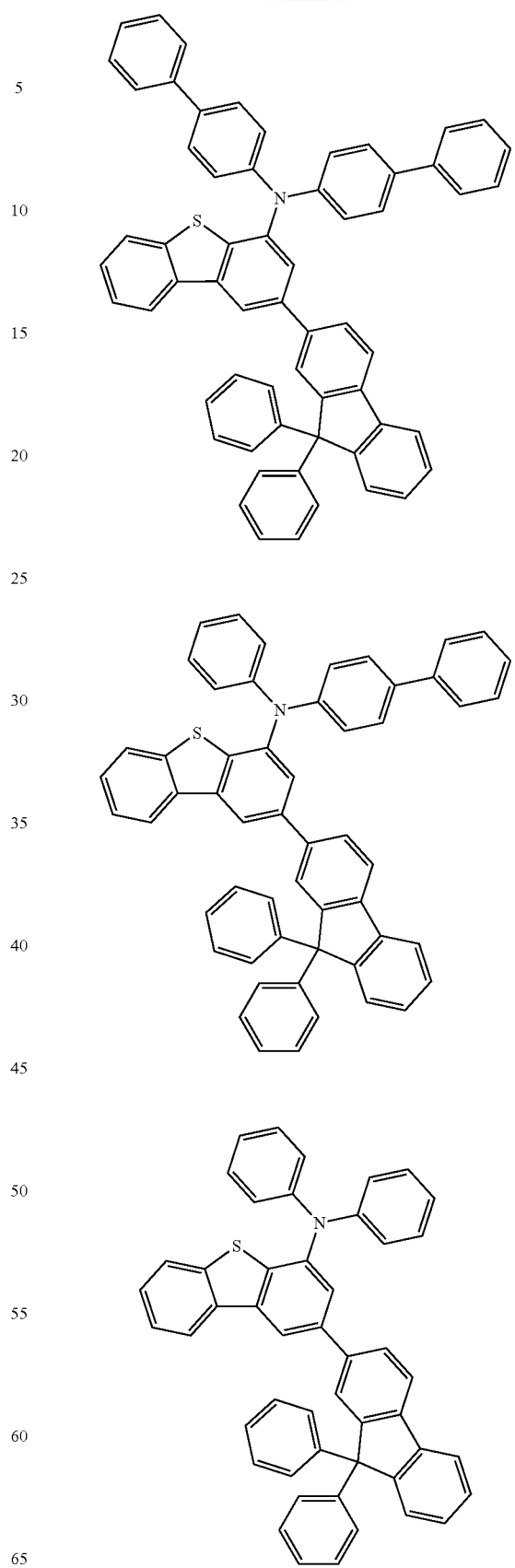

141
-continued
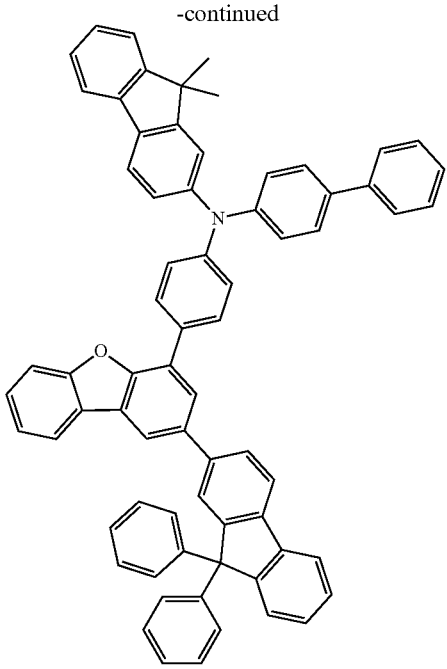
142
-continued
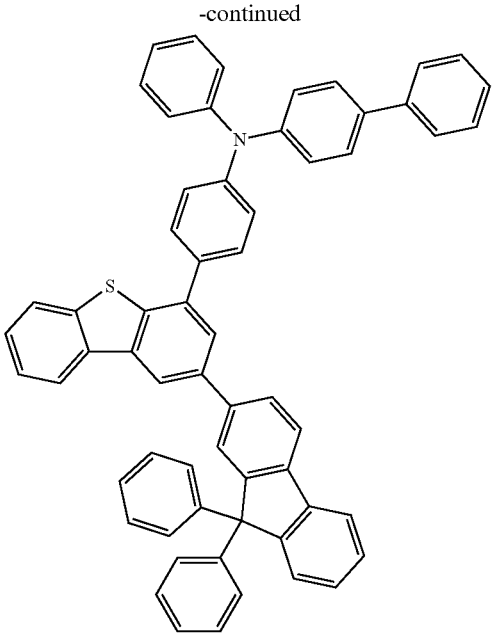

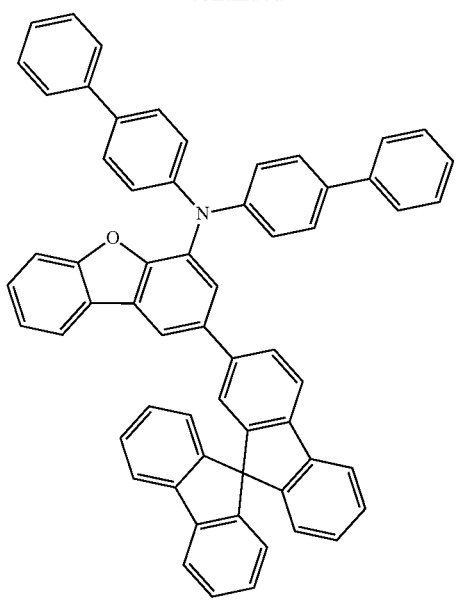
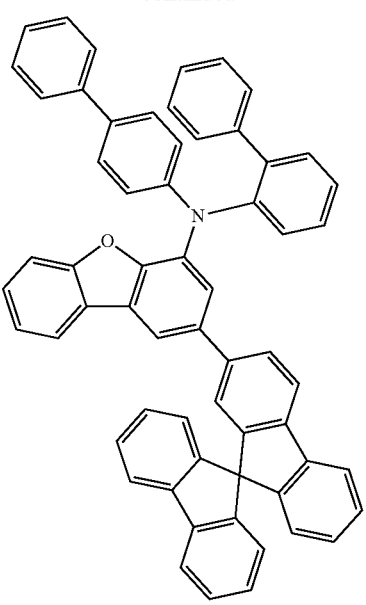
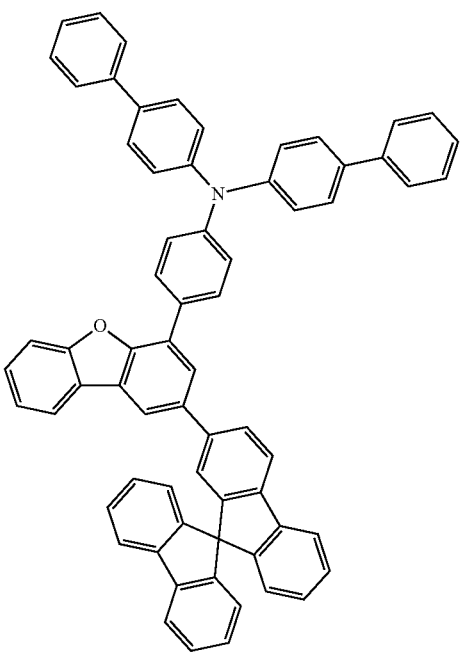

145
-continued
146
-continued
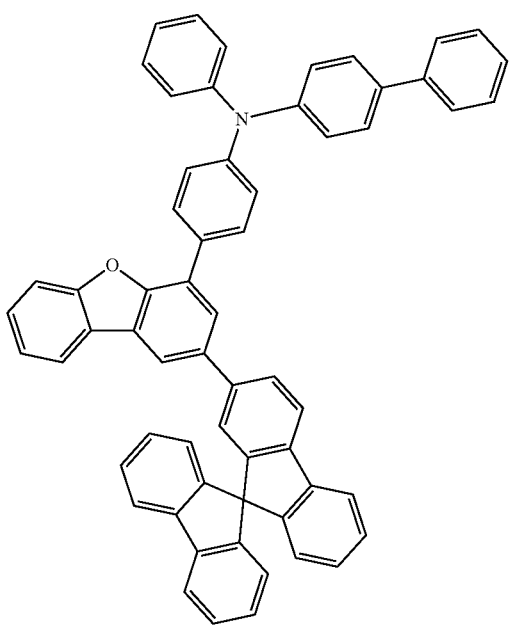
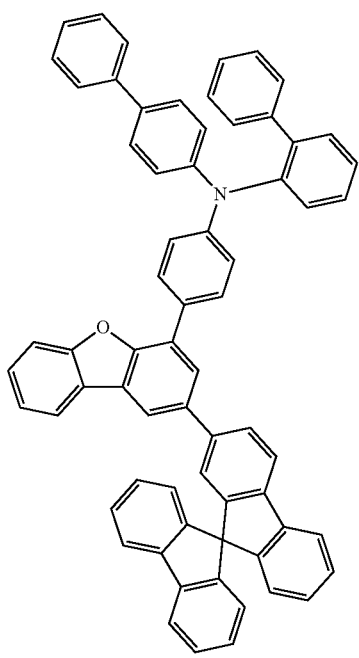

147
-continued
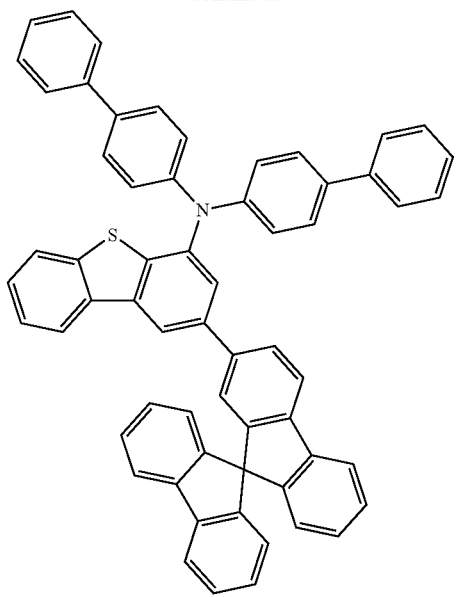
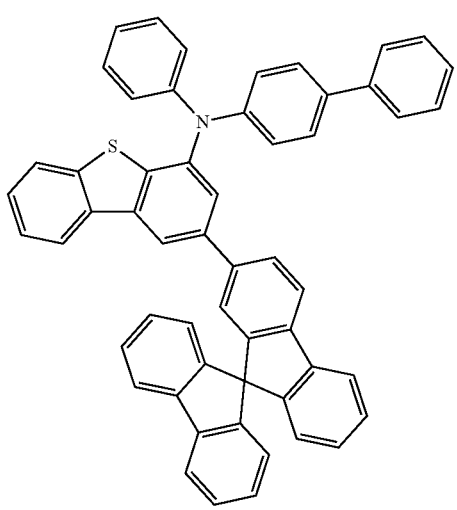
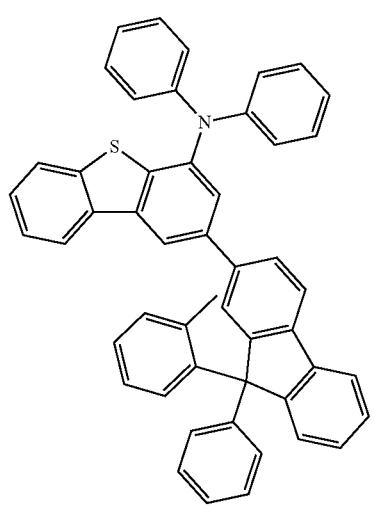
148
-continued
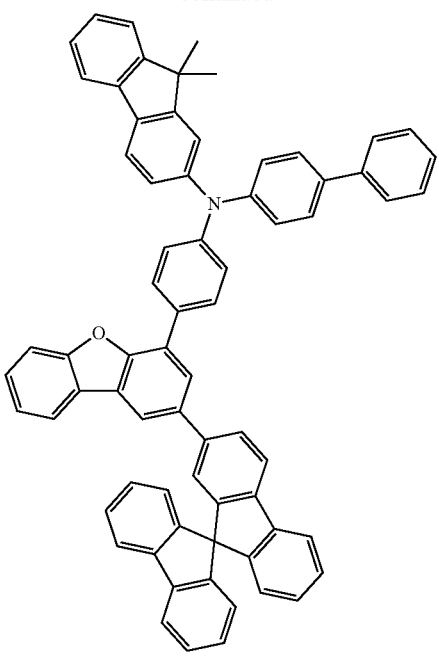
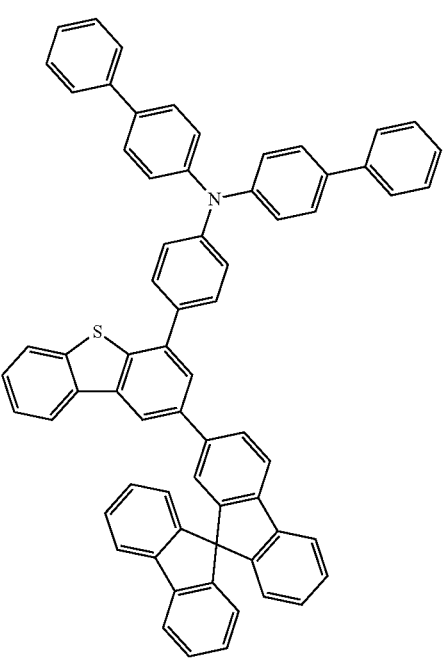

149
-continued
150
-continued
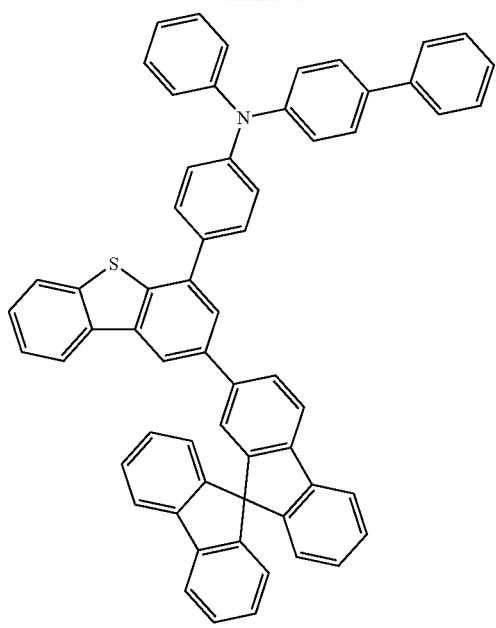
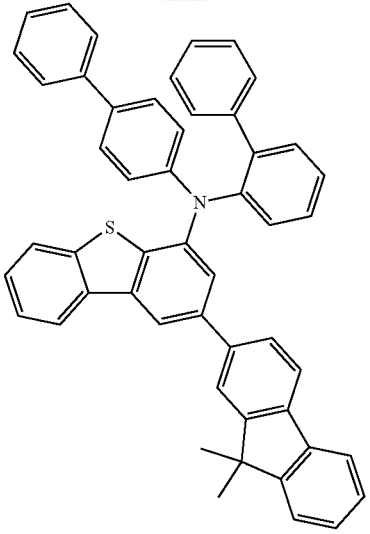
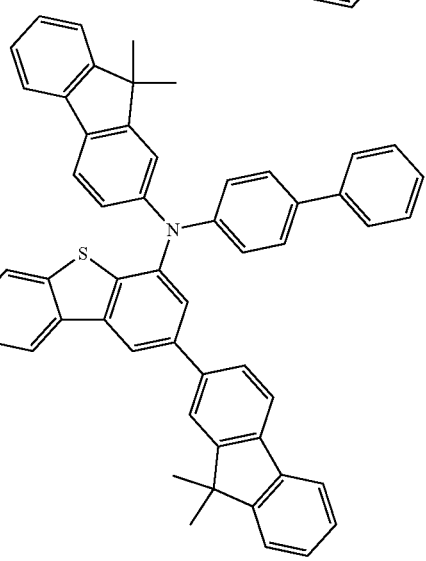
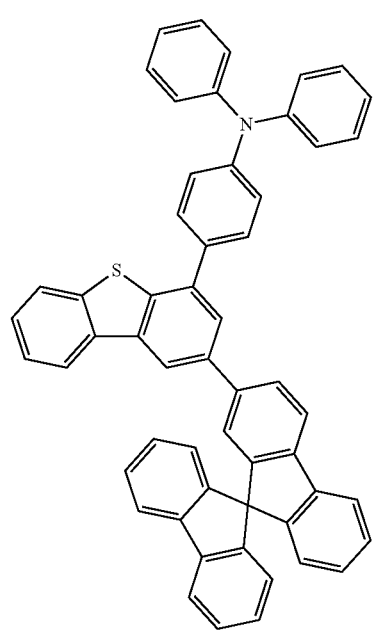

151
-continued
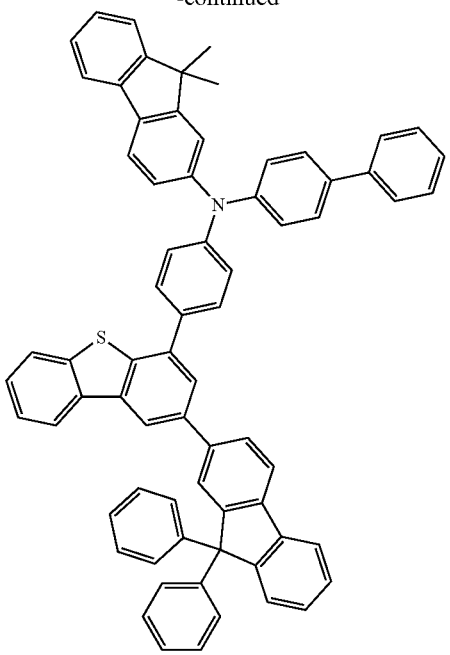
152
-continued
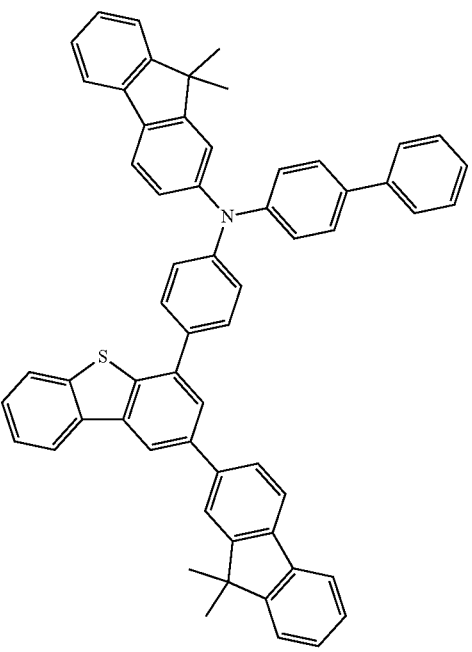
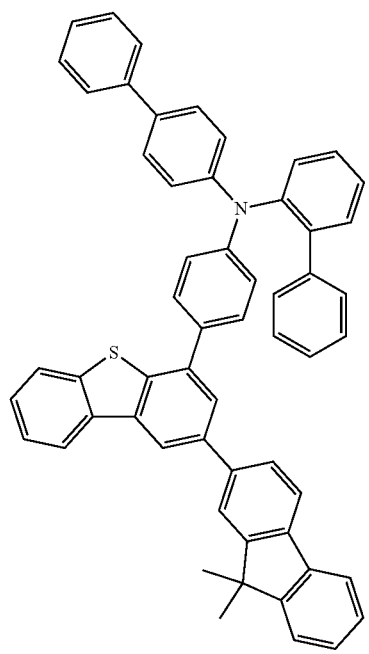
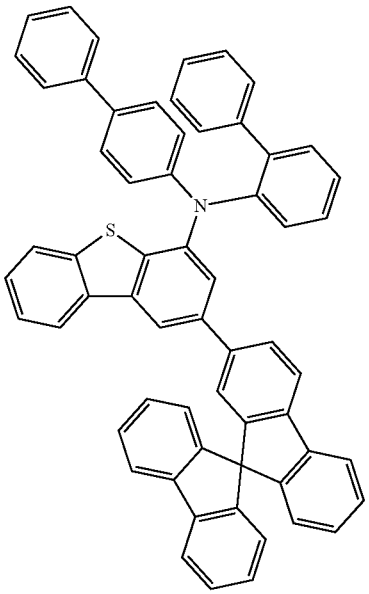

153
-continued
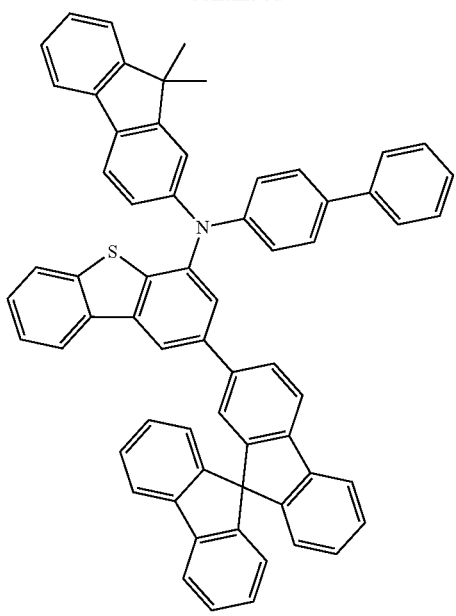
154
-continued
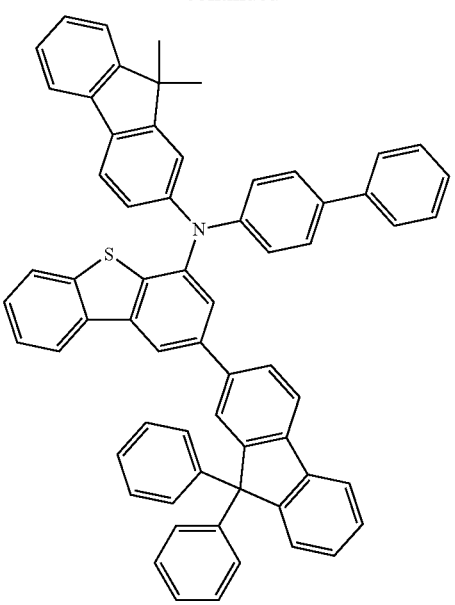
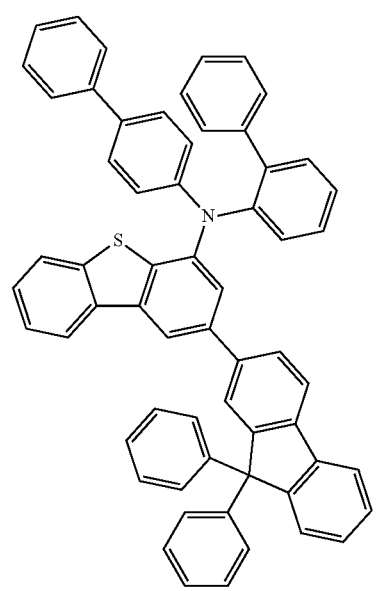

155
-continued
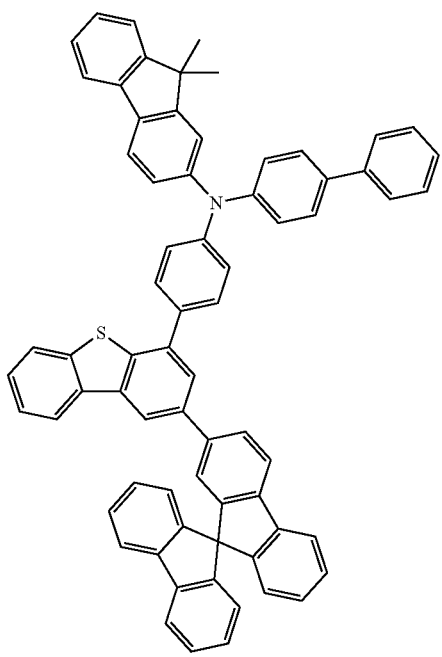
156
-continued
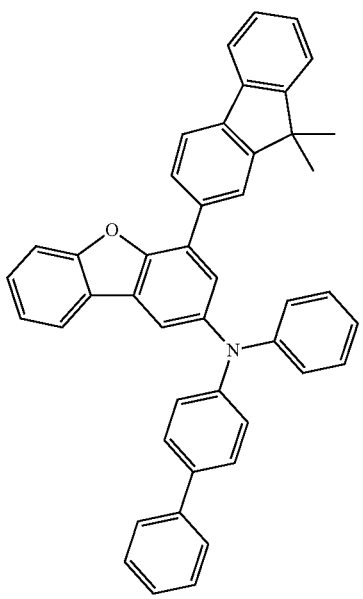
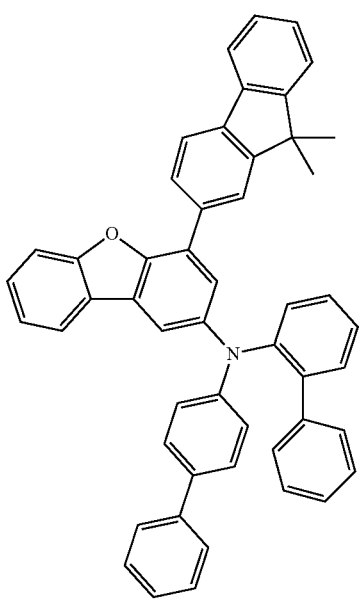

157
-continued
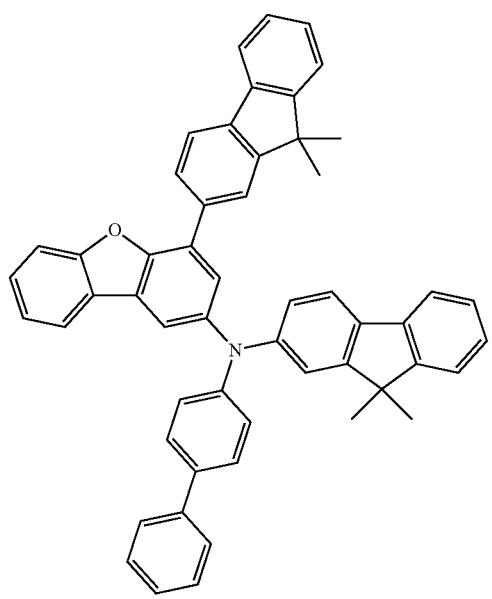
158
-continued
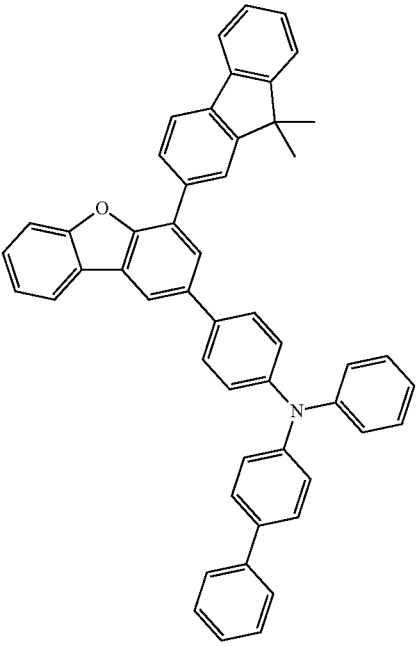
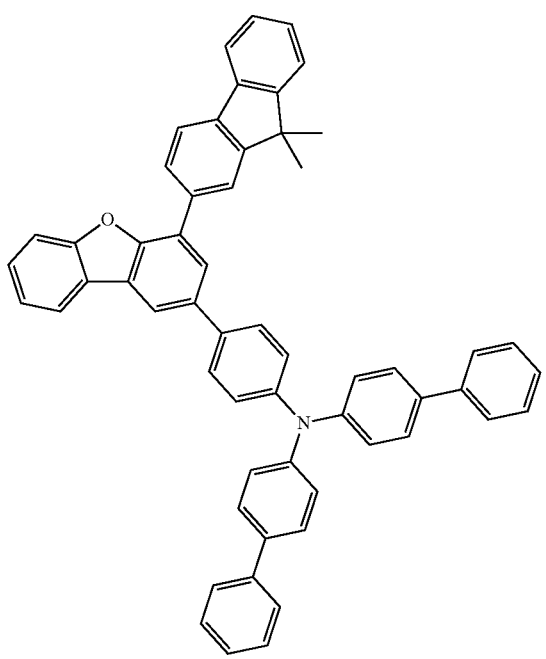
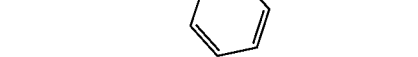

159
-continued
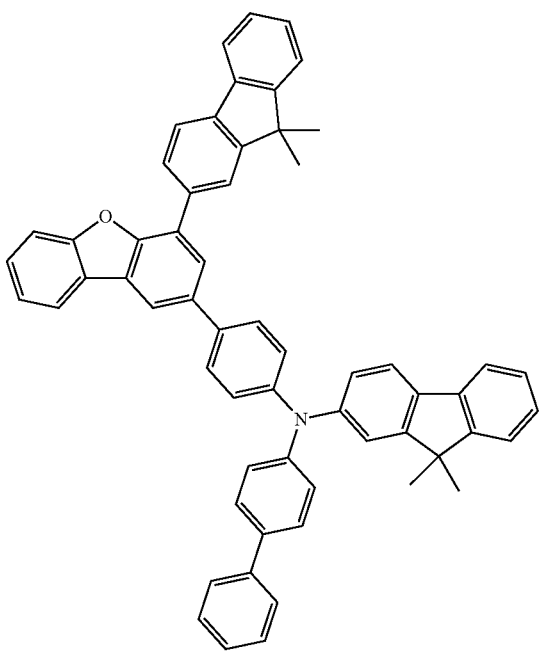
160
-continued
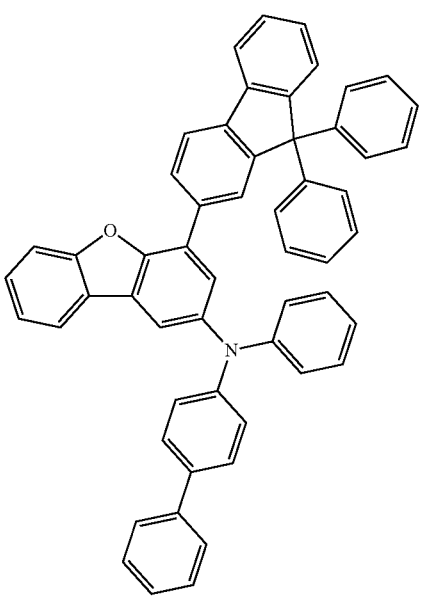
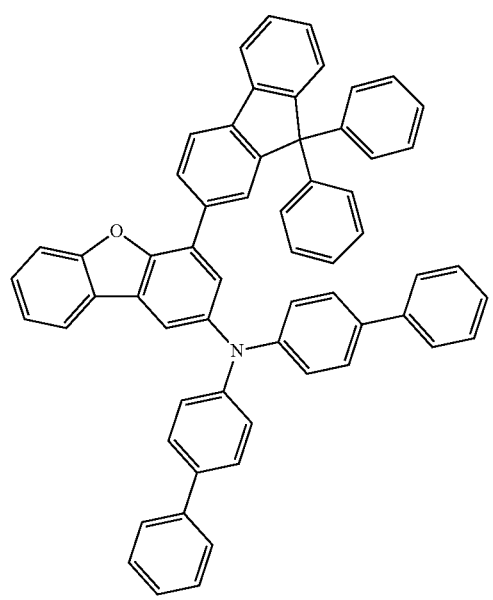
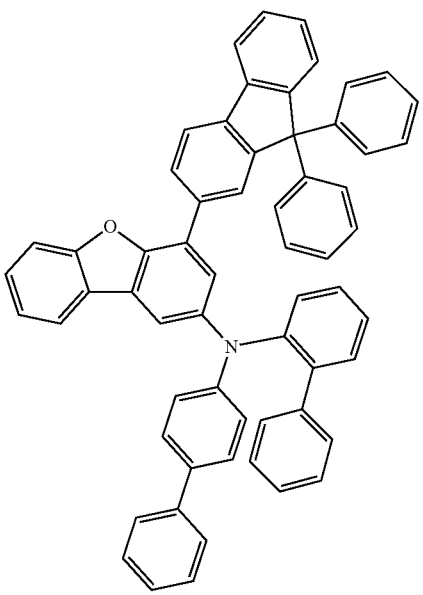

161
-continued
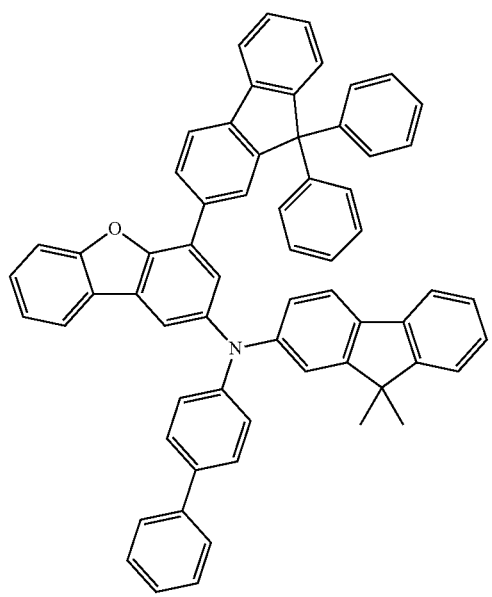
162
-continued
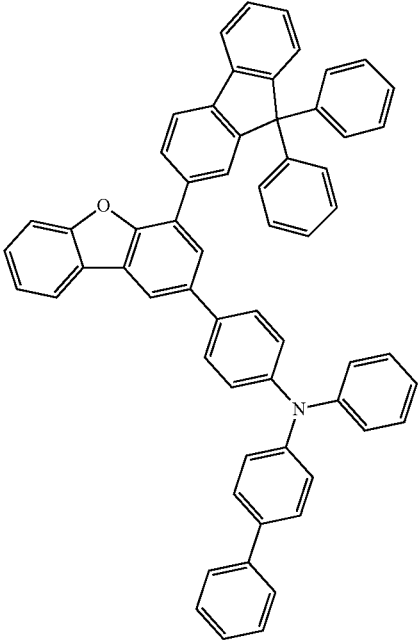
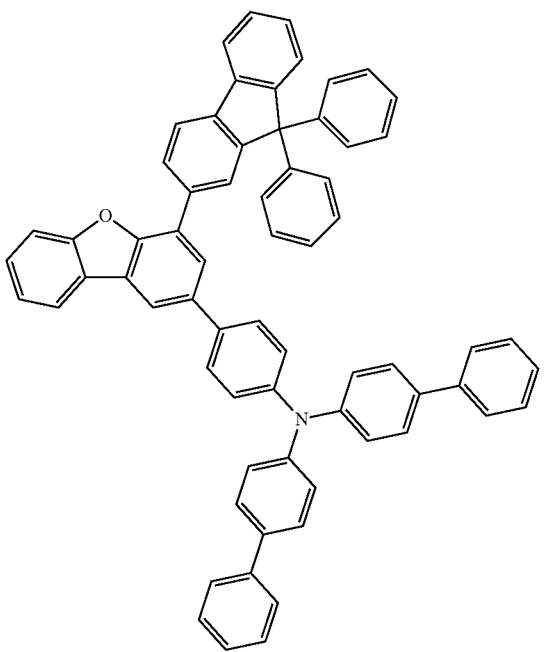
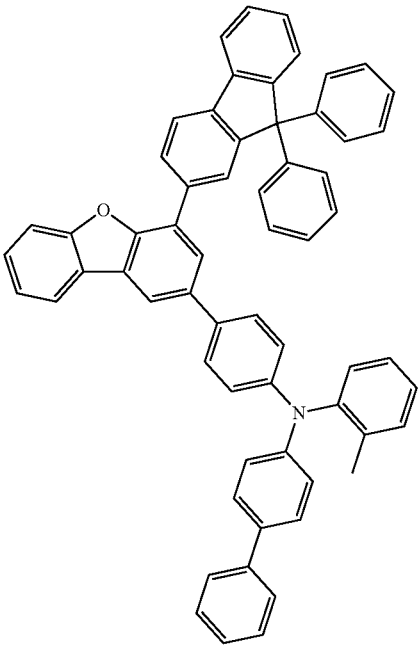

163
-continued
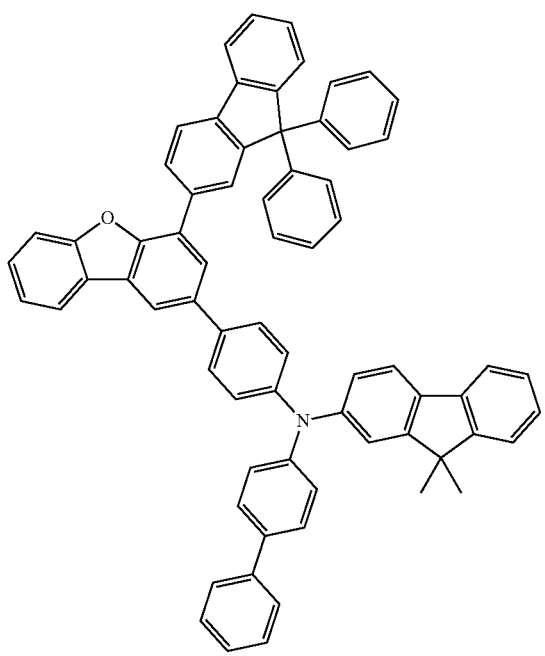
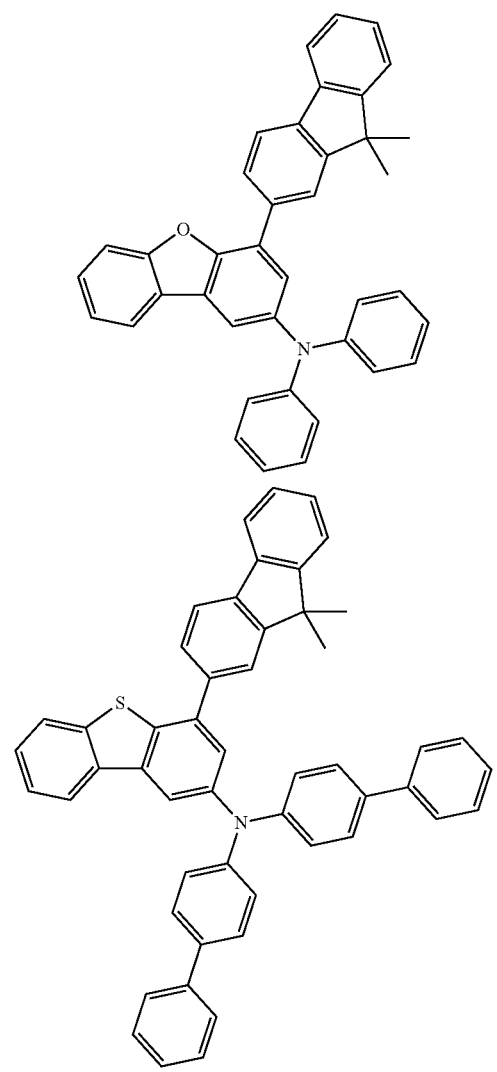
164
-continued
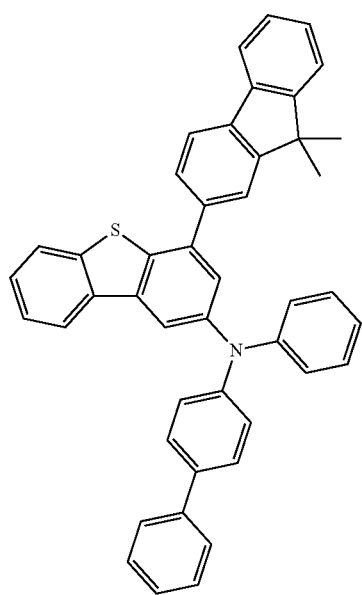
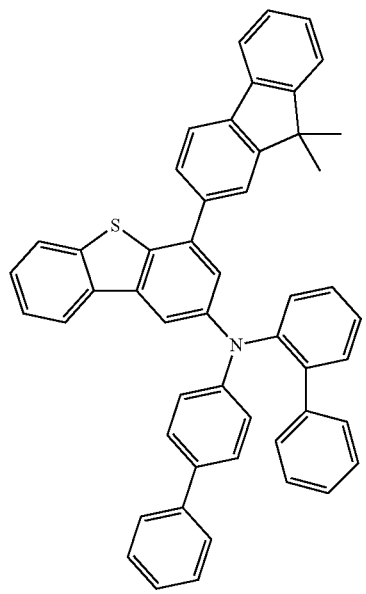

165
-continued
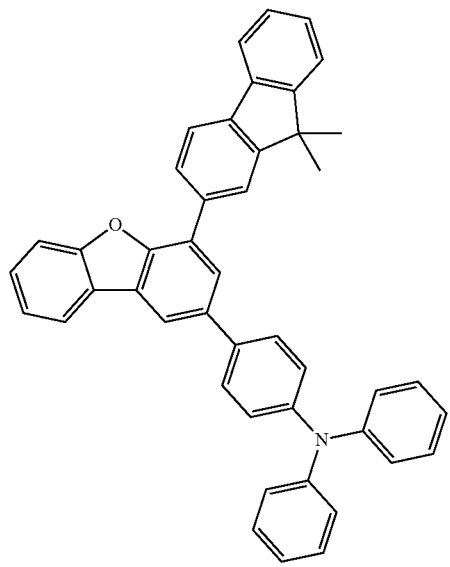
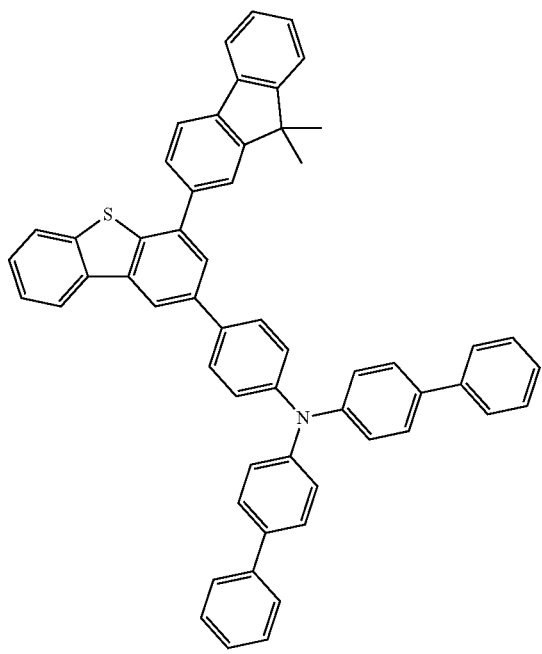
166
-continued
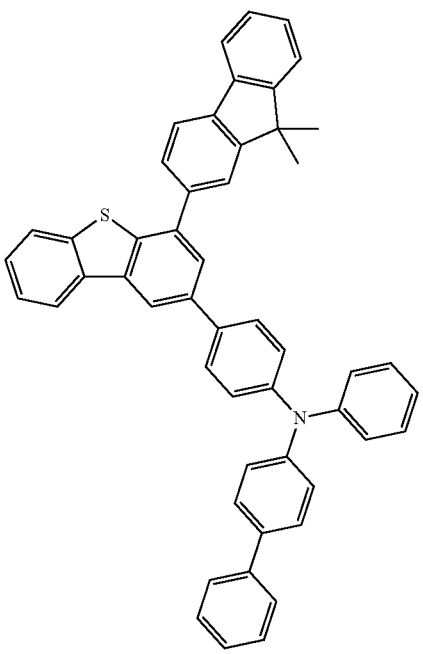
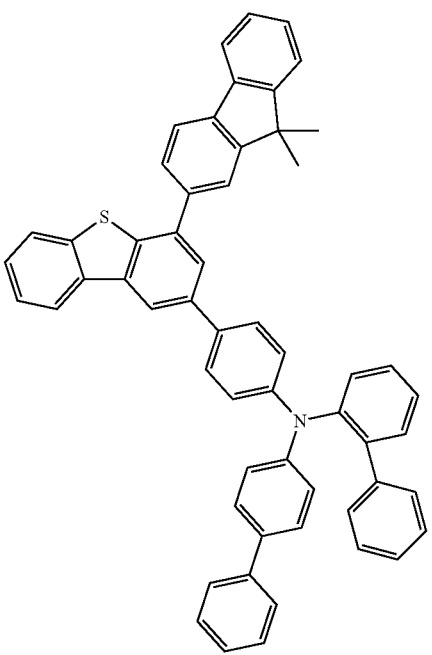

-continued
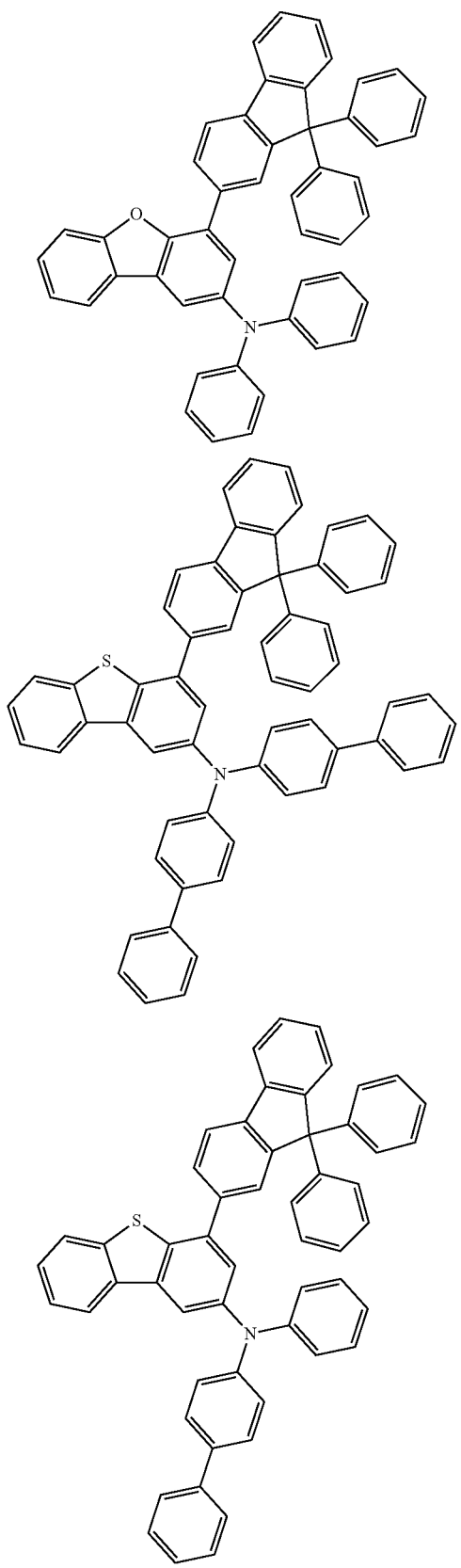
-continued
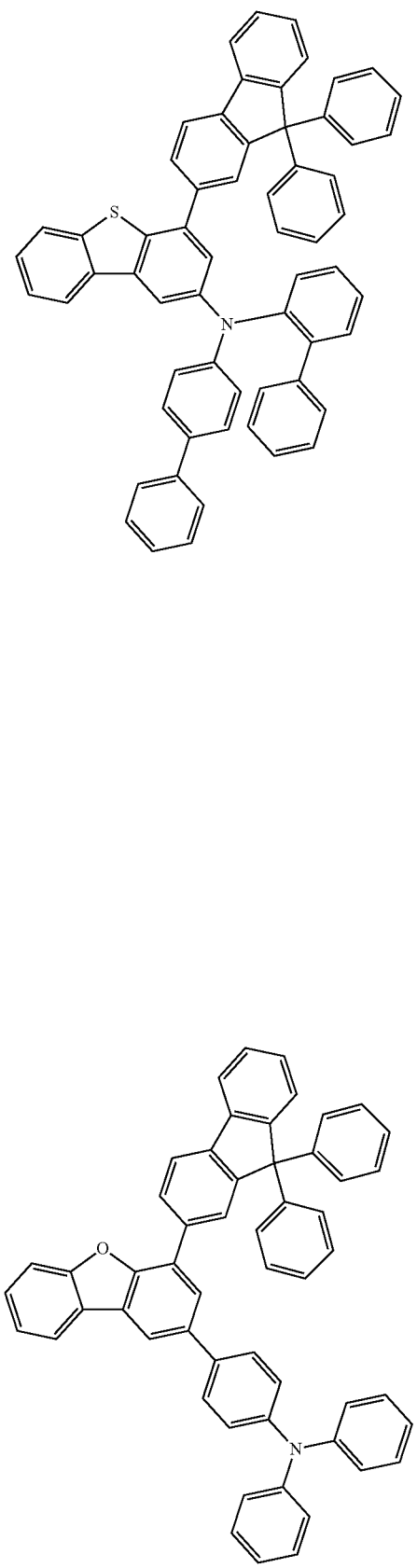

169
-continued
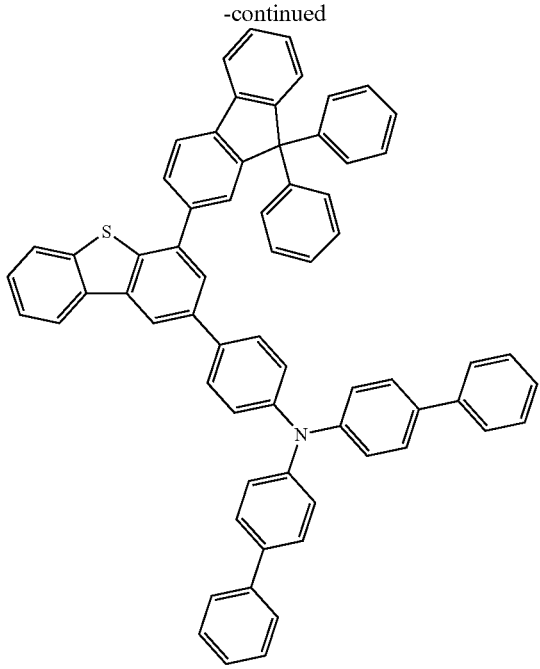
170
-continued
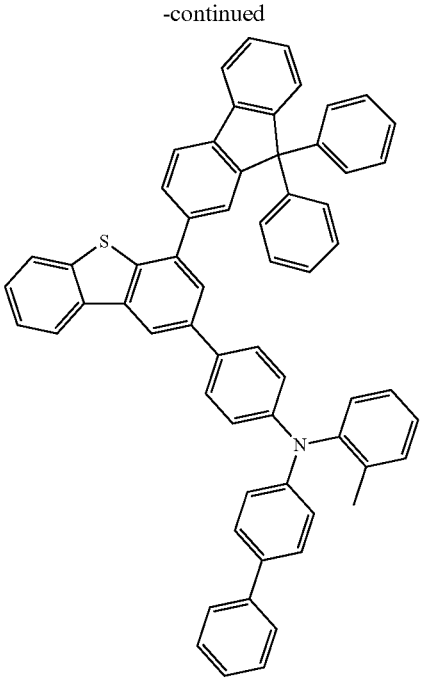
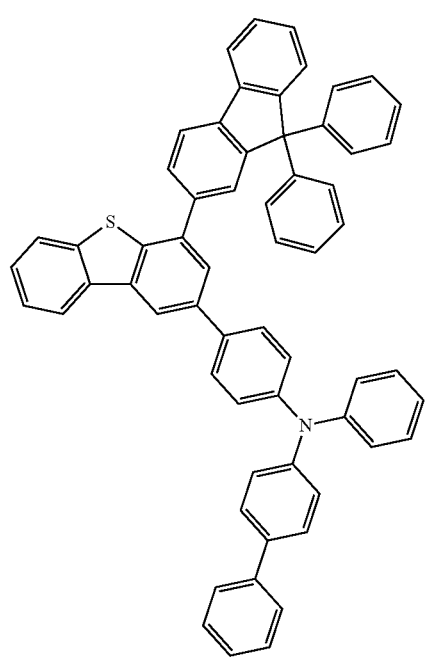
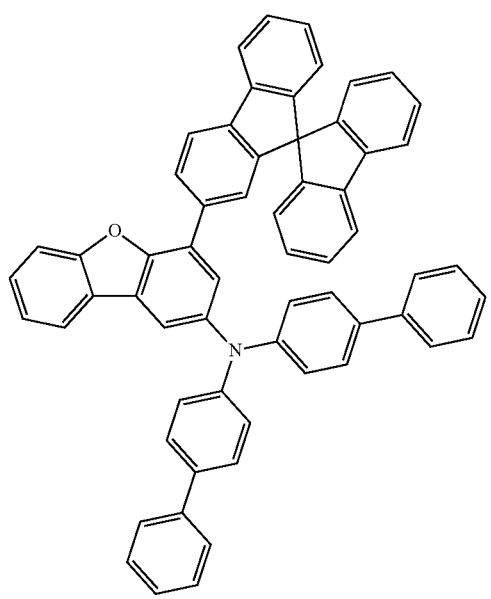

171
-continued
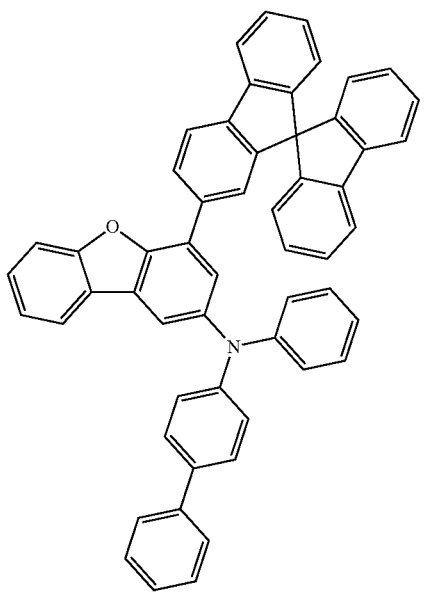
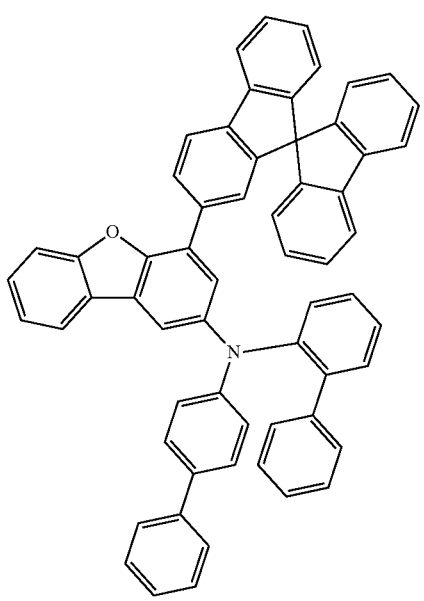
172
-continued
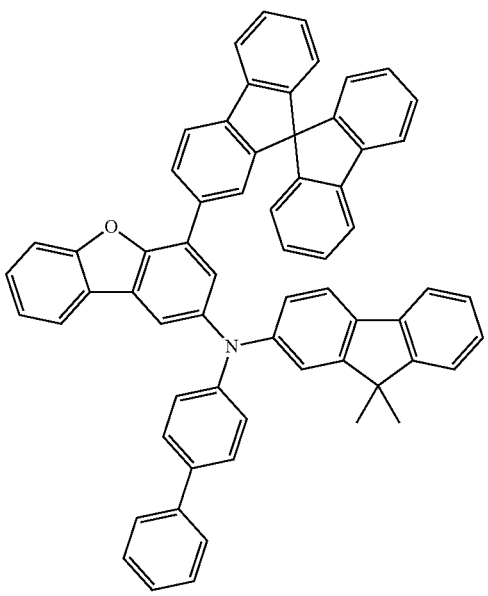
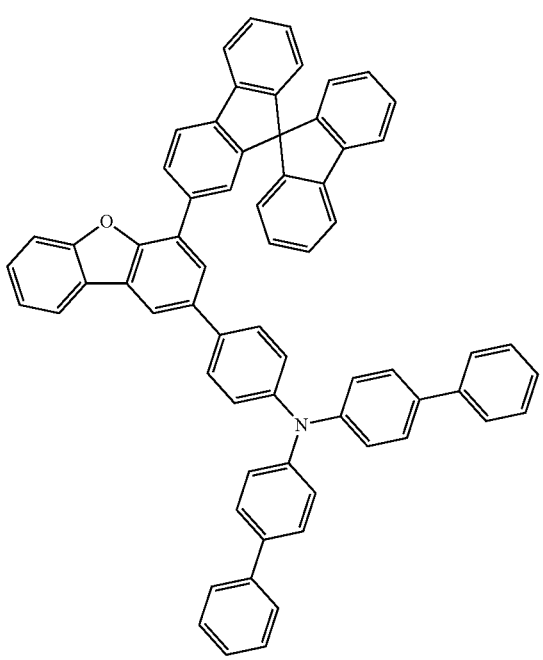

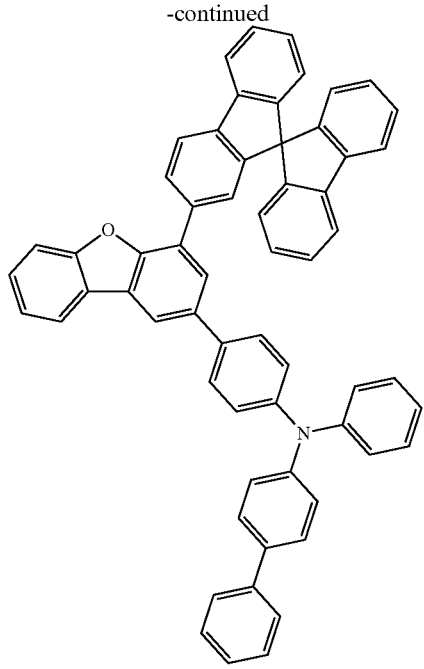
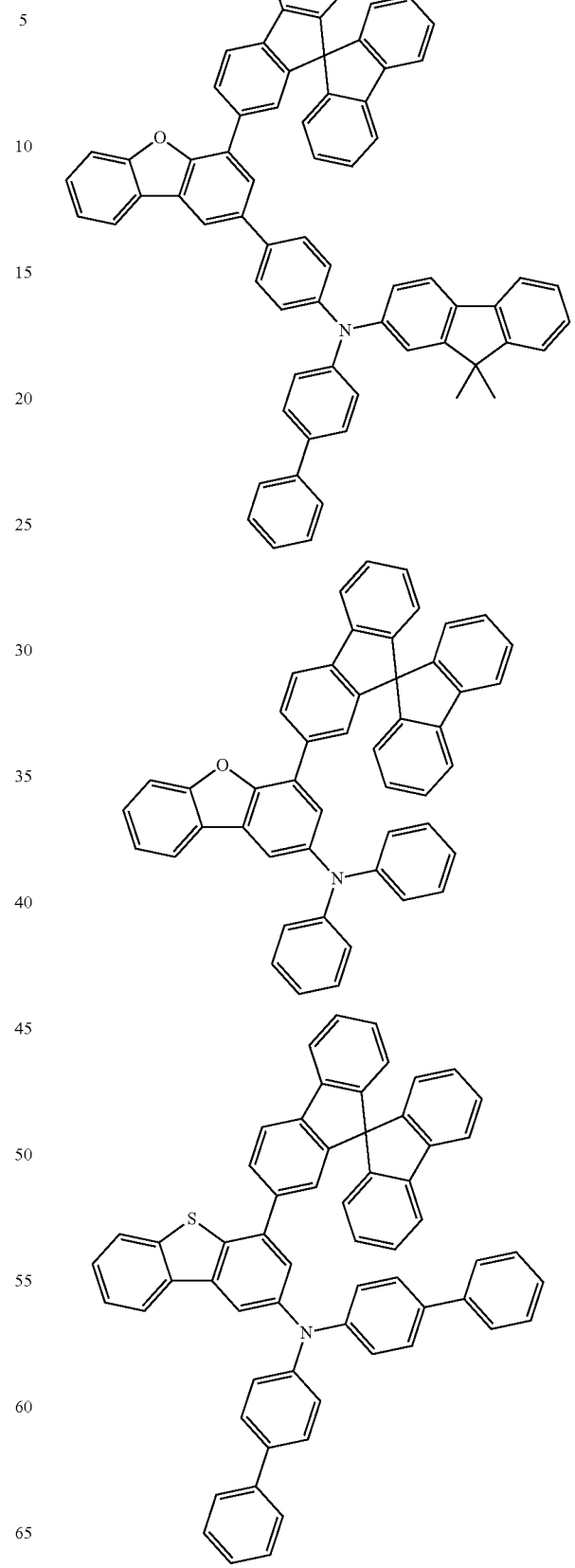

-continued
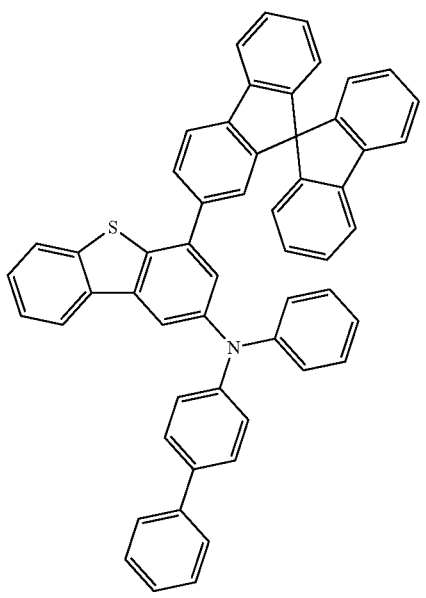
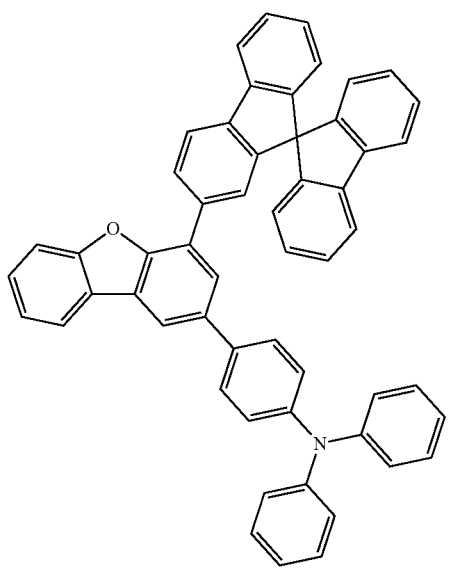
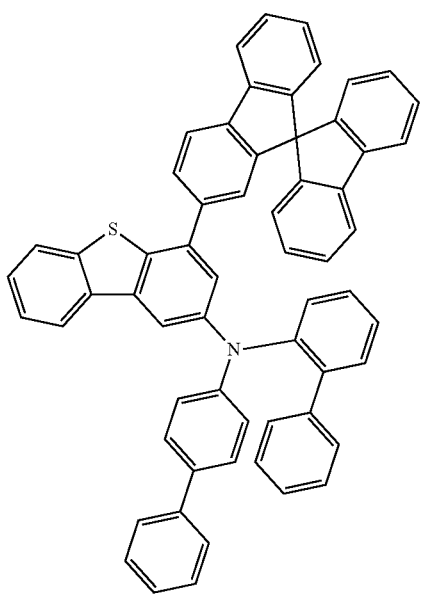
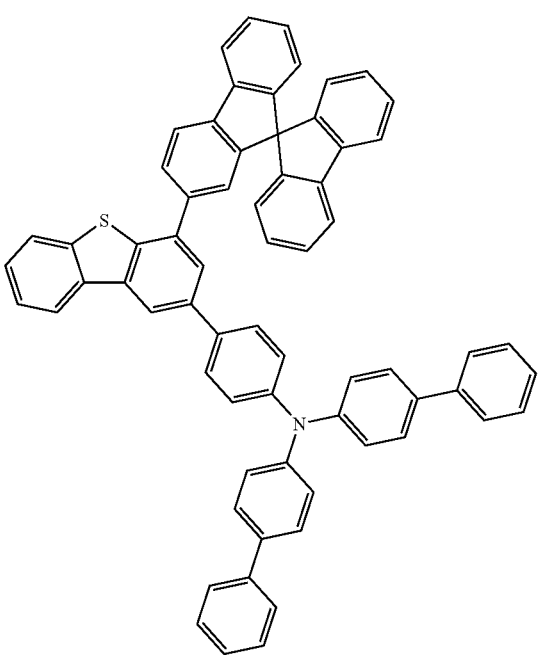

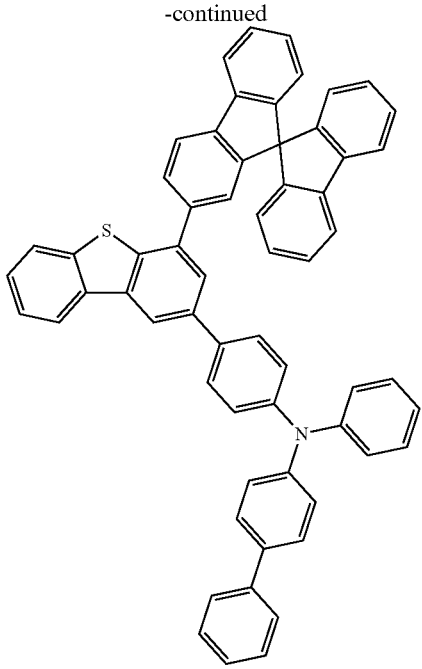
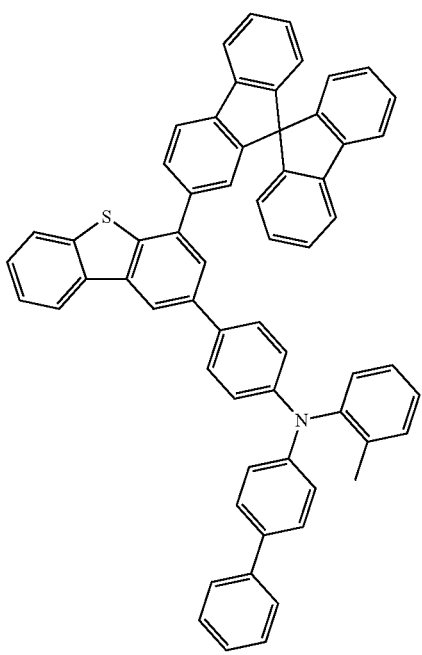
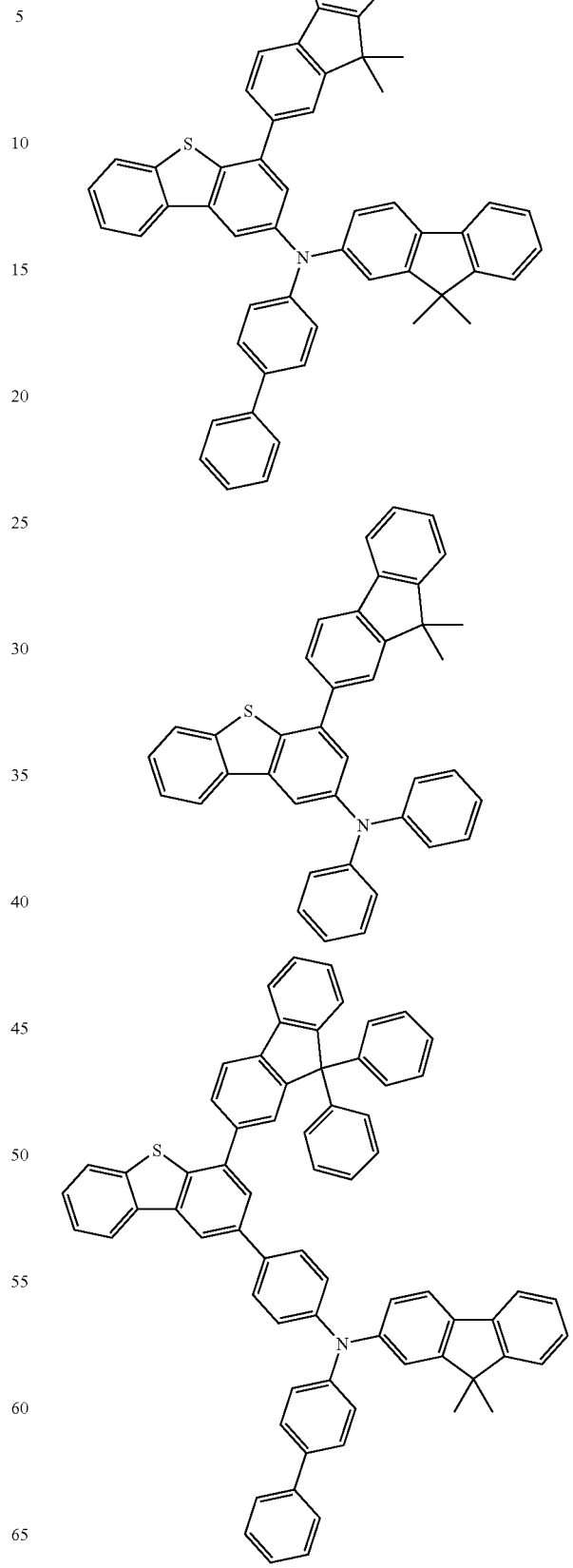

-continued
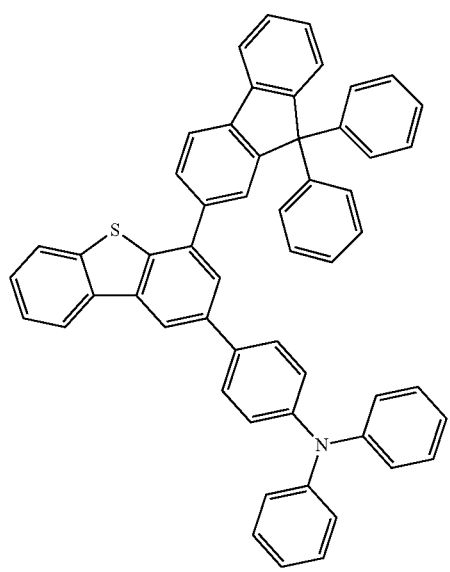
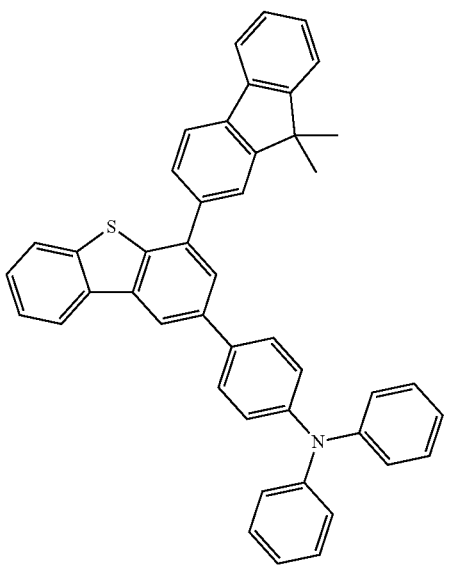
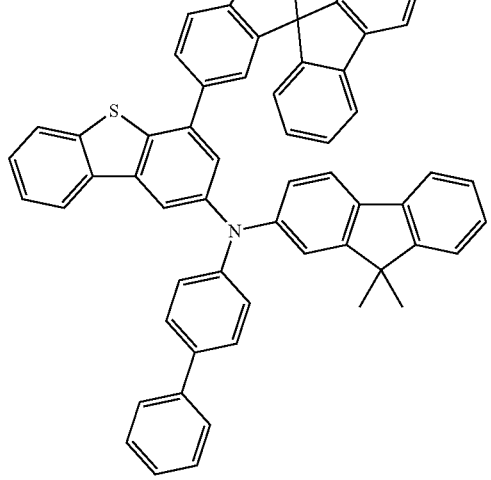
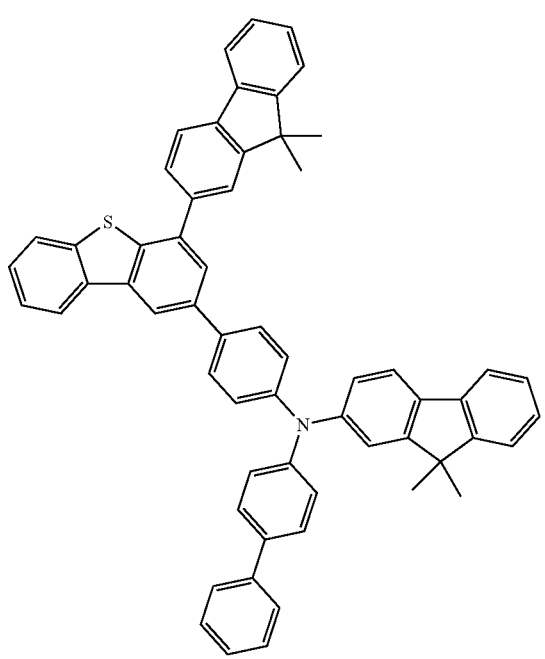
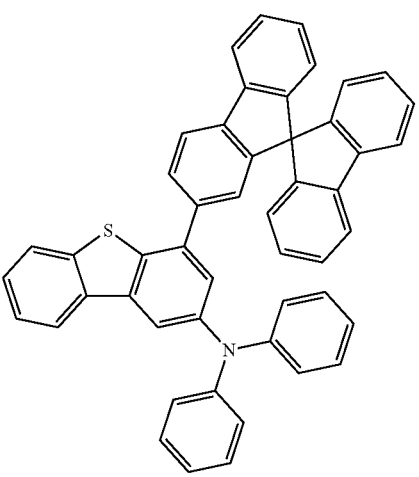

181
-continued
182
-continued
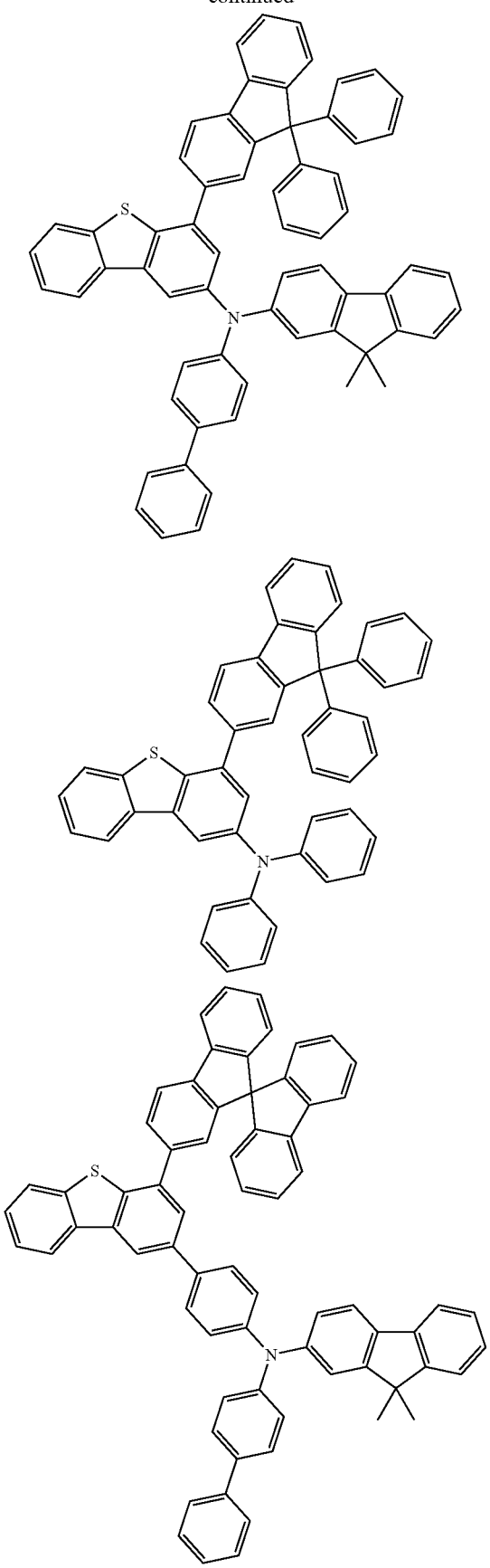

183
-continued
184
-continued
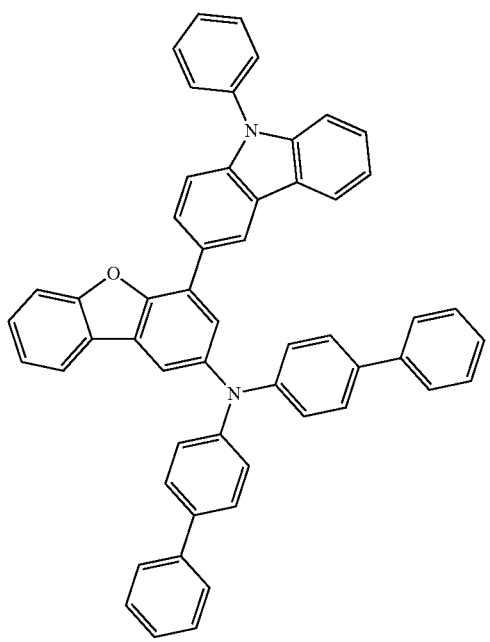
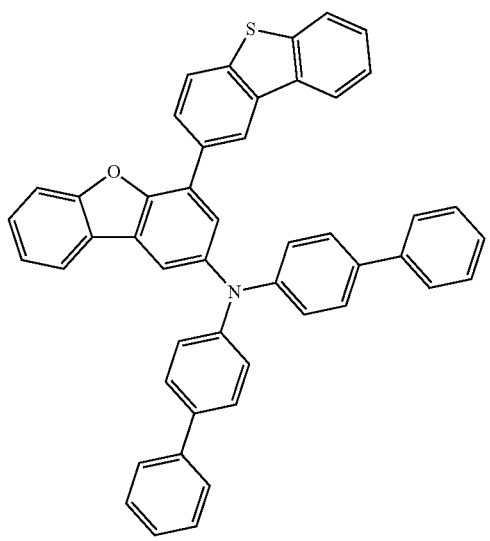
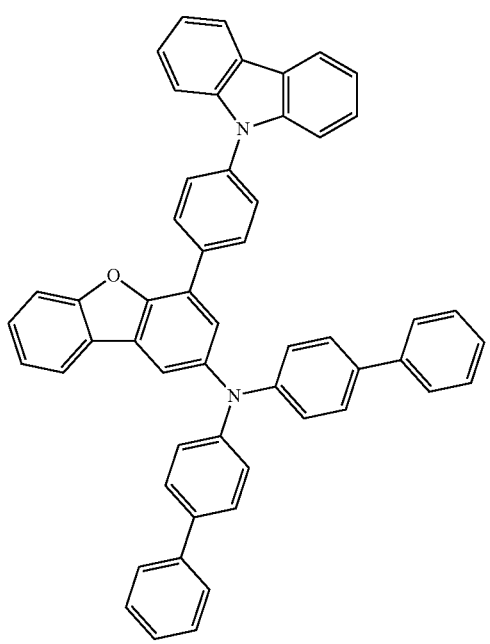

185
-continued
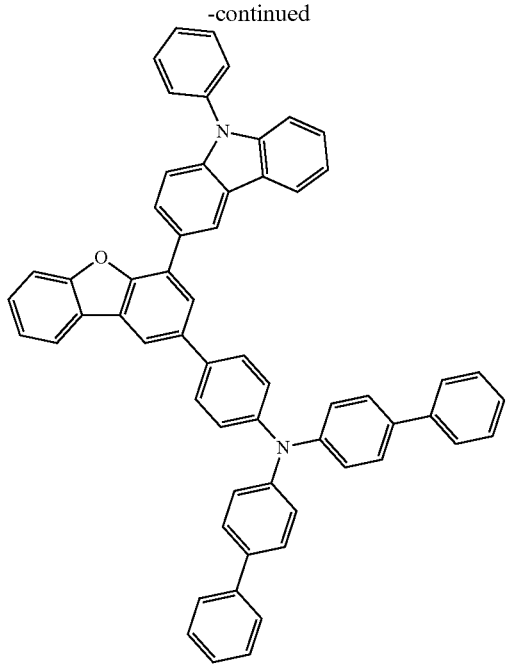
186
-continued
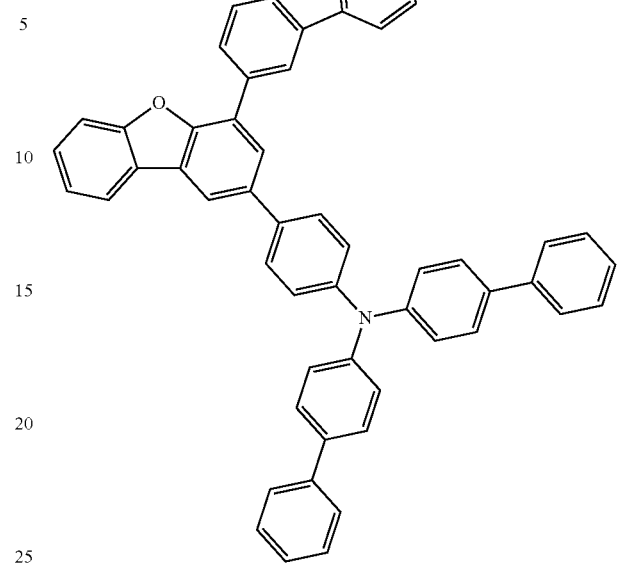
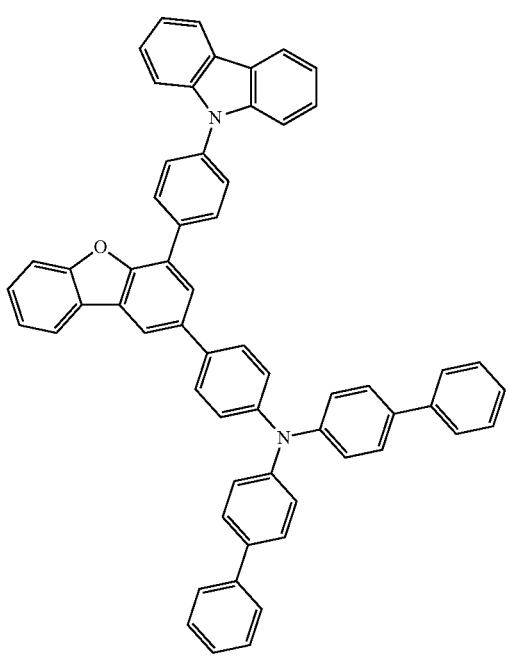
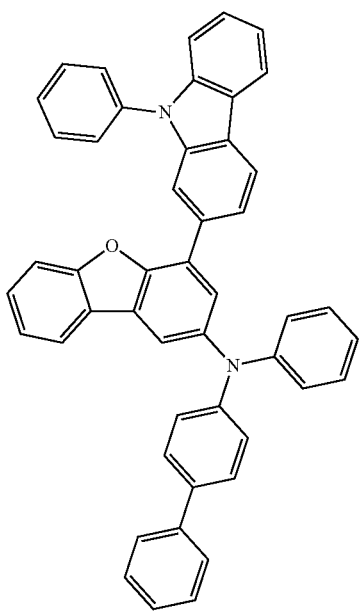

187
-continued
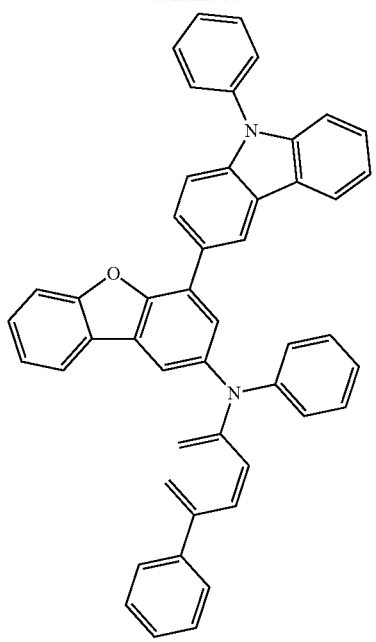
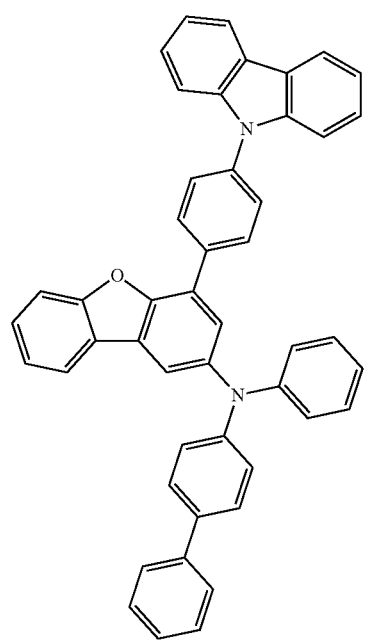
188
-continued
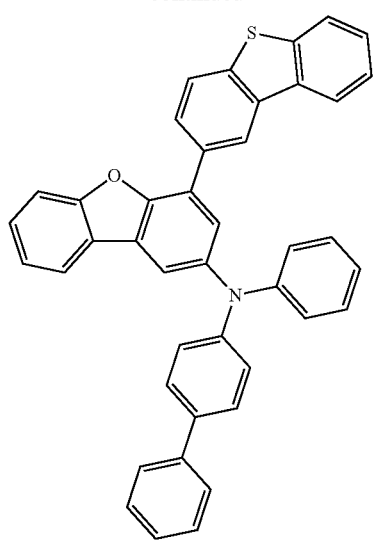
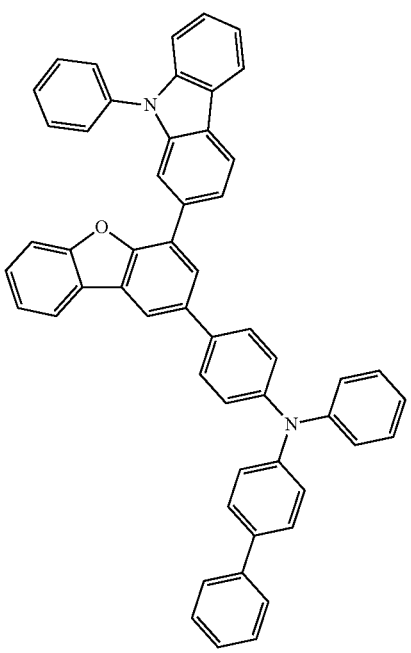

189
-continued
190
-continued
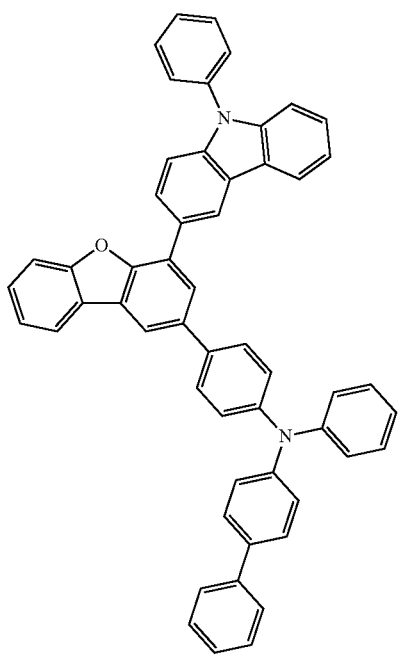
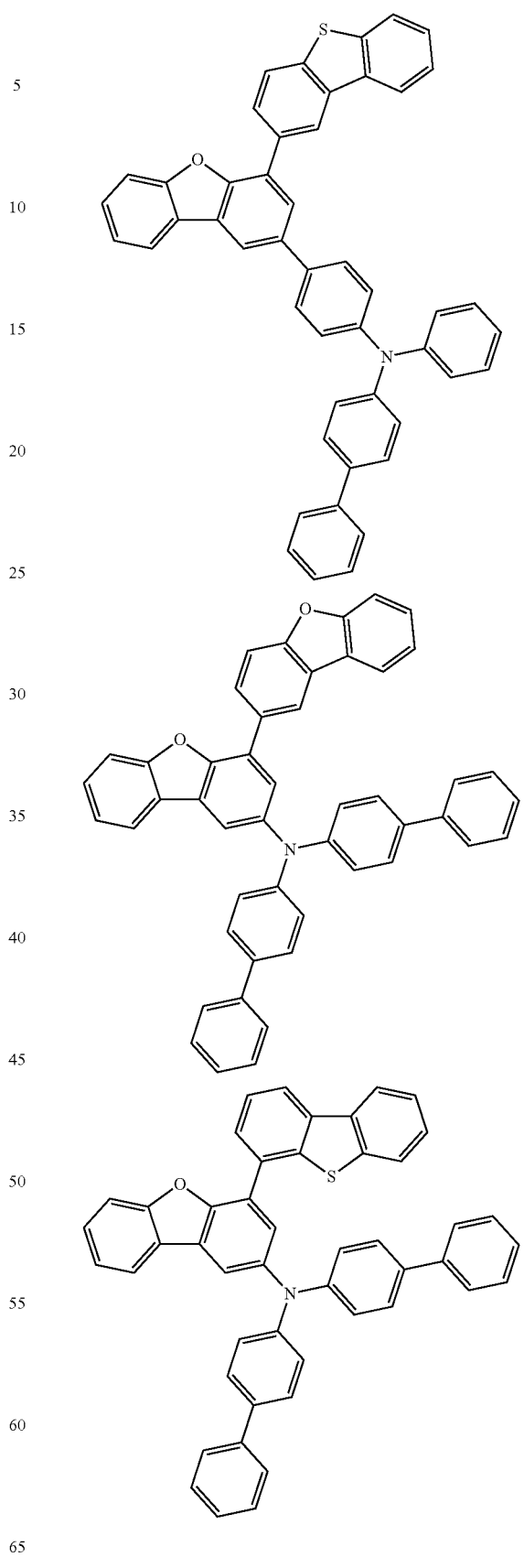

191
-continued
192
-continued
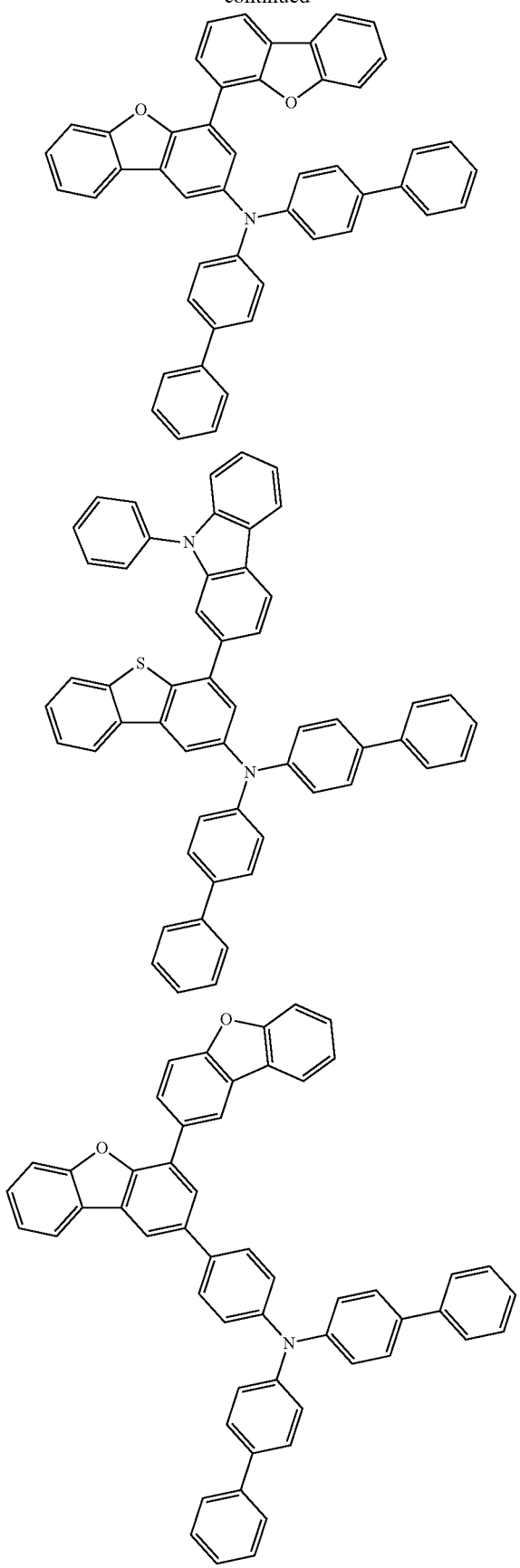
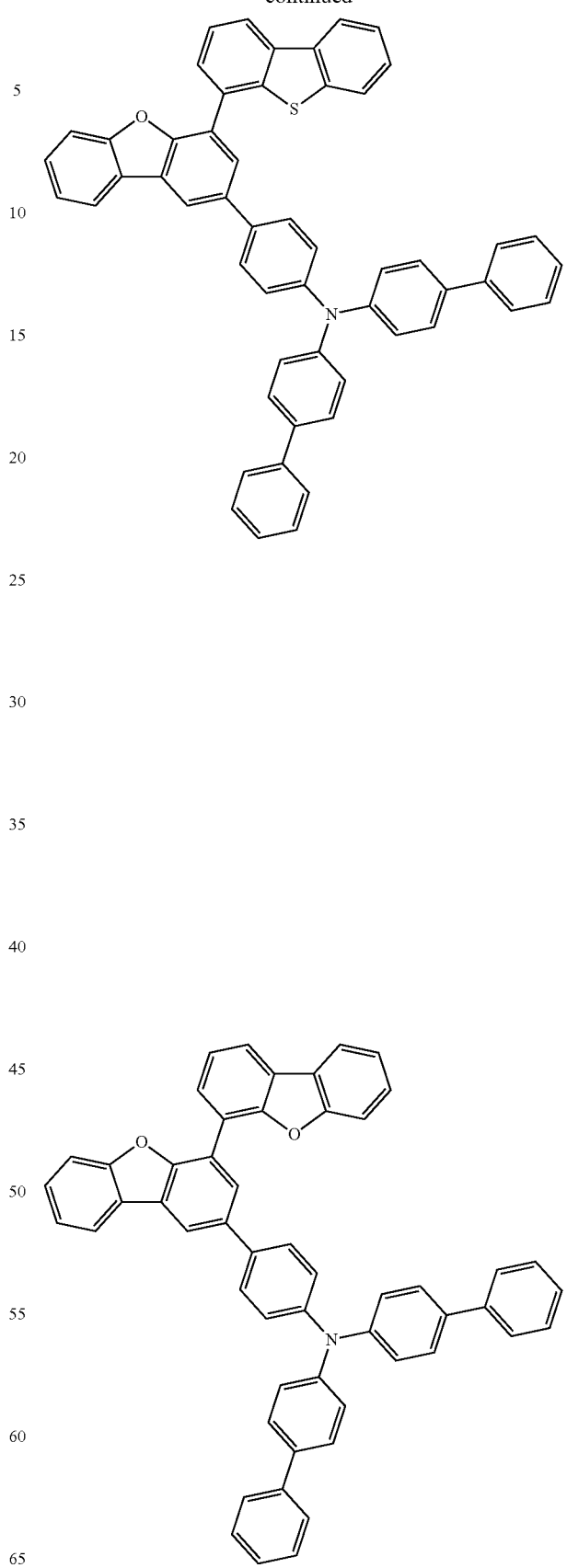

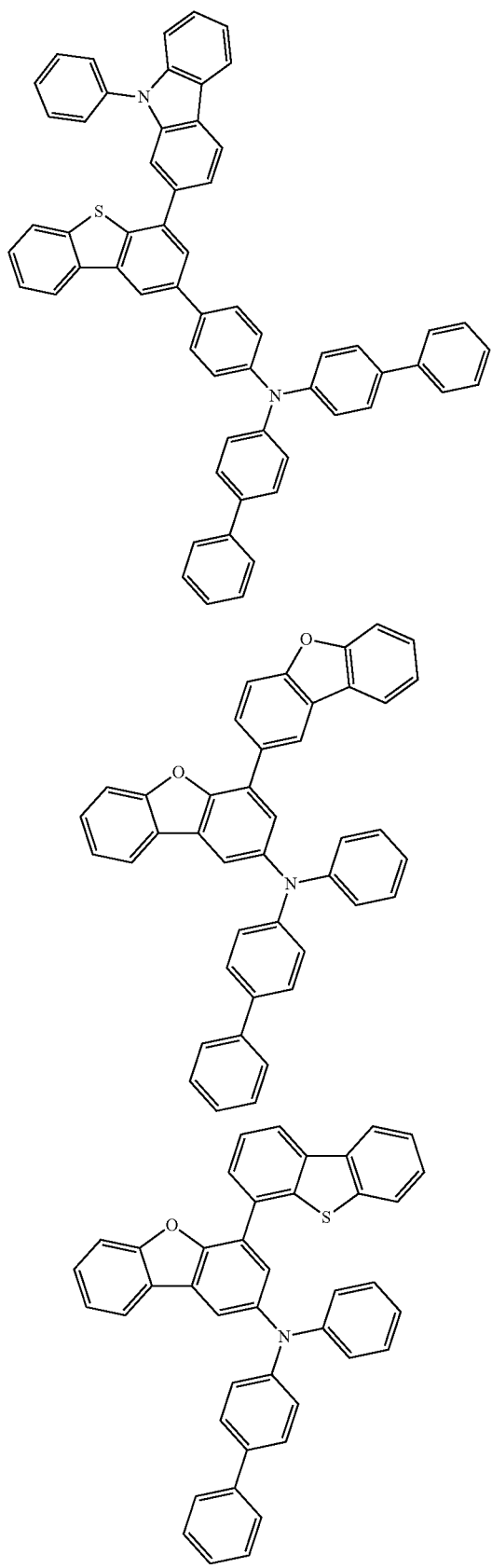
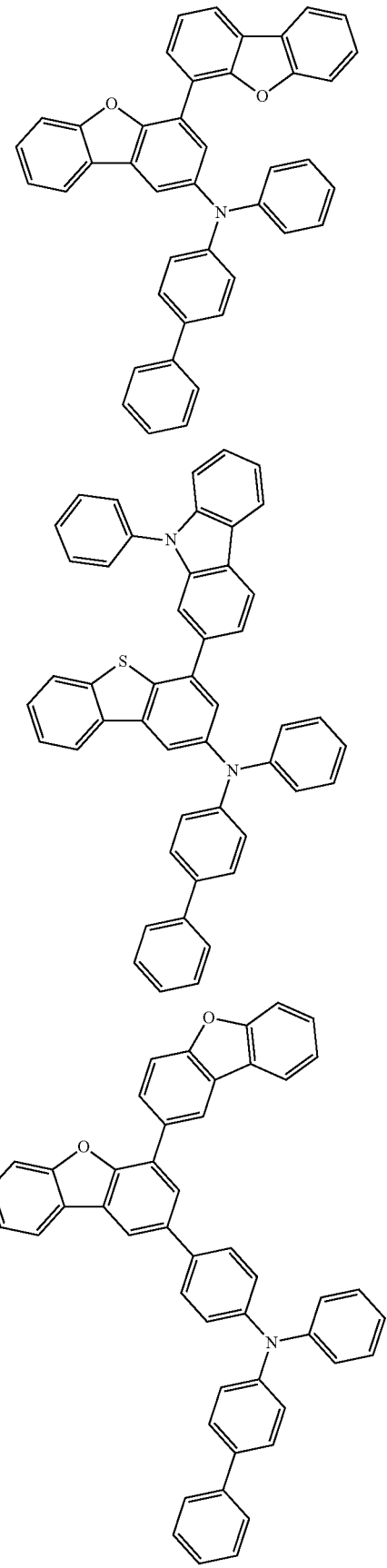

195
-continued
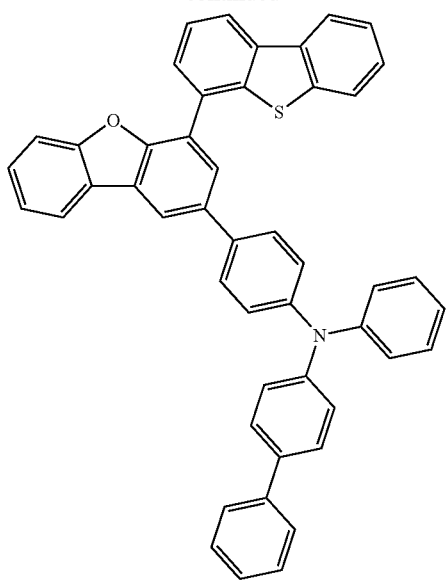
196
-continued
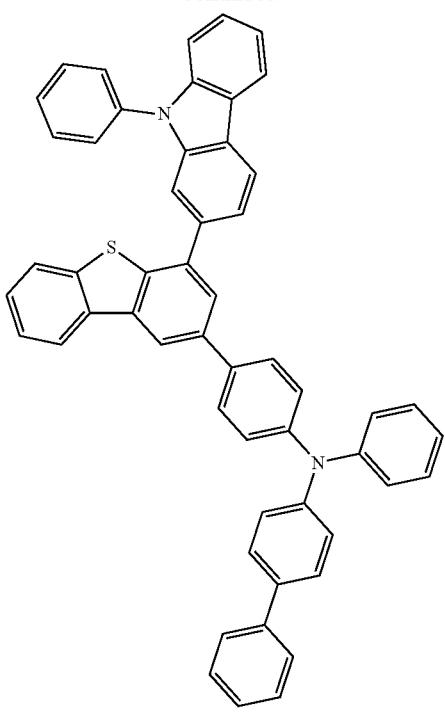
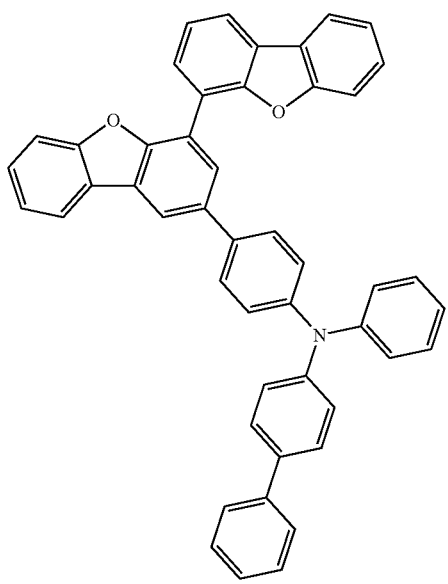

197
-continued
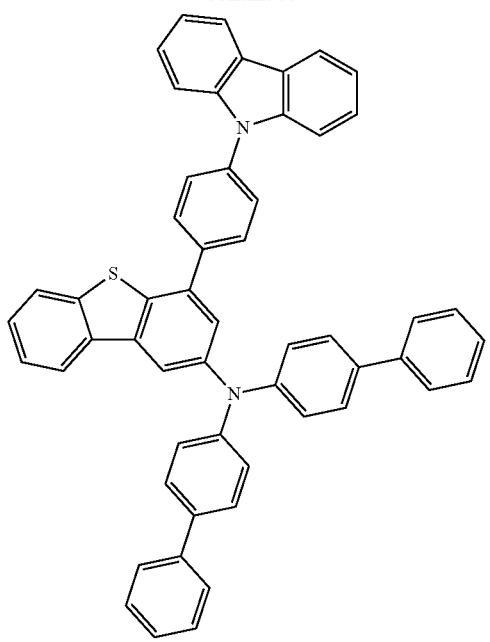
198
-continued
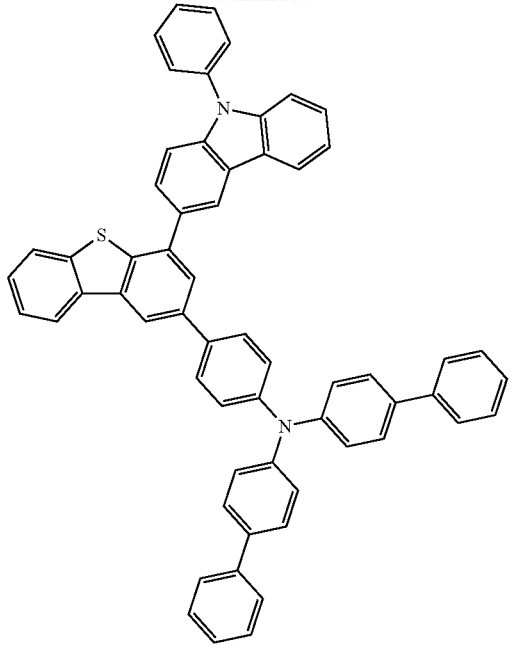
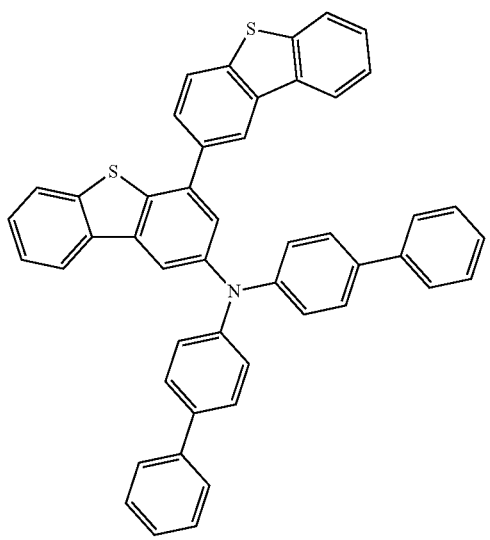
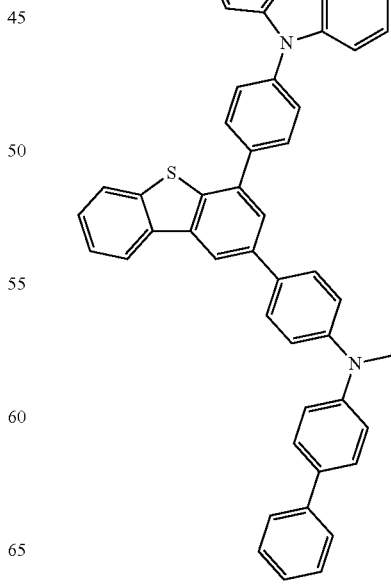

199
-continued
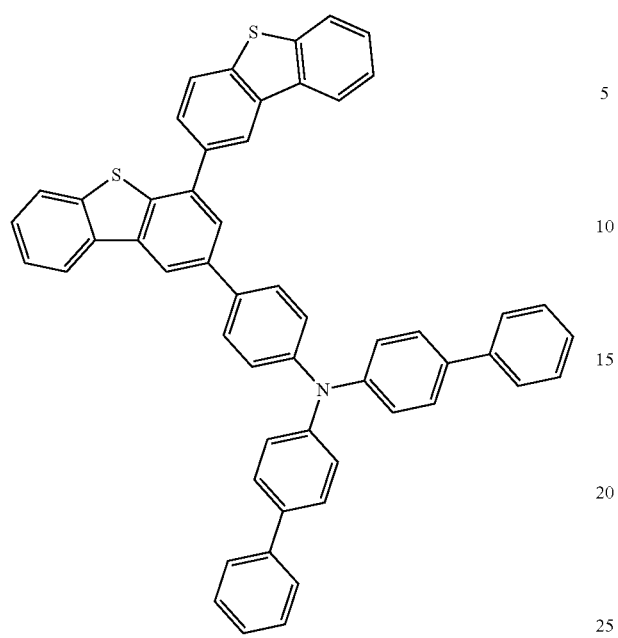
200
-continued
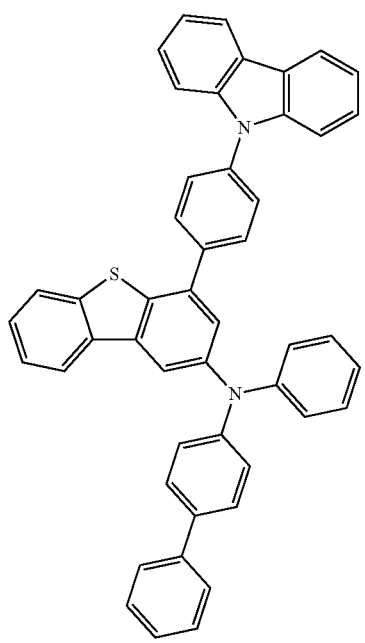
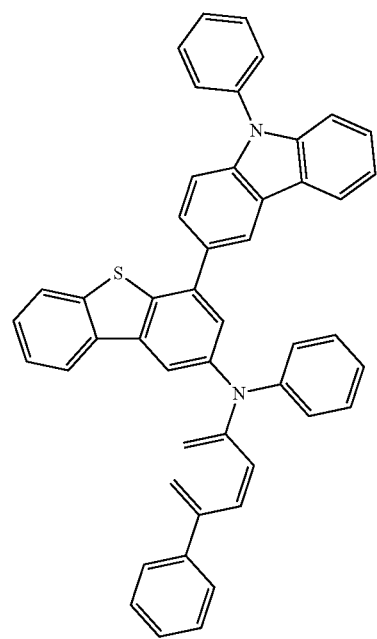
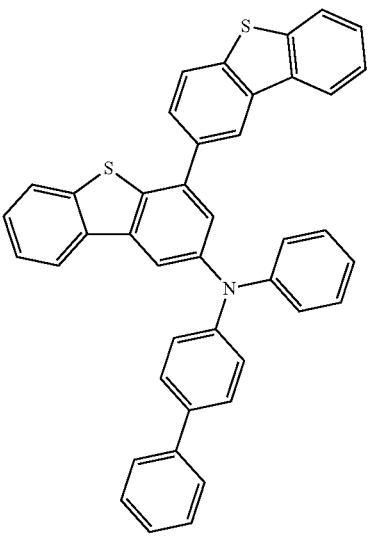

201
-continued
202
-continued
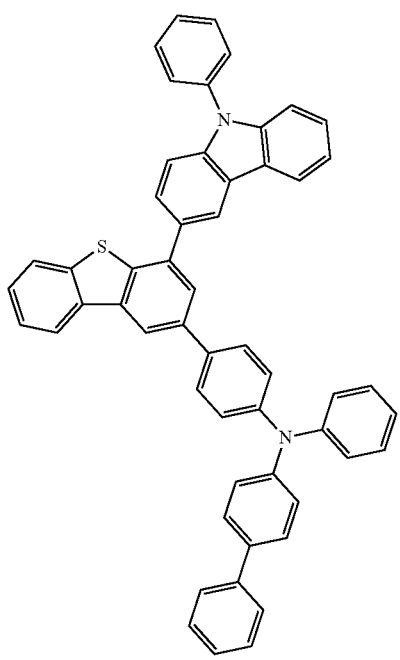
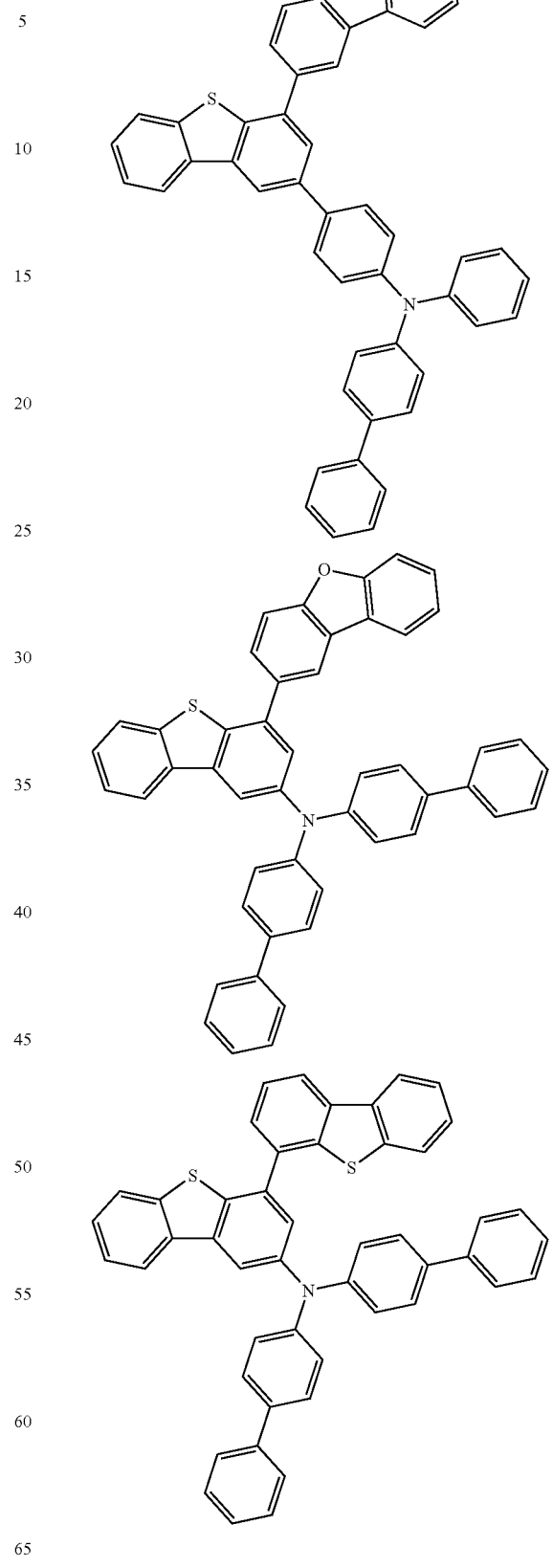

203
-continued
204
-continued
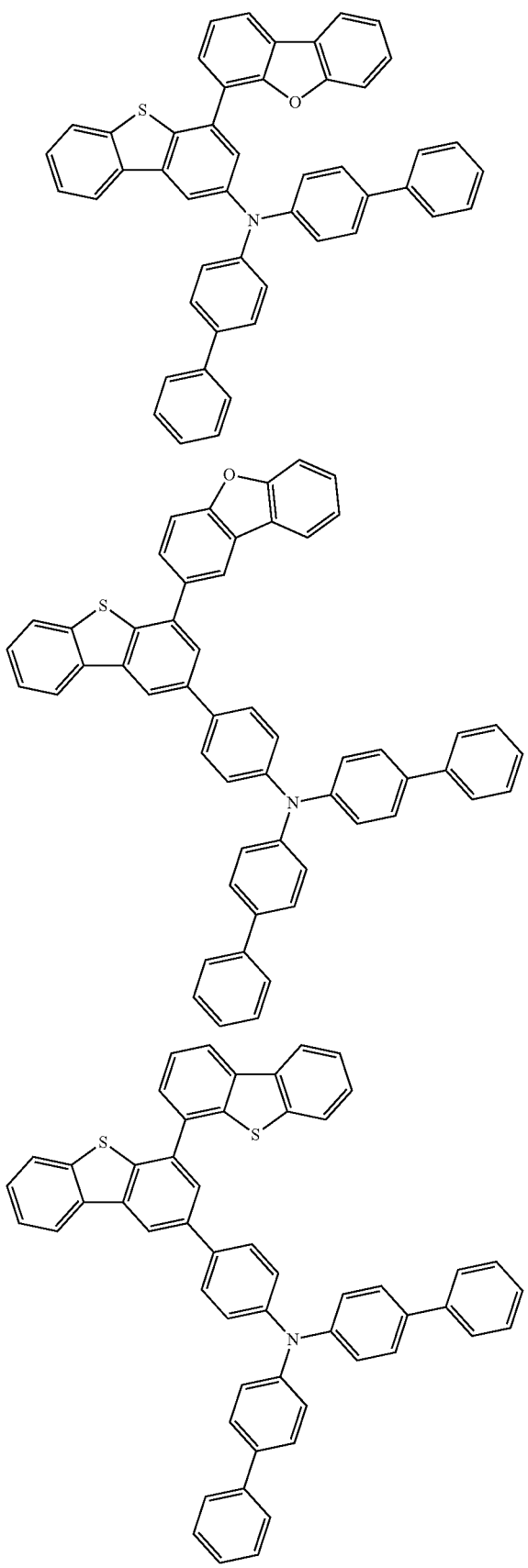

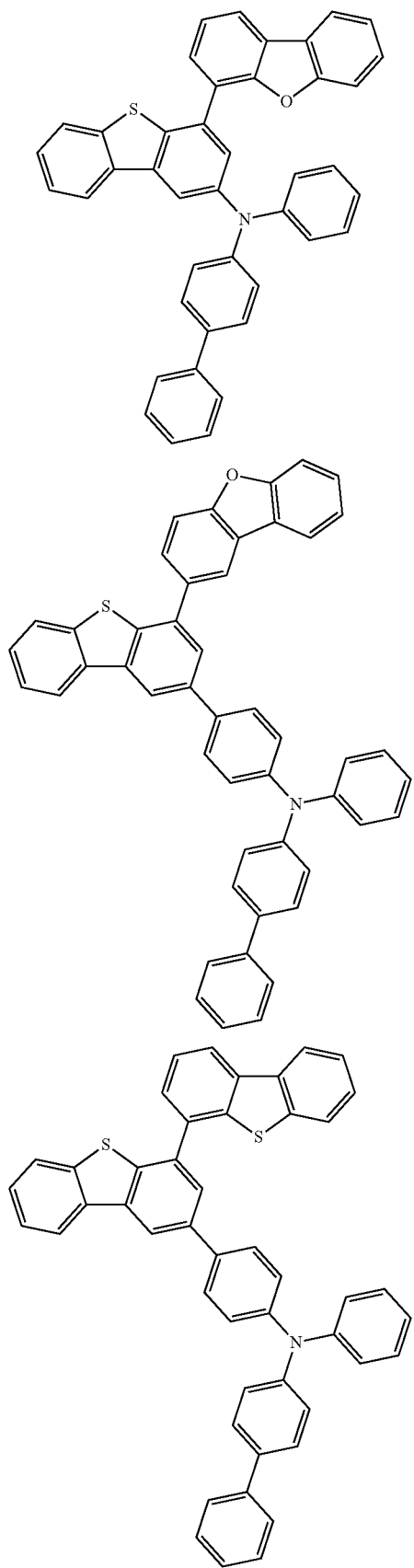
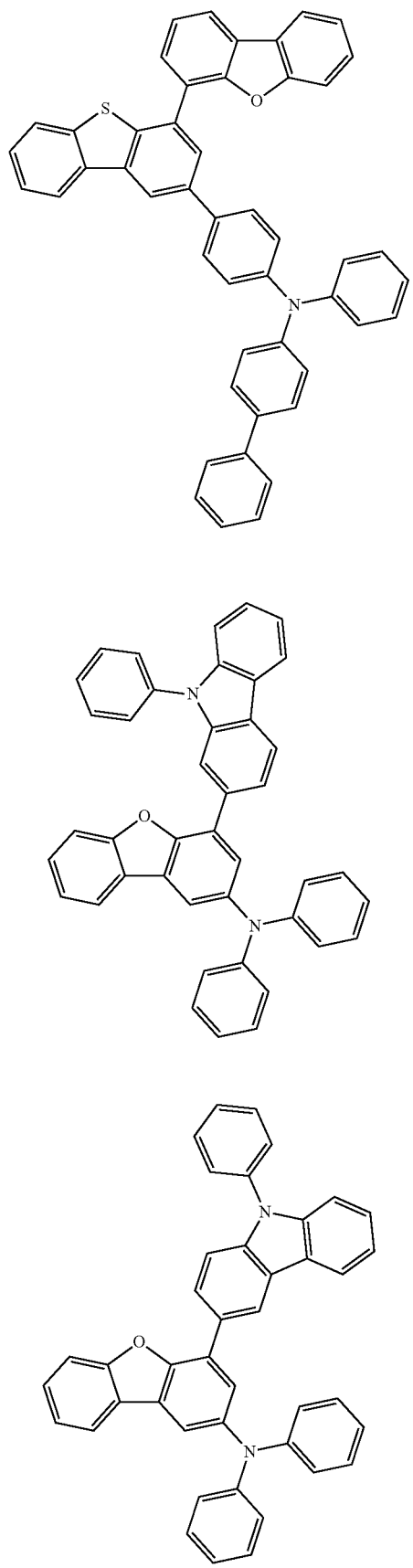

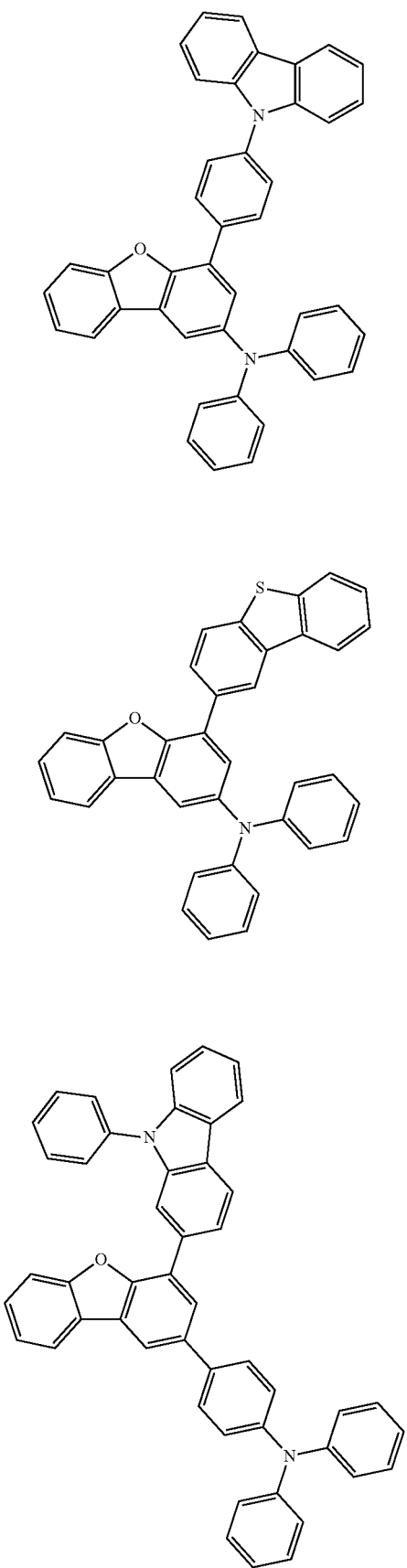

209
-continued
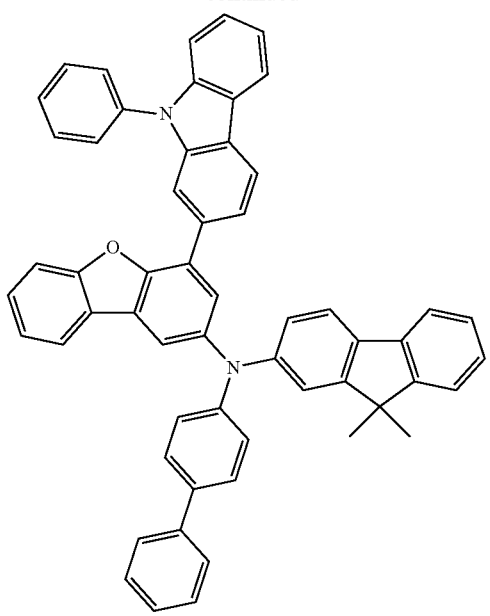
210
-continued
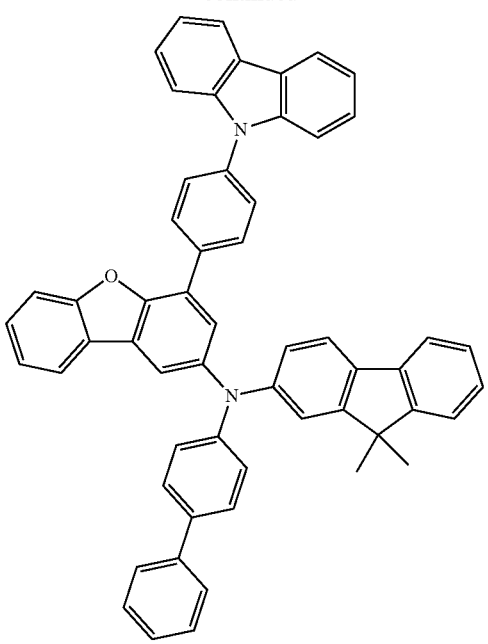
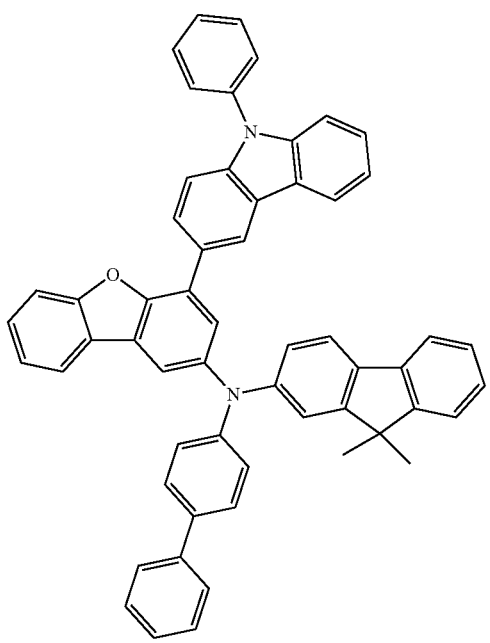
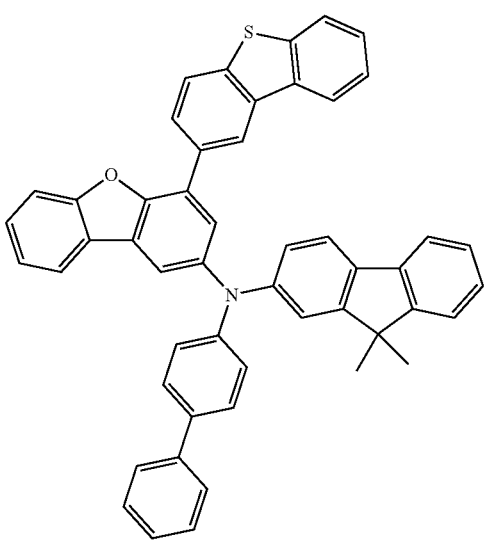

211
-continued
212
-continued
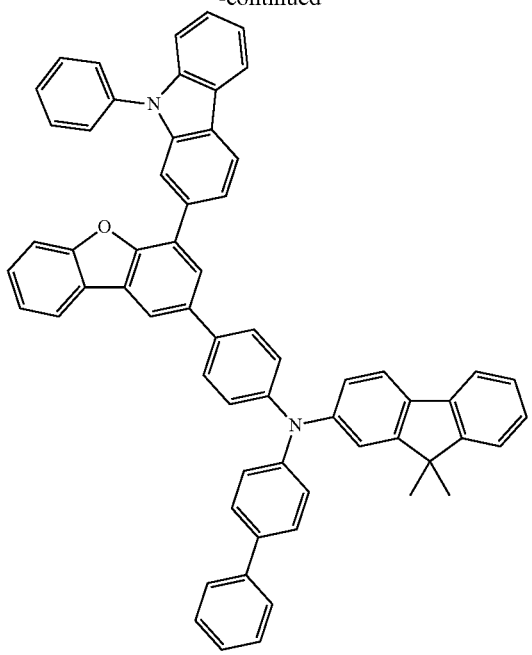
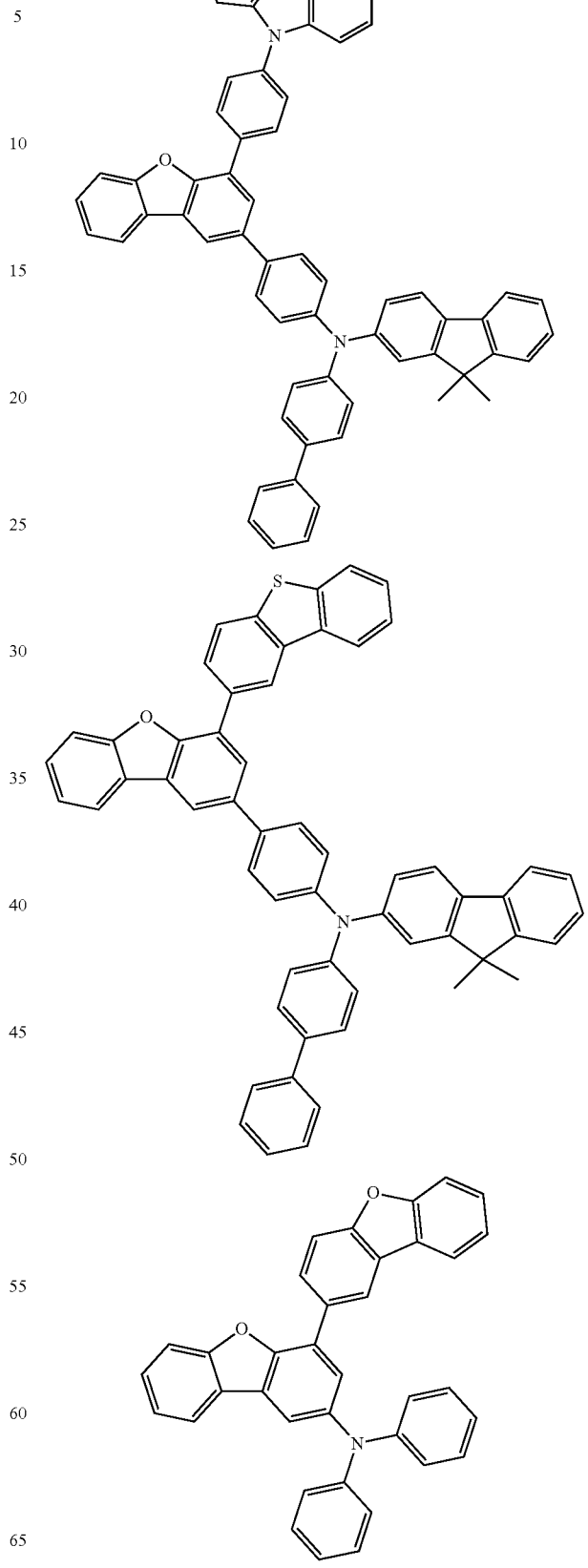

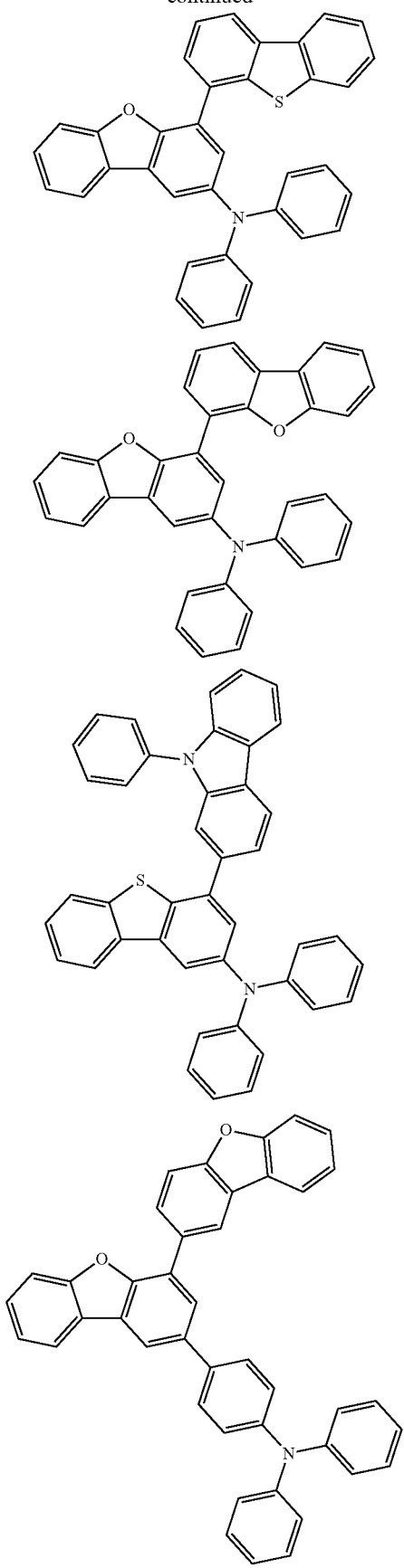
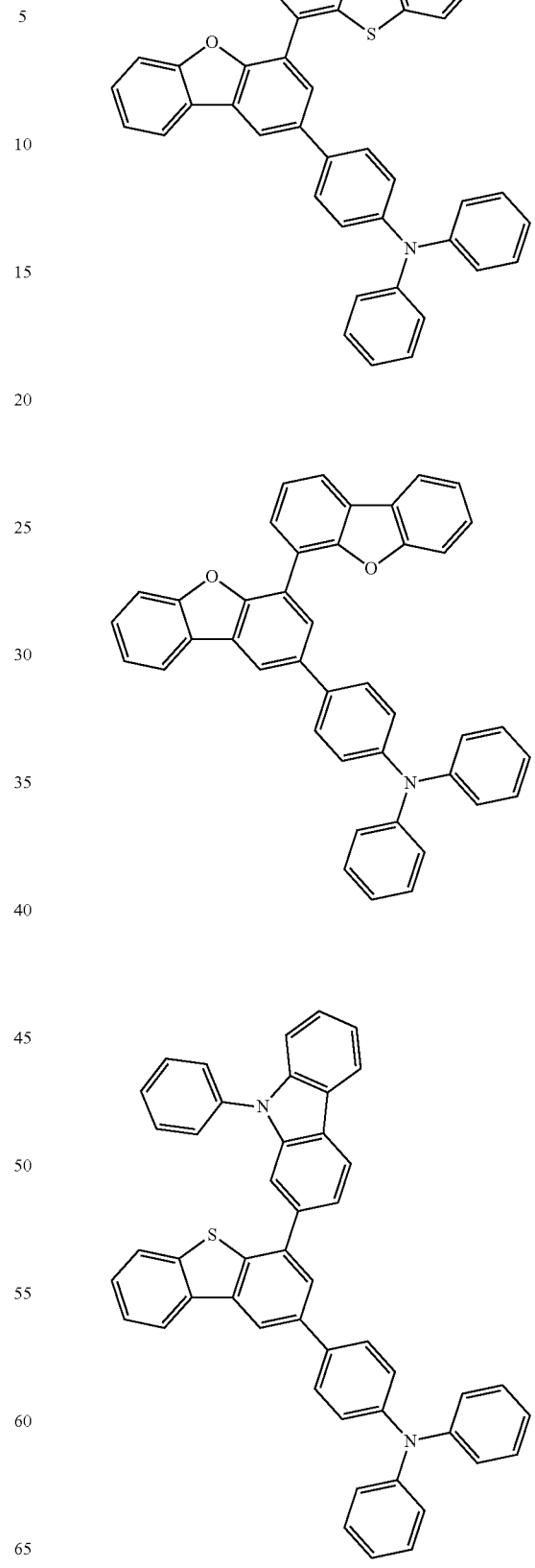

215
-continued
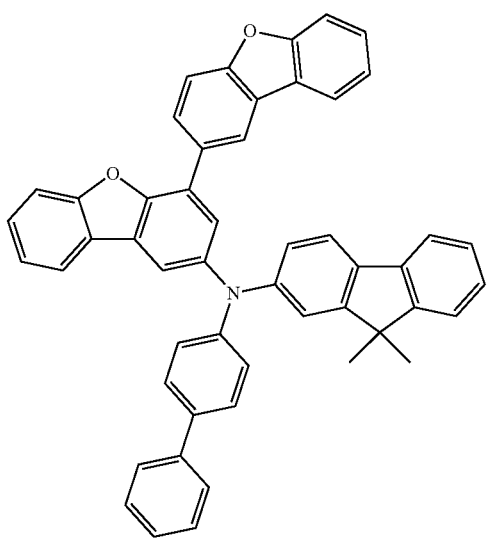
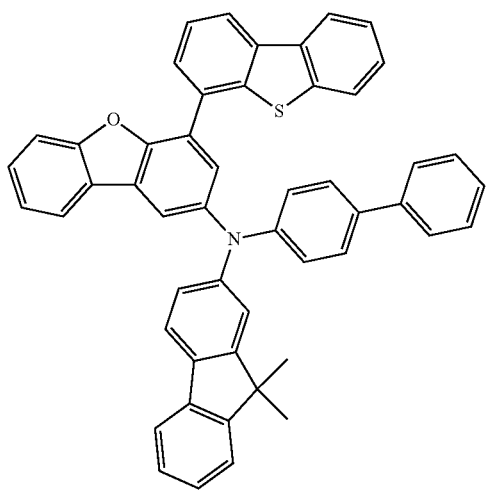
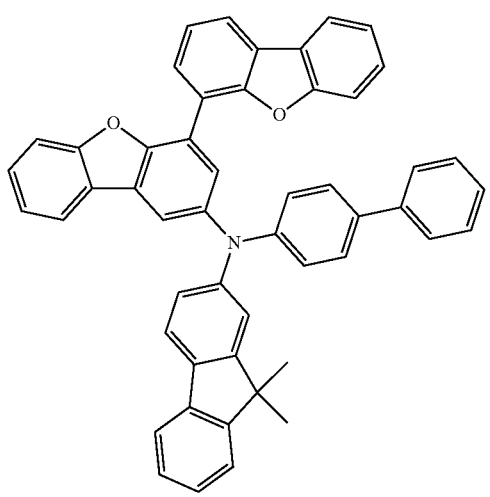
216
-continued
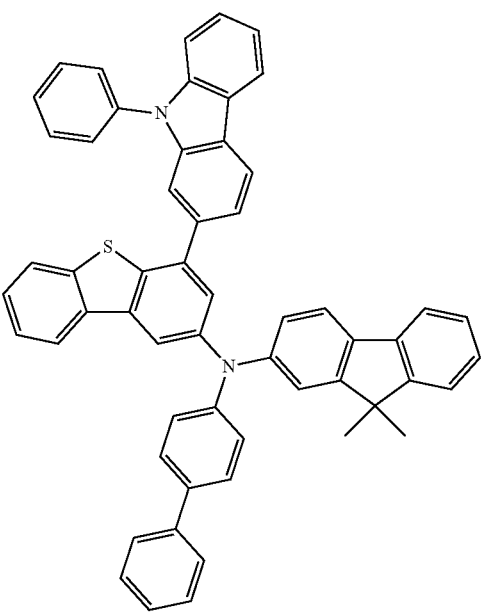
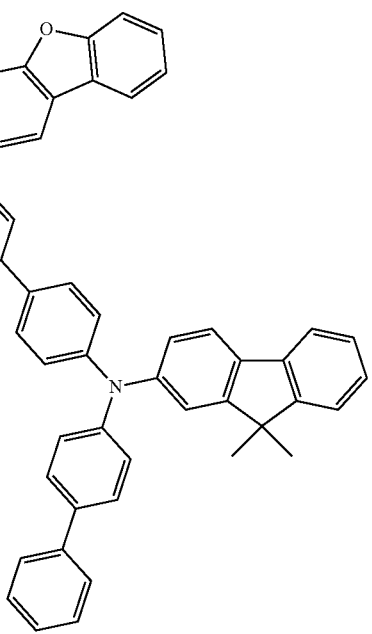

217
-continued
218
-continued
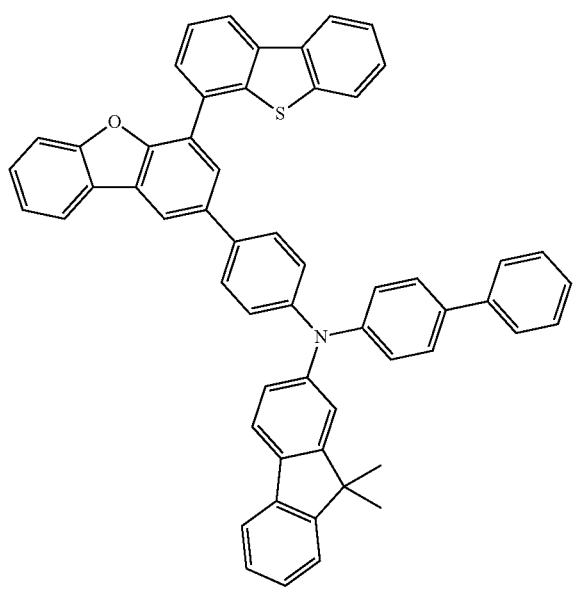
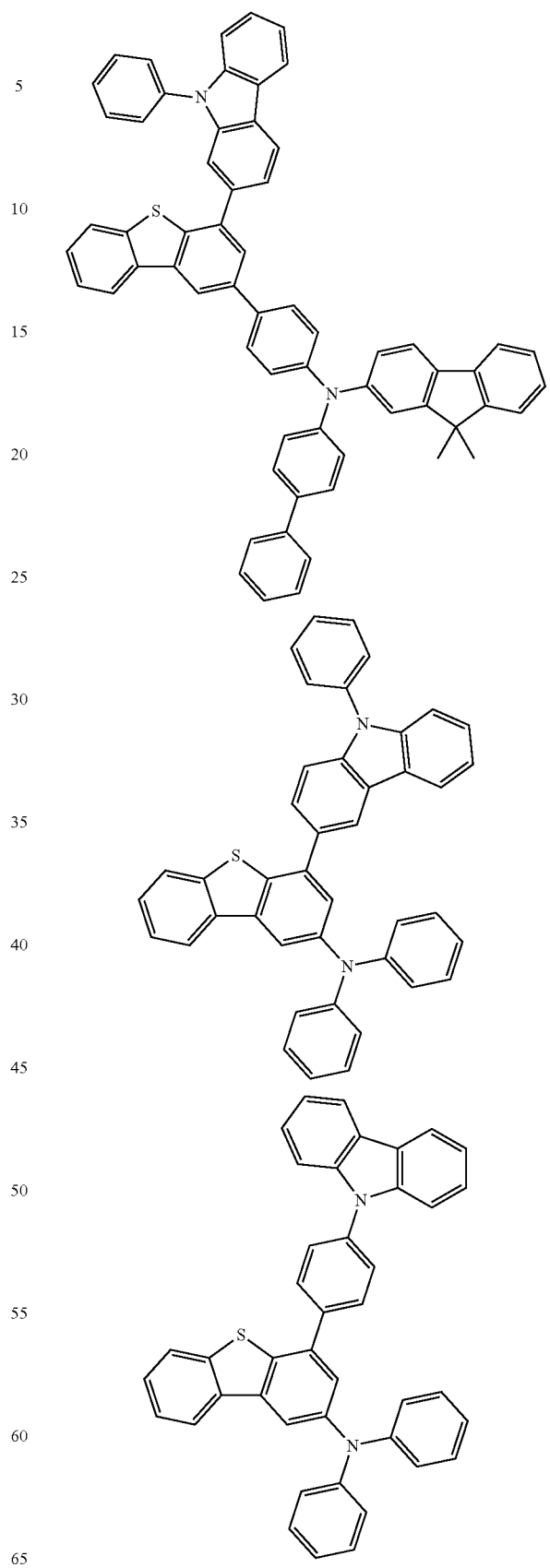

219
-continued
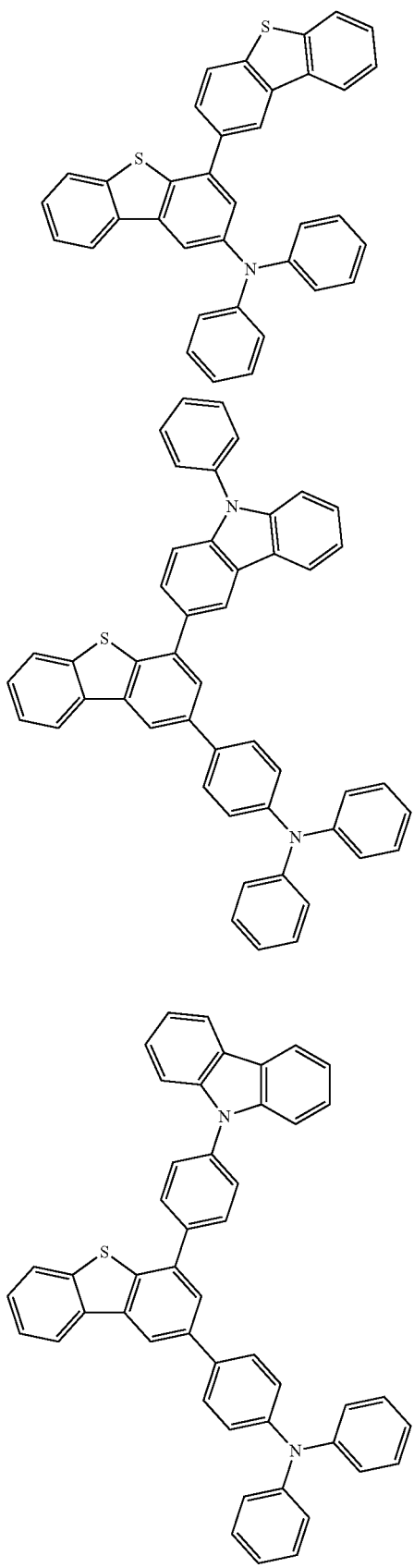
220
-continued
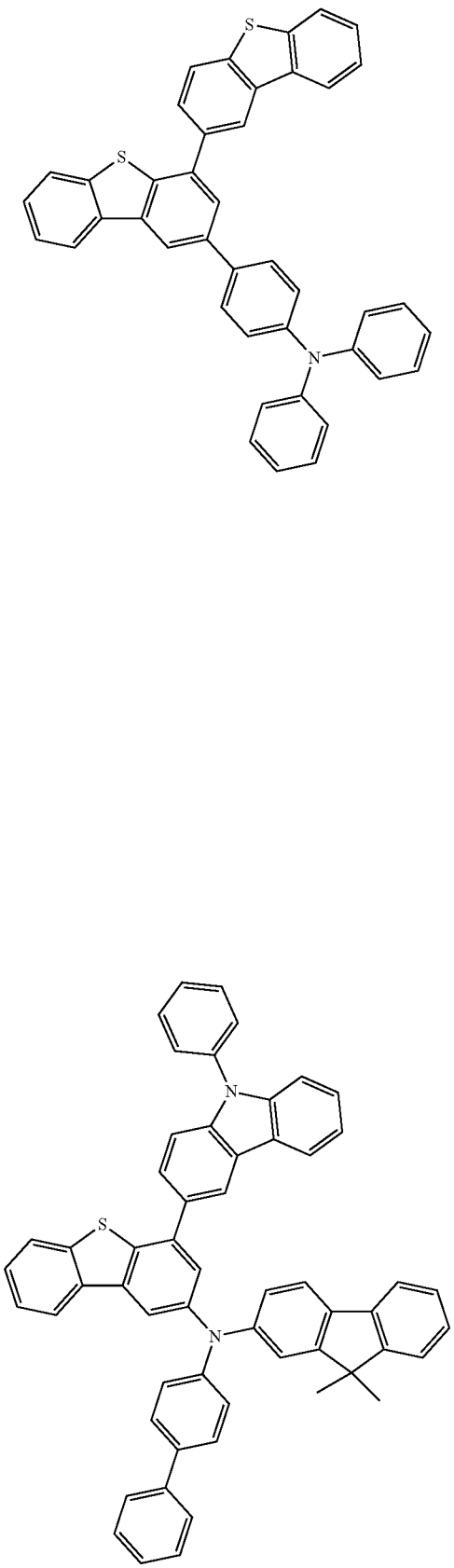

221
-continued
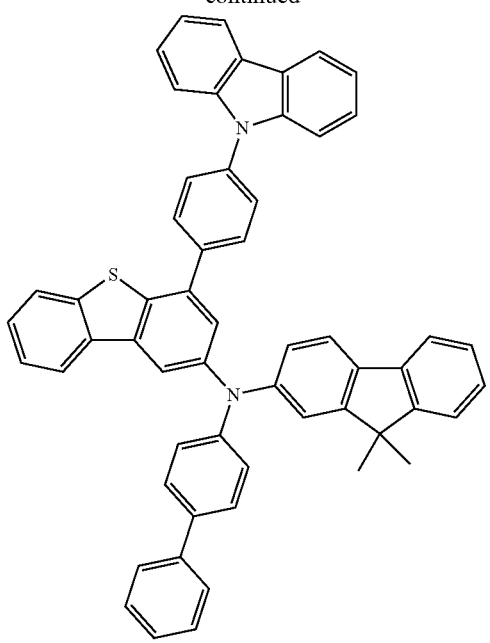
222
-continued
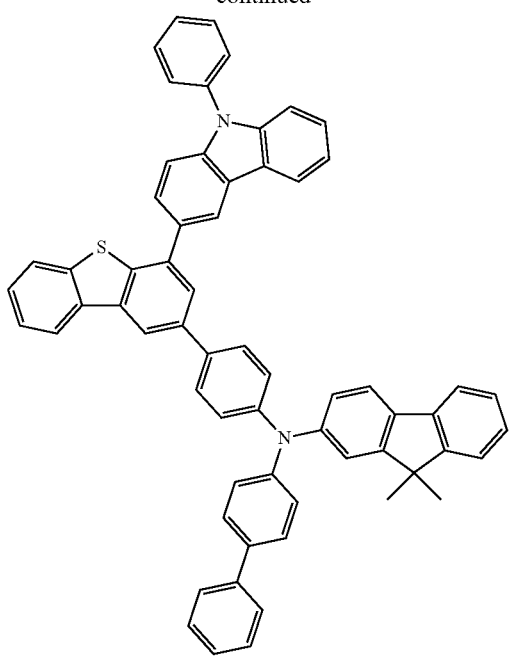
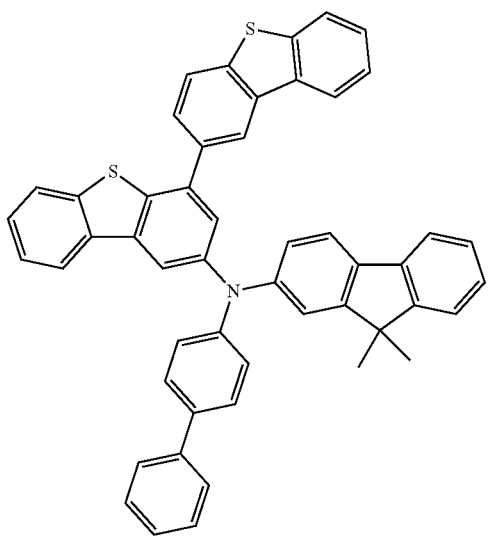
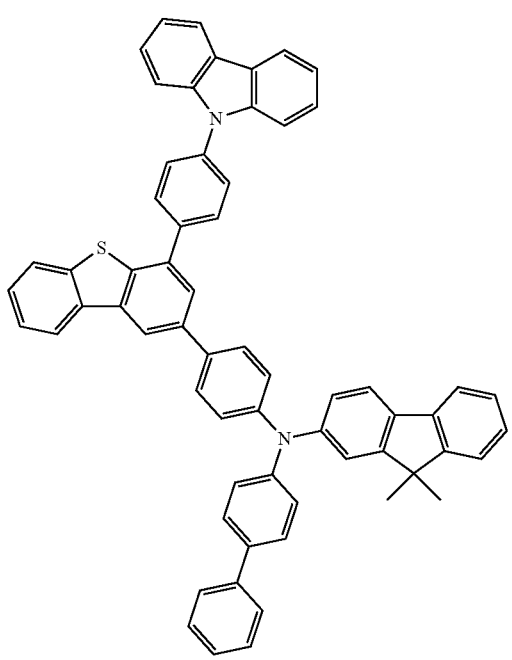

223
-continued
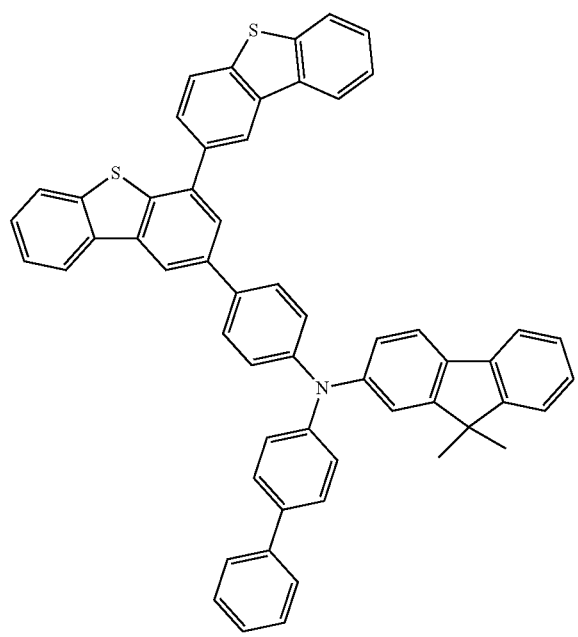
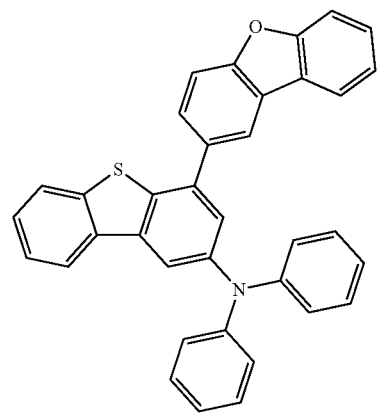
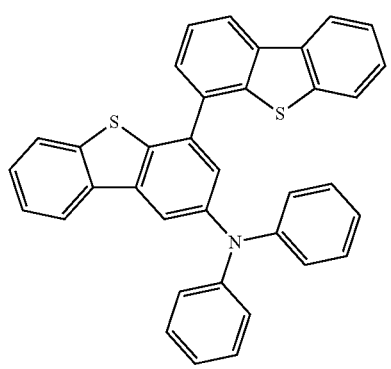
224
-continued
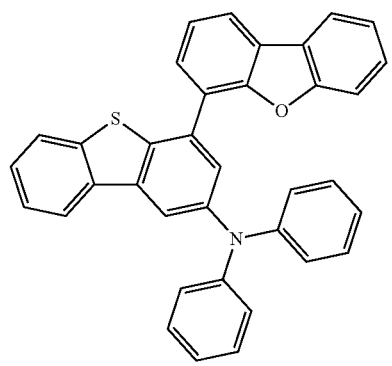
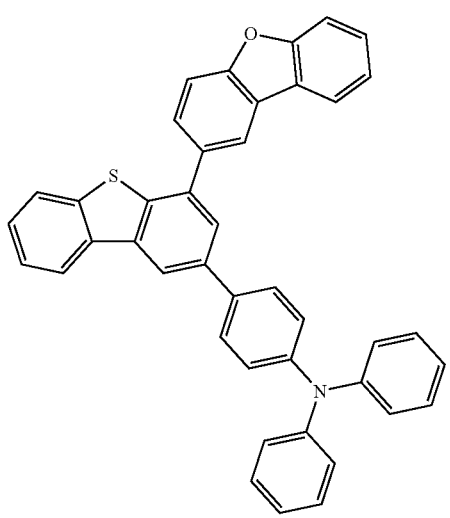
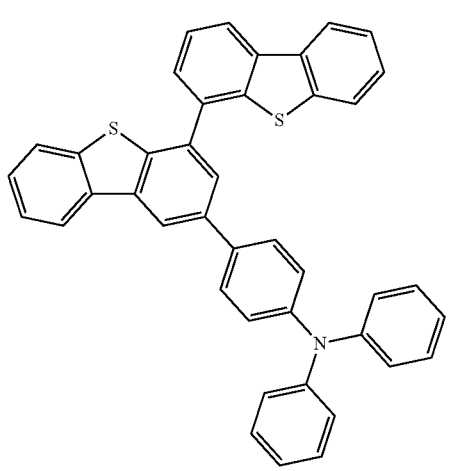

225
-continued
226
-continued
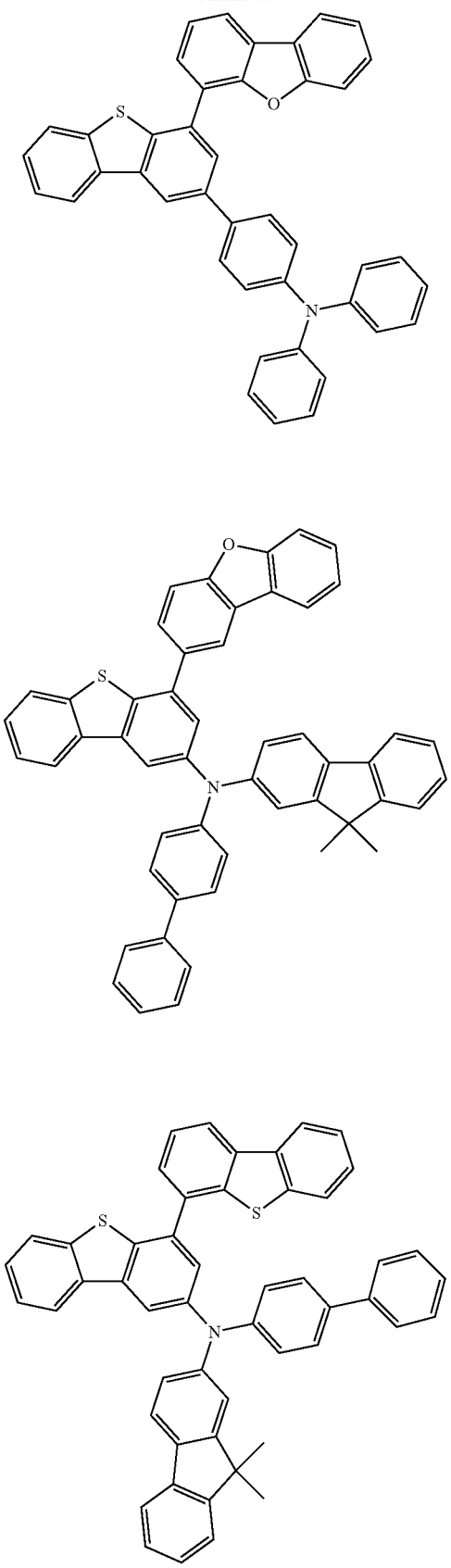
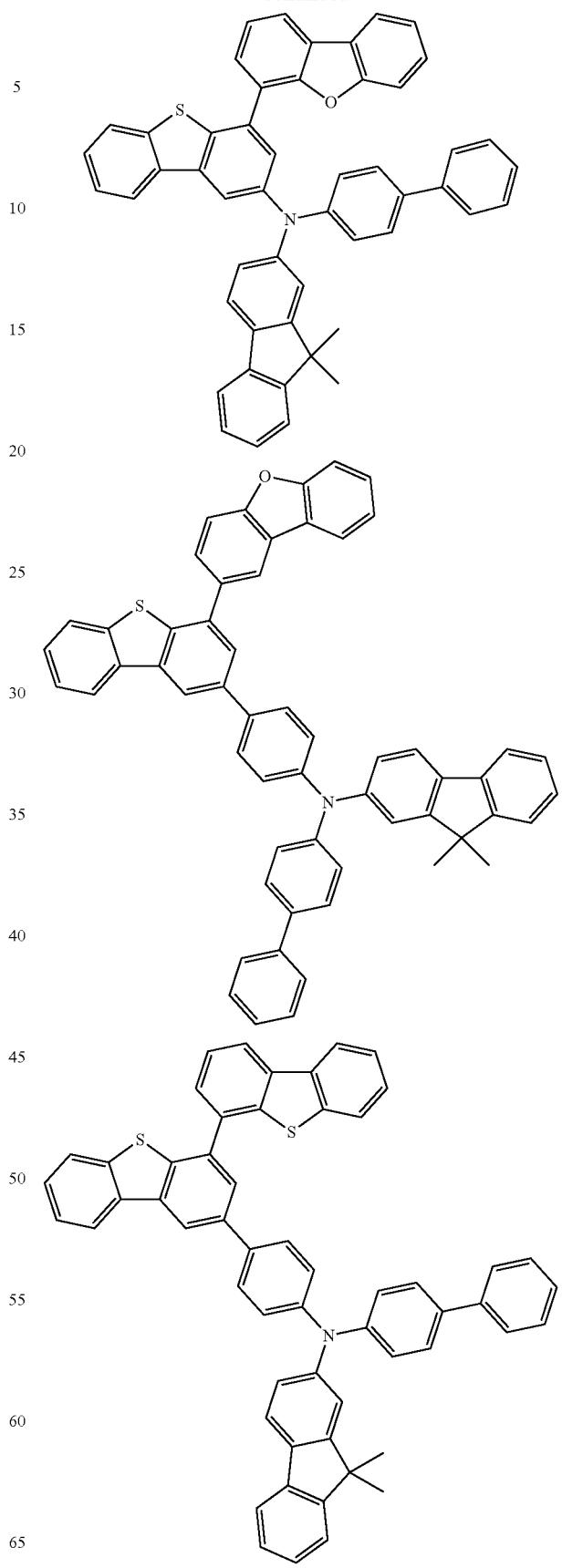

227
-continued
228
-continued
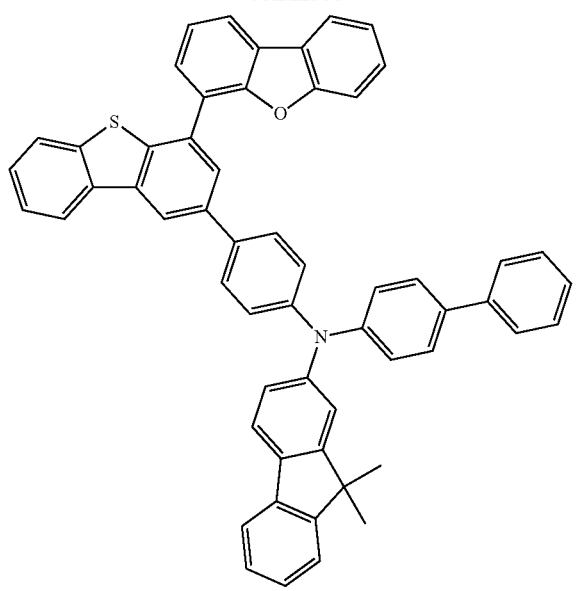
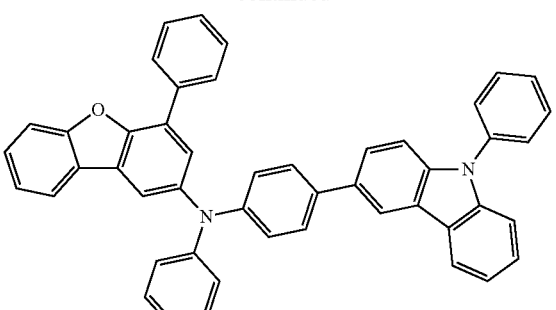
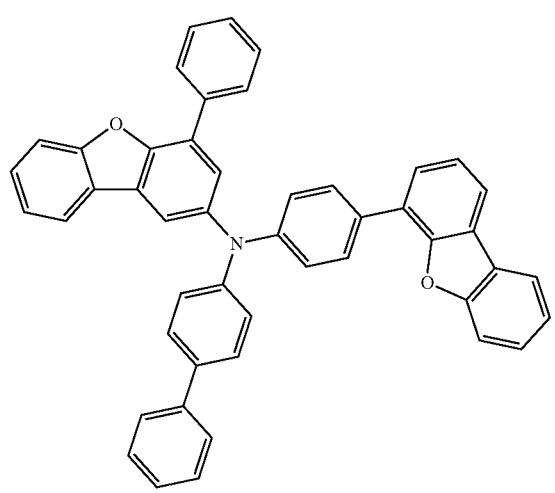
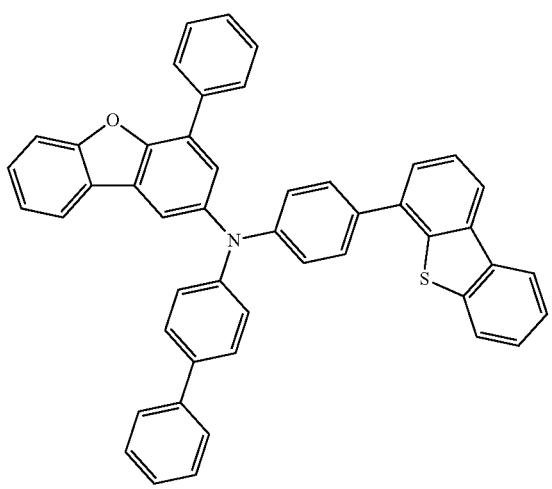
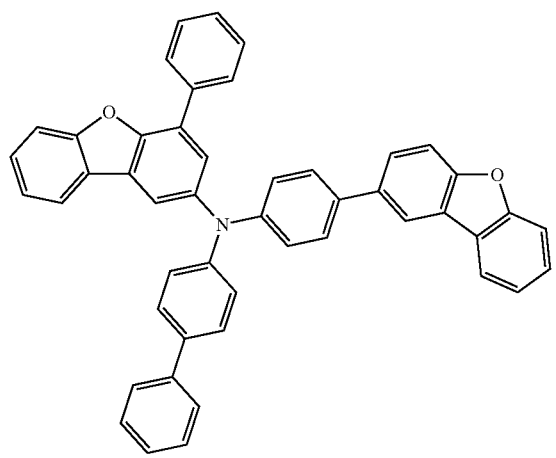
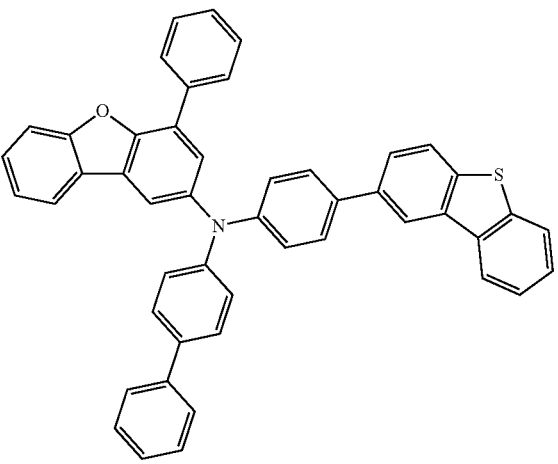

229
-continued
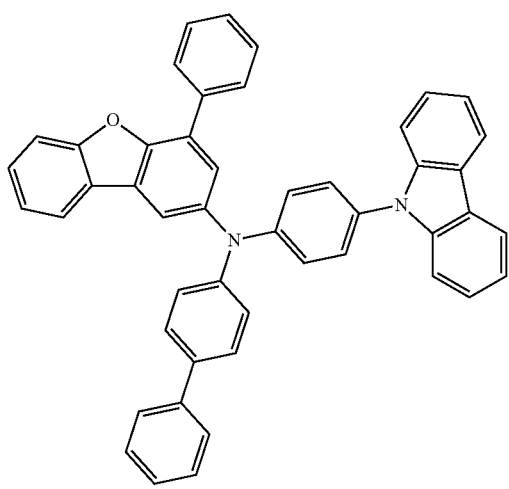
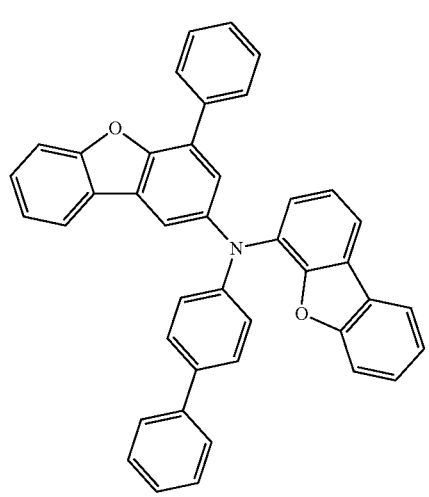
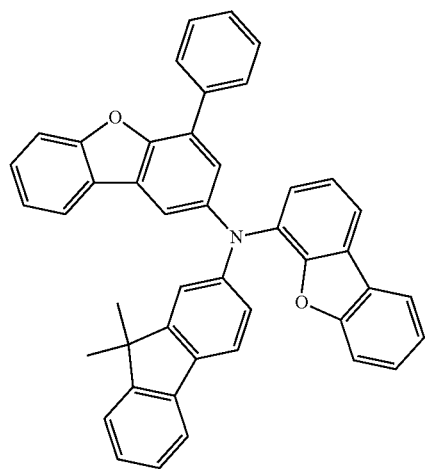
230
-continued
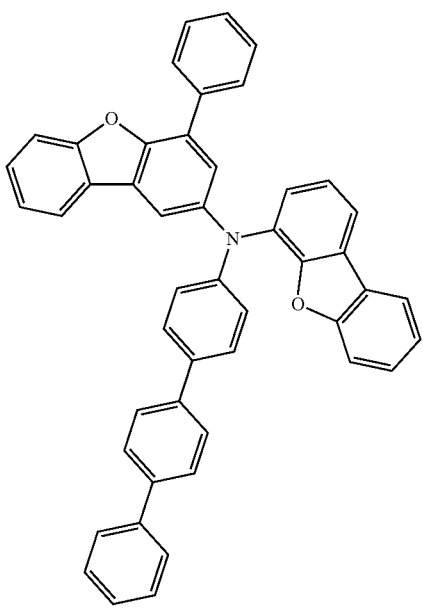
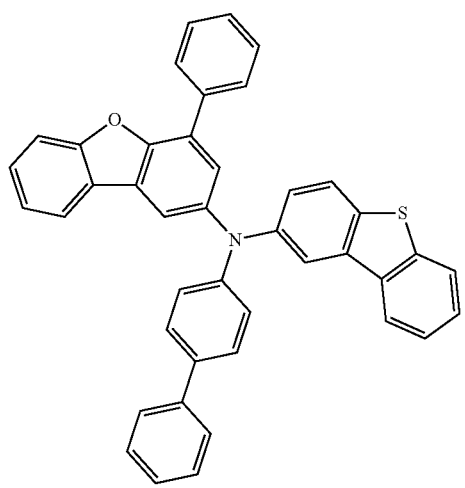
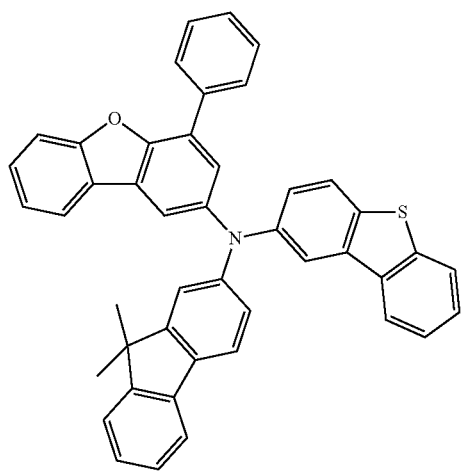

231
-continued
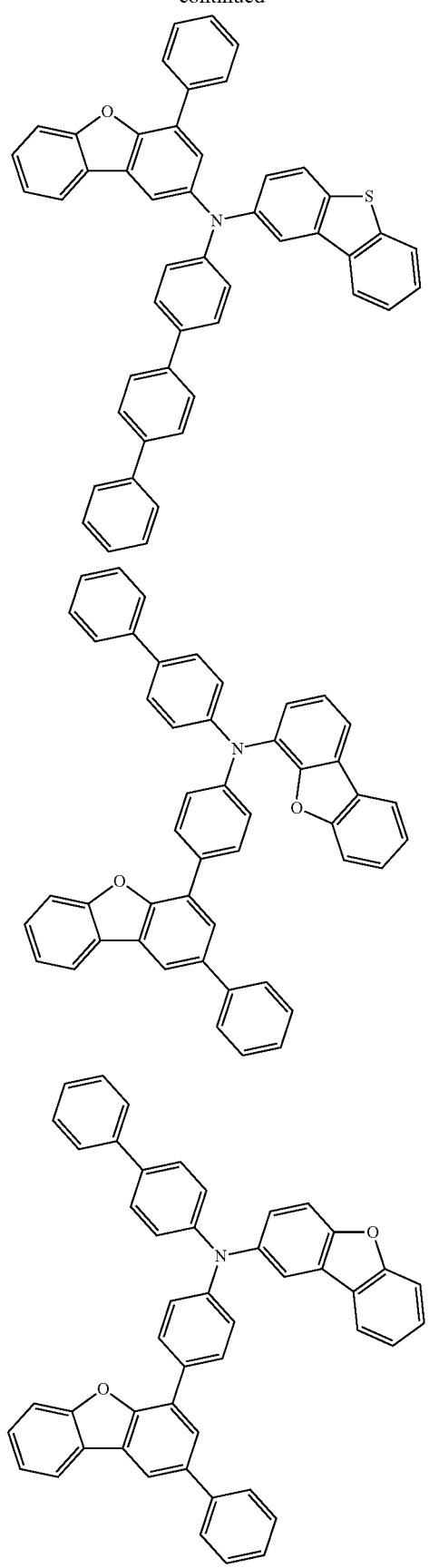
232
-continued
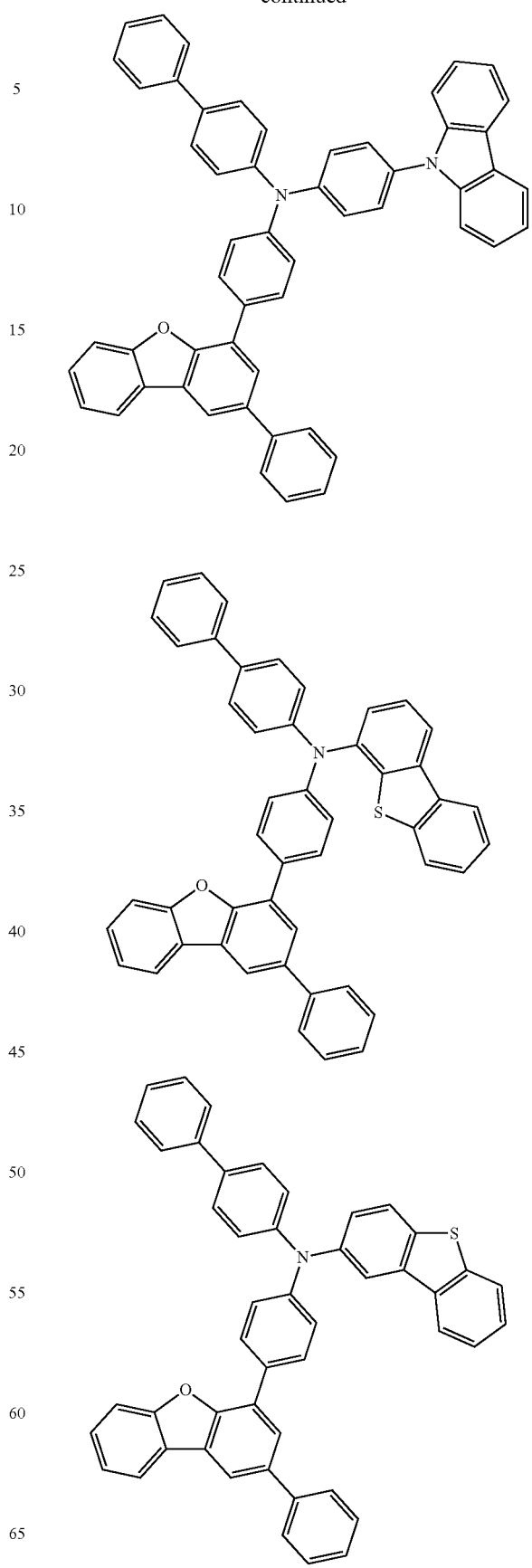

233
-continued
234
-continued
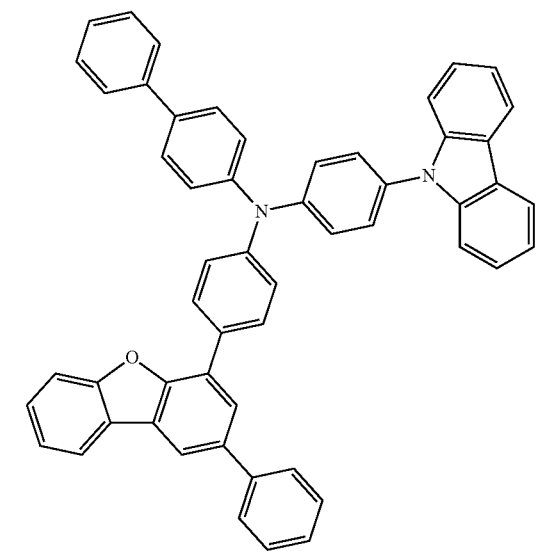
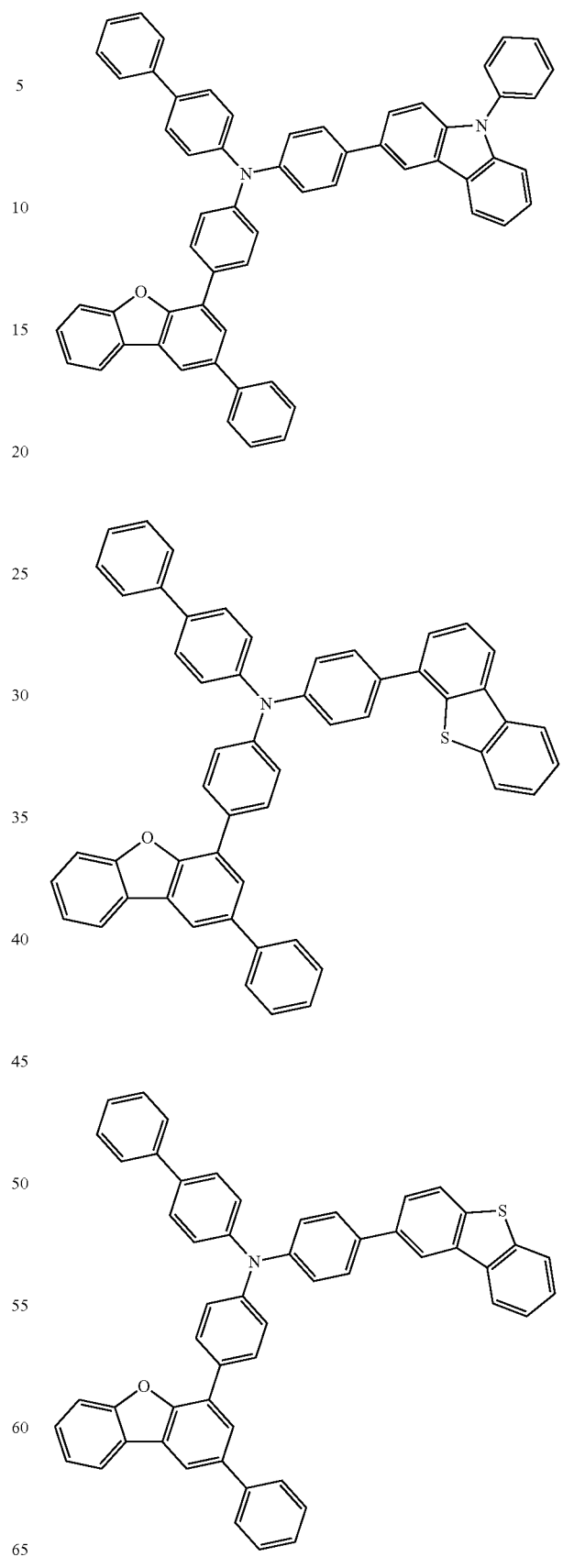

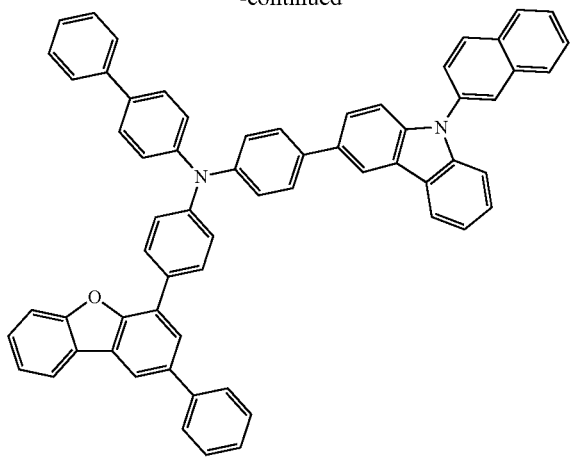

A conjugation length of a compound and an energy band gap thereof are closely related. Specifically, as a conjugation length of a compound increases, an energy band gap thereof decreases.

In the present disclosure, compounds having various energy band gaps may be synthesized by introducing various substituents to A and B positions of the core structure. Normally, an energy band gap is readily controlled by introducing substituents to a core structure having a large energy band gap, however, when a core structure has a small energy band gap, controlling the energy band gap to become large is difficult. In addition, in the present disclosure, HOMO and LUMO energy levels may be controlled as well by introducing various substituents to A and B positions of the core structure.

Furthermore, by introducing various substituents to a core structure having structures as above, compounds having unique properties of the introduced substituents may be synthesized. For example, by introducing substituents normally used as hole injection layer materials, electron blocking layer materials, hole transfer layer materials, light emitting layer materials and electron transfer layer materials used for manufacturing an organic light emitting device to the core structure, materials satisfying needs required for each organic material layer may be synthesized.

In addition, an organic light emitting device according to the present disclosure includes a first electrode, a second electrode, and one or more organic material layers disposed between the first electrode and the second electrode, wherein one or more layers of the organic material layers include the above-mentioned compound.

The organic light emitting device of the present disclosure may be manufactured using common methods and materials for manufacturing organic light emitting devices, except that one or more layers of the organic material layers are formed using the compounds described above.

The organic material layer of the organic light emitting device of the present disclosure may be formed in a single layer structure, but may be formed in a multilayer structure in which two or more organic material layers are laminated. For example, the organic light emitting device of the present disclosure may have a structure including a hole injection layer, a hole transfer layer, an electron blocking layer, a light emitting layer, an electron transfer layer, an electron injection layer and the like as the organic material layer. However, the structure of the organic light emitting device is not limited thereto, and may include less numbers of organic material layers.

Accordingly, in the organic light emitting device of the present disclosure, the organic material layer may include one or more layers of a hole injection layer, an electron blocking layer, a hole transfer layer, and a layer carrying out hole injection and hole transfer at the same time, and one or more layers of the layers may include the compound represented by Chemical Formula 1.

In another embodiment, the organic material layer includes a light emitting layer, and the light emitting layer includes the compound represented by Chemical Formula 1. As one example, the compound represented by Chemical Formula 1 may be included as a host of the light emitting layer. As another example, the compound represented by Chemical Formula 1 may be included as a phosphorescent host of the light emitting layer.

As another example, the organic material layer including the compound represented by Chemical Formula 1 includes the compound represented by Chemical Formula 1 as a host, and includes other organic compounds, metals or metal compounds as a dopant.

As another example, the organic material layer including the compound represented by Chemical Formula 1 includes the compound represented by Chemical Formula 1 as a host, and the compound may be used together with an iridium (Ir)-based dopant.

In addition, the organic material layer may include one or more layers of an electron transfer layer, an electron injection layer, and a layer carrying out electron transfer and electron injection at the same time, and one or more layers of the layers may include the compound.

In another embodiment, the organic material layer of the organic light emitting device includes a hole transfer layer, and the hole transfer layer includes the compound represented by Chemical Formula 1.

In such an organic material layer having a multilayer structure, the compound may be included in a light emitting layer, a layer carrying out hole injection/hole transfer and light emitting at the same time, a layer carrying out hole transfer and light emitting at the same time, or a layer carrying out electron transfer and light emitting at the same time, and the like.

In one embodiment of the present specification, the organic material layer includes a light emitting layer, and the light emitting layer includes a compound represented by the following Chemical Formula A-1.

[Chemcial Formula A-1]

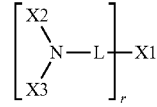

In Chemical Formula A-1,

X1 is a substituted or unsubstituted monovalent or higher benzofluorene group; a substituted or unsubstituted monovalent or higher fluoranthene group; a substituted or unsubstituted monovalent or higher pyrene group; or a substituted or unsubstituted monovalent or higher chrysene group, L is a direct bond; a substituted or unsubstituted arylene group; or a substituted or unsubstituted heteroarylene group, X2 and X3 are the same as or different from each other, and each independently a substituted or unsubstituted aryl group; a substituted or unsubstituted silyl group; a substituted or unsubstituted alkyl group; a substituted or unsubstituted aralkyl group; or a substituted or unsubstituted heteroaryl group, or may bond to each other to form a substituted or unsubstituted ring, r is an integer of 1 or greater, and when r is 2 or greater, substituents in the parentheses are the same as or different from each other.

According to one embodiment of the present specification, the organic material layer includes a light emitting layer, and the light emitting layer includes the compound represented by Chemical Formula A-1 as a dopant of the light emitting layer.

In one embodiment of the present specification, L is a direct bond.

In one embodiment of the present specification, r is 2.

According to one embodiment of the present specification, X1 is a substituted or unsubstituted divalent pyrene group.

In another embodiment, X1 is a divalent pyrene group unsubstituted or substituted with an alkyl group.

In another embodiment, X1 is a divalent pyrene group.

In one embodiment of the present specification, X2 and X3 are the same as or different from each other, and each independently a substituted or unsubstituted aryl group having 6 to 30 carbon atoms; a substituted or unsubstituted alkyl group having 1 to 30 carbon atoms; or a substituted or unsubstituted heteroaryl group having 2 to 30 carbon atoms.

According to one embodiment of the present specification, X2 and X3 are the same as or different from each other, and each independently a substituted or unsubstituted aryl group having 6 to 30 carbon atoms.

In one embodiment of the present specification, X2 and X3 are the same as or different from each other, and each independently an aryl group having 6 to 30 carbon atoms unsubstituted or substituted with a germanium group.

In one embodiment of the present specification, X2 and X3 are a phenyl group unsubstituted or substituted with a trimethylgermanium group.

In one embodiment of the present specification, the organic material layer includes a light emitting layer, and the light emitting layer includes a compound represented by the following Chemical Formula A-2.

[Chemical Formula A-2]

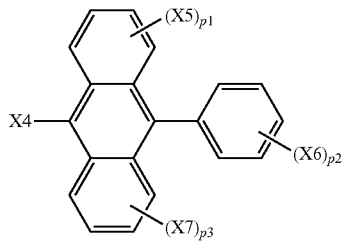

In Chemical Formula A-2,

X4 is a 1-naphthyl group, a 2-naphthyl group, a 1-anthryl group, a 2-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 3-methyl-2-naphthyl group, a 4-methyl-1-naphthyl group or the following chemical formula

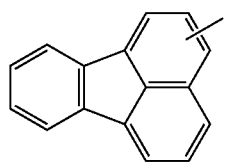

X6 is a phenyl group, a 1-naphthyl group, a 2-naphthyl group, a 1-anthryl group, a 2-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, a 4"-t-butyl-p-terphenyl-4-yl group or a 3-fluoranthenyl group, X5 and X7 are the same as or different from each other, and each independently hydrogen; a substituted or unsubstituted alkyl group; a substituted or unsubstituted alkoxy group; a substituted or unsubstituted aryl group; or a substituted or unsubstituted heteroaryl group, p2 is an integer of 1 to 5, p1 and p3 are each an integer of 1 to 4, and when p1 to p3 are each 2 or greater, substituents in the parentheses are the same as or different from each other.

According to one embodiment of the present specification, the organic material layer includes a light emitting layer, and the light emitting layer includes the compound represented by Chemical Formula A-2 as a host of the light emitting layer.

In one embodiment of the present specification, X4 is a 1-naphthyl group, a 2-naphthyl group, a 1-anthryl group, a 2-anthryl group, a 1-phenanthryl group, a 2-phenanthryl group, a 4-phenanthryl group, a 1-naphthacenyl group or a 1-pyrenyl group.

In one embodiment of the present specification, X4 is a 1-naphthyl group, a 2-naphthyl group or a 1-anthryl group.

In one embodiment of the present specification, X4 is a 1-naphthyl group.

In one embodiment of the present specification, X6 is a phenyl group, a 1-naphthyl group, a 2-naphthyl group, a 1-anthryl group, a 2-anthryl group, a 1-phenanthryl group, a 2-phenanthryl group, a 4-phenanthryl group, a 1-naphthacenyl group or a 1-pyrenyl group.

In one embodiment of the present specification, X6 is a phenyl group, a 1-naphthyl group, a 2-naphthyl group or a 1-anthryl group.

According to one embodiment of the present specification, X6 is a 2-naphthyl group, and p2 is 1.

In one embodiment of the present specification, X5 and X7 are hydrogen.

For example, the structure of the organic light emitting device of the present disclosure may have structures as shown in FIG. 1 and FIG. 2, however, the structure is not limited thereto.

FIG. 1 illustrates a structure of an organic light emitting device in which an anode (2), a light emitting layer (3) and a cathode (4) are consecutively laminated on a substrate (1). In such a structure, the compound may be included in the light emitting layer (3).

FIG. 2 illustrates a structure of an organic light emitting device in which an anode (2), a hole injection layer (5), a hole transfer layer (6), a light emitting layer (7), an electron transfer layer (8) and a cathode (4) are consecutively laminated on a substrate (1). In such a structure, the compound may be included in the hole injection layer (5), the hole transfer layer (6), the light emitting layer (7) or the electron transfer layer (8).

According to one embodiment of the present specification, the organic material layer includes one or more layers of an electron transfer layer, an electron injection layer, and a layer carrying out electron transfer and electron injection at the same time, and one or more layers of the layers include the compound represented by Chemical Formula 1.

According to one embodiment of the present specification, the organic material layer includes a light emitting layer, and the light emitting layer includes the compound represented by Chemical Formula 1 as a host of the light emitting layer.

In one embodiment of the present specification, the organic material layer includes one or more layers of a hole transfer layer, an electron blocking layer, and a layer carrying out hole transfer and electron blocking at the same time, and one layer of the layers includes the compound represented by Chemical Formula 1.

In another embodiment, the organic material layer includes a hole transfer layer and an electron blocking layer, and the hole transfer layer or the electron blocking layer includes the compound represented by Chemical Formula 1.

According to one embodiment of the present specification, the organic material layer includes one or more layers of a hole injection layer, a hole transfer layer, and a layer carrying out hole injection and hole transfer at the same time, and one layer of the layers includes the compound represented by Chemical Formula 1.

In one embodiment of the present specification, the organic material layer includes the compound represented by Chemical Formula 1 as a host, and includes other organic compounds, metals or metal compounds as a dopant.

For example, the organic light emitting device according to the present disclosure may be manufactured by forming an anode on a substrate by depositing a metal, a metal oxide having conductivity, or an alloy thereof using a physical vapor deposition (PVD) method such as sputtering or e-beam evaporation, forming an organic material layer including a hole injection layer, a hole transfer layer, a light emitting layer and an electron transfer layer thereon, and then depositing a material capable of being used as a cathode thereon. In addition to such a method, the organic light emitting device may also be manufactured by consecutively depositing a cathode material, an organic material layer, and an anode material on a substrate.

The organic material layer may have a multilayer structure including a hole injection layer, a hole transfer layer, an electron blocking layer, a light emitting layer, an electron transfer layer and the like, but is not limited thereto, and may have a single layer structure. In addition, the organic material layer may be prepared into less numbers of layers using various polymer materials through a solvent process such as spin coating, dip coating, doctor blading, screen printing, ink jet printing or a thermal transfer method instead of a deposition method.

According to one embodiment of the present specification, the first electrode is an anode, and the second electrode is a cathode.

According to another embodiment of the present specification, the first electrode is a cathode, and the second electrode is an anode.

As the anode material, materials having large work function are normally preferable so that hole injection to an organic material layer is smooth. Specific examples of the anode material capable of being used in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as $ZnO:Al$ or $SnO_2:Sb$; conductive polymers such as poly(3-methyl compound), poly[3,4-(ethylene-1,2-dioxy) compound] (PEDT), polypyrrole and polyaniline, but are not limited thereto.

As the cathode material, materials having small work function are normally preferable so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

As the hole injection material, materials having a highest occupied molecular orbital (HOMO) between the work function of an anode material and the HOMO of surrounding organic material layers are preferable as materials favorably receiving holes from an anode at a low voltage. Specific examples of the hole injection material include metal porphyrins, oligothiophene, arylamine-based organic materials, hexanitrile hexazatriphenylene-based organic materials, quinacridone-based organic materials, perylene-based organic materials, anthraquinone, and polyaniline- and polycompound-based conductive polymers, and the like, but are not limited thereto.

As the hole transfer material, materials having high mobility for holes are suitable as materials receiving holes from an anode or a hole injection layer and transfers the holes to a light emitting layer. Specific examples thereof include arylamine-based organic materials, conductive polymers, block copolymers having conjugated parts and non-conjugated parts together, and the like, but are not limited thereto.

As the light emitting material, materials having favorable quantum efficiency for fluorescence or phosphorescence are preferable as materials capable of emitting light in a visible light region by receiving holes and electrons from a hole transfer layer and an electron transfer layer, respectively, and binding the holes and the electrons. Specific examples thereof include 8-hydroxy-quinoline aluminum complexes ($Alq_3$); carbazole-based compounds; dimerized styryl compounds; BAlq; 10-hydroxybenzo quinoline-metal compounds; benzoxazole-, benzothiazole- and benzimidazole-based compounds; poly(p-phenylenevinylene) (PPV)-based polymers; spiro compounds; polyfluorene, rubrene, and the like, but are not limited thereto.

The organic material layer including the compound represented by Chemical Formula 1 includes the compound represented by Chemical Formula 1 as a host, and the compound may be used together with an iridium (Ir)-based dopant.

The iridium-based complexes used as the dopant are as follows.

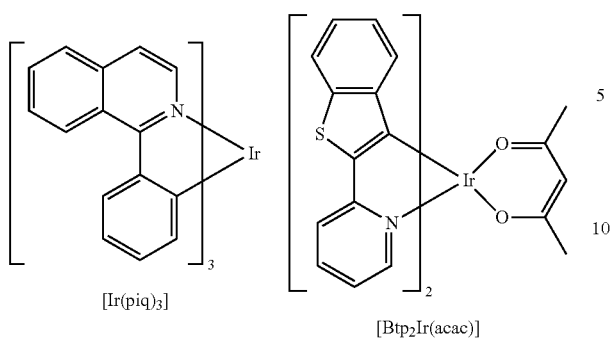

[Ir(piq)₃]    [Btp₂Ir(acac)]

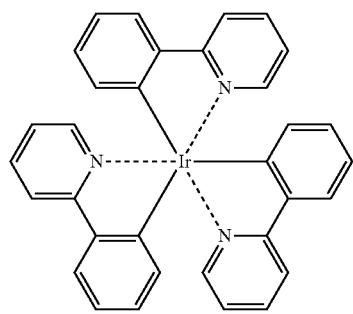

[Ir(mpyp)₃]

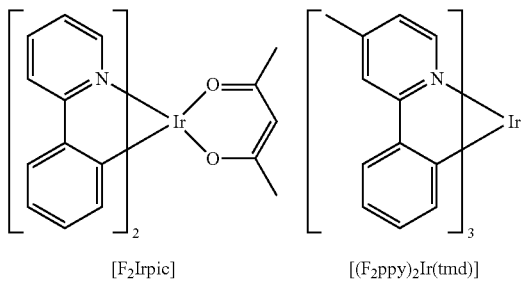

[F₂Irpic]    [(F₂ppy)₂Ir(tmd)]

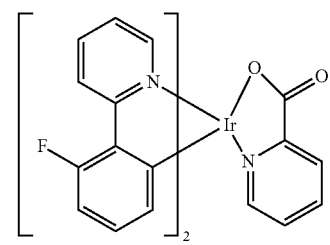

[Ir(dfppz)₃]

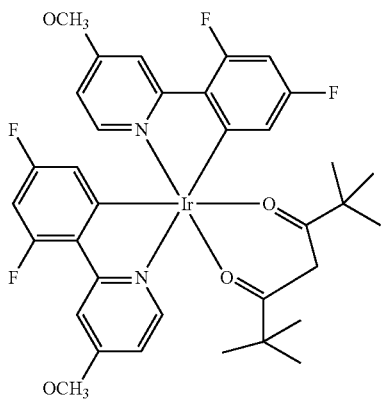

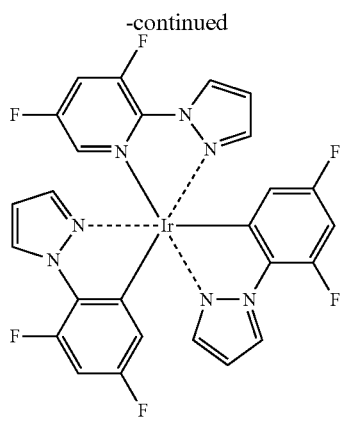

As the electron transfer material, materials having high mobility for electrons are suitable as materials favorably receiving electrons from a cathode and transferring the electrons to a light emitting layer. Specific examples thereof include Al complexes of 8-hydroxyquinoline; complexes including Alq₃; organic radical compounds; hydroxyflavon-metal complexes and the like, but are not limited thereto.

The organic light emitting device according to the present specification may be a top-emission type, a bottom-emission type or a dual-emission type depending on the materials used.

The compound according to the present disclosure may also be used in organic electronic devices including organic solar cells, organic photoconductors, organic transistors and the like on a similar principle as in the organic light emitting device.

Methods for preparing the compound of Chemical Formula 1, and manufacture of an organic light emitting device using the same will be described in detail in the following examples. However, the following examples are for illustrative purposes only, and the scope of the present disclosure is not limited thereto.

Synthesis Example of Intermediate

Intermediates C to J were synthesized according to the following reaction formulae.

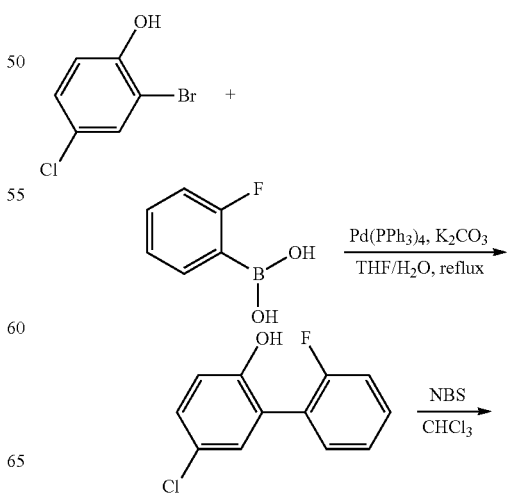

243
-continued
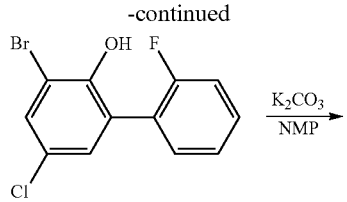
$\xrightarrow{K_2CO_3}{NMP}$
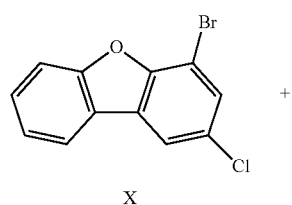
X
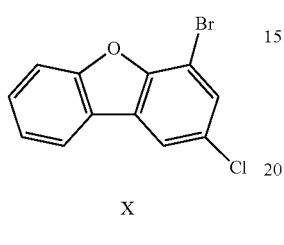 +
X
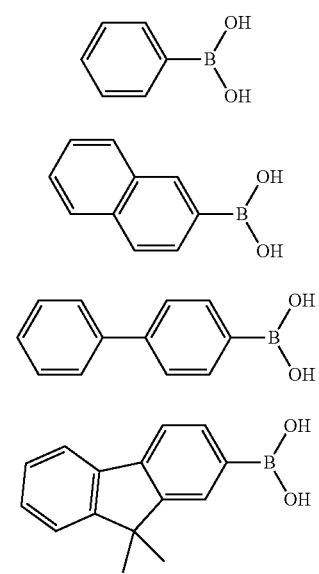
$\xrightarrow{Pd(PPh_3)_4, K_2CO_3}{THF/H_2O, reflux}$
244
-continued
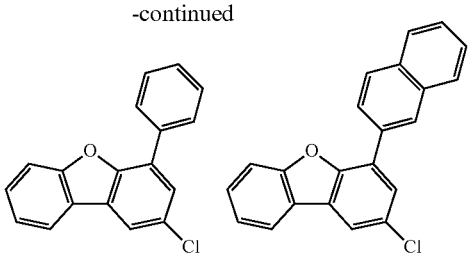
C            D
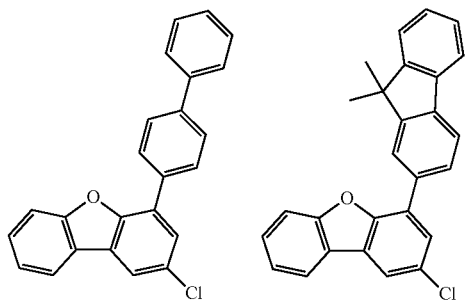
E            F
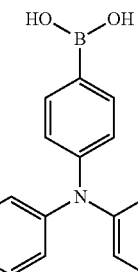
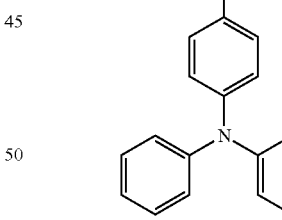 +
X
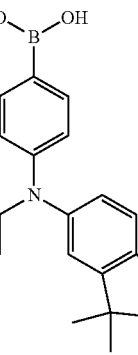
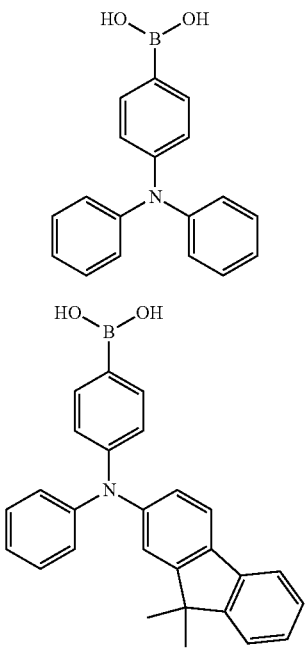
$\xrightarrow{Pd(PPh_3)_4, K_2CO_3}{THF/H_2O, reflux}$

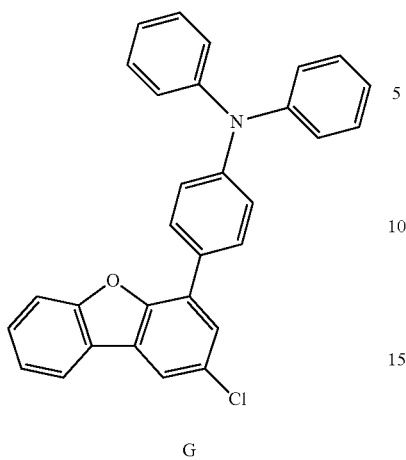
G
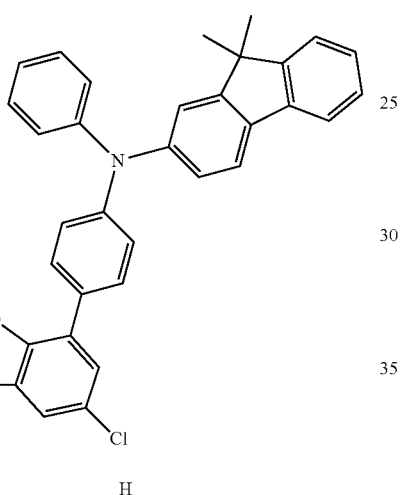
H
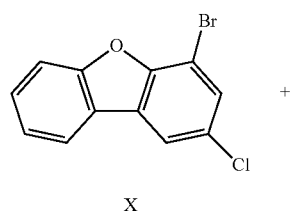
X
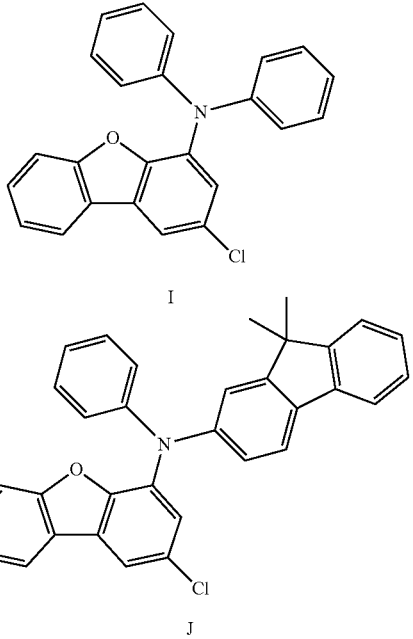
I
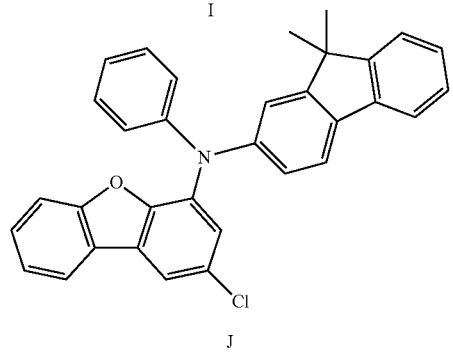
J
In addition, Intermediate X may introduce an amine group to A or B position of Chemical Formula 1 through reaction formulae as follows.
① Introducing an amine group to A position
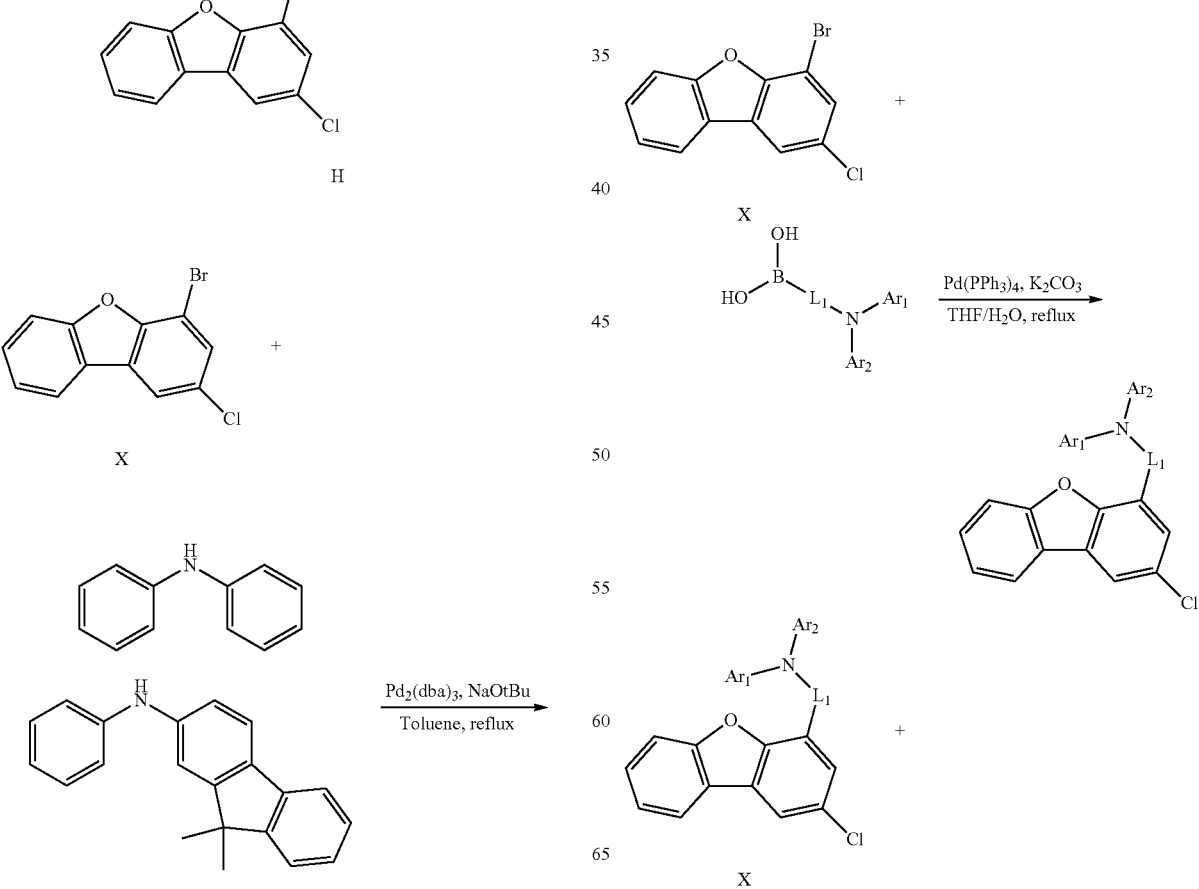

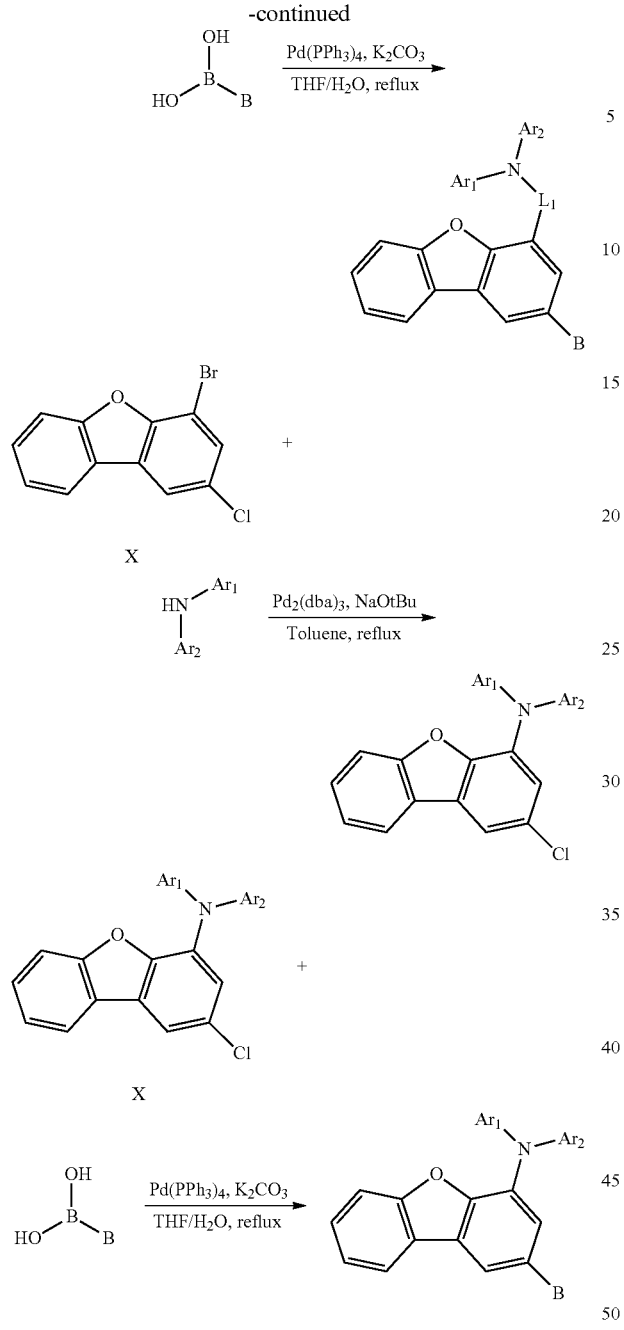

Preparation Example 1-1

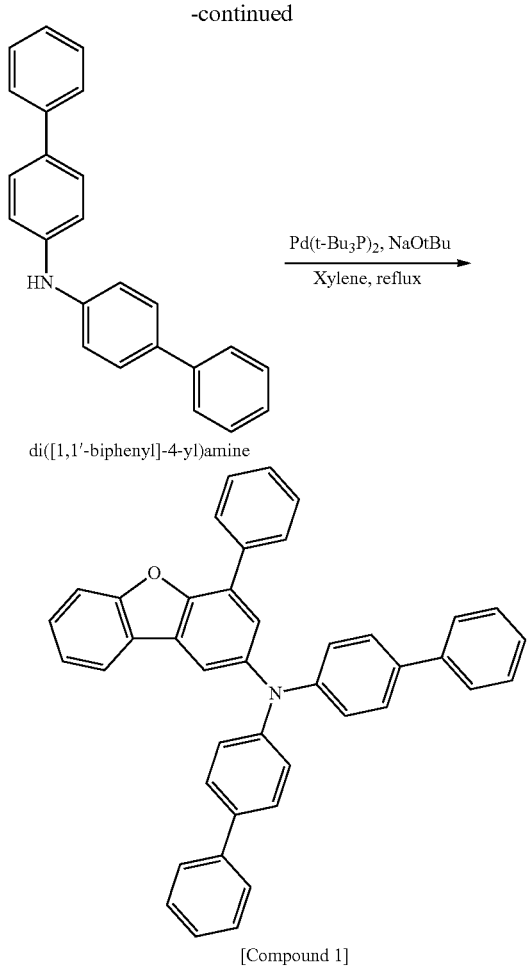

[Compound 1]

After completely dissolving Chemical Formula C (10 g, 35.97 mmol) and di([1,1'-biphenyl]-4-yl)amine (12.70 g, 39.57 mmol) in 150 ml of xylene in a 500 ml round bottom flask under nitrogen atmosphere, sodium tert-butoxide (4.49 g, 46.76 mmol) and then bis(tri-tert-butylphosphine) palladium(0) (0.18 g, 0.36 mmol) were added thereto, and the result was heated and stirred for 3 hours. The temperature was lowered to room temperature, the result was filtered to remove the salts, then xylene was vacuum concentrated, and the result was recrystallized with 230 ml of ethyl acetate to prepare Compound 1 (15.37 g, yield: 76%).

MS[M+H]$^+$=564

Preparation Example 1-2

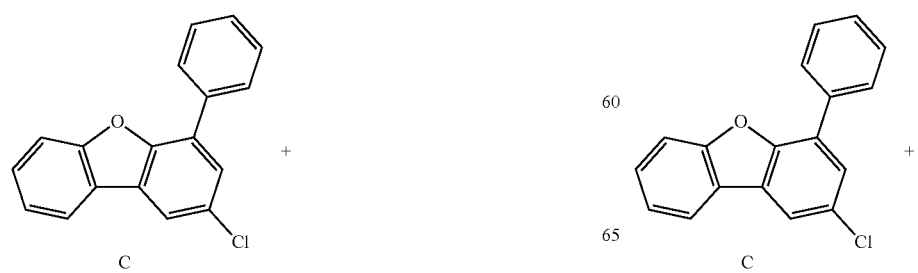

-continued

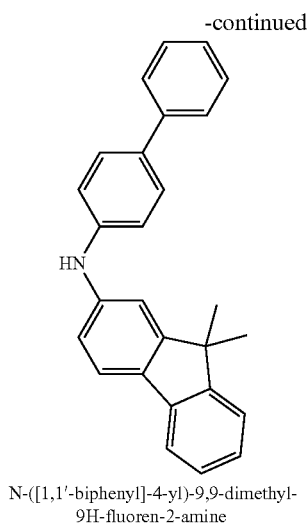

N-([1,1'-biphenyl]-4-yl)-9,9-dimethyl-
9H-fluoren-2-amine

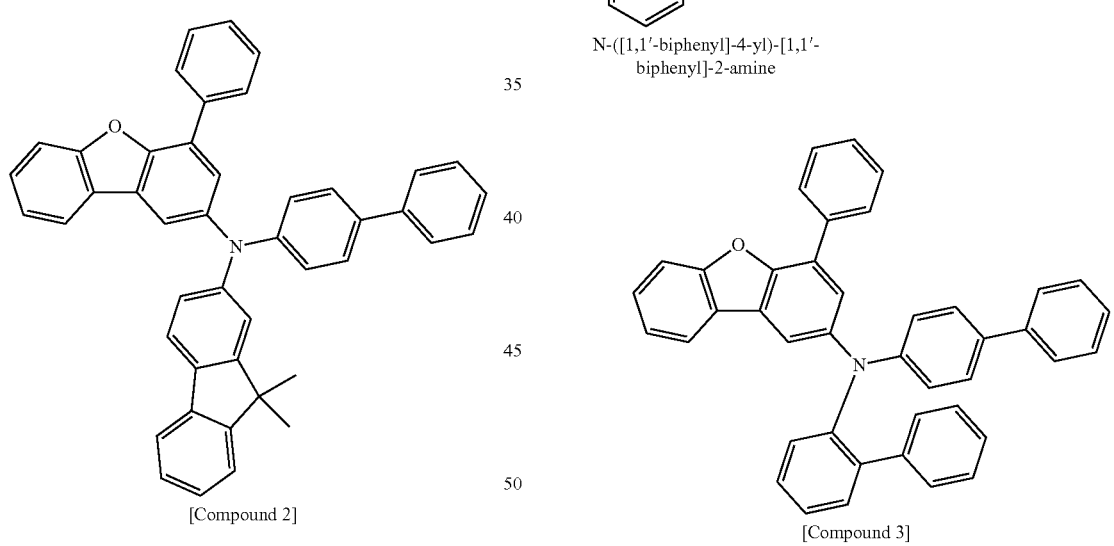

[Compound 2]

After completely dissolving Chemical Formula C (10 g, 35.97 mmol) and N-([1,1'-biphenyl]-4-yl)-9,9-dimethyl-9H-fluoren-2-amine (14.28 g, 39.57 mmol) in 120 ml of xylene in a 500 ml round bottom flask under nitrogen atmosphere, sodium tert-butoxide (4.49 g, 46.76 mmol) and then bis(tri-tert-butylphosphine) palladium(0) (0.18 g, 0.36 mmol) were added thereto, and the result was heated and stirred for 2 hours. The temperature was lowered to room temperature, the result was filtered to remove the salts, then xylene was vacuum concentrated, and the result was recrystallized with 160 ml of ethyl acetate to prepare Compound 2 (13.75 g, yield: 63%).

MS[M+H]$^+$=604

Preparation Example 1-3

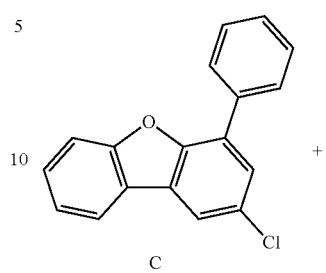

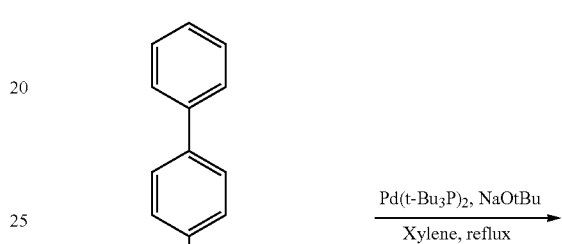

N-([1,1'-biphenyl]-4-yl)-[1,1'-biphenyl]-2-amine

[Compound 3]

After completely dissolving Chemical Formula C (10 g, 35.97 mmol) and N-([1,1'-biphenyl]-4-yl)-[1,1'-biphenyl]-2-amine (12.70 g, 39.57 mmol) in 150 ml of xylene in a 500 ml round bottom flask under nitrogen atmosphere, sodium tert-butoxide (4.49 g, 46.76 mmol) and then bis(tri-tert-butylphosphine) palladium(0) (0.18 g, 0.36 mmol) were added thereto, and the result was heated and stirred for 3 hours. The temperature was lowered to room temperature, the result was filtered to remove the salts, then xylene was vacuum concentrated, and the result was recrystallized with 220 ml of ethyl acetate to prepare Compound 3 (13.84 g, yield: 68%).

MS[M+H]$^+$=564

Preparation Example 1-4

[Compound 4]

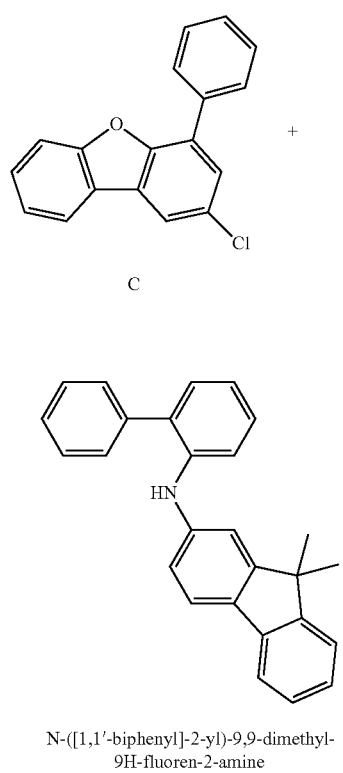

N-([1,1'-biphenyl]-2-yl)-9,9-dimethyl-9H-fluoren-2-amine

Pd(t-Bu₃P)₂, NaOtBu
Xylene, reflux

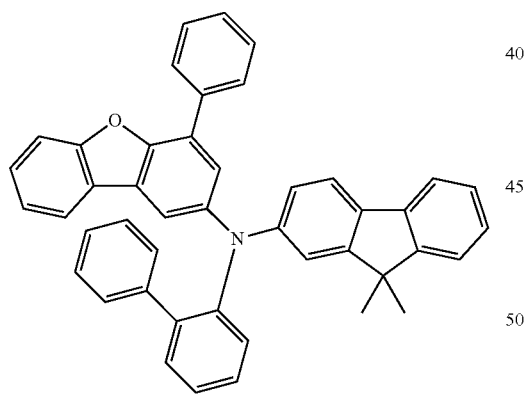

After completely dissolving Chemical Formula C (10 g, 35.97 mmol) and N-([1,1'-biphenyl]-2-yl)-9,9-dimethyl-9H-fluoren-2-amine (14.28 g, 39.57 mmol) in 120 ml of xylene in a 500 ml round bottom flask under nitrogen atmosphere, sodium tert-butoxide (4.49 g, 46.76 mmol) and then bis(tri-tert-butylphosphine) palladium(0) (0.18 g, 0.36 mmol) were added thereto, and the result was heated and stirred for 4 hours. The temperature was lowered to room temperature, the result was filtered to remove the salts, then xylene was vacuum concentrated, and the result was recrystallized with 130 ml of ethyl acetate to prepare Compound 4 (11.92 g, yield: 55%).
MS[M+H]¹=604

Preparation Example 1-5

[Compound 5]

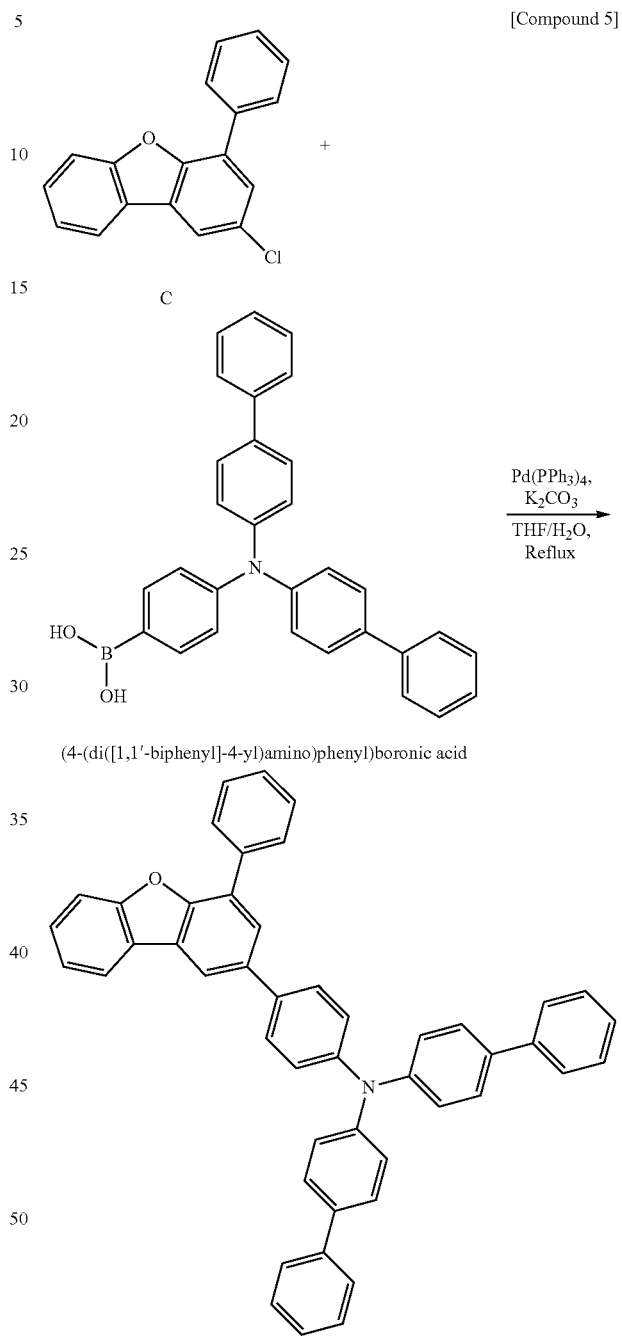

(4-(di([1,1'-biphenyl]-4-yl)amino)phenyl)boronic acid

Pd(PPh₃)₄, K₂CO₃
THF/H₂O, Reflux

After completely dissolving Compound C (10.0 g, 35.97 mmol) and (4-(di([1,1'-biphenyl]-4-yl)amino)phenyl)boronic acid (18.24 g, 41.37 mmol) in 320 ml of tetrahydrofuran in a 500 ml round bottom flask under nitrogen atmosphere, an aqueous 2 M potassium carbonate solution (160 ml) and then tetrakis-(triphenylphosphine) palladium (0.42 g, 0.36 mmol) were added thereto, and the result was heated and stirred for 5 hours. The temperature was lowered to room temperature, the water layer was removed, and the result was dried with anhydrous magnesium sulfate, vacuum concentrated, and then recrystallized with 340 ml of ethyl acetate to prepare Compound 5 (18.66 g, yield: 81%).
MS[M+H]⁺=640

Preparation Example 1-6

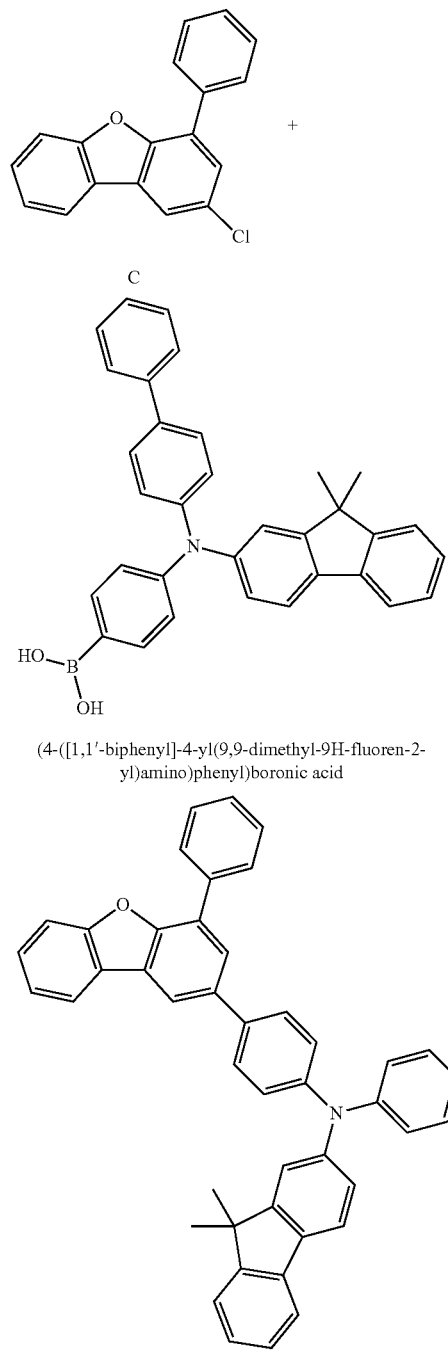

(4-([1,1'-biphenyl]-4-yl(9,9-dimethyl-9H-fluoren-2-yl)amino)phenyl)boronic acid

After completely dissolving Compound C (10.0 g, 35.97 mmol) and (4-([1,1'-biphenyl]-4-yl(9,9-dimethyl-9H-fluoren-2-yl)amino)phenyl)boronic acid (19.90 g, 41.37 mmol) in 280 ml of tetrahydrofuran in a 500 ml round bottom flask under nitrogen atmosphere, an aqueous 2 M potassium carbonate solution (140 ml) and then tetrakis-(triphenylphosphine)palladium (0.42 g, 0.36 mmol) were added thereto, and the result was heated and stirred for 4 hours. The temperature was lowered to room temperature, the water layer was removed, and the result was dried with anhydrous magnesium sulfate, vacuum concentrated, and then recrystallized with 270 ml of ethyl acetate to prepare Compound 6 (16.11 g, yield: 66%).

MS[M+H]$^+$=680

Preparation Example 1-7

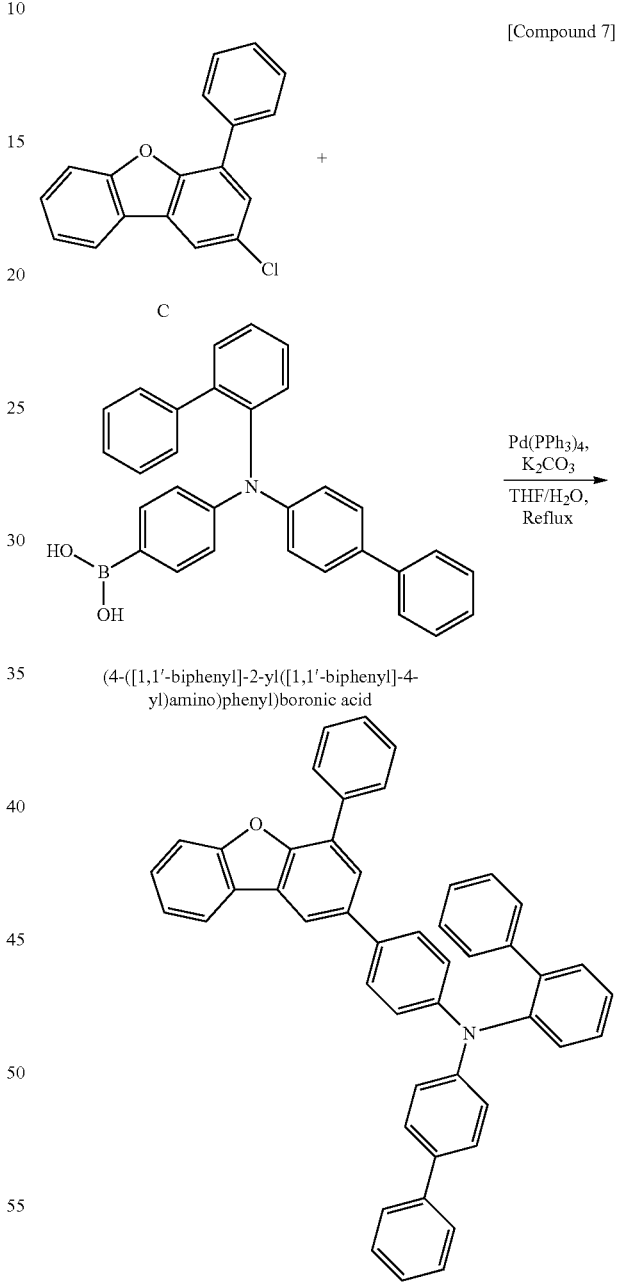

(4-([1,1'-biphenyl]-2-yl([1,1'-biphenyl]-4-yl)amino)phenyl)boronic acid

After completely dissolving Compound C (10.0 g, 35.97 mmol) and (4-([1,1'-biphenyl]-2-yl([1,1'-biphenyl]-4-yl)amino)phenyl)boronic acid (18.24 g, 41.37 mmol) in 260 ml of tetrahydrofuran in a 500 ml round bottom flask under nitrogen atmosphere, an aqueous 2 M potassium carbonate solution (130 ml) and then tetrakis-(triphenylphosphine) palladium (0.42 g, 0.36 mmol) were added thereto, and the result was heated and stirred for 8 hours. The temperature was lowered to room temperature, the water layer was removed, and the result was dried with anhydrous magnesium sulfate, vacuum concentrated, and then recrystallized with 290 ml of ethyl acetate to prepare Compound 7 (16.79 g, yield: 72%).

MS[M+H]$^+$=640

Preparation Example 1-8

After completely dissolving Compound C (10.0 g, 35.97 mmol) and (4-([1,1'-biphenyl]-2-yl(9,9-dimethyl-9H-fluoren-2-yl)amino)phenyl)boronic acid (19.90 g, 41.37 mmol) in 240 ml of tetrahydrofuran in a 500 ml round bottom flask under nitrogen atmosphere, an aqueous 2 M potassium carbonate solution (120 ml) and then tetrakis-(triphenylphosphine)palladium (0.42 g, 0.36 mmol) were added thereto, and the result was heated and stirred for 4 hours. The temperature was lowered to room temperature, the water layer was removed, and the result was dried with anhydrous magnesium sulfate, vacuum concentrated, and then recrystallized with 280 ml of ethyl acetate to prepare Compound 8 (14.50 g, yield: 59%).

MS[M+H]$^+$=680

Preparation Example 1-9

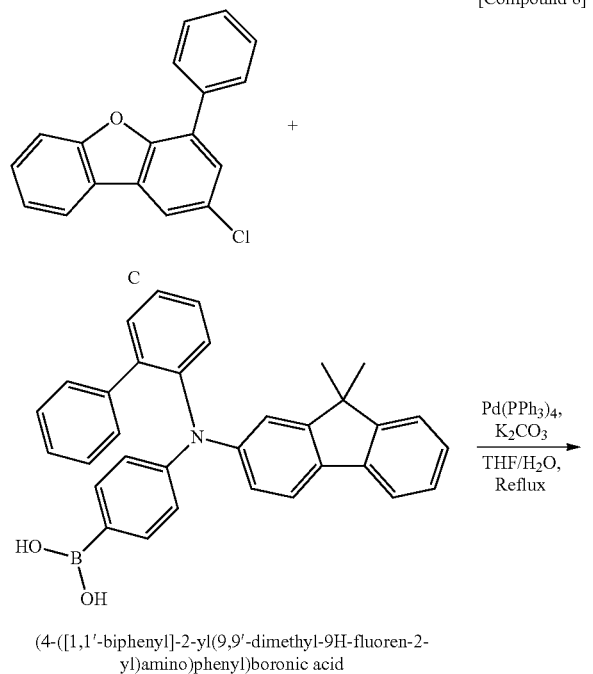

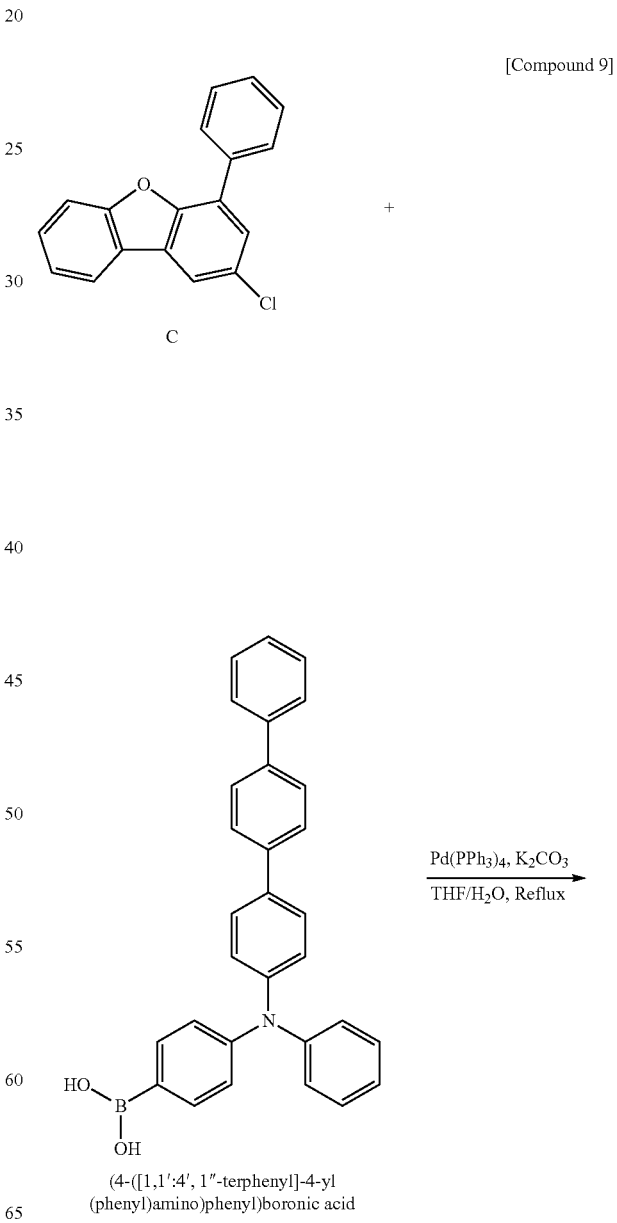

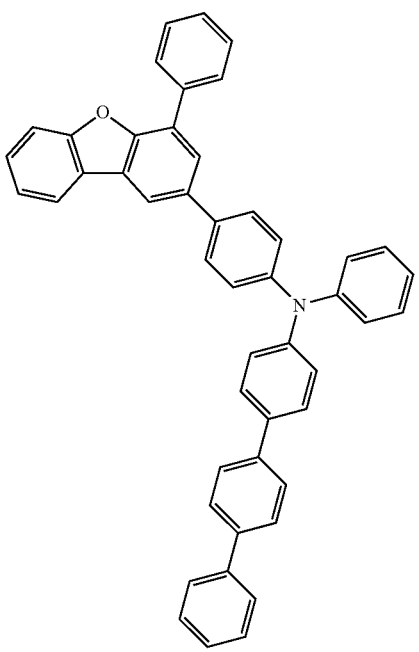

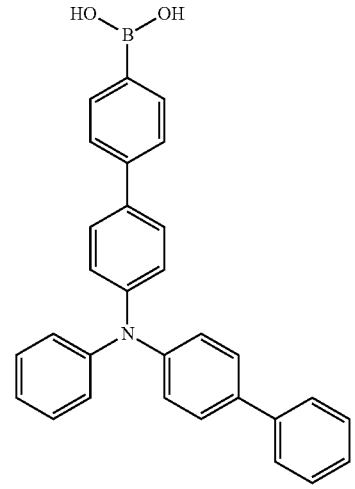

(4'-([1,1'-biphenyl]-4-yl(phenyl)amino)-[1,1'-biphenyl]-4-yl)boronic acid

After completely dissolving Compound C (10.0 g, 35.97 mmol) and (4-([1,1':4',1"-terphenyl]-4-yl(phenyl)amino)phenyl)boronic acid (18.24 g, 41.37 mmol) in 320 ml of tetrahydrofuran in a 500 ml round bottom flask under nitrogen atmosphere, an aqueous 2 M potassium carbonate solution (160 ml) and then tetrakis-(triphenylphosphine)palladium (0.42 g, 0.36 mmol) were added thereto, and the result was heated and stirred for 5 hours. The temperature was lowered to room temperature, the water layer was removed, and the result was dried with anhydrous magnesium sulfate, vacuum concentrated, and then recrystallized with 340 ml of ethyl acetate to prepare Compound 9 (17.45 g, yield: 76%).

MS[M+H]$^+$=640

Preparation Example 1-10

[Compound 10]

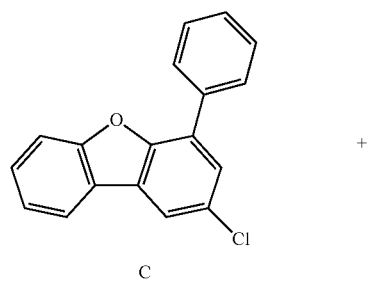

+

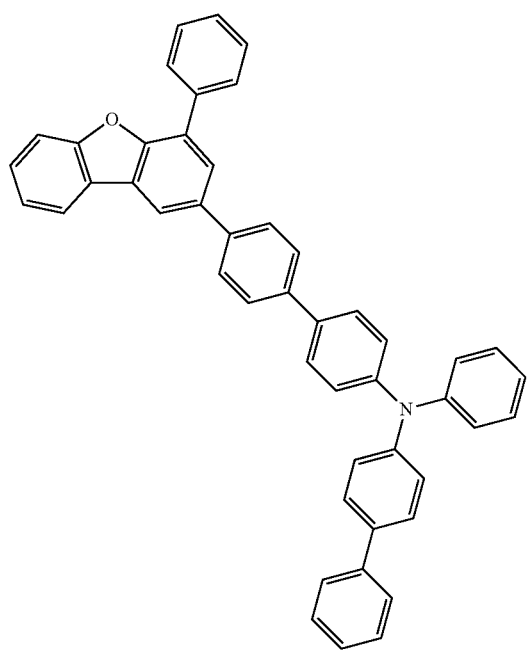

After completely dissolving Compound C (10.0 g, 35.97 mmol) and (4'-([1,1'-biphenyl]-4-yl(phenyl)amino)-[1,1'-biphenyl]-4-yl)boronic acid (18.24 g, 41.37 mmol) in 320 ml of tetrahydrofuran in a 500 ml round bottom flask under nitrogen atmosphere, an aqueous 2 M potassium carbonate solution (160 ml) and then tetrakis-(triphenylphosphine)palladium (0.42 g, 0.36 mmol) were added thereto, and the result was heated and stirred for 5 hours. The temperature was lowered to room temperature, the water layer was removed, and the result was dried with anhydrous magnesium sulfate, vacuum concentrated, and then recrystallized with 340 ml of ethyl acetate to prepare Compound 10 (20.44 g, yield: 89%).

MS[M+H]$^+$=640

Preparation Example 1-11

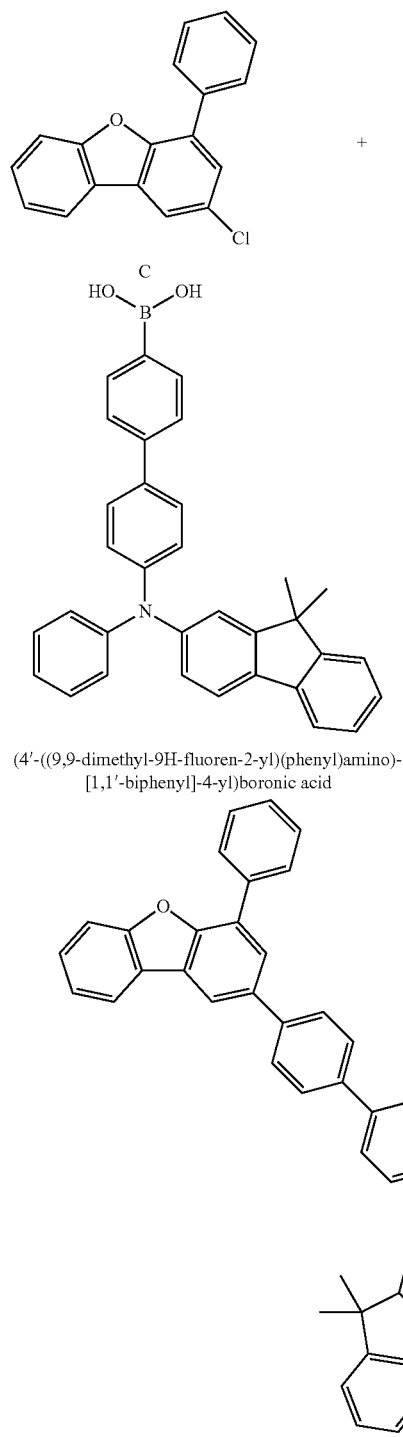

(4'-((9,9-dimethyl-9H-fluoren-2-yl)(phenyl)amino)-[1,1'-biphenyl]-4-yl)boronic acid After completely dissolving Compound C (10.0 g, 35.97 mmol) and (4'-((9,9-dimethyl-9H-fluoren-2-yl)(phenyl)amino)-[1,1'-biphenyl]-4-yl)boronic acid (19.90 g, 41.37 mmol) in 240 ml of tetrahydrofuran in a 500 ml round bottom flask under nitrogen atmosphere, an aqueous 2 M potassium carbonate solution (120 ml) and then tetrakis-(triphenylphosphine) palladium (0.42 g, 0.36 mmol) were added thereto, and the result was heated and stirred for 9 hours. The temperature was lowered to room temperature, the water layer was removed, and the result was dried with anhydrous magnesium sulfate, vacuum concentrated, and then recrystallized with 220 ml of ethyl acetate to prepare Compound 11 (18.69 g, yield: 76%).

MS[M+H]$^+$=680

Preparation Example 1-12

Syntheses of Following Compounds 12 to 22

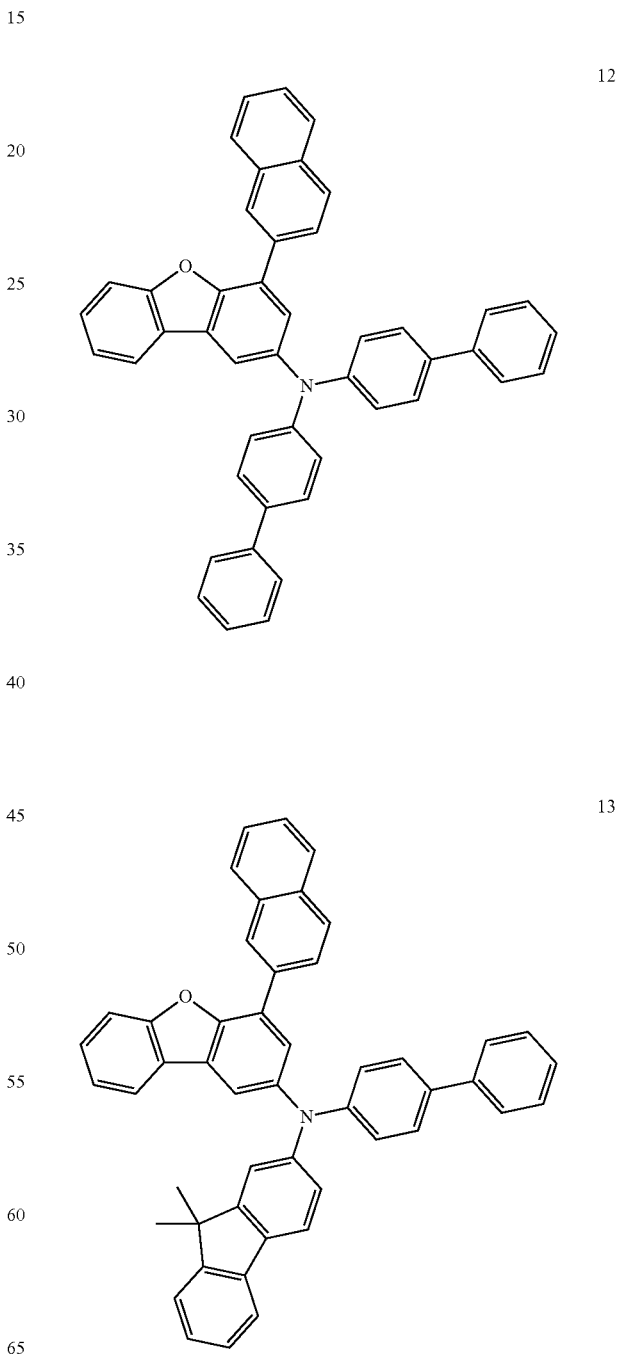

261
14
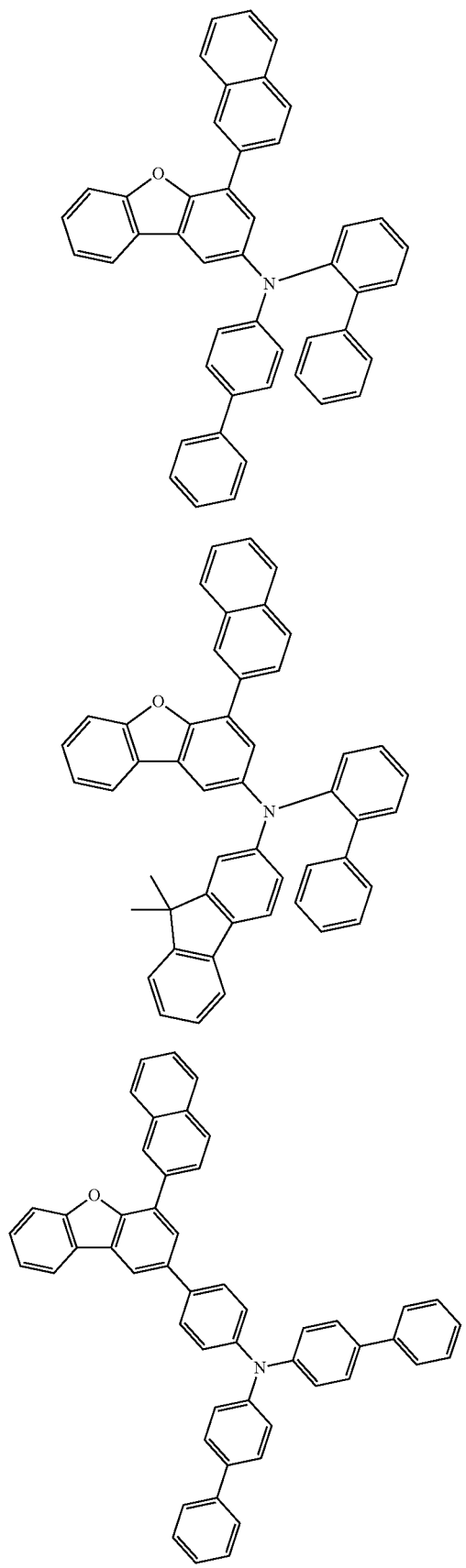
262
17
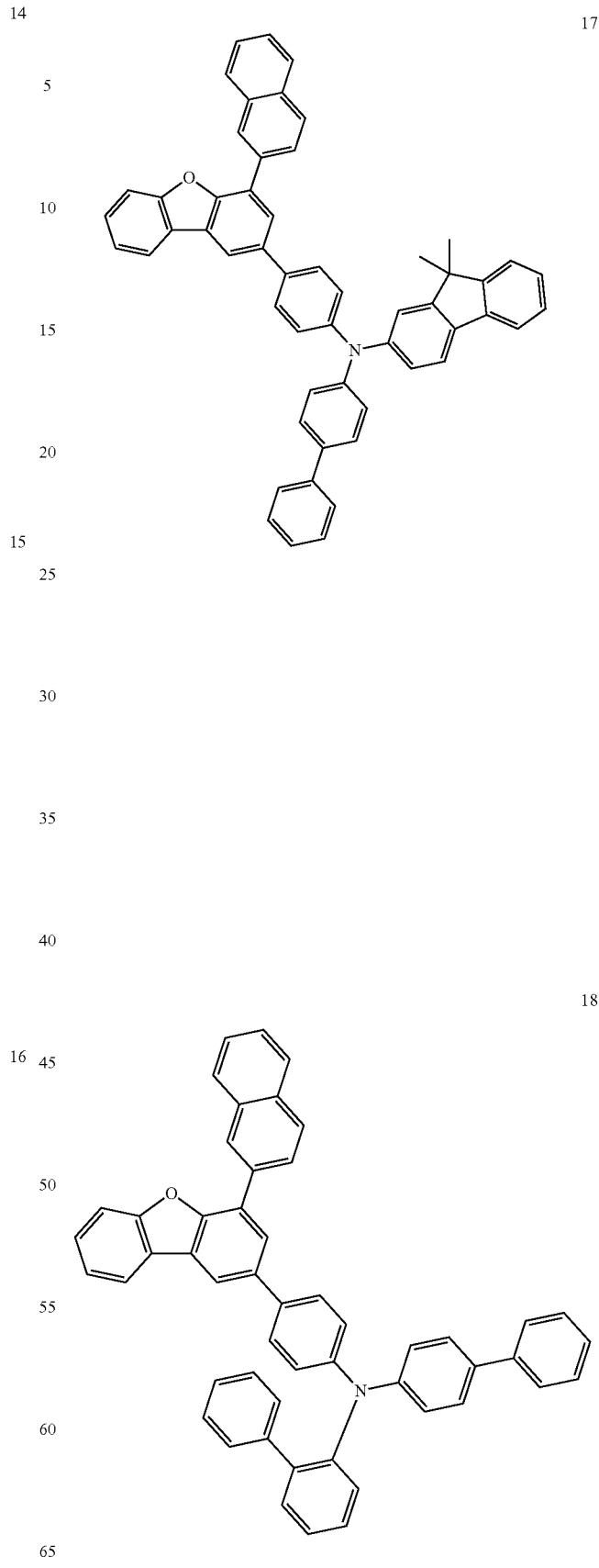
18

19
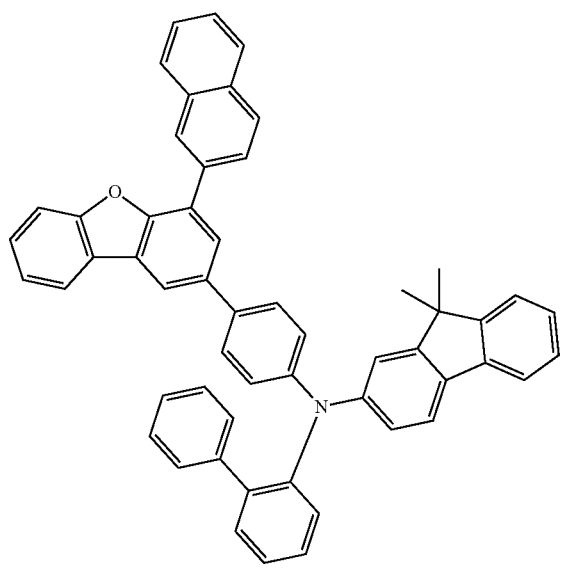
20
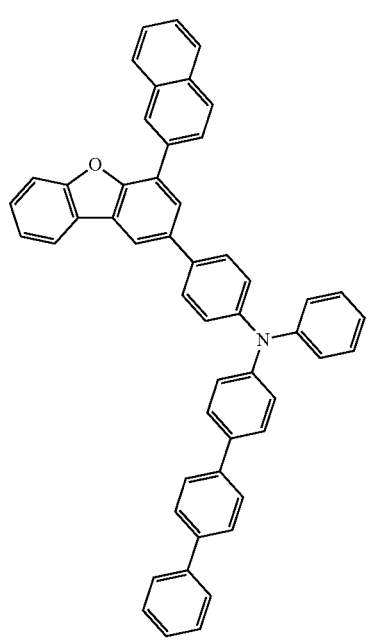
21
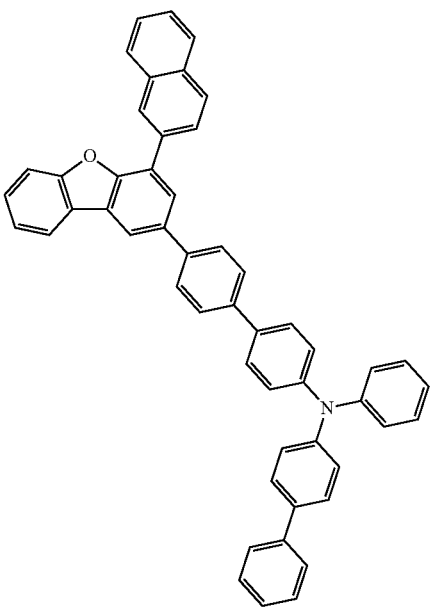
22
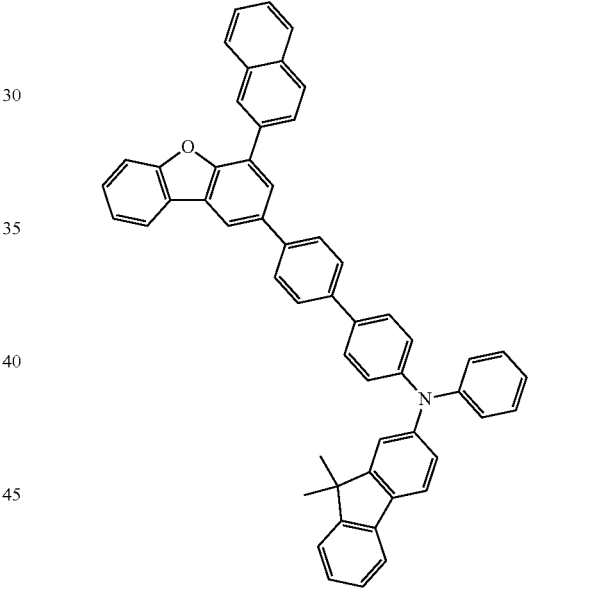
Compounds 12 to 22 were prepared in the same manner as in Preparation Examples 1-1 to 1-11 preparing Compounds 1 to 11, except that the material of Chemical Formula D was used as the starting material instead of Chemical Formula C.
| Compound | MS [M + H]$^+$ |
|---|---|
| 12 | 614 |
| 13 | 654 |
| 14 | 614 |
| 15 | 654 |
| 16 | 690 |
| 17 | 730 |
| 18 | 690 |
| 19 | 730 |
| 20 | 690 |

-continued
| Compound | MS [M + H]+ |
|---|---|
| 21 | 690 |
| 22 | 730 |
Preparation Example 1-13
Syntheses of Following Compounds 23 to 33
23
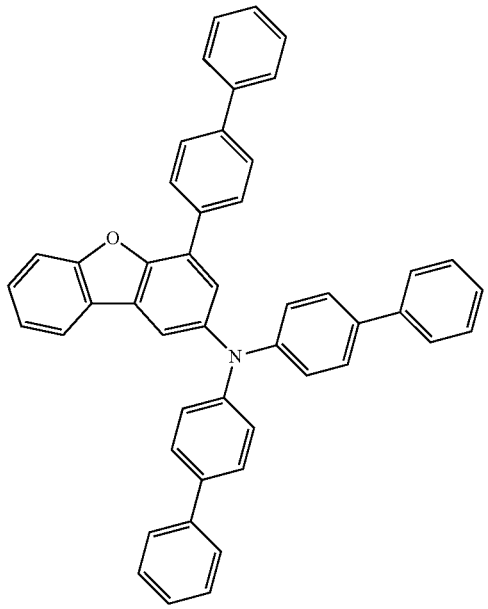
24
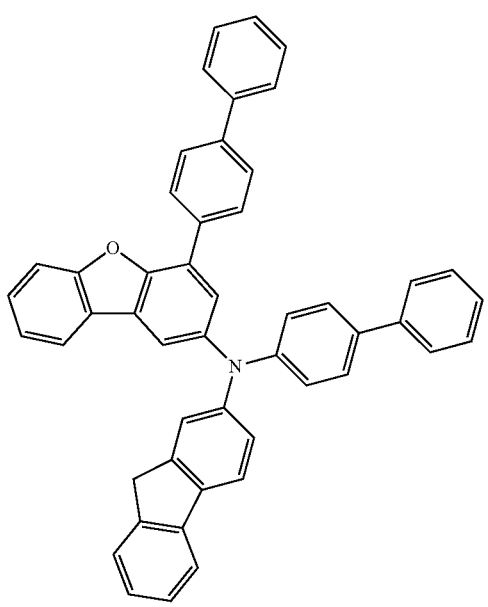
25
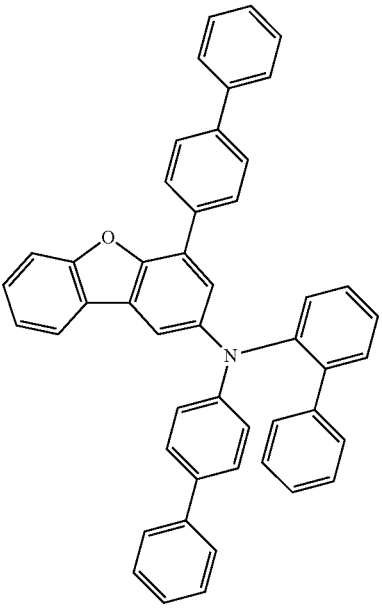
26
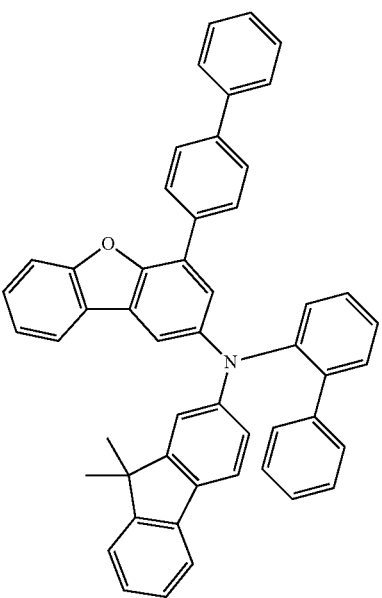

27
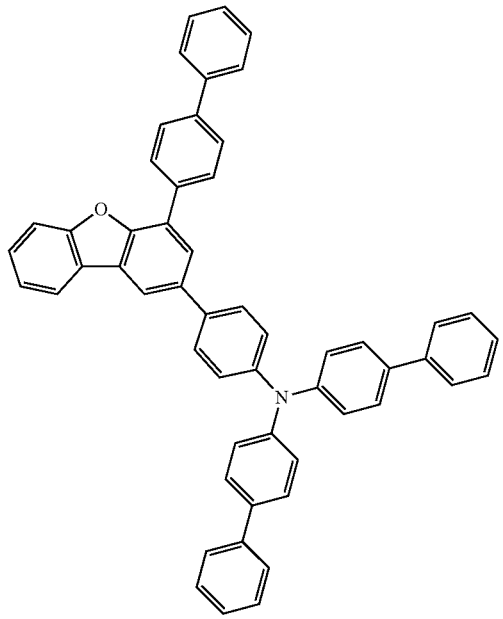
28
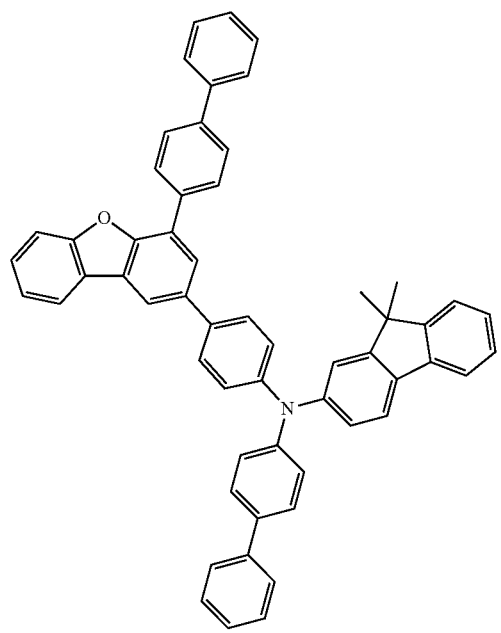
29
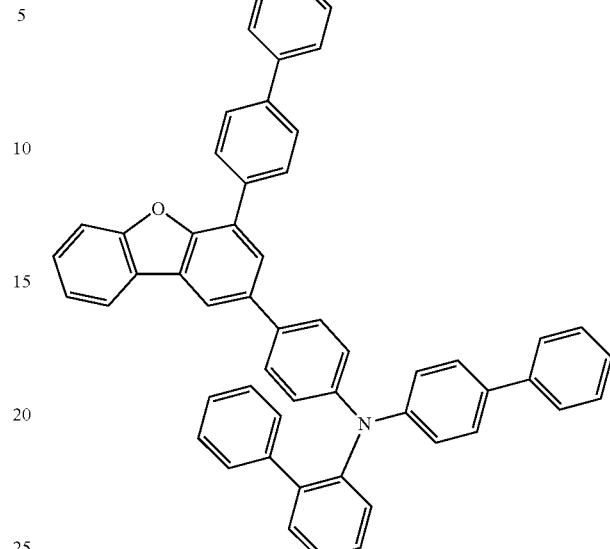
30
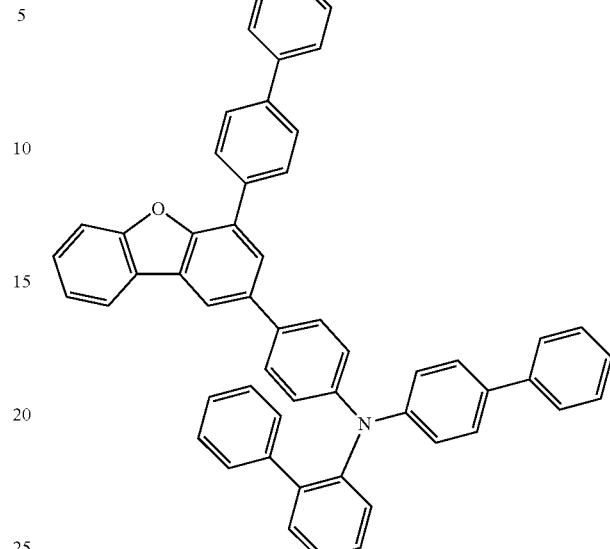

31
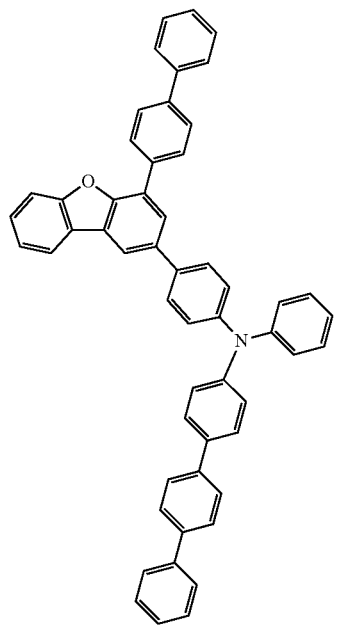
32
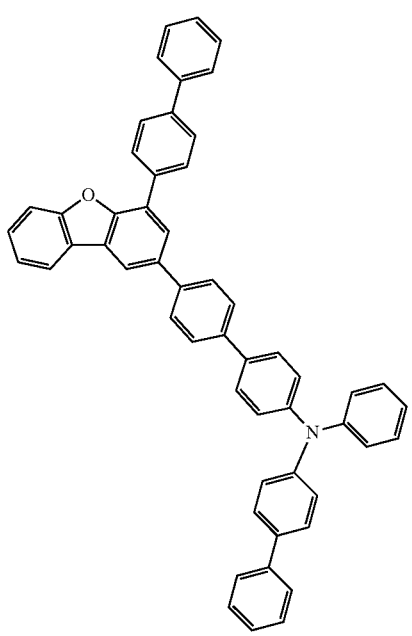
33
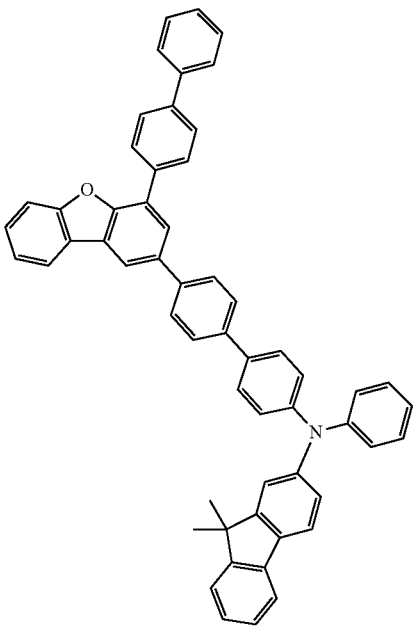
Compounds 23 to 33 were prepared in the same manner as in Preparation Examples 1-1 to 1-11 preparing Compounds 1 to 11, except that the material of Chemical Formula E was used as the starting material instead of Chemical Formula C.
| Compound | MS [M + H]$^+$ |
|---|---|
| 23 | 640 |
| 24 | 680 |
| 25 | 640 |
| 26 | 680 |
| 27 | 716 |
| 28 | 756 |
| 29 | 716 |
| 30 | 756 |
| 31 | 716 |
| 32 | 716 |
| 33 | 756 |

Preparation Example 1-14
Syntheses of Following Compounds 34 to 44
34
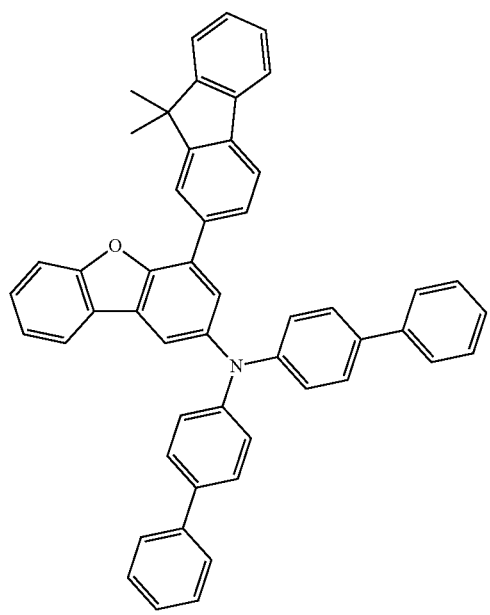
35
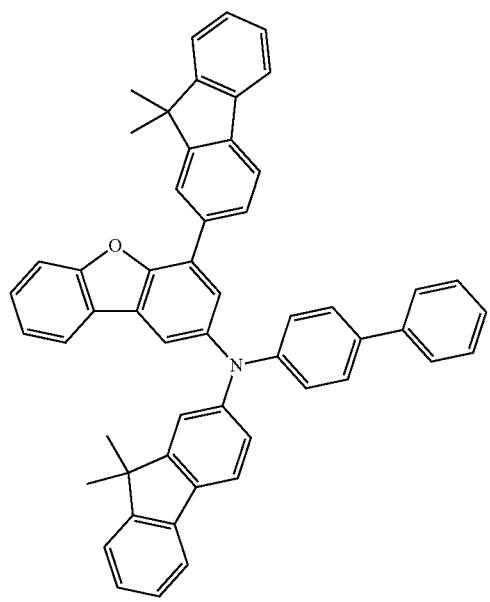
36
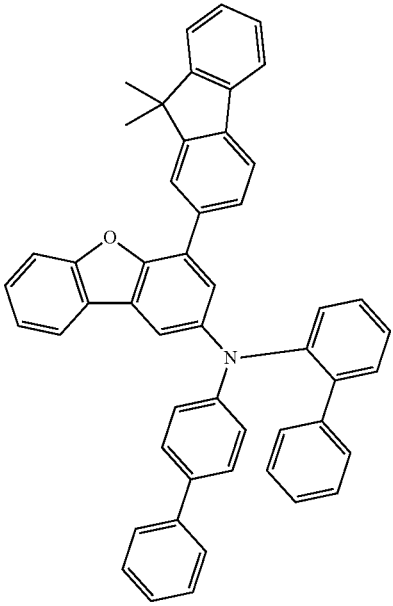
37
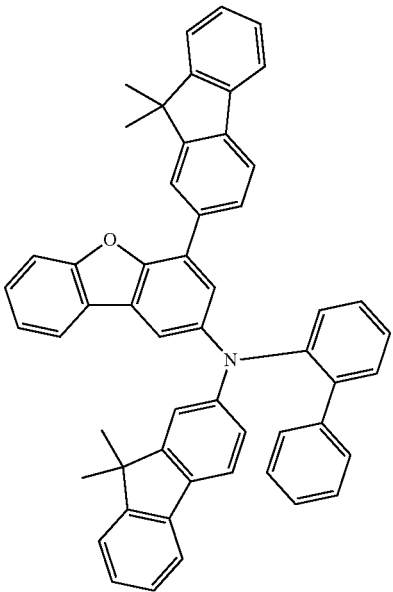

38
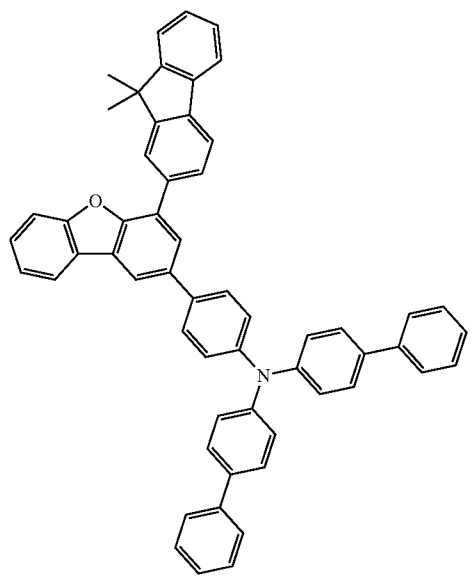
273
39
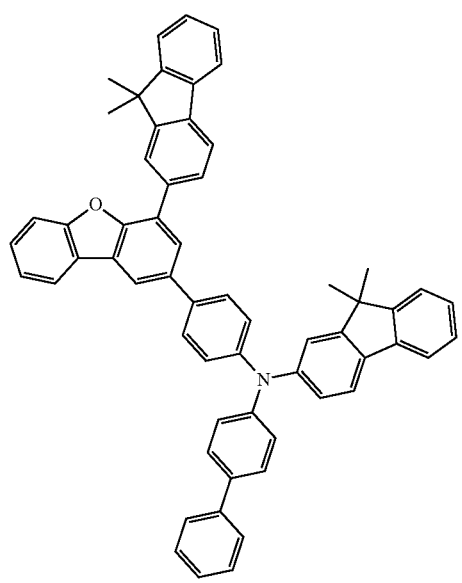
40
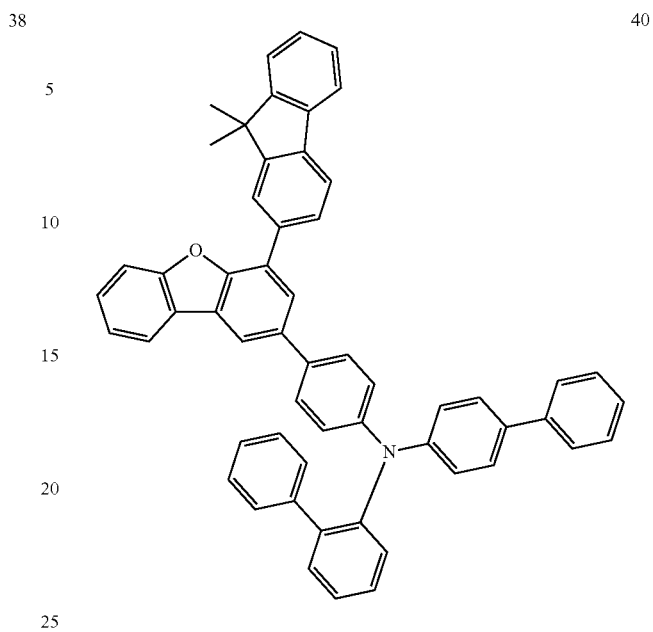
274
41
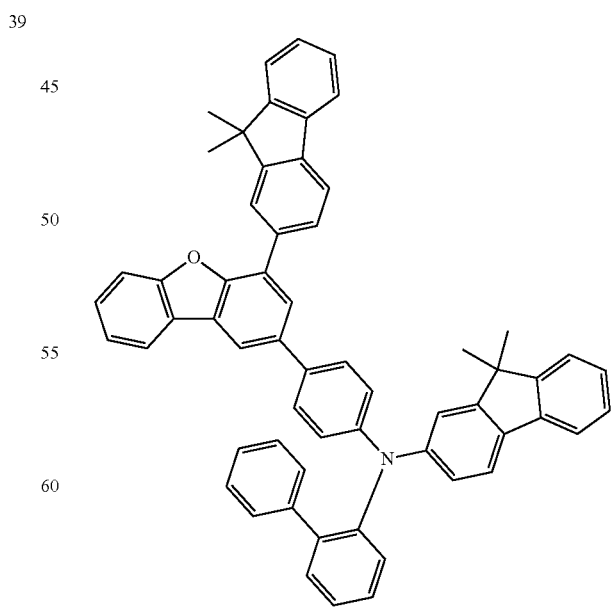

42
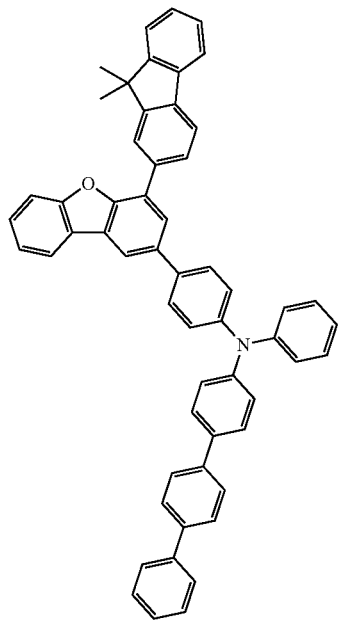
43
44
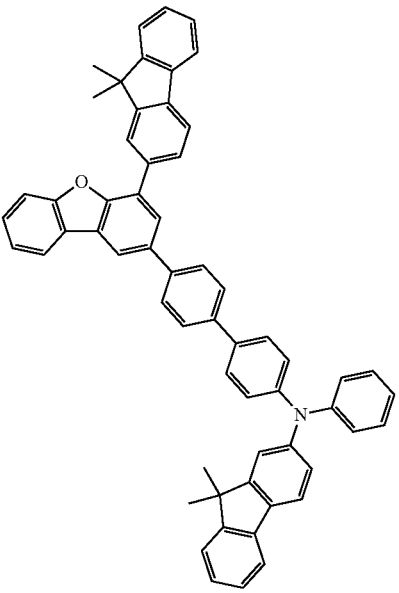
Compounds 34 to 44 were prepared in the same manner as in Preparation Examples 1-1 to 1-11 preparing Compounds 1 to 11, except that the material of Chemical Formula F was used as the starting material instead of Chemical Formula C.
| Compound | MS [M + H]+ |
| --- | --- |
| 34 | 680 |
| 35 | 720 |
| 36 | 680 |
| 37 | 720 |
| 38 | 756 |
| 39 | 796 |
| 40 | 756 |
| 41 | 796 |
| 42 | 756 |
| 43 | 756 |
| 44 | 796 |

Preparation Example 1-15

1) Synthesis of the Following Compound 1-45

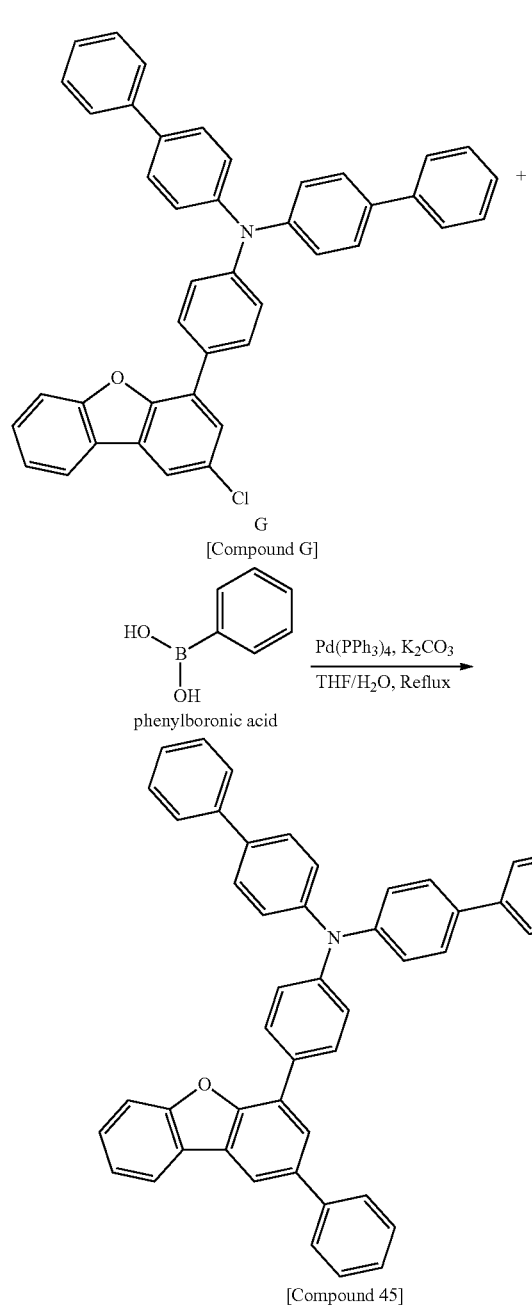

[Compound G]

[Compound 45]

After completely dissolving Compound G (15.0 g, 25.13 mmol) and phenyl boronic acid (4.83 g, 39.57 mmol) in 300 ml of tetrahydrofuran in a 500 ml round bottom flask under nitrogen atmosphere, an aqueous 2 M potassium carbonate solution (150 ml) and then tetrakis-(triphenylphosphine) palladium (0.42 g, 0.36 mmol) were added thereto, and the result was heated and stirred for 3 hours. The temperature was lowered to room temperature, the water layer was removed, and the result was dried with anhydrous magnesium sulfate, vacuum concentrated, and then recrystallized with 250 ml of ethyl acetate to prepare Compound 45 (14.98 g, yield: 87%).

MS[M+H]$^+$=640

Preparation Example 1-16

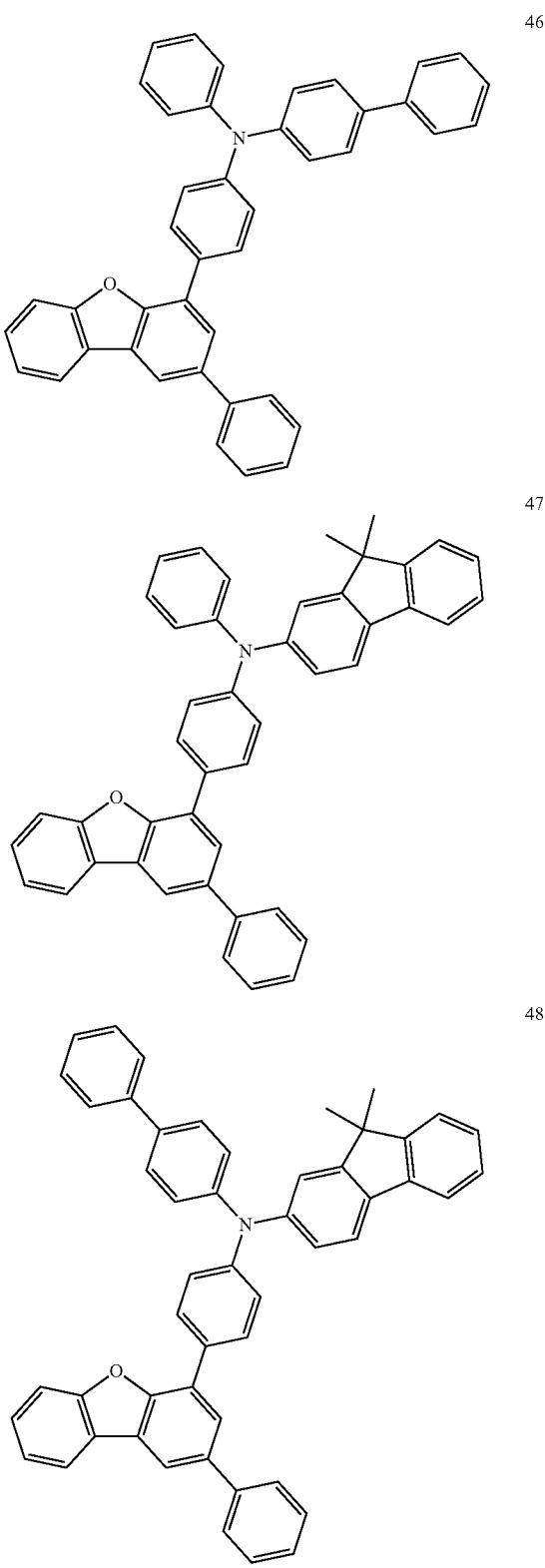

Compounds 46 to 48 were prepared in the same manner as in Preparation Example 1-15 preparing Compound 45, except that Chemical Formulae H, I and J were used as the starting material instead of Chemical Formula G.

| Compound | MS [M + H]⁺ |
|---|---|
| 46 | 564 |
| 47 | 604 |
| 48 | 680 |

Preparation Example 1-17

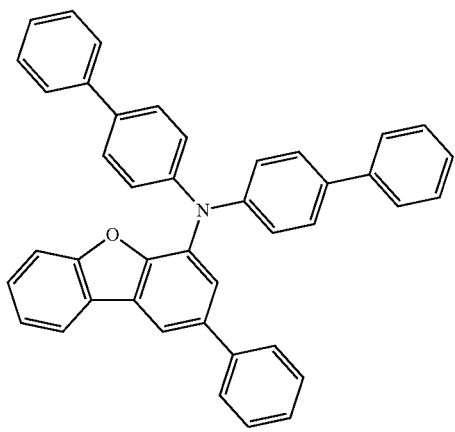

49

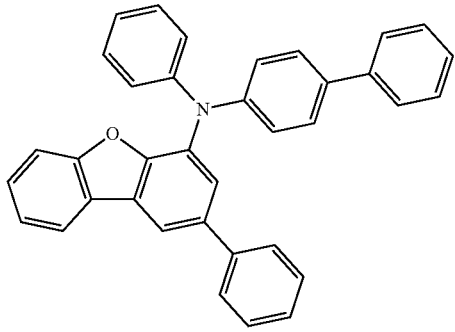

50

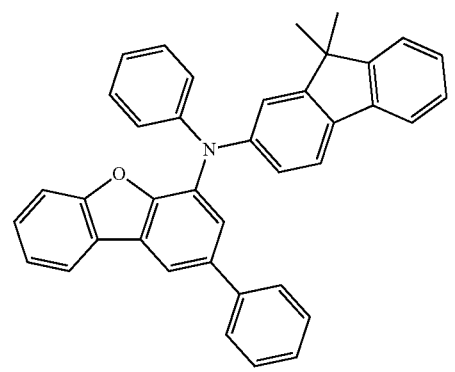

51

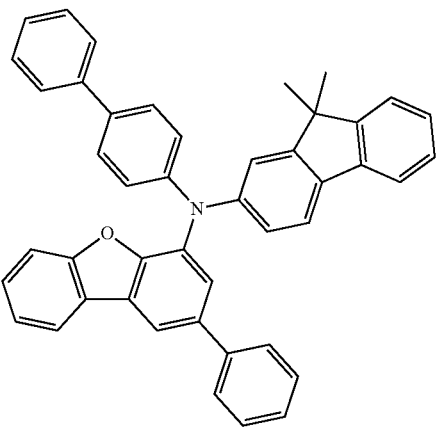

52

Compounds 49 to 52 were prepared in the same manner as in Preparation Example 1-15 preparing Compound 45, except that Chemical Formulae K, L, M and N were used as the starting material instead of Chemical Formula G.

| Compound | MS [M + H]⁺ |
|---|---|
| 49 | 564 |
| 50 | 488 |
| 51 | 528 |
| 52 | 604 |

Preparation Example 1-18

Syntheses of Following Compounds 1-53 to 1-59

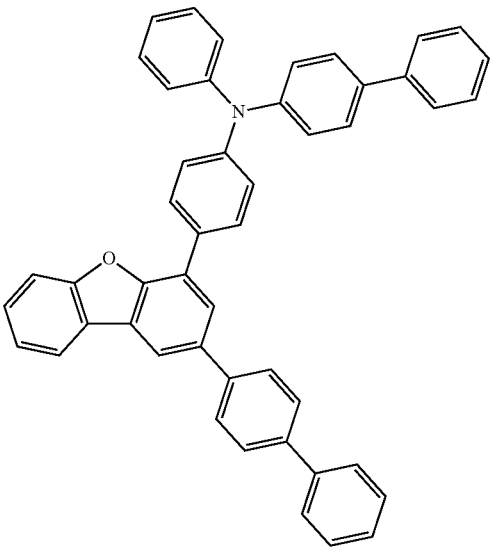

53

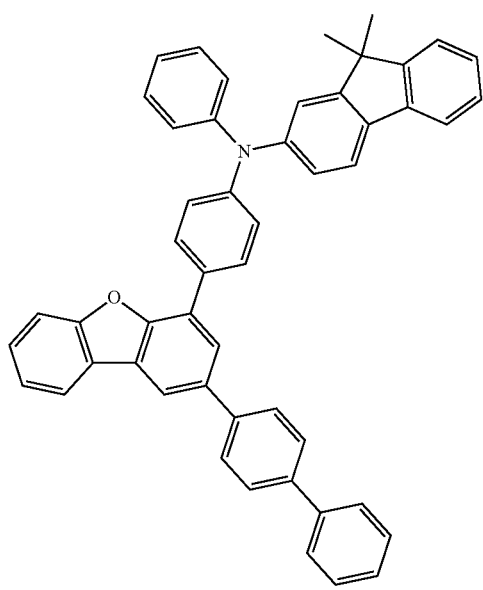
54
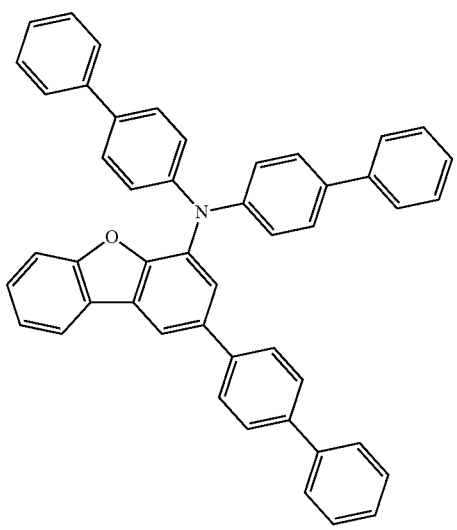
56
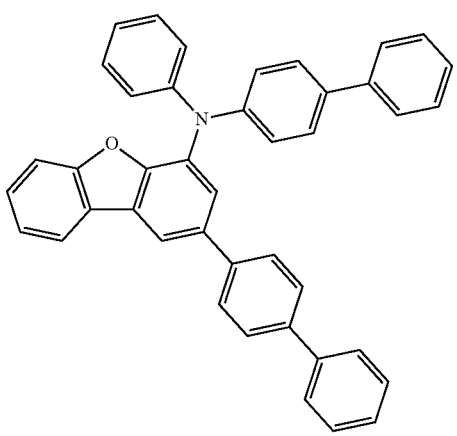
57
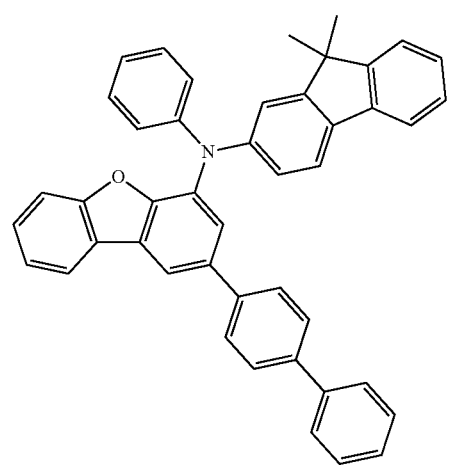
58

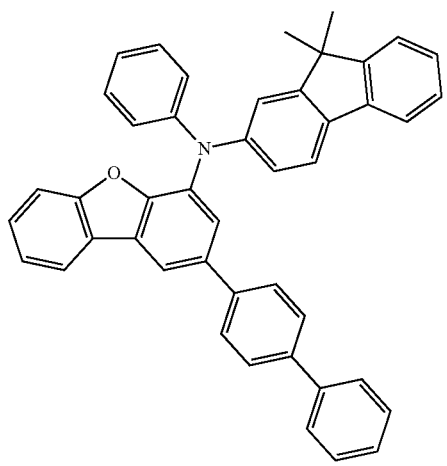

Compounds 53 to 59 were prepared in the same manner as in Preparation Example 1-15 preparing Compound 45, except that Chemical Formulae H, I, J, K, L, M and N were used as the starting material instead of Chemical Formula G, and biphenyl boronic acid was used instead of phenyl boronic acid.

| Compound | MS [M + H]⁺ |
|---|---|
| 53 | 640 |
| 54 | 680 |
| 55 | 680 |
| 56 | 640 |
| 57 | 564 |
| 58 | 604 |
| 59 | 604 |

Example 1-1

A glass substrate on which indium tin oxide (ITO) was coated as a thin film to a thickness of 1,000 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

On the transparent ITO electrode prepared as above, a hole injection layer was formed by thermal vacuum depositing hexanitrile hexaazatriphenylene (HAT) of the following chemical formula to a thickness of 500 Å.

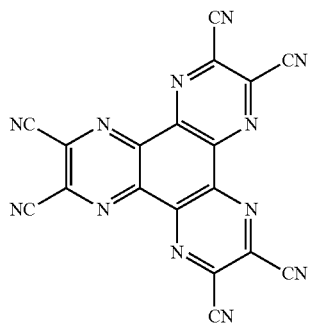

[HAT]

A hole transfer layer was formed on the hole injection layer by vacuum depositing the following compound 4-4'-bis[N-(1-naphthyl)-N-phenylamino]biphenyl (NPB) (300 Å), a material transferring holes.

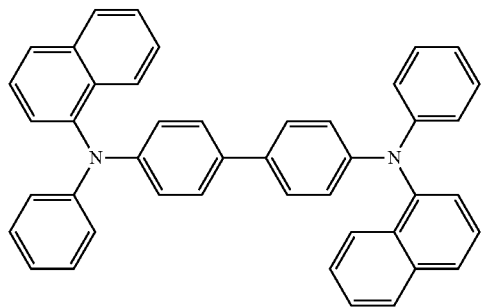

[NPB]

Subsequently, an electron blocking layer was formed on the hole transfer layer to a film thickness of 100 Å by vacuum depositing the following Compound 1.

[Compound 1]

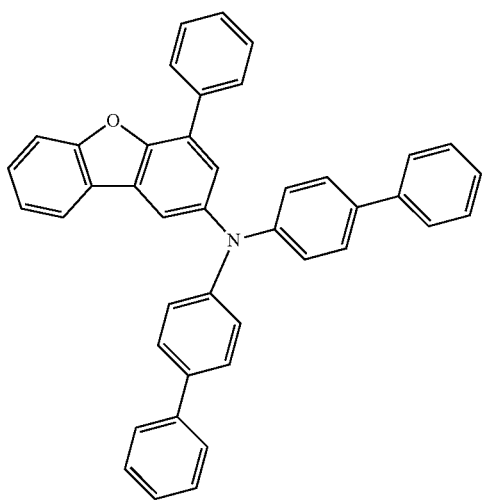

Next, a light emitting layer was formed on the electron blocking layer to a film thickness of 300 Å by vacuum depositing BH and BD shown below in a weight ratio of 25:1.

[BH]

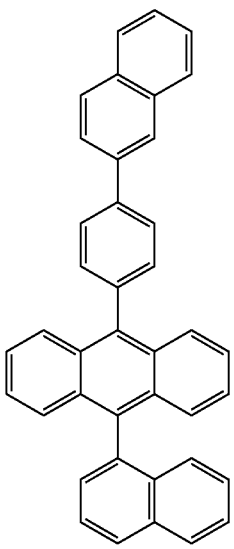

[BD]

[ET1]

[LiQ]

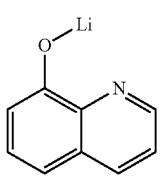

An electron injection and transfer layer was formed on the light emitting layer to a thickness of 300 Å by vacuum depositing the compound ET1 and the compound lithium quinolate (LiQ) in a weight ratio of 1:1. A cathode was formed on the electron injection and transfer layer by depositing lithium fluoride (LiF) to a thickness of 12 Å and aluminum to a thickness of 2,000 Å in consecutive order.

An organic light emitting device was manufactured by maintaining, in the above-mentioned processes, the deposition rates of the organic materials at 0.4 Å/sec to 0.7 Å/sec, the deposition rates of the lithium fluoride and the aluminum of the cathode at 0.3 Å/sec and 2 Å/sec, respectively, and the degree of vacuum during the deposition at $2 \times 10^{-7}$ torr to $5 \times 10^{-6}$ torr.

Example 1-2

An organic light emitting device was manufactured in the same manner as in Example 1-1 except that Compound 2 was used instead of Compound 1.

Example 1-3

An organic light emitting device was manufactured in the same manner as in Example 1-1 except that Compound 5 was used instead of Compound 1.

Example 1-4

An organic light emitting device was manufactured in the same manner as in Example 1-1 except that Compound 6 was used instead of Compound 1.

Example 1-5

An organic light emitting device was manufactured in the same manner as in Example 1-1 except that Compound 8 was used instead of Compound 1.

Example 1-6

An organic light emitting device was manufactured in the same manner as in Example 1-1 except that Compound 10 was used instead of Compound 1.

Example 1-7

An organic light emitting device was manufactured in the same manner as in Example 1-1 except that Compound 11 was used instead of Compound 1.

Example 1-8

An organic light emitting device was manufactured in the same manner as in Example 1-1 except that Compound 12 was used instead of Compound 1.

Example 1-9

An organic light emitting device was manufactured in the same manner as in Example 1-1 except that Compound 13 was used instead of Compound 1.

Example 1-10

An organic light emitting device was manufactured in the same manner as in Example 1-1 except that Compound 16 was used instead of Compound 1.

Example 1-11

An organic light emitting device was manufactured in the same manner as in Example 1-1 except that Compound 17 was used instead of Compound 1.

Example 1-12

An organic light emitting device was manufactured in the same manner as in Example 1-1 except that Compound 25 was used instead of Compound 1.

Example 1-13

An organic light emitting device was manufactured in the same manner as in Example 1-1 except that Compound 26 was used instead of Compound 1.

Example 1-14

An organic light emitting device was manufactured in the same manner as in Example 1-1 except that Compound 29 was used instead of Compound 1.

Example 1-15

An organic light emitting device was manufactured in the same manner as in Example 1-1 except that Compound 30 was used instead of Compound 1.

Example 1-16

An organic light emitting device was manufactured in the same manner as in Example 1-1 except that Compound 34 was used instead of Compound 1.

Example 1-17

An organic light emitting device was manufactured in the same manner as in Example 1-1 except that Compound 45 was used instead of Compound 1.

Example 1-18

An organic light emitting device was manufactured in the same manner as in Example 1-1 except that Compound 48 was used instead of Compound 1.

Example 1-19

An organic light emitting device was manufactured in the same manner as in Example 1-1 except that Compound 49 was used instead of Compound 1.

Example 1-20

An organic light emitting device was manufactured in the same manner as in Example 1-1 except that Compound 52 was used instead of Compound 1.

Example 1-21

An organic light emitting device was manufactured in the same manner as in Example 1-1 except that Compound 53 was used instead of Compound 1.

Comparative Example 1-1

An organic light emitting device was manufactured in the same manner as in Example 1-1 except that the following compound of EB1 was used instead of Compound 1.

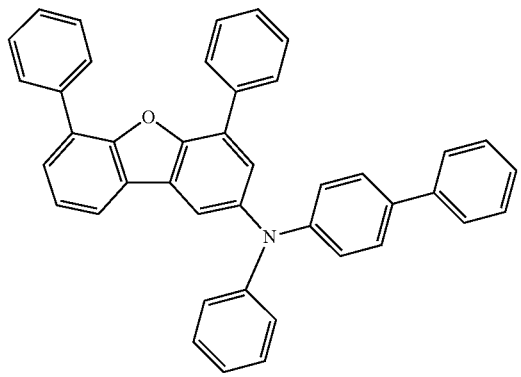

[EB1]

Comparative Example 1-2

An organic light emitting device was manufactured in the same manner as in Example 1-1 except that the following compound of EB2 was used instead of Compound 1.

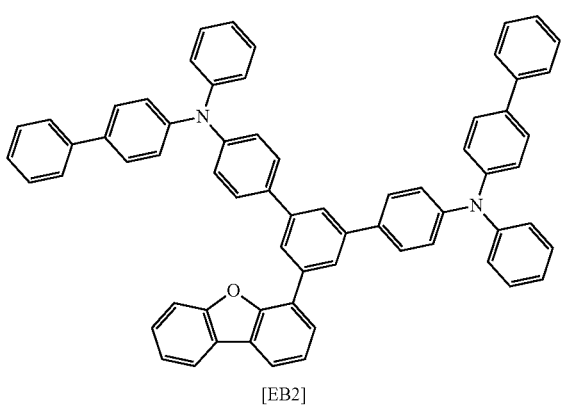 [SMILES: c1ccc(-c2ccc(N(c3ccccc3)c3ccc(-c4cc(-c5ccc(N(c6ccccc6)c6ccc(-c7ccccc7)cc6)cc5)cc(-c5cccc6c5oc5ccccc56)c4)cc3)cc2)cc1]

[EB2]

Comparative Example 1-3

An organic light emitting device was manufactured in the same manner as in Example 1-1 except that the following compound of EB3 was used instead of Compound 1.

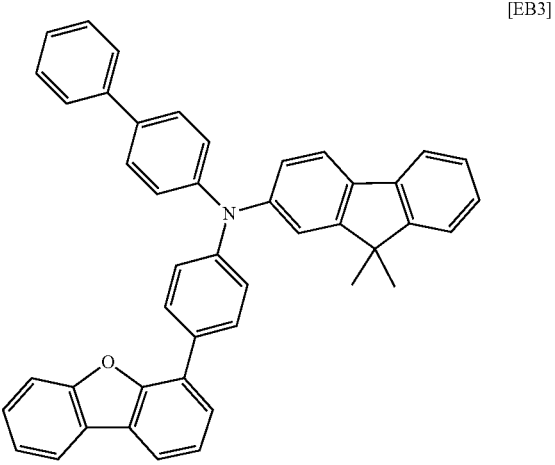 [SMILES: CC1(C)c2ccccc2-c2ccc(N(c3ccc(-c4ccccc4)cc3)c3ccc(-c4cccc5c4oc4ccccc45)cc3)cc21]

[EB3]

When a current was applied to the organic light emitting devices manufactured in Examples 1-1 to 1-21 and Comparative Examples 1-1 to 1-3, results of Table 1 were obtained.

TABLE 1

| | Compound (Electron Blocking Layer) | Voltage (V@10 mA/cm²) | Efficiency (cd/A@10 mA/cm²) | Color Coordinate (x, y) |
|---|---|---|---|---|
| Example 1-1 | Compound 1 | 3.89 | 6.50 | (0.138, 0.127) |
| Example 1-2 | Compound 2 | 3.84 | 6.52 | (0.139, 0.122) |
| Example 1-3 | Compound 5 | 3.85 | 6.33 | (0.138, 0.126) |
| Example 1-4 | Compound 6 | 3.81 | 6.32 | (0.138, 0.127) |
| Example 1-5 | Compound 8 | 3.89 | 6.30 | (0.137, 0.125) |
| Example 1-6 | Compound 10 | 3.89 | 6.50 | (0.136, 0.125) |
| Example 1-7 | Compound 11 | 3.84 | 6.52 | (0.136, 0.127) |
| Example 1-8 | Compound 12 | 3.62 | 6.53 | (0.136, 0.125) |
| Example 1-9 | Compound 13 | 3.61 | 6.67 | (0.137, 0.125) |
| Example 1-10 | Compound 16 | 3.68 | 6.68 | (0.138, 0.125) |
| Example 1-11 | Compound 17 | 3.66 | 6.65 | (0.136, 0.125) |
| Example 1-12 | Compound 25 | 3.64 | 6.66 | (0.137, 0.125) |
| Example 1-13 | Compound 26 | 3.85 | 6.33 | (0.136, 0.125) |
| Example 1-14 | Compound 29 | 3.81 | 6.32 | (0.138, 0.126) |
| Example 1-15 | Compound 30 | 3.89 | 6.30 | (0.137, 0.125) |
| Example 1-16 | Compound 34 | 3.89 | 6.50 | (0.136, 0.127) |
| Example 1-17 | Compound 45 | 3.84 | 6.52 | (0.135, 0.127) |
| Example 1-18 | Compound 48 | 3.85 | 6.33 | (0.138, 0.127) |
| Example 1-19 | Compound 49 | 3.81 | 6.32 | (0.137, 0.125) |
| Example 1-20 | Compound 52 | 3.89 | 6.30 | (0.137, 0.125) |
| Example 1-21 | Compound 53 | 3.89 | 6.50 | (0.136, 0.125) |
| Comparative Example 1-1 | EB1 | 4.53 | 5.41 | (0.136, 0.127) |
| Comparative Example 1-2 | EB2 | 4.83 | 5.17 | (0.136, 0.127) |
| Comparative Example 1-3 | EB3 | 4.65 | 5.34 | (0.136, 0.127) |

As shown in Table 1, when comparing the organic light emitting devices using the compounds of the present disclosure with the organic light emitting devices using the compound in which other substituents that are not hydrogen are linked to positions that are not A or B position of the compound of the present disclosure (Comparative Example 1), using the compound having two amine groups on A position (Comparative Example 2), and using the compound having an amine group and not having an aryl group (Comparative Example 3), the compounds of the present disclosure exhibited excellent properties in terms of efficiency, driving voltage and/or stability of the organic light emitting devices since the compounds of the present disclosure performed a role of electron blocking.

As shown in the results of Table 1, it was identified that the compounds of the present disclosure had an excellent electron blocking ability and therefor were capable of being used in an organic light emitting device.

Example 2-1

Experiments were carried out in the same manner as in Example 1-1 except that the following compound TCTA was used as the electron blocking layer, and the compounds of Examples 1-1 to 1-21 were used as the hole transfer layer instead of NPB.

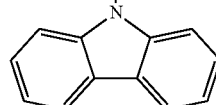

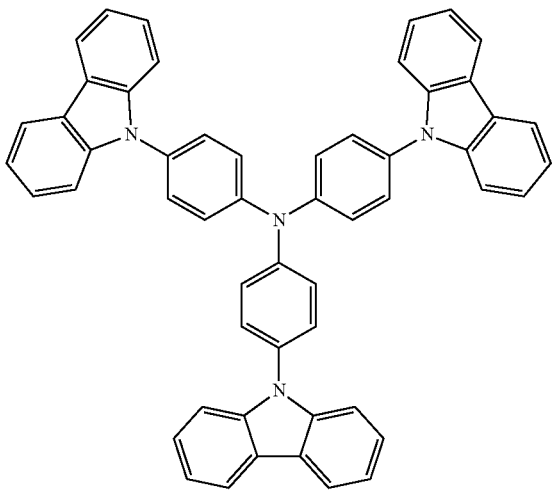

TCTA

Comparative Example 2-1

An organic light emitting device was manufactured in the same manner as in Example 2-1 except that the following compound of HT1 was used instead of Compound 1.

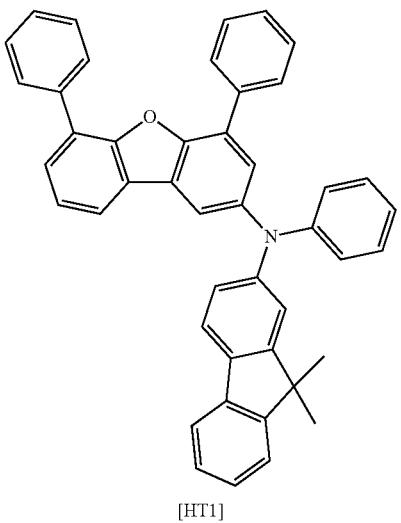

[HT1]

Comparative Example 2-2

An organic light emitting device was manufactured in the same manner as in Example 2-1 except that the following compound of HT2 was used instead of Compound 1.

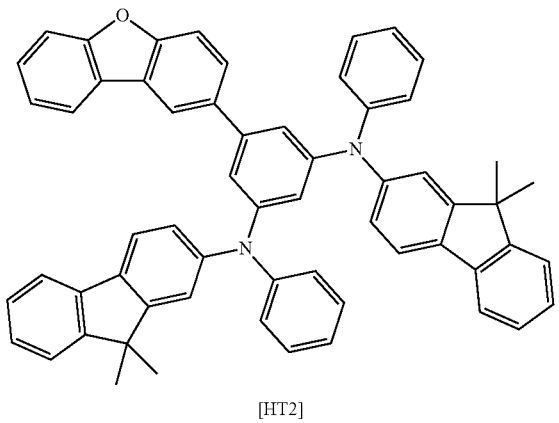

[HT2]

Comparative Example 2-3

An organic light emitting device was manufactured in the same manner as in Example 2-1 except that the following compound of HT3 was used instead of Compound 1.

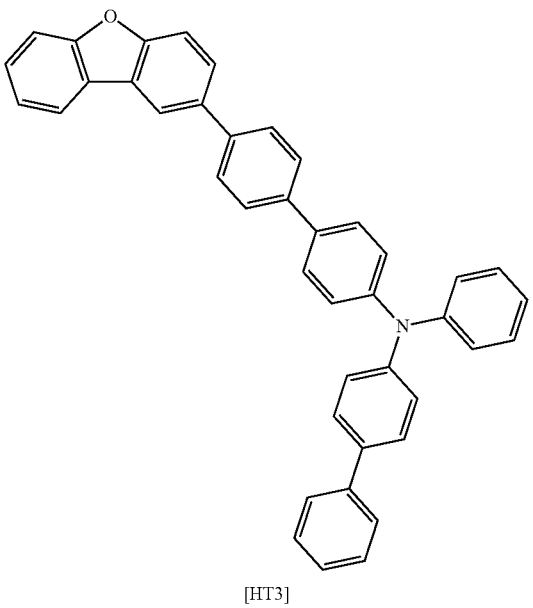

[HT3]

When a current was applied to the organic light emitting devices manufactured in Examples 2-1 to Example 2-21 and Comparative Examples 2-1 to 2-3, results of Table 2 were obtained.

TABLE 2

| | Compound (Hole Transfer Layer) | Voltage (V@10 mA/ $cm^2$) | Efficiency (cd/A@10 mA/ $cm^2$) | Color Coordinate (x, y) |
|---|---|---|---|---|
| Example 2-1 | Compound 1 | 3.65 | 5.15 | (0.138, 0.127) |
| Example 2-2 | Compound 2 | 3.74 | 5.21 | (0.139, 0.122) |
| Example 2-3 | Compound 5 | 3.71 | 5.18 | (0.138, 0.126) |
| Example 2-4 | Compound 6 | 3.61 | 5.20 | (0.138, 0.127) |
| Example 2-5 | Compound 8 | 3.62 | 5.11 | (0.137, 0.125) |
| Example 2-6 | Compound 10 | 3.74 | 4.92 | (0.136, 0.125) |
| Example 2-7 | Compound 11 | 3.84 | 4.91 | (0.136, 0.127) |
| Example 2-8 | Compound 12 | 3.81 | 5.05 | (0.136, 0.125) |
| Example 2-9 | Compound 13 | 3.83 | 4.90 | (0.137, 0.125) |
| Example 2-10 | Compound 16 | 3.75 | 4.88 | (0.138, 0.125) |
| Example 2-11 | Compound 17 | 3.72 | 4.76 | (0.136, 0.125) |
| Example 2-12 | Compound 25 | 3.78 | 4.95 | (0.137, 0.125) |
| Example 2-13 | Compound 26 | 3.73 | 5.05 | (0.136, 0.125) |
| Example 2-14 | Compound 29 | 3.70 | 4.93 | (0.138, 0.126) |
| Example 2-15 | Compound 30 | 3.74 | 4.89 | (0.137, 0.125) |
| Example 2-16 | Compound 34 | 3.65 | 5.15 | (0.136, 0.127) |
| Example 2-17 | Compound 45 | 3.74 | 5.21 | (0.135, 0.127) |
| Example 2-18 | Compound 48 | 3.71 | 5.18 | (0.138, 0.127) |
| Example 2-19 | Compound 49 | 3.61 | 5.20 | (0.137, 0.125) |
| Example 2-20 | Compound 52 | 3.62 | 5.16 | (0.137, 0.125) |
| Example 2-21 | Compound 53 | 3.78 | 5.01 | (0.136, 0.125) |
| Comparative Example 2-1 | HT1 | 4.21 | 4.53 | (0.136, 0.127) |
| Comparative Example 2-2 | HT2 | 4.65 | 4.12 | (0.136, 0.127) |
| Comparative Example 2-3 | HT3 | 4.31 | 4.45 | (0.136, 0.127) |

As shown in Table 2, when comparing the organic light emitting devices using the compounds of the present disclosure with the organic light emitting devices using the compound in which other substituents that are not hydrogen are linked to positions that are not A or B position of the compound of the present disclosure (Comparative Example 1), using the compound having two amine groups on A position (Comparative Example 2), and using the compound having an amine group and not having an aryl group (Comparative Example 3), the compounds of the present disclosure exhibited excellent properties in terms of efficiency, driving voltage and/or stability of the organic light emitting devices since the compounds of the present disclosure performed a role of hole transfer. Accordingly, it was identified that the compounds of the present disclosure had an excellent hole transfer ability and therefore were capable of being used in an organic light emitting device.

As shown in the results of Table 1 and Table 2, it was identified that the compounds of the present disclosure had an excellent hole transfer ability as well as an electron blocking ability, and therefore, were capable of being used in an organic light emitting device.

Hereinbefore, preferred embodiments of the present disclosure (electron blocking layer, hole transfer layer) have been described, however, the present disclosure is not limited thereto, and various modifications may be made within the scope of the claims and the detailed descriptions, and the modifications are also included in the scope of the present disclosure.

The invention claimed is:

1. An organic light emitting device comprising:
a first electrode;
a second electrode; and
an organic material layer disposed between the first electrode and the second electrode,
wherein the organic material layer comprises at least one selected from an electron transfer layer, an electron injection layer, a layer carrying out electron transfer and electron injection at the same time, a hole transfer layer, an electron blocking layer, a layer carrying out hole transfer and electron blocking at the same time, a hole injection layer, or a layer carrying out hole injection and hole transfer at the same time, and the electron transfer layer, the electron injection layer, the layer carrying out electron transfer and electron injection at the same time, the hole transfer layer, the electron blocking layer, the layer carrying out hole transfer and electron blocking at the same time, the hole injection layer, or the layer carrying out hole injection and hole transfer at the same time comprises a compound represented by the following Chemical Formula 1:

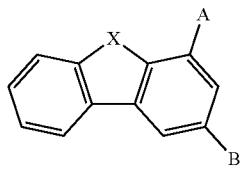

[Chemical Formula 1]

wherein, in Chemical Formula 1,
X is O or S;
one of A or B has a structure of the following Chemical Formula 1-1, and the other one of A or B is an aryl group that is optionally substituted with a substituent that is not a carbazole group, wherein a carbon atom of the aryl group is directly bonded to the

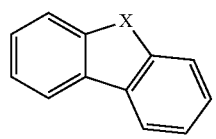

of Chemical Formula 1; or a heterocyclic group selected from a dibenzothiophene group optionally substituted with an aryl group, or a dibenzofuranyl group that is optionally substituted, and a carbon atom of the heterocyclic group is directly bonded to the

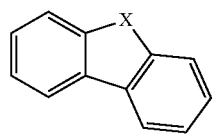

of Chemical Formula 1,

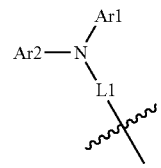

[Chemical Formula 1-1]

wherein, in Chemical Formula 1-1, L1 is a direct bond; or a substituted or unsubstituted arylene group; and Ar1 and Ar2 are the same as or different from each other, and each independently hydrogen; deuterium; a halogen group; a nitrile group; a nitro group; a hydroxyl group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylphosphine group; a substituted or unsubstituted phosphine oxide group; a substituted or unsubstituted aryl group; or a substituted or unsubstituted heterocyclic group, provided that Ar1 and Ar2 are not both a naphthyl group, and that when Ar1 and Ar2 are both a phenyl group, L1 is a substituted or unsubstituted arylene group.

2. The organic light emitting device of claim 1, wherein the compound represented by Chemical Formula 1 is represented by the following Chemical Formula 1-A or Chemical Formula 1-B:

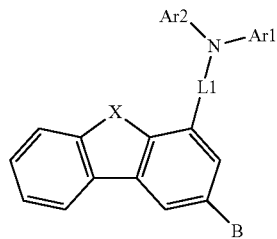

[Chemical Formula 1-A]

[Chemical Formula 1-B]

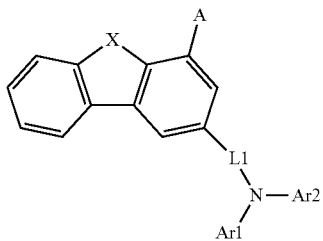

wherein, in Chemical Formulae 1-A and 1-B,
definitions of X, L1, Ar1 and Ar2 are the same as in Chemical Formula 1 and Chemical Formula 1-1, and
A and B are each independently an aryl group that is optionally substituted with a substituent that is not a carbazole group, wherein a carbon atom of the aryl group is directly bonded to the

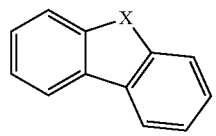

of Chemical Formula 1-A and 1-B, respectively; or a heterocyclic group selected from a dibenzothiophene group optionally substituted with an aryl group, or a dibenzofuranyl group that is optionally substituted, and a carbon atom of the heterocyclic group is directly bonded to the

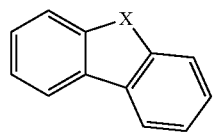

of Chemical Formulae 1-A and 1-B, respectively.

3. The organic light emitting device of claim 1, wherein the compound represented by Chemical Formula 1 is represented by any one of the following Chemical Formula 21 to Chemical Formula 24:

[Chemical Formula 21]

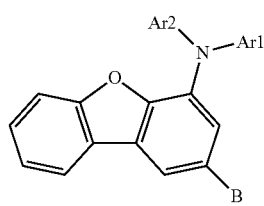

[Chemical Formula 22]

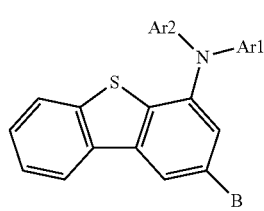

[Chemical Formula 23]

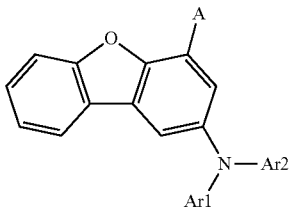

[Chemical Formula 24]

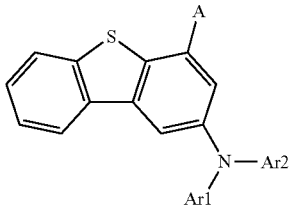

wherein, in Chemical Formulae 21 to 24,
definitions of Ar1 and Ar2 are the same as in Chemical Formula 1 and Chemical Formula 1-1, and
A and B are each independently an aryl group that is optionally substituted with a substituent that is not a carbazole group, wherein a carbon atom of the aryl group is directly bonded to the

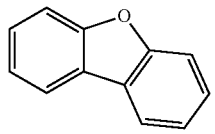

of Chemical Formulae 21 and 23, and

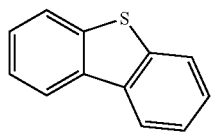

of Chemical Formulae 22 and 24, respectively; or a heterocyclic group that is optionally substituted, wherein the heterocyclic group is a dibenzothiophene group or a dibenzofuranyl group, and a carbon atom of the heterocyclic group is directly bonded to the

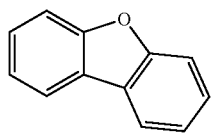 [SMILES: c1ccc2c(c1)oc1ccccc12]

of Chemical Formulae 21 and 23, and

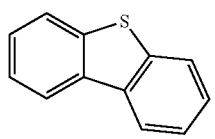

of Chemical Formulae 22 and 24, respectively.

4. The organic light emitting device of claim 1, wherein L1 is any one selected from among the following structures:

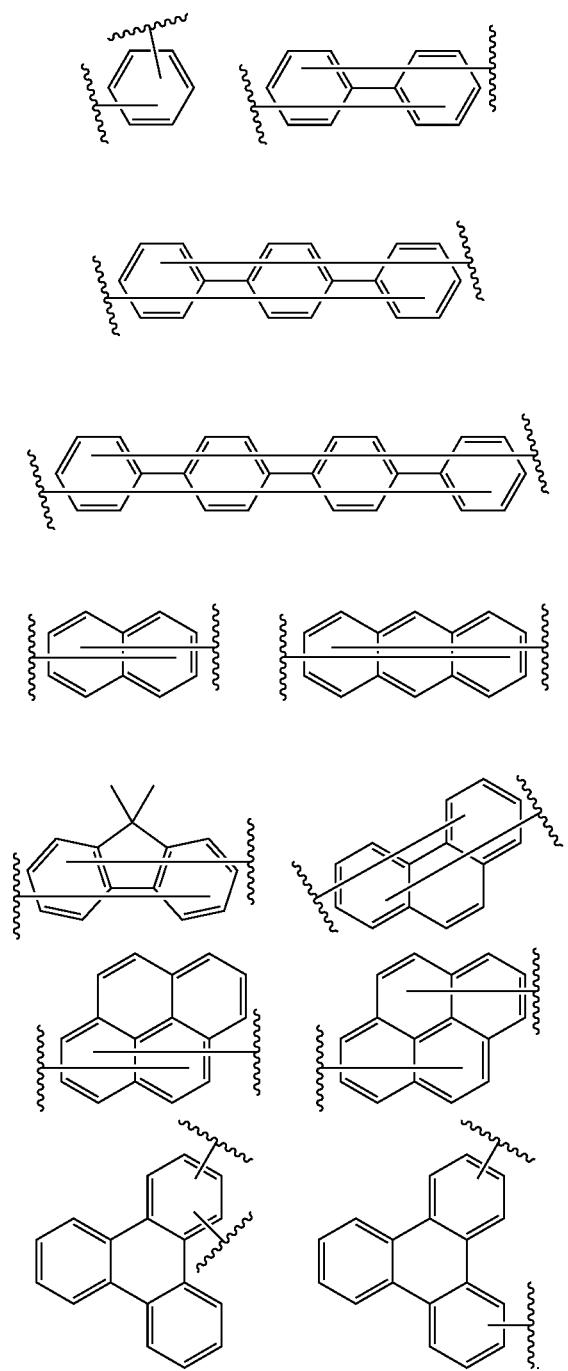

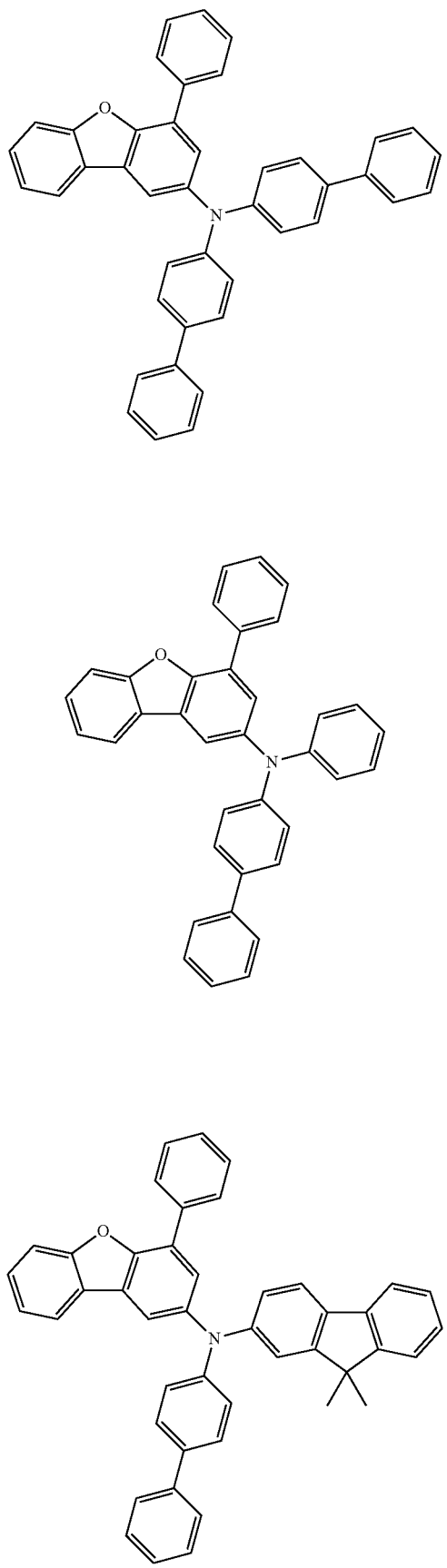

5. The organic light emitting device of claim 1, wherein Ar1 and Ar2 are the same as or different from each other, and each independently hydrogen, a substituted or unsubstituted aryl group having 6 to 40 carbon atoms; or a substituted or unsubstituted heterocyclic group having 2 to 40 carbon atoms.

6. The organic light emitting device of claim 1, wherein the compound of Chemical Formula 1 is any one selected from among the following structures:

299
-continued
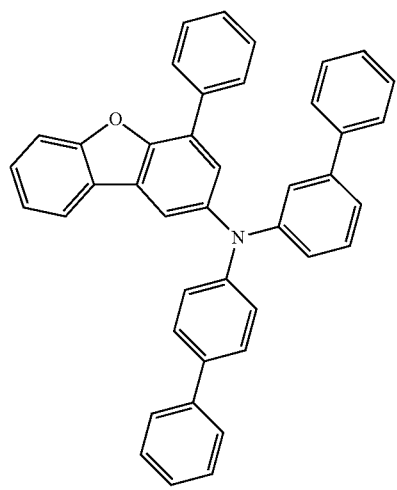
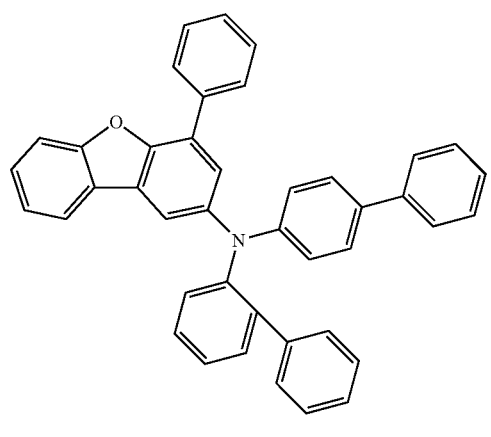
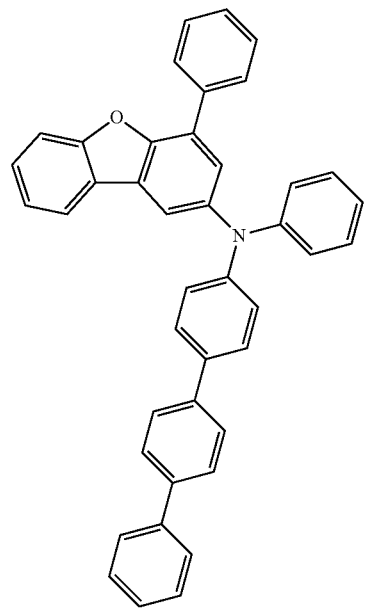
300
-continued
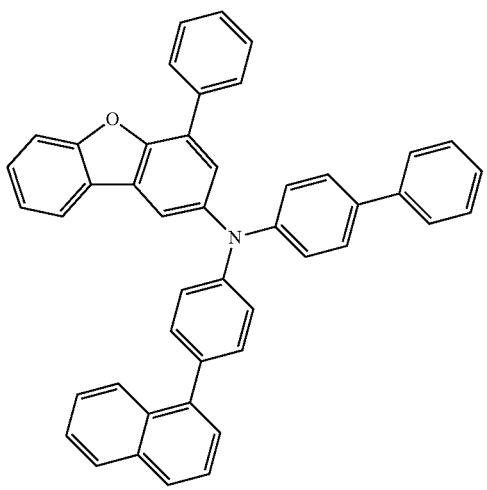
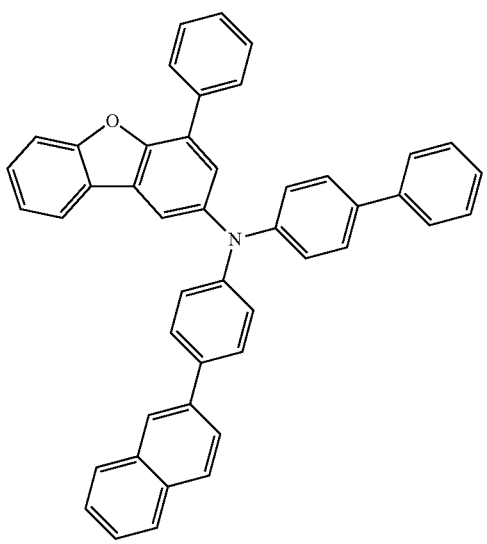
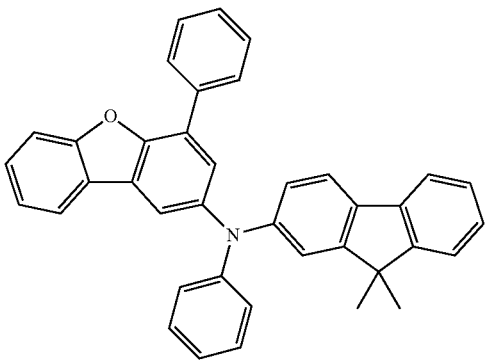

301
-continued
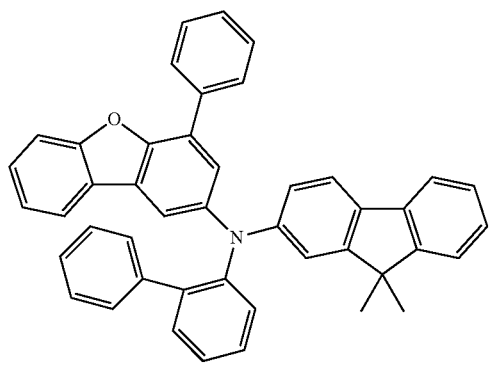
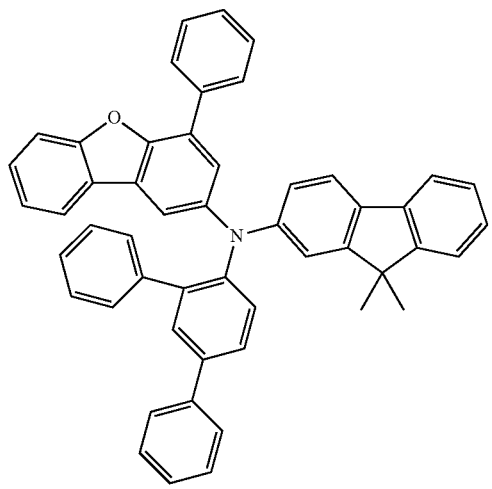
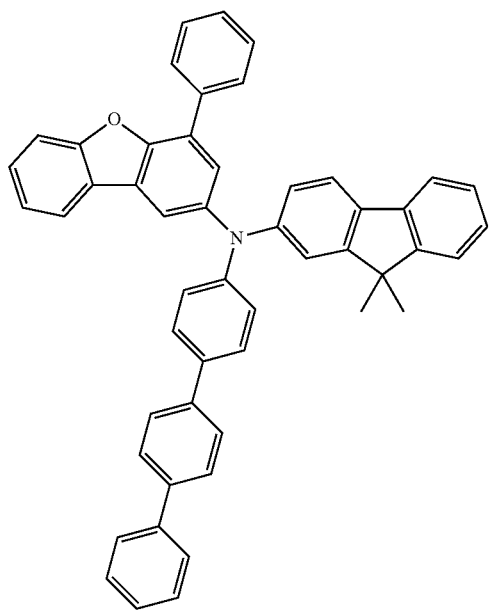
302
-continued
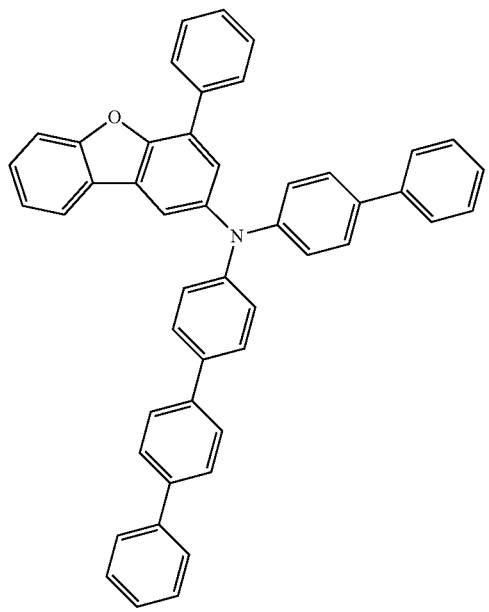
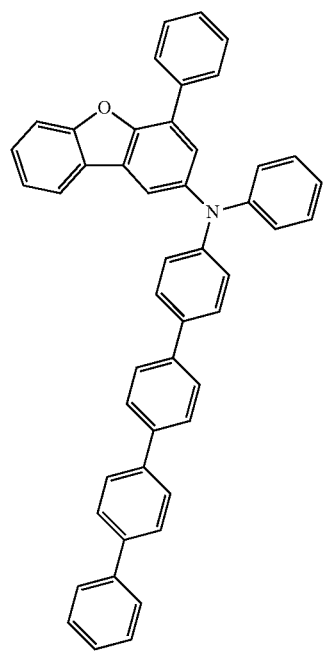

303
-continued
304
-continued
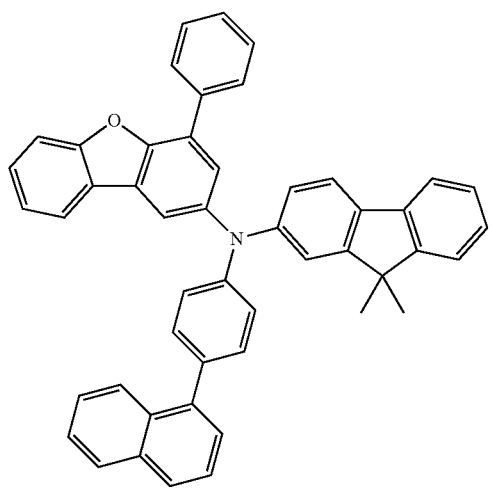
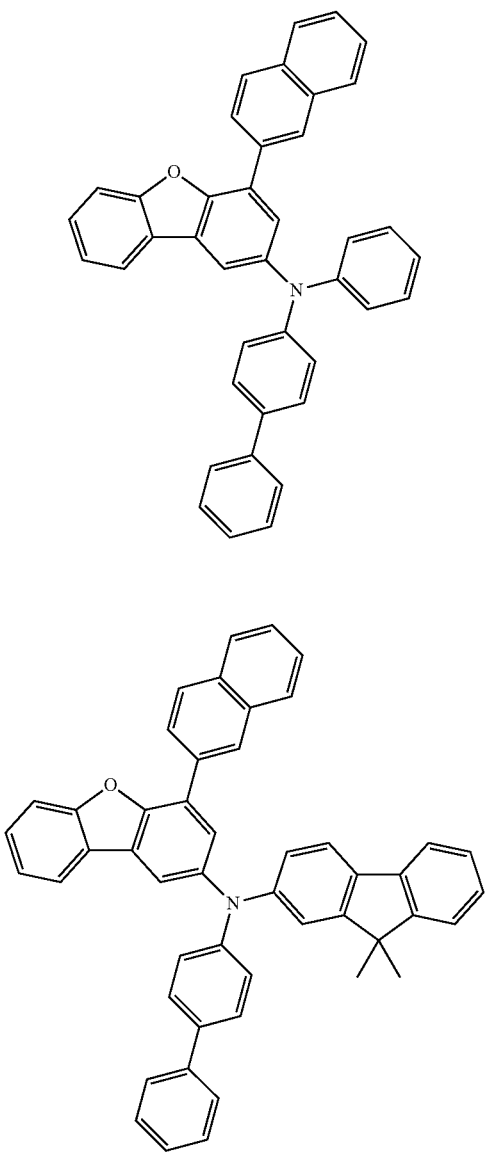
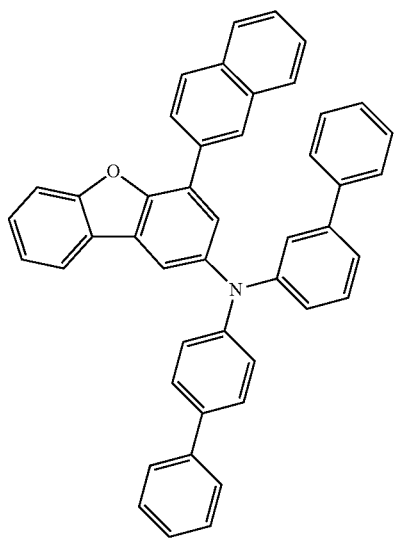

| 305 -continued | 306 -continued |
|---|---|
| 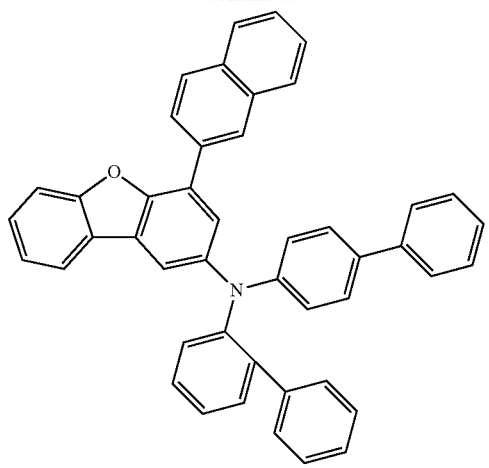 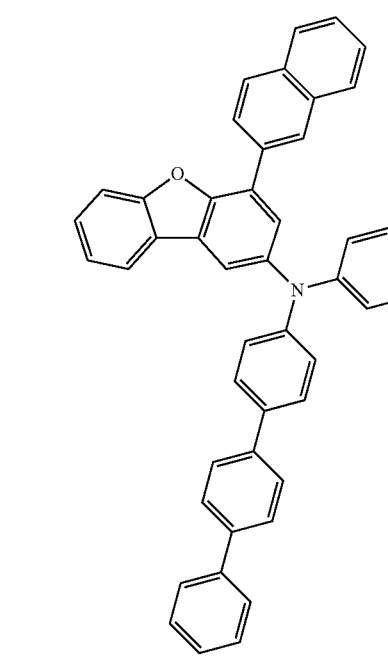 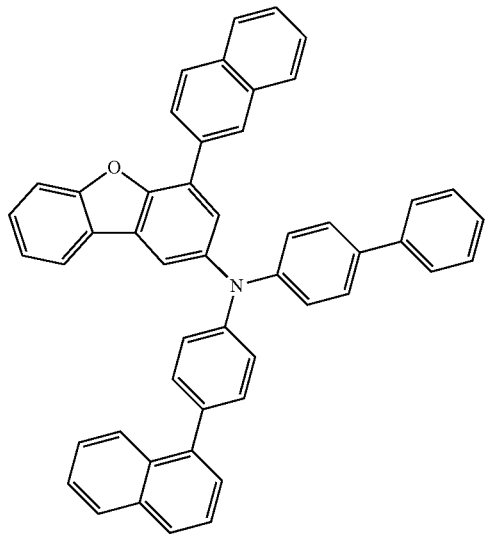 | 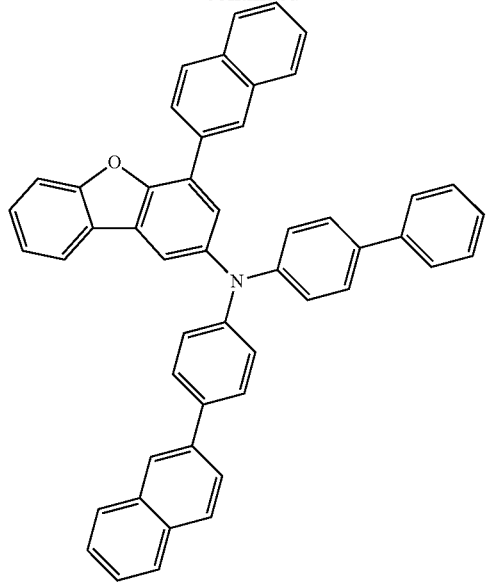 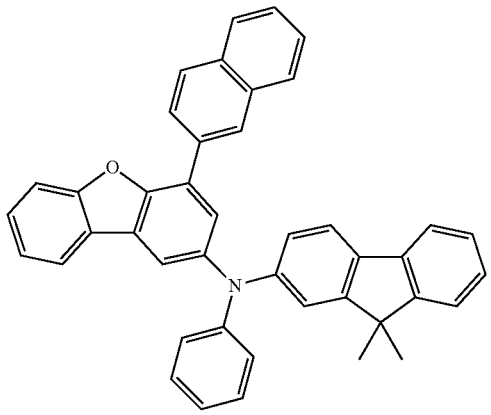 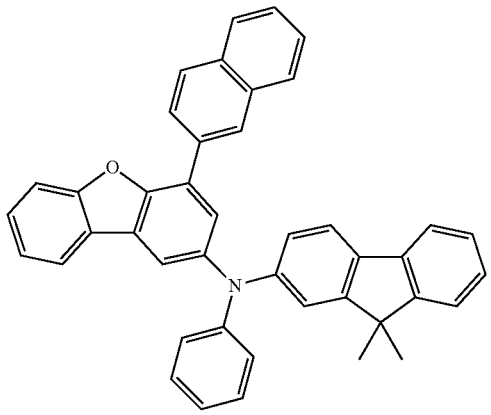 |

307
-continued
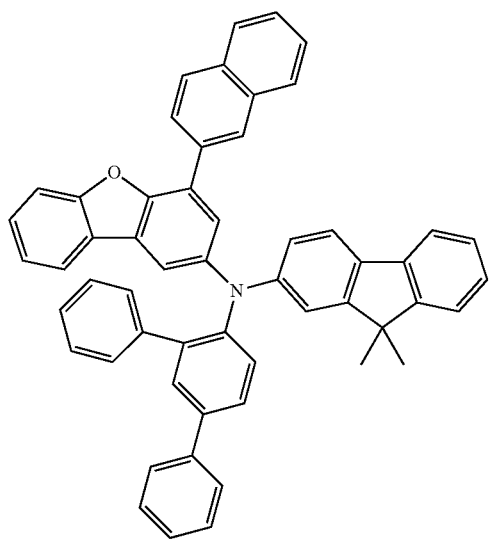
308
-continued
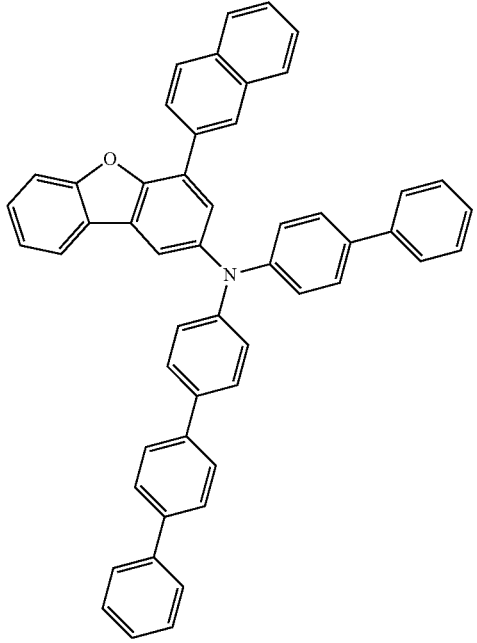
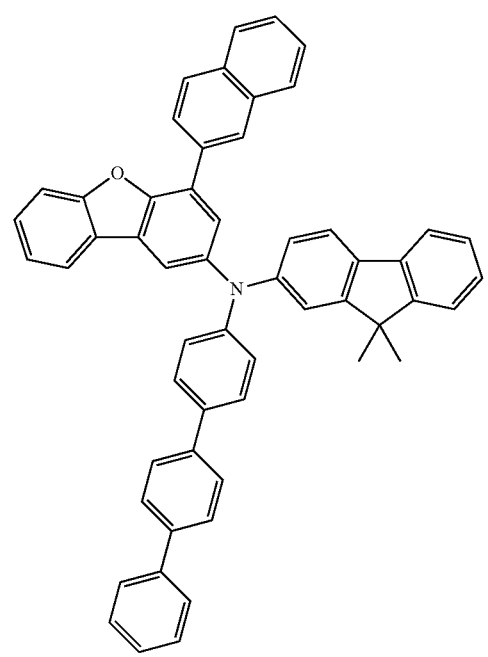
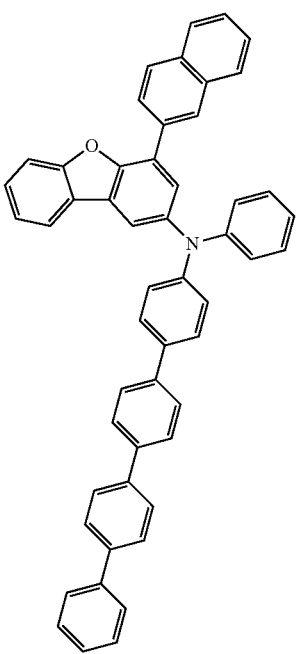

309
-continued
310
-continued
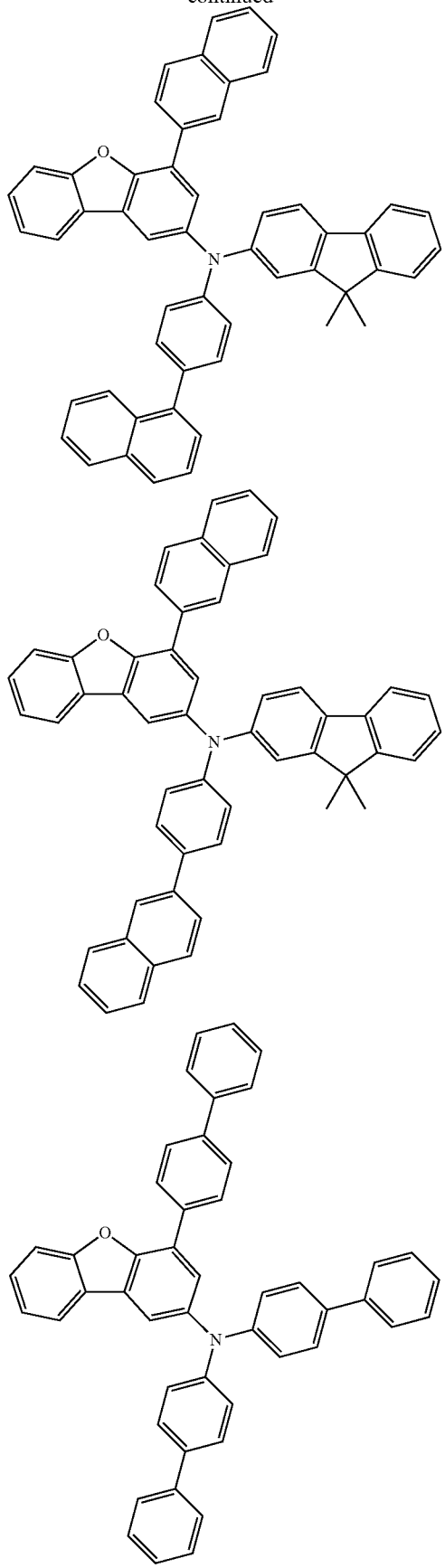

311
-continued
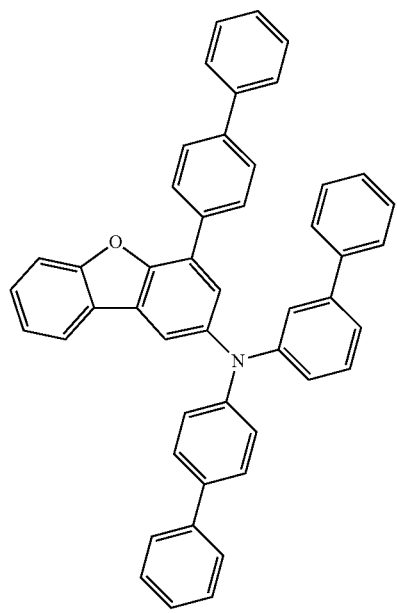
312
-continued
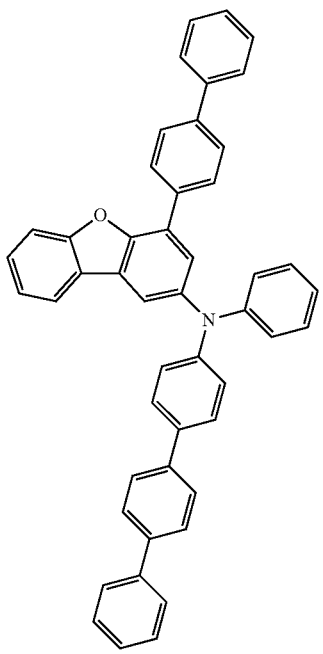
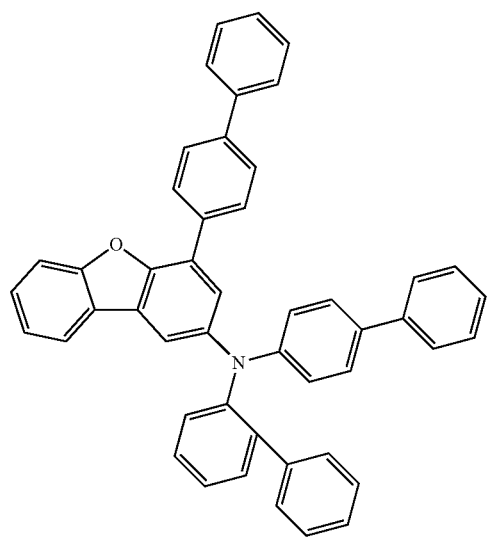
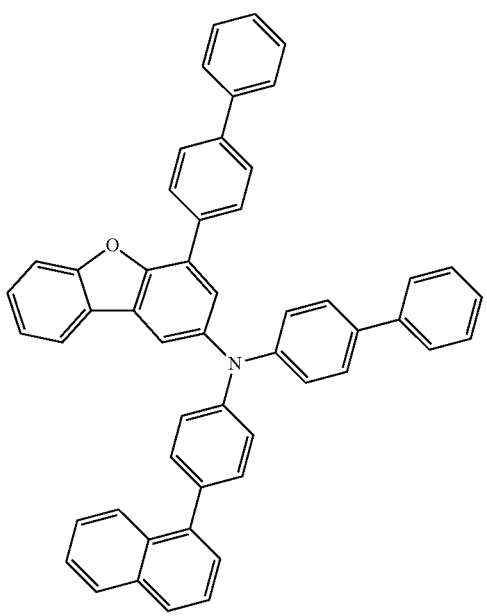

313
-continued
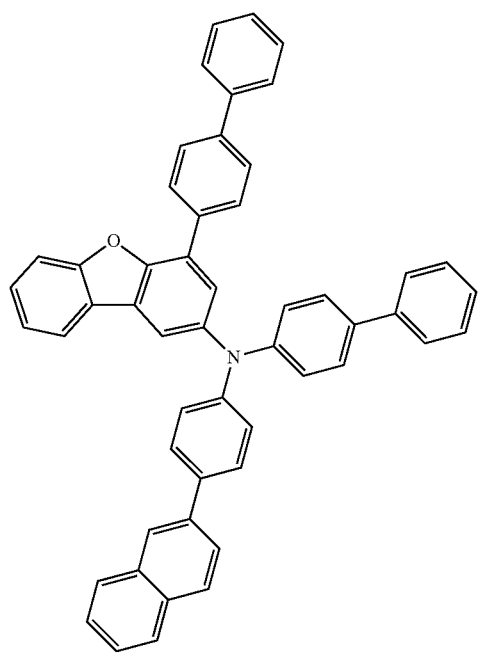
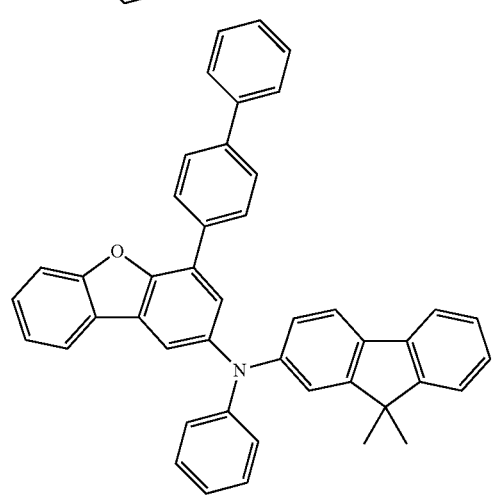
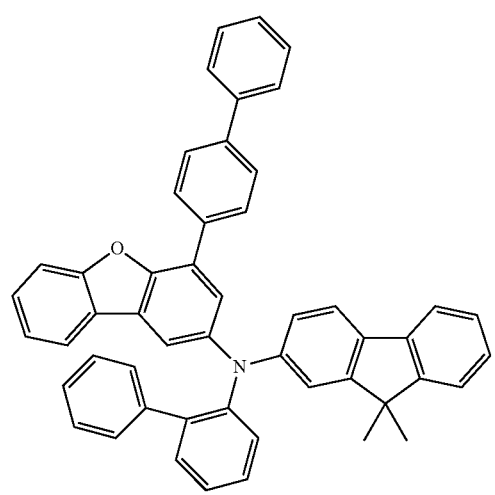
314
-continued
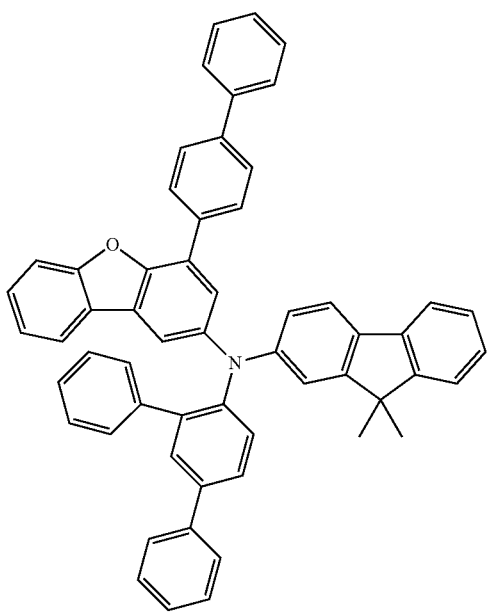
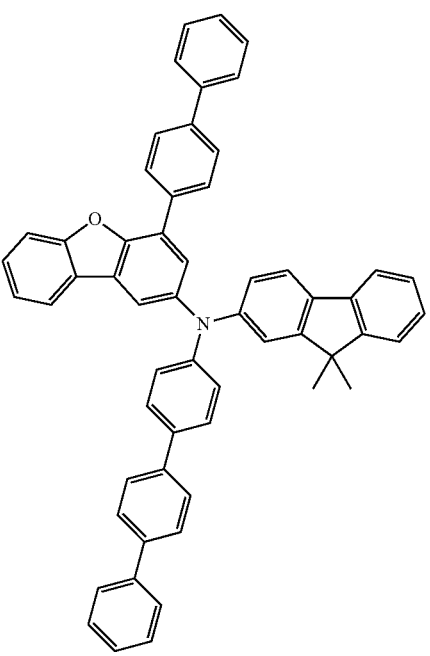

315
-continued
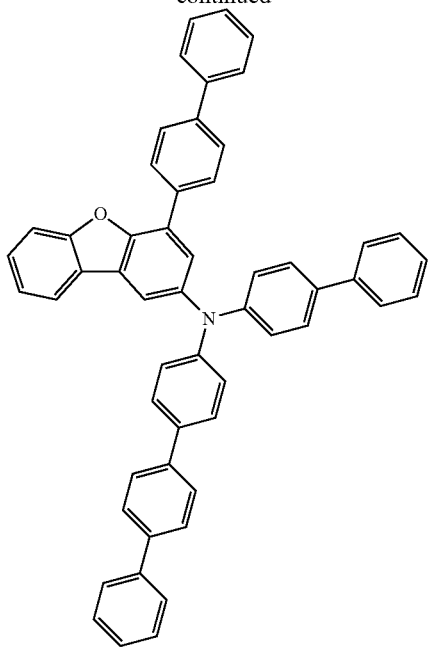
316
-continued
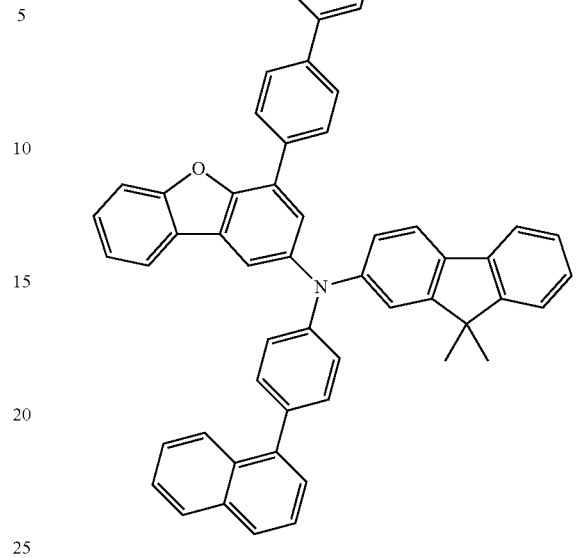
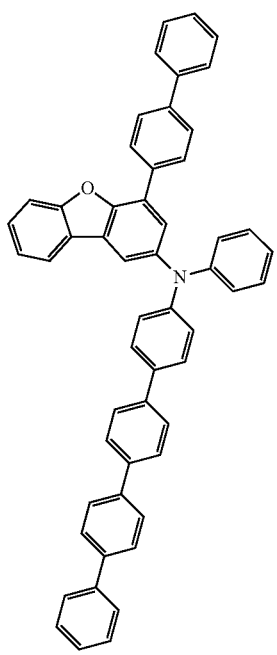
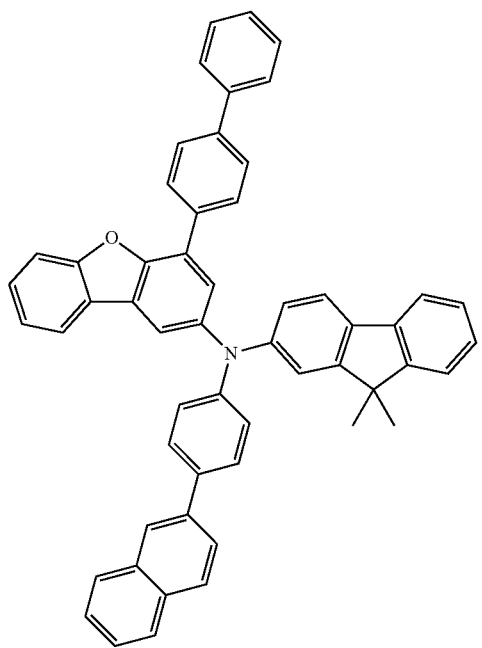

317
-continued
318
-continued
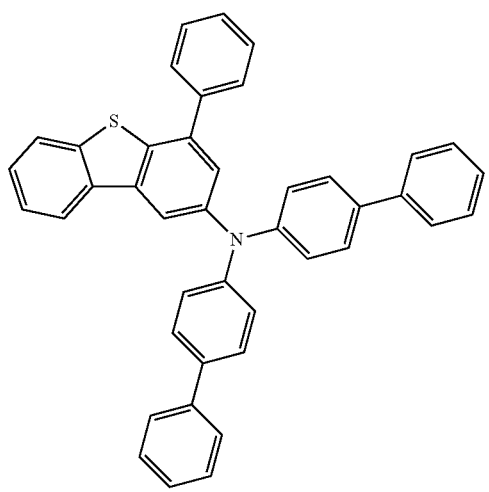
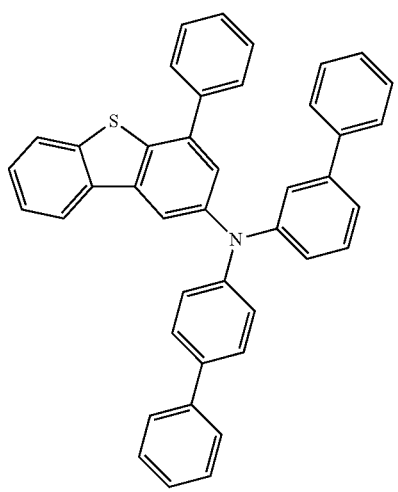
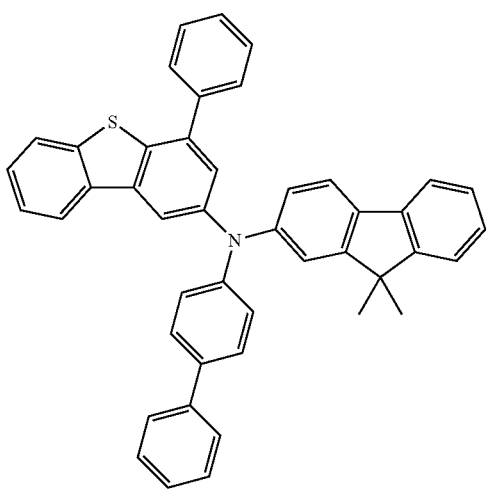
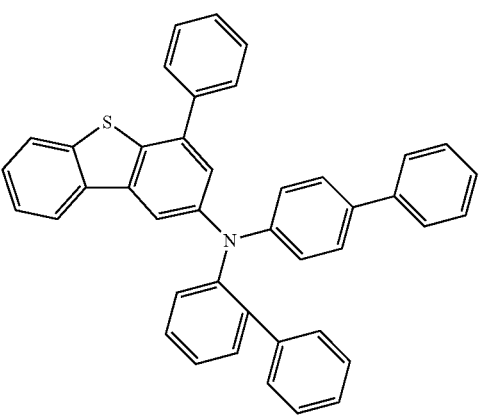
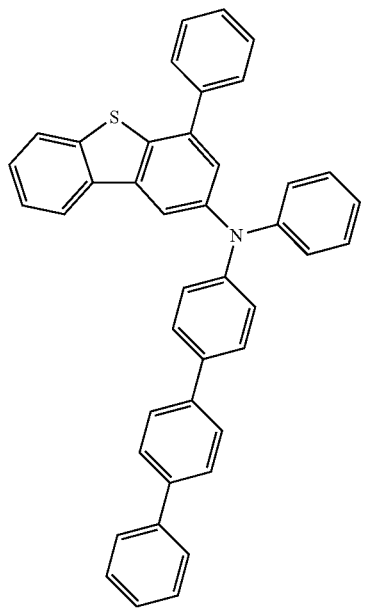

319
-continued
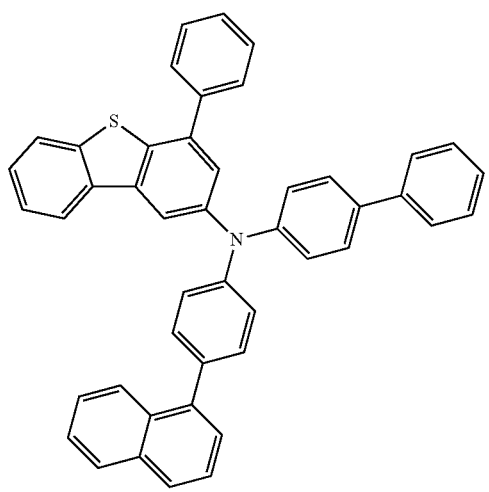
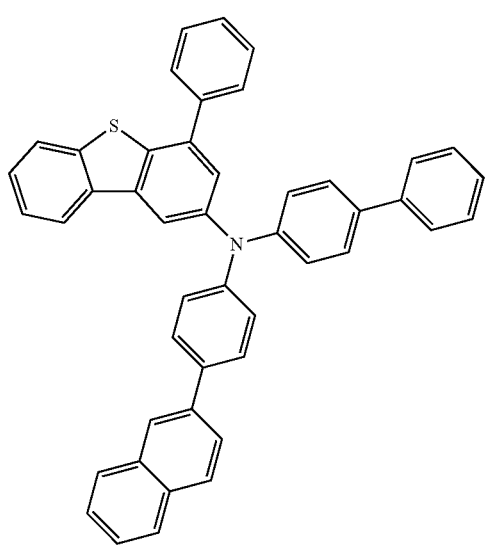
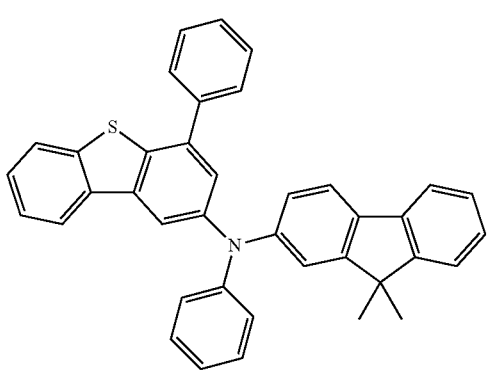
320
-continued
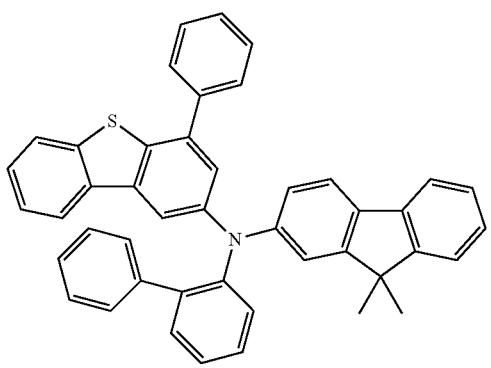
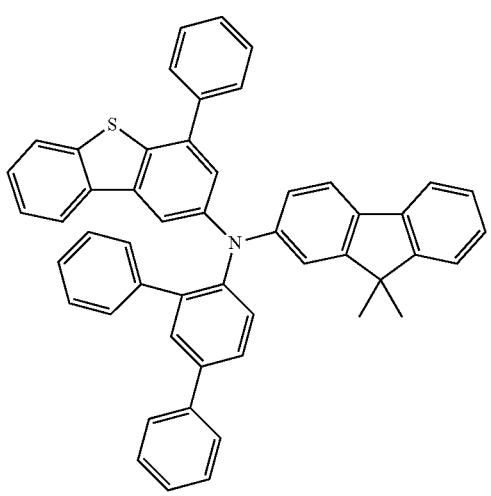
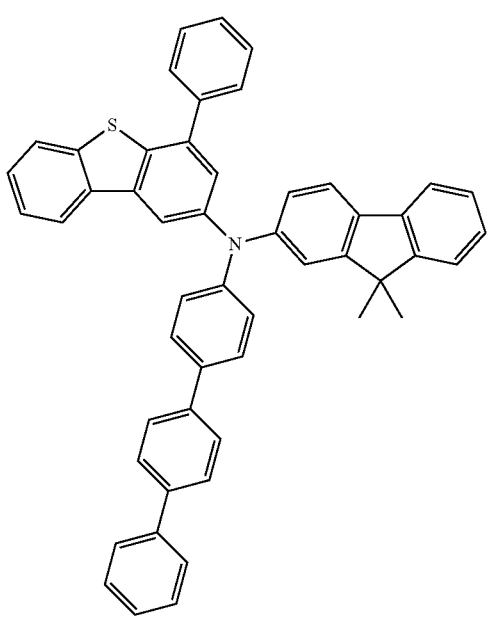

321
-continued
322
-continued
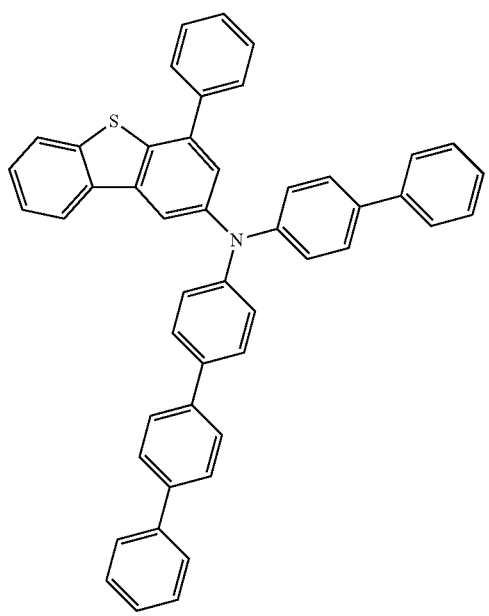
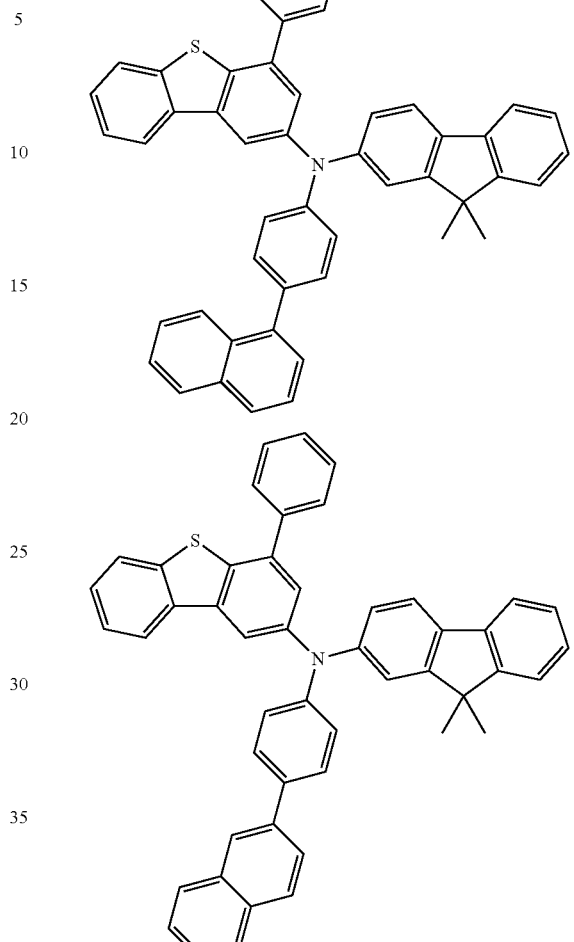
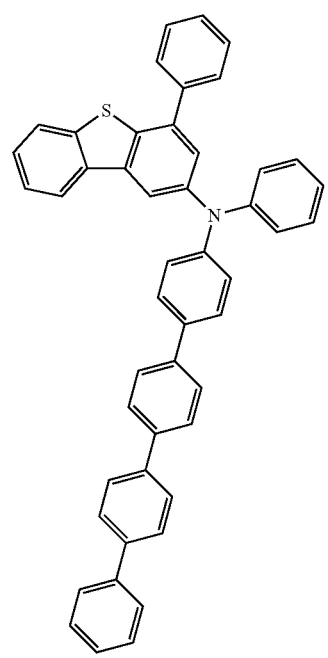
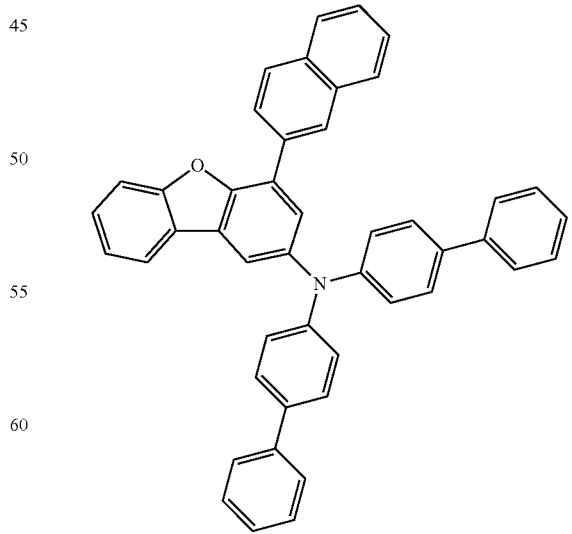

323
-continued
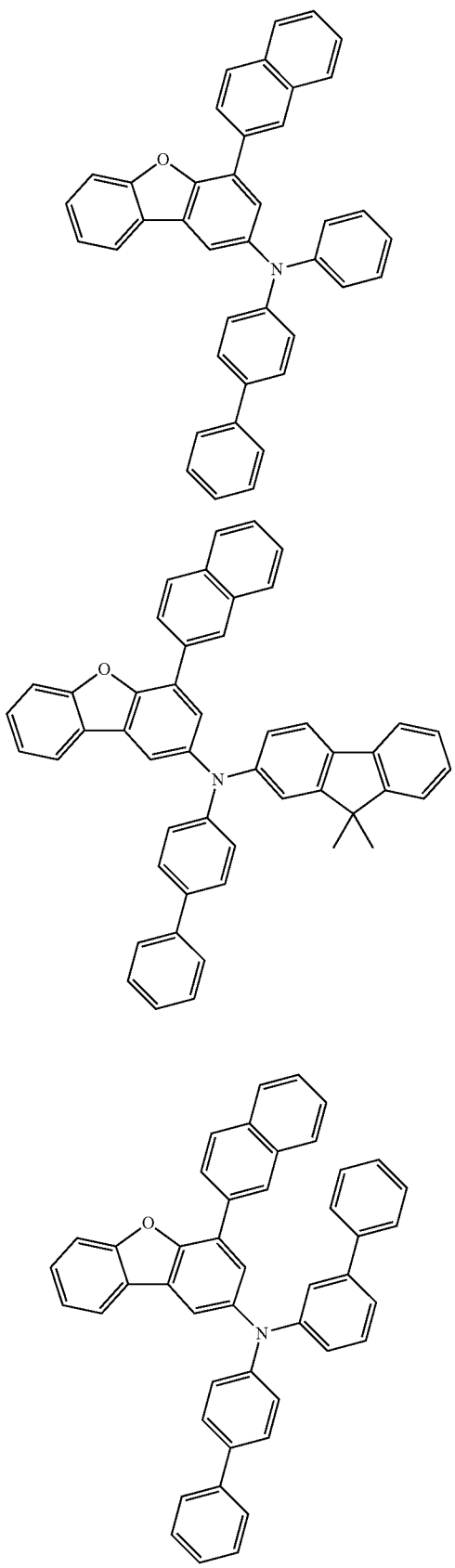
324
-continued
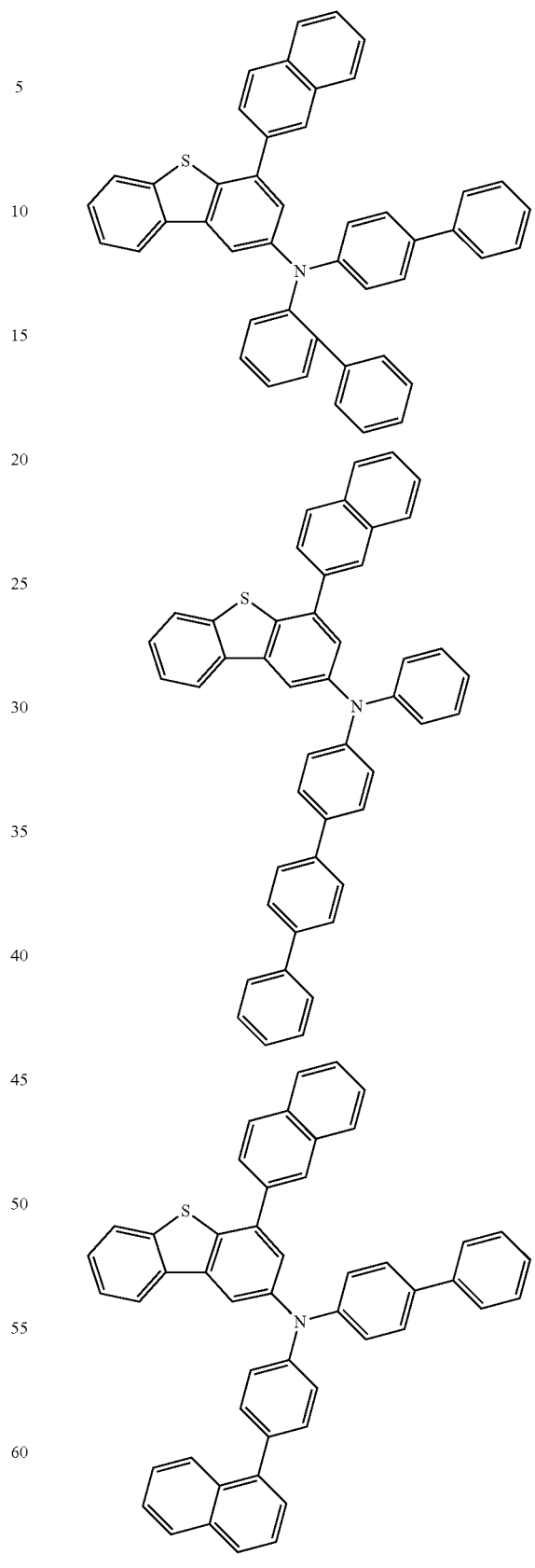

325
-continued
326
-continued
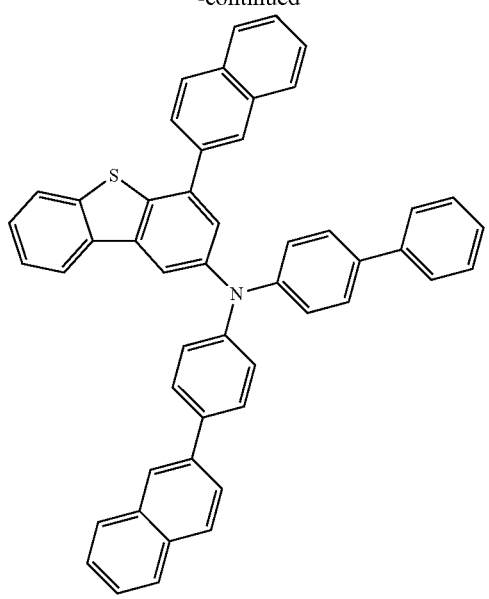
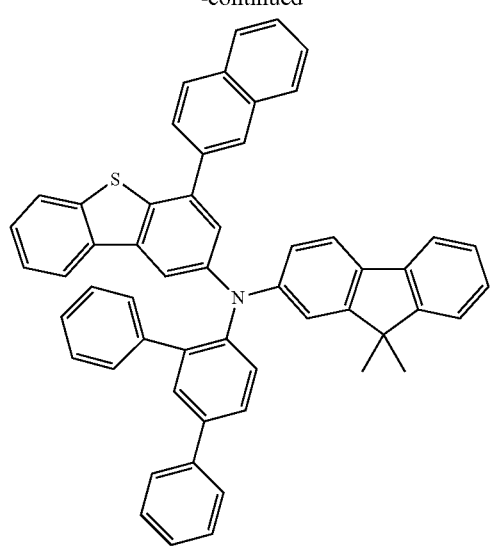
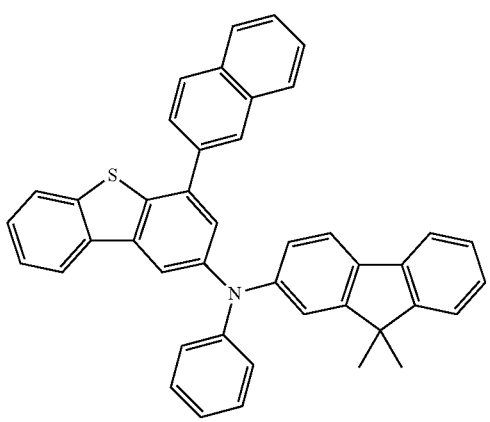
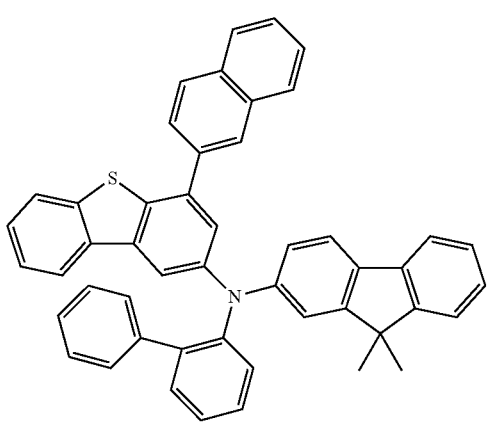
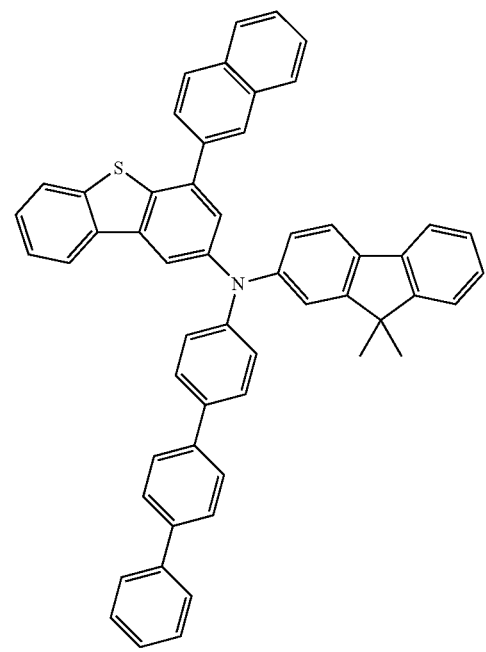

327 -continued
328 -continued
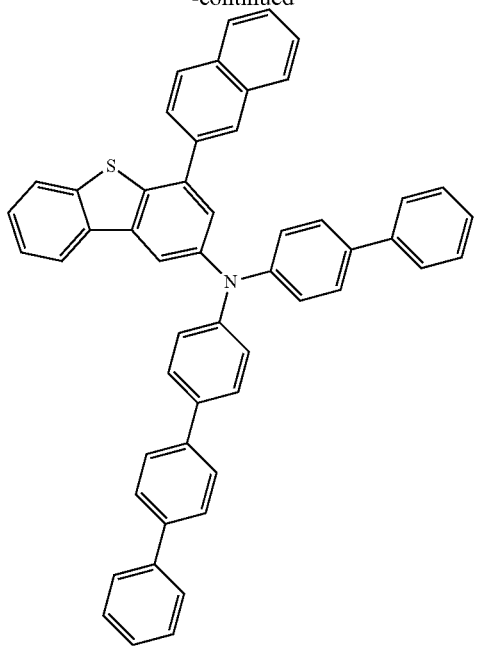
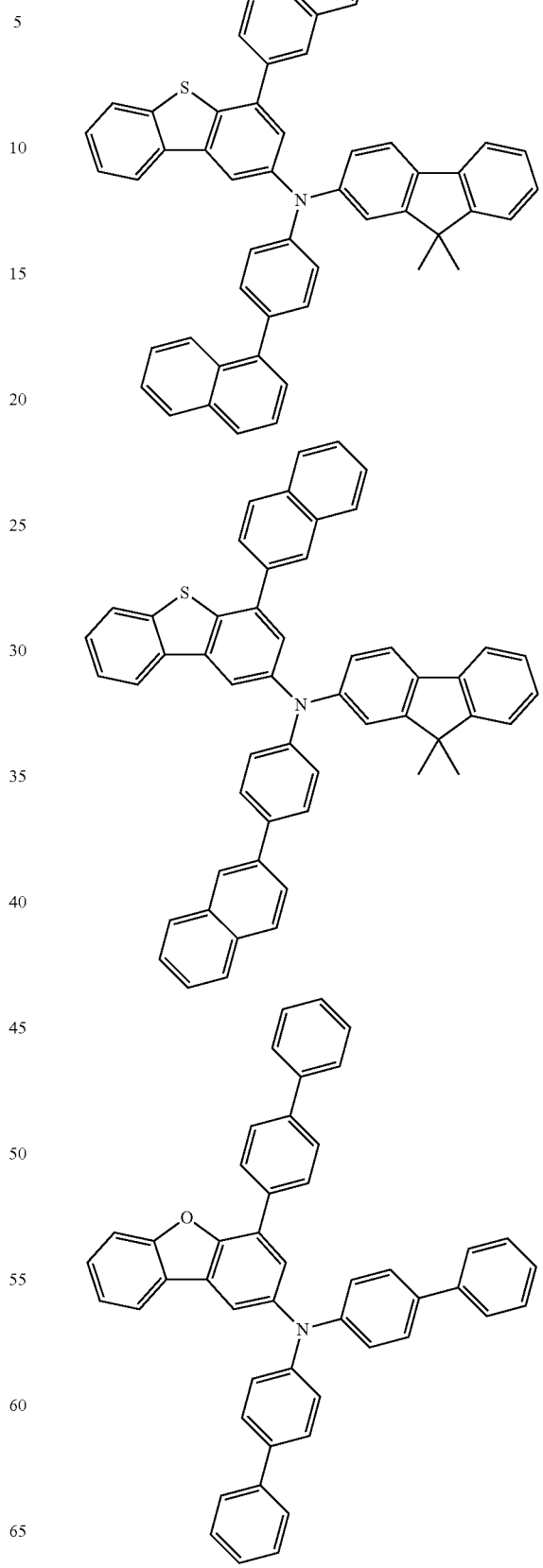
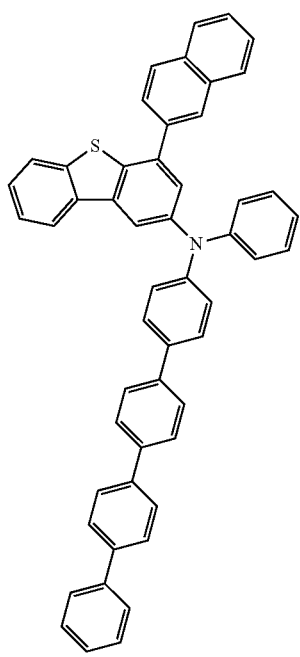

329
-continued
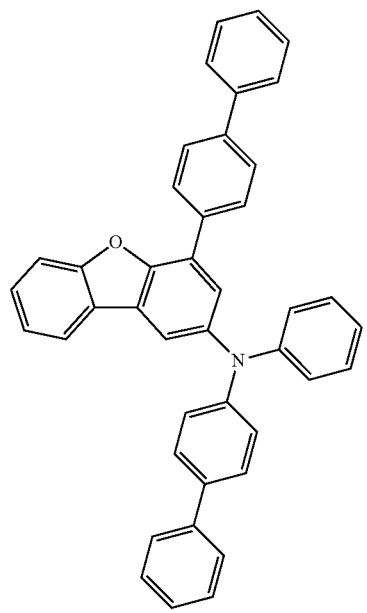
330
-continued
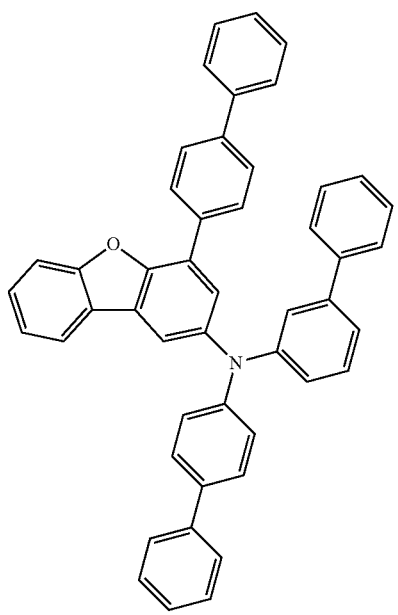
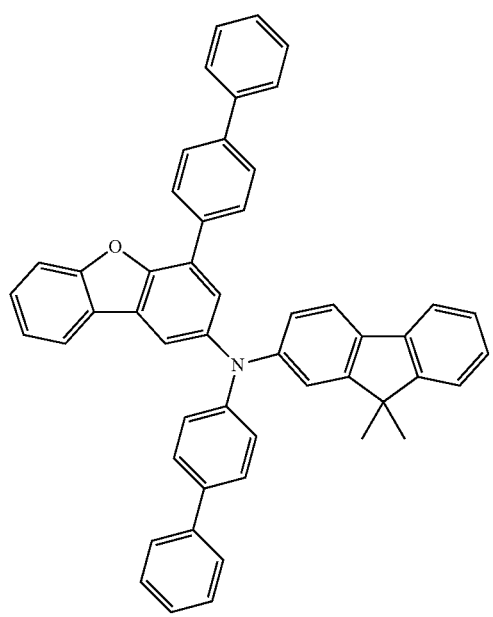
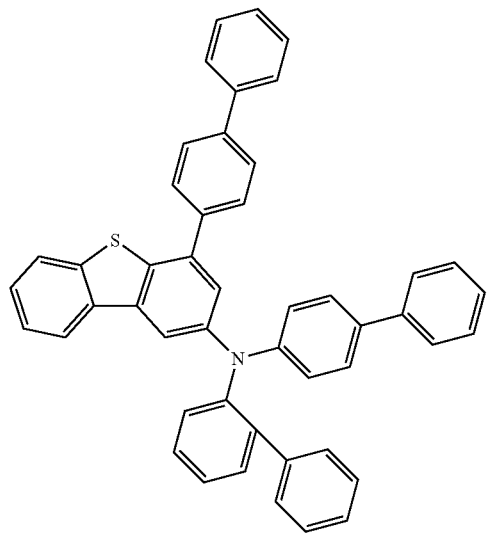

331
-continued
332
-continued
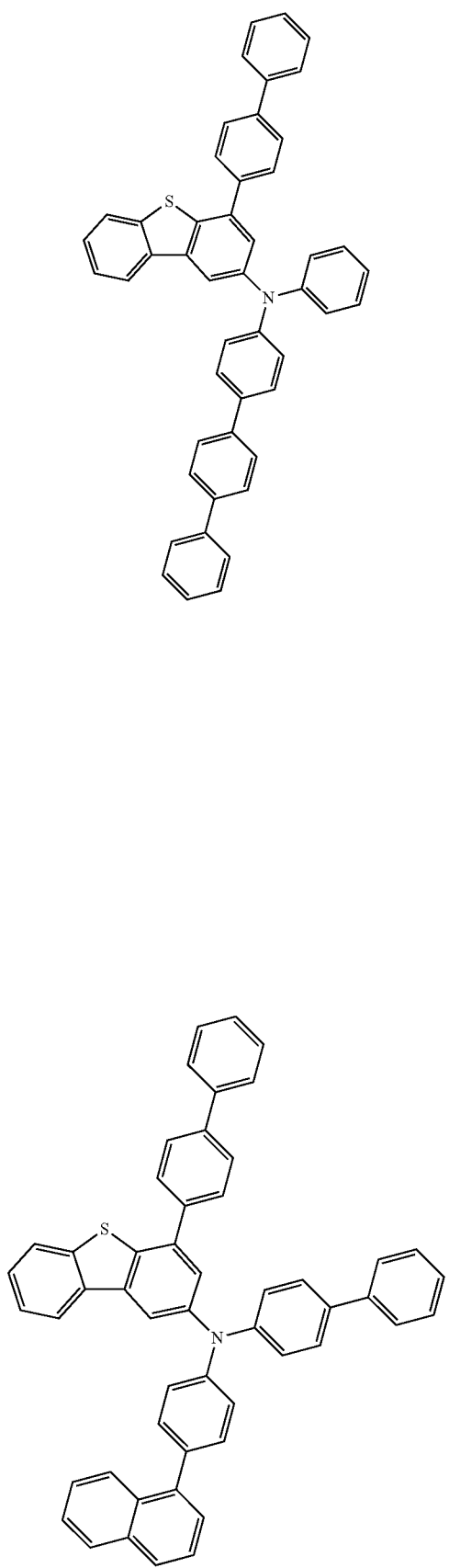
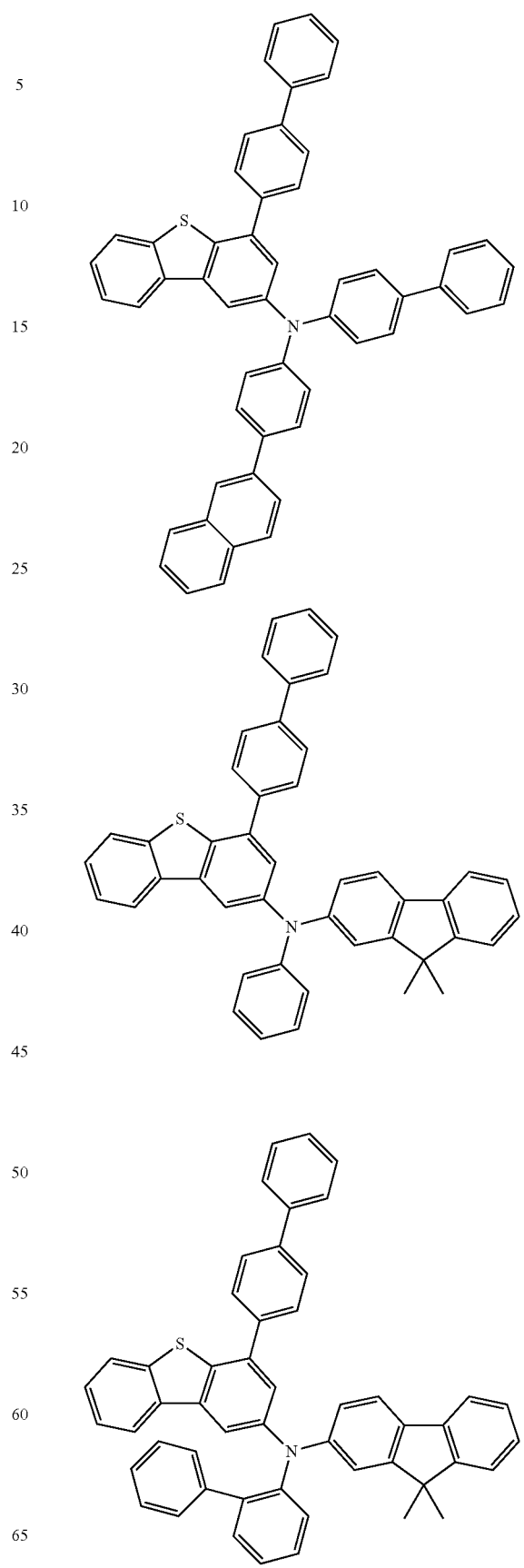

333
-continued
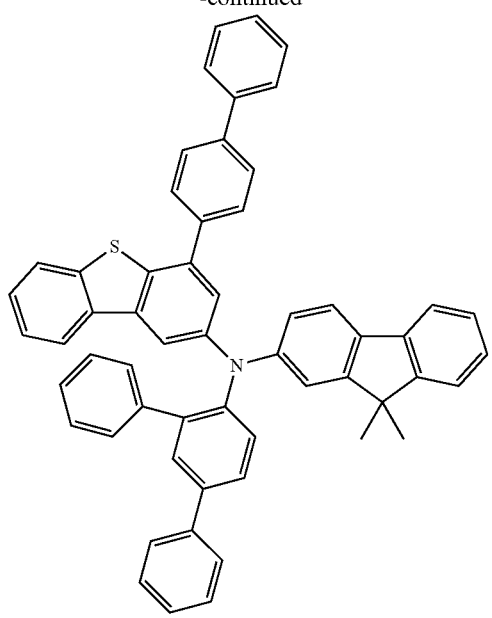
334
-continued
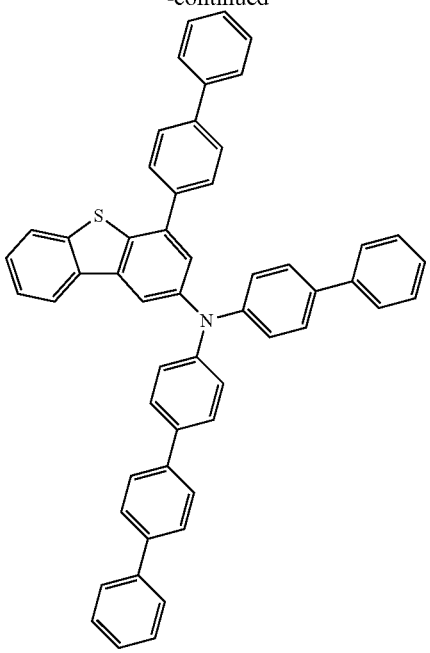
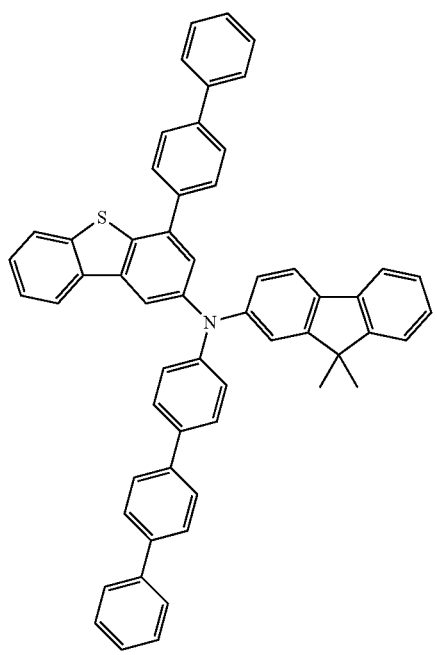
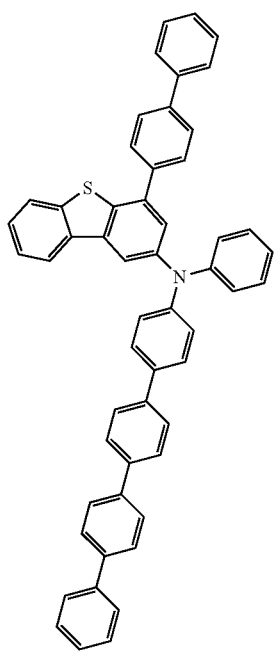

335
-continued
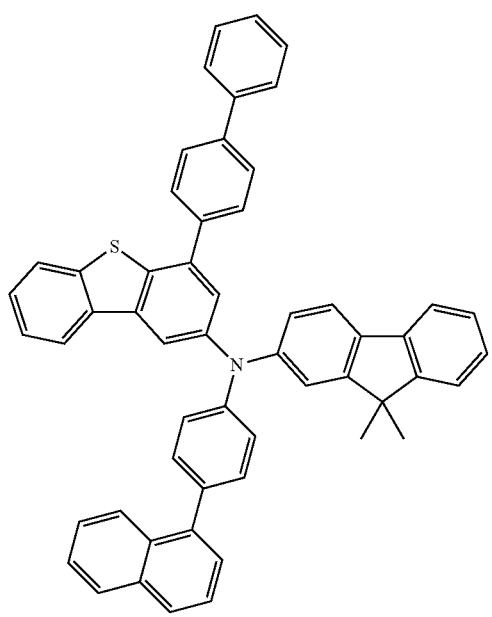
336
-continued
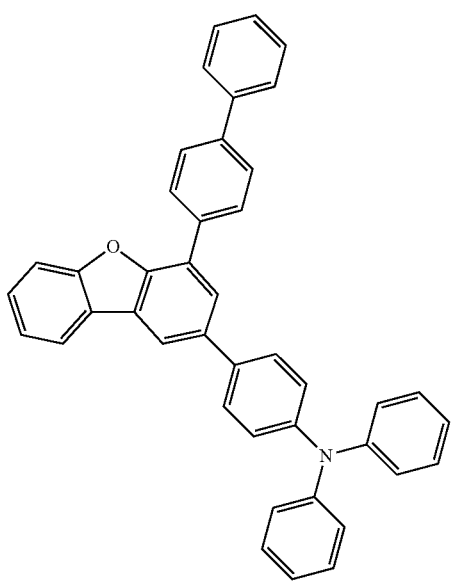
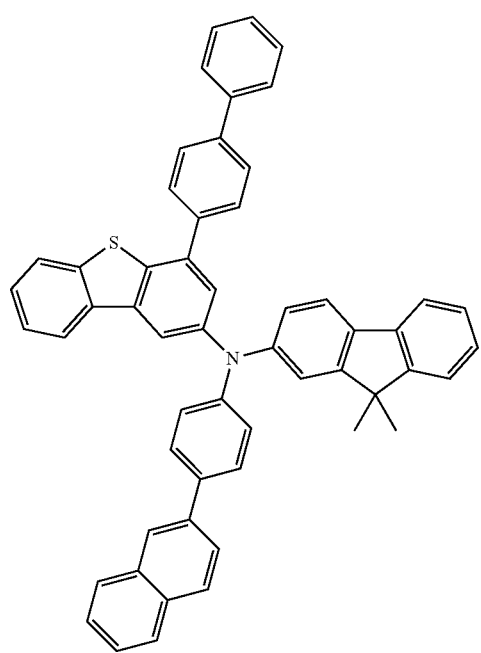
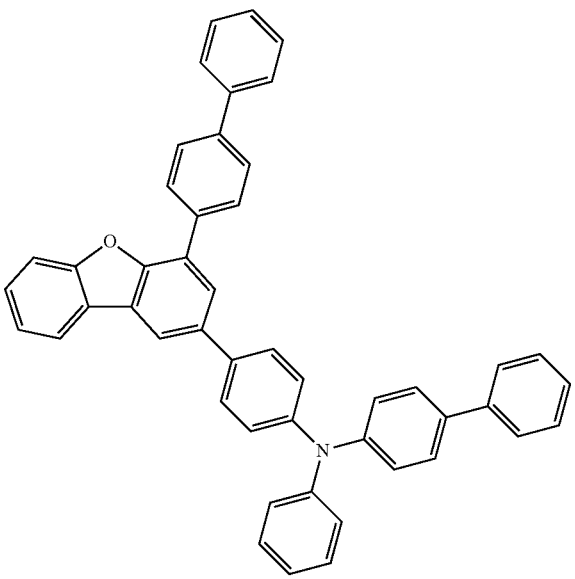

337
-continued
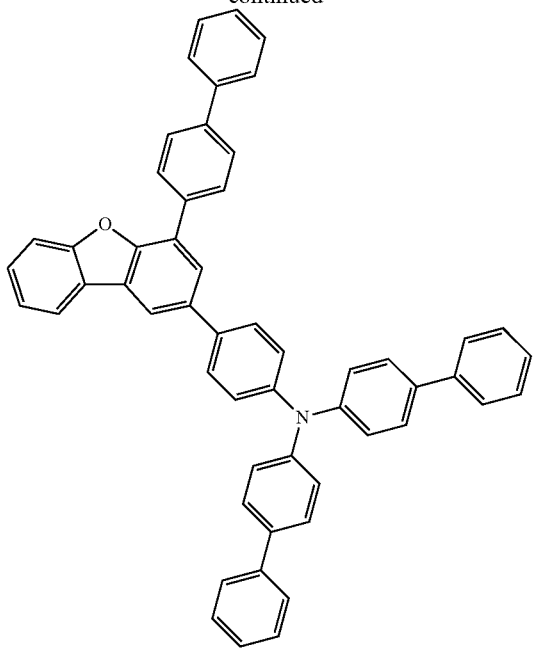
338
-continued
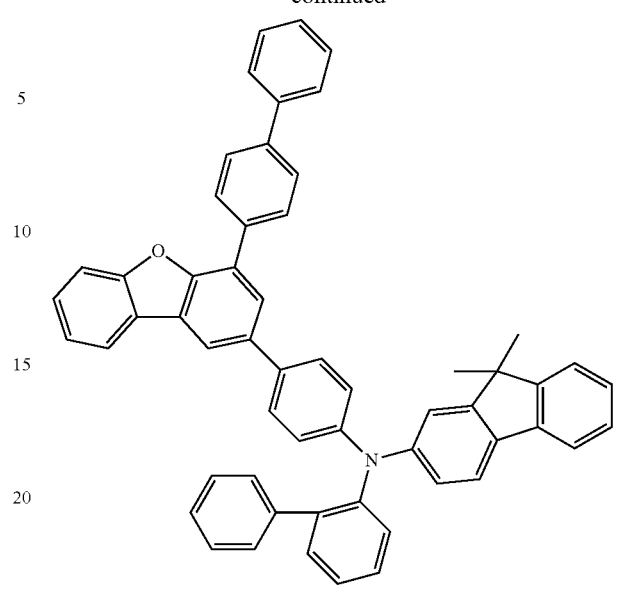
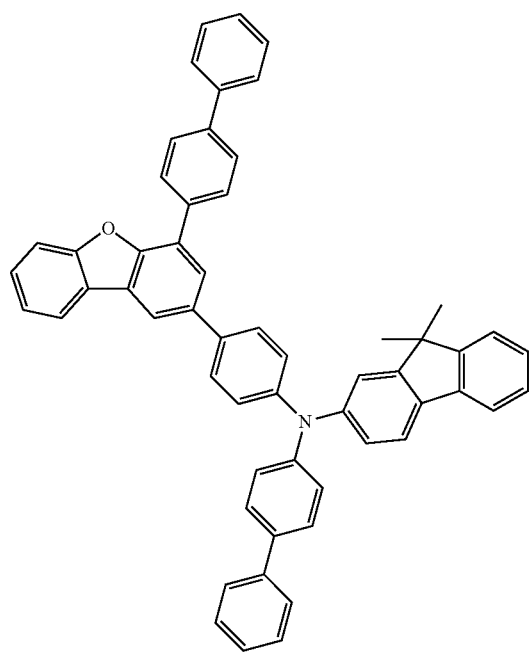
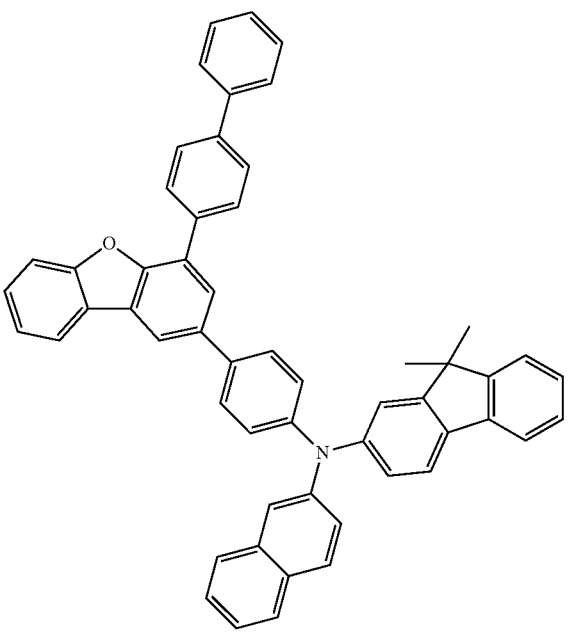

339
-continued
340
-continued
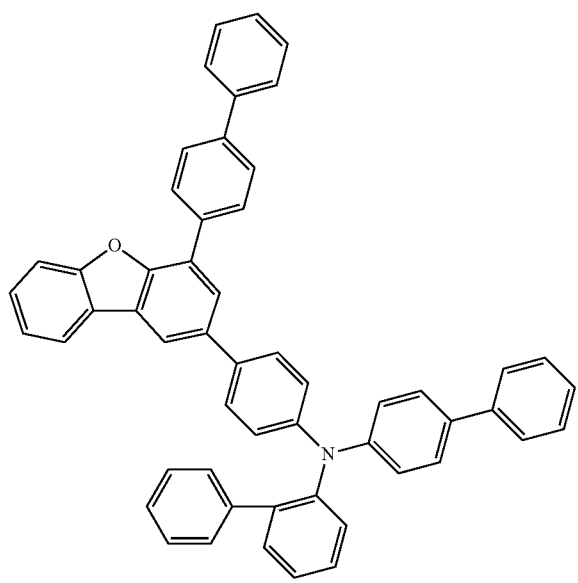
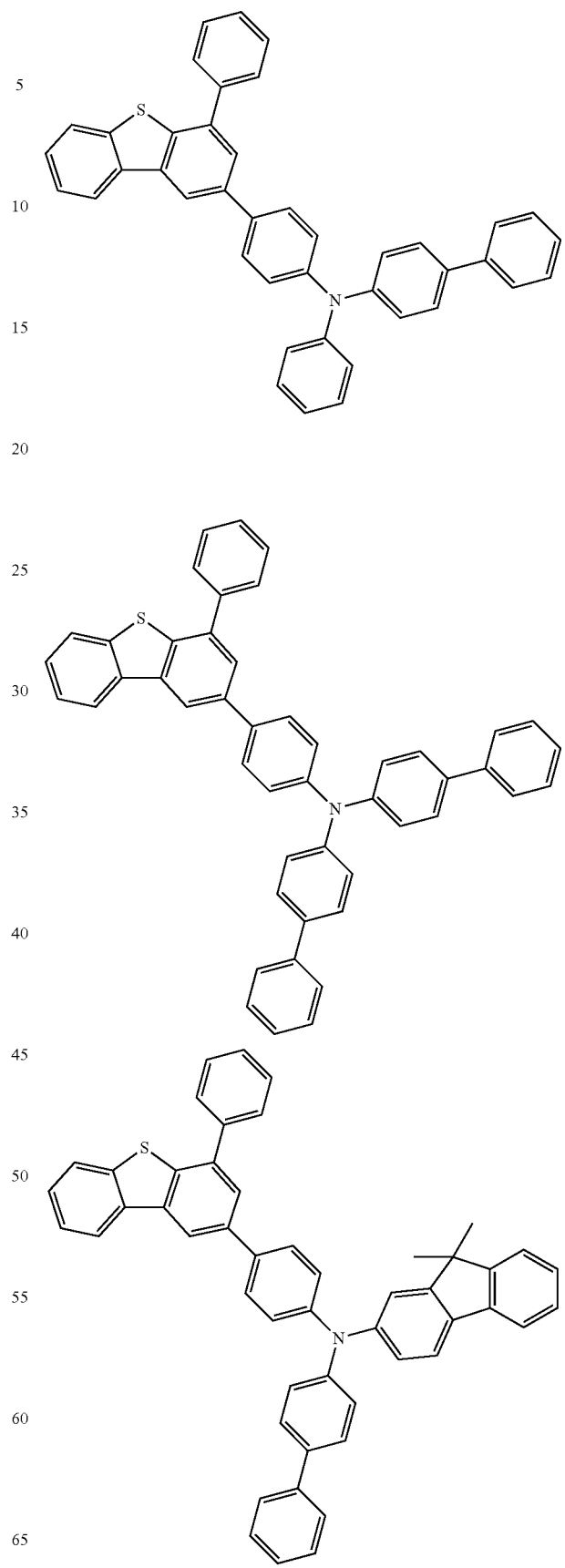

341
-continued
342
-continued
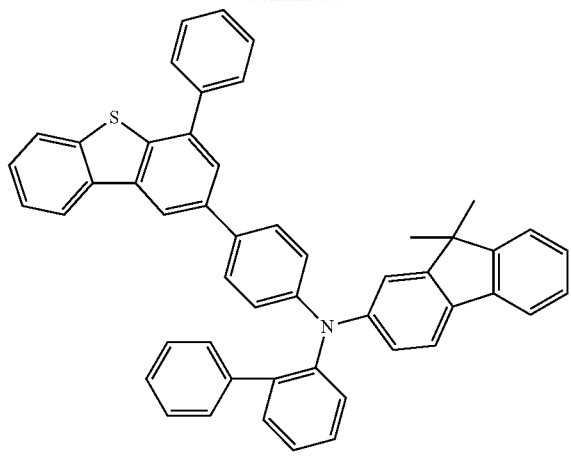
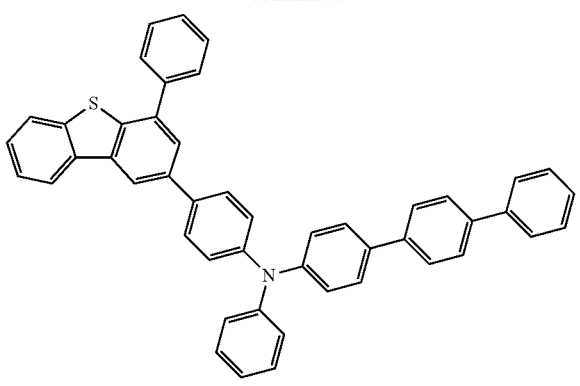
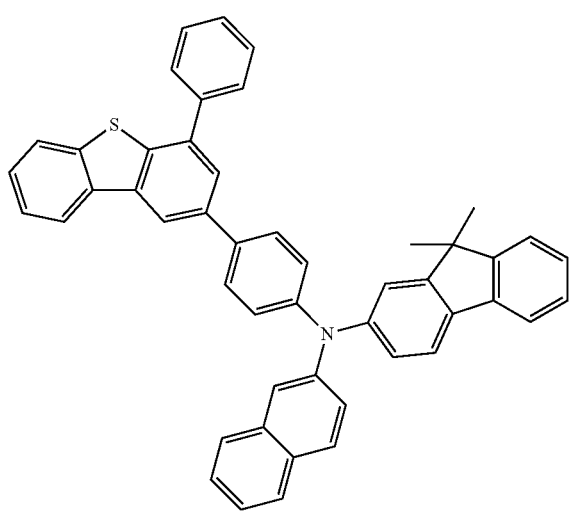
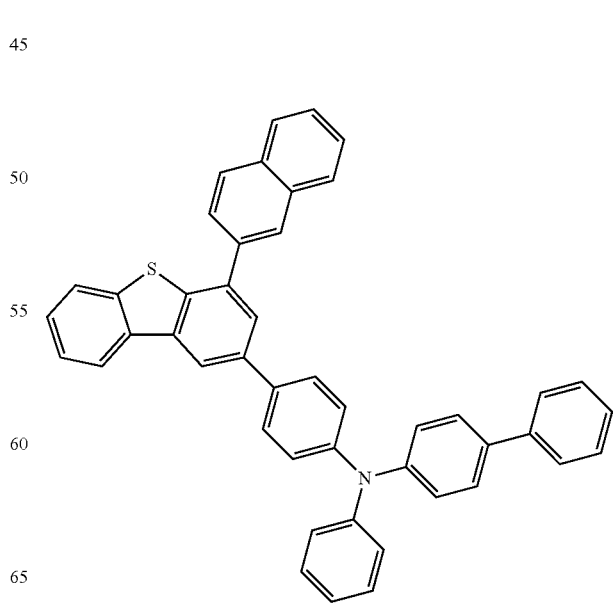
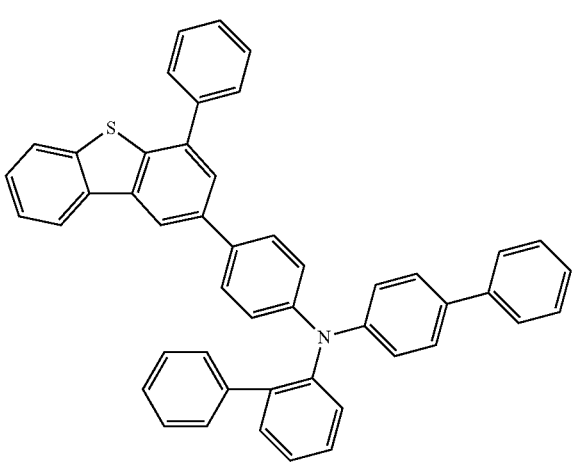

343
-continued
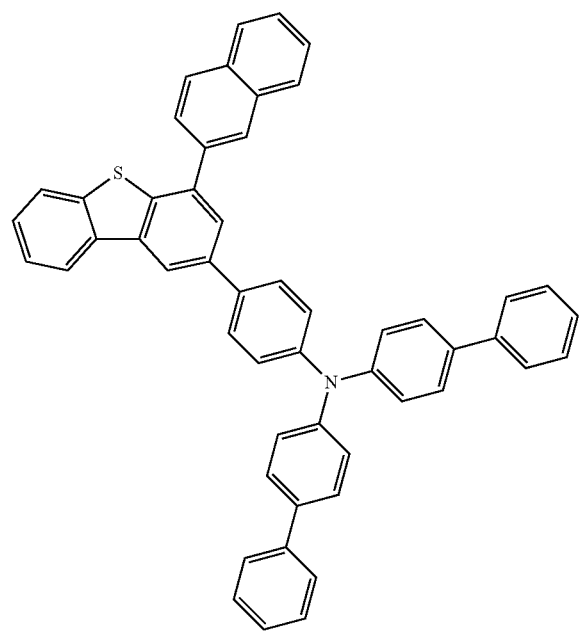
344
-continued
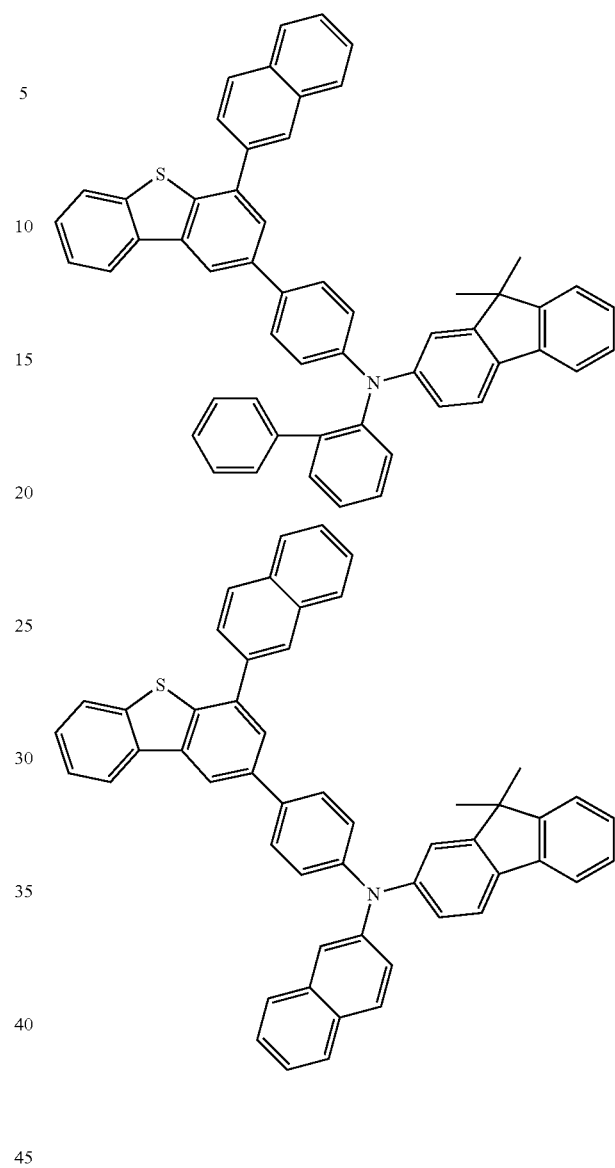
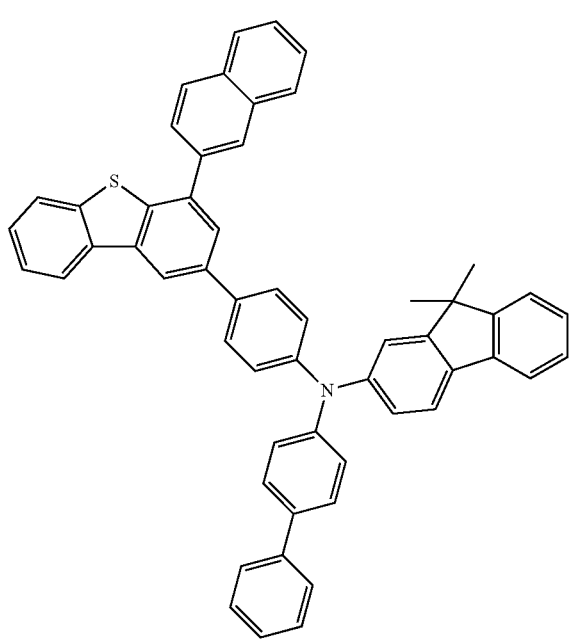
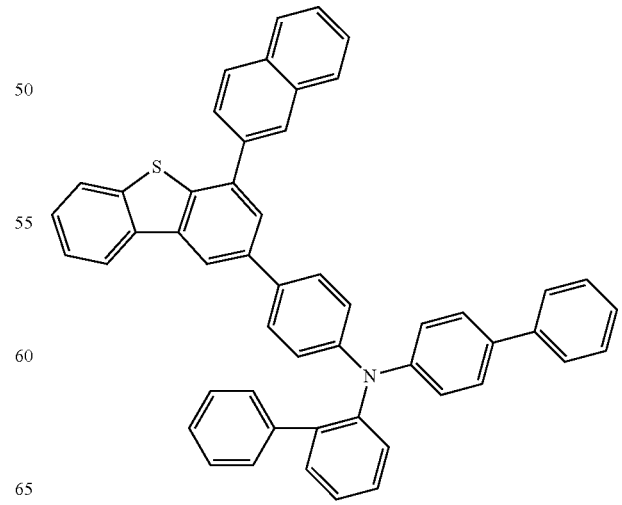

345
-continued
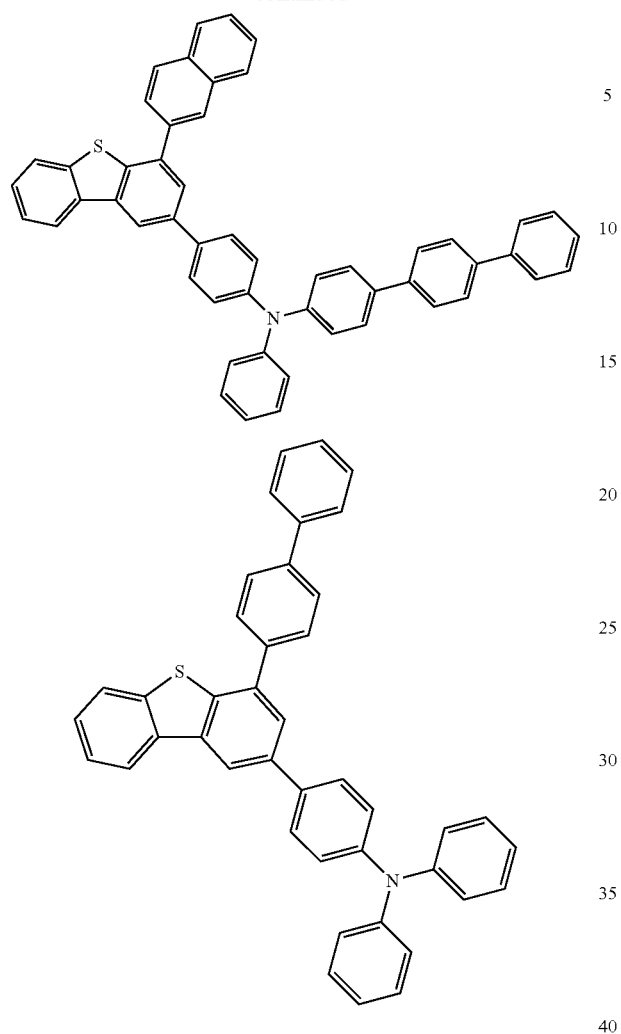
346
-continued
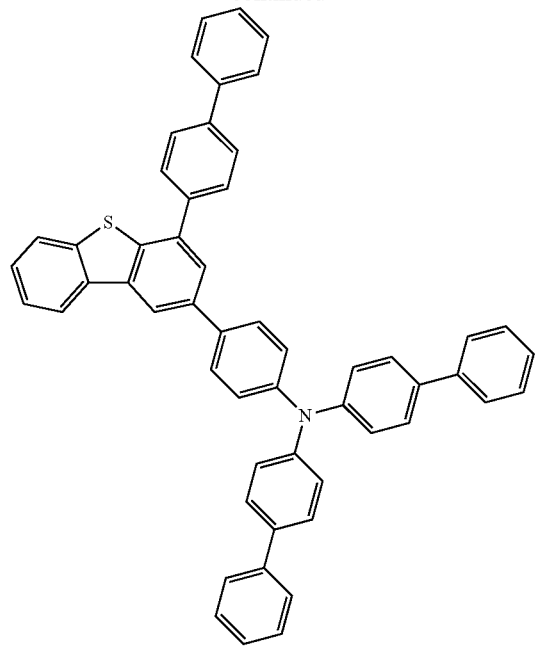
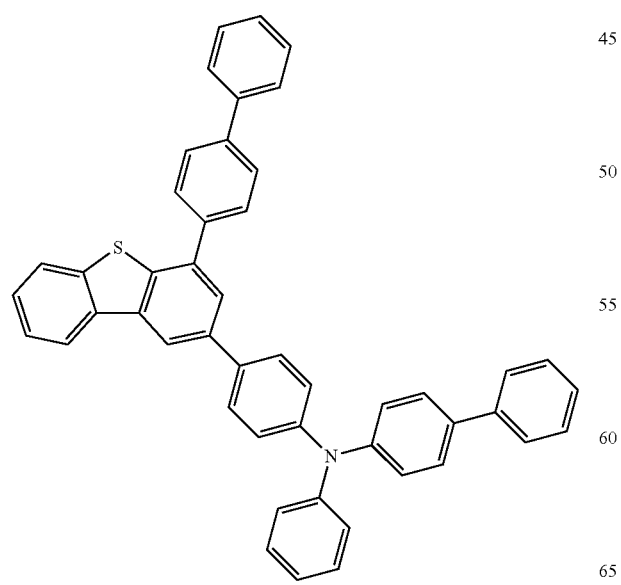
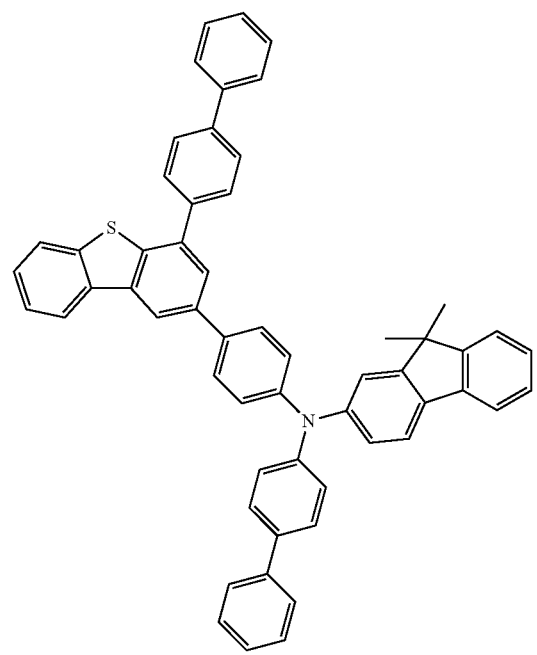

347
-continued
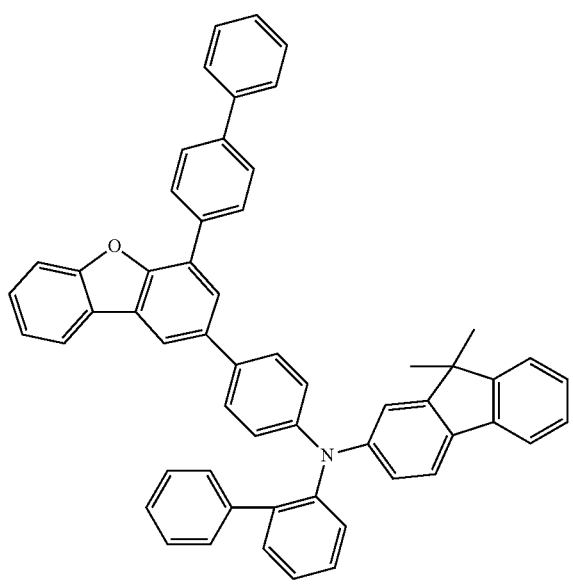
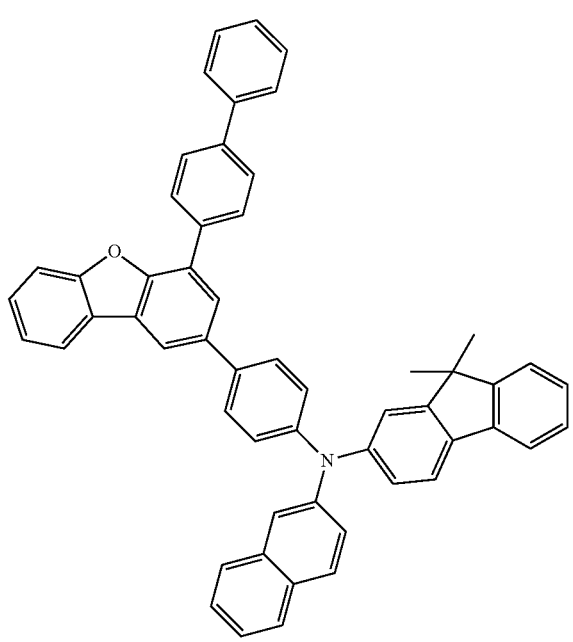
348
-continued
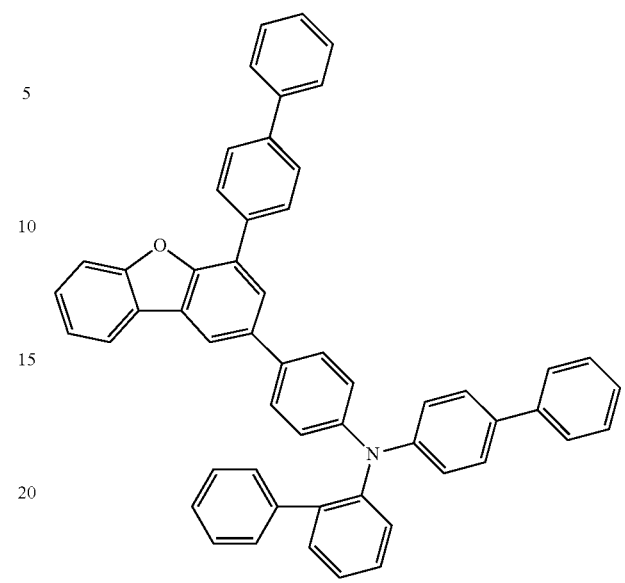
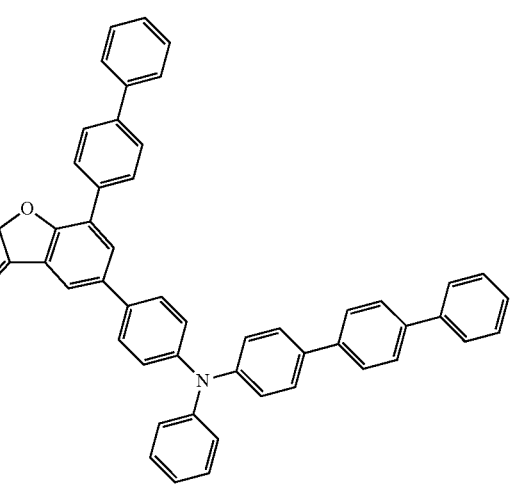
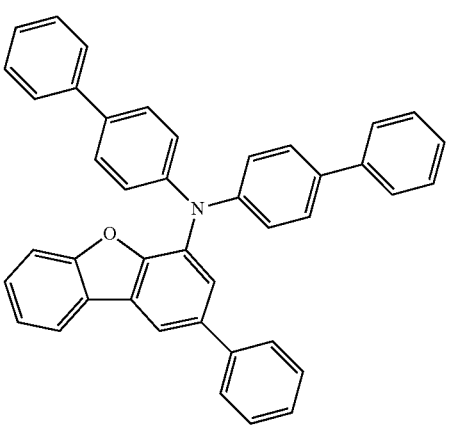

349
-continued
350
-continued
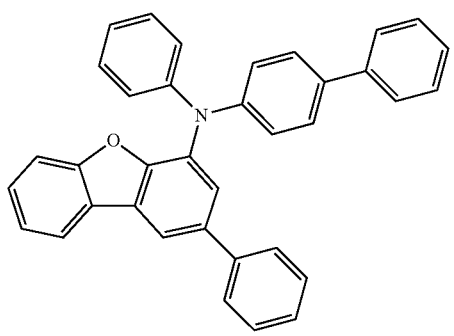
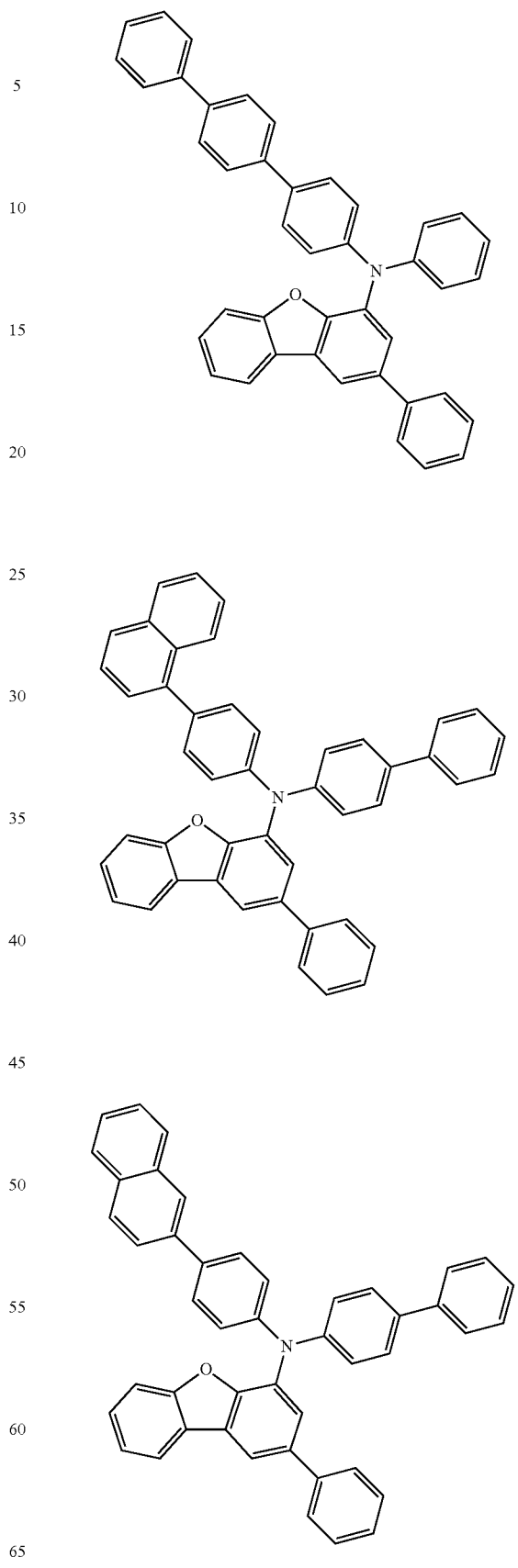

351
-continued
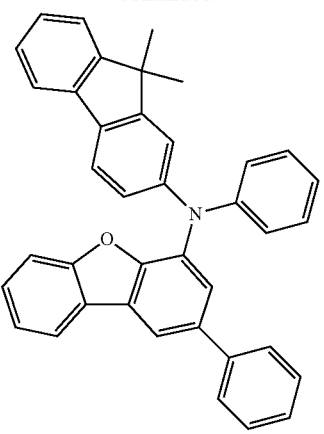
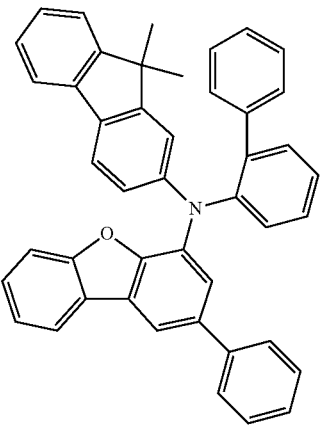
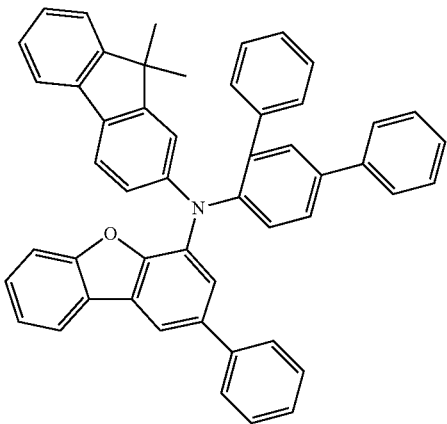
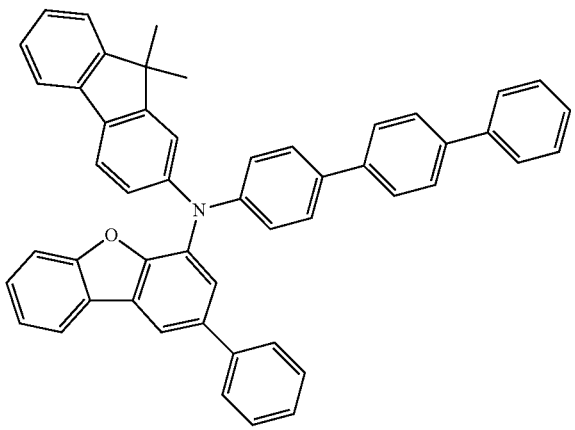
352
-continued
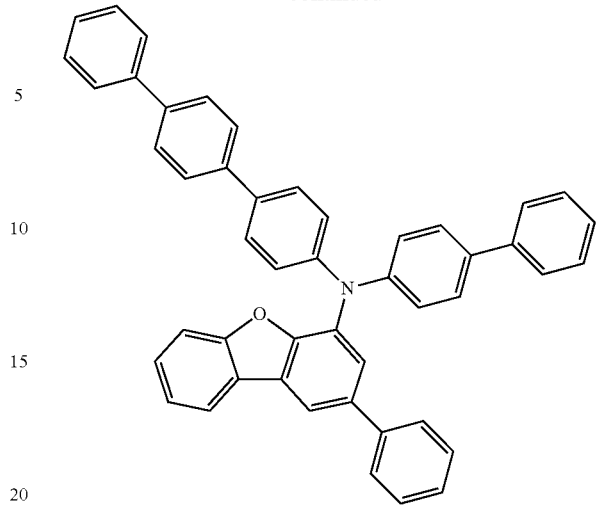
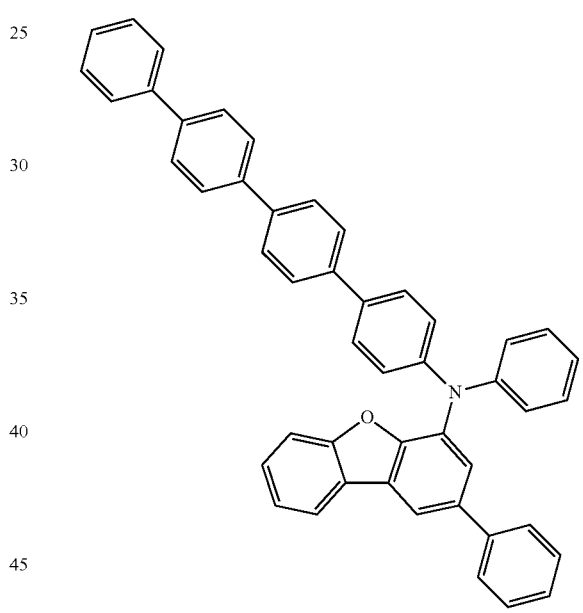
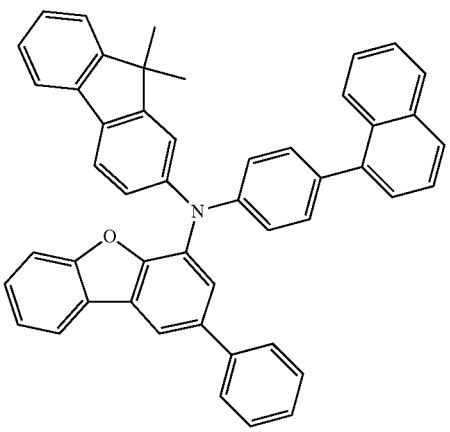

353
-continued
354
-continued
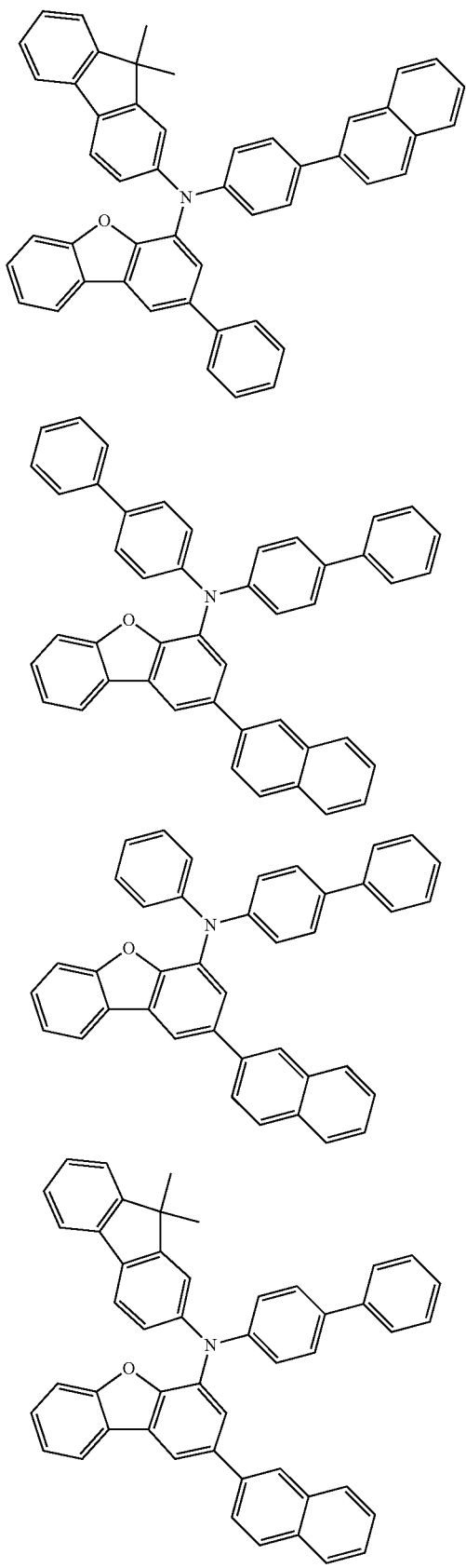
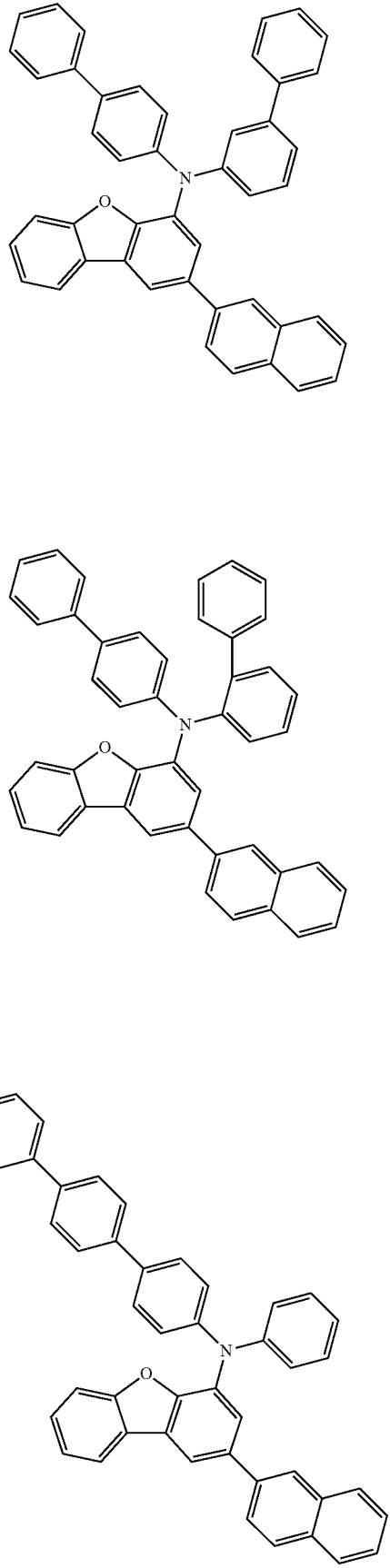

355
-continued
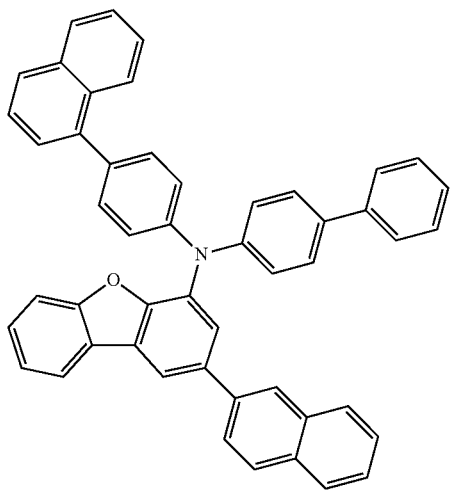
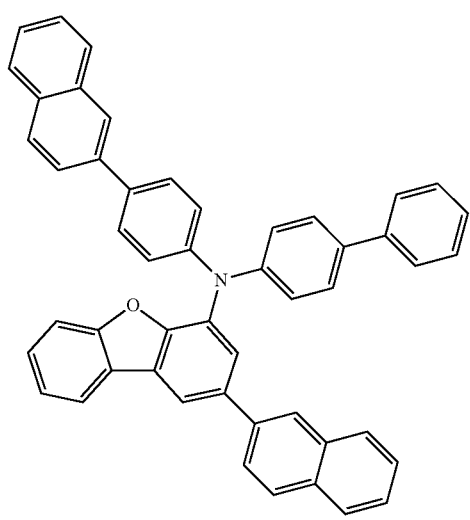
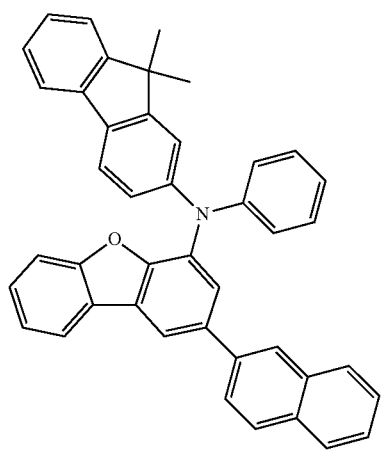
356
-continued
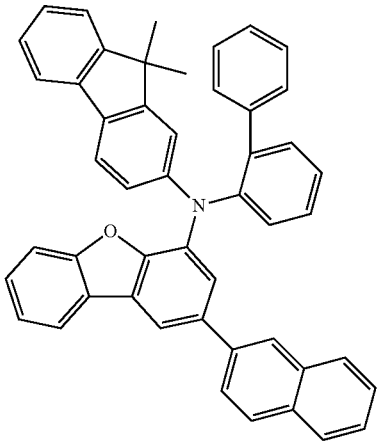
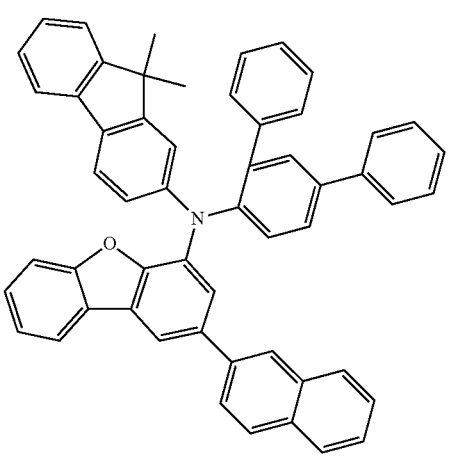
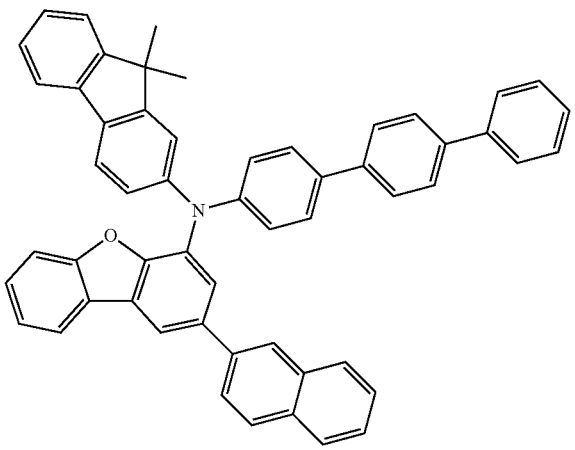

357
-continued
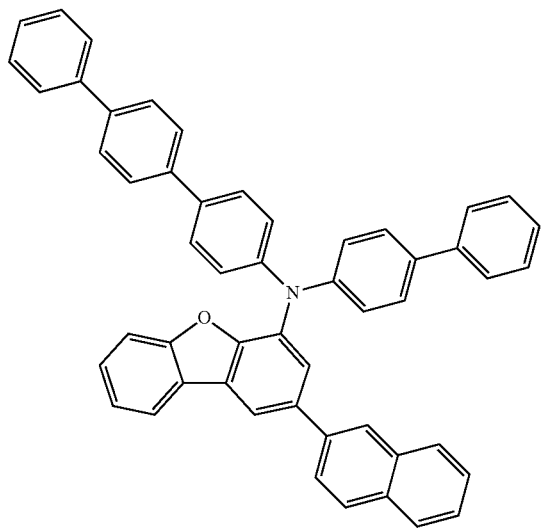
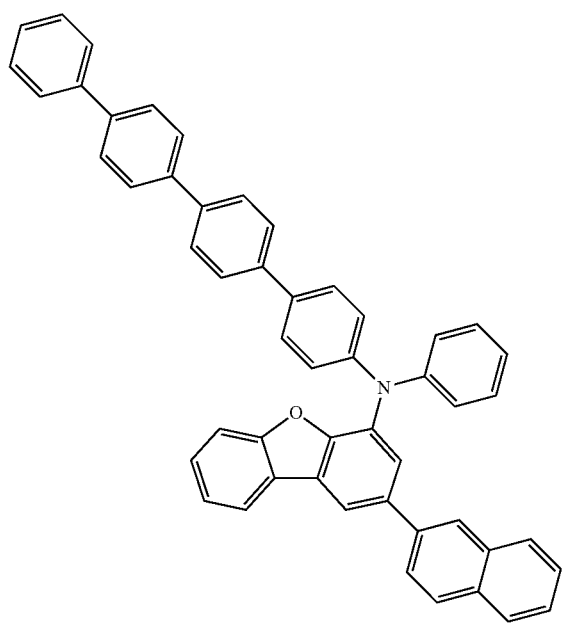
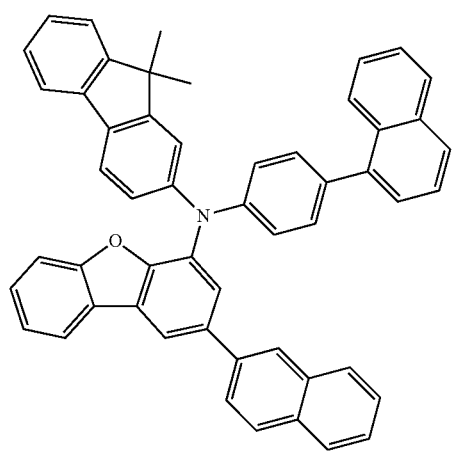
358
-continued
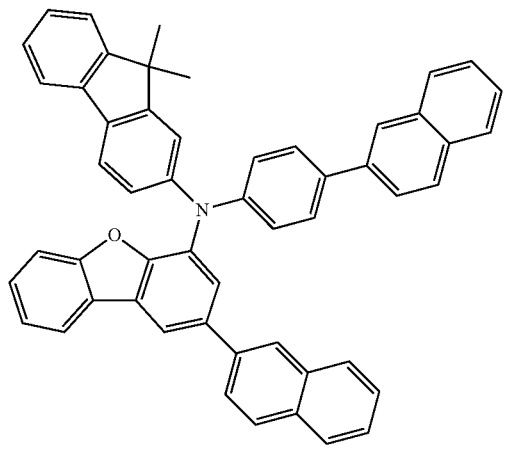
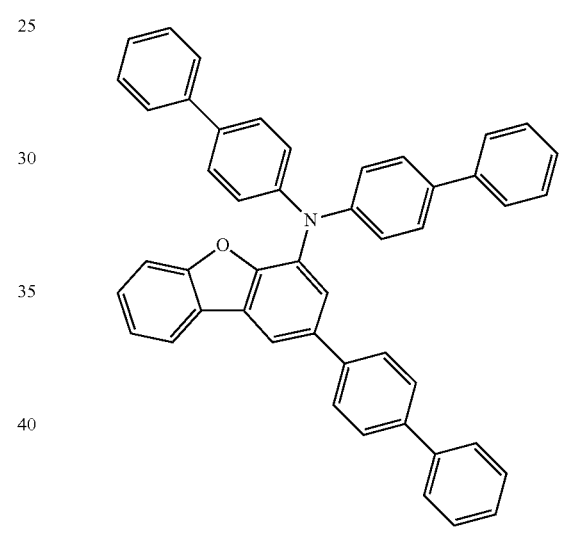
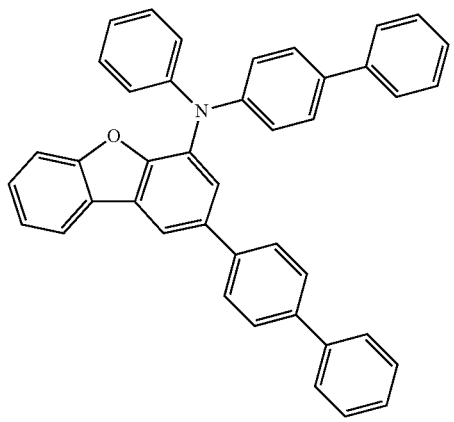

359
-continued
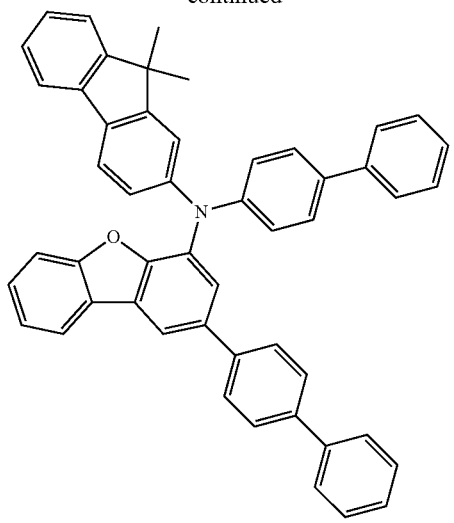
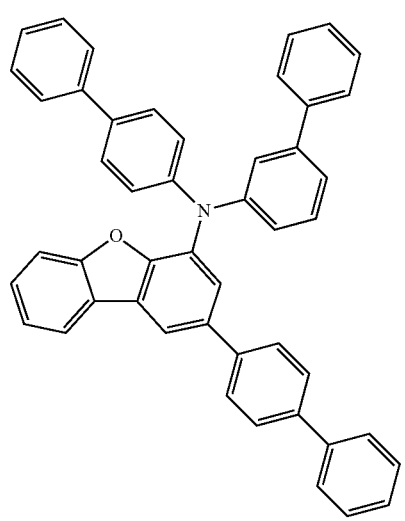 [SMILES: c1ccc(-c2ccc(-c3cc(N(c4ccc(-c5ccccc5)cc4)c4cccc(-c5ccccc5)c4)c4oc5ccccc5c4c3)cc2)cc1]
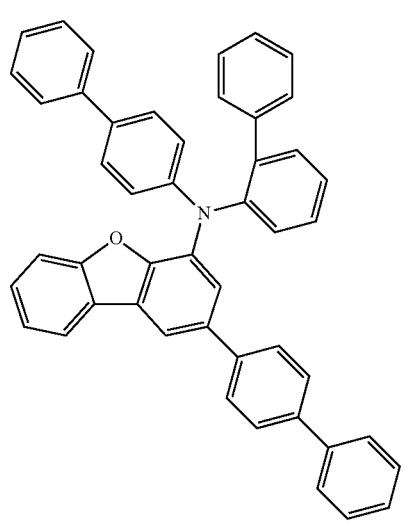
360
-continued
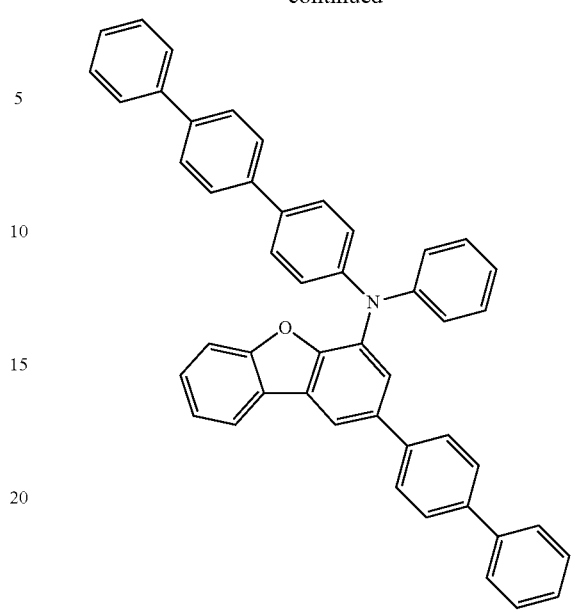
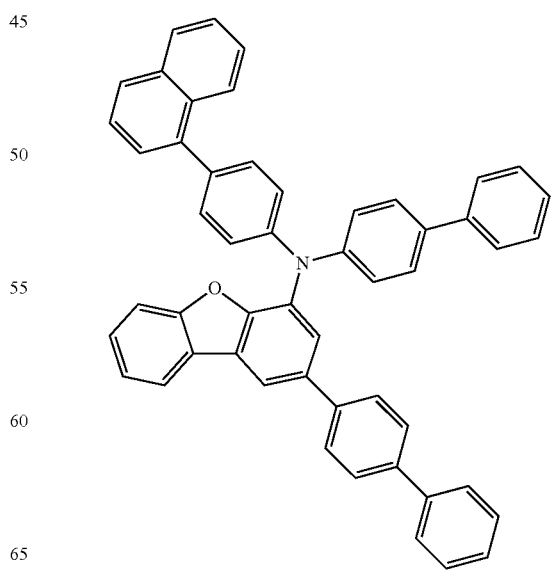

361
-continued
362
-continued
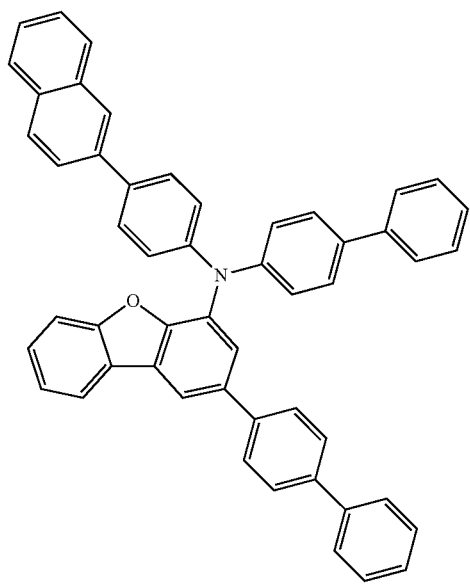
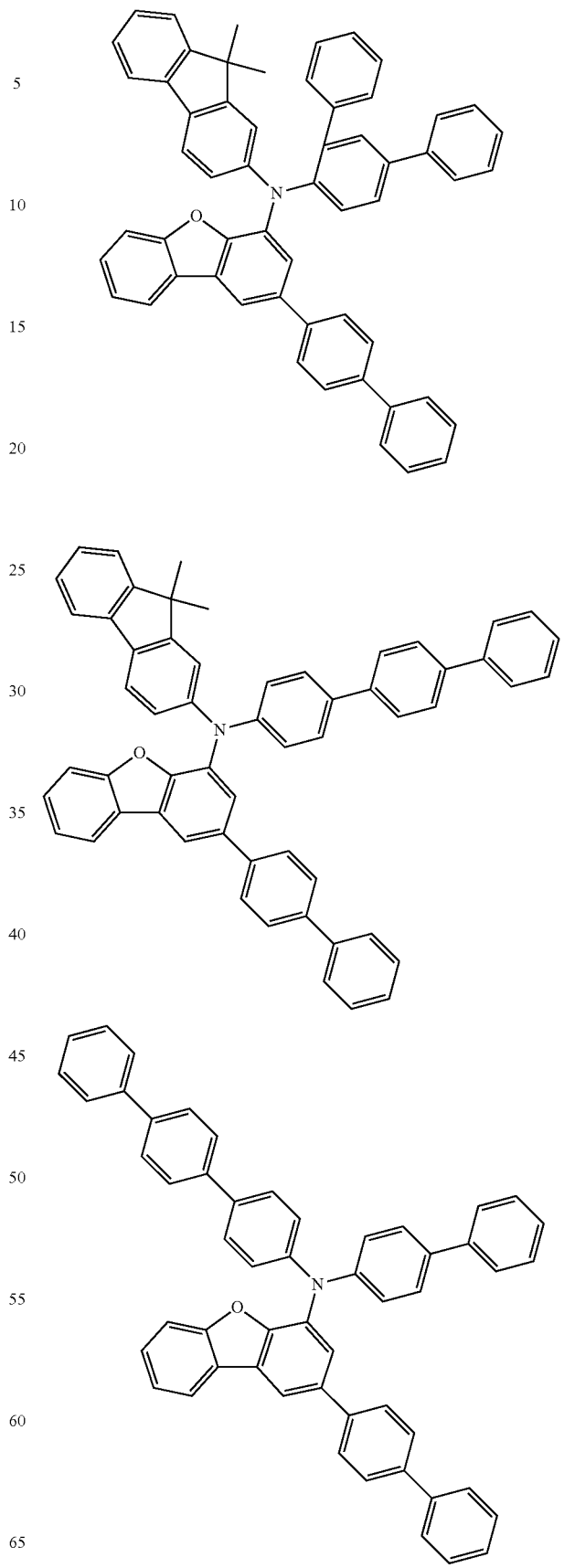

363
-continued
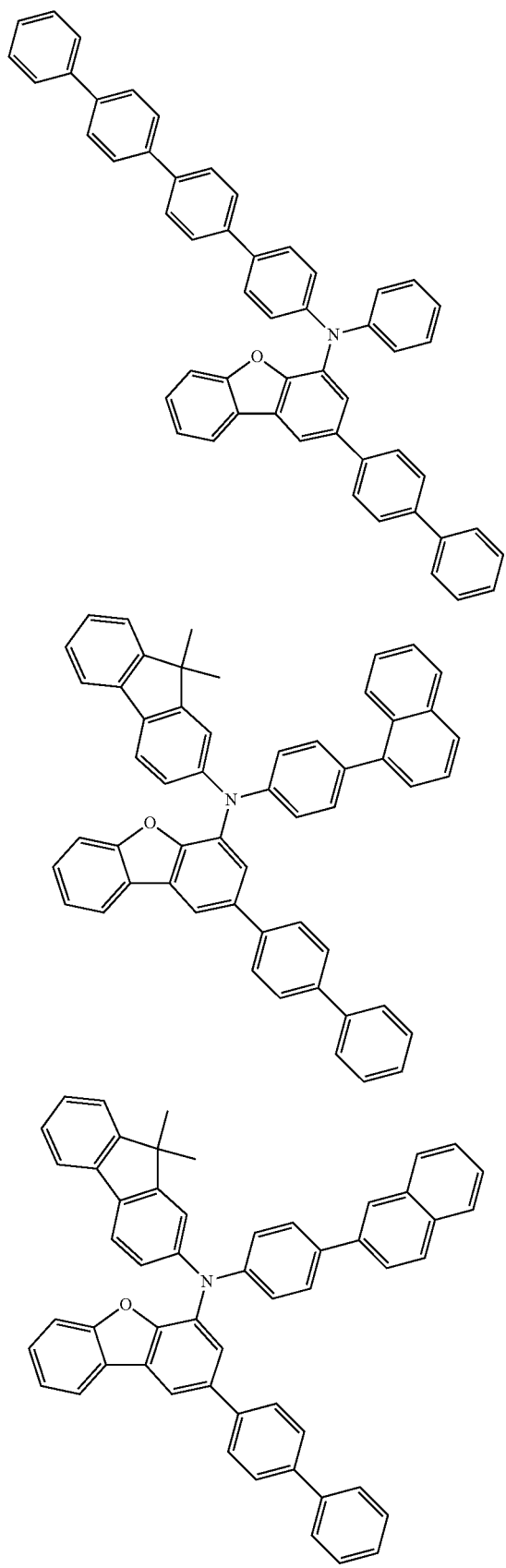
364
-continued
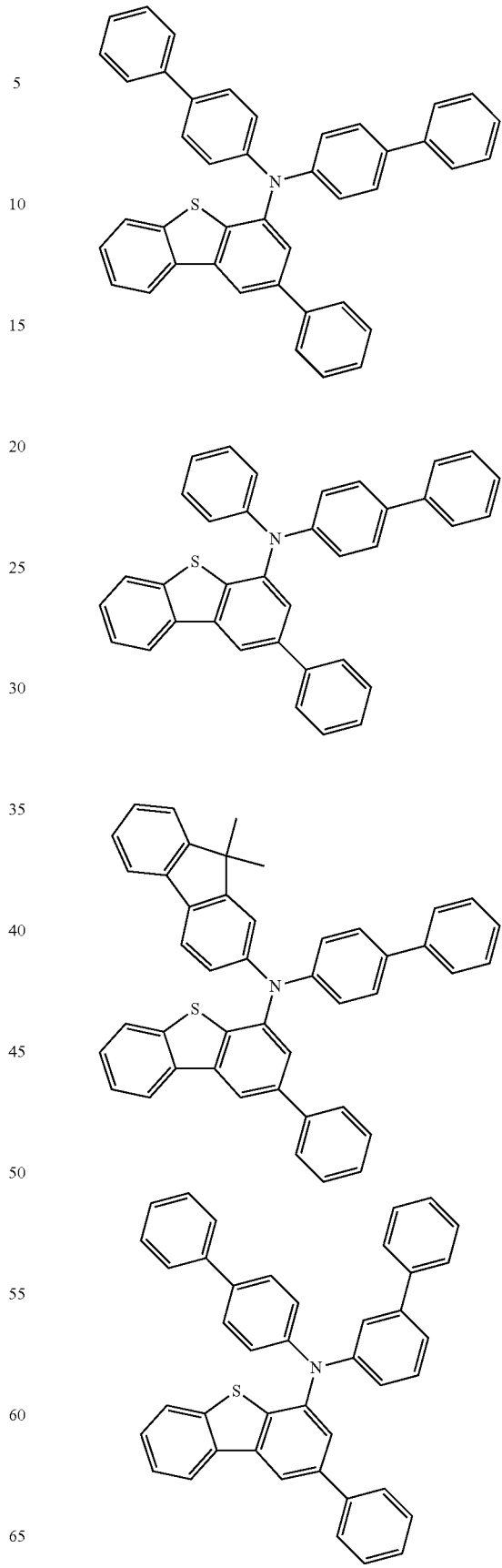

365
-continued
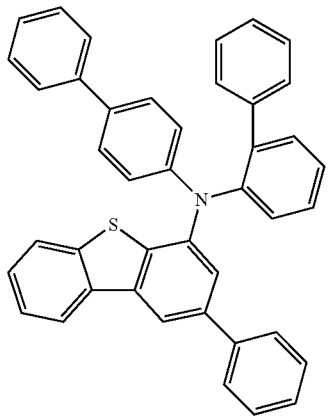
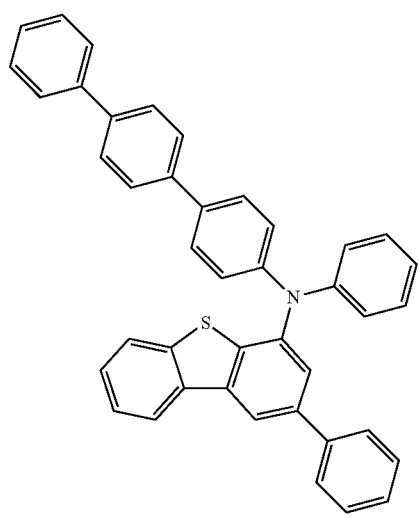
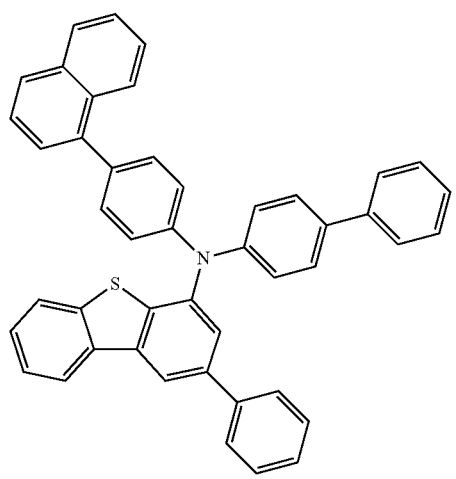
366
-continued
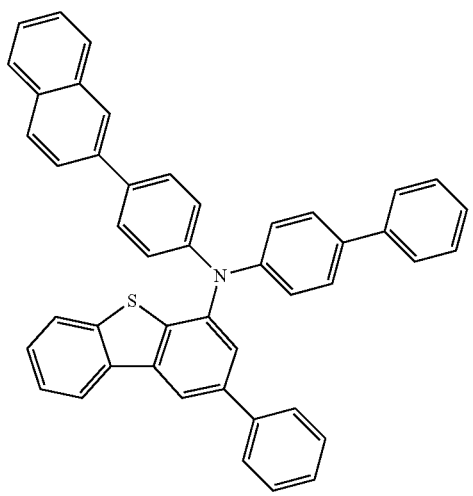
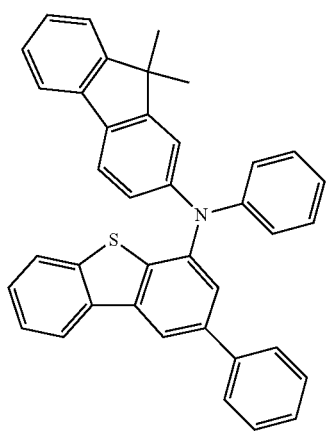
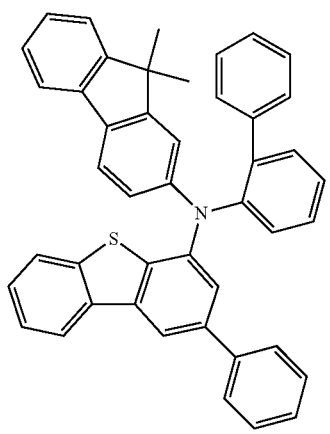

367
-continued
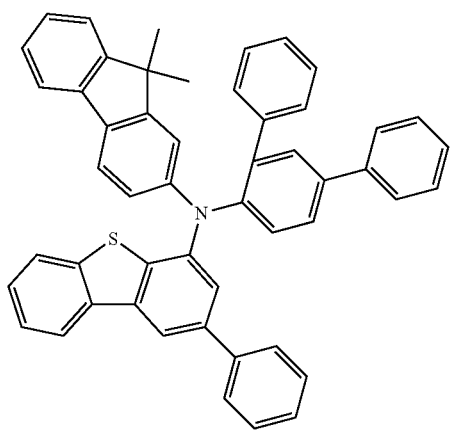
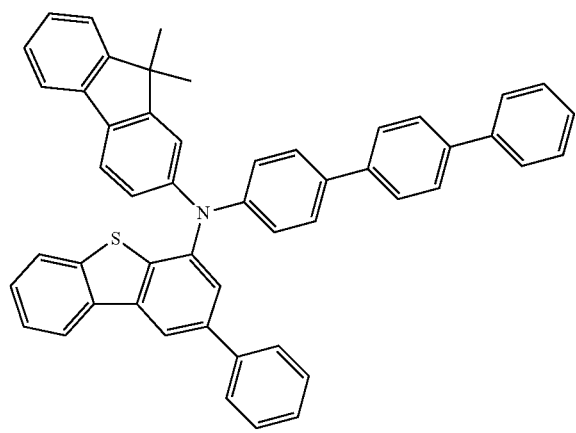
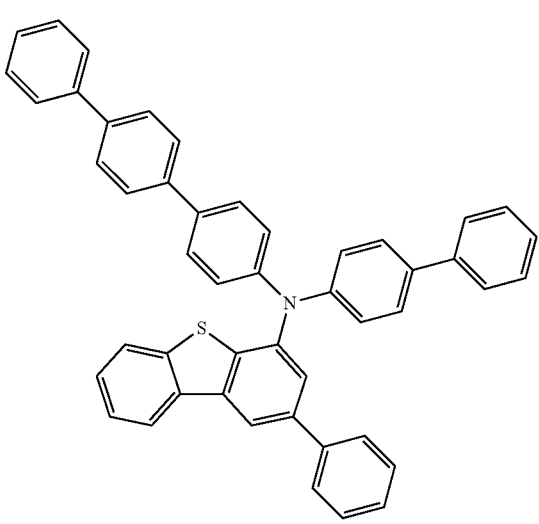
368
-continued
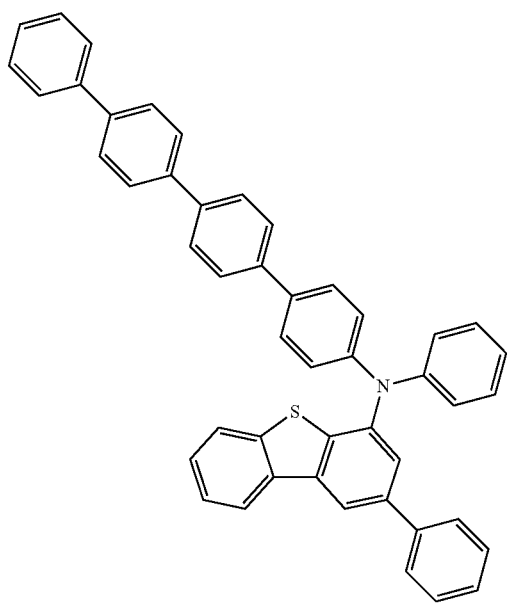
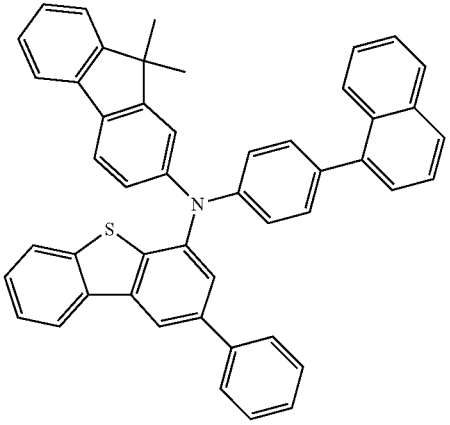
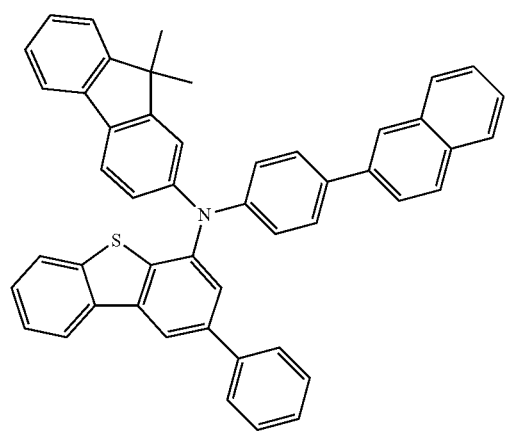

369
-continued
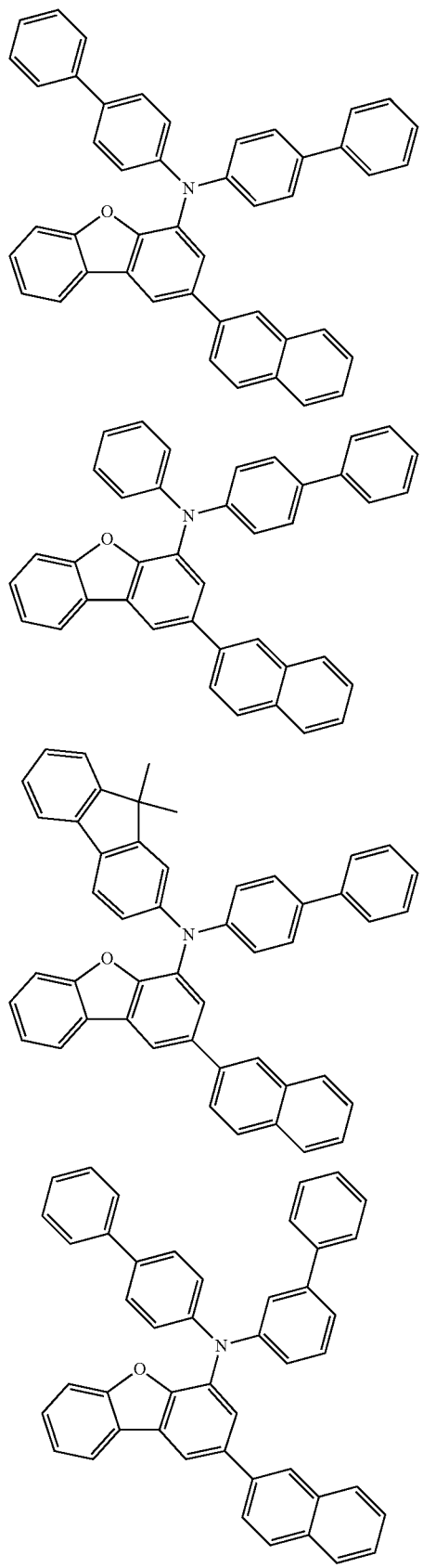
370
-continued
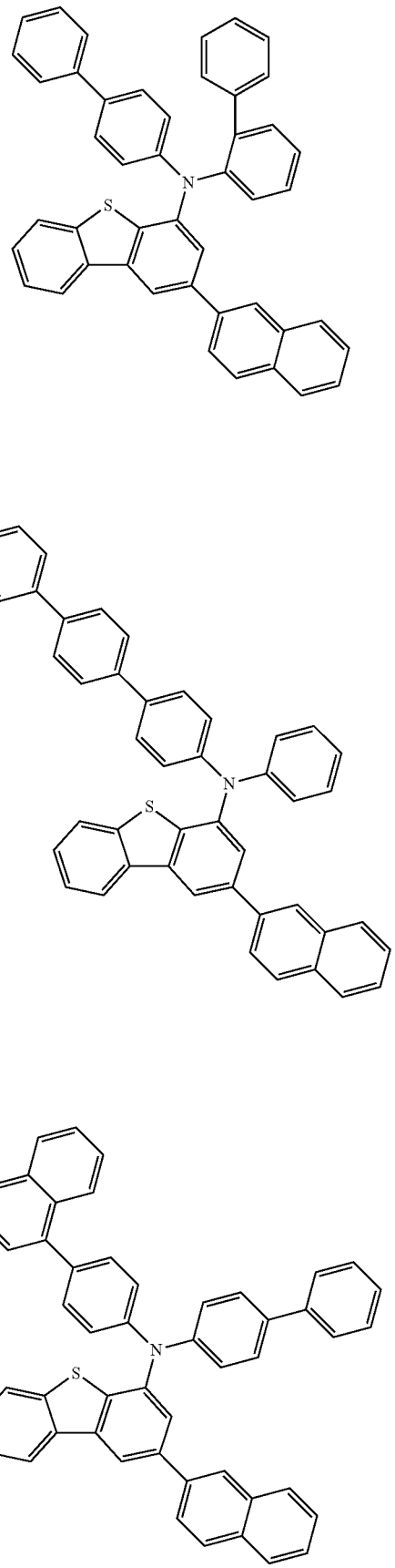

371
-continued
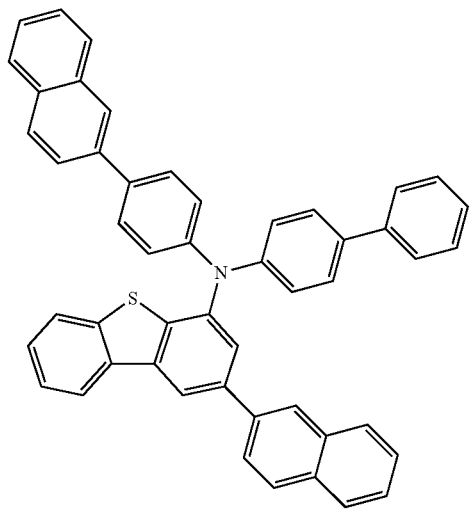
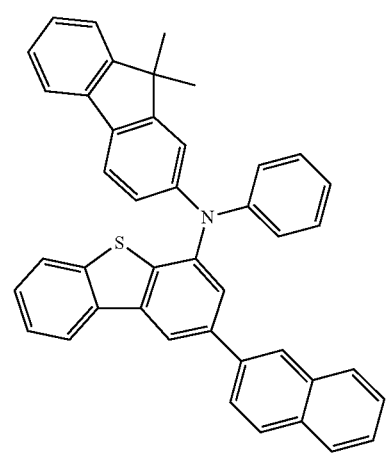
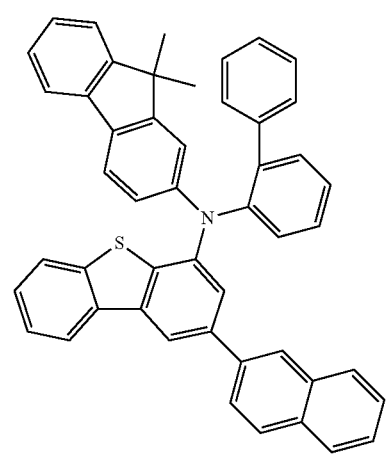
372
-continued
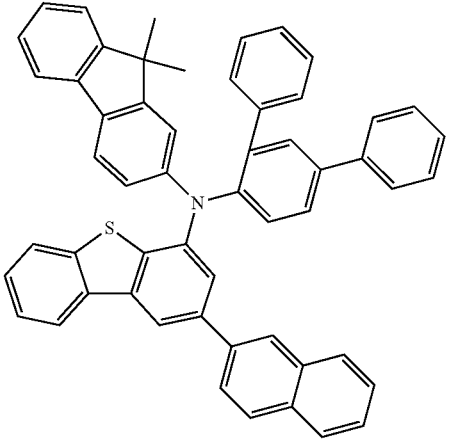
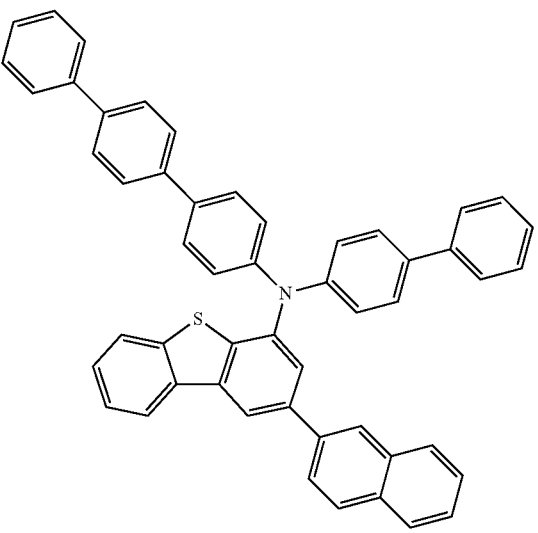

373
-continued
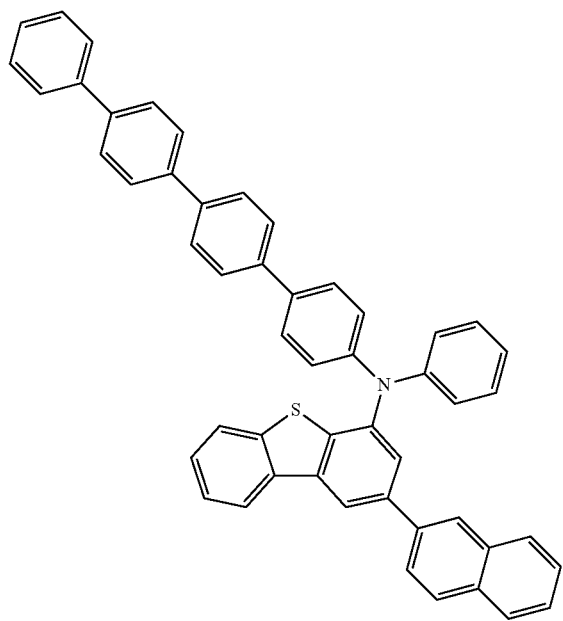
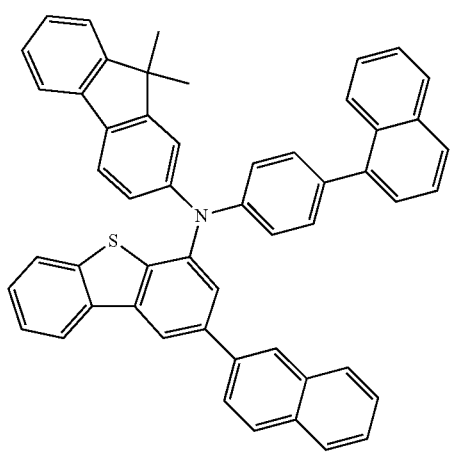
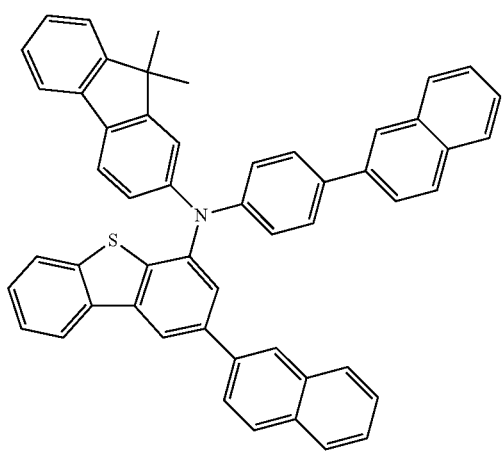
374
-continued
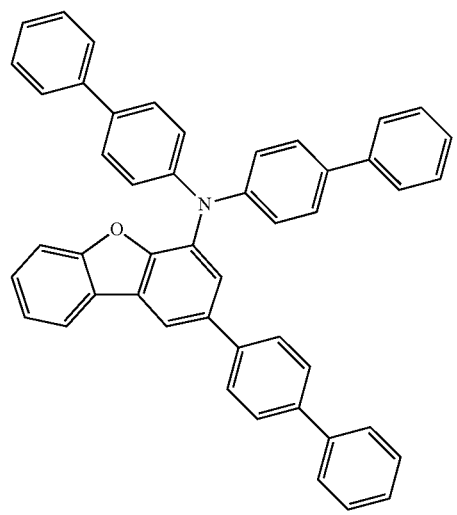
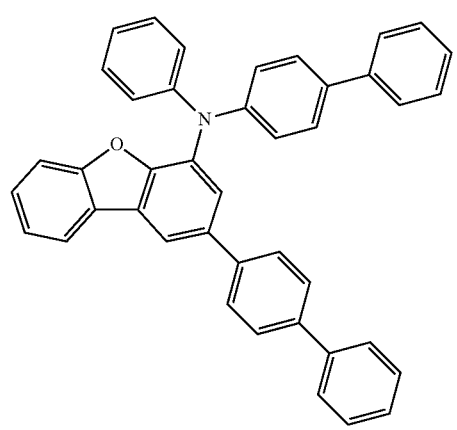
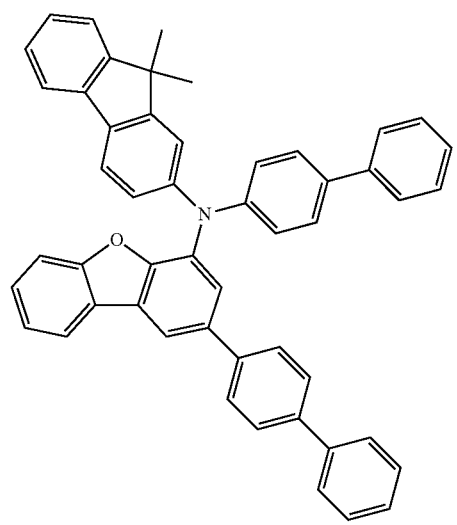

375
-continued
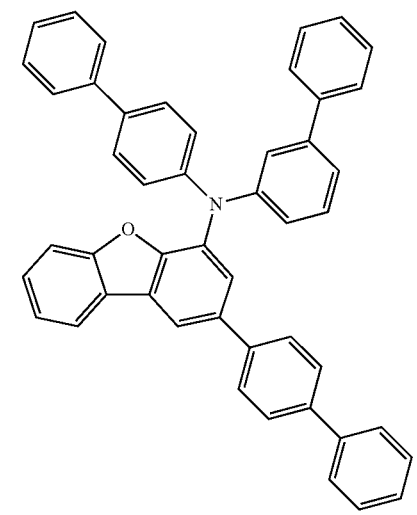 [SMILES: c1ccc(-c2ccc(-c3cc(N(c4ccc(-c5ccccc5)cc4)c4cccc(-c5ccccc5)c4)c4oc5ccccc5c4c3)cc2)cc1]
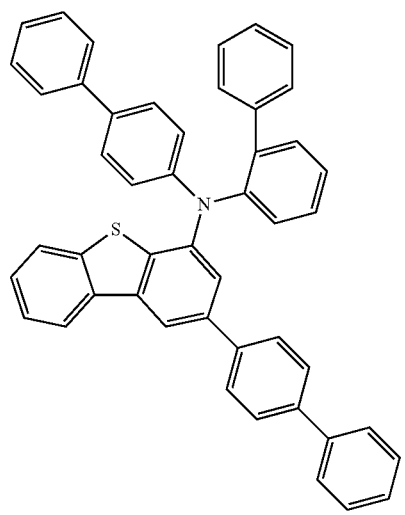
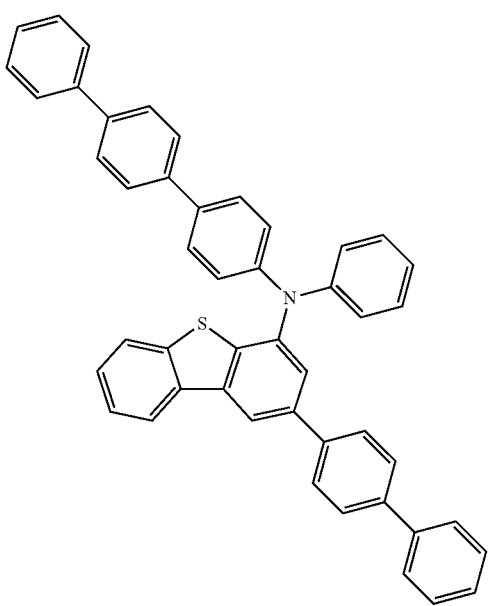
376
-continued
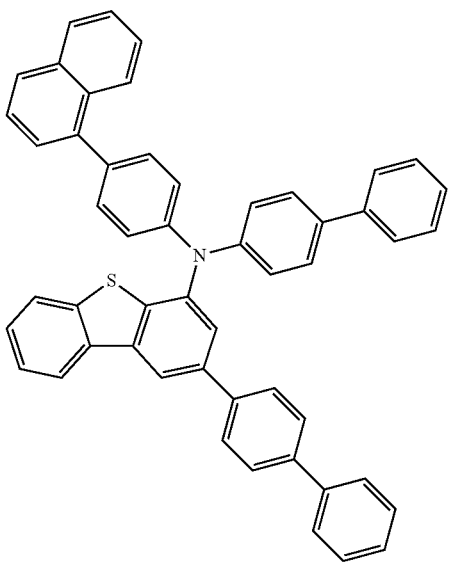
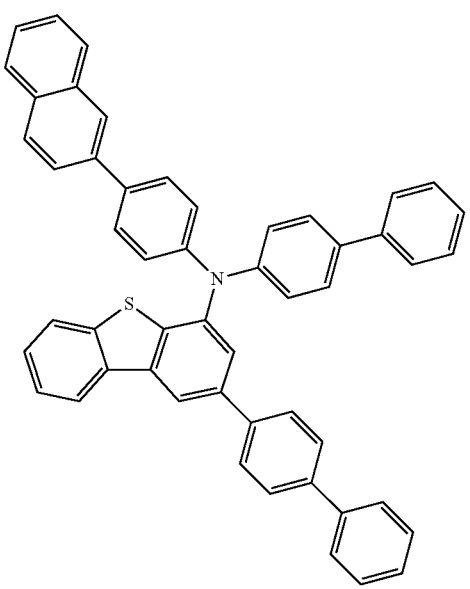
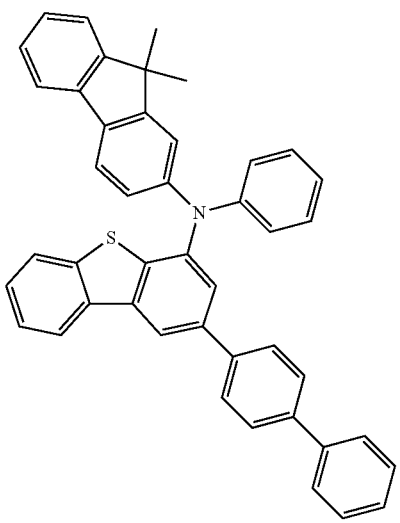

377
-continued
378
-continued
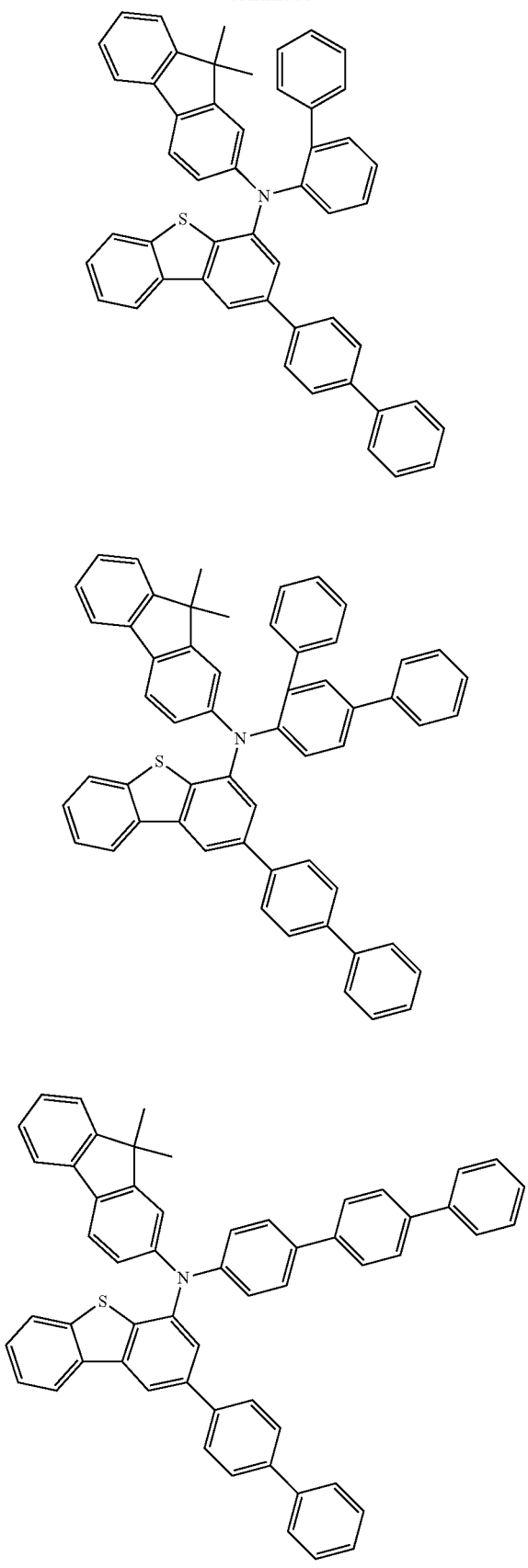
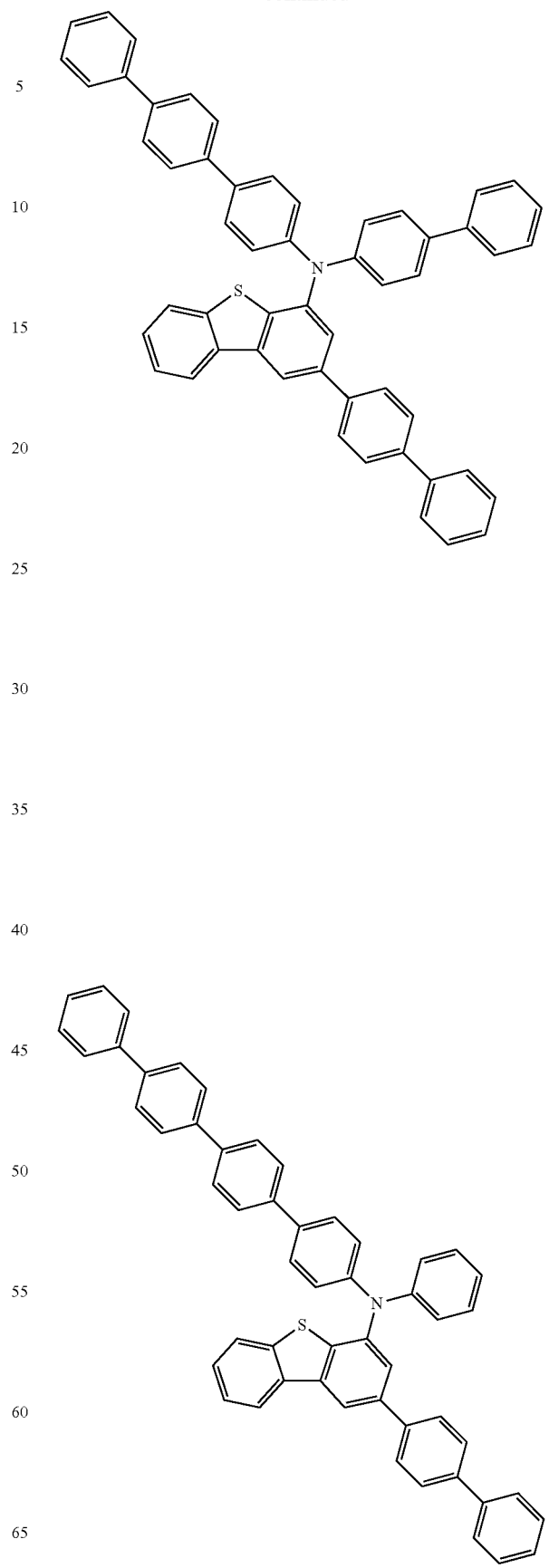

379
-continued
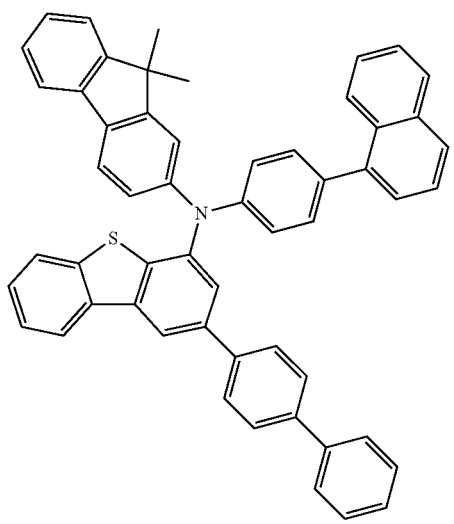
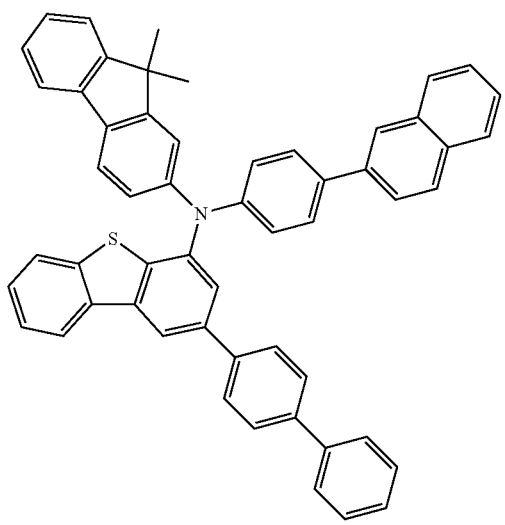
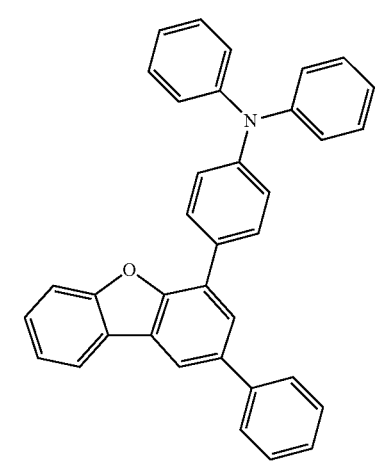
380
-continued
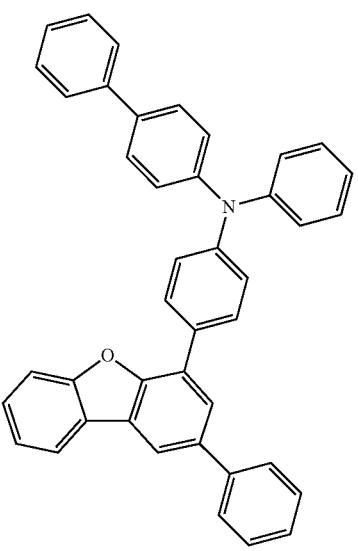
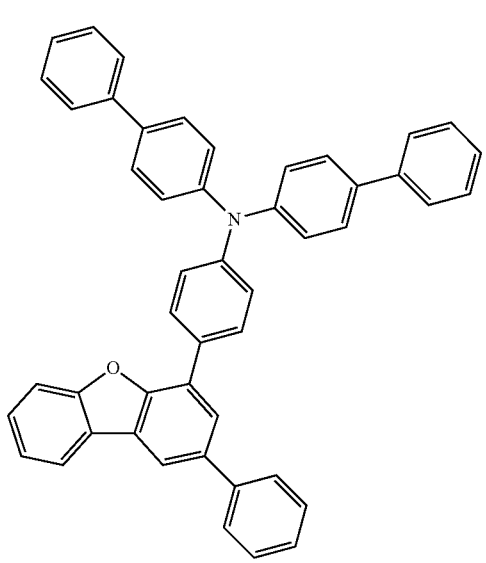
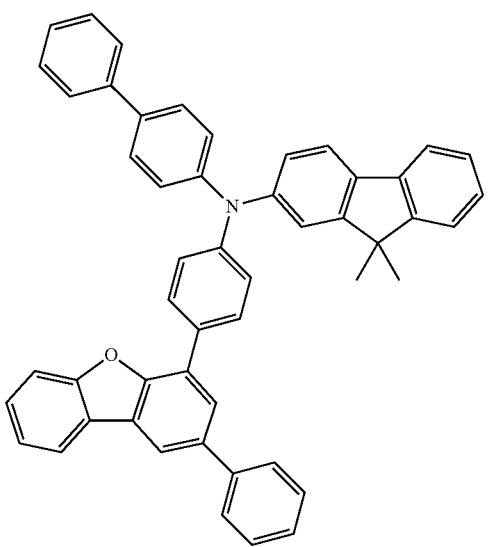

381
-continued
382
-continued
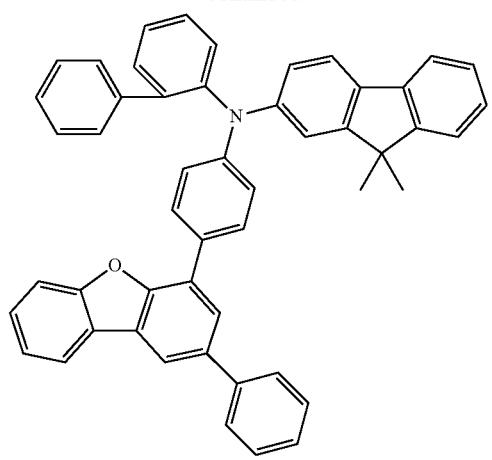
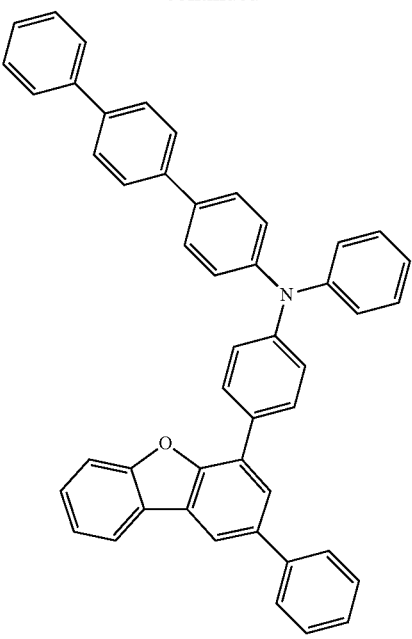
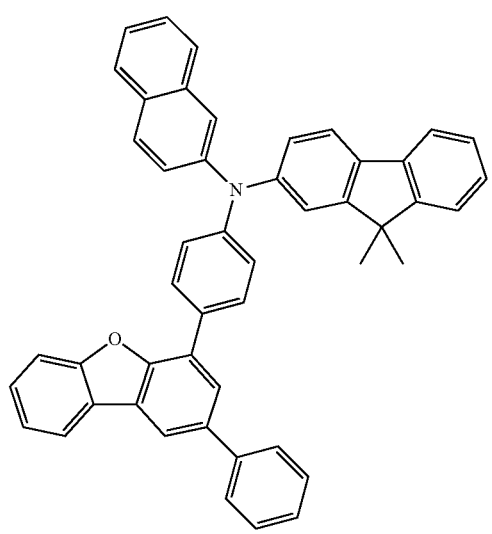
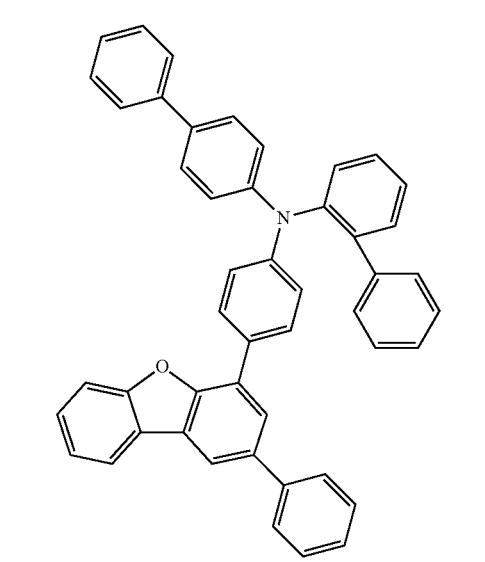
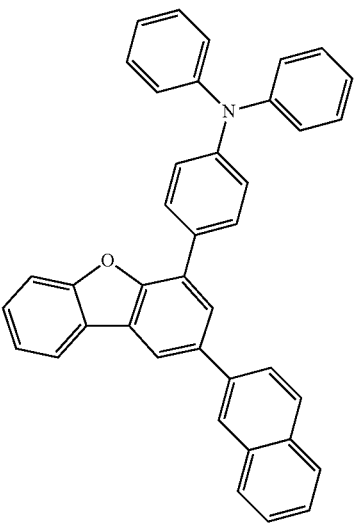

383
-continued
384
-continued
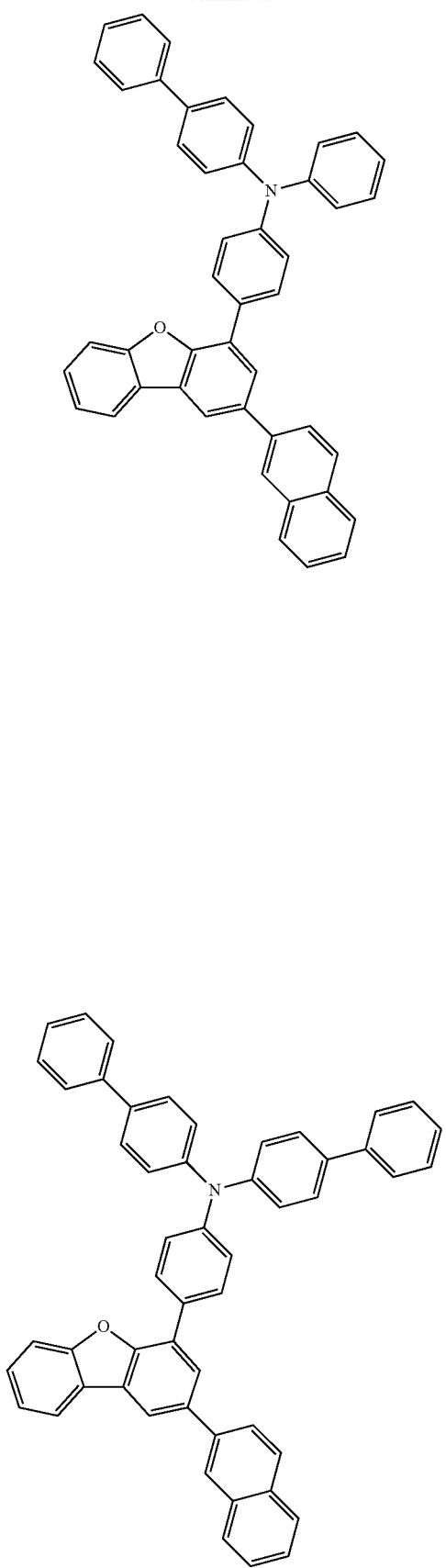
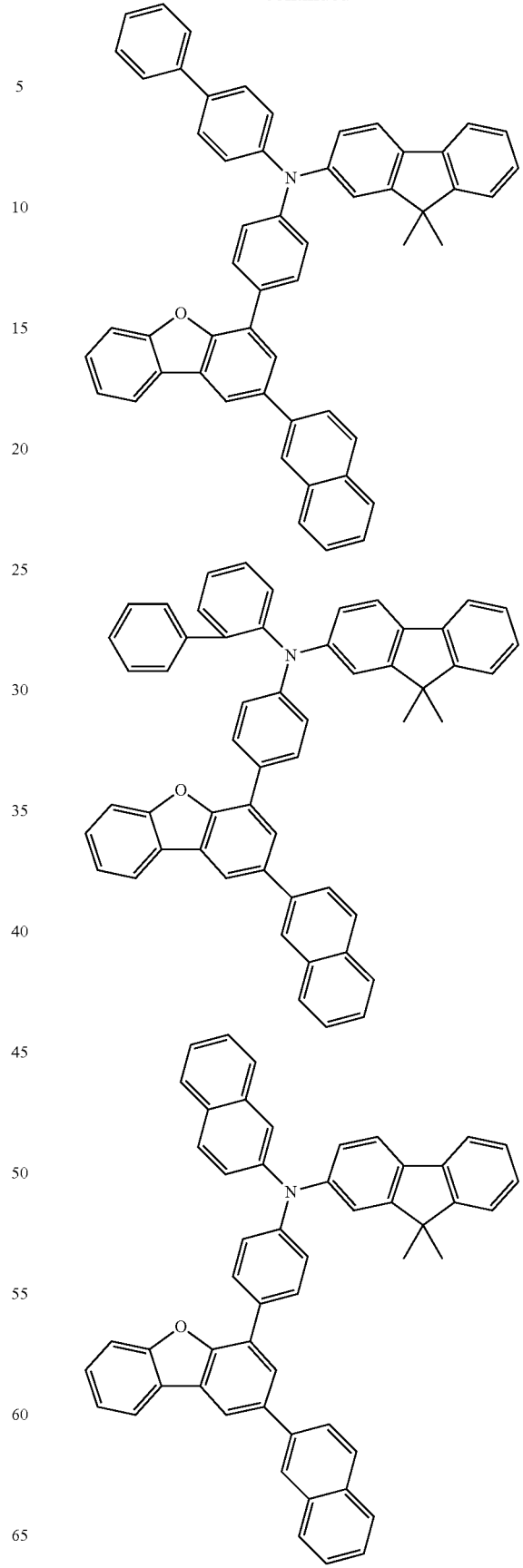

385
-continued
386
-continued
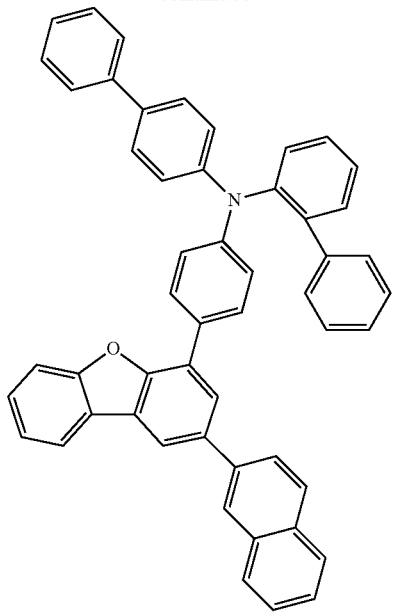
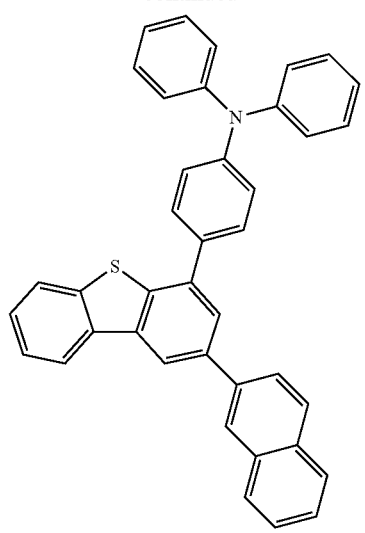

387
-continued
388
-continued
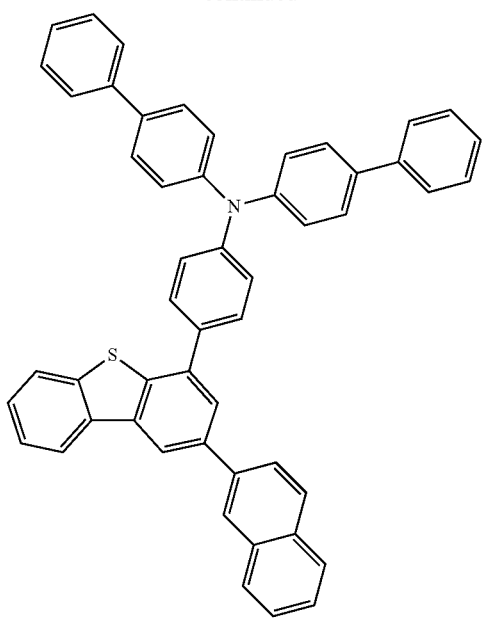
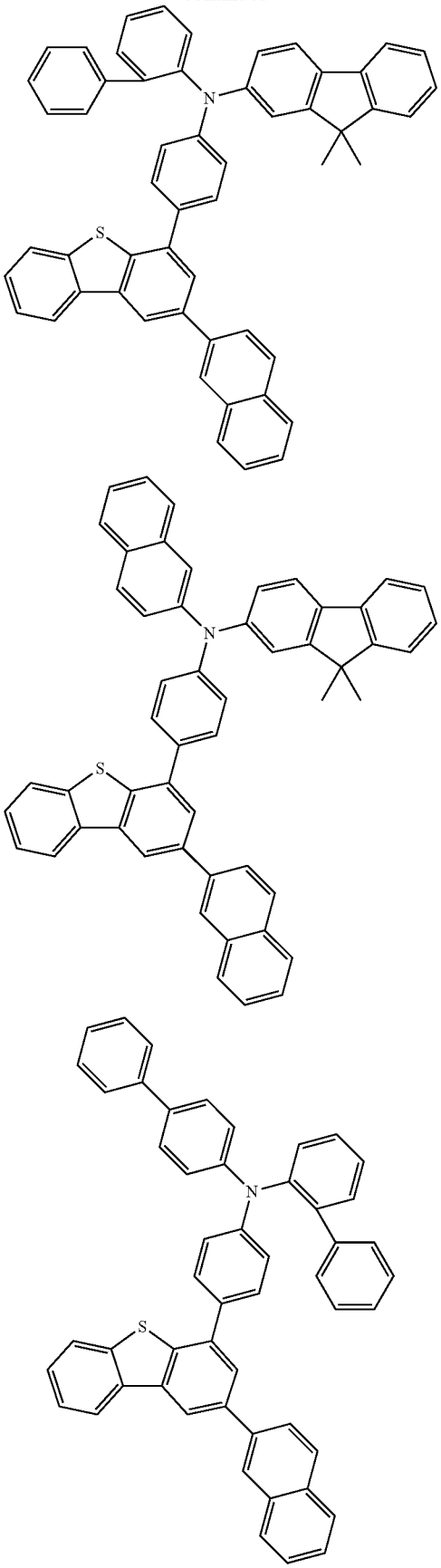

389
-continued
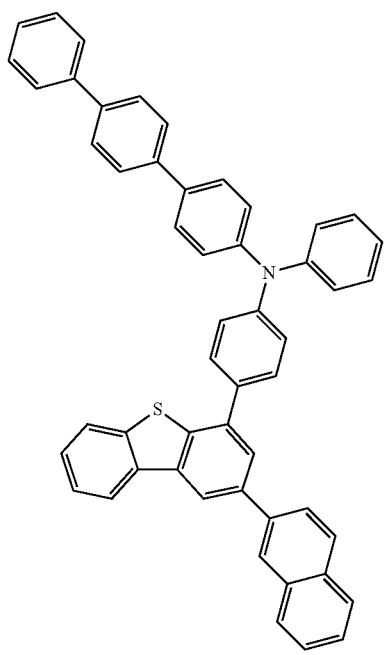
390
-continued
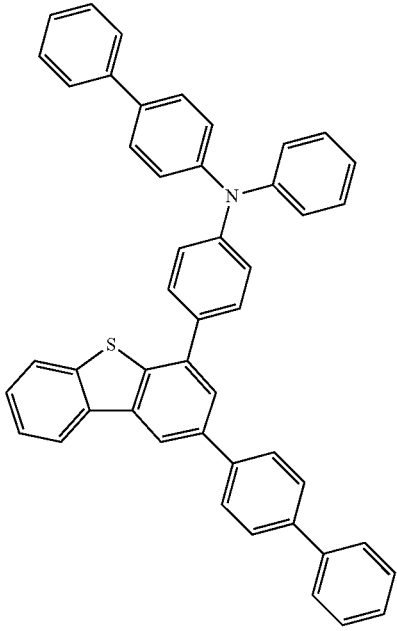
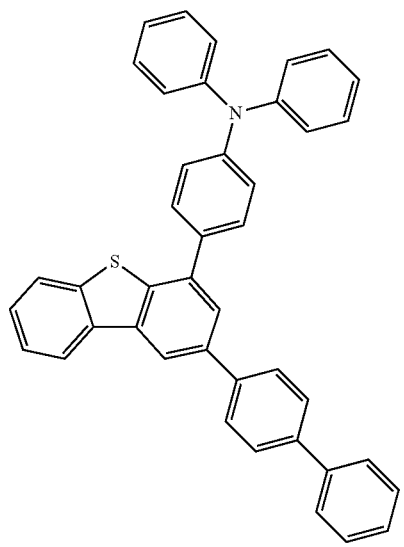
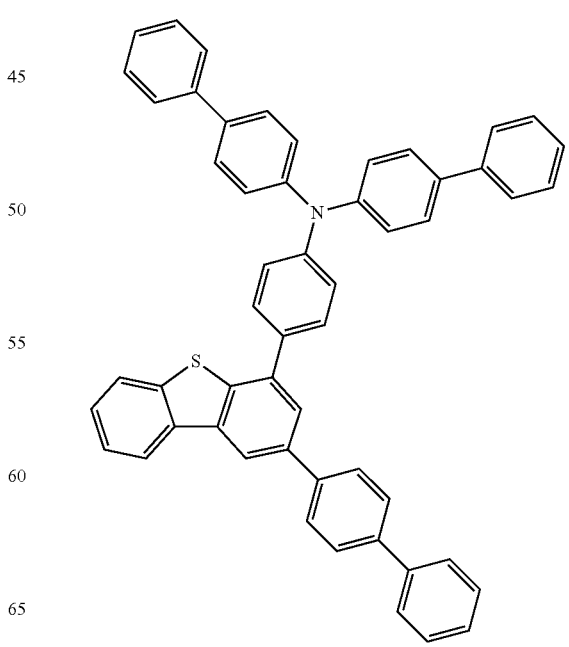

391
-continued
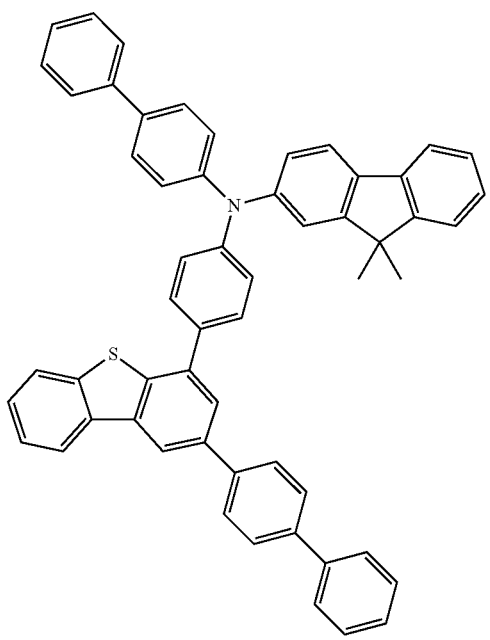
392
-continued
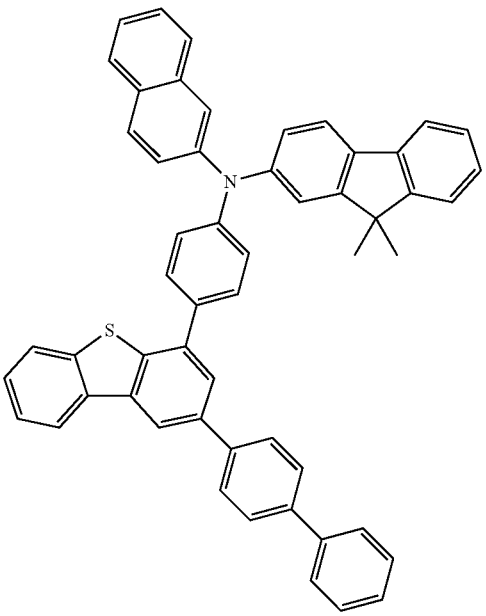
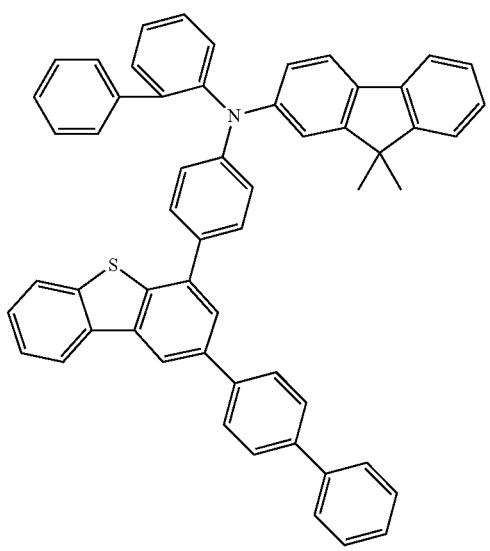
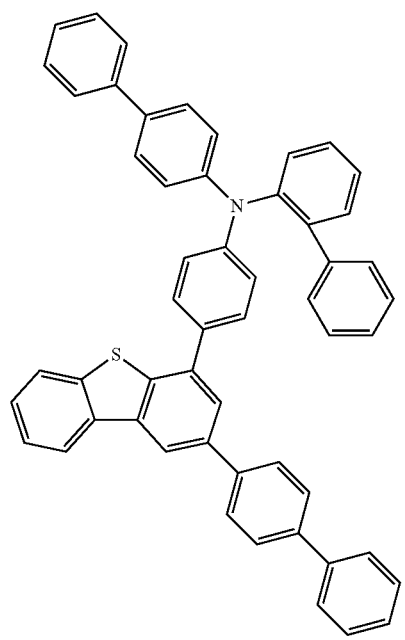

393
-continued
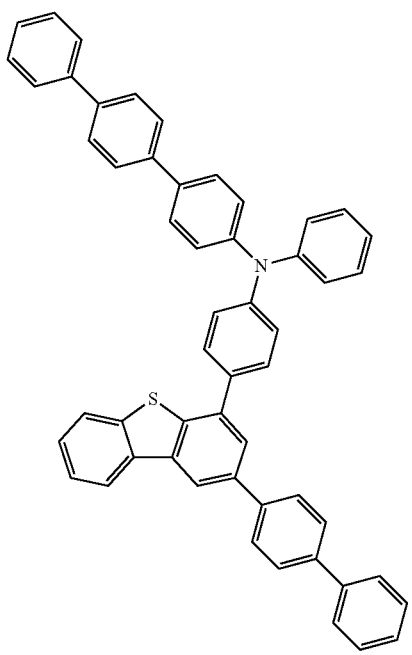
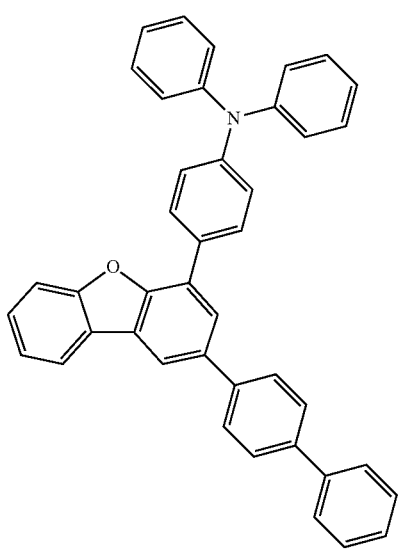
394
-continued
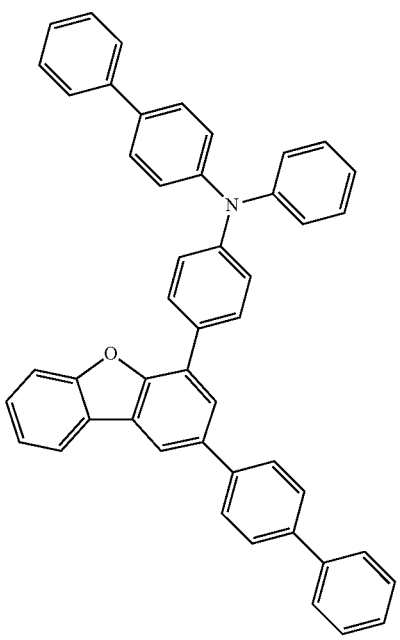
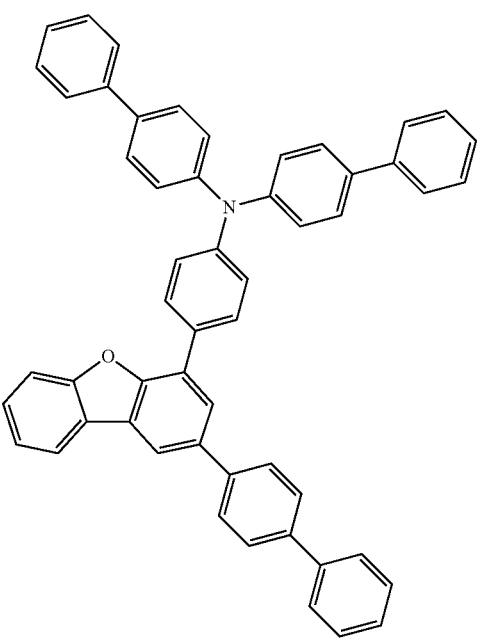

395
-continued
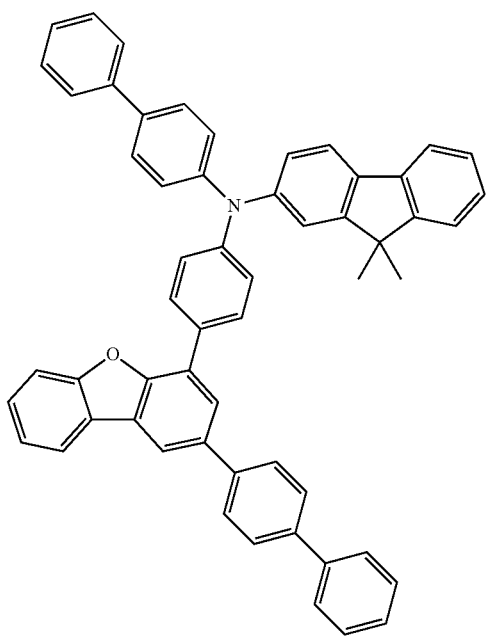
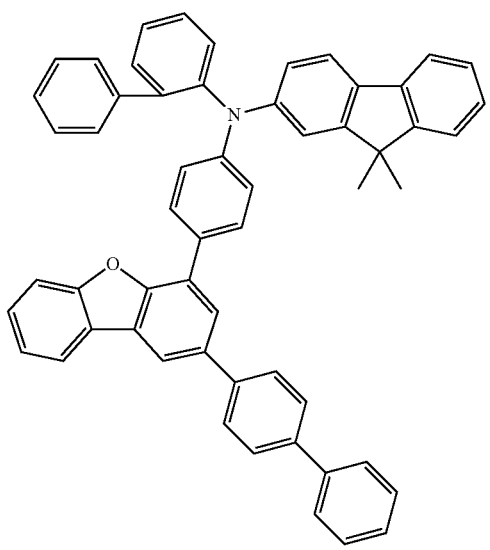
396
-continued
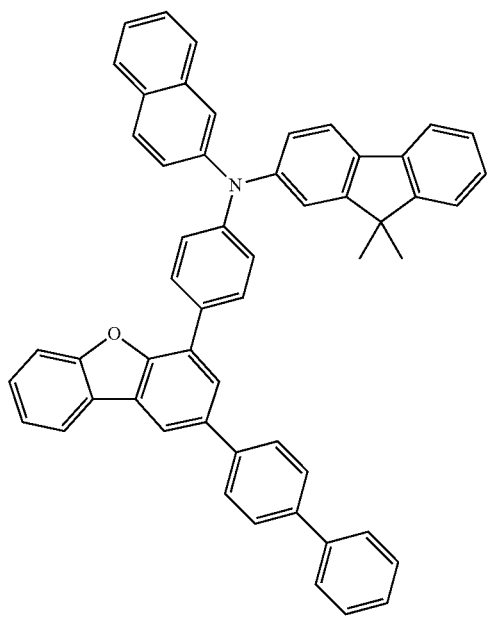
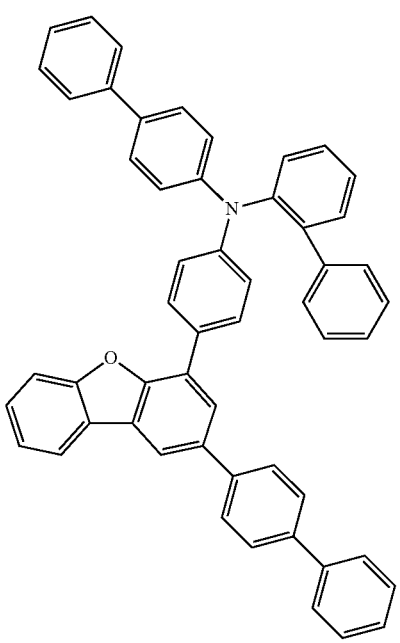

397
-continued
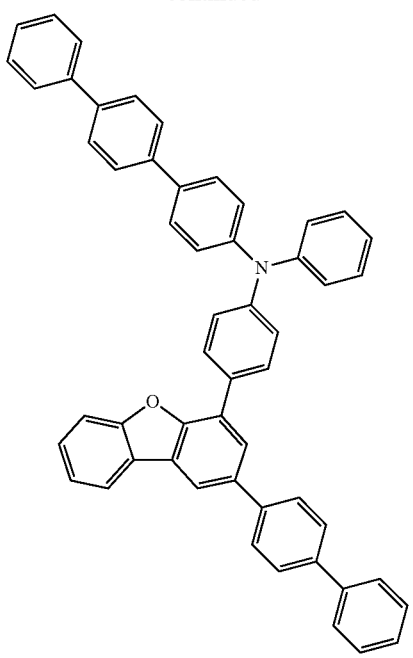
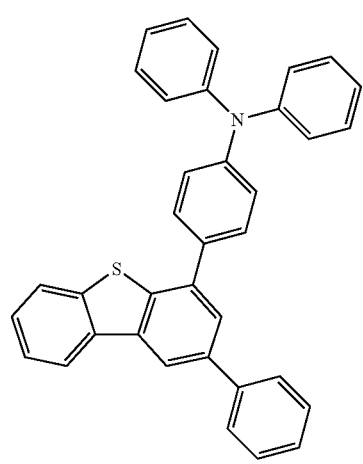
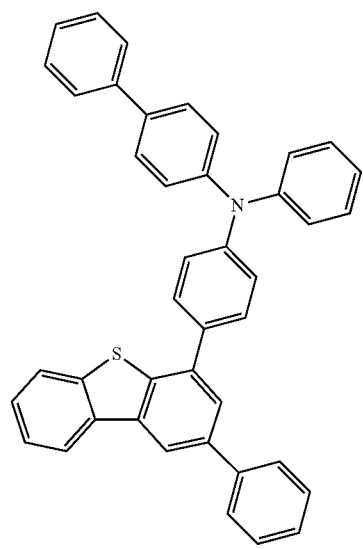
398
-continued
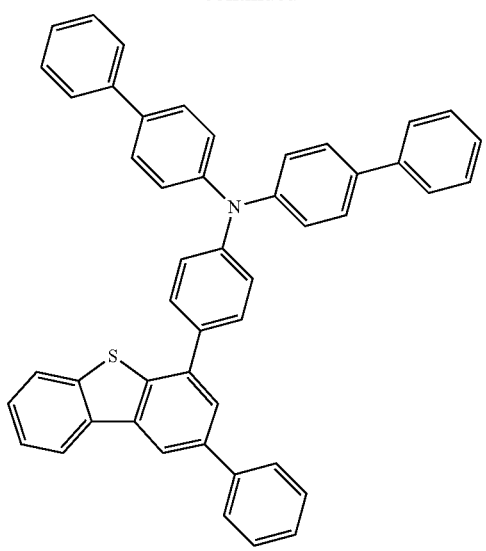
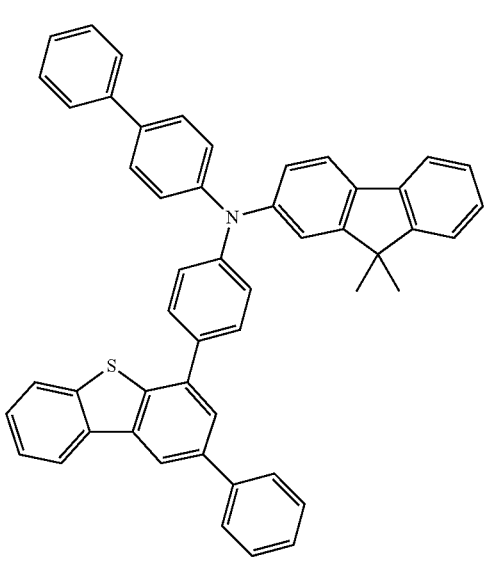
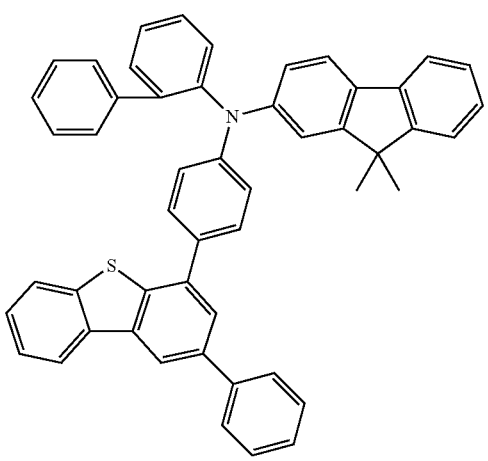

399
-continued
400
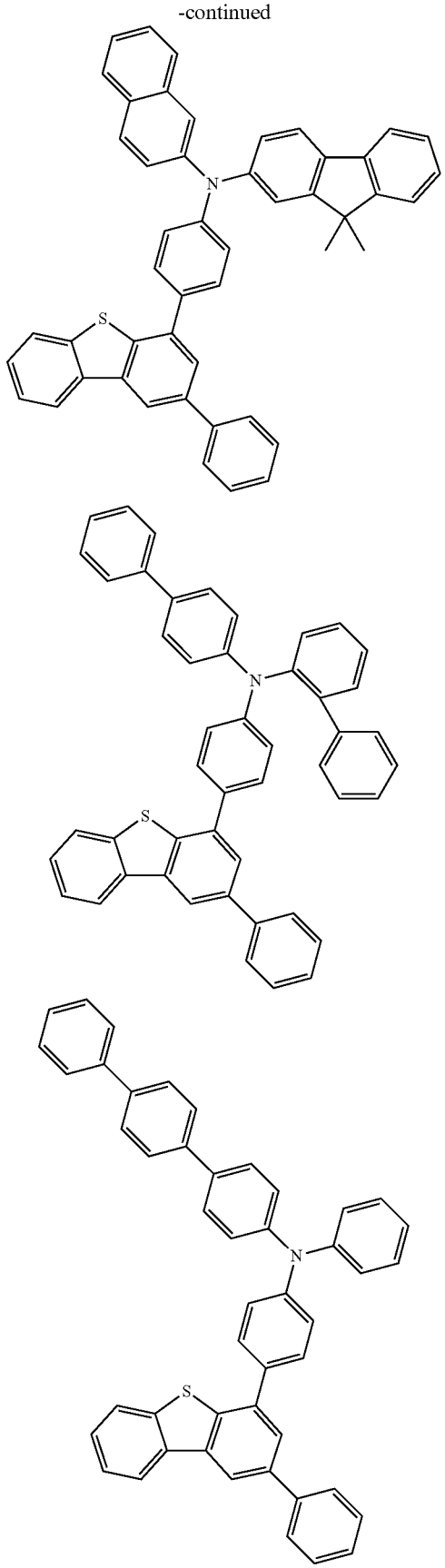
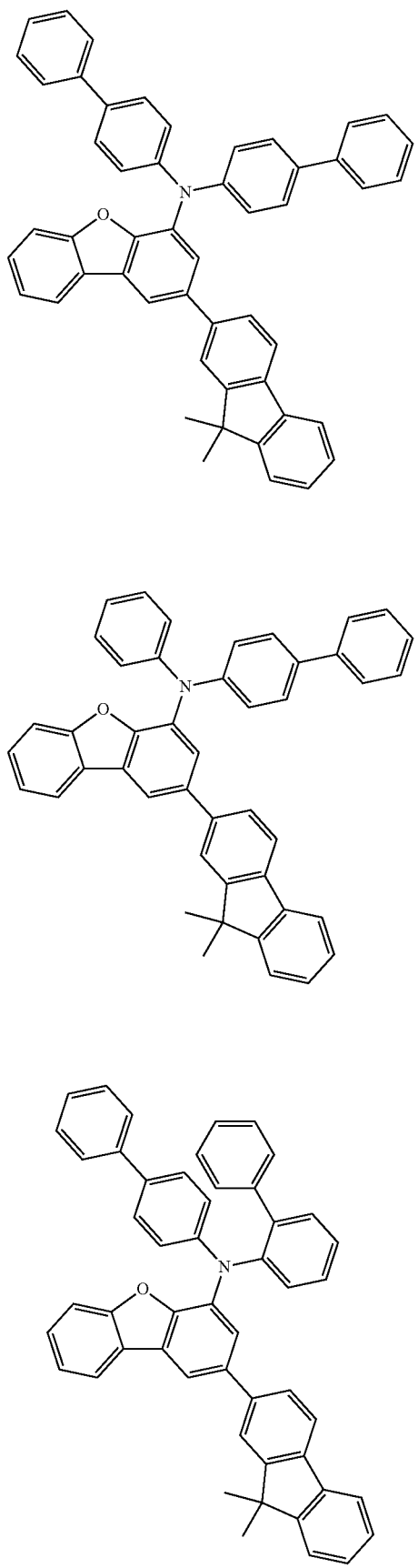

401
-continued
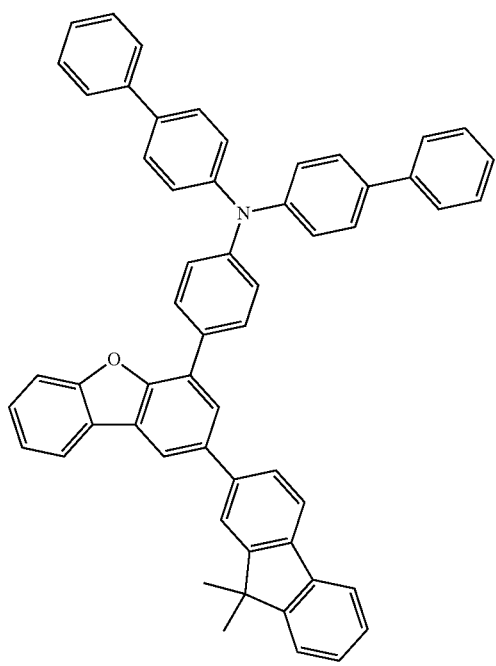
402
-continued
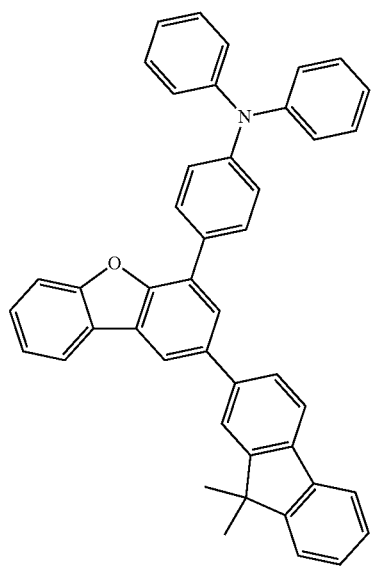
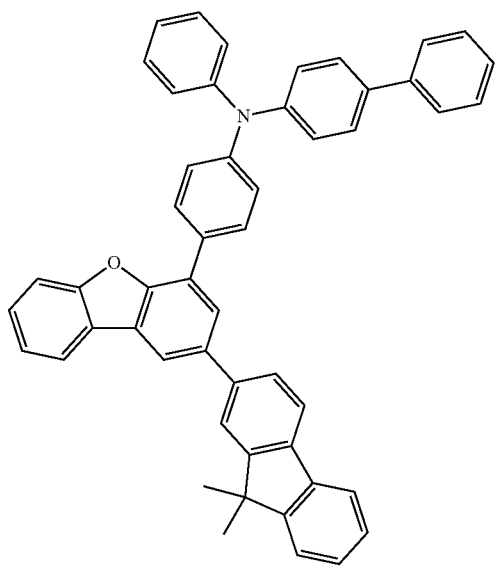
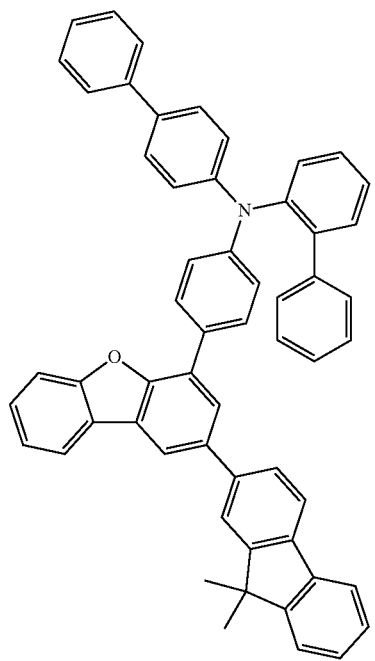

403
-continued
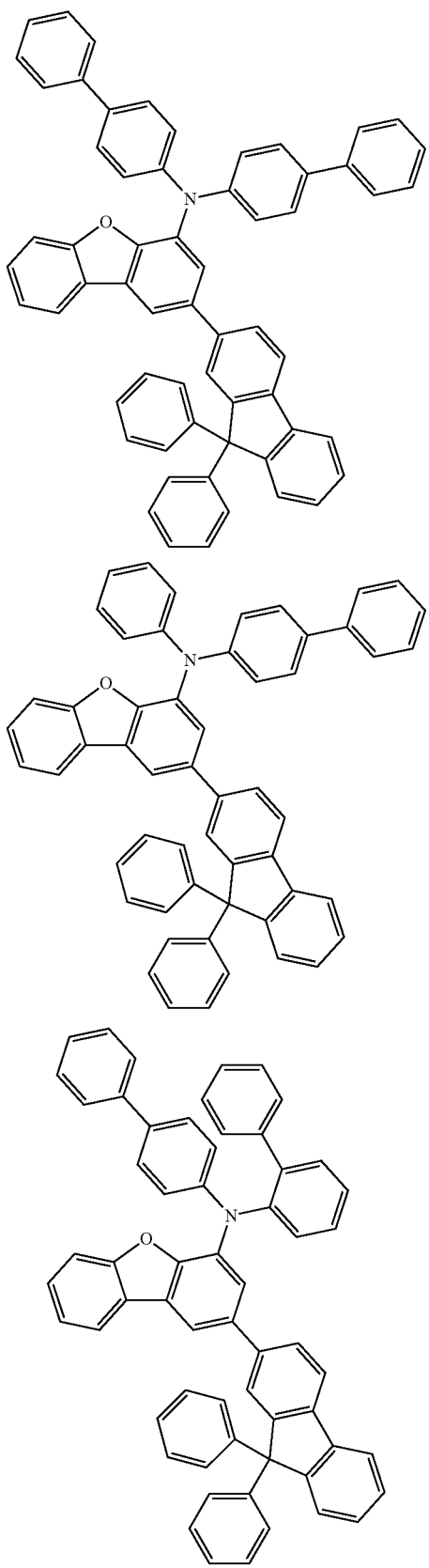
404
-continued

405
-continued
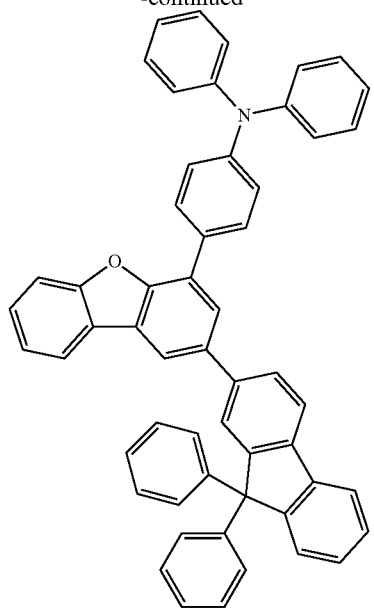
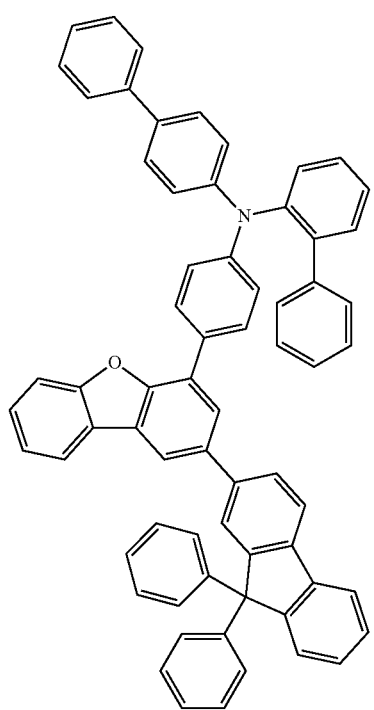
406
-continued
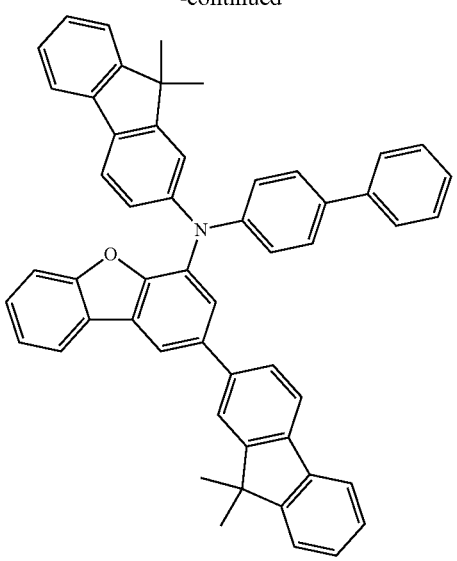
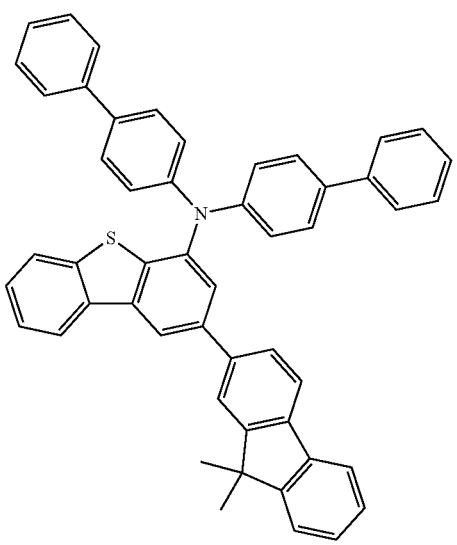
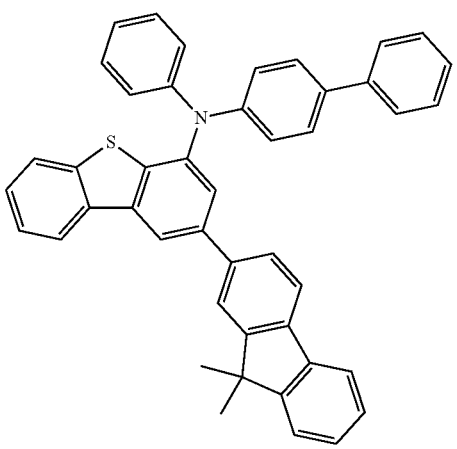

407
-continued
408
-continued
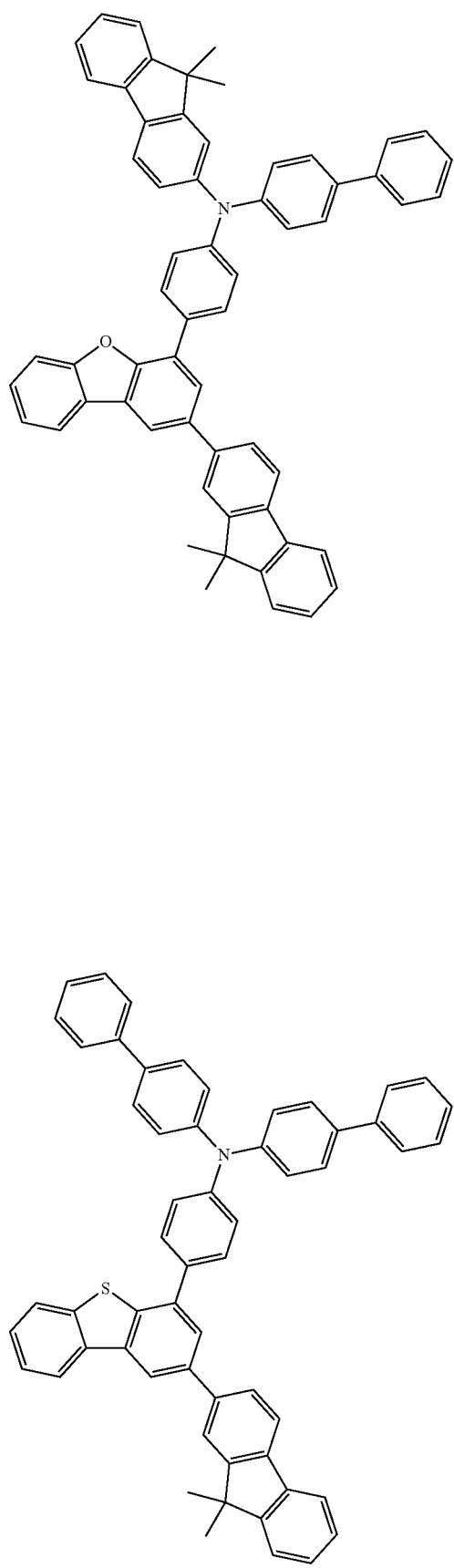
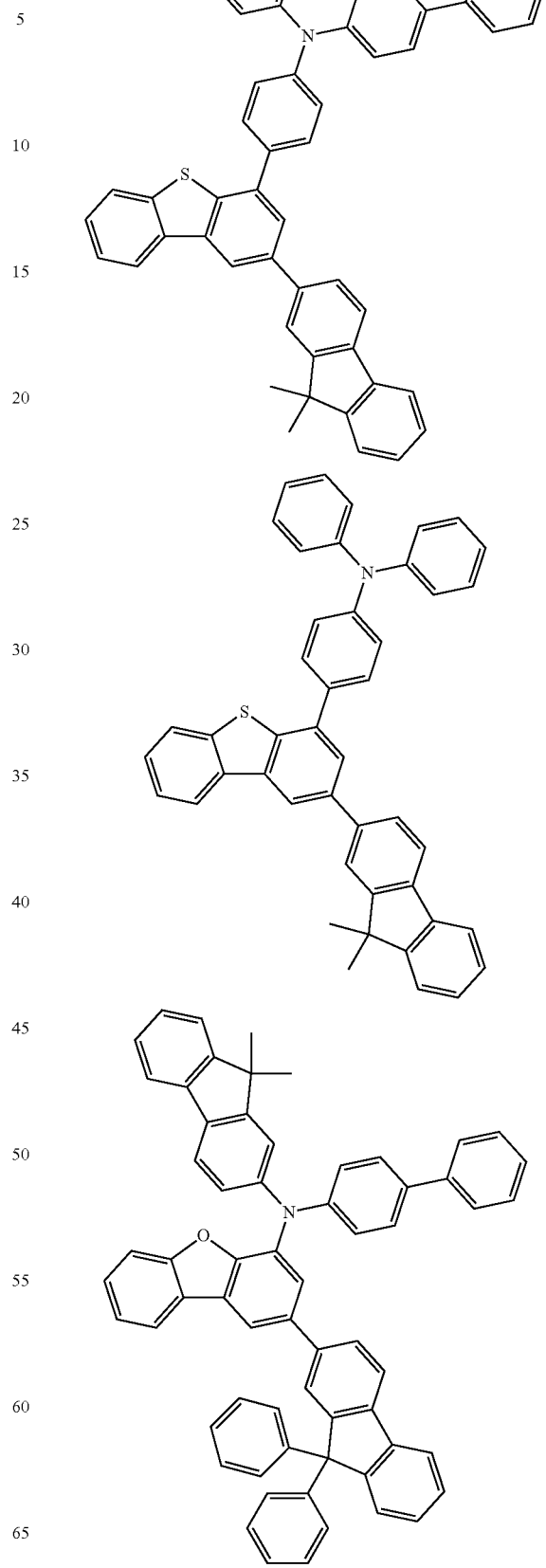

409
-continued
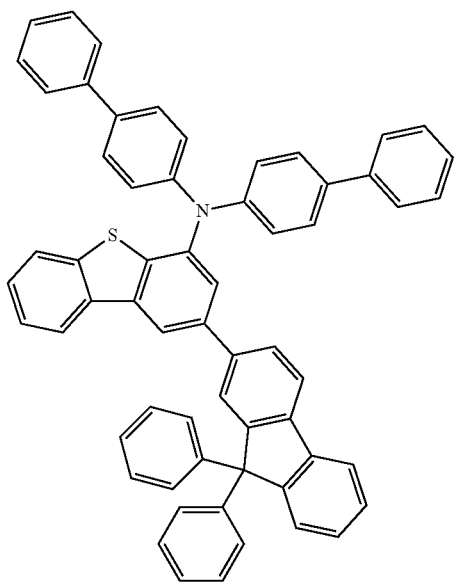
410
-continued
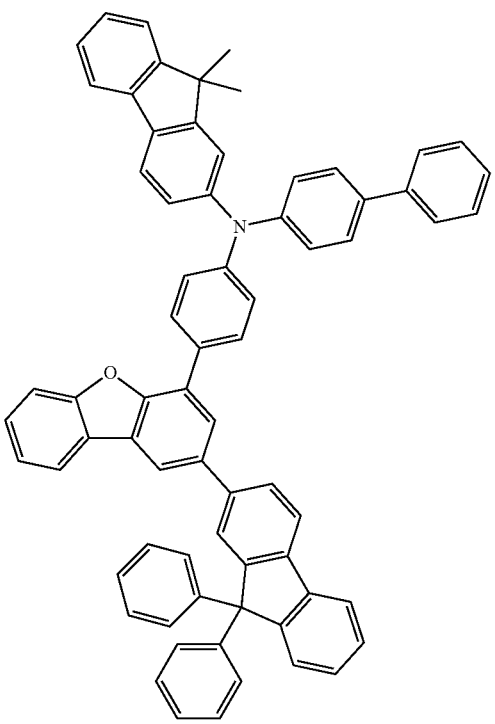
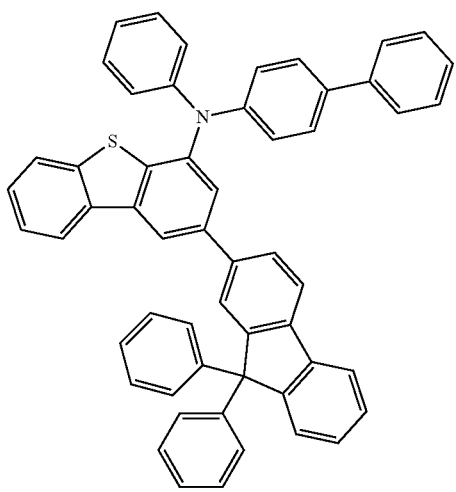
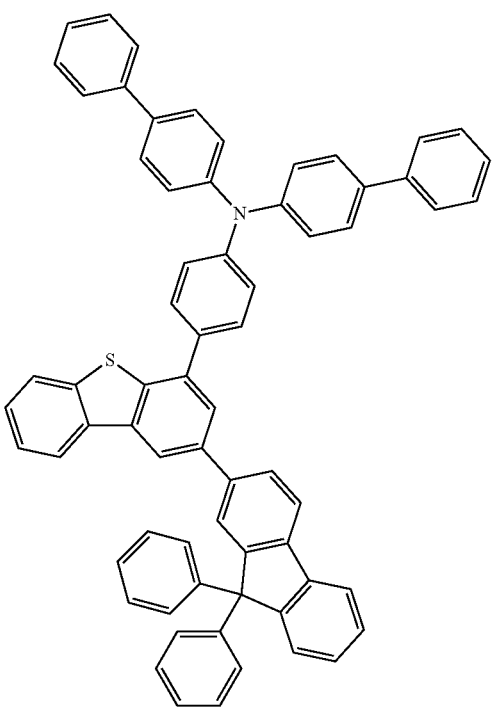

411
-continued
412
-continued
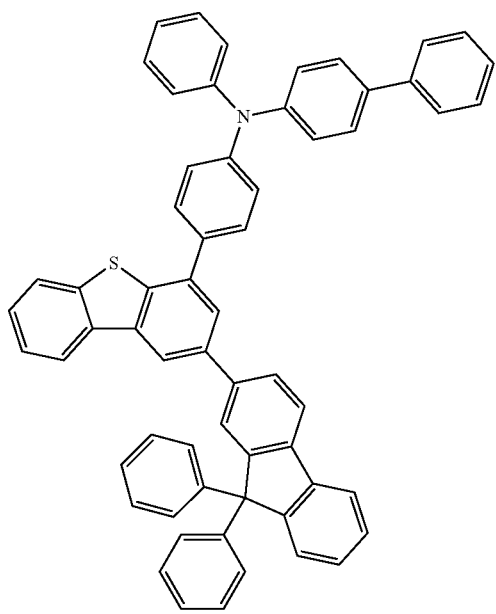
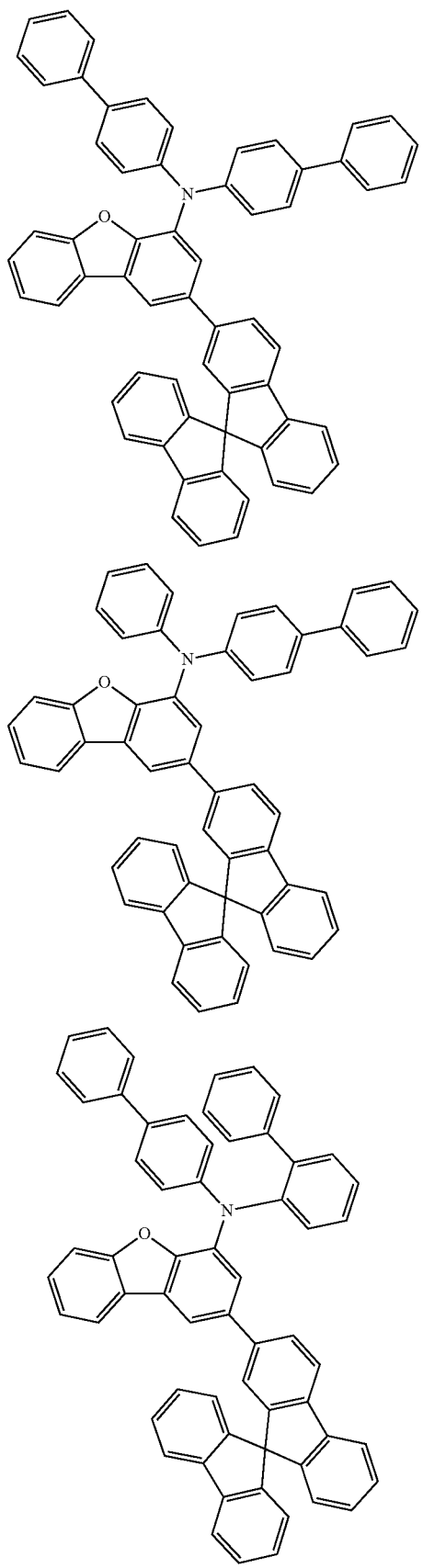

413
-continued
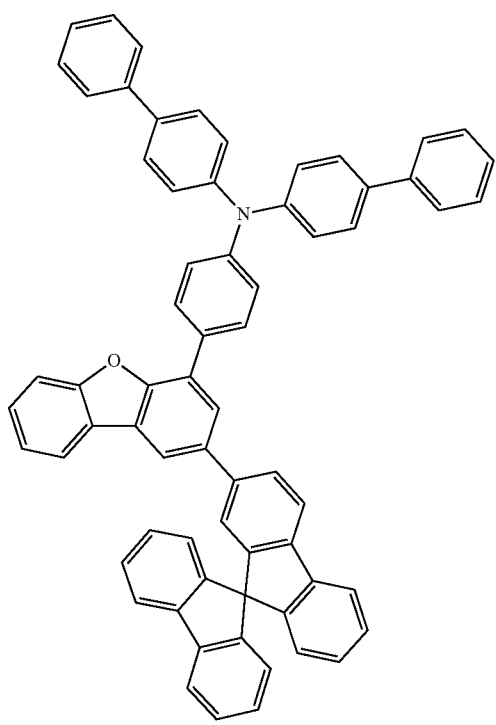
414
-continued
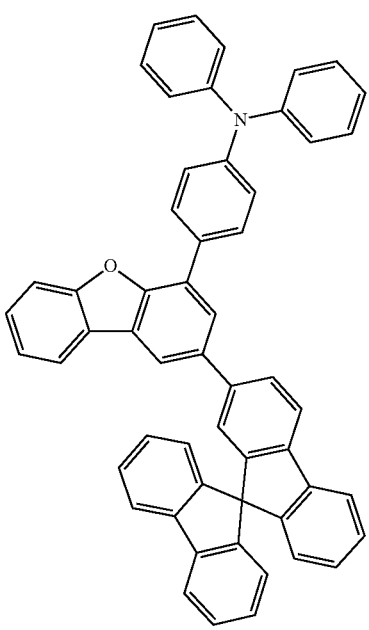
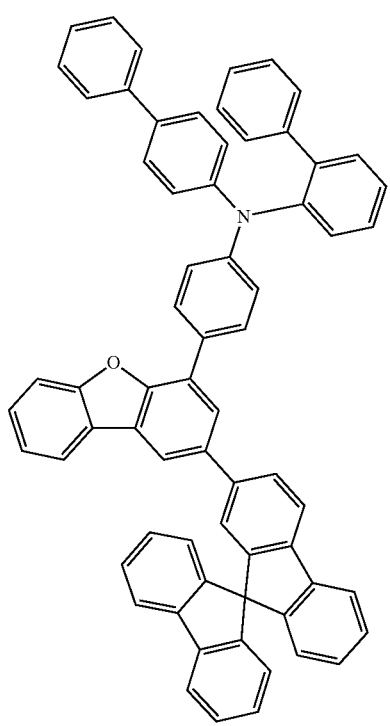

415
-continued
416
-continued
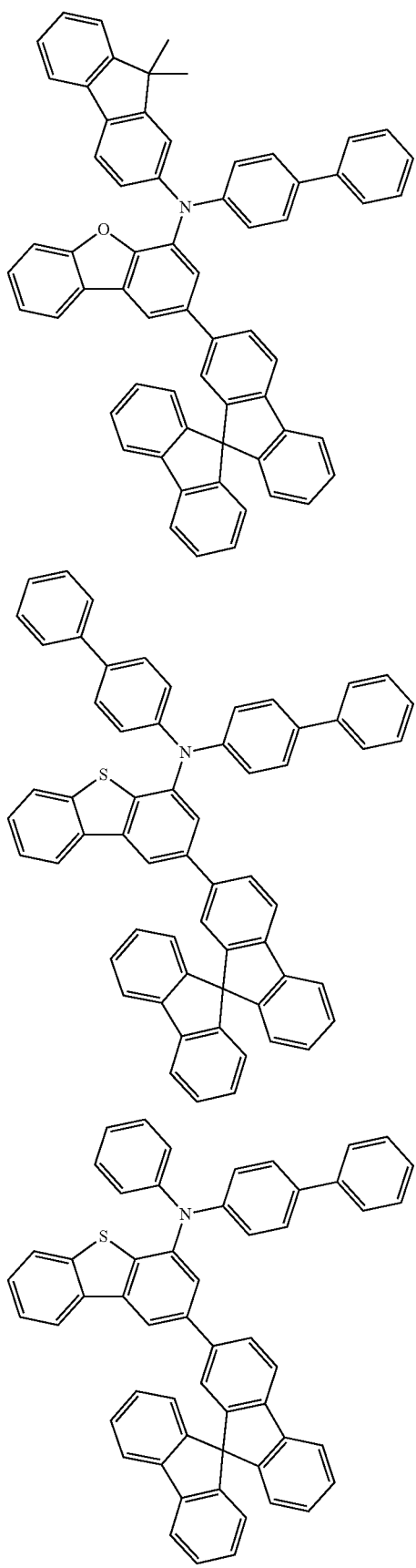
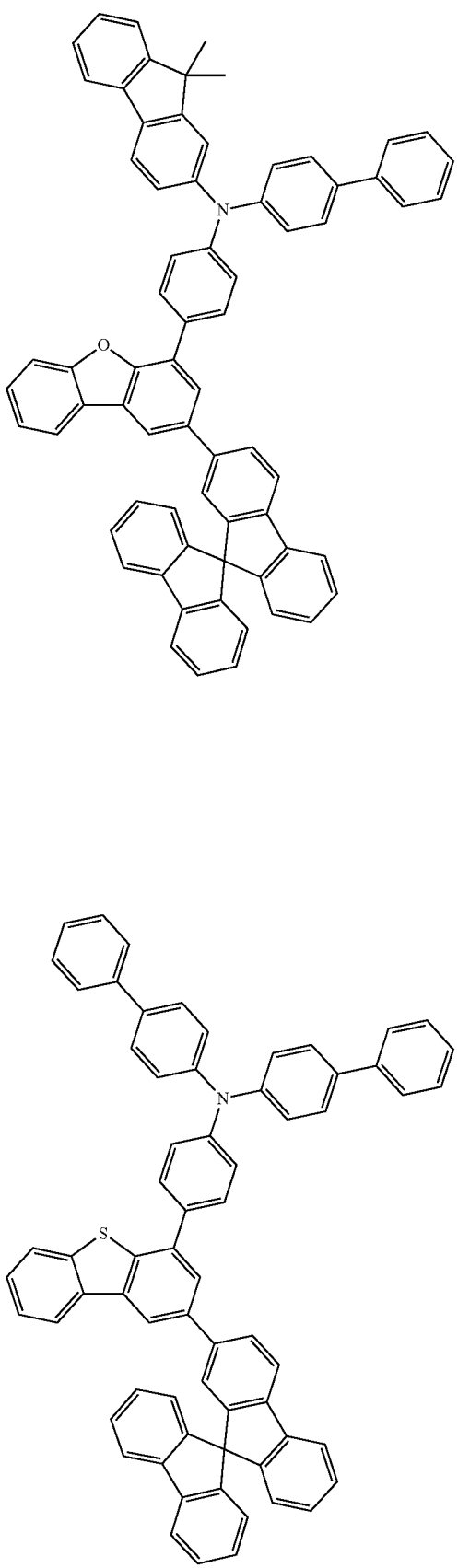

417
-continued
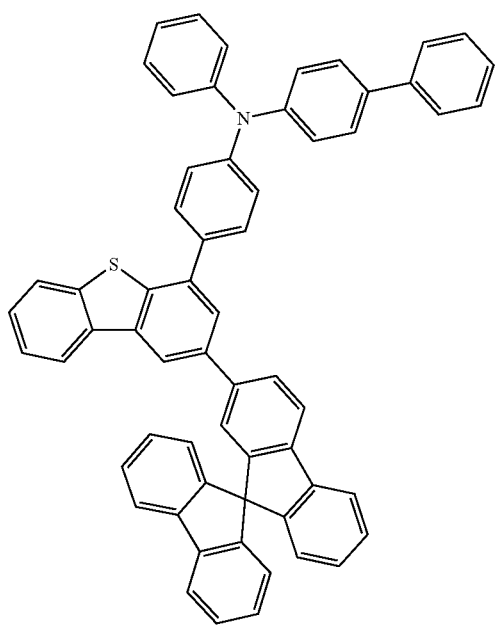
418
-continued
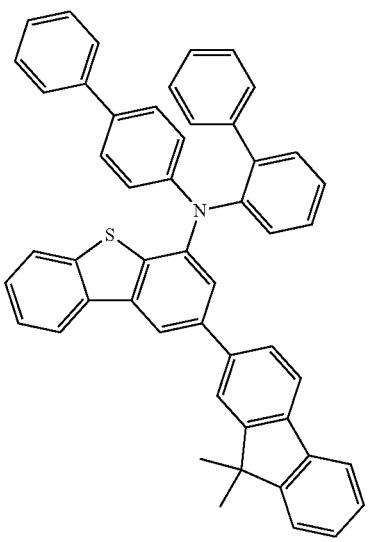
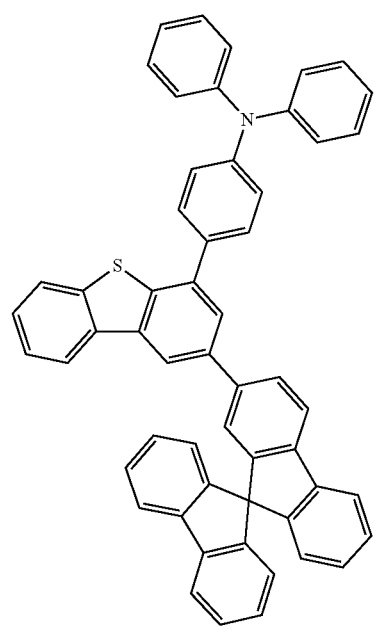
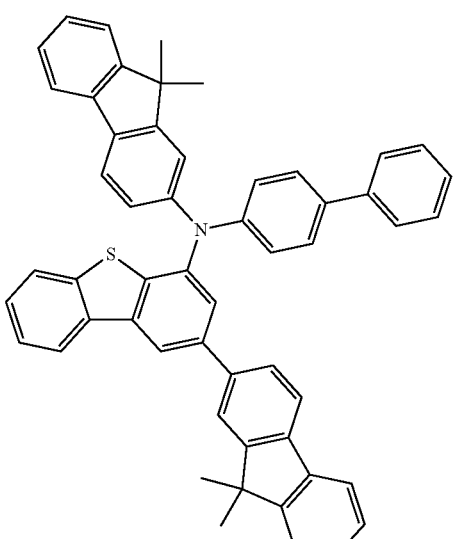

419
-continued
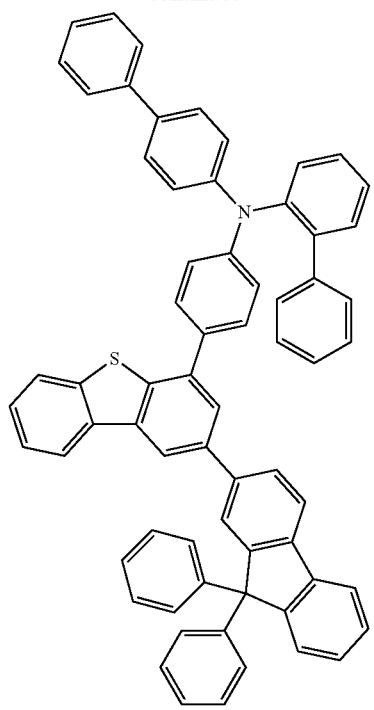
420
-continued
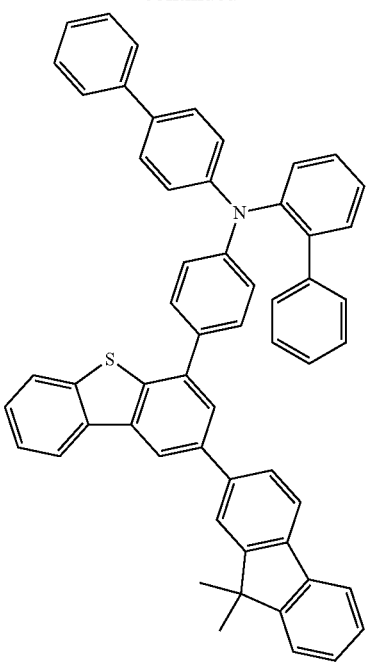
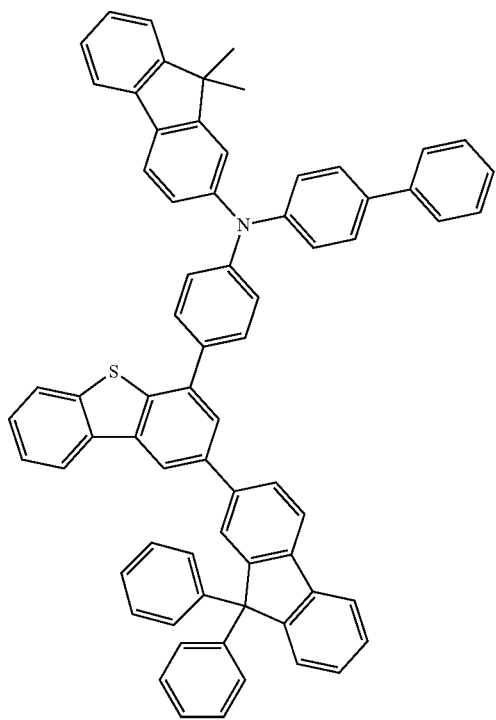

421
-continued
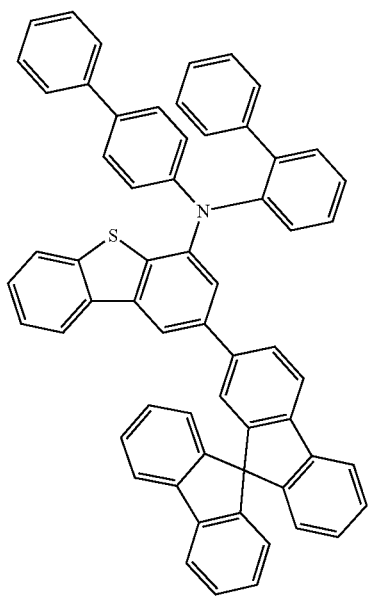
422
-continued
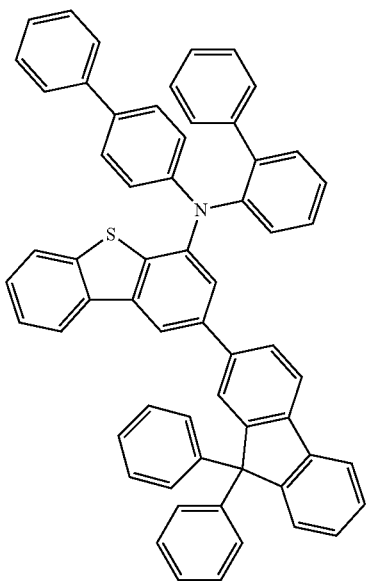
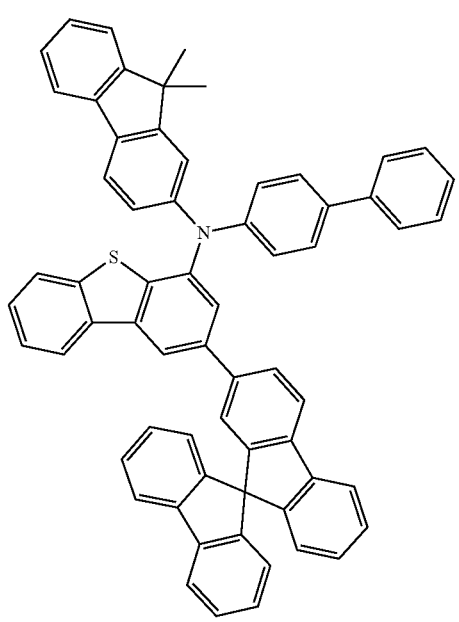
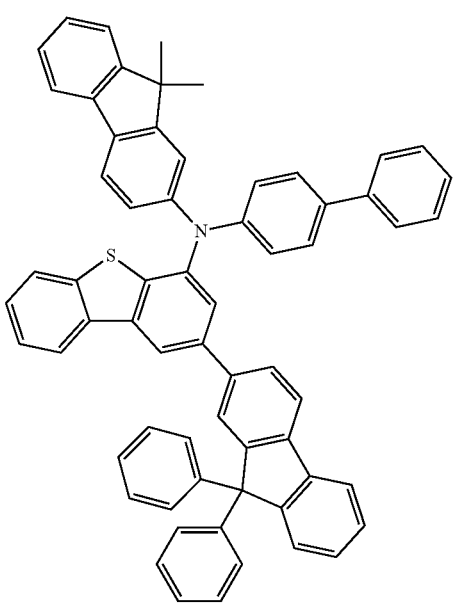

423
-continued
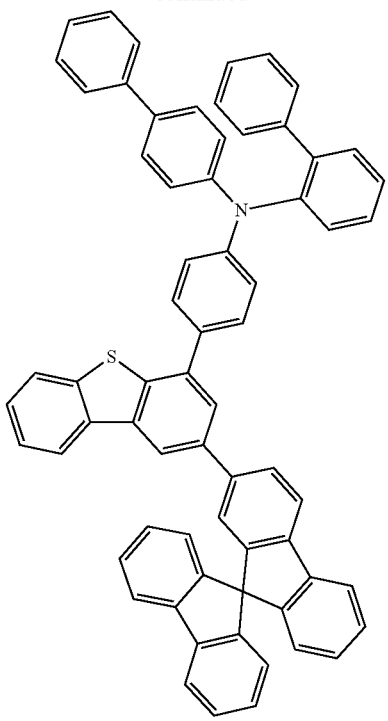
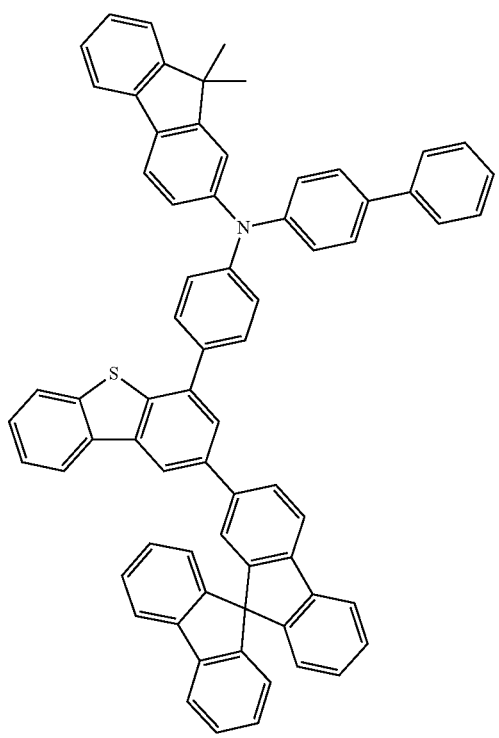
424
-continued
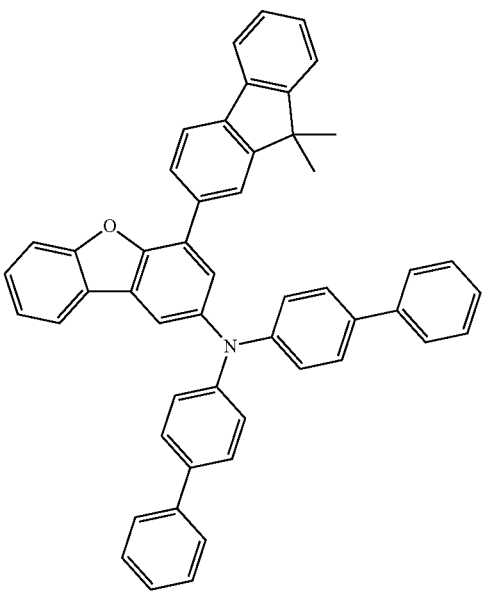
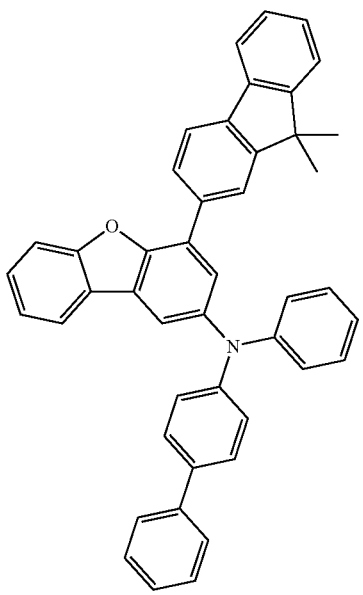

425
-continued
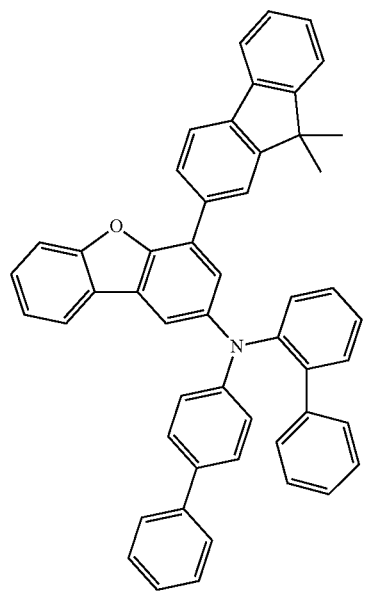
426
-continued
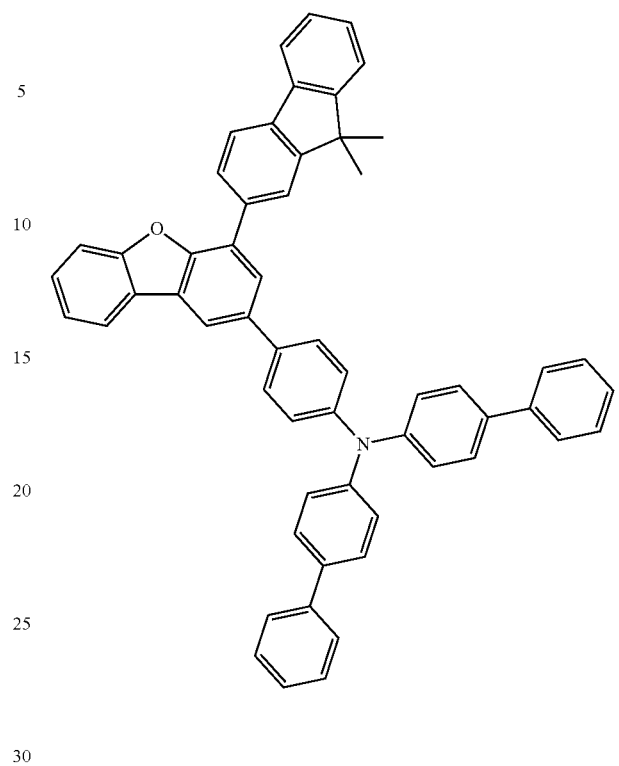
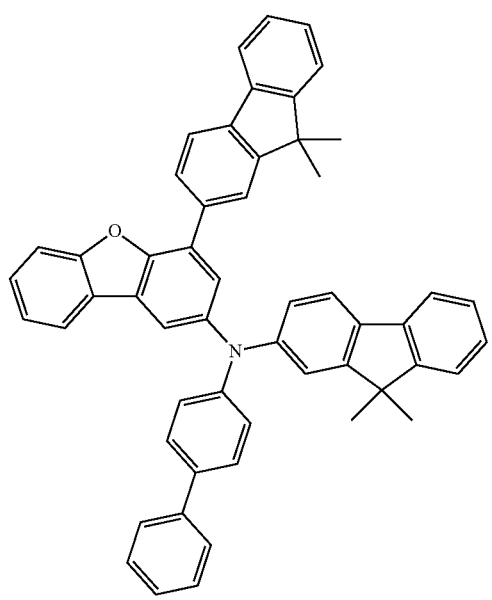 [SMILES: CC1(C)c2ccccc2-c2ccc(-c3cc(N(c4ccc(-c5ccccc5)cc4)c4ccc5c(c4)C(C)(C)c4ccccc4-5)cc4c3oc3ccccc34)cc21]
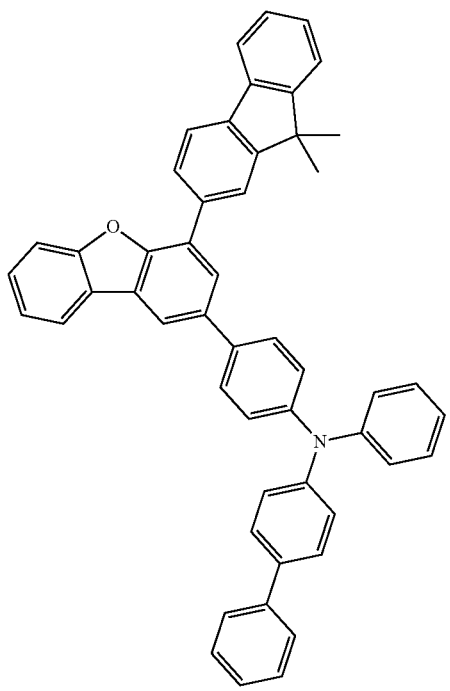

427
-continued
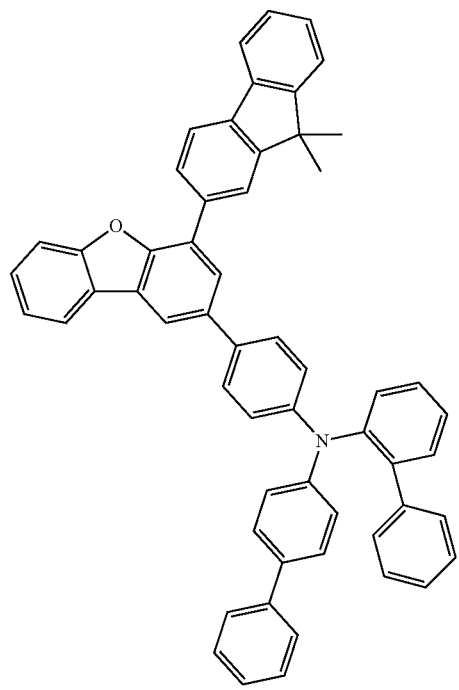
428
-continued
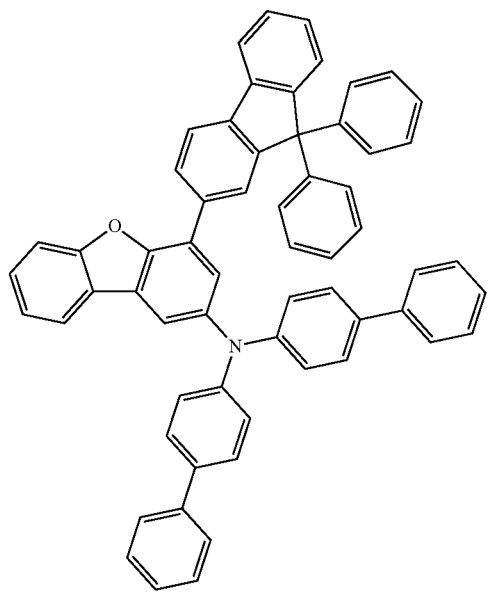
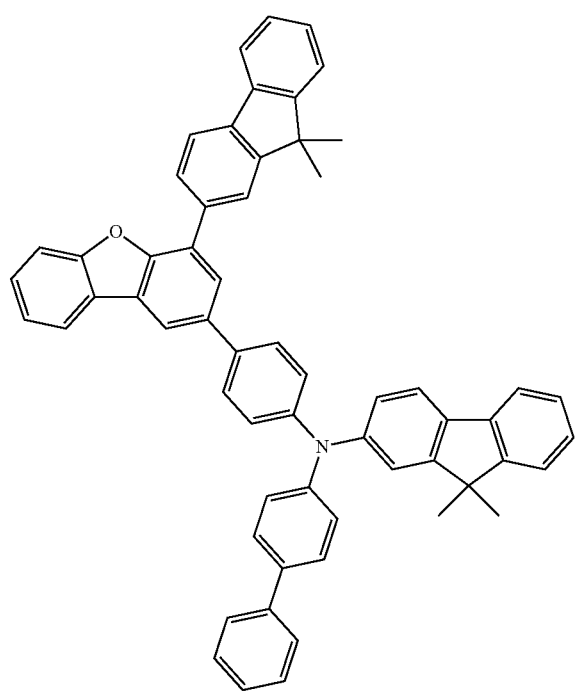
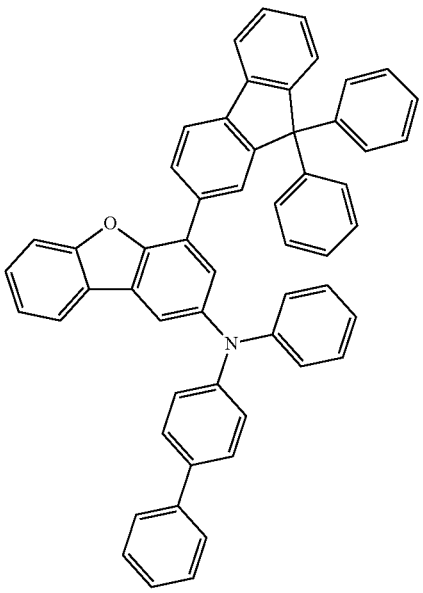

429
-continued
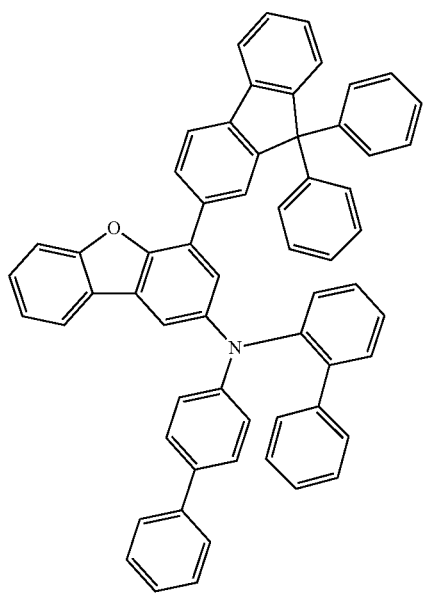
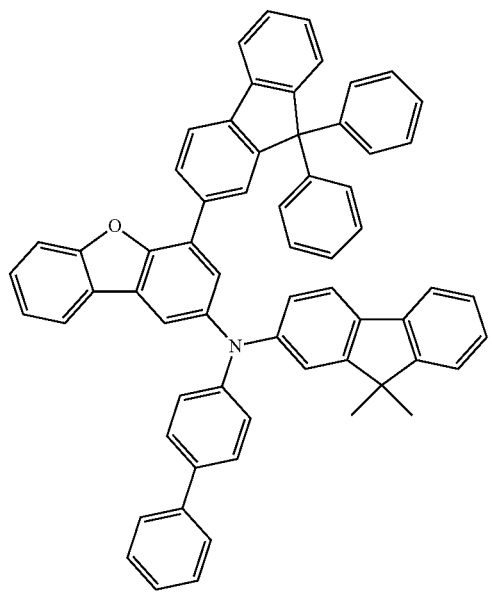 [SMILES: CC1(C)c2ccccc2-c2ccc(N(c3ccc(-c4ccccc4)cc3)c3cc(-c4ccc5c(c4)C(c4ccccc4)(c4ccccc4)c4ccccc4-5)c4oc5ccccc5c4c3)cc21]
430
-continued
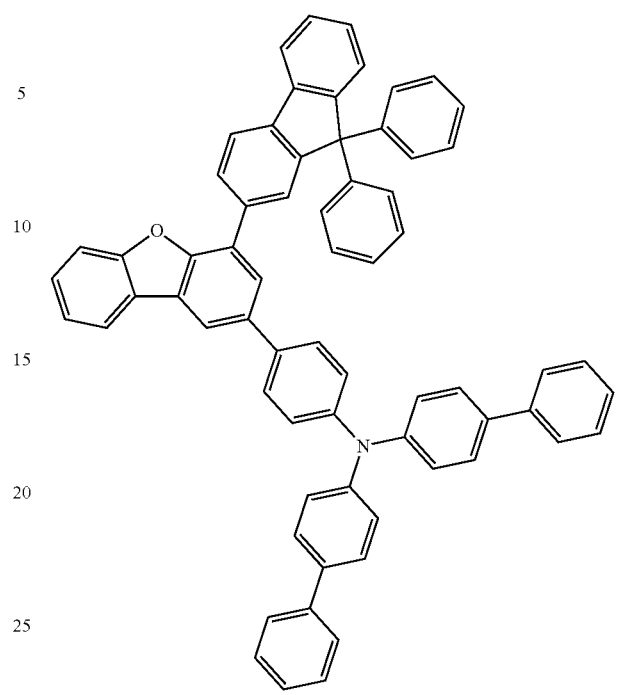
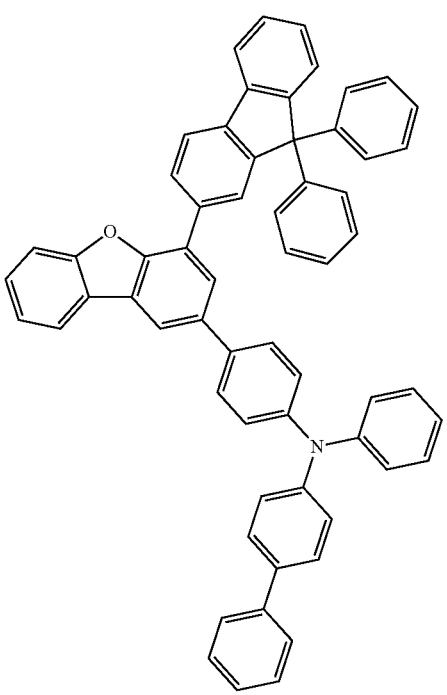

431
-continued
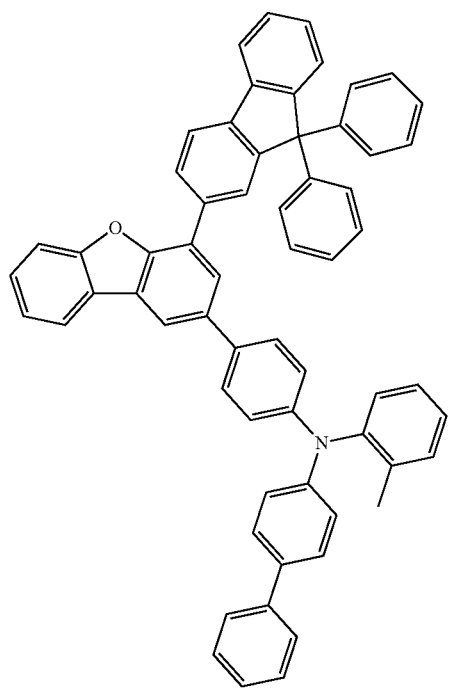
432
-continued
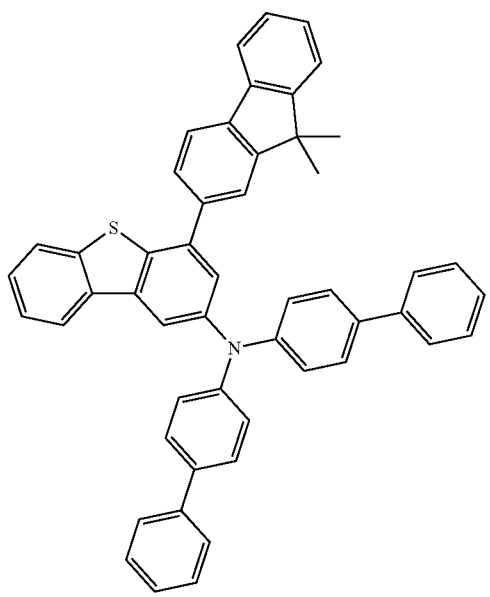
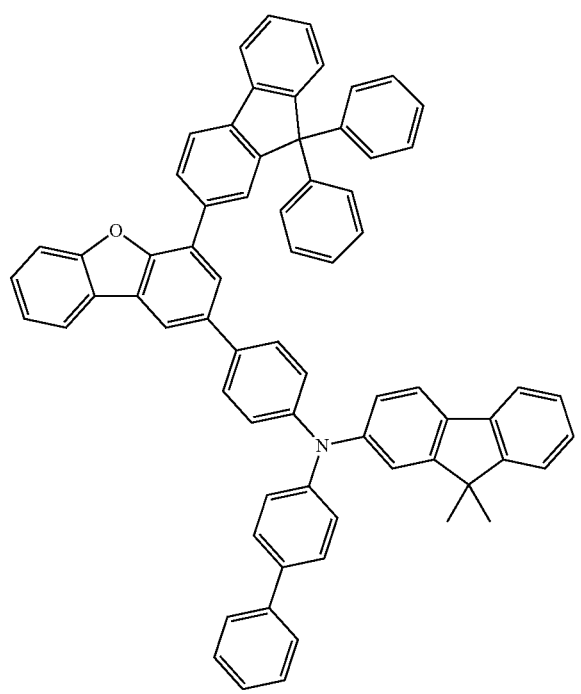
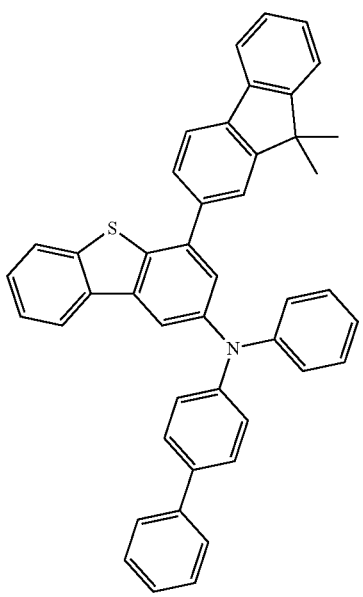

433
-continued
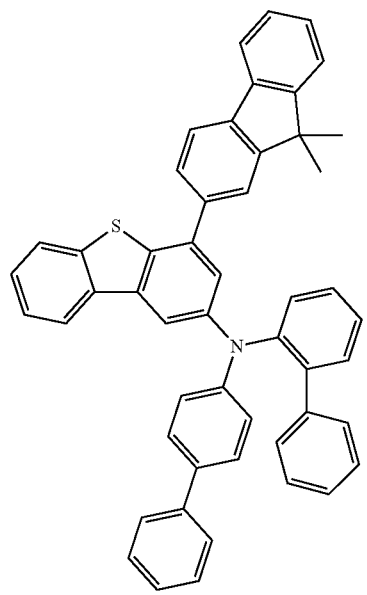
434
-continued
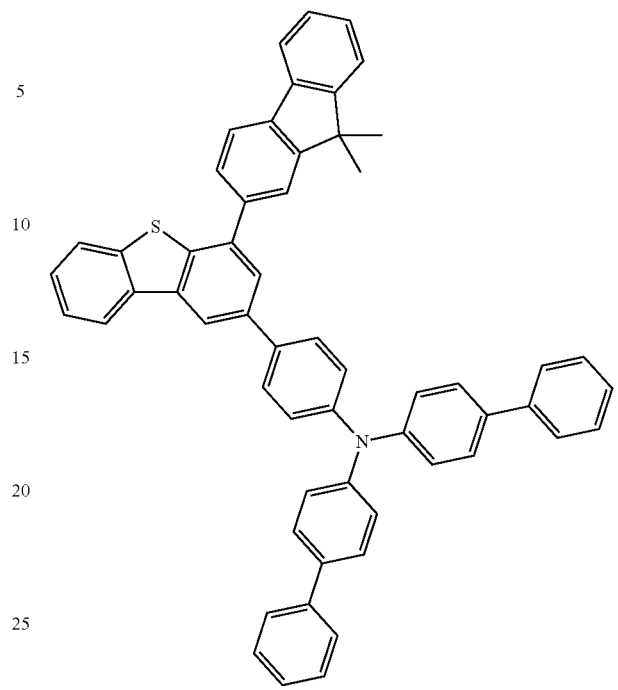
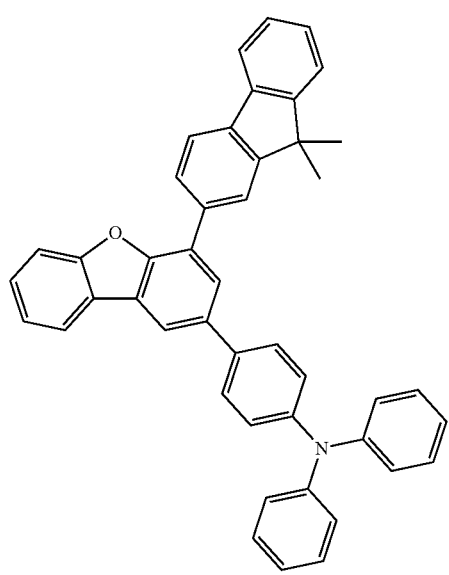
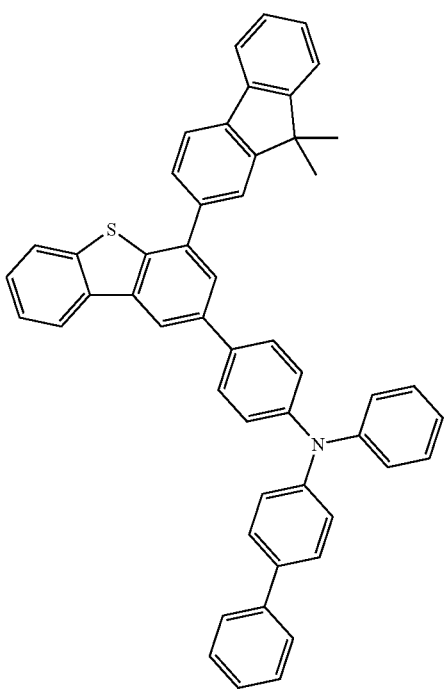

435
-continued
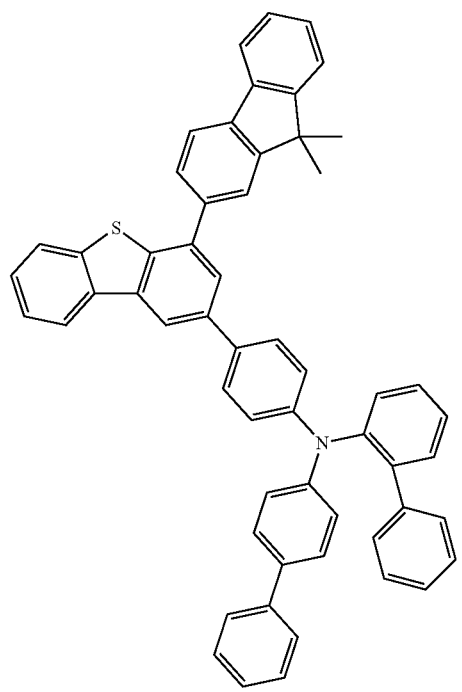
436
-continued
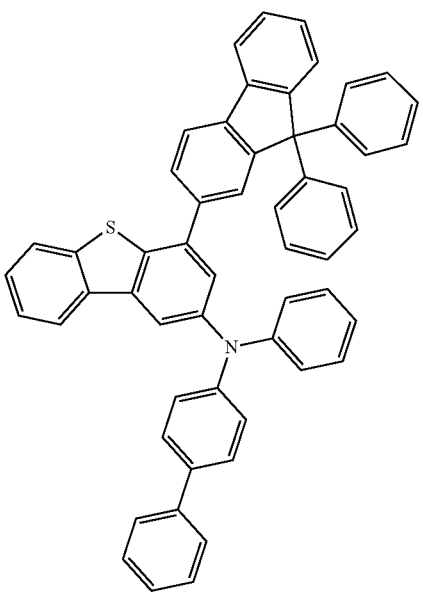
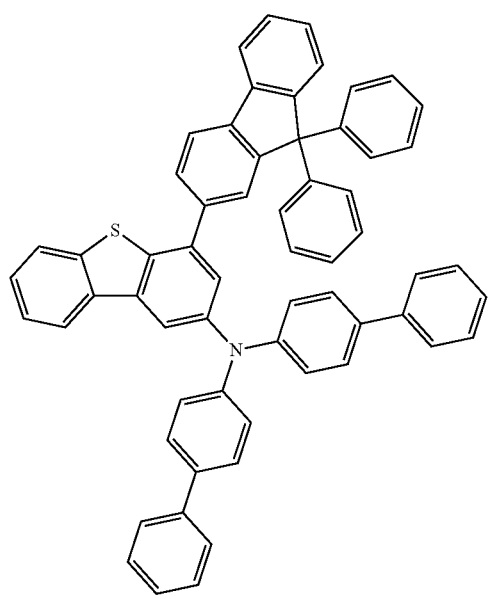
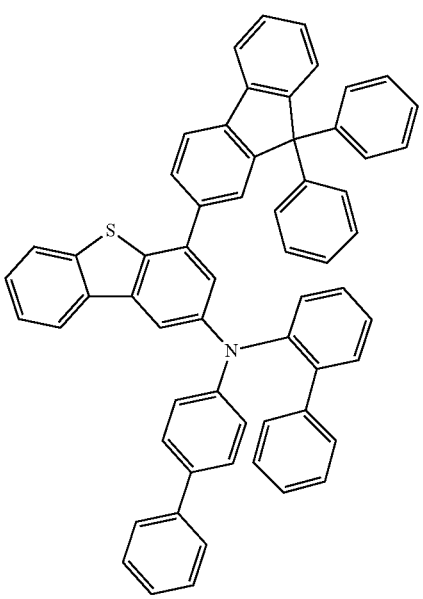

437
-continued
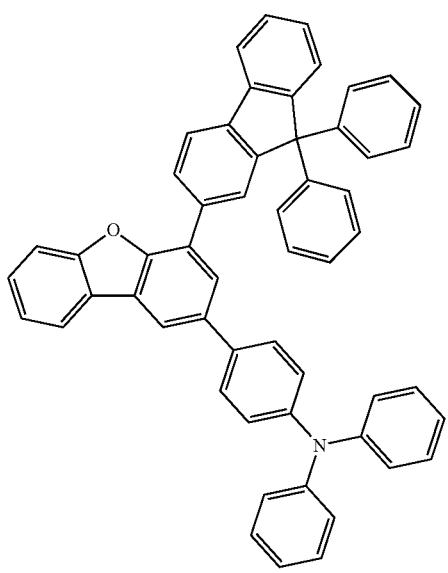
438
-continued
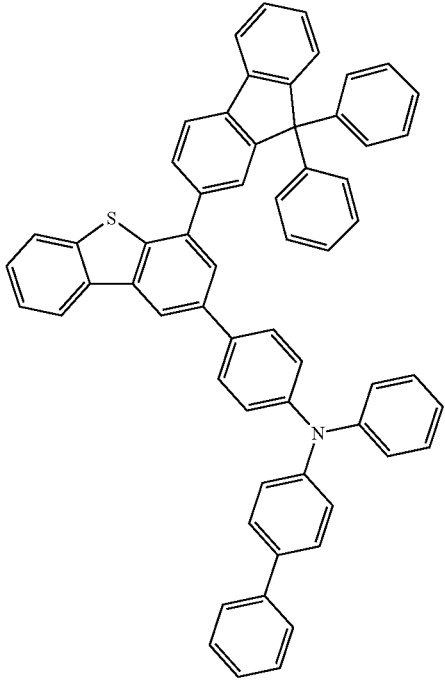
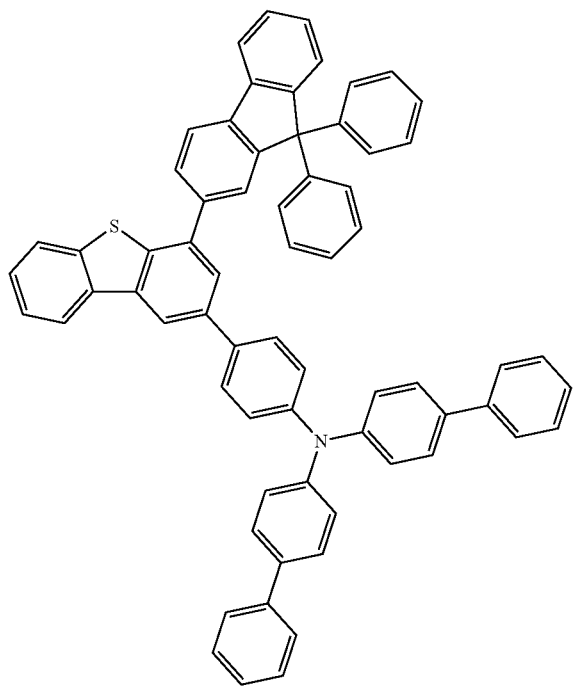
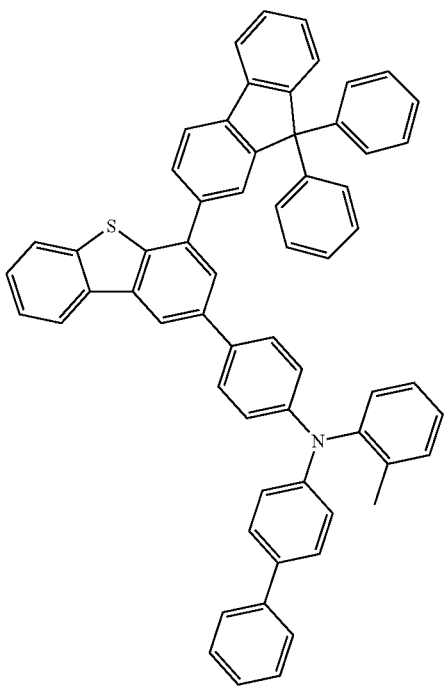

439
-continued
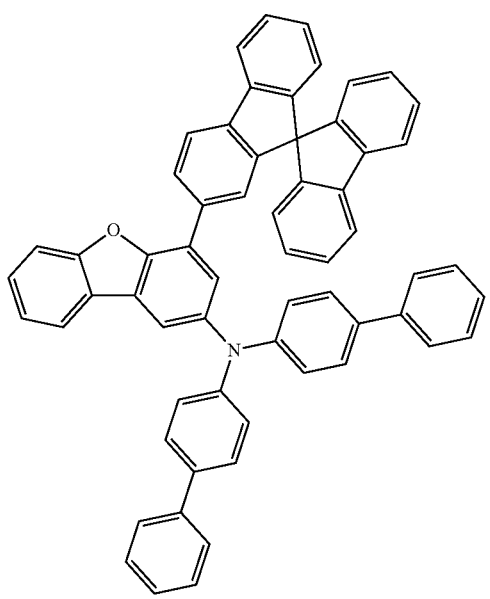
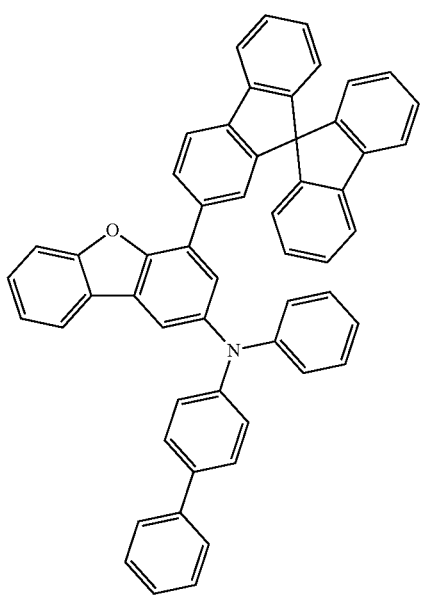
440
-continued
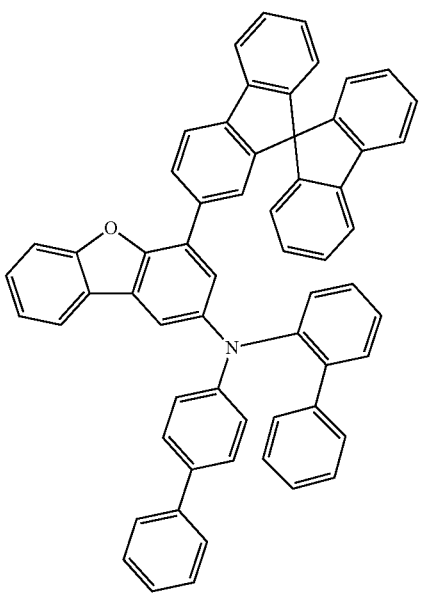
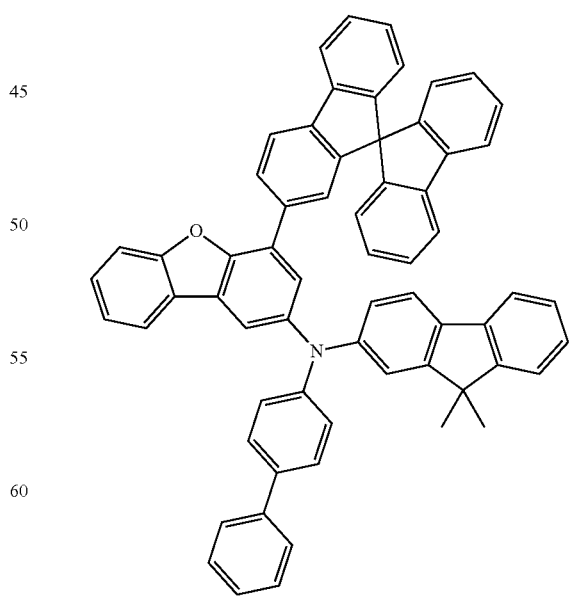

441
-continued
442
-continued
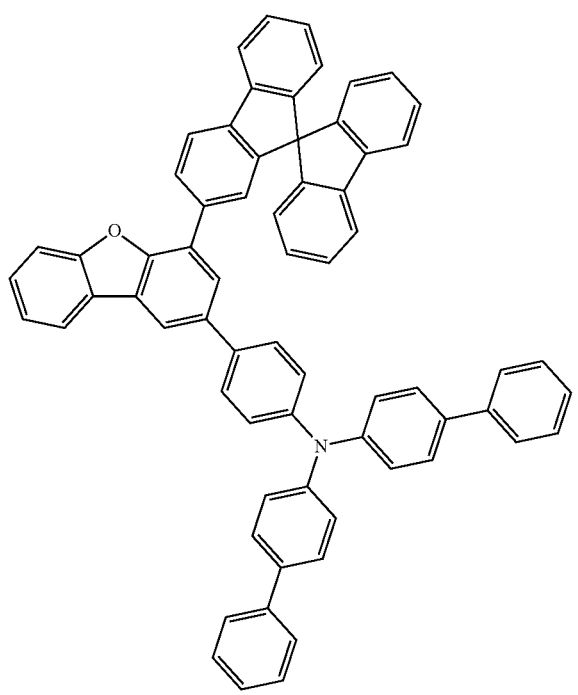
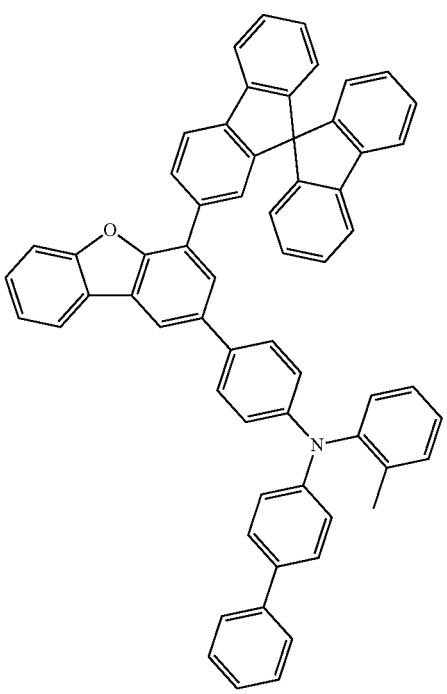

443
-continued
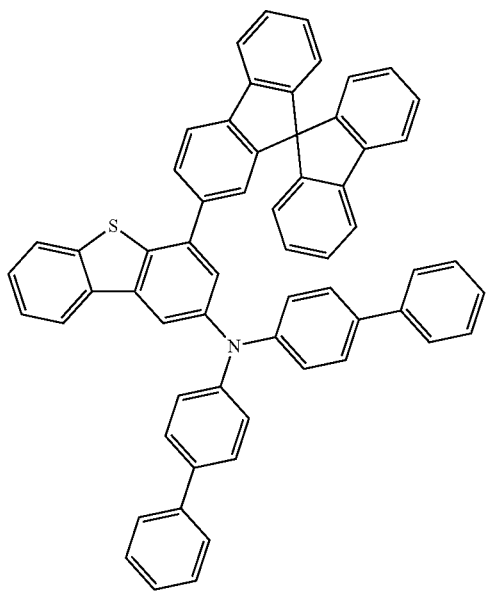
444
-continued
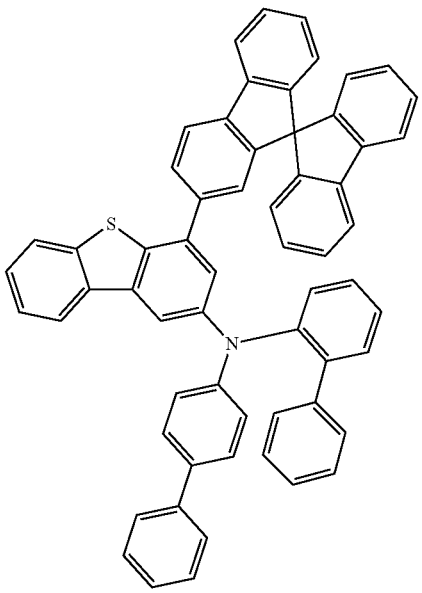
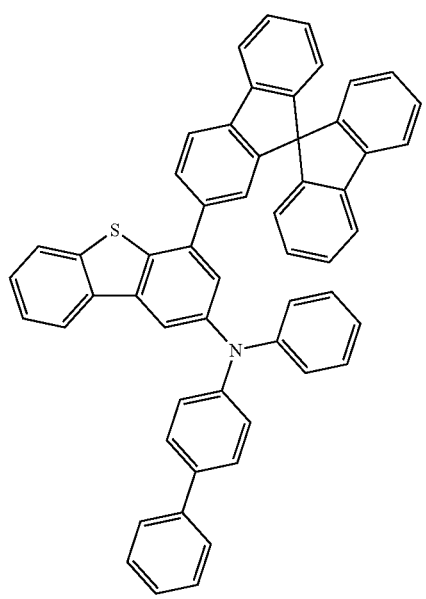
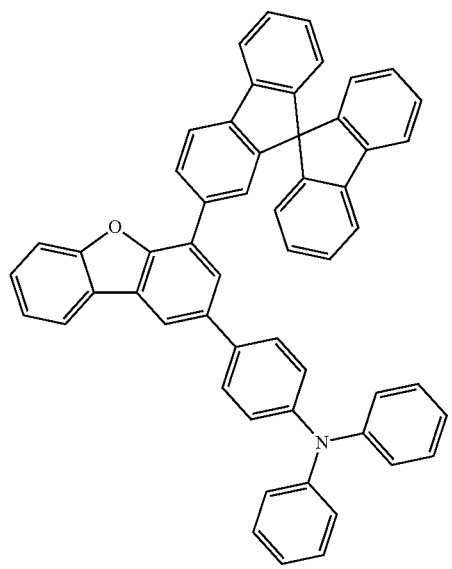

445
-continued
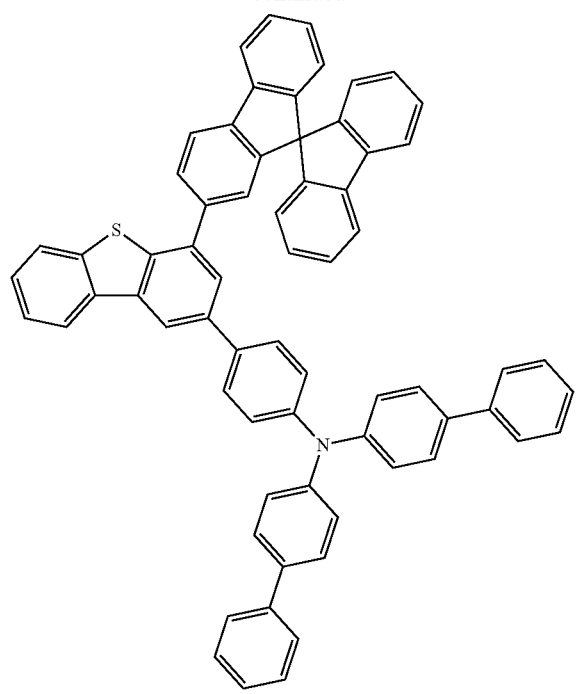
446
-continued
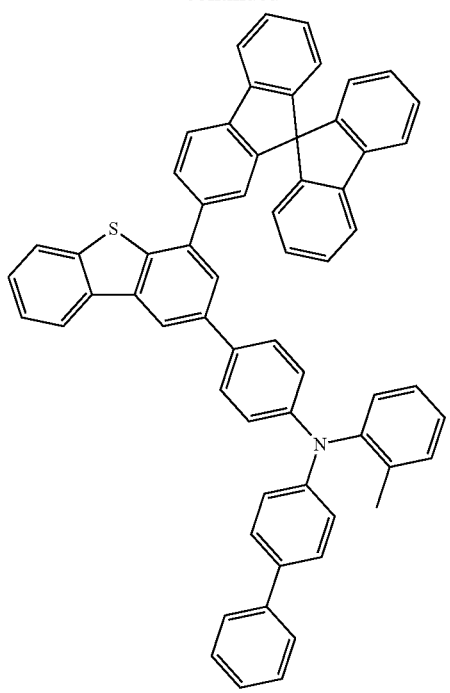
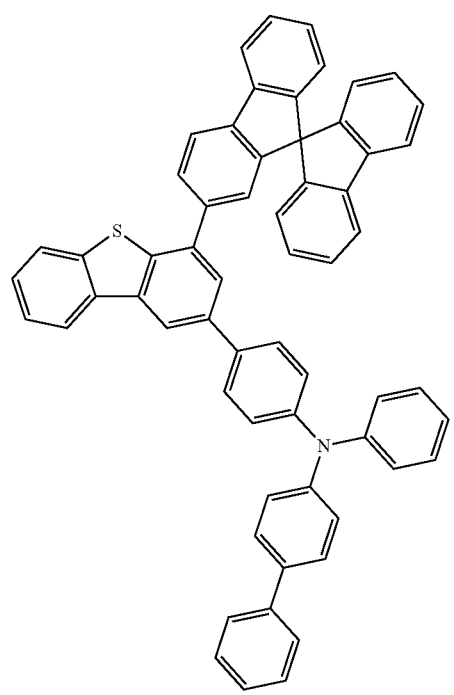
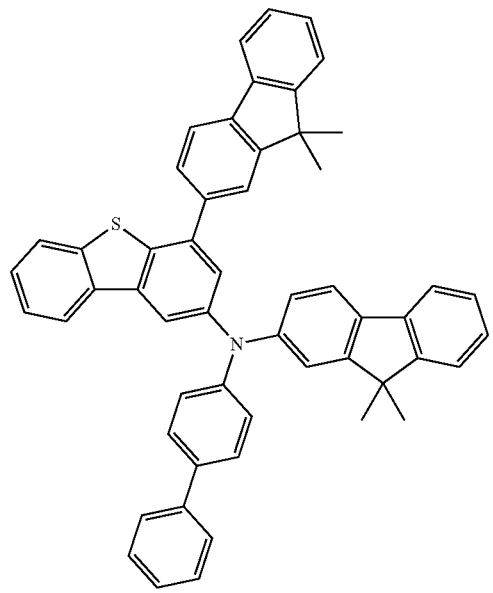

447
-continued
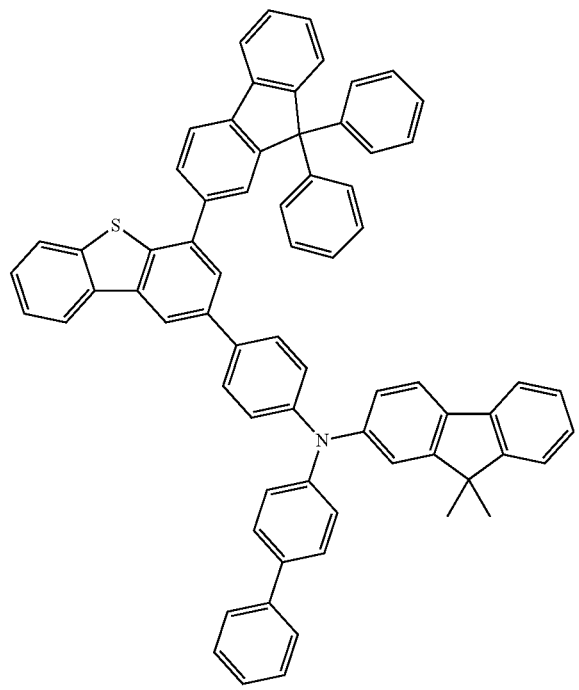
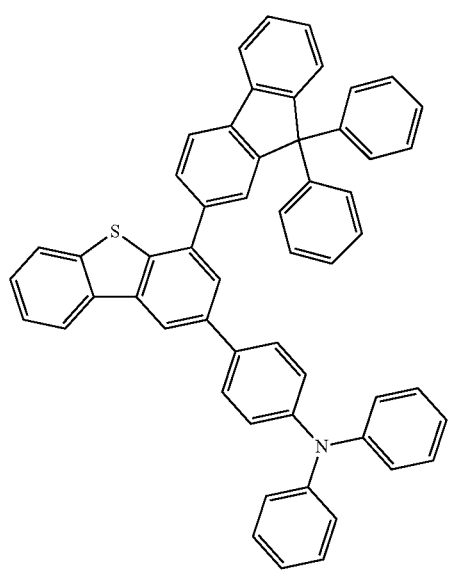
448
-continued
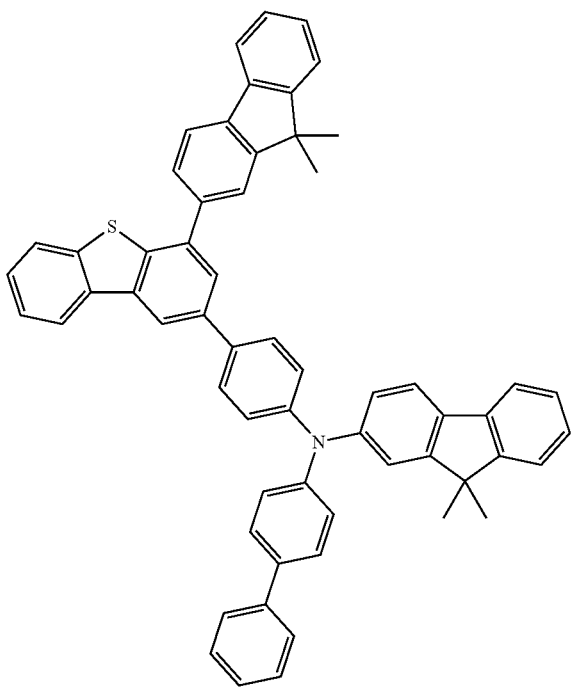
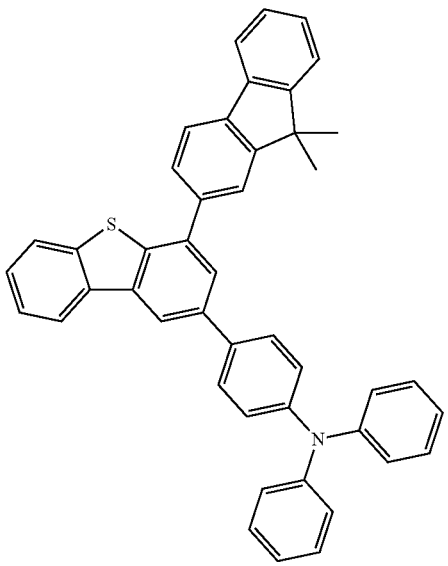

449
-continued
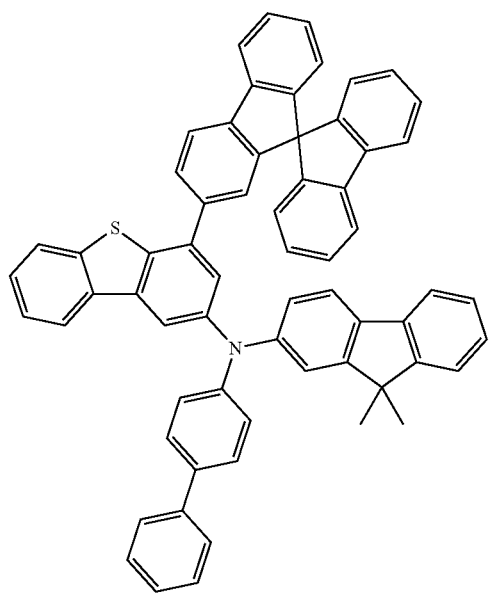 [SMILES: CC1(C)c2ccccc2-c2ccc(N(c3ccc(-c4ccccc4)cc3)c3cc(-c4ccc5c(c4)C4(c6ccccc6-c6ccccc64)c4ccccc4-5)c4oc5ccccc5c4c3)cc21]
450
-continued
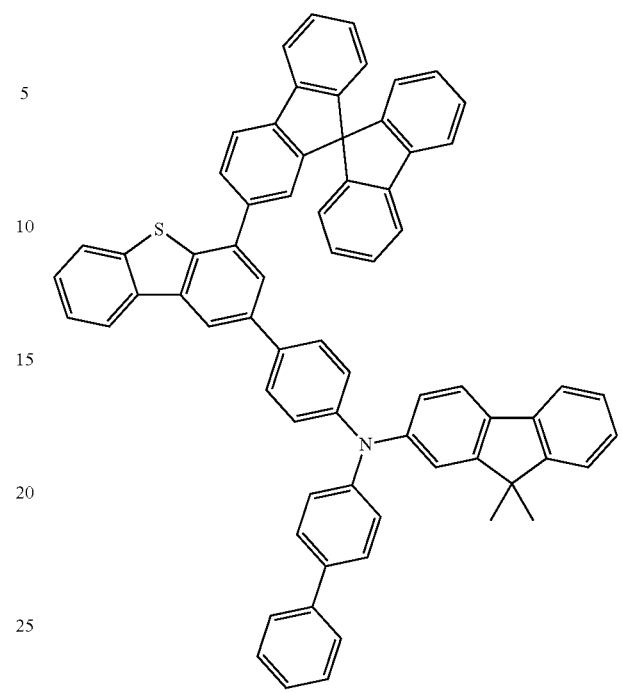
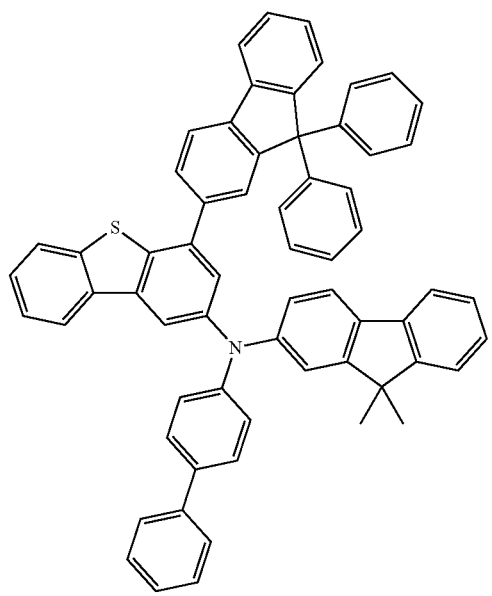
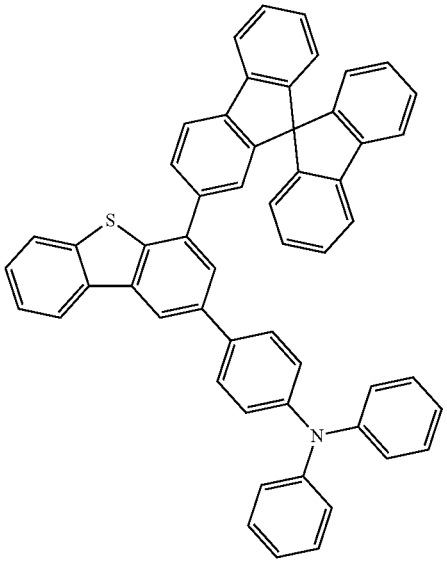

451
-continued
452
-continued
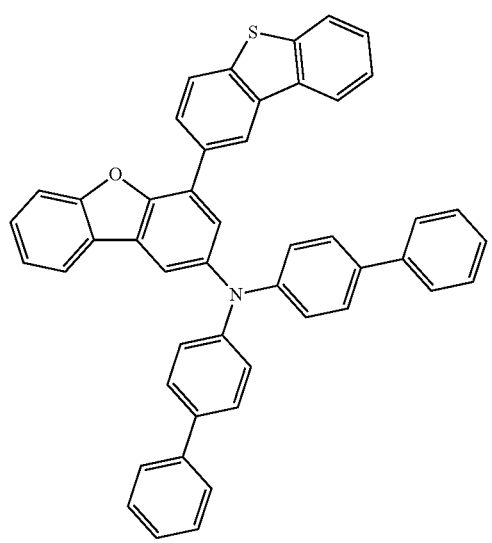
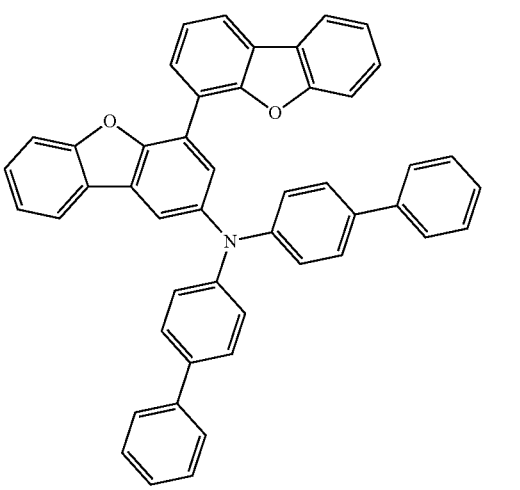
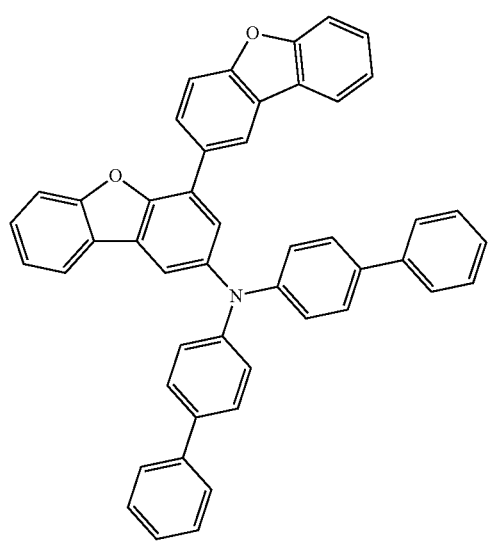
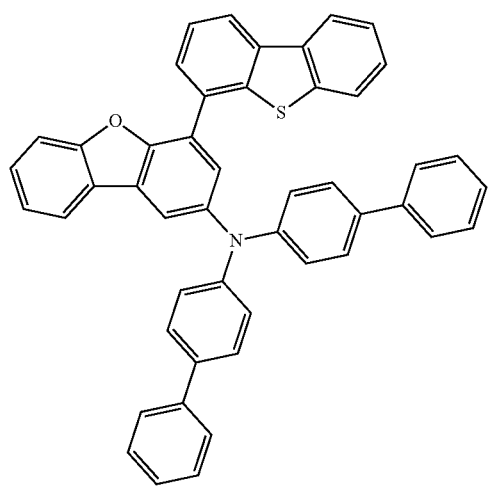 [SMILES: c1ccc(-c2ccc(N(c3ccc(-c4ccccc4)cc3)c3cc(-c4cccc5c4oc4ccccc45)c4oc5ccccc5c4c3)cc2)cc1]
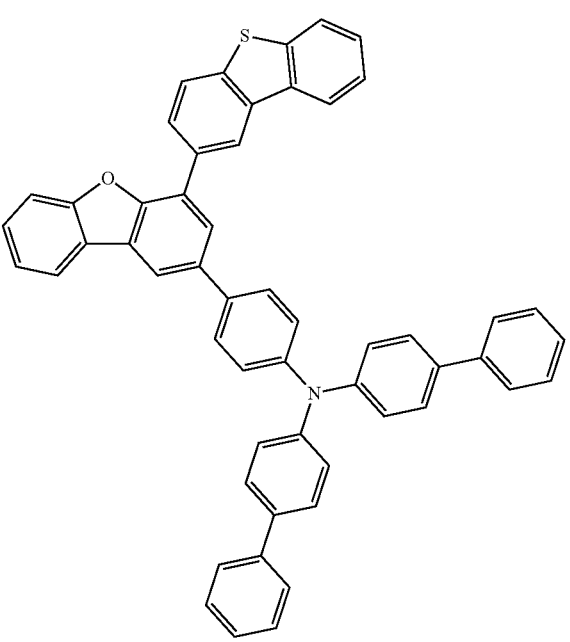

453
-continued
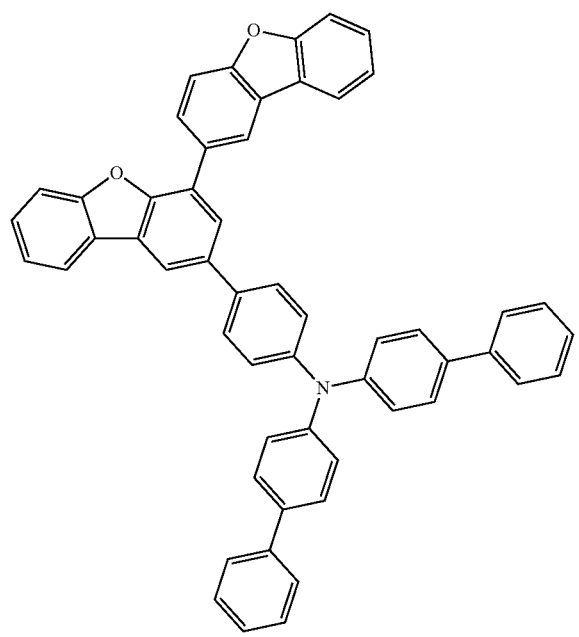
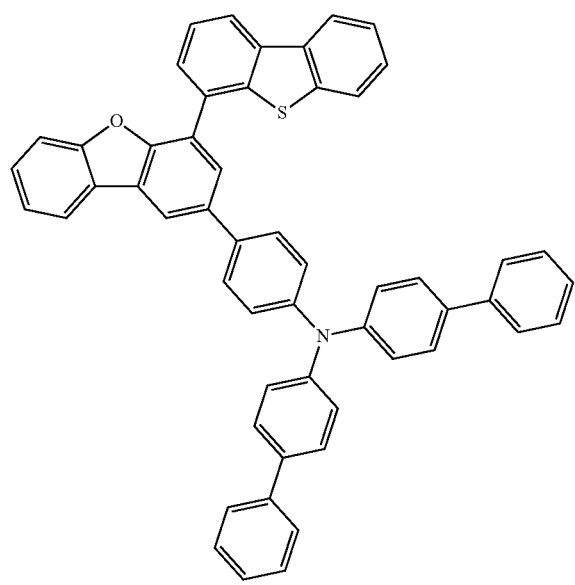
454
-continued
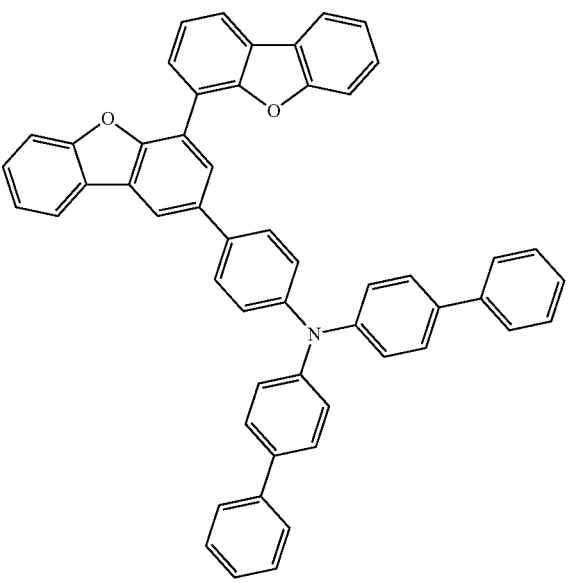
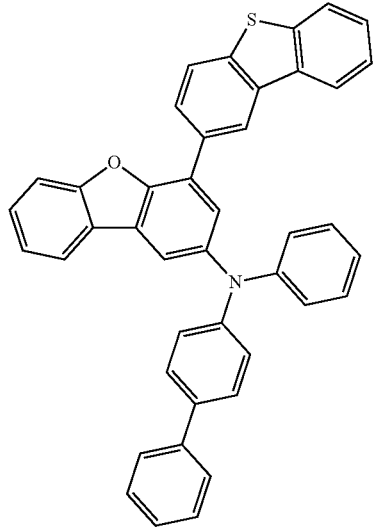
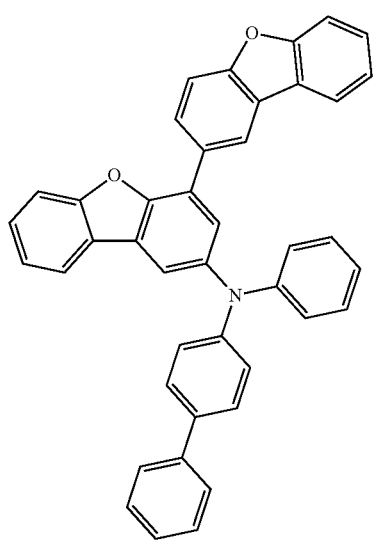

455
-continued
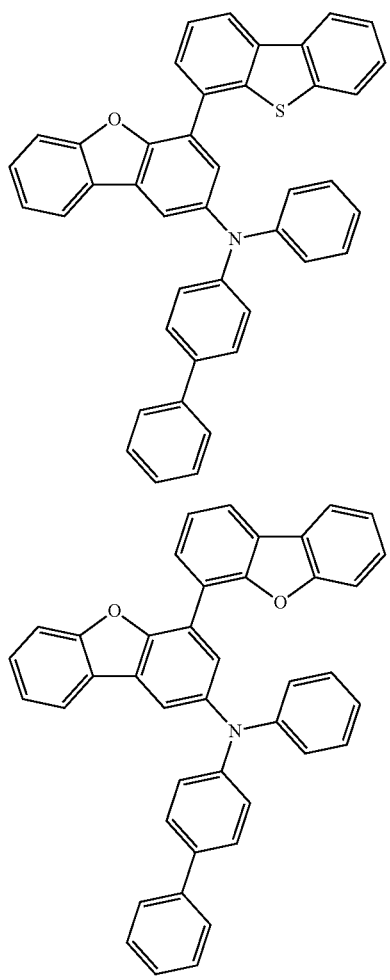
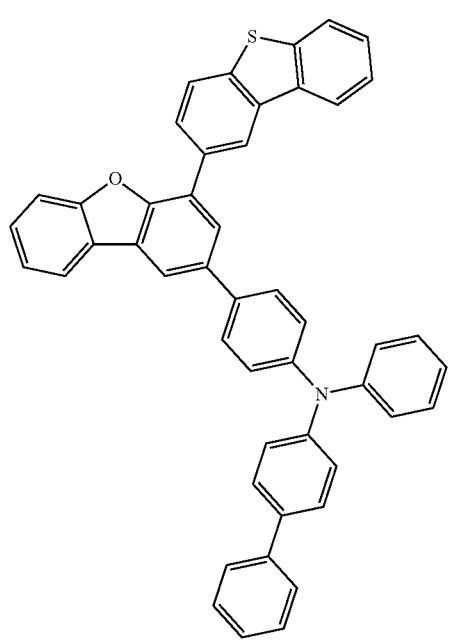
456
-continued
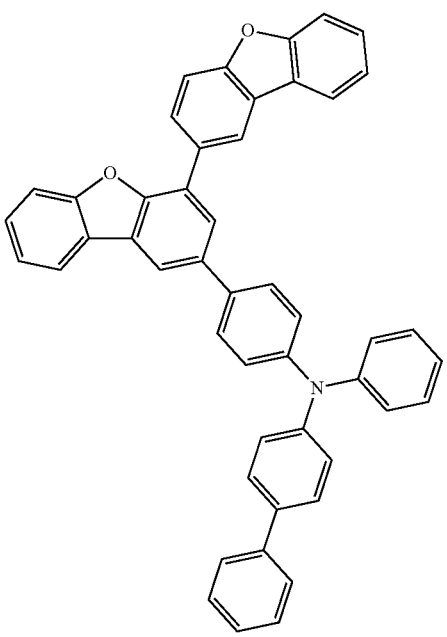
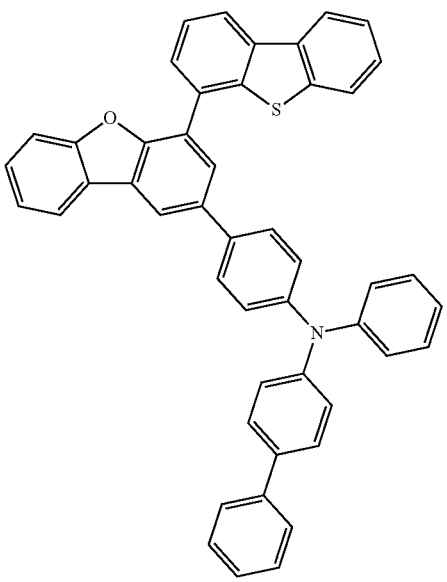

457
-continued
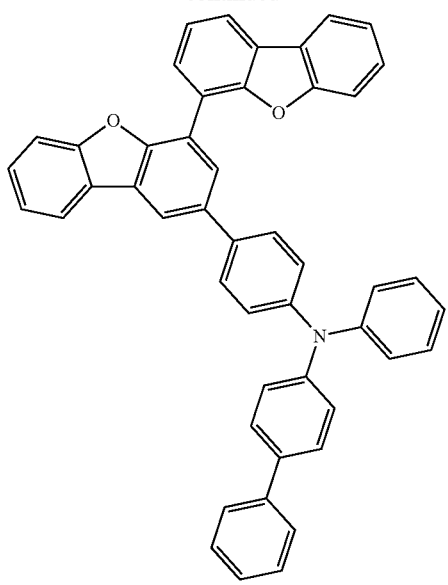
458
-continued
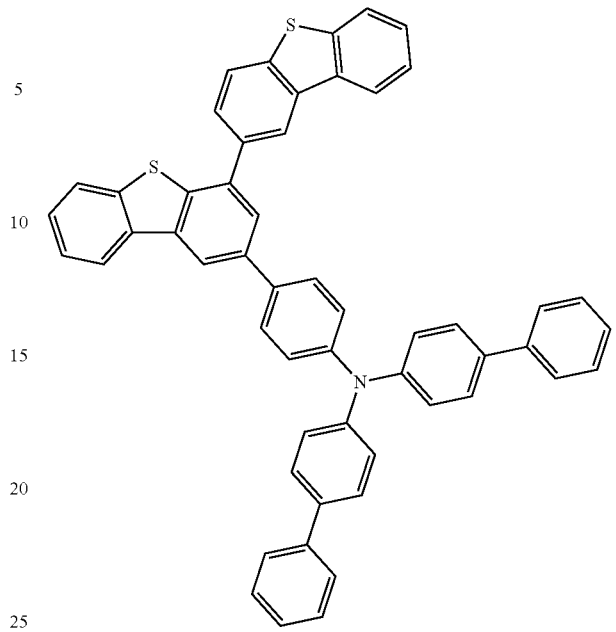
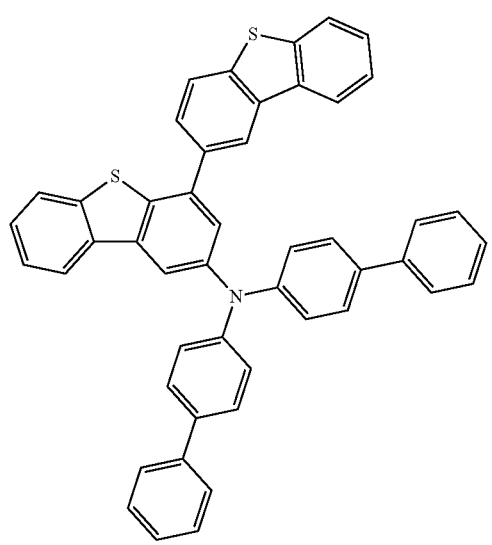
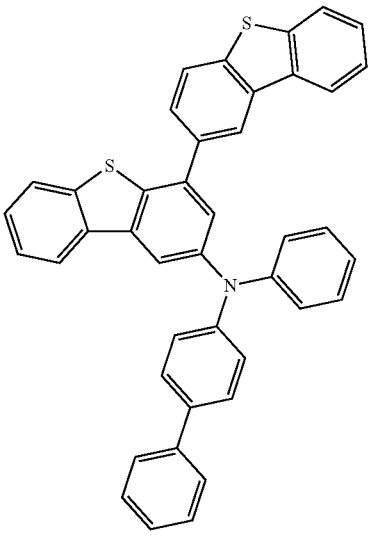

459
-continued
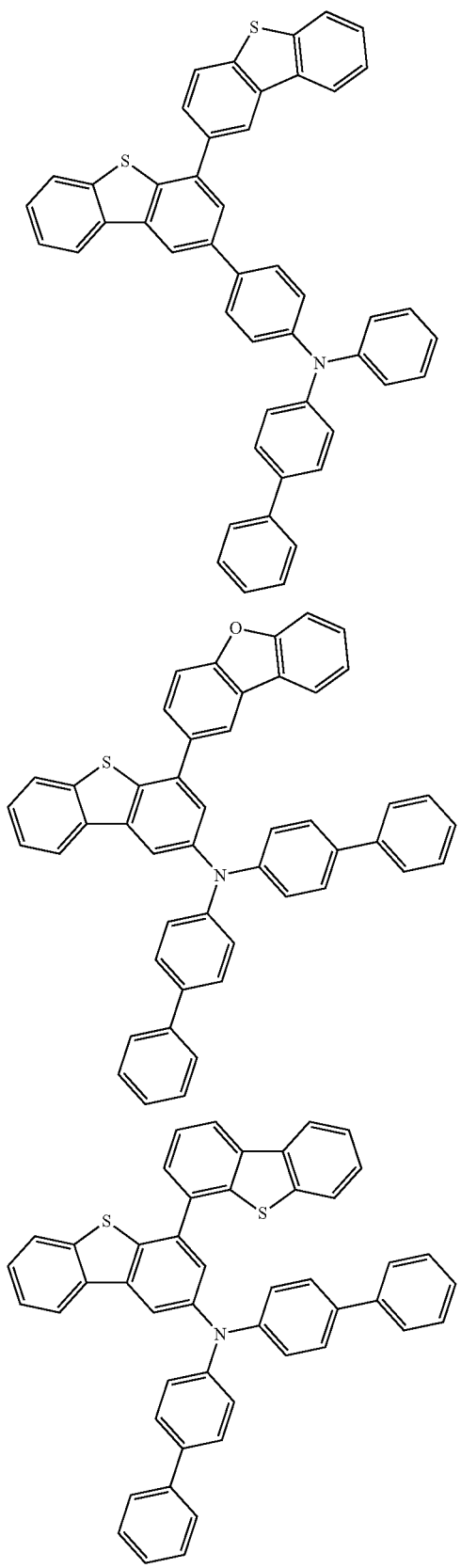
460
-continued
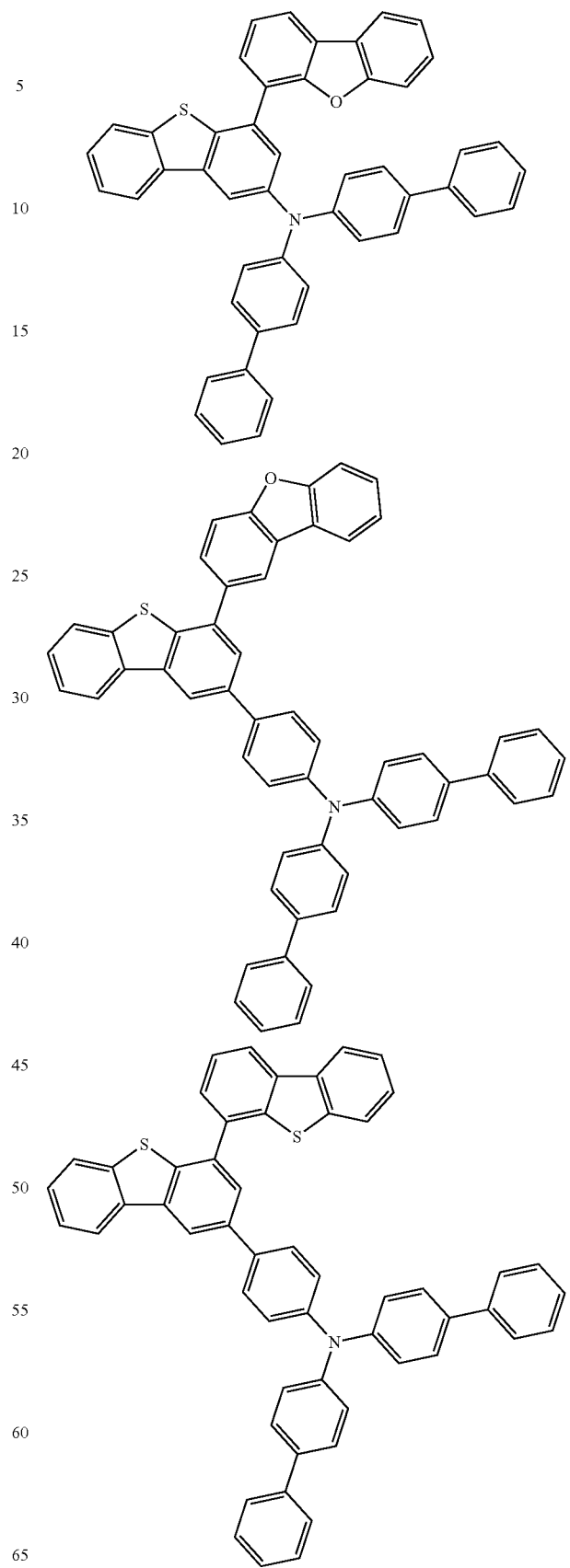

461
-continued
462
-continued
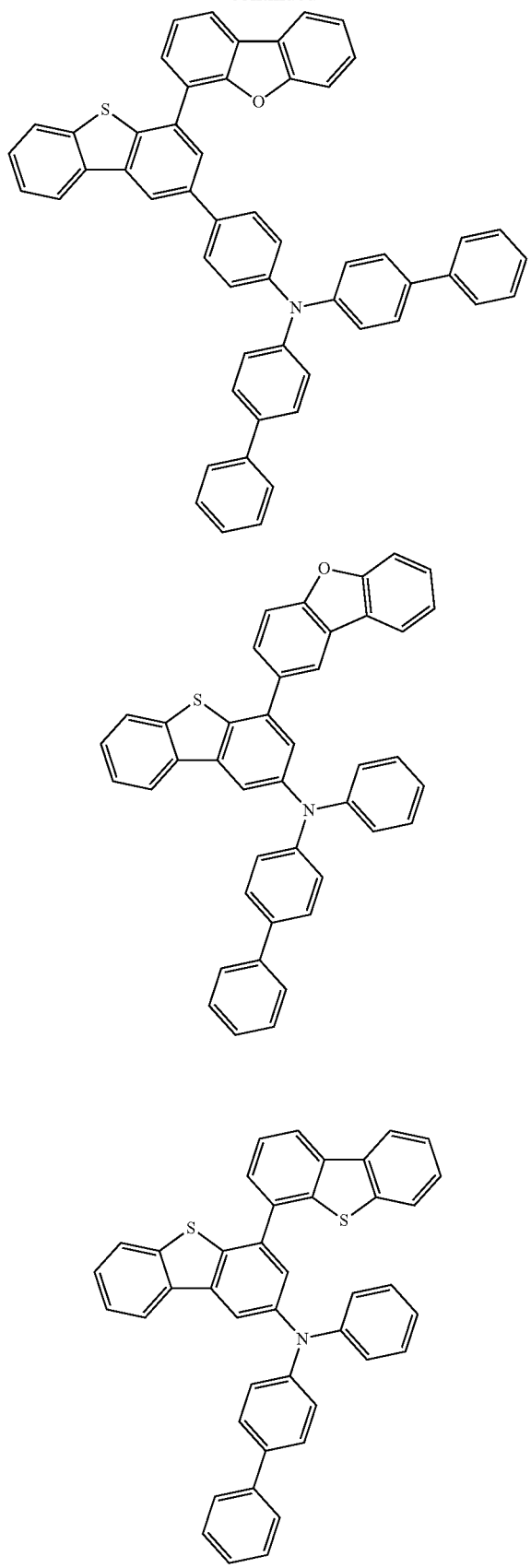
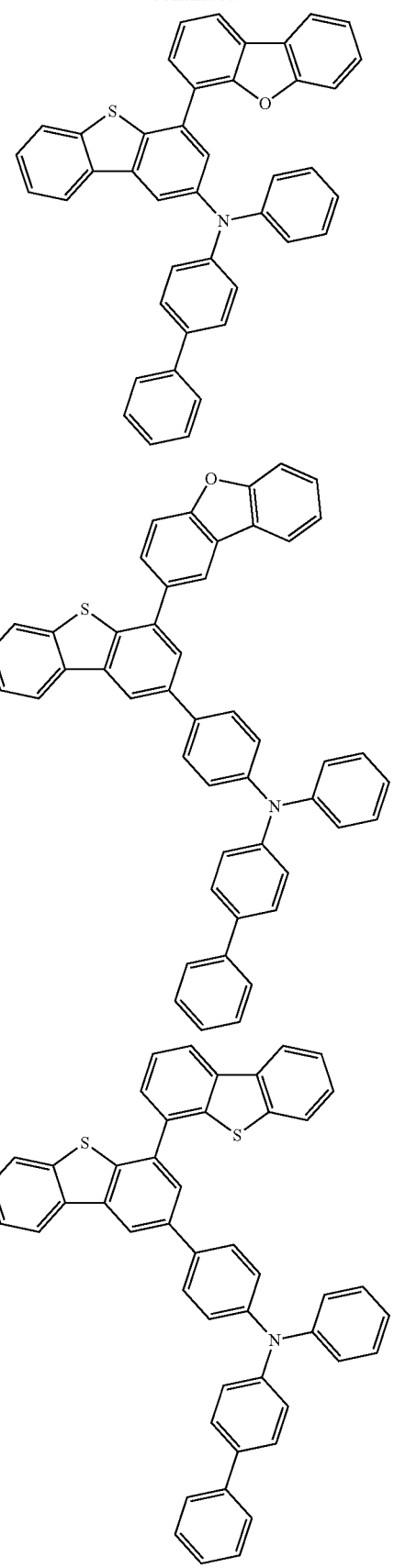

463
-continued
464
-continued
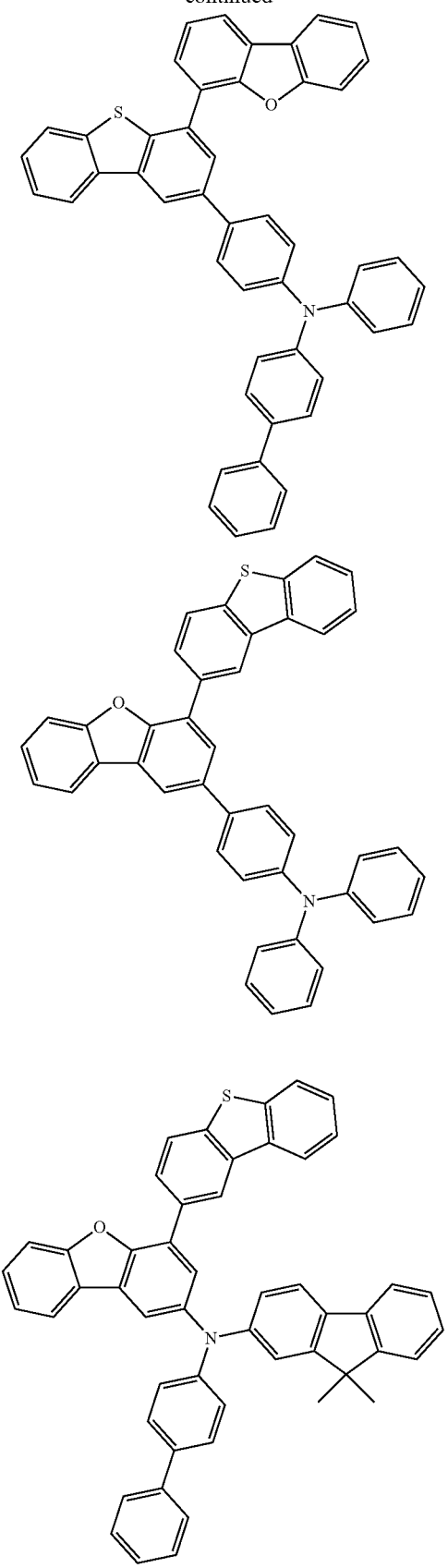
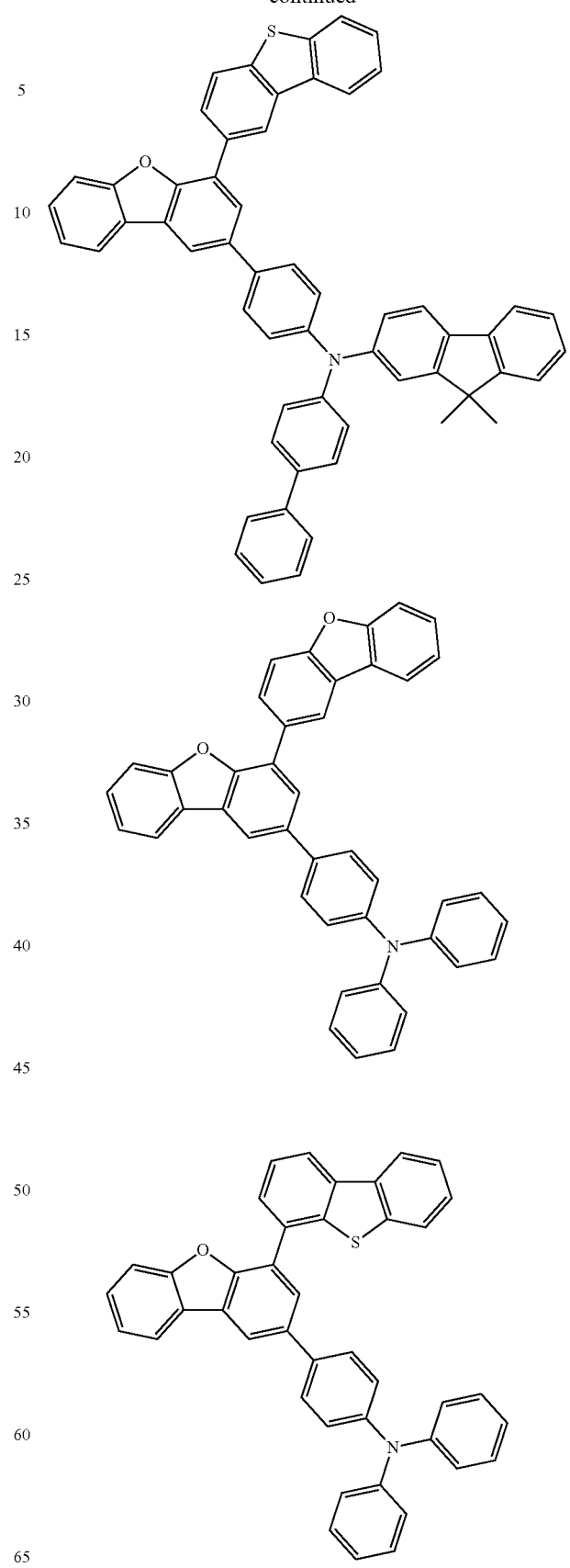

465
-continued
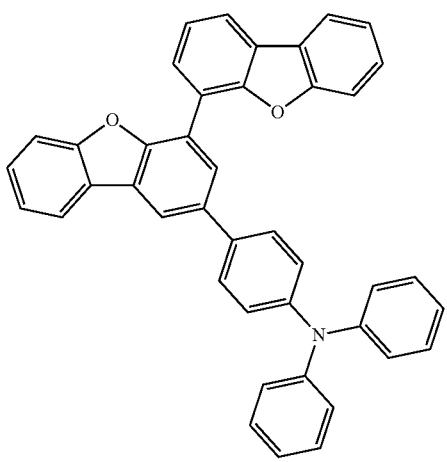
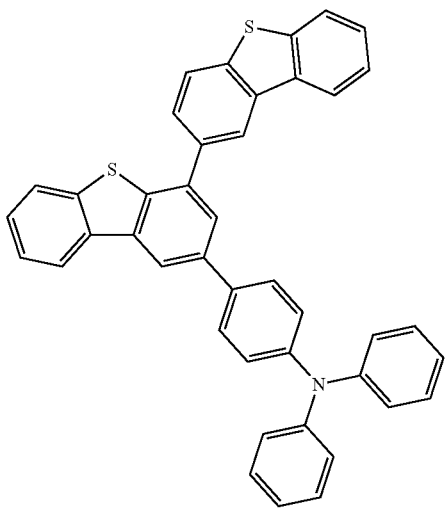
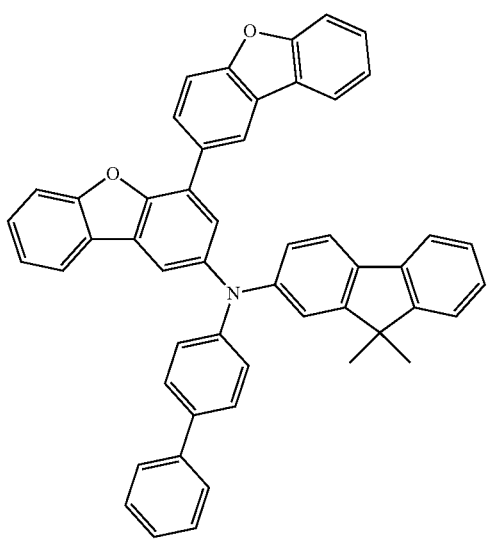
466
-continued
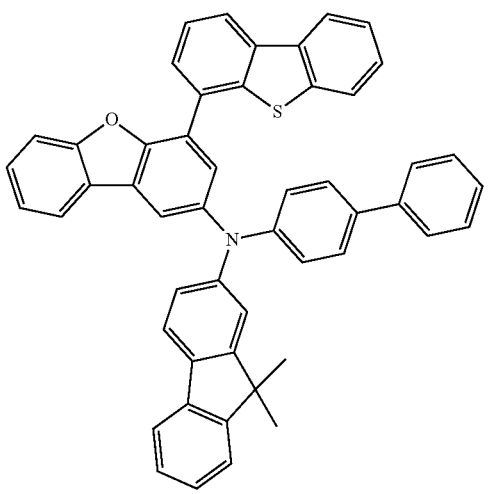
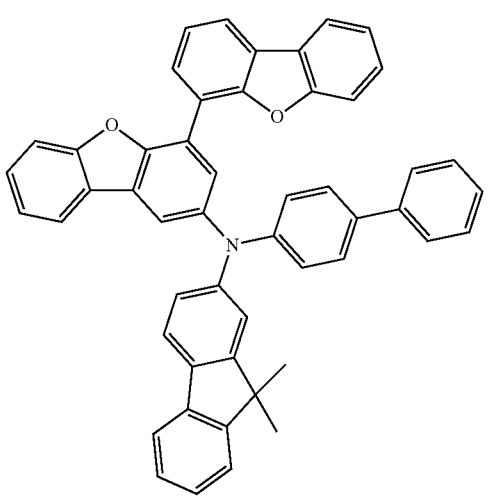
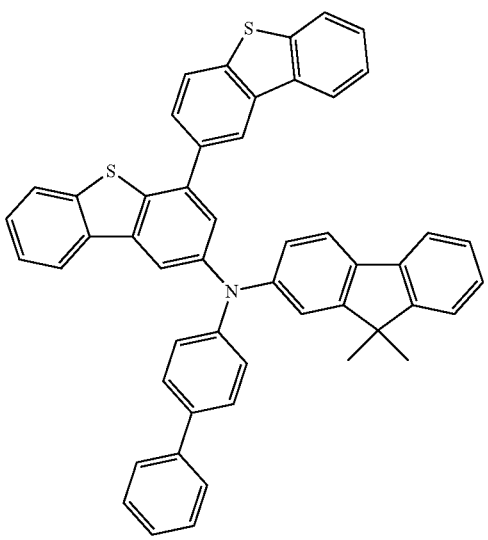

467
-continued
468
-continued
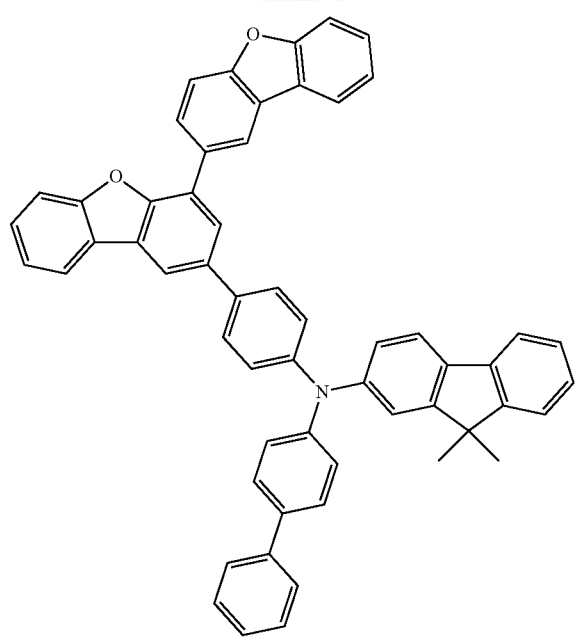
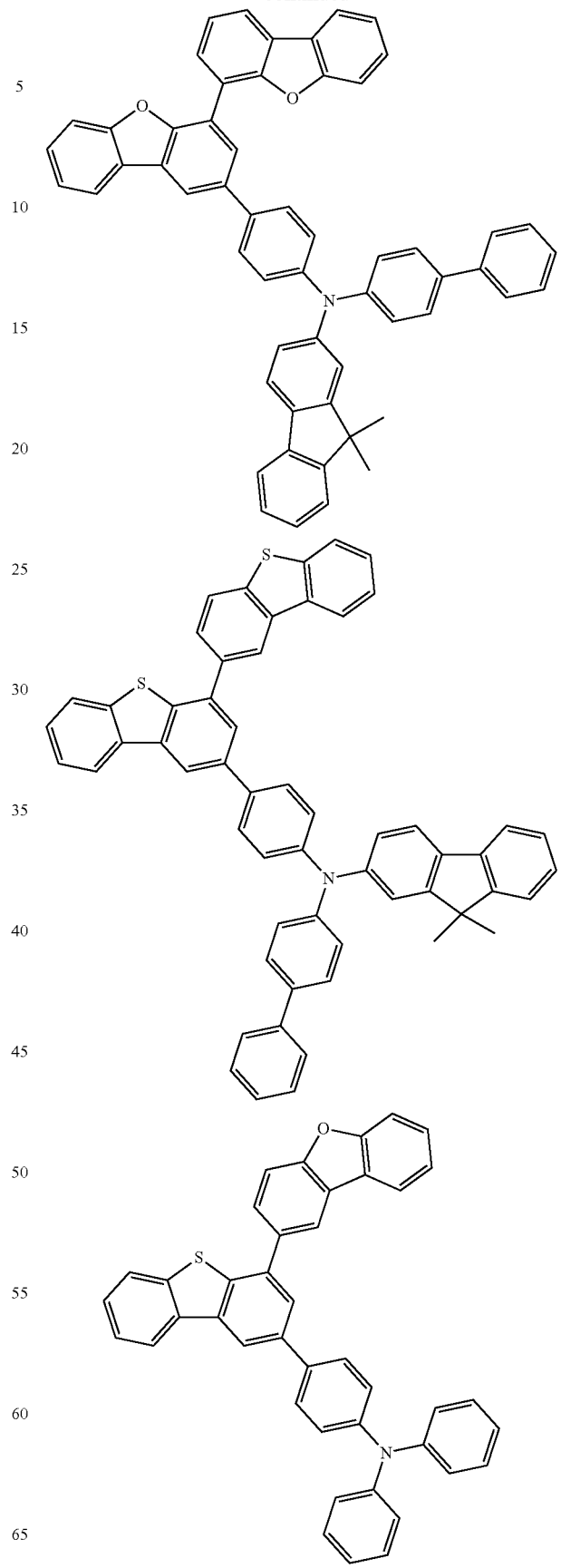
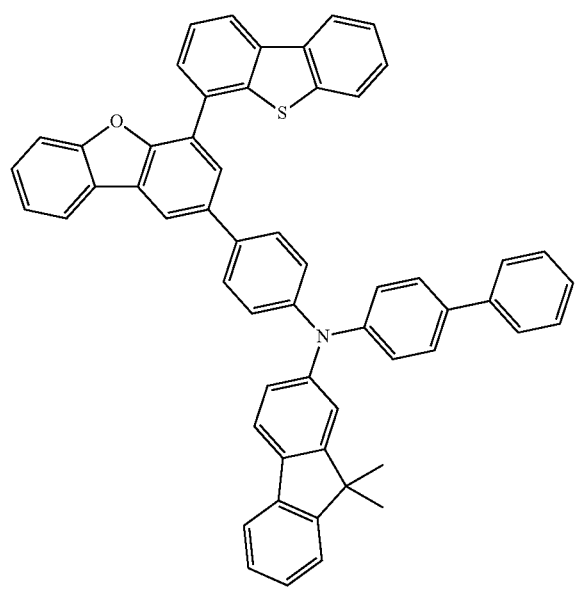

469
-continued
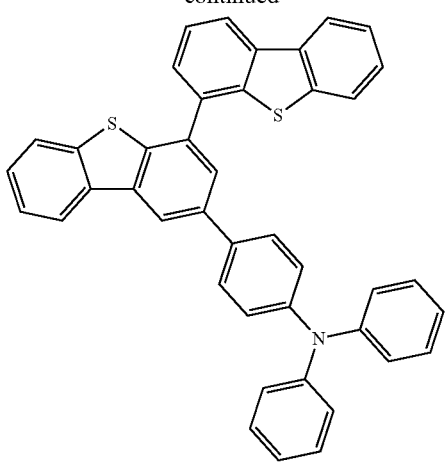
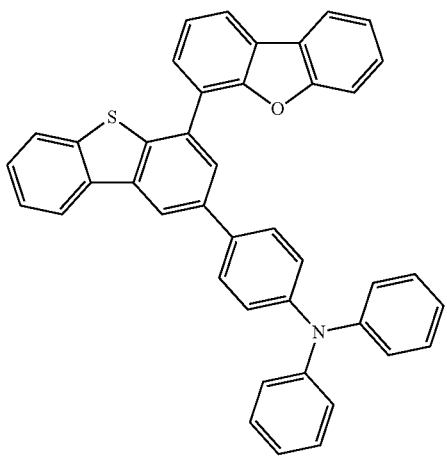
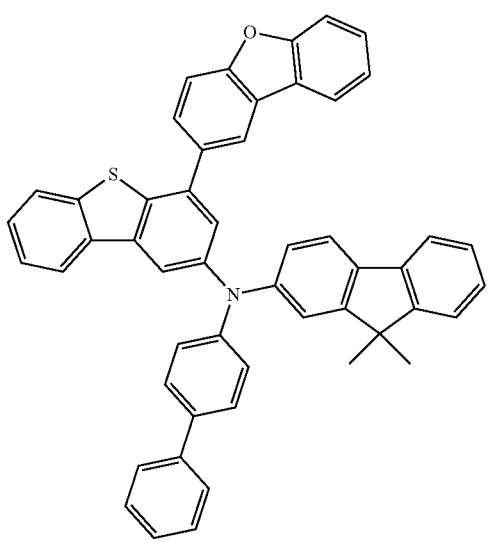
470
-continued
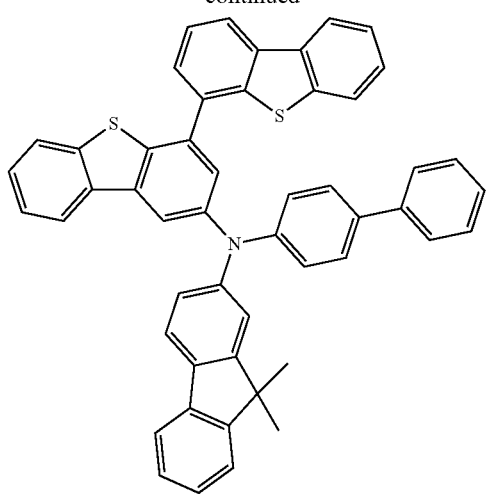
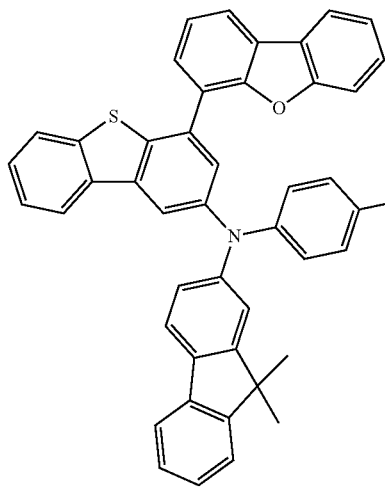
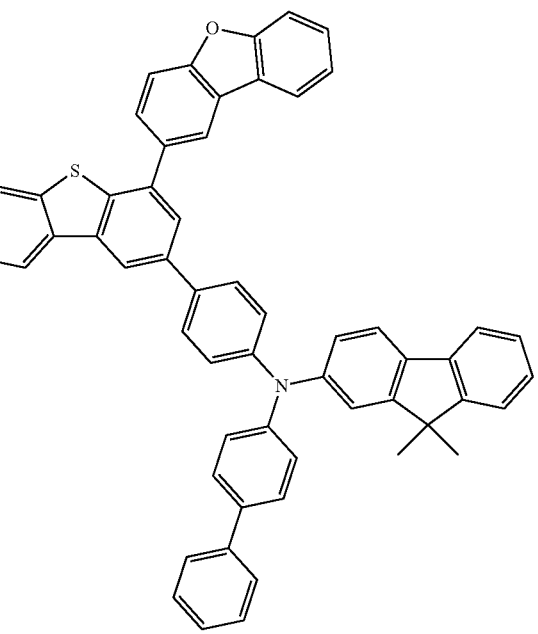

471
-continued
472
-continued
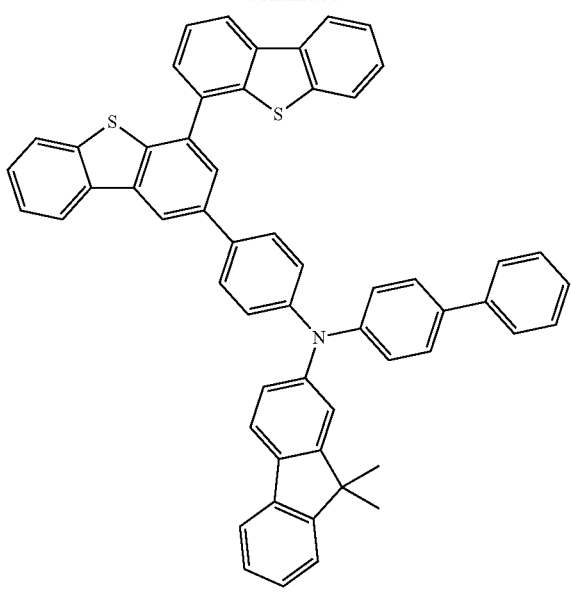
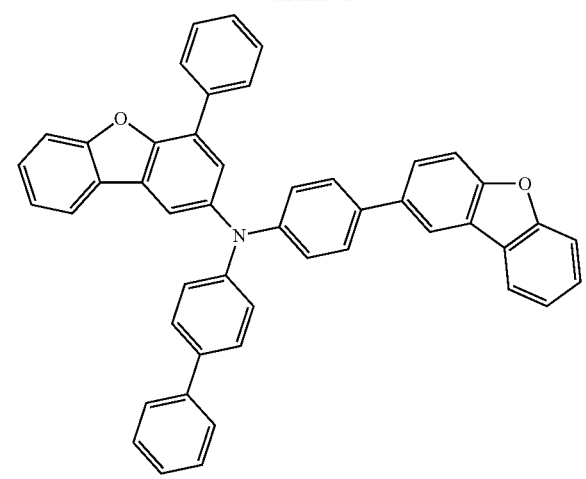
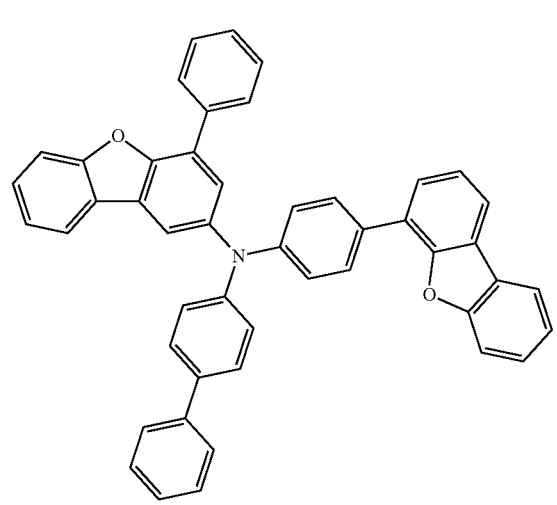
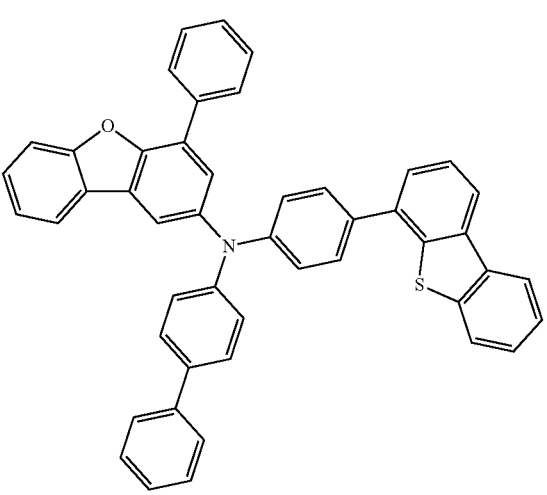

473
-continued
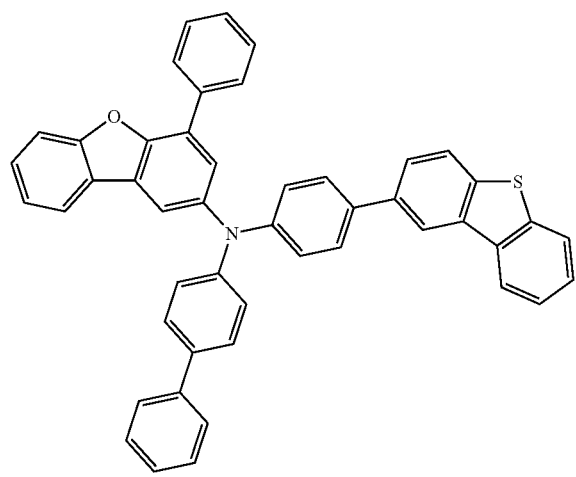
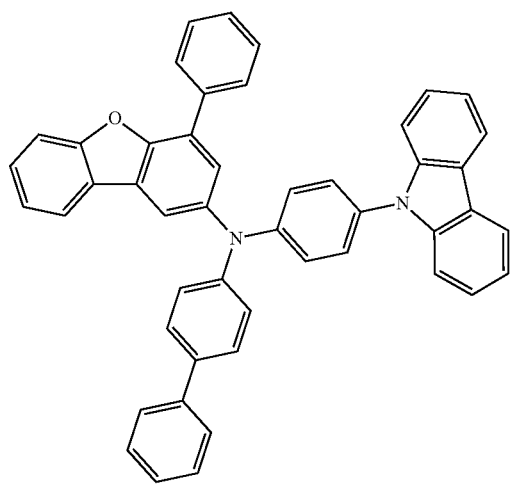
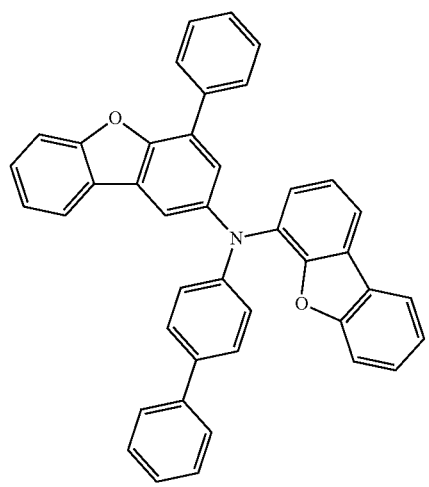
474
-continued
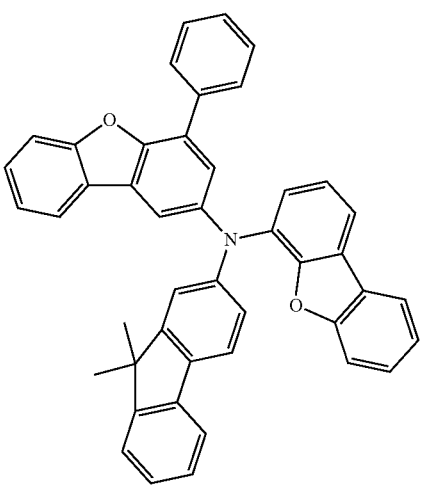
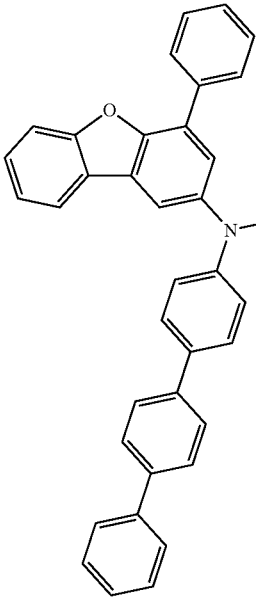
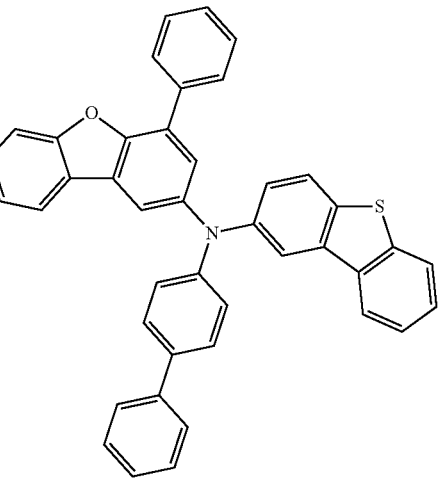

475
-continued
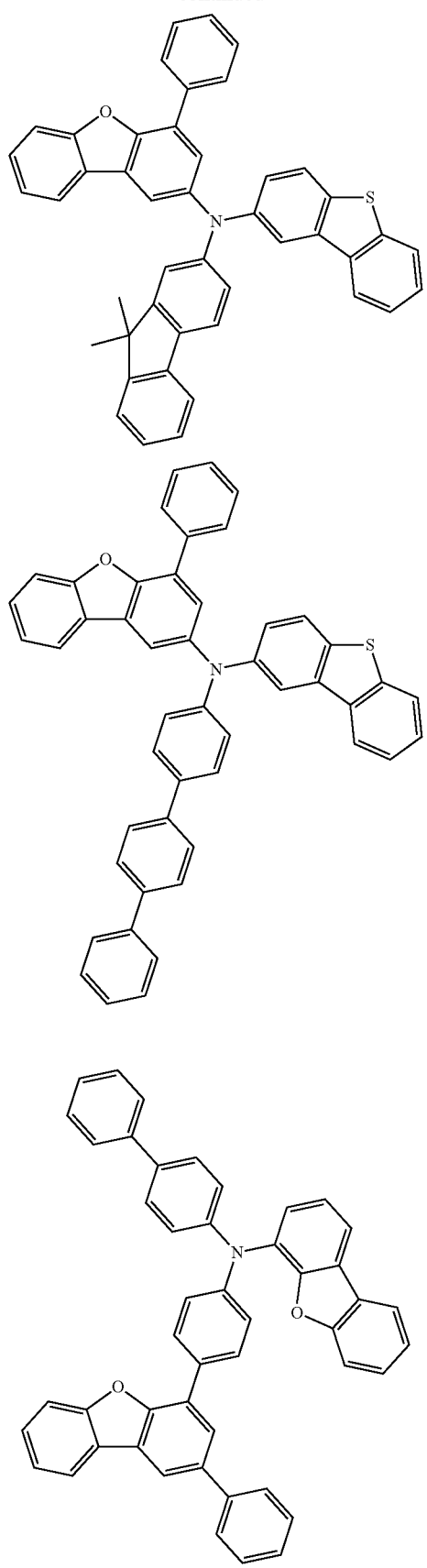
476
-continued
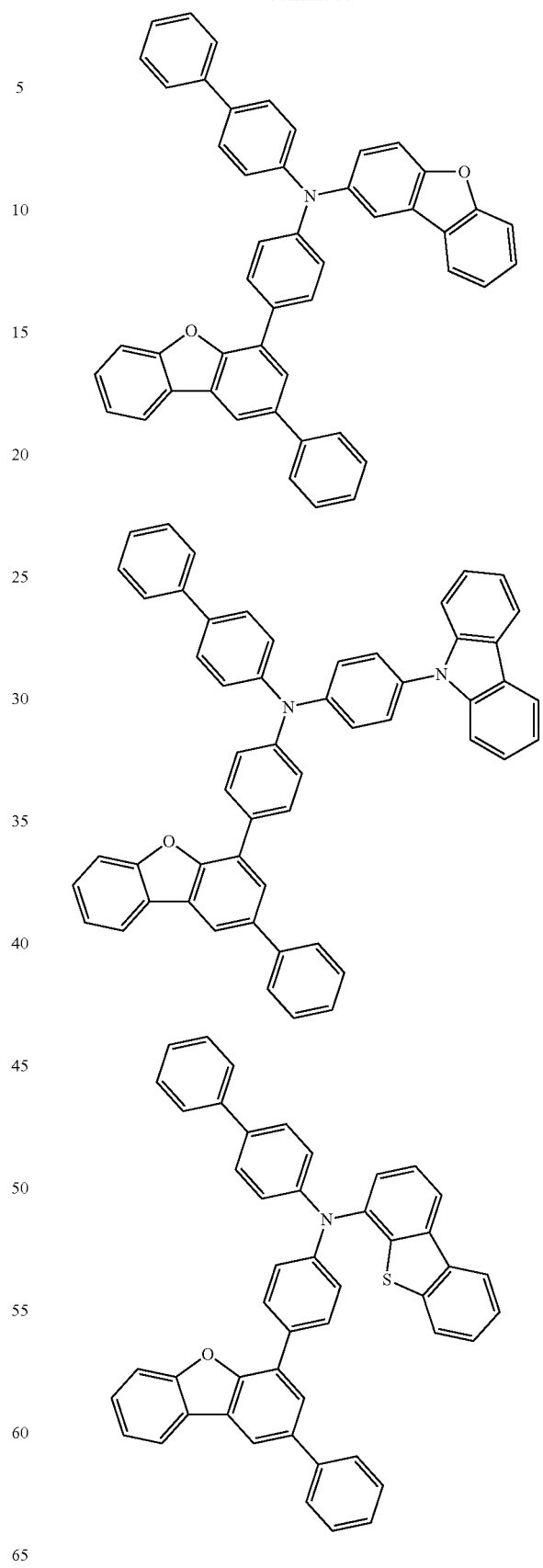

477
-continued
478
-continued
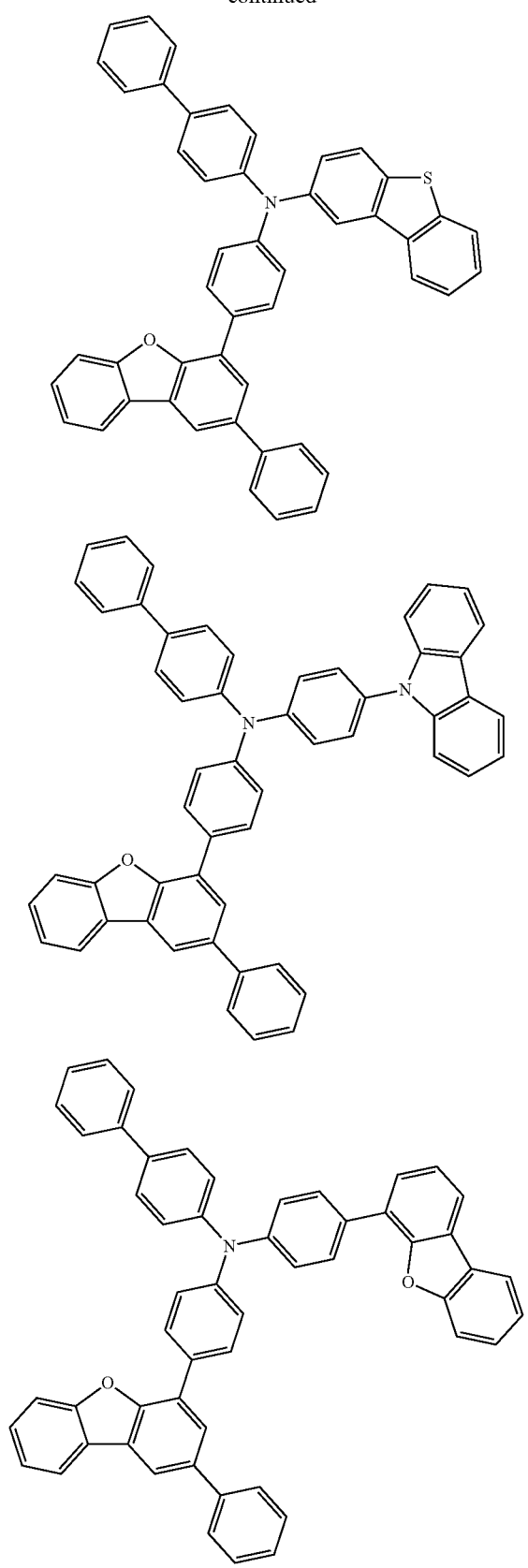
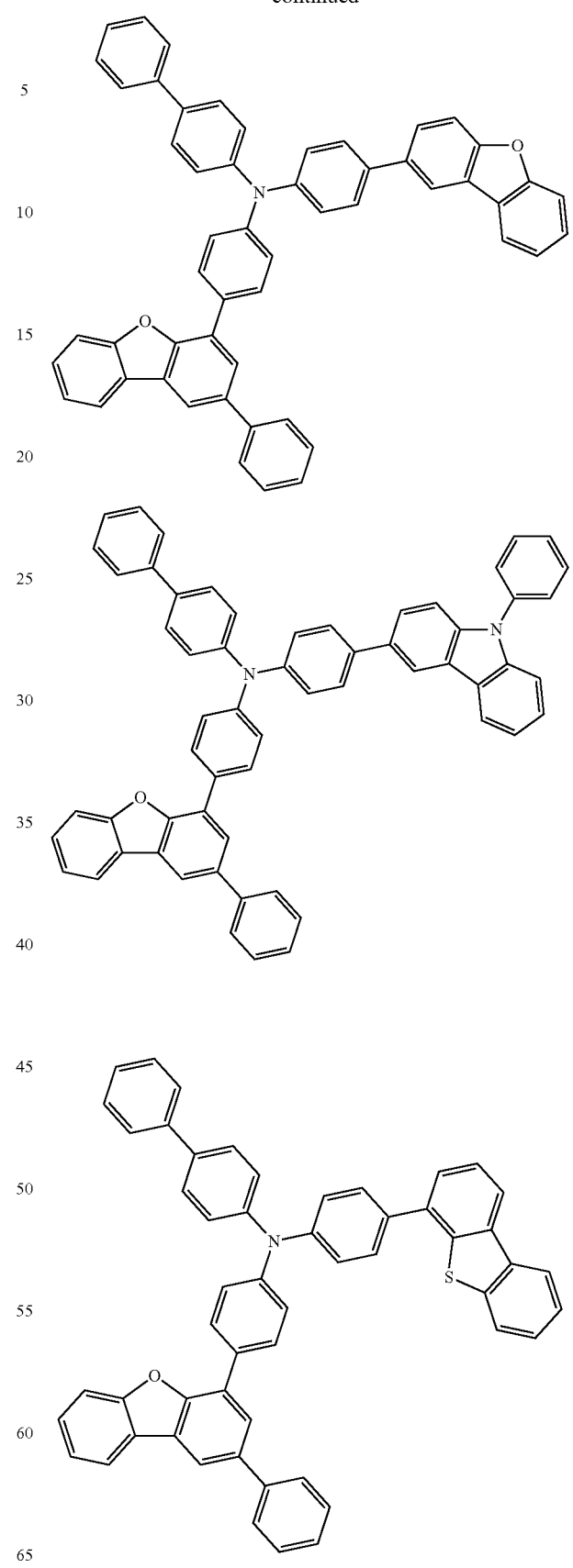

-continued

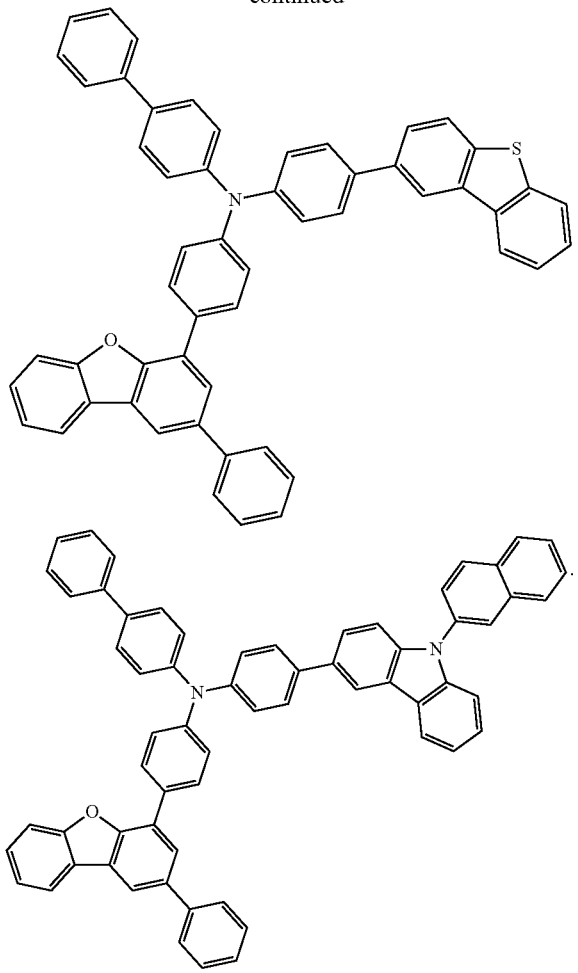

7. The organic light emitting device of claim 1, wherein the organic material layer comprises at least one of an electron transfer layer, an electron injection layer, or a layer carrying out electron transfer and electron injection at the same time, and the electron transfer layer, the electron injection layer, or the layer carrying out electron transfer and electron injection at the same time comprises the compound.

8. The organic light emitting device of claim 1, wherein the organic material layer comprises at lease one of a hole transfer layer, an electron blocking layer, or a layer carrying out hole transfer and electron blocking at the same time, and the hole transfer layer, the electron blocking layer, or the layer carrying out hole transfer and electron blocking at the same time comprises the compound.

9. The organic light emitting device of claim 1, wherein the organic material layer comprises at least one of a hole injection layer, a hole transfer layer, or a layer carrying out hole injection and hole transfer at the same time, and the hole injection layer, the hole transfer layer, or the layer carrying out hole injection and hole transfer at the same time comprises the compound.

10. The organic light emitting device of claim 1, wherein the organic material layer comprises the compound represented by Chemical Formula 1 as a host, and comprises other organic compounds, metals or metal compounds as a dopant.

11. The organic light emitting device of claim 1, wherein the organic material layer further comprises a light emitting layer, and the light emitting layer comprises a compound represented by the following Chemical Formula A-1:

[Chemica Formula A-1]

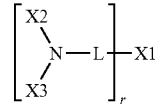

wherein, in Chemical Formula A-1,

X1 is a substituted or unsubstituted monovalent or higher benzofluorene group; a substituted or unsubstituted monovalent or higher fluoranthene group; a substituted or unsubstituted monovalent or higher pyrene group; or a substituted or unsubstituted monovalent or higher chrysene group;

L is a direct bond; a substituted or unsubstituted arylene group; or a substituted or unsubstituted heteroarylene group;

X2 and X3 are the same as or different from each other, and each independently a substituted or unsubstituted aryl group; a substituted or unsubstituted silyl group; a substituted or unsubstituted alkyl group; a substituted or unsubstituted aralkyl group; or a substituted or unsubstituted heteroaryl group, or bond to each other to form a substituted or unsubstituted ring;

r is an integer of 1 or greater; and when r is 2 or greater, each NX2X3L is the same as or different from each other.

12. The organic light emitting device of claim 11, wherein L is a direct bond, X1 is a substituted or unsubstituted divalent pyrene group, X2 and X3 are the same as or different from each other and each independently an aryl group unsubstituted or substituted with a germanium group, and r is 2.

13. The organic light emitting device of claim 1, wherein the organic material layer further comprises a light emitting layer, and the light emitting layer comprises a compound represented by the following Chemical Formula A-2:

[Chemical Formula A-2]

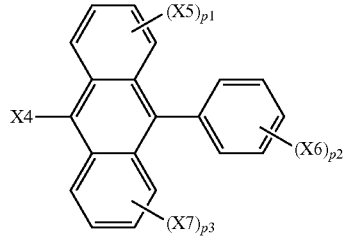

wherein, in Chemical Formula A-2,

X4 is a 1-naphthyl group, a 2-naphthyl group, a 1-anthryl group, a 2-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 3-methyl-2-naphthyl group, a 4-methyl-1-naphthyl group or the following chemical formula

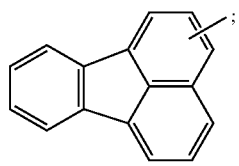

X6 is a phenyl group, a 1-naphthyl group, a 2-naphthyl group, a 1-anthryl group, a 2-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenyl group, a 4''-t-butyl-p-terphenyl-4-yl group or a 3-fluoranthenyl group;

X5 and X7 are the same as or different from each other, and each independently hydrogen; a substituted or unsubstituted alkyl group; a substituted or unsubstituted alkoxy group; a substituted or unsubstituted aryl group; or a substituted or unsubstituted heteroaryl group;

p2 is an integer of 1 to 5;

p1 and p3 are each an integer of 1 to 4; and when p1 to p3 are each 2 or greater, each of X5, X6 and X7 is the same as or different from each other.

14. The organic light emitting device of claim 13, wherein X4 is a 1-naphthyl group and X6 is a 2-naphthyl group.

15. The organic light emitting device of claim 11, wherein the light emitting layer further comprises a compound represented by the following Chemical Formula A-2:

[Chemical Formula A-2]

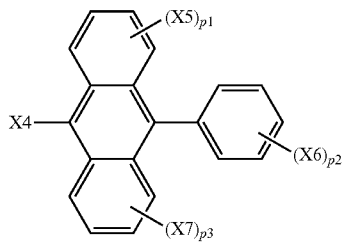

wherein, in Chemical Formula A-2,

X4 is a 1-naphthyl group, a 2-naphthyl group, a 1-anthryl group, a 2-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 3-methyl-2-naphthyl group, a 4-methyl-1-naphthyl group or the following chemical formula

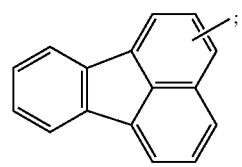

X6 is a phenyl group, a 1-naphthyl group, a 2-naphthyl group, a 1-anthryl group, a 2-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenyl group, a 4''-t-butyl-p-terphenyl-4-yl group or a 3-fluoranthenyl group;

X5 and X7 are the same as or different from each other, and each independently hydrogen; a substituted or unsubstituted alkyl group; a substituted or unsubstituted alkoxy group; a substituted or unsubstituted aryl group; or a substituted or unsubstituted heteroaryl group;

p2 is an integer of 1 to 5;

p1 and p3 are each an integer of 1 to 4; and when p1 to p3 are each 2 or greater, each of X5, X6 and X7 is the same as or different from each other.

* * * * *